United States Patent
Jimenez Nunez et al.

(10) Patent No.: US 10,421,742 B2
(45) Date of Patent: Sep. 24, 2019

(54) SUBSTITUTED OXOPYRIDINE DERIVATIVES

(71) Applicant: BAYER PHARMA AKTIENGESELLSCHAFT, Berlin (DE)

(72) Inventors: Eloisa Jimenez Nunez, Freiburg im Breisgau (DE); Jens Ackerstaff, Düsseldorf (DE); Susanne Röhrig, Hilden (DE); Alexander Hillisch, Solingen (DE); Katharina Meier, Mettmann (DE); Stefan Heitmeier, Wülfrath (DE); Adrian Tersteegen, Wuppertal (DE); Jan Stampfuß, Düsseldorf (DE); Pascal Ellerbrock, Düsseldorf (DE); Daniel Meibom, Wuppertal (DE); Dieter Lang, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/742,063

(22) PCT Filed: Jul. 5, 2016

(86) PCT No.: PCT/EP2016/065787
§ 371 (c)(1),
(2) Date: Jan. 5, 2018

(87) PCT Pub. No.: WO2017/005725
PCT Pub. Date: Jan. 12, 2017

(65) Prior Publication Data
US 2018/0194745 A1     Jul. 12, 2018

(30) Foreign Application Priority Data

Jul. 9, 2015  (EP) .................................... 15176099
Feb. 25, 2016  (EP) .................................... 16157350

(51) Int. Cl.
| | | |
|---|---|---|
| *C07D 401/10* | (2006.01) | |
| *C07D 401/14* | (2006.01) | |
| *C07D 413/14* | (2006.01) | |
| *C07D 413/10* | (2006.01) | |
| *A61P 7/02* | (2006.01) | |

(52) U.S. Cl.
CPC .............. *C07D 401/10* (2013.01); *A61P 7/02* (2018.01); *C07D 401/14* (2013.01); *C07D 413/10* (2013.01); *C07D 413/14* (2013.01)

(58) Field of Classification Search
CPC .................................................... C07D 401/10
USPC ....................................... 546/268.4; 514/340
See application file for complete search history.

(56) References Cited

U.S. PATENT DOCUMENTS

2018/0222889 A1*  8/2018  Corte .................. C07D 401/14

FOREIGN PATENT DOCUMENTS

| | | |
|---|---|---|
| EP | 1526131 A1 | 4/2005 |
| GB | 2497806 A | 6/2013 |
| WO | 2002042273 A2 | 5/2002 |
| WO | 2006030032 A1 | 3/2006 |
| WO | 2007131179 A1 | 11/2007 |
| WO | 2008079787 A2 | 7/2008 |
| WO | 2013056034 A1 | 4/2013 |
| WO | 2013093484 A1 | 6/2013 |
| WO | WO 2014/154794 | 10/2014 |
| WO | WO 2014/160592 | 10/2014 |
| WO | 2015011087 A1 | 1/2015 |
| WO | 2015063093 A1 | 5/2015 |
| WO | 2015120777 A1 | 8/2015 |
| WO | 2016046156 A1 | 3/2016 |
| WO | 2016046157 A1 | 3/2016 |
| WO | 2016046158 A1 | 3/2016 |
| WO | 2016046159 A1 | 3/2016 |
| WO | 2016046164 A1 | 3/2016 |
| WO | 2016046166 A1 | 3/2016 |

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*
International Preliminary Report on Patentability received for PCT Patent Application No. PCT/EP2016/065787, dated Jan. 9, 2018, 7 pages.
Ansell et al., "Managing Oral Anticoagulant Therapy", Sixth ACCP Consensus Conference on Antithrombotic Therapy, Chest, vol. 119, No. 1, Jan. 2001, pp. 22S-38S.

(Continued)

*Primary Examiner* — Patricia L Morris
(74) *Attorney, Agent, or Firm* — McBee Moore Woodward & Vanik IP, LLC

(57) ABSTRACT

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

9 Claims, No Drawings

(56) References Cited

OTHER PUBLICATIONS

Aponick et al., "Chirality Transfer in Au-Catalyzed Cyclization Reactions of Monoallylic Diols: Selective Access to Specific Enantiomers Based on Olefin Geometry", Organic Letters, vol. 13, No. 6, 2011, pp. 1330-1333.

Baker et al., "(BDP)CuH: A "Hot" Stryker's Reagent for Use in Achiral Conjugate Reductions", Organic Letters, vol. 10, No. 2, 2008, pp. 289-292.

Braunwald, Eugene, "Heart Disease: A Textbook of Cardiovascular Medicine", 5th edition, Includes Bibliographical References and Index, 1997, 23 pages.

Castells et al., "1-Alkoxycarbonylalkylidenetriphenylarsoranes: Preparation and Reactions", Tetrahedron, vol. 50, No. 48, 1994, pp. 13765-13774.

Dellinger et al., "Surviving Sepsis Campaign Guidelines for Management of Severe Sepsis and Septic Shock", Crit Care Med, vol. 32, No. 3, 2004, pp. 858-873.

Fier et al., "Synthesis of Difluoromethyl Ethers with Difluoromethyltriflate", Angew. Chem. Int. Ed., vol. 52, 2013, pp. 2092-2095.

Hirsh et al., "Oral Anticoagulants: Mechanism of Action, Clinical Effectiveness, and Optimal Therapeutic Range", Sixth ACCP Consensus Conference on Antithrombotic Therapy, Chest, vol. 119, No. 1, Jan. 2001, pp. 8S-21S.

Ikemoto et al., "A Practical Synthesis of the Chronic Renal Disease Agent, 4,5-Dihydro-3H-1,4,8b-triazaacenaphthylen-3-one Derivatives, Using Regioselective Chlorination of Ethyl 5-methylimidazo[1,2-a]pyridine-3-carboxylate with N-Chlorosuccinimide", Tetrahedron, vol. 56, 2000, pp. 7915-7921.

Kendall et al., "Discovery of pyrazolo[1,5-a]pyridines as p110α-selective PI3 Kinase Inhibitors", Bioorganic & Medicinal Chemistry, vol. 20, 2012, pp. 69-85.

Kinzel et al., "A New Palladium Precatalyst Allows for the Fast Suzuki-Miyaura Coupling Reactions of Unstable Polyfluorophenyl and 2-Heteroaryl Boronic Acids", J. Am. Chem. Soc., vol. 132, No. 40, 2010, pp. 14073-14075.

Levin et al., "Reaction of the Ruppert-Prakash Reagent with perfluorosulfonic Acids", Journal of Fluorine Chemistry, vol. 130, 2009, pp. 667-670.

Levy et al., "2001 SCCM/ESICM/ACCP/ATS/SIS International Sepsis Definitions Conference", Crit Care Med, vol. 31, No. 4, 2003, pp. 1250-1256.

Nakashima et al., "Pharmacokinetics of the New Antiplatelet Agent 2-methyl-3-(1,4,5,6-tetrahydronicotinoyl)pyrazolo[1,5-a]pyridine in Human Subjects", Arzneimittel Forschung. Drug Research, vol. 42, No. 1, 1992, pp. 60-64.

Pschyrembel, Willibald, "Pschyrembel: Klinisches Wörterbuch", 257, reworked edition with 2339 illustrations and 268 tables, 1994, pp. 610 (Official copy only). See attached communication under 37 CFR § 1.98(a) (3).

Römpp's, Chemistry L., "Heparin", Version 1.5, Stuttgart/New York: Georg Thieme Verlag, 1998, 2 pages (Official copy only). See attached communication under 37 CFR § 1.98(a) (3).

Wells et al., "Interactions of Warfarin with Drugs and Food", Annals of Internal Medicine, vol. 121, No. 9, Nov. 1, 1994, pp. 676-683

Williams & Wilkins, "American College of Chest Physicians/Society of Critical Care Medicine Consensus Conference: Definitions for Sepsis and Organ Failure and Guidelines for the Use of Innovative Therapies in Sepsis", Critical Care Medicine, vol. 20, No. 6, 1992, pp. 864-874.

International Search Report for PCT/EP2016/065787, dated Aug. 8, 2016, 2 pages.

* cited by examiner

SUBSTITUTED OXOPYRIDINE DERIVATIVES

This application is the U.S. national phase of International Application No. PCT/EP2016/065787 filed 5 Jul. 2016, which designated the U.S. and claims priority to EP Patent Application No. 15176099.8 filed 9 Jul. 2015, and EP Patent Application No. 16157350.6 filed 25 Feb. 2016, the entire contents of each of which are hereby incorporated by reference.

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood.

In the more recent past, the traditional theory of two separate regions of the coagulation cascade (extrinsic and intrinsic path) has been modified owing to new findings: In these models, coagulation is initiated by binding of activated factor VIIa to tissue factor (TF). The resulting complex activates factor X, which in turn leads to generation of thrombin with subsequent production of fibrin and platelet activation (via PAR-1) as injury-sealing end products of haemostasis. Compared to the subsequent amplification/propagation phase, the thrombin production rate in this first phase is low and as a result of the occurrence of TFPI as inhibitor of the TF-FVIIa-FX complex is limited in time.

A central component of the transition from initiation to amplification and propagation of coagulation is factor XIa: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

In addition, it becomes the focus that, in addition to the stimulation via tissue factor, the coagulation system can be activated particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa which subsequently activates factor XI, attached to cell surfaces, to factor XIa. This leads to further activation of the coagulation cascade as described above. In addition, factor XIIa also activates bound plasma prokallikrein to plasma kallikrein (PK) which, in a potentiation loop, firstly leads to further factor XII activation, overall resulting in amplification of the initiation of the coagulation cascade. In addition, PK is an important bradikinin-releasing protease which, inter alia, thus leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Uncontrolled activation of the coagulation system or defective inhibition of the activation processes may lead to the formation of local thromboses or embolisms in vessels (arteries, veins, lymph vessels) or cardiac cavities. In addition, systemic hypercoagulability may lead to system-wide formation of thrombi and finally to consumption coagulopathy in the context of a disseminated intravasal coagulation. Thromboembolic complications may also occur in extracorporeal circulatory systems such as during haemodialysis and also in vascular prostheses or prosthetic heart valves and stents.

In the course of many cardiovascular and metabolic disorders, there is an increased tendency for coagulation and platelet activation owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis. This unwanted and excessive activation of coagulation may, by formation of fibrin- and platelet-rich thrombi, lead to thromboembolic disorders and thrombotic complications with life-threatening conditions. Inflammable processes may also be involved here. Accordingly, thromboembolic disorders are still one of the most frequent causes of morbidity and mortality in most industrialized countries.

The anticoagulants known from the prior art, that is to say substances for inhibiting or preventing blood coagulation, have various disadvantages. Accordingly, in practice, efficient treatment methods or the prophylaxis of thrombotic/thromboembolic disorders is found to be very difficult and unsatisfactory.

In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral haemorrhages and bleeding in the gastrointestinal tract, and there may be thrombopaenia, alopecia medicomentosa or osteoporosis. Low-molecular-weight heparins do have a lower probability of leading to the development of heparin-induced thrombocytopaenia; however, they can also only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other coumarin derivatives which nonselectively inhibit the synthesis of various products of certain vitamin K-dependent coagulation factors in the liver. Owing to the mechanism of action, the onset of action is only very slow (latency to the onset of action 36 to 48 hours). The compounds can be administered orally; however, owing to the high risk of bleeding and the narrow therapeutic index complicated individual adjustment and monitoring of the patient are required. In addition, other side-effects such as gastrointestinal problems, hair loss and skin necroses have been described.

More recent approaches for oral anticoagulants are in various phases of clinical evaluation or in clinical use, and have demonstrated their effectiveness in various studies. However, taking these medicaments can also lead to bleeding complications, particularly in predisposed patients. Thus, for antithrombotic medicaments, the therapeutic window is of central importance: The interval between the therapeutically active dose for coagulation inhibition and the dose where bleeding may occur should be as large as possible so that maximum therapeutic activity is achieved at a minimum risk profile.

In various in vitro and in vivo models with, for example, antibodies as factor XIa inhibitors, but also in factor XIa knock-out models, the antithrombotic effect with small/no prolongation of bleeding time or extension of blood volume was confirmed. In clinical studies, elevated factor XIa concentrations were associated with an increased event rate. In contrast, factor XI deficiency (haemophilia C) did not lead to spontaneous bleeding and was apparent only in the course of surgical operations and traumata, but did show protection with respect to certain thromboembolic events.

In addition, plasma kallikrein (PK) is associated with other disorders, which are associated with increased vascular permeability or chronic inflammatory disorders such as is the case in diabetic retinopathy, macular oedema and hereditary angiooedema or chronic inflammatory intestinal disorders. Diabetic retinopathy is primarily caused by microvascular deficiency, which leads to basal membrane thickening of the vessels and loss of vascularized pericytes followed by vascular occlusion and retinal ischaemia which, owing to the retinal hypoxia thus caused, may lead to enhanced vessel permeability with subsequent formation of a macular oedema and, due to all of the processes present, to the patient going blind. In hereditary angiooedema (HAE), reduced formation of the physiological kallikrein inhibitor C1-esterase inhibitor causes uncontrolled plasma kallikrein activation leading to inflammations with fulminant oedema formation and strong pains. From experimental animal models, there are indications that inhibition of plasma kallikrein inhibits increased vascular permeability and may therefore prevent formation of a macular oedema and/or diabetic retinopathy or may improve the acute symptoms of HAE. Oral plasma kallikrein inhibitors could also be used for prophylaxis of HAE.

The kinins generated by means of plasma kallikrein especially have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Furthermore, for many disorders the combination of antithrombotic and antiinflammatory principles may also be particularly attractive to prevent the mutual enhancement of coagulation and inflammation.

WO 2006/030032 describes inter alia substituted pyridinones as allosteric modulators of the mGluR2 receptor, and WO 2008/079787 describes substituted pyridin-2-ones and their use as glucokinase activators. WO 2014/154794, WO 2014/160592, WO 2015/011087, WO 2015/063093, WO 2016/046158, WO 2016/046157, WO 2016/046159, WO 2016/046164, WO 2016/046166 and WO 2016/046156 describe substituted pyridin-2-one and their use as factor XIa inhibitors.

It is therefore an object of the present invention to provide novel compounds for the treatment of cardiovascular disorders, in particular of thrombotic or thromboembolic disorders, in humans and animals, which compounds have a wide therapeutic window and, in addition, a good pharmacokinetic behavior.

Surprisingly, it has now been found that certain substituted oxopyridine derivatives represent highly potent factor XIa inhibitors exhibiting a significantly enhanced pharmacokinetic behavior, in particular a longer exposure of such a compound in the blood above the minimal effective concentration within a given dosing interval.

The invention provides compounds of the formula

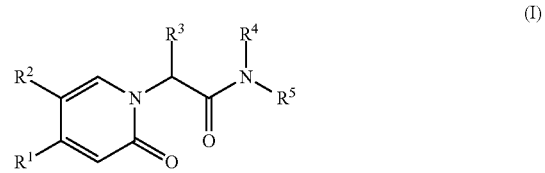

in which
$R^1$ represents a group of the formula

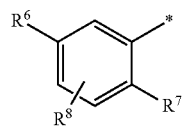

where * is the point of attachment to the oxopyridine ring,
$R^6$ represents chlorine or methyl,
$R^7$ represents 5- or 6-membered heterocyclyl,
where heterocyclyl may be substituted by a substituent selected from the group consisting of oxo, chlorine, fluorine, hydroxy, methyl, difluoromethyl, trifluoromethyl and 2,2,2-trifluoroethyl,
$R^8$ represents hydrogen or fluorine,
$R^2$ represents chlorine, methyl or methoxy,
$R^3$ represents hydrogen, $C_1$-$C_5$-alkyl, 1,1-difluoroethyl, 3,3,3-trifluoro-2-methoxyprop-1-yl or 3,3,3-trifluoro-2-ethoxyprop-1-yl,
where alkyl may be substituted by a substituent selected from the group consisting of fluorine, hydroxy, difluoromethyl, trifluoromethyl, methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl, pyridyl, $C_3$-$C_6$-cycloalkyloxy and 4- to 6-membered oxoheterocyclyloxy,
in which tert-butoxy and isopropoxy may be substituted by 1 to 3 fluorine substituents, and
where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy,
and
in which oxoheterocyclyl may be substituted by 1 to 2 substituents independently of one another selected from the group consisting of fluorine, methyl, ethyl, difluoromethyl and trifluoromethyl,
and
in which pyrazolyl is substituted by 1 or 2 substituents independently of one another selected from the group consisting of fluorine, methyl and ethyl,
and
in which cycloalkyloxy and oxoheterocyclyloxy may be substituted by 1 to 2 substituents independently of one another selected from the group consisting of fluorine and methyl,
$R^4$ represents hydrogen,
$R^5$ represents a group of the formula

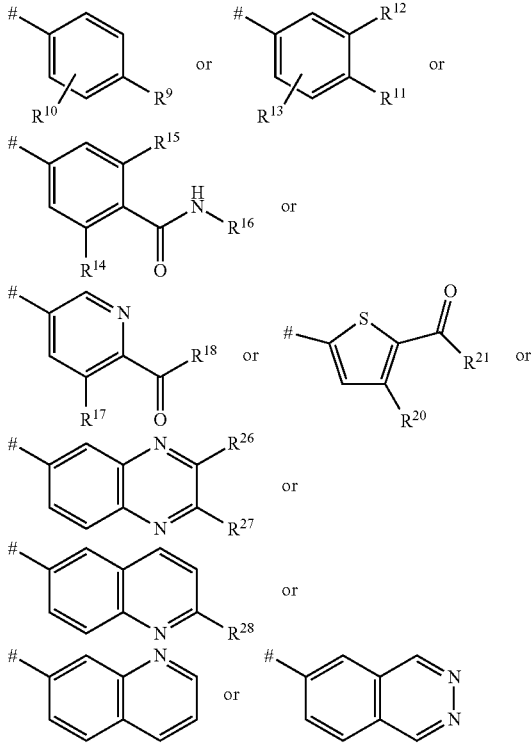

where # is the point of attachment to the nitrogen atom,
$R^9$ represents hydroxycarbonyl or 5-membered heterocyclyl,
$R^{10}$ represents hydrogen or fluorine,
$R^{11}$ and $R^{12}$ together with the carbon atoms to which they are attached form a 5-membered heterocycle,
where the heterocycle may be substituted by 1 to 2 substituents independently of one another selected from the group consisting of oxo, hydroxy, hydroxycarbonyl, methyl, ethyl, 2-hydroxyethyl, difluoromethyl, trifluoromethyl, cyclopropylmethyl, trideuteromethyl, 2,2-difluoroethyl and 2,2,2-trifluoroethyl,
$R^{13}$ represents hydrogen or fluorine,
$R^{14}$ represents hydrogen or fluorine,
$R^{15}$ represents hydrogen or fluorine,
$R^{16}$ represents hydrogen, $C_1$-$C_4$-alkyl or cyclopropyl,
$R^{17}$ represents hydrogen or fluorine,
$R^{18}$ represents hydroxy or —$NHR^{19}$,
in which
$R^{19}$ represents hydrogen, $C_1$-$C_4$-alkyl or cyclopropyl,
$R^{20}$ represents hydrogen or fluorine,
$R^{21}$ represents hydroxy or —$NHR^{22}$,
in which
$R^{22}$ represents hydrogen, $C_1$-$C_4$-alkyl or cyclopropyl,
$R^{26}$ represents hydrogen, methyl or trifluoromethyl,
$R^{27}$ represents hydrogen, methyl or trifluoromethyl,
$R^{28}$ represents hydrogen, cyano, methyl, trifluoromethyl or amino,
and the salts thereof, the solvates thereof and the solvates of the salts thereof.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

In the context of the present invention, the term "enantiomerically pure" is to be understood as meaning that the compound in question with respect to the absolute configuration of the chiral centre is present in an enantiomeric excess of more than 95%, preferably more than 97%. The enantiomeric excess, ee, is calculated here by evaluating the corresponding HPLC chromatogram on a chiral phase using the formula below:

$$ee=[E^A(\text{area \%})-E^B(\text{area \%})]\times 100\%/[E^A(\text{area \%})+E^B(\text{area \%})]$$

($E^A$: major enantiomer, $E^B$: minor enantiomer)

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Designated as solvates in the context of the invention are those forms of the compounds according to the invention which form a complex in the solid or liquid state by coordination with solvent molecules. Hydrates are a specific form of the solvates in which the coordination is with water.

The present invention additionally also encompasses prodrugs of the compounds of the invention. The term "prodrugs" encompasses compounds which for their part may be biologically active or inactive but are converted during their residence time in the body into compounds according to the invention (for example by metabolism or hydrolysis).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is used here synonymously with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, unless specified otherwise, the substituents are defined as follows:

Alkyl represents a straight-chain or branched alkyl radical having 1 to 5 carbon atoms, preferably 1 to 4 carbon atoms, particularly preferably 1 to 3 carbon atoms, by way of example and with preference methyl, ethyl, n-propyl, isopropyl, 2-methylprop-1-yl, n-butyl, tert-butyl and 2,2-dimethylprop-1-yl.

Alkoxy represents a straight-chain or branched alkoxy radical having 1 to 4 carbon atoms, preferably 1 to 3 carbon atoms, by way of example and with preference methoxy, ethoxy, n-propoxy, isopropoxy, 2-methylprop-1-oxy, n-butoxy and tert-butoxy.

Cycloalkyl represents a monocyclic cycloalkyl group having 3 to 6 carbon atoms, cycloalkyl which may be mentioned by way of example and with preference being cyclopropyl, cyclobutyl, cyclopentyl and cyclohexyl.

4- to 6-membered oxoheterocyclyl in the definition of the radical $R^3$ represents a saturated monocyclic radical having 4 to 6 ring atoms in which one ring atom is an oxygen atom, by way of example and with preference oxetanyl, tetrahydrofuranyl and tetrahydro-2H-pyranyl.

4- to 6-membered thioheterocyclyl in the definition of the radical $R^3$ represents a saturated monocyclic radical having 4 to 6 ring atoms in which one ring atom is a sulphur atom, by way of example and with preference thientanyl, tetrahydrothienyl and tetrahydro-2H-thiopyranyl.

5- or 6-membered heterocyclyl in the definition of the radical $R^7$ represents a saturated, partially unsaturated or aromatic monocyclic radical having 5 or 6 ring atoms and up to 4 heteroatoms from the group consisting of S, O and N, where a nitrogen atom may also form an N-oxide, by way of example and with preference furyl, pyrrolyl, thiazolyl, oxazolyl, isoxazolyl, oxadiazolyl, thiadiazolyl, pyrazolyl, imidazolyl, triazolyl, tetrazolyl, dihydro-1,2-oxazolyl, dihydro-1,3-oxazolyl, dihydroimidazolyl, dihydropyrazolyl, dihydrothiazolyl, dihydropyrrolyl and dihydrodioxazinyl.

5-membered heterocyclyl in the definition of the radical $R^9$ represents a saturated, partially unsaturated or aromatic monocyclic radical having 5 ring atoms and up to 4 heteroatoms from the group consisting of S, O and N, where a nitrogen atom may also form an N-oxide, by way of example and with preference thienyl, furyl, pyrrolyl, thiazolyl, oxazolyl, isoxazolyl, oxadiazolyl, thiadiazolyl, pyrazolyl, imidazolyl, triazolyl, tetrazolyl, dihydrooxazolyl and dihydroimidazolyl.

5-membered heterocycle in the definition of the radicals $R^{11}$ and $R^{12}$ represents a saturated, partially unsaturated or aromatic monocyclic radical having 5 ring atoms and up to 3 heteroatoms, preferably up to 2 heteroatoms, from the group consisting of S, O and N, where a nitrogen atom may also form an N-oxide. This 5-membered heterocycle together with the phenyl ring to which it is attached represents, by way of example and with preference indolin-5-yl, isoindolin-5-yl, 2,3-dihydro-1H-indazol-5-yl, 2,3-dihydro-1H-benzimidazol-5-yl, 1,3-dihydro-2,1-benzoxazol-5-yl, 2,3-dihydro-1,3-benzoxazol-5-yl, 1,3-dihydro-2,1-benzothiazol-5-yl, 2,3-dihydro-1,3-benzothiazol-5-yl, 1H-benzimidazol-5-yl, 1H-indazol-5-yl, 2H-indazol-5-yl, 1,2-benzoxazol-5-yl, benzotriazol-5-yl, benzofuran-5-yl, benzothiophen-5-yl, indolin-6-yl, isoindolin-6-yl, 2,3-dihydro-1H-indazol-6-yl, 2,3-dihydro-1H-benzimidazol-6-yl, 1,3-dihydro-2,1-benzoxazol-6-yl, 2,3-dihydro-1,3-benzoxazol-6-yl, 1,3-dihydro-2,1-benzothiazol-6-yl, 2,3-dihydro-1,3-benzothiazol-6-yl, 1H-benzimidazol-6-yl, 1H-indazol-6-yl, 2H-indazol-6-yl, 1,2-benzoxazol-6-yl, benzotriazol-6-yl, benzofuran-6-yl and benzothiophen-6-yl.

In the formulae of the group which may represent $R^1$, the end point of the line marked by * in each case does not represent a carbon atom or a $CH_2$ group, but is part of the bond to the atom to which $R^1$ is attached.

In the formulae of the group which may represent $R^5$, the end point of the line marked by # in each case does not represent a carbon atom or a $CH_2$ group, but is part of the bond to the atom to which $R^5$ is attached.

Preference is given to compounds of the formula (I) in which
$R^1$ represents a group of the formula

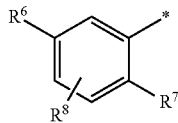

where * is the point of attachment to the oxopyridine ring,
$R^6$ represents chlorine or methyl,
$R^7$ represents 5- or 6-membered heterocyclyl,
where heterocyclyl may be substituted by a substituent selected from the group consisting of oxo, chlorine, fluorine, hydroxy, methyl, difluoromethyl, trifluoromethyl and 2,2,2-trifluoroethyl,
$R^8$ represents hydrogen or fluorine,
$R^2$ represents chlorine, methyl or methoxy,
$R^3$ represents hydrogen, $C_1$-$C_5$-alkyl, 1,1-difluoroethyl, 3,3,3-trifluoro-2-methoxyprop-1-yl or 3,3,3-trifluoro-2-ethoxyprop-1-yl,
where alkyl may be substituted by a substituent selected from the group consisting of fluorine, hydroxy, difluoromethyl, trifluoromethyl, methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl, pyridyl, $C_3$-$C_6$-cycloalkyloxy and 4- to 6-membered oxoheterocyclyloxy,
in which tert-butoxy and isopropoxy may be substituted by 1 to 3 fluorine substituents,
and
where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy,
and
in which oxoheterocyclyl may be substituted by 1 to 2 substituents independently of one another selected from the group consisting of fluorine, methyl, ethyl, difluoromethyl and trifluoromethyl,
and
in which pyrazolyl is substituted by 1 or 2 substituents independently of one another selected from the group consisting of fluorine, methyl and ethyl,
and
in which cycloalkyloxy and oxoheterocyclyloxy may be substituted by 1 to 2 substituents independently of one another selected from the group consisting of fluorine and methyl, $R^4$ represents hydrogen,
$R^5$ represents a group of the formula

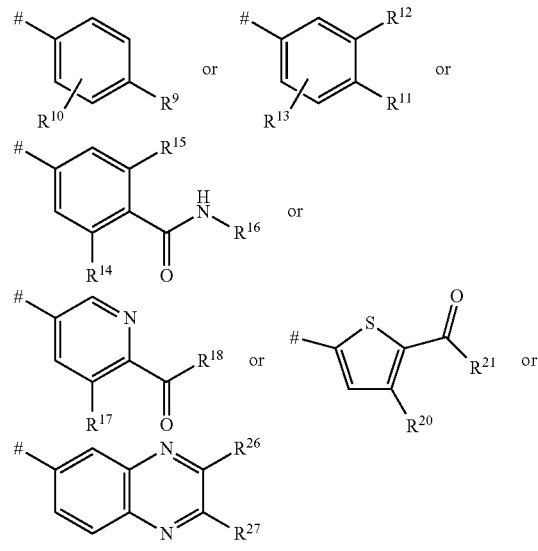

where # is the point of attachment to the nitrogen atom,
$R^9$ represents hydroxycarbonyl or 5-membered heterocyclyl,
$R^{10}$ represents hydrogen or fluorine,
$R^{11}$ and $R^{12}$ together with the carbon atoms to which they are attached form a 5-membered heterocycle,
where the heterocycle may be substituted by 1 to 2 substituents independently of one another selected from the group consisting of oxo, hydroxy, hydroxycarbonyl, methyl, difluoromethyl and trifluoromethyl,
$R^{13}$ represents hydrogen or fluorine,
$R^{14}$ represents hydrogen or fluorine,
$R^{15}$ represents hydrogen or fluorine,
$R^{16}$ represents hydrogen, $C_1$-$C_4$-alkyl or cyclopropyl,
$R^{17}$ represents hydrogen or fluorine,
$R^{18}$ represents hydroxy or —$NHR^{19}$,
in which
$R^{19}$ represents hydrogen, $C_1$-$C_4$-alkyl or cyclopropyl,
$R^{20}$ represents hydrogen or fluorine,
$R^{21}$ represents hydroxy or —$NHR^{22}$,
in which
$R^{22}$ represents hydrogen, $C_1$-$C_4$-alkyl or cyclopropyl,
$R^{26}$ represents hydrogen,
$R^{27}$ represents hydrogen,
and the salts thereof, the solvates thereof and the solvates of the salts thereof.

Preference is also given to compounds of the formula (I) in which
$R^1$ represents a group of the formula

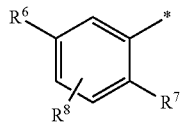

where * is the point of attachment to the oxopyridine ring,
$R^6$ represents chlorine or methyl,
$R^7$ represents 5- or 6-membered heterocyclyl, where heterocyclyl may be substituted by a substituent selected from the group consisting of oxo, chlorine, fluorine and hydroxy, $R^8$ represents hydrogen or fluorine, $R^2$ represents chlorine, methyl or methoxy, $R^3$ represents $C_1$-$C_5$-alkyl, 1,1-difluoroethyl, 3,3,3-trifluoro-2-methoxyprop-1-yl or 3,3,3-trifluoro-2-ethoxyprop-1-yl, where alkyl may be substituted by a substituent selected from the group consisting of fluorine, hydroxy, difluoromethyl, trifluoromethyl, methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl, pyridyl, $C_3$-$C_6$-cycloalkyloxy and 4- to 6-membered oxoheterocyclyloxy, in which tert-butoxy and isopropoxy may be substituted by 1 to 3 fluorine substituents, and where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy, and in which oxoheterocyclyl may be substituted by 1 to 2 substituents independently of one another selected from the group consisting of fluorine, methyl, ethyl, difluoromethyl and trifluoromethyl, and in which pyrazolyl is substituted by 1 or 2 substituents independently of one another selected from the group consisting of fluorine, methyl and ethyl, and in which cycloalkyloxy and oxoheterocyclyloxy may be substituted by 1 to 2 substituents independently of one another selected from the group consisting of fluorine and methyl, $R^4$ represents hydrogen, $R^5$ represents a group of the formula

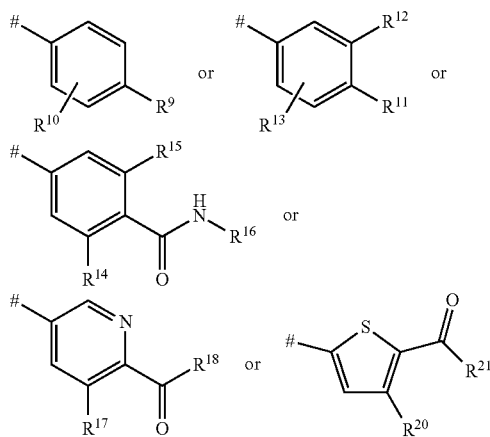

where # is the point of attachment to the nitrogen atom, $R^9$ represents hydroxycarbonyl or 5-membered heterocyclyl, $R^{10}$ represents hydrogen or fluorine, $R^{11}$ and $R^{12}$ together with the carbon atoms to which they are attached form a 5-membered heterocycle, where the heterocycle may be substituted by 1 to 2 substituents independently of one another selected from the group consisting of oxo, hydroxy, hydroxycarbonyl, methyl, difluoromethyl and trifluoromethyl, $R^{13}$ represents hydrogen or fluorine, $R^{14}$ represents hydrogen or fluorine, $R^{15}$ represents hydrogen or fluorine, $R^{16}$ represents hydrogen, $C_1$-$C_4$-alkyl or cyclopropyl, $R^{17}$ represents hydrogen or fluorine, $R^{18}$ represents hydroxy or —$NHR^{19}$, in which $R^{19}$ represents hydrogen, $C_1$-$C_4$-alkyl or cyclopropyl, $R^{20}$ represents hydrogen or fluorine, $R^{21}$ represents hydroxy or —$NHR^{22}$, in which $R^{22}$ represents hydrogen, $C_1$-$C_4$-alkyl or cyclopropyl, and the salts thereof, the solvates thereof and the solvates of the salts thereof.

Preference is also given to compounds of the formula (I) in which $R^1$ represents a group of the formula

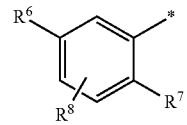

where * is the point of attachment to the oxopyridine ring, $R^6$ represents chlorine, $R^7$ represents furyl, pyrrolyl, oxazolyl, isoxazolyl, oxadiazolyl, dihydro-1,2-oxazolyl, dihydro-1,3-oxazolyl, imidazolyl, pyrazolyl, triazolyl, tetrazolyl, dihydroimidazolyl, dihydropyrazolyl, dihydropyrrolyl or dihydrodioxazinyl, where furyl, pyrrolyl, oxazolyl, isoxazolyl, oxadiazolyl, dihydro-1,2-oxazolyl, dihydro-1,3-oxazolyl, imidazolyl, pyrazolyl, triazolyl, tetrazolyl, dihydroimidazolyl, dihydropyrazolyl, dihydropyrrolyl and dihydrodioxazinyl may be substituted by a substituent selected from the group consisting of oxo, chlorine, fluorine, hydroxy, methyl, difluoromethyl, trifluoromethyl and 2,2,2-trifluoroethyl, $R^8$ represents hydrogen, $R^2$ represents chlorine or methoxy, $R^3$ represents hydrogen or $C_1$-$C_5$-alkyl, where alkyl may be substituted by a substituent selected from the group consisting of difluoromethyl, trifluoromethyl, methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl and $C_3$-$C_6$-cycloalkyloxy, in which tert-butoxy and isopropoxy may be substituted by 1 to 3 fluorine substituents, and where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy, and in which oxoheterocyclyl may be substituted by 1 to 2 substituents independently of one another selected from the group consisting of fluorine, methyl, ethyl, difluoromethyl and trifluoromethyl, and
in which pyrazolyl is substituted by 1 or 2 substituents independently of one another selected from the group consisting of methyl and ethyl,
and
in which cycloalkyloxy may be substituted by 1 or 2 substituents independently of one another selected from the group consisting of fluorine and methyl, $R^4$ represents hydrogen,
$R^5$ represents a group of the formula

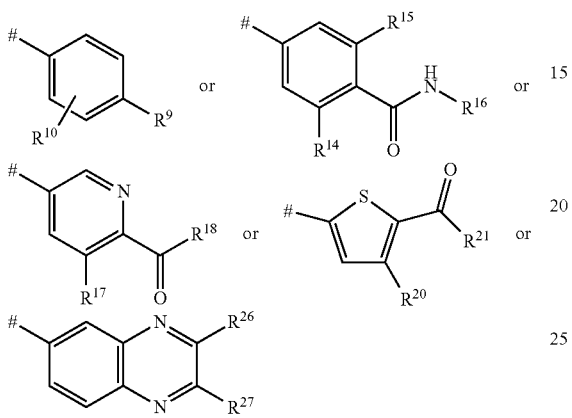

where # is the point of attachment to the nitrogen atom,
$R^9$ represents hydroxycarbonyl,
$R^{10}$ represents hydrogen or fluorine,
$R^{14}$ represents hydrogen or fluorine,
$R^{15}$ represents hydrogen,
$R^{16}$ represents hydrogen, methyl or ethyl,
$R^{17}$ represents hydrogen or fluorine,
$R^{18}$ represents —$NHR^{19}$,
in which
$R^{19}$ represents hydrogen, methyl or ethyl,
$R^{20}$ represents hydrogen or fluorine,
$R^{21}$ represents —$NHR^{22}$,
in which
$R^{22}$ represents hydrogen, methyl, ethyl or cyclopropyl,
$R^{26}$ represents hydrogen,
$R^{27}$ represents hydrogen,
or
$R^5$ represents 2H-indazol-5-yl,
where the 5-membered heterocycle in 2H-indazol-5-yl may be substituted by a substituent selected from the group consisting of methyl, difluoromethyl and trifluoromethyl,
and
where the benzyl ring in 2H-indazol-5-yl may be substituted by a fluorine substituent, and the salts thereof, the solvates thereof and the solvates of the salts thereof.

Preference is also given to compounds of the formula (I) in which
$R^1$ represents a group of the formula

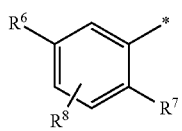

where * is the point of attachment to the oxopyridine ring,
$R^6$ represents chlorine,
$R^7$ represents furyl, pyrrolyl, oxazolyl, isoxazolyl, oxadiazolyl, dihydro-1,2-oxazolyl, dihydro-1,3-oxazolyl, imidazolyl, pyrazolyl, triazolyl, tetrazolyl, dihydroimidazolyl, dihydropyrazolyl, dihydropyrrolyl or dihydrodioxazinyl,
where furyl, pyrrolyl, oxazolyl, isoxazolyl, oxadiazolyl, dihydro-1,2-oxazolyl, dihydro-1,3-oxazolyl, imidazolyl, pyrazolyl, triazolyl, tetrazolyl, dihydroimidazolyl, dihydropyrazolyl, dihydropyrrolyl and dihydrodioxazinyl may be substituted by a substituent selected from the group consisting of oxo, chlorine, fluorine and hydroxy, $R^8$ represents hydrogen,
$R^2$ represents chlorine or methoxy,
$R^3$ is $C_1$-$C_5$-alkyl;
where alkyl may be substituted by a substituent selected from the group consisting of methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl and $C_3$-$C_6$-cycloalkyloxy,
in which tert-butoxy and isopropoxy may be substituted by 1 to 3 fluorine substituents,
and
where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy,
and
in which oxoheterocyclyl may be substituted by 1 to 2 substituents independently of one another selected from the group consisting of fluorine, methyl, ethyl, difluoromethyl and trifluoromethyl,
and
in which pyrazolyl is substituted by 1 or 2 substituents independently of one another selected from the group consisting of methyl and ethyl,
and
in which cycloalkyloxy may be substituted by 1 or 2 substituents independently of one another selected from the group consisting of fluorine and methyl, $R^4$ represents hydrogen,
$R^5$ represents a group of the formula

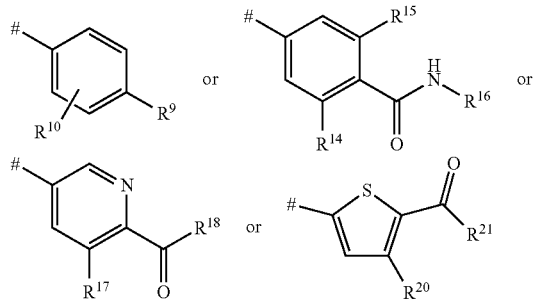

where # is the point of attachment to the nitrogen atom,
$R^9$ represents hydroxycarbonyl,
$R^{10}$ represents hydrogen or fluorine,
$R^{14}$ represents hydrogen or fluorine,
$R^{15}$ represents hydrogen, $R^{16}$ represents hydrogen, methyl or ethyl,
$R^{17}$ represents hydrogen or fluorine,
$R^{18}$ represents —NHR$^{19}$,
in which
$R^{19}$ represents hydrogen, methyl or ethyl,
$R^{20}$ represents hydrogen or fluorine,
$R^{21}$ represents —NHR$^{22}$,
in which
$R^{22}$ represents hydrogen, methyl, ethyl or cyclopropyl,
or
$R^5$ represents 2H-indazol-5-yl,
where the 5-membered heterocycle in 2H-indazol-5-yl may be substituted by a substituent selected from the group consisting of methyl, difluoromethyl and trifluoromethyl,
and
where the benzyl ring in 2H-indazol-5-yl may be substituted by a fluorine substituent, and the salts thereof, the solvates thereof and the solvates of the salts thereof.

Preference is also given to compounds of the formula (I) in which
$R^1$ represents a group of the formula

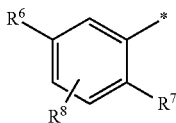

where * is the point of attachment to the oxopyridine ring,
$R^6$ represents chlorine,
$R^7$ represents oxazolyl, oxadiazolyl, dihydro-1,2-oxazolyl, imidazolyl, pyrazolyl, tetrazolyl or dihydrodioxazinyl,
where oxazolyl, oxadiazolyl, dihydro-1,2-oxazolyl, imidazolyl, pyrazolyl, tetrazolyl and dihydrodioxazinyl may be substituted by a fluorine substituent,
$R^8$ represents hydrogen,
$R^2$ represents methoxy,
$R^3$ represents ethyl,
where ethyl may be substituted by a substituent selected from the group consisting of methoxy, tert-butoxy, trifluoromethoxy and tetrahydro-2H-pyranyl,
$R^4$ represents hydrogen,
$R^5$ represents a group of the formula

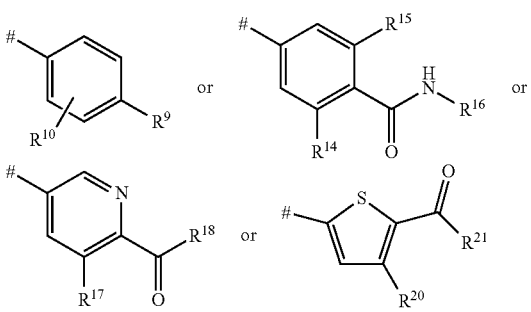

where # is the point of attachment to the nitrogen atom,
$R^9$ represents hydroxycarbonyl,
$R^{10}$ represents hydrogen,
$R^{14}$ represents fluorine,
$R^{15}$ represents hydrogen,
$R^{16}$ represents hydrogen or methyl,
$R^{17}$ represents hydrogen,
$R^{18}$ represents —NHR$^{19}$,
in which
$R^{19}$ represents hydrogen or methyl,
$R^{20}$ represents hydrogen,
$R^{21}$ represents —NHR$^{22}$,
in which
$R^{22}$ represents cyclopropyl,
or
$R^5$ represents 2H-indazol-5-yl,
where the 5-membered heterocycle in 2H-indazol-5-yl is substituted by a methyl substituent.
and the salts thereof, the solvates thereof and the solvates of the salts thereof.

Preference is also given to compounds of the formula (I) in which
$R^1$ represents a group of the formula

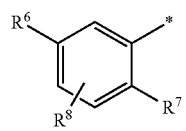

where * is the point of attachment to the oxopyridine ring,
$R^6$ represents chlorine,
$R^7$ represents oxazolyl, oxadiazolyl or dihydro-1,2-oxazolyl,
$R^8$ represents hydrogen,
$R^2$ represents methoxy,
$R^3$ represents ethyl,
where ethyl may be substituted by a substituent selected from the group consisting of methoxy and tetrahydro-2H-pyranyl,
$R^4$ represents hydrogen,
$R^5$ represents a group of the formula

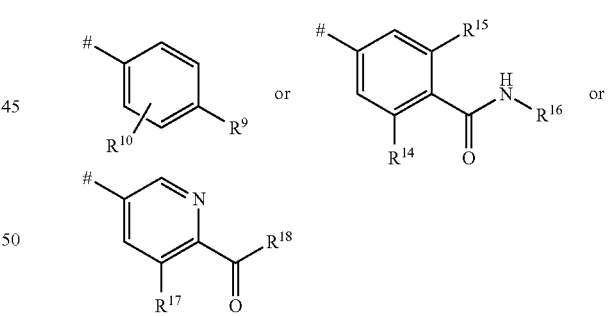

where # is the point of attachment to the nitrogen atom,
$R^9$ represents hydroxycarbonyl,
$R^{10}$ represents hydrogen,
$R^{14}$ represents fluorine,
$R^{15}$ represents hydrogen,
$R^{16}$ represents hydrogen,
$R^{17}$ represents hydrogen,
$R^{18}$ represents —NHR$^{19}$,
in which
$R^{19}$ represents hydrogen or methyl,
and the salts thereof, the solvates thereof and the solvates of the salts thereof.

Preference is also given to compounds of the formula (I) in which $R^1$ represents a group of the formula

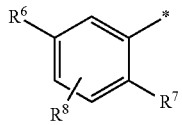

where * is the point of attachment to the oxopyridine ring,
$R^6$ represents chlorine,
$R^7$ represents isoxazolyl, oxadiazolyl or triazolyl,
where isoxazolyl, oxadiazolyl and triazolyl may be substituted by a substituent selected from the group consisting of chlorine, methyl, difluoromethyl and trifluoromethyl,
$R^8$ represents hydrogen,
$R^2$ represents methoxy,
$R^3$ represents methyl, ethyl, n-propyl or n-butyl,
where methyl may be substituted by a cyclobutyl substituent,
and
where ethyl may be substituted by a substituent selected from the group consisting of methoxy and tert-butoxy,
$R^4$ represents hydrogen,
$R^5$ represents a group of the formula

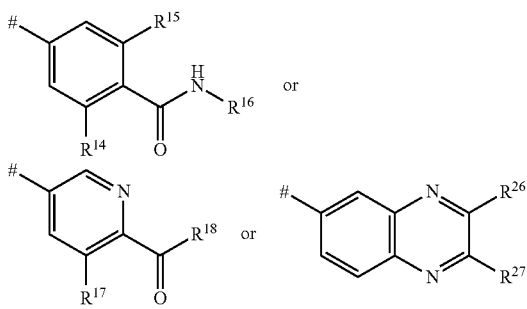

where # is the point of attachment to the nitrogen atom,
$R^{14}$ represents fluorine,
$R^{15}$ represents hydrogen,
$R^{16}$ represents hydrogen,
$R^{17}$ represents hydrogen, $R^{18}$ represents —NHR$^{19}$,
in which
$R^{19}$ represents methyl,
$R^{26}$ represents hydrogen,
$R^{27}$ represents hydrogen,
or
$R^5$ represents 2H-indazol-5-yl,
where the 5-membered heterocycle in 2H-indazol-5-yl is substituted by a methyl substituent.
and the salts thereof, the solvates thereof and the solvates of the salts thereof.

Preference is also given to compounds of the formula (I) in which $R^1$ represents a group of the formula

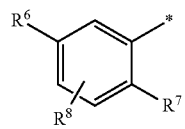

where * is the point of attachment to the oxopyridine ring,
$R^6$ represents chlorine,
$R^7$ represents triazolyl,
where triazolyl is substituted by a substituent selected from the group consisting of chlorine and difluoromethyl,
$R^8$ represents hydrogen,
$R^2$ represents methoxy,
$R^3$ represents methyl, ethyl, n-propyl or n-butyl,
$R^4$ represents hydrogen,
$R^5$ represents a group of the formula

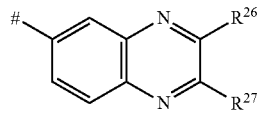

where # is the point of attachment to the nitrogen atom,
$R^{26}$ represents hydrogen,
$R^{27}$ represents hydrogen,
or
$R^5$ represents 2H-indazol-5-yl,
where the 5-membered heterocycle in 2H-indazol-5-yl is substituted by a methyl substituent.
and the salts thereof, the solvates thereof and the solvates of the salts thereof.

Particular preference is given to compounds of the formula (I) in which
$R^1$ represents a group of the formula

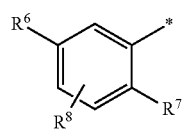

where * is the point of attachment to the oxopyridine ring,
$R^6$ represents chlorine,
$R^7$ represents triazolyl,
where triazolyl is substituted by a substituent selected from the group consisting of chlorine, difluoromethyl and trifluoromethyl,
$R^8$ represents hydrogen,
$R^2$ represents methoxy,
$R^3$ represents methyl, ethyl or n-propyl,
$R^4$ represents hydrogen,
$R^5$ represents a group of the formula

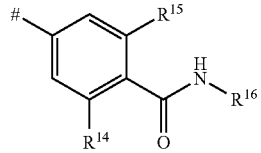

where # is the point of attachment to the nitrogen atom, $R^{14}$ represents fluorine,
$R^{15}$ represents hydrogen,
$R^{16}$ represents hydrogen,
and the salts thereof, the solvates thereof and the solvates of the salts thereof.

Particular preference is also given to compounds of the formula (I) in which
$R^1$ represents a group of the formula

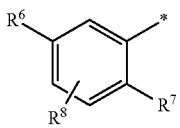

where * is the point of attachment to the oxopyridine ring,
$R^6$ represents chlorine,
$R^7$ represents triazolyl,
  where triazolyl is substituted by a substituent selected from the group consisting of chlorine and trifluoromethyl,
$R^8$ represents hydrogen,
$R^2$ represents methoxy,
$R^3$ represents ethyl,
$R^4$ represents hydrogen,
$R^5$ represents a group of the formula

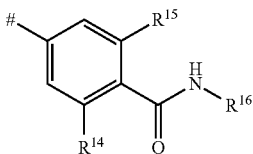

where # is the point of attachment to the nitrogen atom,
$R^{14}$ represents fluorine,
$R^{15}$ represents hydrogen,
$R^{16}$ represents hydrogen,
and the salts thereof, the solvates thereof and the solvates of the salts thereof.

Preference is also given to compounds of the formula (I) in which
$R^1$ represents a group of the formula

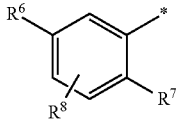

where * is the point of attachment to the oxopyridine ring,
$R^6$ represents chlorine,
$R^7$ represents oxazolyl, oxadiazolyl or dihydro-1,2-oxazolyl,
$R^8$ represents hydrogen.

Preference is also given to compounds of the formula (I) in which $R^2$ represents methoxy.

Preference is also given to compounds of the formula (I) in which $R^3$ represents ethyl.

Preference is also given to compounds of the formula (I) in which $R^3$ represents n-propyl.

Preference is also given to compounds of the formula (I) in which $R^3$ represents $C_1$-$C_5$-alkyl, 1,1-difluoroethyl, 3,3,3-trifluoro-2-methoxyprop-1-yl or 3,3,3-trifluoro-2-ethoxyprop-1-yl,
  where alkyl may be substituted by a substituent selected from the group consisting of fluorine, hydroxy, difluoromethyl, trifluoromethyl, methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl, pyridyl, $C_3$-$C_6$-cycloalkyloxy and 4- to 6-membered oxoheterocyclyloxy,
    in which tert-butoxy and isopropoxy may be substituted by 1 to 3 fluorine substituents,
    and
    in which cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy,
    and
    in which oxoheterocyclyl may be substituted by 1 to 2 substituents independently of one another selected from the group consisting of fluorine, methyl, ethyl, difluoromethyl and trifluoromethyl,
    and
    in which pyrazolyl is substituted by 1 or 2 substituents independently of one another selected from the group consisting of fluorine, methyl and ethyl,
    and
    in which cycloalkyloxy and oxoheterocyclyloxy may be substituted by 1 to 2 substituents independently of one another selected from the group consisting of fluorine and methyl.

Preference is also given to compounds of the formula (I) in which
$R^3$ represents $C_1$-$C_5$-alkyl;
  where alkyl may be substituted by a substituent selected from the group consisting of difluoromethyl, trifluoromethyl, methoxy, ethoxy, tert-butoxy, isopropoxy, difluoromethoxy, trifluoromethoxy, $C_3$-$C_6$-cycloalkyl, 4- to 6-membered oxoheterocyclyl, 1,4-dioxanyl, pyrazolyl, phenyl and $C_3$-$C_6$-cycloalkyloxy,
    in which tert-butoxy and isopropoxy may be substituted by 1 to 3 fluorine substituents,
    and
    in which cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy,
    and
    in which oxoheterocyclyl may be substituted by 1 to 2 substituents independently of one another selected from the group consisting of fluorine, methyl, ethyl, difluoromethyl and trifluoromethyl,
    and
    in which pyrazolyl is substituted by 1 or 2 substituents independently of one another selected from the group consisting of methyl and ethyl,
    and
    in which cycloalkyloxy may be substituted by 1 or 2 substituents independently of one another selected from the group consisting of fluorine and methyl.

Preference is also given to compounds of the formula (I) in which $R^3$ represents hydrogen.

Preference is also given to compounds of the formula (I) in which $R^5$ represents a group of the formula

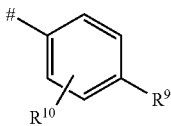

where # is the point of attachment to the nitrogen atom,
$R^9$ represents hydroxycarbonyl,
$R^{10}$ represents hydrogen.

Preference is also given to compounds of the formula (Ia)

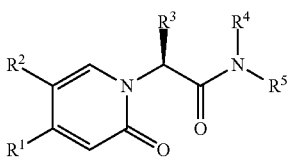

(Ia)

in which $R^1$, $R^2$, $R^3$, $R^4$ and $R^5$ are as defined above.

The invention further provides a process for preparing the compounds of the formula (I), or the salts thereof, solvates thereof or the solvates of the salts thereof, wherein
[A] the compounds of the formula

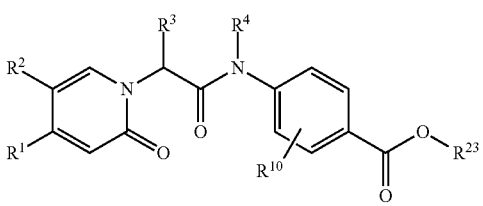

(IIa)

in which
 $R^1$, $R^2$, $R^3$, $R^4$ and $R^{10}$ have the meaning given above and
 $R^{23}$ represents tert-butyl,
are reacted with an acid to give compounds of the formula

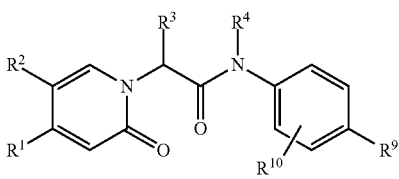

(Ib)

in which
$R^1$, $R^2$, $R^3$, $R^4$ and $R^{10}$ have the meaning given above and
$R^9$ represents hydroxycarbonyl,
or
[B] the compounds of the formula

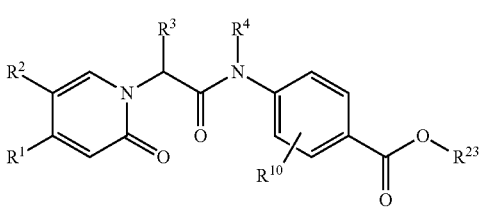

(IIb)

in which
$R^1$, $R^2$, $R^3$, $R^4$ and $R^{10}$ have the meaning given above and
$R^{23}$ represents methyl or ethyl,
are reacted with a base to give compounds of the formula

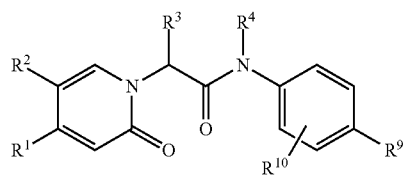

(Ib)

in which
$R^1$, $R^2$, $R^3$, $R^4$ and $R^{10}$ have the meaning given above and
$R^9$ represents hydroxycarbonyl,
or
[C] the compounds of the formula

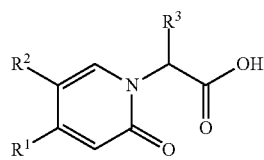

(III)

in which
$R^1$, $R^2$ and $R^3$ have the meaning given above
are reacted with compounds of the formula

(IV)

in which
$R^4$ and $R^5$ have the meaning given above,
in the presence of a dehydrating agent to give compounds of the formula (I),
or
[D] the compounds of the formula

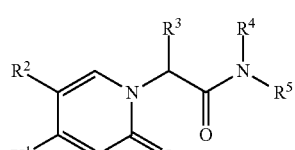

(V)

in which
$R^2$, $R^3$, $R^4$ and $R^5$ have the meaning given above and
$X^1$ represents chlorine, bromine or iodine,
are reacted with compounds of the formula $R^1\text{-}Q^1$ (VI)

in which
$R^1$ is as defined above, and
$Q^1$ represents —B(OH)$_2$, a boronic ester, preferably pinacol boronate, or —BF$_3^-$K$^+$, under Suzuki coupling conditions to give compounds of the formula (I).

The compounds of the formula (Ib) are a subset of the compounds of the formula (I).

The compounds of the formulae (IIa) and (IIb) together form the group of the compounds of the formula (II).

The reaction according to process [A] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

The reaction according to process [B] is generally carried out in inert solvents, preferably in a temperature range from room temperature up to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to a mixture of tetrahydrofuran and water or a mixture of methanol and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide or caesium carbonate.

The reaction according to process [C] is generally carried out in inert solvents, if appropriate in the presence of a base, preferably in a temperature range from 0° C. to room temperature at atmospheric pressure.

Suitable dehydrating agents here are, for example, carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or 2,4,6-tripropyl-1,3,5,2,4,6-trioxatriphosphinane 2,4,6-trioxide (T3P), or mixtures of these, with bases. The condensation is preferably carried out using HATU or T3P.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine. The condensation is preferably carried out using diisopropylethylamine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The reaction according to process [D] is generally carried out in inert solvents, in the presence of a catalyst, optionally in the presence of an additional reagent, optionally in a microwave, preferably in a temperature range from room temperature to 150° C. at atmospheric pressure to 3 bar.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphaneferrocenyl)palladium (II) chloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene) palladium, palladium(II) acetate/dicyclohexyl(2',4',6'-triisopropylbiphenyl-2-yl)phosphine, [1,1-bis (diphenylphosphino)ferocene]palladium(II) chloride monodichloromethane adduct or XPhos precatalyst [(2'-aminobiphenyl-2-yl)(chloro)palladium dicyclohexyl(2',4', 6'-triisopropylbiphenyl-2-yl)phosphane (1:1)], preference being given to tetrakistriphenylphosphinepalladium(0), [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2', 4',6'-triisopropylbiphenyl-2-yl)phosphane (1:1)].

Additional reagents are, for example, potassium acetate, caesium carbonate, potassium carbonate or sodium carbonate, potassium tert-butoxide, caesium fluoride or potassium phosphate, where these may be present in aqueous solution; preferred are additional reagents such as potassium carbonate or aqueous potassium phosphate solution.

Inert solvents are, for example, ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, or N-methylpyrrolidone or acetonitrile, or mixtures of the solvents with alcohols such as methanol or ethanol and/or water; preference is given to tetrahydrofuran, dioxane or acetonitrile.

The compounds of the formula (IV) are known, can be synthesized from the corresponding starting compounds by known processes or can be prepared analogously to the processes described in the Examples section.

The compounds of the formula (VI) are known or can be synthesized by known processes from the corresponding starting compounds.

The compounds of the formula (II) are known or can be prepared by reacting compounds of the formula (III)

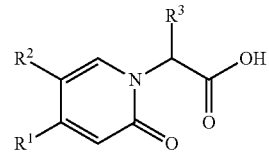

in which
$R^1$, $R^2$ and $R^3$ have the meaning given above
with compounds of the formula

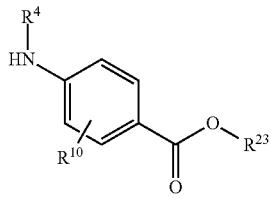
(VII)

in which
$R^4$ and $R^{10}$ have the meaning given above, and
$R^{23}$ represents methyl, ethyl or tert-butyl,
in the presence of a dehydrating reagent.

The reaction is carried out as described for process [C].

The compounds of the formula (VII) are known, can be synthesized from the corresponding starting compounds by known processes or can be prepared analogously to the processes described in the Examples section.

The compounds of the formula (III) are known or can be prepared by
[E] reacting compounds of the formula

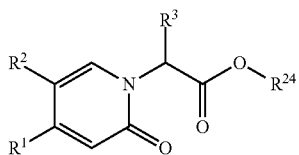
(VIIIa)

in which
$R^1$, $R^2$ and $R^3$ have the meaning given above and
$R^{24}$ represents tert-butyl,
with an acid,
or
[F] reacting compounds of the formula

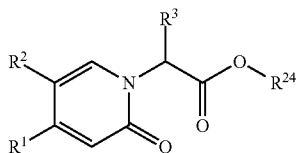
(VIIIb)

in which
$R^1$, $R^2$ and $R^3$ have the meaning given above and
$R^{24}$ represents methyl, ethyl or benzyl,
with a base.

The compounds of the formulae (VIIIa) and (VIIIb) together form the group of the compounds of the formula (VIII).

The reaction according to process [E] is carried out as described for process [A].

The reaction in process [F] is carried out as described for process [B].

The compounds of the formula (VIII) are known or can be prepared by

[G] reacting compounds of the formula

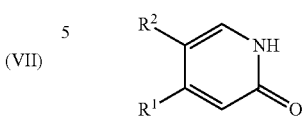
(IX)

in which
$R^1$ and $R^2$ have the meaning given above,
with compounds of the formula

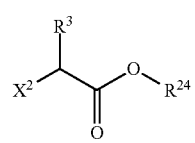
(X)

in which
$R^3$ has the meaning given above,
$R^{24}$ represents methyl, ethyl, benzyl or tert-butyl, and
$X^2$ represents chlorine, bromine, iodine, methanesulphonyloxy or trifluoromethanesulphonyloxy,
or
[H] reacting compounds of the formula

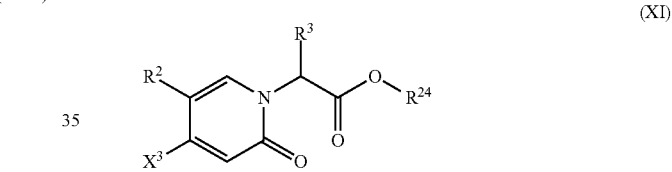
(XI)

in which
$R^2$ and $R^3$ have the meaning given above,
$R^{24}$ represents methyl, ethyl, benzyl or tert-butyl and
$X^3$ represents chlorine, bromine or iodine,
with compounds of the formula (VI) under Suzuki coupling conditions.

The reaction according to process [G] is generally carried out in inert solvents, optionally in the presence of a base, preferably in a temperature range from room temperature to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water; preference is given to dimethylformamide.

Bases are, for example, alkali metal hydroxides such as sodium hydroxide, lithium hydroxide or potassium hydroxide, or alkali metal carbonates such as caesium carbonate, sodium carbonate or potassium carbonate, or potassium tert-butoxide or sodium tert-butoxide, sodium hydride or a mixture of these bases or a mixture of sodium hydride and lithium bromide; preference is given to potassium carbonate or sodium hydride.

The compounds of the formula (X) are known or can be synthesized by known processes from the appropriate starting materials.

The reaction according to process [H] is carried out as described for process [D].

The compounds of the formula (IX) are known or can be prepared by reacting compounds of the formula

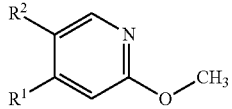 (XII)

in which
R¹ and R² have the meaning given above,
with pyridinium hydrochloride or pyridinium hydrobromide.

The reaction is generally carried out in inert solvents, preferably in a temperature range of from 80° C. to 120° C. at atmospheric pressure.

Inert solvents are, for example, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The compounds of the formula (XII) are known or can be prepared by reacting compounds of the formula

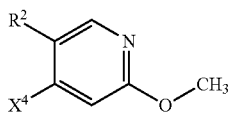 (XIII)

in which
R² has the meaning given above and
X⁴ represents chlorine, bromine or iodine,
with compounds of the formula (VI) under Suzuki coupling conditions.

The reaction is carried out as described for process [D].

The compounds of the formula (XIII) are known or can be synthesized by known processes from the appropriate starting materials.

The compounds of the formula (XI) are known or can be prepared by reacting compounds of the formula

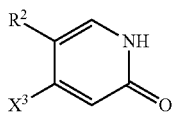 (XIV)

in which
R² has the meaning given above and
X³ represents chlorine, bromine or iodine,
with compounds of the formula (X).

The reaction is carried out as described for process [G].

The compounds of the formula (XIV) are known or can be synthesized by known processes from the appropriate starting materials.

The compounds of the formula (V) are known or can be prepared by reacting compounds of the formula

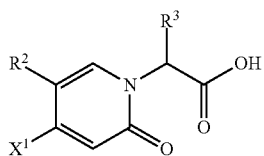 (XV)

in which
R² and R³ have the meaning given above, and
X¹ represents chlorine, bromine or iodine,
with compounds of the formula (IV) in the presence of a dehydrating reagent.

The reaction is carried out as described for process [C].

The compounds of the formula (XV) are known or can be prepared by

[I] reacting compounds of the formula

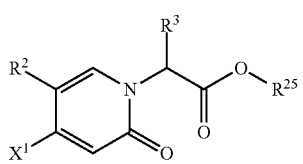 (XVIa)

in which
R² and R³ have the meaning given above,
R²⁵ represents tert-butyl and
X¹ represents chlorine, bromine or iodine,
with an acid,
or
[J] reacting compounds of the formula

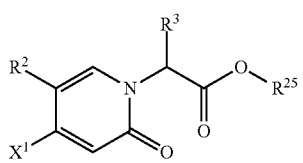 (XVIb)

in which
R² and R³ have the meaning given above,
R²⁵ represents methyl, ethyl or benzyl and
X¹ represents chlorine, bromine or iodine,
with a base.

The compounds of the formulae (XVIa) and (XVIb) together form the group of the compounds of the formula (XVI).

The reaction according to process [I] is carried out as described for process [A].

The reaction according to process [J] is carried out as described for process [B].

The compounds of the formula (XVI) are known or can be prepared by reacting compounds of the formula

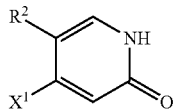 (XVII)

in which
R² has the meaning given above and
X¹ represents chlorine, bromine or iodine,
with compounds of the formula

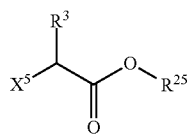 (XVIII)

in which
R³ has the meaning given above,
R²⁵ represents methyl, ethyl, benzyl or tert-butyl, and
X⁵ represents chlorine, bromine, iodine, methanesulphonyloxy or trifluoromethanesulphonyloxy.

The reaction is carried out as described for process [G].

The compounds of the formulae (XVII) and (XVIII) are known or can be synthesized by known processes from the appropriate starting materials.

In an alternative process, the compounds of the formula (VIII) can be prepared by reacting compounds of the formula

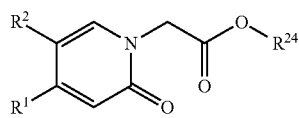 (XIX)

in which
R¹ and R² have the meaning given above, and
R²⁴ represents methyl, ethyl, benzyl or tert-butyl,
with compounds of the formula

 (XX)

in which
R³ has the meaning given above and
X⁶ represents chlorine, bromine, iodine, methanesulphonyloxy, trifluoromethanesulphonyloxy or para-toluenesulphonyloxy.

The reaction is generally carried out in inert solvents, if appropriate in the presence of a base, preferably in a temperature range from −78° C. to room temperature at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride, N-butyllithium or bis(trimethylsilyl)lithium amide, preference is given to bis(trimethylsilyl)lithium amide.

The compounds of the formula (XIX) are known or can be synthesized by the processes described above, for example process [G], from the appropriate starting materials.

The compounds of the formula (XX) are known or can be synthesized by known processes from the appropriate starting materials.

In an alternative process, the compounds of the formula (VIII) can be prepared by reacting compounds of the formula

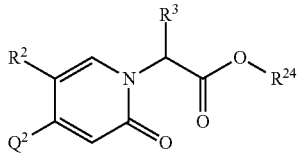 (XXI)

in which
R² and R³ have the meaning given above,
R²⁴ represents methyl, ethyl, benzyl or tert-butyl and
Q² represents —B(OH)₂, a boronic ester, preferably pinacol boronate, or —BF₃⁻K⁺, with compounds of the formula

 (XXII)

in which
R¹ is as defined above, and
X⁷ represents chlorine, bromine or iodine,
under Suzuki coupling conditions.

The reaction is carried out as described for process [D].

The compounds of the formula (XXI) are known or can be synthesized by known processes from the appropriate starting materials, for example from compounds of the formula (XI).

The compounds of the formula (XXII) are known or can be synthesized by known processes from the appropriate starting materials.

In an alternative process, the compounds of the formula (III) can be prepared by reacting compounds of the formula

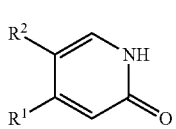 (IX)

in which
R¹ and R² have the meaning given above,
with compounds of the formula

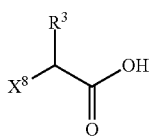 (XXIII)

in which
R³ has the meaning given above and
X⁸ represents chlorine, bromine or iodine.

The reaction is generally carried out in inert solvents, if appropriate in the presence of a base, preferably in a temperature range from −10° C. to 90° C. at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride or bis(trimethylsilyl)lithium amide or a mixture of magnesium di-tert-butoxide and potassium tert-butoxide, preference is given to a mixture of magnesium di-tert-butoxide and potassium tert-butoxide.

The compounds of the formula (XXIII) are known or can be synthesized by known processes from the appropriate starting materials.

In an alternative process, the compounds of the formula (XV) can be prepared by reacting compounds of the formula

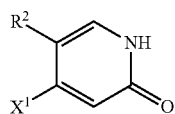
(XVII)

in which
$R^2$ has the meaning given above and
$X^1$ represents chlorine, bromine or iodine,
with compounds of the formula

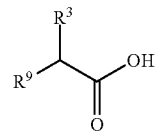
(XXIV)

in which
$R^3$ has the meaning given above and
$X^9$ represents chlorine, bromine or iodine.

The reaction is carried out as described for the reaction of compounds of the formula (IX) with compounds of the formula (XXIII).

The compounds of the formula (XXIV) are known or can be synthesized by known processes from the appropriate starting materials.

The preparation of the starting compounds and of the compounds of the formula (I) can be illustrated by the synthesis scheme below.

Scheme 1:

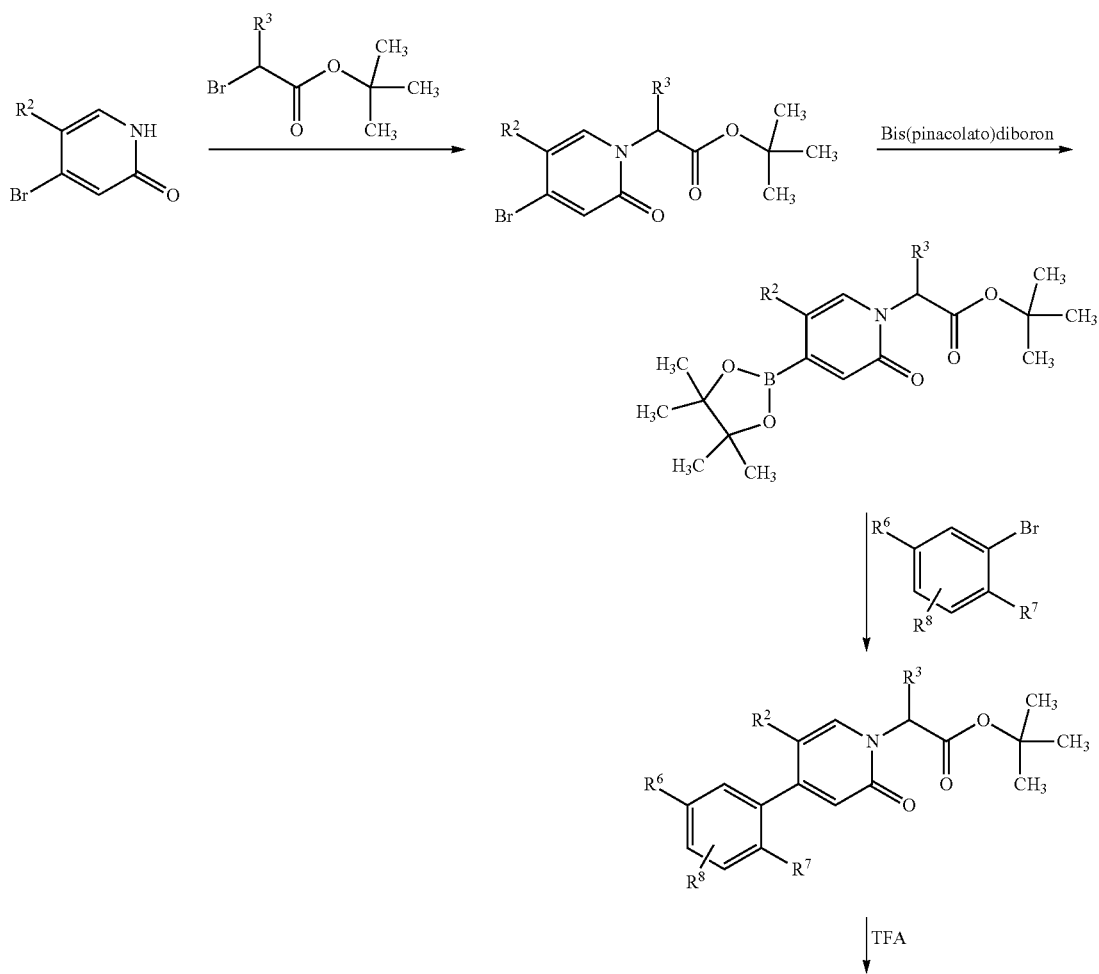

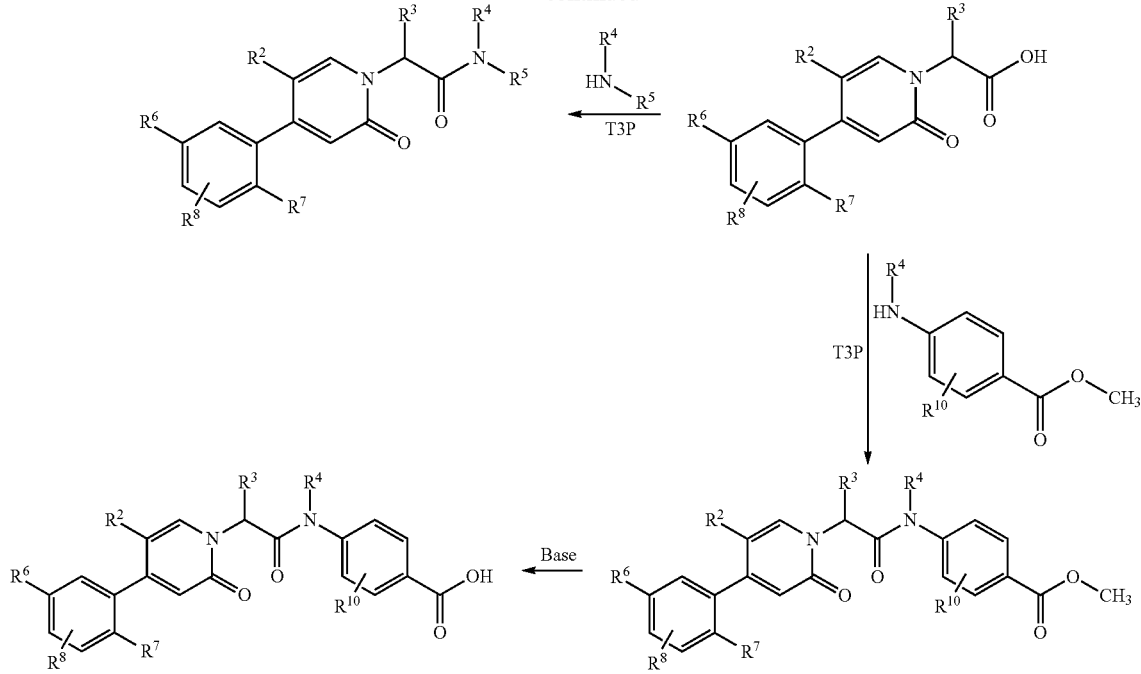

The compounds according to the invention have an unforeseeable useful pharmacological activity spectrum and good pharmacokinetic behavior, in particular a longer exposure of such a compound in the blood above the minimal effective concentration within a given dosing interval. Such a profile results in an improved peak-to-trough ratio (quotient of maximum to minimum concentration) within a given dosing interval, which has the advantage that the compound can be administered less frequently and at a significantly lower dose to achieve an effect. They are compounds that influence the proteolytic activity of the serine protease factor XIa (FXIa) and/or the serine protease plasma kallikrein (PK). The compounds according to the invention inhibit the enzymatic cleavage of substrates, catalysed by FXIa and/or PK, which have essential roles in the activation of blood coagulation, in the aggregation of blood platelets via reduction of the thrombin necessary for the PAR-1 activation of the platelets, and in inflammatory processes, which particularly involve an increase in vascular permeability.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmic disorders, in particular of diabetic retinopathy or macular oedema, and/or inflammatory disorders, in particular those associated with excess plasma kallikrein activity, such as hereditary angiooedema (HAE) or chronic inflammatory disorders, particularly of the intestine such as Crohn's disease.

Factor XIa (FXIa) is an important enzyme in the context of coagulation, which can be activated both by thrombin and factor XIIa (FXIIa), and is therefore involved in two essential processes of coagulation: It is a central component of the transition from initiation to amplification and propagation of coagulation: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated, leading to strong thrombus growth and stabilizing the thrombus.

Moreover, factor XIa is an important component for the intrinsic initiation of coagulation: In addition to the stimulation via tissue factor (TF), the coagulation system can be activated also particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa (FXIIA) which subsequently activates FXI, attached to cell surfaces, to FXIa. This leads to further activation of the coagulation cascade as described above.

In contrast, thrombin generation in the initiation phase remains uninfluenced via TF/factor VIIa and factor X activation and finally thrombin formation, the physiological reaction on vascular injuries. This could explain why no prolongations of bleeding times were found in FXIa knock-out mice, as in rabbits and other species, with administration of FXIa inhibitor. This low bleeding tendency caused by the substance is of great advantage for use in humans, particularly in patients with increased risk of bleeding.

In addition, factor XIIa also activates plasma prokallikrein to plasma kallikrein (PK) in the context of the intrinsic activation which, inter alia, in a potentiation loop, leads to further factor XII activation, overall resulting in amplification of the initiation of the coagulation cascade on surfaces. A PK-inhibiting activity of a compound according to the invention thus reduces coagulation via surface activation and thus has an anticoagulatory effect. An advantage could be in the combination of factor XIa inhibitory activity and PK inhibitory activity allowing a balanced antithrombotic effect.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

The inventive compounds are therefore also suitable for the prevention and treatment of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves.

In addition, the inventive compounds are suitable for the treatment and prevention of disseminated intravascular coagulation (DIC) which may occur in connection with sepsis inter alia, but also owing to surgical interventions, neoplastic disorders, burns or other injuries and may lead to severe organ damage through microthromboses.

Thromboembolic complications furthermore occur in microangiopathic haemolytical anaemias and by the blood coming into contact with foreign surfaces in the context of extracorporeal circulation such as, for example, haemodialysis, ECMO ("extracorporeal membrane oxygenation"), LVAD ("left ventricular assist device") and similar methods, AV fistulas, vascular and heart valve prostheses.

Moreover, the compounds according to the invention are suitable for the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component also plays an essential role. Mutual enhancement of coagulation and inflammation in particular can be prevented by the compounds according to the invention, thus decisively lowering the probability of thrombotic complications. In this case, both the factor XIa-inhibitory component (via inhibition of thrombin production) and the PK-inhibitory component can contribute to the anticoagulant and antiinflammatory effect (e.g. via bradykinin). Therefore, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Kinins generated by means of plasma kallikrein, inter alia, have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Moreover, the compounds according to the invention can be used for inhibiting tumour growth and the formation of metastases, and also for the prophylaxis and/or treatment of thromboembolic complications, such as, for example, venous thromboembolisms, for tumour patients, in particular those undergoing major surgical interventions or chemo- or radiotherapy.

In addition, the inventive compounds are also suitable for the prophylaxis and/or treatment of pulmonary hypertension.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" includes idiopathic pulmonary arterial hypertension (IPAH, formerly also referred to as primary pulmonary hypertension), familial pulmonary arterial hypertension (FPAH) and associated pulmonary arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonatants.

Pulmonary hypertension associated with disorders of the left heart includes a diseased left atrium or ventricle and mitral or aorta valve defects.

Pulmonary hypertension associated with pulmonary disorders and/or hypoxia includes chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention further provides for the use of the inventive compounds for production of medicaments for the treatment and/or prophylaxis of pulmonary hypertension associated with sarcoidosis, histiocytosis X and lymphangiomatosis.

In addition, the substances according to the invention are also useful for the treatment of pulmonary and hepatic fibroses.

In addition, the compounds according to the invention are also suitable for the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and diffusion of fluid and proteins into the extravasal space. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or crosslinked extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

Compounds according to the invention which inhibit plasma kallikrein alone or in combination with factor XIa, are also useful for the treatment and/or prophylaxis of disorders in the course of which plasma kallikrein is involved. In addition to the anticoagulant activity, plasma kallikrein is an important bradikinin-releasing protease which, inter alia, thus leads to increased endothelial permeability. The compounds can therefore be used for the treatment and/or prophylaxis of disorders involving oedema formations such as ophthalmic disorders, in particular, diabetic retinopathy or macular oedema or hereditary angiooedema.

"Ophthalmic disorders" in the context of the present invention include in particular disorders such as diabetic retinopathy, diabetic macular oedema (DME), macular oedema, macular oedema associated with retinal vein occlusion, age-related macular degeneration (AMD), choroidal neovascularization (CNV), choroidal neovascular membranes (CNVM), cystoid macular oedema (CME), epiretinal membranes (ERM) and macular perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorders such as uveitis, scleritis or endophthalmitis, cataract, refraction anomalies such as myopia, hyperopia or astigmatism and keratoconus, disorders of the anterior eye such as corneal angiogenesis as sequela of, for example, keratitis, cornea transplantation or keratoplasty, corneal angiogenesis as sequela of hypoxia (for example by excessive use of contact lenses), pterygium conjunctivae, subcorneal oedema and intracorneal oedema.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

Particular the present invention provides the compounds according to the invention for use in a method for the treatment and/or prophylaxis of thrombotic or thromboembolic disorders using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa or plasma kallikrein.

The present invention furthermore provides a method for preventing the coagulation of blood in vitro, in particular in banked blood or biological samples which may comprise factor XIa or plasma kallikrein or both enzymes, which method is characterized in that an anticoagulatory effective amount of the compound according to the invention is added.

The present invention further provides medicaments comprising a compound according to the invention and one or more further active compounds, in particular for the treatment and/or prophylaxis of the disorders mentioned above. Preferred examples of active compounds suitable for combinations include:

lipid-lowering substances, especially HMG-CoA (3-hydroxy-3-methylglutaryl-coenzyme A) reductase inhibitors, for example lovastatin (Mevacor), simvastatin (Zocor), pravastatin (Pravachol), fluvastatin (Lescol) and atorvastatin (Lipitor);

coronary therapeutics/vasodilatators, especially ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan, losartan, valsartan, irbesartan, candesartan, eprosartan and temisartan, or β-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase, for example riociguat;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA, for example Actilyse®), streptokinase, reteplase and urokinase or plasminogen-modulating substances causing increased formation of plasmin;

anticoagulatory substances (anticoagulants) such as, for example, heparin (UFH), low-molecular-weight heparins (LMW), for example tinzaparin, certoparin, parnaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI) such as, for example, Pradaxa (dabigatran), atecegatran (AZD-0837), DP-4088, SSR-182289A, argatroban, bivalirudin and tanogitran (BIBT-986 and prodrug BIBT-1011), hirudin;

direct factor Xa inhibitors such as, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, substances which inhibit the aggregation of platelets (platelet aggregation inhibitors, thrombocyte aggregation inhibitors), such as, for example, acetylsalicylic acid (such as, for example, aspirin), P2Y12 antagonists such as, for example, ticlopidine (Ticlid), clopidogrel (Plavix), prasugrel, ticagrelor, cangrelor, elinogrel, PAR-1 antagonists such as, for example, vorapaxar, PAR-4 antagonists, EP3 antagonists such as, for example, DG041;

platelet adhesion inhibitors such as GPVI and/or GPIb antagonists such as, for example, Revacept or caplacizumab;

fibrinogen receptor antagonists (glycoprotein-IIb/IIIa antagonists), for example abciximab, eptifibatide, tirofiban, lamifiban, lefradafiban and fradafiban;

recombinant human activated protein C such as, for example, Xigris or recombinant thrombomudulin;

and also antiarrhythmics;

inhibitors of VEGF and/or PDGF signal paths such as, for example, aflibercept, ranibizumab, bevacizumab, KH-902, pegaptanib, ramucirumab, squalamin or bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, Vargatef and E-10030;

inhibitors of angiopoietin-Tie signal paths such as, for example, AMG386;

inhibitors of Tie2 receptor tyrosine kinase;

inhibitors of the integrin signal paths such as, for example, volociximab, cilengitide and ALG1001;

inhibitors of the PI3K-Akt-mTor signal paths such as, for example, XL-147, perifosine, MK2206, sirolimus, temsirolimus and everolimus;

corticosteroids such as, for example, anecortave, betamethasone, dexamethasone, triamcinolone, fluocinolone and fluocinolone acetonide;

inhibitors of the ALK1-Smad1/5 signal path such as, for example, ACE041;

cyclooxygenase inhibitors such as, for example, bromfenac and nepafenac;

inhibitors of the kallikrein-kinin system such as, for example, safotibant and ecallantide;

inhibitors of the sphingosine 1-phosphate signal paths such as, for example, sonepcizumab;

inhibitors of the complement-C5a receptor such as, for example, eculizumab;

inhibitors of the 5HT1a receptor such as, for example, tandospirone;

inhibitors of the Ras-Raf-Mek-Erk signal path; inhibitors of the MAPK signal paths; inhibitors of the FGF signal paths; inhibitors of endothelial cell proliferation; apoptosis-inducing active compounds;

photodynamic therapy consisting of an active compound and the action of light, the active compound being, for example, verteporfin.

"Combinations" for the purpose of the invention mean not only dosage forms which contain all the components (so-called fixed combinations) and combination packs which contain the components separate from one another, but also components which are administered simultaneously or sequentially, provided that they are used for the prophylaxis and/or treatment of the same disease.

It is likewise possible to combine two or more active ingredients with one another, meaning that they are thus each in two-component or multicomponent combinations.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Suitable for extraocular (topic) administration are administration forms which operate in accordance with the prior art, which release the active compound rapidly and/or in a modified or controlled manner and which contain the active compound in crystalline and/or amorphized and/or dissolved form such as, for example, eye drops, sprays and lotions (e.g. solutions, suspensions, vesicular/colloidal systems, emulsions, aerosols), powders for eye drops, sprays and lotions (e.g. ground active compound, mixtures, lyophilisates, precipitated active compound), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable for intraocular administration are administration forms which operate in accordance with the prior art, which release the active compound rapidly and/or in a modified or controlled manner and which contain the active compound in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active compound, mixtures, lyophilisates, precipitated active compound), gels for preparations for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds of the invention can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments comprising at least one inventive compound, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary, if appropriate, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

A) EXAMPLES

Abbreviations

Boc tert-butyloxycarbonyl
brs or br s broad singlet (in NMR)
Ex. Example
d day(s), doublet (in NMR)
TLC thin-layer chromatography
DCM dichloromethane
DCI direct chemical ionization (in MS)
dd doublet of doublets (in NMR)
DIC N,N'-diisopropylcarbodiimide
DIEA N,N-diisopropylethylamine
DMAP 4-dimethylaminopyridine
DMF N,N-dimethylformamide
DMSO dimethyl sulphoxide
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
HV high vacuum
LC/MS liquid chromatography-coupled mass spectroscopy
LDA lithium diisopropylamide
m multiplet (in NMR)
min minute(s)
MS mass spectroscopy
NMR nuclear magnetic resonance spectroscopy
Oxima ethyl hydroxyiminocyanoac etate
q quartet (in NMR)
quant. quantitative
quin quintet (in NMR)
RP reversed phase (in HPLC)
RT room temperature
$R_t$ retention time (in HPLC)

s singlet (in NMR)
sxt sextet (in NMR)
SFC supercritical fluid chromatography (with supercritical carbon dioxide as mobile phase)
t triplet (in NMR)
THF tetrahydrofuran
TFA trifluoroacetic acid
T3P 2,4,6-tripropyl-1,3,5,2,4,6-trioxatriphosphinane 2,4,6-trioxide HPLC, LC-MS and GC Methods:

Method 1:
Instrument: Waters ACQUITY SQD UPLC system; column: Waters Acquity UPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→+1.2 min 5% A→2.0 min 5% A; oven: 50° C.; flow rate: 0.40 ml/min; UV detection: 208-400 nm.

Method 2:
Instrument: Waters ACQUITY SQD UPLC system; column: Waters Acquity UPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 3:
Instrument: Micromass Quattro Premier with Waters UPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4:
MS instrument: Waters (Micromass) Quattro Micro; HPLC instrument: Agilent 1100 series; column: YMC-Triart C18 3µ 50 mm×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 5:
MS instrument: Waters (Micromass) QM; HPLC instrument: Agilent 1100 series; column: Agient ZORBAX Extend-C18 3.0 mm×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 6:
MS instrument: Waters (Micromass) ZQ; HPLC instrument: Agilent 1100 series; column: Agient ZORBAX Extend-C18 3.0 mm×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7:
Instrument: Thermo DFS, Trace GC Ultra; column: Restek RTX-35, 15 m×200 µm×0.33 µm; constant helium flow rate: 1.20 ml/min; oven: 60° C.; inlet: 220° C.; gradient: 60° C., 30° C./min→300° C. (maintained for 3.33 min).

Method 8:
Instrument: Agilent MS Quad 6150; HPLC: Agilent 1290; column: Waters Acquity UPLC HSS T3 1.8µ 50 mm×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 9:
Instrument: Thermo Scientific DSQII, Thermo Scientific Trace GC Ultra; column: Restek RTX-35MS, 15 m×200 µm×0.33 µm; constant helium flow rate: 1.20 ml/min; oven: 60° C.; inlet: 220° C.; gradient: 60° C., 30° C./min→300° C. (maintained for 3.33 min).

Method 10:
MS instrument type: Thermo Scientific FT-MS; instrument type UHPLC+: Thermo Scientific UltiMate 3000; column: Waters, HSST3, 2.1 mm×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm.

Method 11:
MS instrument: Waters (Micromass) Quattro Micro; instrument Waters UPLC Acquity; column: Waters BEH C18 1.7µ 50 mm×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Method 12:
Instrument: SHIMADZU LCMS: UFLC 20-AD and LCMS 2020 MS detector (electrospray ion source (ESI): scan between m/z 90-900 using a scan time of 0.7 s); column: Shim-pack XR-ODS, 2.2 µm, 3.0 mm×50 mm; linear gradient: 95% A (A: 0.05% TFA in water) to 100% B (B: 0.05% TFA in acetonitrile) over 2.2 min with a total run time of 3.6 min; column temperature: 40° C.; flow rate: 1.0 ml/min; UV detection: 190-400 nm.

Method 13:
Instrument: SHIMADZU LCMS: UFLC 20-AD and LCMS 2020 MS detector (electrospray ion source (ESI): scan between m/z 90-900 using a scan time of 0.5-1.0 s); column: Ascentis Express C18, 2.7 µm, 2.1 mm×50 mm; linear gradient: 95% A (A: 0.05% TFA in water) to 100% B (B: 0.05% TFA in acetonitrile) over 1.0 min with a total run time of 2.0 min; column temperature: 40° C.; flow rate: 1.0 ml/min; UV detection: 190-400 nm.

Method 14:
Instrument: SHIMADZU LCMS: UFLC 20-AD and LCMS 2020 MS detector (electrospray ion source (ESI): scan between m/z 90-900 using a scan time of 0.5-1.0 s); column: Ascentis Express C18, 2.7 µm, 2.1 mm×50 mm; linear gradient: 95% A (A: 0.05% TFA in water) to 100% B (B: 0.05% TFA in acetonitrile) over 2.1 min with a total run time of 3.0 min; column temperature: 40° C.; flow rate: 1.0 ml/min; UV detection: 190-400 nm.

Method 15:
Instrument: SHIMADZU LCMS: UFLC 20-AD and LCMS 2020 MS detector (electrospray ion source (ESI): scan between m/z 90-900 using a scan time of 0.5-1.0 s); column: Ascentis Express C18, 2.7 µm, 2.1 mm×50 mm; linear gradient: 95% A (A: 0.05% TFA in water) to 95% B (B: 0.05% TFA in acetonitrile) over 2.0 min with a total run time of 3.0 min; column temperature: 40° C.; flow rate: 1.0 ml/min; UV detection: 190-400 nm.

Method 16:
Instrument: SHIMADZU LCMS: UFLC 20-AD and LCMS 2020 MS detector (electrospray ion source (ESI):

scan between m/z 90-900 using a scan time of 0.5-1.0 s); column: CORTECS C18, 2.7 µm, 2.1 mm×50 mm; linear gradient: 95% A (A: 0.09% formic acid in water) to 100% B (B: 0.1% formic acid in acetonitrile) over 1.2 min with a total run time of 2.0 min; column temperature: 40° C.; flow rate: 1.0 ml/min; UV detection: 190-400 nm.

Method 17:
Instrument: SHIMADZU LCMS: UFLC 20-AD and LCMS 2020 MS detector (electrospray ion source (ESI): scan between m/z 90-900 using a scan time of 0.5-1.0 s); column: CORTECS C18, 2.7 µm, 2.1 mm×50 mm; linear gradient: 95% A (A: 0.09% formic acid in water) to 95% B (B: 0.1% formic acid in acetonitrile) over 2.0 min with a total run time of 3.0 min; column temperature: 40° C.; flow rate: 1.0 ml/min; UV detection: 190-400 nm.

Method 18:
Instrument: SHIMADZU LCMS: UFLC 20-AD and LCMS 2020 MS detector (electrospray ion source (ESI): scan between m/z 90-900 using a scan time of 0.5-1.0 s); column: Ascentis C18, 2.7 µm, 2.1 mm×50 mm; linear gradient: 95% A (A: 0.05% TFA in water) to 100% B (B: 0.05% TFA in acetonitrile) over 1.1 min with a total run time of 2.0 min; column temperature: 45° C.; flow rate: 1.0 ml/min; UV detection: 190-400 nm.

Method 19:
Instrument: SHIMADZU LCMS: UFLC 20-AD and LCMS 2020 MS detector (electrospray ion source (ESI): scan between m/z 90-900 using a scan time of 0.5-1.0 s); column: Ascentis C18, 2.7 µm, 2.1 mm×50 mm; linear gradient: 95% A (A: 0.05% TFA in water) to 100% B (B: 0.05% TFA in acetonitrile) over 1.2 min with a total run time of 2.0 min; column temperature: 40° C.; flow rate: 1.0 ml/min; UV detection: 190-400 nm.

Method 20:
column: Ascentis Express C18, 2.7 µm, 2.1 mm×50 mm; linear gradient: 50% A (A: 0.05% TFA in water) to 95% B (B: 0.05% TFA in acetonitrile) over 3.0 min with a total run time of 4.0 min; column temperature: 40° C.; flow rate: 1.0 ml/min.

Method 21:
Instrument: ThermoFisherScientific LTQ-Orbitrap-XL; Geritetyp HPLC: Agilent 1200SL; column: Agilent, POROSHELL 120, 3 mm×150 mm, SB—C18 2.7 µm; mobile phase A: 1 l Wasser+0.1% trifluoroacetic acid; mobile phase B: 1 l acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV-detection: 210 nm.

Method 22:
Instrument: SHIMADZU LCMS: UFLC 20-AD and LCMS 2020 MS detector (electrospray ion source (ESI): scan between m/z 90-900 using a scan time of 0.5-1.0 s); column: CORTECS-C18, 2.7 µm, 2.1 mm×50 mm; linear gradient: 95% A (A: 0.1% TFA in water) to 95% B (B: 0.1% TFA in acetonitrile) over 2.0 min with a total run time of 3.0 min; column temperature: 40° C.; flow rate: 1.0 ml/min; UV detection: 190-400 nm.

Method 23:
Instrument: SHIMADZU LCMS: UFLC 20-AD and LCMS 2020 MS detector (electrospray ion source (ESI): scan between m/z 90-900 using a scan time of 0.5-1.0 s); column: Poroshell HPH-C18, 2.7 µm, 3.0 mm×50 mm; linear gradient: 90% A (A: 5 mM ammonium bicarbonate in water) to 95% B (B: acetonitrile) over 1.1 min with a total run time of 1.8 min; column temperature: 45° C.; flow rate: 1.2 ml/min; UV detection: 190-400 nm.

Microwave:
The microwave reactor used was a "single-mode" instrument of the Emrys™ Optimizer type.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Compounds

General Method 1A: Preparation of a Boronic Acid

At −78° C., lithium diisopropylamide (2 M in tetrahydrofuran/heptane/ethylbenzene) was added to a solution of the appropriate pyridine derivative in tetrahydrofuran (about 3 ml/mmol), the mixture was stirred for 2 to 4 h and triisopropyl borate was then added quickly. The reaction mixture was maintained at −78° C. for a further 2 to 3 h and then slowly thawed to RT overnight. After addition of water, the tetrahydrofuran was removed under reduced pressure and the aqueous phase was extracted twice with ethyl acetate. The aqueous phase was acidified with aqueous hydrochloric acid (2M), generally resulting in formation of a precipitate which was filtered off, washed with water and dried. The aqueous phase was extracted three times with ethyl acetate. The combined organic phases were dried (sodium sulphate or magnesium sulphate), filtered and concentrated under reduced pressure.

General Method 2A: Suzuki Coupling

In a flask which had been dried by heating and flushed with argon, 1.0 eq. of the appropriate boronic acids, 1.0 eq. of the aryl bromide or aryl iodide, 3.0 eq. of potassium carbonate and 0.1 eq. of [1,1-bis(diphenylphosphino)ferrocene]palladium(II) chloride/monodichloromethane adduct or tetrakis(triphenylphosphine)palladium(0) were initially charged. The flask was then evacuated three times and in each case vented with argon. Dioxane (about 6 ml/mmol) was added, and the reaction mixture was stirred at 110° C. for a number of hours until substantially complete conversion had been achieved. The reaction mixture was then filtered through Celite and the filtrate was concentrated under reduced pressure. Water was added to the residue. After addition of ethyl acetate and phase separation, the organic phase was washed once with water and once with saturated aqueous sodium chloride solution, dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 3A: Methoxypyridine Cleavage 20 eq. of pyridinium hydrochloride or pyridinium hydrobromide were added to a solution of the appropriate methoxypyridine in dimethylformamide (10-12.5 ml/mmol) and the mixture was stirred at 100° C. for a number of hours to days, with further pyridinium hydrochloride or pyridinium hydrobromide possibly being added, until substantially complete conversion had been achieved. Subsequently, the reaction solution was concentrated under reduced pressure and the residue was triturated with water. The precipitate formed was filtered off, washed with water and dried under reduced pressure.

General Method 4A: N-Alkylation of 2-pyridinone Derivatives with the Appropriate 2-bromo- or 2-chloropropanoic ester Derivatives in the Presence of Potassium Carbonate Under argon and at RT, 1.2 eq. of the appropriate 2-bromo- or 2-chloropropanoic ester derivative and 1.5 eq. of potassium carbonate were added to a solution of 1.0 eq. of the appropriate 2-pyridinone derivative in dimethylformamide (5-10 ml/mmol), and the mixture was stirred at 100° C. After removal of the dimethylformamide and addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 5A: Amide Coupling Using T3P/pyridine

A solution of the appropriate carboxylic acid (1 eq.) and the appropriate amine (1.1-1.5 eq.) in pyridine (about 0.1M) was heated to 60 to 80° C., and T3P (50% in ethyl acetate, 1.5 to 4 eq.) was added dropwise. Alternatively, T3P was added at RT and the mixture was then stirred at RT or heated to RT to 90° C. After 1-20 h, the reaction mixture was cooled to RT, and water and ethyl acetate were added. The aqueous phase was extracted with ethyl acetate. The combined organic phases were washed with aqueous buffer solution (pH=5), with saturated aqueous sodium bicarbonate solution and with saturated aqueous sodium chloride solution, dried over sodium sulphate and concentrated under reduced pressure. The crude product was then optionally purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 5B: Amide coupling with HATU/DIEA

Under argon and at RT, the amine (1.1 eq.), N,N-diisopropylethylamine (2.2 eq.) and a solution of HATU (1.2 eq.) in a little dimethylformamide were added to a solution of the appropriate carboxylic acid (1.0 eq.) in dimethylformamide (7-15 ml/mmol). The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 6A: Hydrolysis of a tert-butyl ester or a Boc-Protected Amine Using TFA At RT, 20 eq. of TFA were added to a solution of 1.0 eq. of the appropriate tert-butyl ester derivative in dichloromethane (about 5-10 ml/mmol), and the mixture was stirred at RT for 1 to 8 h. The reaction mixture was then concentrated under reduced pressure and the residue was co-evaporated repeatedly with dichloromethane and toluene and dried under reduced pressure. The crude product was then optionally purified either by normal phase chromatography (cyclohexane/ethyl acetate mixtures or dichloromethane/methanol mixtures) or preparative RP-HPLC (water/acetonitrile gradient or water/methanol gradient).

General Method 6B: Hydrolysis of a methyl/ethyl or benzyl ester with Lithium Hydroxide At RT, lithium hydroxide (2-4 eq.) was added to a solution of 1.0 eq. of the appropriate methyl or ethyl ester in tetrahydrofuran/water (3:1, about 7-15 ml/mmol). The reaction mixture was stirred at RT to 60° C. and then adjusted to pH 1 using aqueous hydrochloric acid (1N). After addition of water/ethyl acetate and phase separation, the aqueous phase was extracted three times with ethyl acetate. The combined organic phases were dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 6C: Hydrolysis of a tert-butyl ester Using Lithium Hydroxide

At RT, lithium hydroxide (2-5 eq.) was added to a solution of 1.0 eq. of the appropriate tert-butyl ester in tetrahydrofuran/ethanol (1:2, 15-50 ml/mmol). The reaction mixture was stirred at RT to 60° C., saturated aqueous ammonium chloride solution was then added and the mixture was adjusted to pH 1 using aqueous hydrochloric acid (1N). After addition of water/ethyl acetate and phase separation, the aqueous phase was extracted three times with ethyl acetate. The combined organic phases were dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 6D: Hydrolysis of a tert-butyl ester Using Hydrogen Chloride in Dioxane A solution of 1.0 eq. of the appropriate tert-butyl ester derivative in 4M hydrogen chloride in dioxane (concentration of the tert-butyl ester derivative about 0.1M) was either stirred at RT for 2 to 48 h or treated in an ultrasonic bath for 2 to 5 h. The reaction mixture was then concentrated under reduced pressure and the residue was co-evaporated repeatedly with tetrahydrofuran and dried under reduced pressure. The crude product was converted without further purification.

General Method 7A: Preparation of Triflates

A solution of the appropriate alcohol (1 eq.) was initially charged in dichloromethane (0.1-1M), and at −78° C. to 0° C. lutidine (1.1-1.5 eq.) or triethylamine (1.1-1.5 eq.) or N,N-diisopropylethylamine (1.1-1.5 eq.) and trifluoromethanesulphonic anhydride (1.05-1.5 eq.) were added in succession. The reaction mixture was stirred at −78° C. to 0° C. for another 1 h and then diluted with triple the amount (based on the reaction volume) of methyl tert-butyl ether. The organic phase was washed three times with a 3:1 mixture of saturated aqueous sodium chloride solution/1N hydrochloric acid and finally with saturated aqueous sodium bicarbonate solution, dried (sodium sulphate or magnesium sulphate) and filtered, and the solvent was removed under reduced pressure. The crude product was used in the next step without further purification.

General Method 8A: Alkylation of Acetic Esters with Triflates

Under argon and at −78° C., bis(trimethylsilyl)lithium amide (1.0M in THF, 1.1-1.3 eq.) was added dropwise to a solution of the appropriate acetic ester (1 eq.) in tetrahydrofuran (0.1-0.2M), and the mixture was stirred for 15 min. The appropriate alkyl triflate (1.5-2.0 eq.) was then added neat or as a solution in THF. The resulting reaction mixture was stirred at −78° C. for another 15 min and at RT for another 1 h. Saturated aqueous ammonium chloride solution was added to the reaction mixture.

After phase separation, the aqueous phase was extracted with ethyl acetate. The combined organic phases were dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 9A: Nitro Reduction with Iron

The appropriate nitro compound was dissolved in an ethanol/water mixture (5:1) (about 2-3M), and concentrated hydrochloric acid (0.5-1 eq.) and iron powder (3-8 eq.) were added. The reaction mixture was heated at 80 to 100° C. until the reaction had gone to completion (about 1 to 6 h). The hot reaction mixture was filtered through kieselguhr. The filter cake was washed with methanol and the filtrate was concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

Example 1.1A

2-Fluoro-4-nitrobenzamide

5.00 g (27 mmol) of 2-fluoro-4-nitrobenzoic acid and 2.17 g (40.5 mmol, 1.5 eq.) of ammonium chloride were reacted according to General Method 5A. The crude product was purified by normal phase chromatography (mobile phase: dichloromethane/methanol 2-5%). Yield: 2.65 g (53% of theory)

LC/MS [Method 1]: $R_t$=0.48 min; MS (ESIpos): m/z=185 (M+H)$^+$, $^1$H-NMR (400 MHz, DMSO-$d_6$): δ [ppm]=8.19 (dd, 1H), 8.12 (dd, 1H), 8.05 (br. s, 1H), 7.91 (br. s, 1H), 7.86 (dd, 1H).

Example 1.1B

4-Amino-2-fluorobenzamide

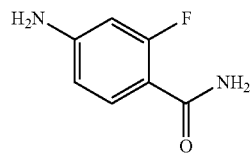 [SMILES: NC(=O)c1ccc(N)cc1F]

2.65 g (14.4 mmol) of 2-fluoro-4-nitrobenzamide were reacted according to General Method 9A. The crude product was purified by normal phase chromatography (mobile phase: dichloromethane/methanol 5-10%). Yield: 1.64 g (74% of theory)

LC/MS [Method 5]: $R_t$=0.89 min; MS (ESIpos): m/z=155 (M+H)$^+$, $^1$H-NMR (400 MHz, DMSO-$d_6$): δ [ppm]=7.48 (t, 1H), 7.15 (br. s, 1H), 6.97 (br. s, 1H), 6.38 (dd, 1H), 6.27 (dd, 1H), 5.93 (s, 2H).

Example 1.2A

2-Fluoro-N-methyl-4-nitrobenzamide

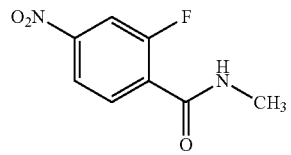

1.00 g (5.40 mmol) of 2-fluoro-4-nitrobenzoic acid and 547 mg (8.10 mmol, 1.5 eq.) of methylamine hydrochloride were reacted according to General Method 5A. Yield: 1.07 g (94% pure, 94% of theory).

LC/MS [Method 1]: $R_t$=0.56 min; MS (ESIpos): m/z=199 (M+H)$^+$, $^1$H-NMR (400 MHz, DMSO-$d_6$): δ [ppm]=8.58 (br. s, 1H), 8.20 (dd, 1H), 8.13 (dd, 1H), 7.85 (dd, 1H), 2.80 (d, 3H).

Example 1.2B

4-Amino-2-fluoro-N-methylbenzamide

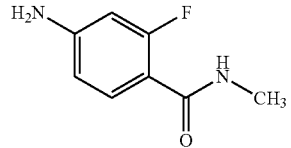

1.07 g (5.07 mmol) of 2-fluoro-N-methyl-4-nitrobenzamide were reacted according to General Method 9A. The crude product was purified by normal phase chromatography (mobile phase: dichloromethane/methanol 5-10%). Yield: 624 mg (72% of theory)

LC/MS [Method 5]: $R_t$=1.20 min; MS (ESIpos): m/z=169 (M+H)$^+$,

¹H-NMR (400 MHz, DMSO-d₆): δ [ppm]=7.54 (br. s, 1H), 7.43 (t, 1H), 6.38 (dd, 1H), 6.27 (dd, 1H), 5.88 (s, 2H), 2.72 (d, 3H).

Example 1.3A

5-Nitropyridine-2-carboxamide

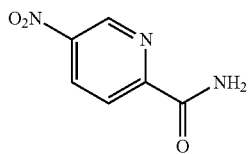 [SMILES: NC(=O)c1ccc([N+](=O)[O-])cn1]

4.00 g (23.8 mmol) of 5-nitropyridine-2-carboxylic acid and 1.91 g (35.7 mmol, 1.5 eq.) of ammonium chloride were reacted according to General Method 5A. After work-up, the crude product was used for the next stage without further purification.

LC/MS [Method 1]: $R_t$=0.39 min; MS (ESIpos): m/z=168 (M+H)⁺,

Example 1.3B

5-Aminopyridine-2-carboxamide

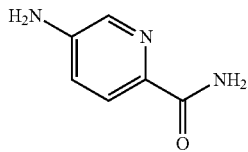

The crude product (about 23.8 mmol) 5-nitropyridine-2-carboxamide was reacted according to General Method 9A. The product obtained was purified by normal phase chromatography (mobile phase: dichloromethane/methanol (9:1) with 1.5% concentrated ammonia). Yield: 1.40 g (42% of theory)

LC/MS [Method 5]: $R_t$=0.50 min; MS (ESIpos): m/z=138 (M+H)⁺,

¹H-NMR (400 MHz, DMSO-d₆): δ [ppm]=7.89 (d, 1H), 7.70 (d, 1H), 7.64 (br. s, 1H), 7.11 (br. s, 1H), 6.95 (dd, 1H), 5.90 (s, 2H).

Example 1.4A

N-Methyl-5-nitropyridine-2-carboxamide

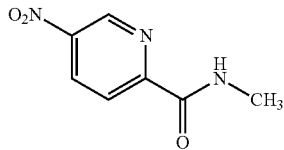

500 mg (2.97 mmol) of 5-nitropyridin-2-carboxylic acid and 301 mg (4.46 mmol, 1.5 eq.) of methylamine hydrochloride were reacted according to General Method 5A. Yield: 459 mg (83% of theory)

LC/MS [Method 3]: $R_t$=1.26 min; MS (ESIpos): m/z=181 (M+H)⁺,

¹H-NMR (400 MHz, DMSO-d₆): δ [ppm]=9.36 (d, 1H), 9.11-8.92 (m, 1H), 8.75 (dd, 1H), 8.26 (d, 1H), 2.85 (d, 3H).

Example 1.4B

5-Amino-N-methylpyridine-2-carboxamide

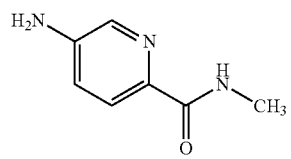

487 mg (2.55 mmol, 1 eq.) of N-methyl-5-nitropyridine-2-carboxamide were reacted according to General Method 9A. The crude product was purified by normal phase chromatography (mobile phase: dichloromethane/methanol 5-10%). Yield: 225 mg (purity 86%, 50% of theory)

¹H-NMR (400 MHz, DMSO-d₆): δ [ppm]=8.32-8.19 (m, 1H), 7.89 (d, 1H), 7.68 (d, 1H), 6.96 (dd, 1H), 5.88 (s, 2H), 2.75 (d, 3H).

Example 1.5A

N-Cyclopropyl-5-nitrothiophene-2-carboxamide

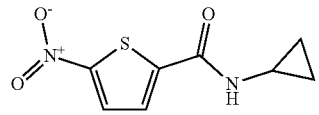 [SMILES: O=C(NC1CC1)c1ccc([N+](=O)[O-])s1]

2.00 g (11.6 mmol) of 5-nitrothiophene-2-carboxylic acid and 1.2 ml (17 mmol, 1.5 eq.) of cyclopropanamine were reacted according to General Method 5A. Yield: 1.67 g (68% of theory)

LC/MS [Method 11]: $R_t$=1.32 min; MS (ESIpos): m/z=213 (M+H)⁺,

¹H-NMR (400 MHz, DMSO-d₆): δ [ppm]=8.94 (d, 1H), 8.12 (d, 1H), 7.74 (d, 1H), 2.87-2.79 (m, 1H), 0.79-0.70 (m, 2H), 0.63-0.54 (m, 2H).

Example 1.5B

5-Amino-N-cyclopropylthiophene-2-carboxamide

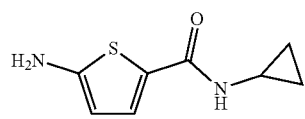 [SMILES: Nc1ccc(C(=O)NC2CC2)s1]

1.67 g (7.87 mmol) of N-cyclopropyl-5-nitrothiophene-2-carboxamide were reacted according to General Method 9A. The crude product was purified by normal phase chromatography (mobile phase: cyclohexane/ethyl acetate 50%-100%). Yield: 791 mg (48% of theory)

LC/MS [Method 11]: $R_t$=0.84 min; MS (ESIpos): m/z=183 (M+H)⁺,

¹H-NMR (400 MHz, DMSO-d₆): δ [ppm]=7.85 (d, 1H), 7.23 (d, 1H), 6.16 (s, 2H), 5.78 (d, 1H), 2.72-2.63 (m, 1H), 0.67-0.55 (m, 2H), 0.50-0.39 (m, 2H).

Example 1.6A (4-Nitro-1,2-phenylene)dimethanol

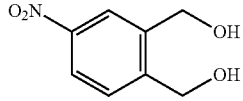 [SMILES: O=[N+]([O-])c1ccc(CO)c(CO)c1]

To a stirred solution of 10.0 g (47.4 mmol) of 4-nitrophthalic acid in 300 ml of tetrahydrofuran was added dropwise 189.5 ml (189.5 mmol, 4.0 eq., 1 mmol/l in tetrahydrofuran) of borane tetrahydrofuran complex at 0° C. After stirring for 2 h at RT, the reaction mixture was cautiously quenched with 200 ml of methanol and then concentrated under reduced pressure. The residue was purified by silica gel chromatography (eluent: petroleum ether-ethyl acetate 100:1 to 2:1). Yield: 6.00 g (65% of theory)

¹H-NMR (300 MHz, DMSO-d₆): δ [ppm]=8.26-8.25 (m, 1H), 8.14-8.10 (m, 1H), 7.71-7.68 (m, 1H), 5.50-5.43 (m, 2H), 4.61-4.58 (m, 4H).

Example 1.6B

6-Nitrophthalazine

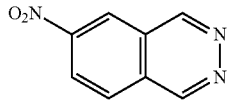 [SMILES: O=[N+]([O-])c1ccc2cnncc2c1]

Under a nitrogen atmosphere, to a solution of 6.3 ml (72.1 mmol, 2.2 eq.) of oxalyl chloride in 240 ml dichloromethane was added a solution of 9.3 ml (131.0 mmol, 4.0 eq.) of dimethyl sulfoxide in 10.0 ml dichloromethane dropwise at −78° C. The resulting solution was stirred for 10 min and then a solution of 6.00 g (32.8 mmol) of (4-nitro-1,2-phenylene)dimethanol in 10 ml dimethyl sulfoxide and 10 ml dichloromethane was added dropwise at −78° C. After stirring for 10 min at the same temperature, 57.0 ml (327.6 mmol, 10.0 eq.) of N,N-diisopropylethylamine was added slowly. The reaction mixture was stirred for 1 h at −78° C. and then allowed to warm to room temperature slowly. To the mixture was added ice-cold water (200 ml) and the aqueous layer was extracted with dichloromethane (2×100 ml). The combined organic phases were dried over anhydrous magnesium sulfate, filtered and the filtrate was used to next step without further purification. This solution of 32.75 mmol of crude 4-nitrophthalaldehyde in 450 ml dichloromethane was diluted with 50.0 ml ethanol and 10.0 ml (164 mmol, 5.0 equiv.) of 80% hydrazine hydrate was added dropwise at 0° C. The reaction solution was stirred for 1 h at room temperature and then concentrated under reduced pressure. The residue was purified by silica gel column chromatography (eluent: petroleum ether-ethyl acetate 1:1 to 0:1). Yield: 2.50 g (41% of theory).

¹H-NMR (300 MHz, DMSO-d₆): δ [ppm]=9.96-9.90 (m, 2H), 9.17-9.16 (m, 1H), 8.76-8.70 (m, 1H), 8.44-8.40 (m, 1H).

Example 1.6C

Phthalazin-6-aminium chloride

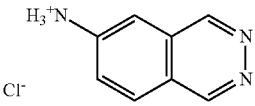

To a solution of 3.70 g (21.2 mmol) of 6-nitrophthalazine in 100.0 ml methanol was added 300 mg of 10% palladium on carbon. The resulting mixture was evacuated and flushed three times with nitrogen, followed by flushing with hydrogen. The reaction mixture was stirred for 24 hours at room temperature under an atmosphere of hydrogen (2 atm). After filtration through celite, the filtrate was concentrated under reduced pressure. The residue was dissolved in 20 ml of methanol and then 30 ml of 4 mol/l solution of hydrogen chloride in dioxane was added to the mixture. The solid was collected by filtration and dried under vacuum. Yield: 1.40 g (35% of theory).

¹H-NMR (300 MHz, DMSO-d₆): δ [ppm]=9.68 (s, 1H), 9.37 (s, 1H), 8.09-8.06 (m, 1H), 7.63 (s, 2H), 7.48-7.45 (m, 1H), 7.06 (m, 1H).

Example 1.7A

6-Bromo-2-(trifluoromethyl)quinoxaline and 7-bromo-2-(trifluoromethyl)quinoxaline (Mixture of Regioisomers)

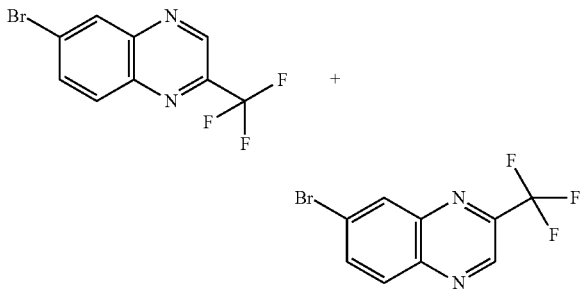

A solution of 14.41 g (53.40 mmol, 2.33 eq.) of 3,3-dibromo-1,1,1-trifluoroacetone and 17.52 g (213.60 mmol, 9.3 eq.) of sodium acetate in 100 ml of methanol and 100 ml of water was heated to 98° C. for 30 min. At this temperature, 4.30 g (22.96 mmol) of 4-bromobenzene-1,2-diamine was added, the reaction mixture was cooled to RT and stirred for 20 h. The resulting suspension was filtered and the solid washed with water. The solid was collected and dried under high vacuum. The product could be used in the following reaction without further purification. Yield: 6.20 g (97% of theory)

¹H-NMR (400 MHz, DMSO-d₆): δ [ppm]=9.50-9.47 (m, 1H), 8.60-8.55 (m, 1H), 8.27-8.17 (m, 2H).

Example 1.7B tert-Butyl [2-(trifluoromethyl)quinoxalin-6-yl]carbamate and tert-butyl [3-(trifluoromethyl)-quinoxalin-6-yl]carbamate (Mixture of Regioisomers)

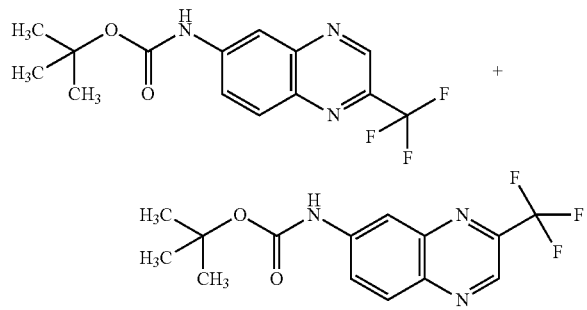

A suspension of 2.0 g (7.2 mmol) of 6-bromo-2-(trifluoromethyl)quinoxaline and 7-bromo-2-(trifluoromethyl)quinoxaline (mixture of regioisomers), 1.27 g (10.83 mmol, 1.5 eq.) of tert-butyl carbamate, 81 mg (0.36 mmol, 0.05 eq.) of palladium(II) acetate, 344 mg (0.722 mmol, 0.1 eq.) of 2-dicyclohexylphosphino-2',4',6'-triisopropylbiphenyl and 4.70 g (14.44 mmol, 2.0 eq.) of cesium carbonate in 100 ml of dioxane was sparged with nitrogen for 5 minutes. The reaction mixture was then heated under nitrogen for 5 hours at 100° C. The reaction mixture was cooled to room temperature. The solids were filtered off and the filtrate was concentrated under reduced pressure. The residue was purified by silica gel column chromatography (100-200 mesh, 100 g, cyclohexane: ethyl acetate 5:1). Yield: 2.0 g (84% of theory).

LC/MS [Method 8]: $R_t$=1.41 min; MS (ESIneg): m/z=312 (M−H)$^-$.

Example 1.7C 2-(Trifluoromethyl)quinoxalin-6-aminium chloride and 3-(trifluoromethyl)quinoxalin-6-aminium chloride (Mixture of Regioisomers)

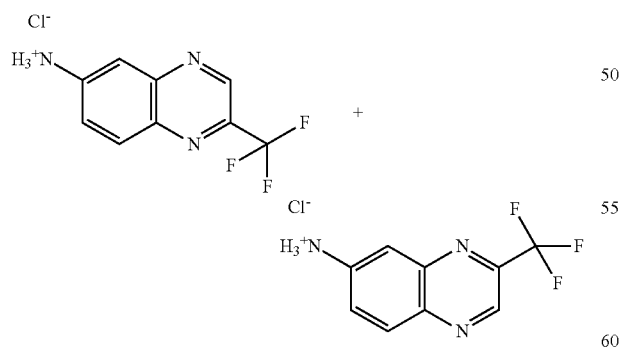

2.0 g (6.4 mmol) of tert-butyl [2-(trifluoromethyl)quinoxalin-6-yl]carbamate and tert-butyl [3-(trifluoromethyl)quinoxalin-6-yl]carbamate (mixture of regioisomers) was dissolved in 16.0 ml (63.840 mmol, 10.0 eq.) of a 4 M solution of hydrogen chloride in dioxane and the reaction mixture was stirred at RT for 24 h. The reaction mixture was treated with diethyl ether and concentrated under reduced pressure. The resulting residue was washed with diethyl ether. The product could be used without further purification. Yield: 1.20 g (76% of theory).

LC/MS [Method 8]: $R_t$=1.00 min; MS (ESIneg): m/z=212 (M−H)$^-$.

Example 1.7D 3-(Trifluoromethyl)quinoxalin-6-amine

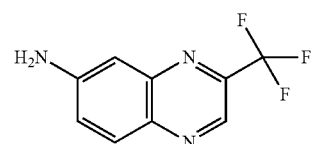

Regioisomer separation of 2-(trifluoromethyl)quinoxalin-6-aminium chloride and 3-(trifluoromethyl)quinoxalin-6-aminium chloride (mixture of regioisomers) (300 mg) (Example 1.7C) gave 110 mg of the title compound.

Separating column: $R_t$=5.06 min.

Separating method: column: Daicel Chiralpak IF 5 μm 250 mm×20 mm; mobile phase: n-heptane 80%/ethanol 20%; temperature: 25° C.; flow rate: 40 ml/min; UV detection: 265 nm.

LC/MS [Method 10]: $R_t$=1.36 min; MS (ESIpos): m/z=214 [M+H]$^+$.

Example 1.7E 2-(Trifluoromethyl)quinoxalin-6-amine

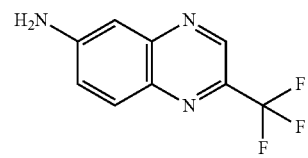 [SMILES: Nc1ccc2nc(C(F)(F)F)cnc2c1]

Regioisomer separation of 2-(trifluoromethyl)quinoxalin-6-aminium chloride and 3-(trifluoromethyl)quinoxalin-6-aminium chloride (mixture of regioisomers) (300 mg) (Example 1.7C) gave 150 mg of the title compound.

Separating column: $R_t$=6.91 min.

Separating method: column: Daicel Chiralpak IF 5 μm 250 mm×20 mm; mobile phase: n-heptane 80%/ethanol 20%; temperature: 25° C.; flow rate: 40 ml/min; UV detection: 265 nm.

LC/MS [Method 10]: $R_t$=1.36 min; MS (ESIpos): m/z=214 [M+H]$^+$.

Example 1.8A

5-Nitro-2-(2,2,2-trifluoroethyl)-2H-indazole

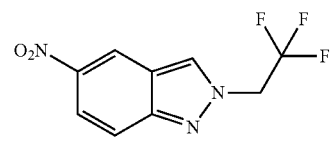

1.00 g (6.13 mmol) 5-nitro-1H-indazole were dissolved in 15.0 ml DMF and 5.99 g (18.39 mmol) cesium carbonate as well as 1.72 ml (7.36 mmol) 2,2,2-trifluoroethyl 1,1,2,2,3,3,4,4,4-nonafluorobutane-1-sulfonate were added. The mixture was then stirred overnight and diluted with 50 ml ethyl acetate and 50 ml water. The aqueous phase was acidified to pH 1 with 1M hydrochloric acid and extracted twice with 20 ml ethyl acetate. The combined organic extracts were washed with 30 ml water and subsequently with 30 ml aqueous saturated sodium chloride solution and then dried over magnesium sulfate, filtered and concentrated under reduced pressure. The residue was taken up in 5 ml dichloromethane and purified by normal phase chromatography (mobile phase: cyclohexane/ethyl acetate-gradient). Yield: 350 mg (23% of theory).

LC/MS [Method 10]: $R_t$=1.58 min; MS (ESIpos): m/z=246 (M+H)$^+$.

$^1$H-NMR (500 MHz, DMSO-d$_6$): δ [ppm]=8.82-8.78 (m, 1H), 8.72-8.69 (m, 1H), 8.07 (d, 1H), 7.87 (dd, 1H), 5.68 (q, 2H).

Example 1.8B 2-(2,2,2-Trifluoroethyl)-2H-indazol-5-amine

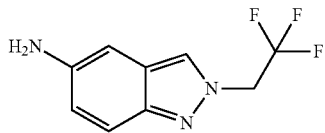

350 mg (1.43 mmol) 5-nitro-2-(2,2,2-trifluoroethyl)-2H-indazole were dissolved in 8.7 ml ethanol. To this solution 76.0 mg palladium (10% on charcoal) were added and the mixture was stirred under 1 atmosphere of hydrogen at room temperature for 4 hours. The mixture was then filtered through Celite, the residue washed with 50 ml ethanol and the combined filtrate was concentrated under reduced pressure to give 296 mg of the product which was used crude in the next step.

LC/MS [Method 1]: $R_t$=0.28 min; MS (ESIpos): m/z=216 (M+H)$^+$.

Example 1.9A 2-(2,2-Difluoroethyl)-5-nitro-2H-indazole

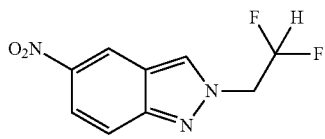

1.00 g (6.13 mmol) 5-nitro-1H-indazole were dissolved in 15.0 ml DMF and 5.99 g (18.39 mmol) cesium carbonate as well as 1.57 g (7.36 mmol) 2,2-difluoroethyl trifluoromethanesulfonate were added. The mixture was then stirred overnight and diluted with 50 ml ethyl acetate and 50 ml water. The aqueous phase was acidified to pH 1 with 1M hydrochloric acid and extracted twice with 20 ml ethyl acetate. The combined organic extracts were washed with 30 ml water and subsequently with 30 ml aqueous saturated sodium chloride solution and then dried over magnesium sulfate, filtered and concentrated under reduced pressure. The residue was purified by normal phase chromatography (mobile phase: cyclohexane/ethyl acetate-gradient). Yield: 352 mg (25% of theory).

LC/MS [Method 10]: $R_t$=1.41 min; MS (ESIpos): m/z=228 (M+H)$^+$, $^1$H-NMR (500 MHz, DMSO-d$_6$): δ [ppm]=8.96 (d, 1H), 8.89 (s, 1H), 8.05 (dd, 1H), 7.83 (d, 1H), 6.41-6.72 (m, 1H), 5.05-5.17 (m, 2H).

Example 1.9B 2-(2,2-Difluoroethyl)-2H-indazol-5-amine

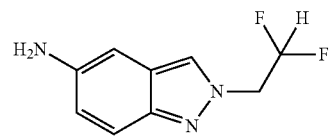 [SMILES: O=[N+]([O-])c1ccc2nn(CC(F)F)cc2c1]

352 mg (1.55 mmol) 2-(2,2-difluoroethyl)-5-nitro-2H-indazole were dissolved in 9.5 ml ethanol. To this solution 82.4 mg palladium (10% on charcoal) were added and the mixture was stirred under 1 atmosphere of hydrogen at room temperature for 4 hours. The mixture was then filtered through Celite, the residue washed with 50 ml ethanol and the combined filtrate was concentrated under reduced pressure to give 307 mg of the product which was used crude in the next step.

LC/MS [Method 21]: $R_t$=3.39 min; MS (ESIpos): m/z=198 (M+H)$^+$.

Example 1.10A 2-(Difluoromethyl)-5-nitro-2H-indazole

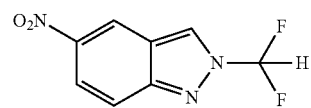 [SMILES: O=[N+]([O-])c1ccc2nn(C(F)F)cc2c1]

0.75 g (4.60 mmol) 5-nitro-1H-indazole were dissolved in 22.5 ml ethyl acetate and 1.27 g (9.20 mmol) potassium carbonate as well as 1.64 g (9.20 mmol) difluoro(fluorosulfonyl)acetic acid were added. The mixture was then stirred for 2 hours at room temperature (until gas evolution ceased) and diluted portionwise with aqueous saturated sodium carbonate solution. The mixture was then extracted three times with ethyl acetate and the combined organic phases were washed with water and subsequently with saturated aqueous sodium chloride solution, then dried (magnesium sulphate), filtered and concentrated under reduced pressure. The residue was purified by normal phase chromatography (mobile phase: cyclohexane/ethyl acetate-gradient). Yield: 617 mg (63% of theory).

$^1$H-NMR (500 MHz, DMSO-d$_6$): δ [ppm]=9.31 (d, 1H), 8.97-8.99 (m, 1H), 8.14-8.41 (m, 1H), 8.12 (dd, 1H), 7.92-7.97 (m, 1H).

Example 1.10B 2-(Difluoromethyl)-2H-indazol-5-amine hydrochloride

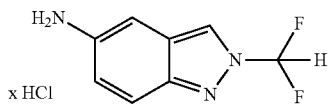 [SMILES: Nc1ccc2nn(C(F)F)cc2c1]

605 mg (2.84 mmol) 2-(difluoromethyl)-5-nitro-2H-indazole were dissolved in 15 ml ethanol. To this solution 151 mg palladium (10% on charcoal) were added and the mixture was stirred under 1 atmosphere of hydrogen at room temperature for 3 hours. The mixture was then filtered through Celite, the residue washed with 100 ml ethanol and the combined filtrate was concentrated under reduced pressure. The residue was taken up in 10 ml dioxane and then 2 ml hydrochloric acid (4M) were added. The resulting suspension was then diluted with 5 ml dioxane and filtered. The filtered off solid was washed with 20 ml diethyl ether and dried under reduced pressure to give 369 mg of the product which was used crude in the next step.

LC/MS [Method 10]: $R_t$=0.52 min; MS (ESIpos): m/z=184 (M+H)$^+$.

Example 1.11A 2-(Cyclopropylmethyl)-5-nitro-2H-indazole

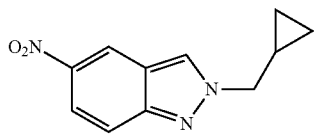 [SMILES: O=[N+]([O-])c1ccc2nn(CC3CC3)cc2c1]

1.50 g (9.20 mmol) 5-nitro-1H-indazole were dissolved in 22.5 ml DMF and 2.54 g (18.39 mmol) potassium carbonate as well as 1.35 ml (13.79 mmol) (bromomethyl)cyclopropane were added. The mixture was then stirred for 1.5 hours at 40° C. and diluted with 50 ml ethyl acetate and 50 ml water. The aqueous phase was acidified with 1M hydrochloric acid and extracted twice with 20 ml ethyl acetate. The combined organic extracts were washed with 30 ml water and subsequently with 30 ml aqueous saturated sodium chloride solution and then dried over magnesium sulfate, filtered and concentrated under reduced pressure. The residue was purified by normal phase chromatography (mobile phase: cyclohexane/ethyl acetate-gradient). Yield: 1.05 g (52% of theory).

LC/MS [Method 10]: $R_t$=1.79 min; MS (ESIpos): m/z=218 (M+H)$^+$, $^1$H-NMR (400 MHz, DMSO-d$_6$): δ [ppm]=8.83 (d, 1H), 8.41 (s, 1H), 8.22 (dd, 1H), 7.94 (d, 1H), 4.40 (d, 2H), 1.23-1.37 (m, 1H), 0.37-0.56 (m, 4H).

Example 1.11B 2-(Cyclopropylmethyl)-2H-indazol-5-amine hydrochloride

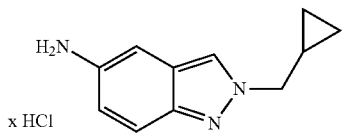 [SMILES: Nc1ccc2nn(CC3CC3)cc2c1]

1.05 g (4.81 mmol) 2-(cyclopropylmethyl)-5-nitro-2H-indazole were dissolved in 25 ml ethanol. To this solution 256 mg palladium (10% on charcoal) were added and the mixture was stirred under 1 atmosphere of hydrogen at room temperature for 3 hours. The mixture was then filtered through Celite, the residue washed with 100 ml ethanol and the combined filtrate was concentrated under reduced pressure. The residue was taken up in 10 ml dioxane and then 5 ml hydrochloric acid (4M) were added. The resulting suspension was concentrated under reduced pressure to give 1.10 g of the product which was used crude in the next step.

LC/MS [Method 10]: $R_t$=0.54 min; MS (ESIpos): m/z=188 (M+H)$^+$.

Example 1.11A 2-(Trideutero)methyl-5-nitro-2H-indazole

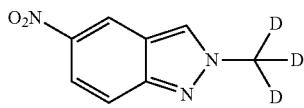

1.00 g (6.13 mmol) 5-nitro-1H-indazole were dissolved in 15.0 ml DMF and 6.00 g (18.39 mmol) cesium carbonate as well as 0.46 ml (7.36 mmol) iodomethane-d$_3$ were added. The mixture was then stirred at room temperature overnight and diluted with 50 ml ethyl acetate as well as 50 ml water. The aqueous phase was acidified with 1M hydrochloric acid and extracted twice with 20 ml ethyl acetate. The combined organic extracts were washed with 30 ml water and subsequently with 30 ml aqueous saturated sodium chloride solution and then dried over magnesium sulfate, filtered and concentrated under reduced pressure. The residue was purified by normal phase chromatography (mobile phase: cyclohexane/ethyl acetate-gradient). Yield: 286 mg (26% of theory).

LC/MS [Method 1]: $R_t$=0.64 min; MS (ESIpos): m/z=181 (M+H)$^+$, $^1$H-NMR (500 MHz, DMSO-d$_6$): δ [ppm]=8.88 (d, 1H), 8.77 (d, 1H), 8.01 (dd, 1H), 7.77 (d, 1H).

Example 1.11B 2-(Trideutero)methyl-2H-indazol-5-amine

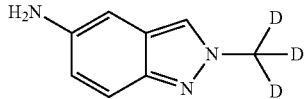 [SMILES: [2H]C([2H])([2H])n1cc2cc([N+](=O)[O-])ccc2n1]

286 mg (1.59 mmol) 2-(trideutero)methyl-5-nitro-2H-indazole were dissolved in 9.7 ml ethanol. To this solution 84 mg palladium (10% on charcoal) were added and the mixture was stirred under 1 atmosphere of hydrogen at room temperature for 4 hours. The mixture was then filtered through Celite, the residue washed with 50 ml ethanol and the combined filtrate was concentrated under reduced pressure. The resulting crude product was used directly in the next step.

Example 1.12A

2-Methylquinoxalin-6-amine

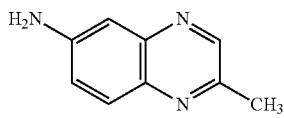

1.16 g (6.13 mmol) 2-methyl-6-nitroquinoxaline (synthesized according to European Journal of Medicinal Chemistry, 2015, 467-479) were dissolved in 32 ml ethanol. To this solution 326 mg palladium (10% on charcoal) were added and the mixture was stirred under 1 atmosphere of hydrogen at room temperature for 3 hours. The mixture was then filtered through Celite, the residue washed with 100 ml ethanol and the combined filtrate was concentrated under reduced pressure. The resulting crude product was purified by normal phase chromatography (mobile phase: cyclohexane/ethyl acetate-gradient). Yield: 416 mg (38% of theory).

Example 1.13A tert-Butyl [2-(trifluoromethyl)quinolin-6-yl]carbamate

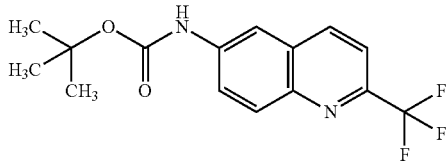 [SMILES: CC(C)(C)OC(=O)Nc1ccc2nc(C(F)(F)F)ccc2c1]

2.00 g (7.2 mmol, 1.0 equiv.) of 16-bromo-2-(trifluoromethyl)quinoline, 1.27 g (10.8 mmol, 1.5 equiv.) of tert-butyl carbamate, 81 mg (0.4 mmol, 0.05 equiv.) of palladium(II) acetate, (0.7 mmol, 0.1 equiv.) of 2-dicyclohexylphosphino-2',4',6'-triisopropyl-1,1'-biphenyl 345 mg and 4.72 g (14.5 mmol, 2.0 equiv.) of cesium carbonate were combined in 15.0 ml of 1,4-dioxane and purged with nitrogen for 5 minutes. The reaction mixture was stirred for half an hour at 100° C. and then cooled to room temperature. After filtration through celite, the filtrate was concentrated under reduced pressure. The residue was purified by silica gel column chromatography (eluent: petroleum ether-ethyl acetate 5:1) to give 1.86 g (81% of theory) of the title compound.
LC/MS [Method 22]: $R_t$=1.21 min; MS (ESIpos): m/z=313 (M+H)$^+$.
$^1$H-NMR (400 MHz, DMSO-d$_6$): δ [ppm]=9.97 (s, 1H), 8.58 (d, 1H), 8.35 (d, 1H), 8.07 (d, 1H), 7.88-7.82 (m, 2H), 1.53 (s, 9H).

Example 1.13B 2-(Trifluoromethyl)quinolin-6-amine hydrochloride

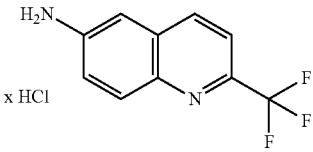 [SMILES: Nc1ccc2nc(C(F)(F)F)ccc2c1]

To a solution of 2.88 g (9.2 mmol, 1.0 equiv.) of tert-butyl [2-(trifluoromethyl)quinolin-6-yl]carbamate in 20 ml of 1,4-dioxane was added 35 ml of a solution of hydrogen chloride in 1,4-dioxane (4M). The resulting mixture was stirred for 16 hours at room temperature. The solid was collected by filtration, washed with acetonitrile (2×200 ml) and then dried in vacuo to give 1.22 g (53% of theory) of the title compound.
LC/MS [Method 23]: $R_t$=1.23 min; MS (ESIpos): m/z=213 (M+H)$^+$.
$^1$H-NMR (400 MHz, DMSO-d$_6$): δ [ppm]=8.24 (d, 1H), 7.86 (d, 1H), 7.74-7.67 (m, 1H), 7.36-7.32 (m, 1H), 6.97 (d, 1H), 5.82 (brs, 2H).
$^{19}$F-NMR (376 MHz, DMSO-d$_6$): δ [ppm]=−65.51 to −65.79 (m, 3F).

Example 1.14A 3-(Trifluoromethyl)-1H-indazol-5-amine

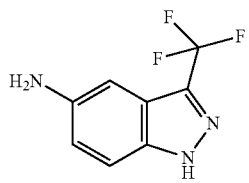

500 mg (2.16 mmol) 5-nitro-3-(trifluoromethyl)-1H-indazole were dissolved in 10 ml ethanol. To this solution 115 mg palladium (10% on charcoal) were added and the mixture was stirred under 1 atmosphere of hydrogen at room temperature for 3 hours. The mixture was then filtered through Celite, the residue washed with 50 ml ethanol and the combined filtrate was concentrated under reduced pressure to give the title compound which was used without further purification. Yield: 462 mg (80% purity, 85% of theory).
LC/MS [Method 10]: $R_t$=0.86 min; MS (ESIpos): m/z=202 (M+H)$^+$.

Example 21A 5-(2-Bromo-4-chlorophenyl)-1,3-oxazole

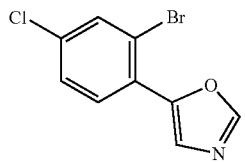 [SMILES: Clc1ccc(-c2cnco2)c(Br)c1]

At RT, 12.7 g (91.8 mmol) of potassium carbonate were added to a mixture of 10.0 g (45.9 mmol) of 2-bromo-4-chlorobenzaldehyde and 9.8 g (50.5 mmol) of isocyanomethyl 4-methylphenyl sulphone in 100 ml of methanol, and the mixture was stirred at 75° C. overnight. After cooling to RT, the reaction mixture was concentrated under reduced pressure. After addition of water, the residue was stirred and the precipitate was filtered off, dried under reduced pressure and triturated with hexane. Yield: 9.8 g (83% of theory)

LC/MS [Method 12]: $R_t$=2.18 min; MS (ESIpos): m/z=259 (M+H)$^+$, $^1$H-NMR (400 MHz, DMSO-$d_6$): δ [ppm]=8.57 (s, 1H), 7.91 (s, 1H), 7.83 (s, 1H), 7.75 (d, 1H), 7.58 (d, 1H).

Example 2.2A 3-(2-Bromo-4-chlorophenyl)prop-2-yn-1-ol

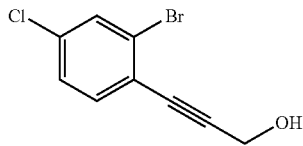 [SMILES: OCC#Cc1ccc(Cl)cc1Br]

32 ml of diethylamine were added to 2.00 g (6.30 mmol) of 2-bromo-4-chloro-1-iodobenzene, 451 μl (7.56 mmol, 1.2 eq.) of prop-2-yn-1-ol, 137 mg (0.19 mmol, 0.03 eq.) of bis(triphenylphosphine)palladium(II) dichloride and 60 mg (0.32 mmol, 0.05 eq.) of copper(I) iodide, and the mixture was stirred at RT overnight. Using ice bath cooling, the reaction mixture was cooled, and 100 ml of dichloromethane and 100 ml of water were added. The aqueous phase was extracted twice with dichloromethane. The combined organic phases were washed with water and then with saturated aqueous sodium chloride solution, dried over sodium sulphate and concentrated. The residue was purified by normal phase chromatography (mobile phase: cyclohexane/ethyl acetate 20-50%). Yield: 1.17 g (76% of theory).

LC/MS [Method 9]: $R_t$=5.85 min; MS (ESIpos): m/z=245.9 (M+H)$^+$, $^1$H-NMR (400 MHz, DMSO-$d_6$): δ [ppm]=7.86 (d, 1H), 7.57-7.53 (m, 1H), 7.50-7.46 (m, 1H), 5.42 (t, 1H), 4.35 (d, 2H).

Example 2.2B

2-{[3-(2-Bromo-4-chlorophenyl)prop-2-yn-1-yl]oxy}-1H-isoindole-1,3(2H)-dione

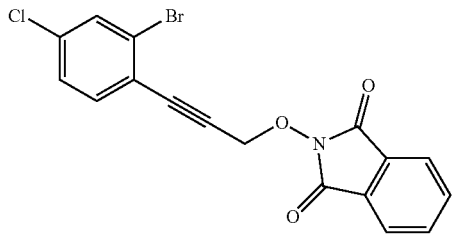 [SMILES: O=C1c2ccccc2C(=O)N1OCC#Cc1ccc(Cl)cc1Br]

A solution of 1.50 g (6.11 mmol) of 3-(2-bromo-4-chlorophenyl)prop-2-yn-1-ol, 1.20 g (7.33 mmol, 1.2 eq.) of 2-hydroxy-1H-isoindole-1,3(2H)-dione and 2.40 g (9.17 mmol, 1.5 eq.) of triphenylphosphine in 24 ml of dichloromethane was cooled to 0° C., 1.80 ml (9.17 mmol, 1.5 eq.) of diisopropyl-(E)-diazene 1,2-dicarboxylate were added and the mixture was stirred at 0° C. for 30 min and then overnight whilst being allowed to warm to RT. The reaction mixture was concentrated and the residue was purified by normal phase chromatography (mobile phase: cyclohexane/ethyl acetate, 10-20%). Yield: 1.63 g (66% of theory).

LC/MS [Method 1]: $R_t$=1.17 min; MS (ESIpos): m/z=390 (M+H)$^+$, $^1$H-NMR (400 MHz, DMSO-$d_6$): δ [ppm]=7.94-7.84 (m, 5H), 7.59-7.47 (m, 2H), 5.20 (s, 2H).

Example 2.2C

1-[3-(Aminooxy)prop-1-yn-1-yl]-2-bromo-4-chlorobenzene

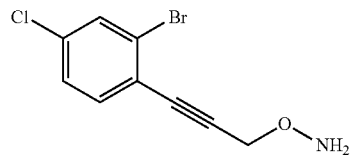 [SMILES: NOCC#Cc1ccc(Cl)cc1Br]

A solution of 1.63 g (4.01 mmol) of 2-{[3-(2-bromo-4-chlorophenyl)prop-2-yn-1-yl]oxy}-1H-isoindole-1,3(2H)-dione in 20 ml of dichloromethane was cooled to 0° C., 974 μl (20.03 mmol, 5 eq.) of hydrazine hydrate were added and the mixture was stirred at 0° C. for 10 min. The reaction mixture was stirred at RT overnight and then diluted with 20 ml of a 5% strength aqueous sodium carbonate solution and extracted three times with in each case 20 ml of ethyl acetate. The combined organic phases were washed with saturated aqueous sodium chloride solution, dried over sodium sulphate and concentrated. The crude product was purified by normal phase chromatography (mobile phase: cyclohexane/ethyl acetate, isocratic 50%). Yield: 997 mg (91% of theory).

LC/MS [Method 10]: $R_t$=1.77 min; MS (ESIpos): m/z=262 (M+H)$^+$, $^1$H-NMR (400 MHz, DMSO-$d_6$): δ [ppm]=7.89-7.87 (m, 1H), 7.62-7.58 (m, 1H), 7.52-7.48 (m, 1H), 6.26 (s, 2H), 4.47 (s, 2H).

Example 2.2D 3-(2-Bromo-4-chlorophenyl)-4,5-dihydro-1,2-oxazole

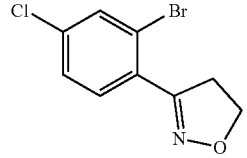 [SMILES: Clc1ccc(C2=NOCC2)c(Br)c1]

997 mg (3.65 mmol) of 1-[3-(aminooxy)prop-1-yn-1-yl]-2-bromo-4-chlorobenzene were dissolved in 39 ml of dichloromethane, 56 mg (0.07 mmol, 0.02 eq.) of [(2-biphenyl)di-tert-butylphosphine]gold(I) hexafluoroantimonate-acetonitrile monoadduct were added and the mixture was stirred at RT for 30 min. 509 µl (3.65 mmol, 1 eq.) of triethylamine were then added. The reaction mixture was filtered though silica gel and washed with dichloromethane. The filtrate was concentrated and the residue was purified by normal phase chromatography (mobile phase: cyclohexane/ethyl acetate, 10-20%). Yield: 705 mg (73% of theory).

LC/MS [Method 2]: $R_t$=2.77 min; MS (ESIpos): m/z=262 (M+H)$^+$, $^1$H-NMR (400 MHz, DMSO-d$_6$): δ [ppm]=7.91-7.89 (m, 1H), 7.60-7.56 (m, 2H), 4.42 (t, 2H), 3.43 (t, 2H).

Example 2.2E 3-(2-Bromo-4-chlorophenyl)-1,2-oxazole

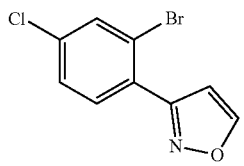 [SMILES: Clc1ccc(-c2ccon2)c(Br)c1]

3.34 g (38.4 mmol) of dioxomanganese were added to a solution of 667 mg (2.56 mmol) of 3-(2-bromo-4-chlorophenyl)-4,5-dihydro-1,2-oxazole in 37 ml of toluene/dioxane (10:1 mixture). A Dean-Stark water separator was connected to the reaction flask and the reaction mixture was heated to reflux. After 24 hours under reflux, 900 mg of dioxomanganese were added and the reaction mixture was heated under reflux for a further 24 hours. The reaction mixture was then cooled, diluted with methanol and filtered through kieselguhr. The filtrate was concentrated and the crude product was purified by normal phase chromatography (mobile phase: cyclohexane/ethyl acetate, 0-15%). Yield: 380 mg (purity 95%, 55% of theory)

$^1$H-NMR (400 MHz, DMSO-d$_6$): δ [ppm]=9.09 (d, 1H), 7.98 (s, 1H), 7.69-7.61 (m, 2H), 6.98 (d, 1H).

Example 2.3A

2-Bromo-4-chloro-N-hydroxybenzamide

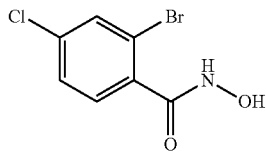 [SMILES: O=C(NO)c1ccc(Cl)cc1Br]

1.00 g (4.25 mmol) of 2-bromo-4-chlorobenzoic acid was initially charged in 30 ml of DMF, 1.30 g (8.49 mmol, 2 eq.) of 1-hydroxy-1H-benzotriazole hydrate and 1.79 g (9.34 mmol, 2.2 eq.) of 1-(3-dimethylaminopropyl)-3-ethylcarbodiimide hydrochloride were added and the mixture was stirred at RT for 1 h. 1.48 g (21.23 mmol, 5 eq.) of hydroxylamine hydrochloride and 2.96 ml (21.23 mmol, 5 eq) of triethylamine were then added, and the mixture was stirred at RT for 20 h. The reaction mixture was filtered off with suction, the filter cake was washed with 3 ml of acetonitrile and the filtrate was purified by preparative HPLC (RP18 column; mobile phase: acetonitrile/water gradient with addition of 0.1% formic acid). Yield: 815 mg (74% of theory)

LC/MS [Method 10]: $R_t$=0.97 min; MS (ESIpos): m/z=252 (M+H)$^+$, $^1$H-NMR (400 MHz, DMSO-d$_6$): δ [ppm]=10.98 (s, 1H), 9.28 (s, 1H), 7.82 (d, 1H), 7.52 (dd, 1H), 7.39 (d, 1H).

Example 2.3B 3-(2-Bromo-4-chlorophenyl)-5,6-dihydro-1,4,2-dioxazine

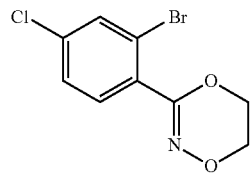 [SMILES: Clc1ccc(C2=NOCCO2)c(Br)c1]

0.81 g (3.14 mmol) of 2-bromo-4-chloro-N-hydroxybenzamide and 1.01 g (7.28 mmol, 2.32 eq.) of potassium carbonate were initially charged in 20 ml of ethanol, 338 µl (3.92 mmol, 1.25 eq.) of 1,2-dibromoethane were added and the mixture was stirred under reflux for 7 h. The reaction mixture was concentrated, and ethyl acetate and water were added to the residue. After phase separation, the organic phase was washed first with water and then with saturated aqueous sodium chloride solution, dried (sodium sulphate) and concentrated. The crude product was purified by normal phase chromatography (mobile phase: cyclohexane/ethyl acetate, 0-20%). Yield: 200 mg (23% of theory).

LC/MS [Method 1]: $R_t$=0.93 min; MS (ESIpos): m/z=278 (M+H)$^+$, $^1$H-NMR (400 MHz, DMSO-d$_6$): δ [ppm]=7.88 (s, 1H), 7.56 (s, 2H), 4.53-4.40 (m, 2H), 4.22-4.09 (m, 2H).

Example 2.4A 1-(2-Bromo-4-chlorophenyl)-1H-tetrazole

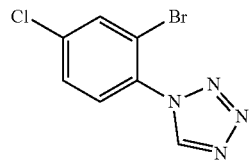 [SMILES: Clc1ccc(-n2cnnn2)c(Br)c1]

529 mg (2.56 mmol) of 2-bromo-4-chloroaniline and 500 mg (7.69 mmol, 3 eq.) of sodium azide were initially charged in 26 ml of acetic acid, 1.28 ml (7.69 mmol, 3 eq.) of triethyl orthoformate were added and the mixture was stirred at 80° C. for 3 h. The reaction mixture was then stirred at RT overnight and concentrated. The residue was stirred in 17.5 ml of saturated aqueous sodium bicarbonate solution, and the mixture was extracted twice with in each case 20 ml of diethyl ether. The combined organic phases were dried over sodium sulphate, concentrated and purified by normal phase chromatography (mobile phase: cyclohexane/ethyl acetate, 20-50%). Yield: 436 mg (81% pure, 53% of theory).

LC/MS [Method 1]: $R_t$=0.84 min; MS (ESIpos): m/z=261 (M+H)$^+$, $^1$H-NMR (400 MHz, DMSO-d$_6$): δ [ppm]=9.91 (s, 1H), 8.18 (d, 1H), 7.86-7.75 (m, 2H).

Example 2.5A 1-(2-Bromo-4-chlorophenyl)-1H-imidazole

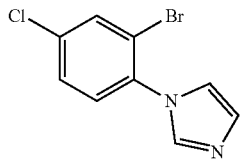 [SMILES: Clc1ccc(-n2ccnc2)c(Br)c1]

4.00 g (19.4 mmol) of 2-bromo-4-chloroaniline were initially charged in 11 ml of methanol, 2.20 ml (19.4 mmol, 1 eq.) of oxalaldehyde were added and the mixture was stirred at RT for 3 h. 88 ml of methanol, 2.07 g (38.7 mmol, 2 eq.) of ammonium chloride and 3.05 ml (40.7 mmol, 2.1 eq.) of formaldehyde (37% in water) were then added, and the mixture was stirred under reflux for 1 h. 2 ml of a 85% strength phosphoric acid were added dropwise over a period of 10 min, and the mixture was stirred under reflux for 6 h. The reaction mixture was substantially concentrated under reduced pressure and 200 ml of ice-water and 200 ml of dichloromethane were added to the residue. With vigorous stirring and using sodium carbonate, the reaction mixture was carefully adjusted to pH 9. The phases were then separated and the aqueous phase was extracted with dichloromethane. The combined organic phases were dried (sodium sulphate) and concentrated. The residue was purified by normal phase chromatography (mobile phase: dichloromethane/methanol, 0-6%). The product fractions were combined and concentrated. 10-15 ml of diethyl ether were added to the residue, the mixture was stirred for 20 min and filtered off with suction and the product was washed with 3 ml of diethyl ether and dried. Yield: 1.40 g (28% of theory)

LC/MS [Method 11]: $R_t$=1.58 min; MS (ESIpos): m/z=259 (M+H)$^+$, $^1$H-NMR (400 MHz, DMSO-d$_6$): δ [ppm]=8.02 (d, 1H), 7.87 (s, 1H), 7.64 (dd, 1H), 7.55 (d, 1H), 7.41 (s, 1H), 7.10 (s, 1H).

Example 2.6A

2-Bromo-1-(2-bromo-4-chlorophenyl)ethanone

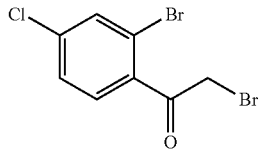 [SMILES: O=C(CBr)c1ccc(Cl)cc1Br]

5.00 g (21.4 mmol) of 2-bromo-4-chloroacetophenone were initially charged in 21.50 ml of glacial acetic acid. 1.10 ml (21.4 mmol) of bromine were then added dropwise and the mixture was stirred at RT for 30 min. With stirring, the mixture was subsequently warmed to 40° C. and then kept below 50° C. by cooling. After the reaction had gone to completion, the temperature returned to RT over a period of 1.5 hours. The mixture was then concentrated under reduced pressure and the residue was reacted without further purification. Yield: 6.60 g (80% purity, 79% of theory).

LC/MS [Method 8]: $R_t$=1.38 min; MS (ESIpos): m/z=310 (M+H)$^+$.

Example 2.6B 4-(2-Bromo-4-chlorophenyl)-1,3-oxazole

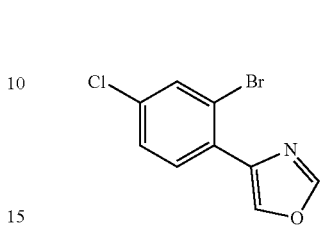

6.60 g (16.90 mmol) of 2-bromo-1-(2-bromo-4-chlorophenyl)ethanone were initially charged in 21.0 ml of formic acid, 4.26 g (67.61 mmol) of anhydrous ammonium formate were then added and the mixture was heated at reflux for 8 hours. Residual formic acid was then removed under reduced pressure, and the residue was diluted with water and ethyl acetate. The mixture was made alkaline using sodium carbonate, the organic phase was separated off and the aqueous phase was washed with ethyl acetate. The collected organic phases were washed with saturated aqueous sodium chloride solution and concentrated under reduced pressure. The residue was separated by flash normal phase chromatography (silica gel, petroleum ether/ethyl acetate gradient) and the crude product obtained in this manner was purified by preparative HPLC (RP18 column, mobile phase: acetonitrile/water gradient with addition of 0.1% formic acid) Yield: 0.9 g (21% of theory).

LC/MS [Method 1]: $R_t$=1.15 min; MS (ESIpos): m/z=258 (M+H)$^+$, $^1$H-NMR (400 MHz, DMSO-d$_6$): δ [ppm]=8.74-8.79 (m, 1H), 8.55-8.59 (m, 1H), 7.96 (d, 1H), 7.89 (d, 1H), 7.60 (dd, 1H).

Example 2.7A

2-Bromo-4-chlorobenzohydrazide

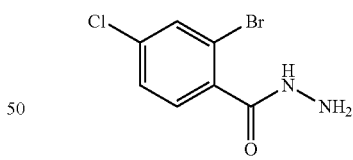

Under argon, 1.50 g (6.18 mmol) of 2-bromo-4-chlorobenzoic acid were initially charged in 58.2 ml of tetrahydrofuran, 1.50 g (9.27 mmol) of 1,1'-carbonyldiimidazole and 0.38 g (3.09 mmol) of 4-dimethylaminopyridine were added and the mixture was stirred at 70° C. for 3 hours. The reaction was subsequently cooled to RT, and 8.03 ml (8.03 mmol) of hydrazine solution (1M in tetrahydrofuran) were then added in one portion. The mixture was 75 min, and a further 8.03 ml of hydrazine solution were then added. After a further 30 min with stirring, 60 ml of dichloromethane and 60 ml of saturated aqueous sodium bicarbonate solution were added. The organic phase was removed and the aqueous phase was extracted twice with dichloromethane. The combined organic phases were washed with water, dried over magnesium sulphate and concentrated under reduced pressure. The residue was purified by flash normal phase chromatography (silica gel, dichloromethane/methanol gradient). Yield: 1.30 g (82% of theory).

LC/MS [Method 11]: $R_t$=1.11 min; MS (ESIpos): m/z=249 (M+H)$^+$, $^1$H-NMR (400 MHz, DMSO-d$_6$): δ [ppm]=9.58 (br. s., 1H), 7.81 (d, 1H), 7.52 (dd, 1H), 7.37 (d, 1H), 4.49 (br. s., 2H).

Example 2.7B 2-(2-Bromo-4-chlorophenyl)-1,3,4-oxadiazole

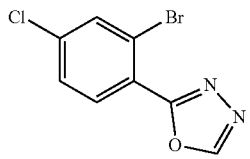 [SMILES: Clc1ccc(-c2nnco2)c(Br)c1]

1.30 g (5.05 mmol) of 2-bromo-4-chlorobenzohydrazide were initially charged in 16.81 ml (101.08 mmol) of triethyl orthoformate, 20 mg of para-toluenesulphonic acid were then added and the mixture was heated at reflux overnight. The solution was then brought to RT, and the crystals formed were filtered off with suction and washed with pentane. The mother liquor was concentrated, the residue was stirred with pentane and the crystals formed were filtered off with suction, washed with pentane and dried. Total yield: 1.11 g (80% of theory).

LC/MS [Method 1]: $R_t$=0.85 min; MS (ESIpos): m/z=258 (M+H)$^+$, $^1$H-NMR (400 MHz, DMSO-d$_6$): δ [ppm]=9.48 (s, 1H), 8.07 (s, 1H), 7.95 (d, 1H), 7.72 (d, 1H).

Example 2.8A 1-(2-Bromo-4-chlorophenyl)-4-fluoro-1H-imidazole

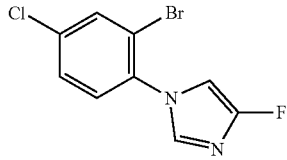 [SMILES: Fc1cn(-c2ccc(Cl)cc2Br)cn1]

930 µl (7.3 mmol) of 2-bromo-4-chloro-1-fluorobenzene, 631 mg (7.33 mmol) of 4-fluoro-1H-imidazole, 3.04 g (22.0 mmol) of potassium carbonate and 32 ml DMF were divided into two microwave vessels and stirred in the microwave at 130° C. for 3 hours. After cooling, the two reaction mixtures were combined and 200 ml of water were added with stirring. This mixture was stirred at 0° C. for 30 min. The suspension was then filtered and the solid was washed with water. The solid was purified by flash normal phase chromatography (mobile phase: cyclohexane/ethyl acetate 0-30% gradient). Yield: 970 mg (48% of theory)

LC/MS [Method 10]: $R_t$=1.78 min; MS (ESIpos): m/z=274 [M+H]$^+$, $^1$H-NMR (400 MHz, DMSO-d$_6$): δ [ppm]=8.04 (d, 1H), 7.68-7.60 (m, 3H), 7.23 (dd, 1H).

Example 2.9A 1-(2-Bromo-4-chlorophenyl)-4-chloro-1H-imidazole

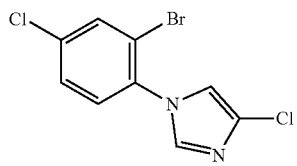 [SMILES: Clc1ccc(-n2cnc(Cl)c2)c(Br)c1]

890 µl (7.0 mmol) of 2-bromo-4-chloro-1-fluorobenzene, 720 mg (7.02 mmol) of 4-chloro-1H-imidazole, 2.91 g (21.1 mmol) of potassium carbonate and 30 ml DMF were divided into two microwave vessels and stirred in the microwave at 130° C. for 3 hours. After cooling, the two reaction mixtures were combined and 150 ml of cold water were added with stirring. This mixture was stirred for 5 min. The suspension was then filtered and the solid was washed with ice-water and pentane and dried under high vacuum. Yield: 1.33 g (64% of theory)

LC/MS [Method 1]: $R_t$=0.97 min; MS (ESIpos): m/z=293 (M+H)$^+$, $^1$H-NMR (400 MHz, DMSO-d$_6$): δ [ppm]=8.05 (d, 1H), 7.89 (d, 1H), 7.68-7.59 (m, 3H).

Example 2.10A 1-(2-Bromo-4-chlorophenyl)-1H-imidazole-4-carbaldehyde

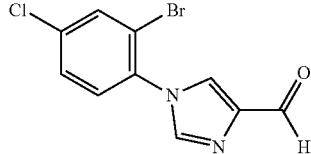 [SMILES: O=Cc1cn(-c2ccc(Cl)cc2Br)cn1]

440 µl (3.4 mmol) of 2-bromo-4-chloro-1-fluorobenzene, 337 mg (3.44 mmol) of 1H-imidazole-4-carbaldehyde, 1.43 g (10.3 mmol) of potassium carbonate and 17 ml DMF were stirred in the microwave at 130° C. for 3 hours. After cooling, methyl tert-butyl ether was added and the organic phase was washed three times with a saturated aqueous sodium chloride solution. The organic phase was dried over sodium sulphate and concentrated under reduced pressure. Yield: 430 mg (43% of theory).

LC/MS [Method 10]: $R_t$=1.44 min; MS (ESIpos): m/z=287 (M+H)$^+$, $^1$H-NMR (400 MHz, DMSO-d$_6$): δ [ppm]=9.83 (s, 1H), 8.36 (d, 1H), 8.13 (d, 1H), 8.08 (d, 1H), 7.72-7.66 (m, 2H).

Example 2.10B 1-(2-Bromo-4-chlorophenyl)-4-(difluoromethyl)-1H-imidazole

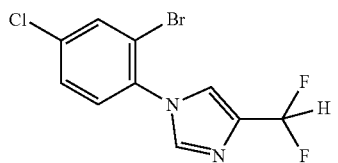 [SMILES: FC(F)c1cn(-c2ccc(Cl)cc2Br)cn1]

At 0° C., 650 µl (purity 90%, 4.4 mmol) of N-ethyl-N-(trifluoro-lambda4-sulphanyl)ethanamine were added to a solution of 430 mg (1.48 mmol) of 1-(2-bromo-4-chlorophenyl)-1H-imidazole-4-carbaldehyde in 8.4 ml of dichloromethane. The reaction mixture was stirred at RT for 20 hours. 25 ml of a saturated aqueous sodium bicarbonate solution were added dropwise until evolution of carbon dioxide could no longer be observed. This mixture was then extracted twice with dichloromethane. The combined organic phases were dried over sodium sulphate and concentrated under reduced pressure. The residue was purified by flash normal phase chromatography (silica gel, cyclohexane/ethyl acetate 0-50% gradient). Yield: 235 mg (52% of theory)

LC/MS [Method 10]: $R_t$=1.77 min; MS (ESIpos): m/z=307 (M+H)$^+$.

Example 2.11A 1-(2-Bromo-4-chlorophenyl)prop-2-en-1-ol (Racemate)

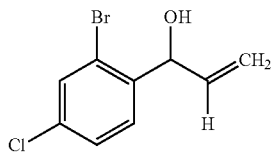

16.0 g (72.9 mmol) of 2-bromo-4-chlorobenzaldehyde were dissolved in 320 ml of THF, and 94.8 ml (c=1 mol/l, 94.8 mmol, 1.3 eq) of a solution of vinylmagnesium bromide in THF were added dropwise with stirring at −70° C. After 2 h at −70° C., saturated aqueous ammonium chloride solution was added and the reaction mixture was extracted with ethyl acetate. The combined organic phases were washed with water and saturated aqueous sodium chloride solution, dried over sodium sulphate, filtered and concentrated under reduced pressure. Yield: 19.0 g (89% of theory).

$^1$H-NMR (400 MHz, DMSO-d$_6$): δ [ppm]=7.70 (d, 1H), 7.56-7.46 (m, 2H), 5.94-5.83 (m, 2H), 5.35-5.32 (m, 1H), 5.28-5.22 (m, 1H), 5.14-5.09 (m, 1H).

Example 2.11B 1-(2-Bromo-4-chlorophenyl)prop-2-en-1-one

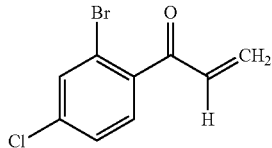

19.0 g (65.2 mmol) of 1-(2-bromo-4-chlorophenyl)prop-2-en-1l-ol (racemate) were dissolved in 600 ml of ethyl acetate, and 54.8 g (195.7 mmol, 3.0 eq.) of 2-iodooxybenzoic acid were added. The reaction mixture was stirred at 100° C. for 12 h and then filtered. The filtrate was concentrated under reduced pressure, the residue was taken up in dichloromethane and the organic phase was washed successively with saturated aqueous sodium sulphite solution, saturated aqueous sodium bicarbonate solution, water and saturated aqueous sodium chloride solution. The organic phase was then dried over magnesium sulphate, filtered and concentrated under reduced pressure. The crude product was purified by HPLC (normal phase, petroleum ether:ethyl acetate 50:1). Yield: 13.0 g (86% purity, 70% of theory).

LC/MS [Method 13]: $R_t$=1.13 min; MS (ESIpos): m/z=247 (M+H)$^+$ $^1$H-NMR (400 MHz, DMSO-d$_6$): δ [ppm]=7.90 (d, 1H), 7.60 (dd, 1H), 7.51 (d, 1H), 6.69-6.76 (m, 1H), 6.28 (d, 1H), 6.03 (d, 1H).

Example 2.11C tert-Butyl 3-(2-bromo-4-chlorophenyl)-4,5-dihydro-1H-pyrazole-1-carboxylate

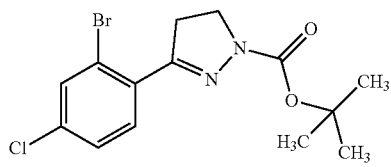 [SMILES: CC(C)(C)OC(=O)N1CCC(c2ccc(Cl)cc2Br)=N1]

4.0 g (16.3 mmol) of 1-(2-bromo-4-chlorophenyl)prop-2-en-1-one were dissolved in 200 ml of methanol, and 3.1 g (48.9 mmol, 3.0 eq.) of hydrazine hydrate were added. The reaction mixture was stirred at 30° C. for 72 h and then concentrated under reduced pressure. The residue was taken up in dichloromethane and the organic phase was washed successively with saturated aqueous sodium bicarbonate solution, water and saturated aqueous sodium chloride solution. The organic phase was dried over sodium sulphate, filtered and concentrated under reduced pressure. The crude product (3.07 g, purity 33%) was dissolved in 40 ml of dichloromethane, and 1.54 g (7.06 mmol, 0.43 eq.) of di-tert-butyl dicarbonate, 0.95 g of triethylamine (9.3 mmol, 0.57 eq.) and 57 mg (0.47 mmol, 0.03 eq.) of 4-dimethylaminopyridine were added. The reaction mixture was stirred at 30° C. for 6 h and then diluted with dichloromethane. The organic phase was washed successively with saturated aqueous sodium bicarbonate solution, water and saturated aqueous sodium chloride solution and then dried over magnesium sulphate and concentrated under reduced pressure. The crude product was purified by HPLC (normal phase, petroleum ether:ethyl acetate 8:1) and then preparative TLC (petroleum ether:ethyl acetate 5:1) of the concentrated product-containing fractions. Yield: 250 mg (94% pure, 14% of theory).

LC/MS [Method 15]: $R_t$=1.87 min; MS (ESIpos): m/z=305 (M-t-Bu+H)$^+$, $^1$H-NMR (400 MHz, DMSO-d$_6$): δ [ppm]=7.88 (d, 1H), 7.63-7.55 (m, 2H), 3.88 (t, 2H), 3.30 (t, 2H), 1.47 (s, 9H).

Example 2.12A 1-(2-Bromo-4-chlorophenyl)-3-(dimethylamino)but-2-en-1-one (One Diastereomer)

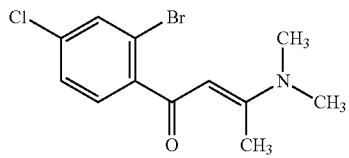 [SMILES: C/C(=C\C(=O)c1ccc(Cl)cc1Br)N(C)C]

1.4 g (6.0 mmol) of 1-(2-bromo-4-chlorophenyl)ethanone and 2.8 g (21.0 mmol, 3.5 eq.) of 1,1-dimethoxy-N,N-dimethylethanamine were dissolved in 20 ml of dioxane, and the mixture was heated under reflux for 24 h. The reaction mixture was subsequently cooled to RT, aqueous saturated sodium bicarbonate solution and ethyl acetate were added and the aqueous phase was separated off. The aqueous phase was extracted with ethyl acetate (twice). The combined organic phases were washed with aqueous saturated ammonium chloride solution, dried over sodium sulphate, filtered and concentrated under reduced pressure. The crude product was purified by flash chromatography (50 g silica, normal phase, cyclohexane/ethyl acetate 5:1 to 1:1). According to $^1$H-NMR, the pure Z or E diastereomer is formed. Yield: 1.35 g (73% of theory).

LC/MS [Method 10]: $R_t$=1.69 min; MS (ESIpos): m/z=302 (M+H)$^+$, $^1$H-NMR (400 MHz, DMSO-d$_6$): δ [ppm]=7.70 (d, 1H), 7.44 (dd, 1H), 7.35 (d, 1H), 5.03 (s, 1H), 3.13-2.89 (m, 6H), 2.56 (s, 3H).

Example 2.12B 5-(2-Bromo-4-chlorophenyl)-3-methyl-1,2-oxazole

1.09 g (3.59 mmol) of (2E)-1-(2-bromo-4-chlorophenyl)-3-(dimethylamino)but-2-en-1-one and 499 mg (7.18 mmol, 2.0 eq.) of hydroxylammonium chloride in 23 ml of water and 23 ml of 1,2-dimethoxyethane were shaken at 60° C. After 24 h, the reaction mixture was cooled and diluted with ethyl acetate, and saturated aqueous sodium bicarbonate solution was added. The aqueous phase was extracted with ethyl acetate (twice). The combined organic phases were dried over sodium sulphate, filtered and concentrated under reduced pressure. Yield: 930 mg (95% of theory).

LC/MS [Method 10]: $R_t$=2.17 min; MS (ESIpos): m/z=272 (M+H)$^+$, $^1$H-NMR (400 MHz, DMSO-d$_6$): δ [ppm]=8.00 (d, 1H), 7.81 (d, 1H), 7.65 (dd, 1H), 6.97 (s, 1H), 2.33 (s, 3H).

Example 2.13A 2-(2-Bromo-4-chlorophenyl)-5-(trifluoromethyl)-1,3,4-oxadiazole

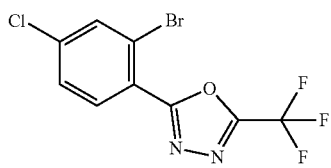 [SMILES: FC(F)(F)c1nnc(-c2ccc(Cl)cc2Br)o1]

5.00 g (20.0 mmol) of 2-bromo-4-chlorobenzohydrazide were dissolved in 100 ml of dichloromethane, and 5.47 g (26.1 mmol, 1.3 eq.) of trifluoroacetic anhydride were added at 0° C. 3.45 g (34.1 mmol, 1.7 eq.) of triethylamine were then added dropwise at 0° C., and the reaction mixture was stirred at RT for 22 h. The reaction mixture was diluted with dichloromethane (300 ml) and the organic phase was washed twice with in each case 300 ml of saturated aqueous sodium bicarbonate solution and twice with in each case 300 ml of saturated aqueous sodium chloride solution. The organic phase was dried over sodium sulphate and filtered and the filtrate was concentrated under reduced pressure. The residue was dissolved in 137 ml of thionyl chloride and the reaction mixture was stirred at 50° C. for 12 h. After cooling to RT, the reaction mixture was concentrated under reduced pressure and the residue was taken up in 500 ml of ethyl acetate. The organic phase was washed once with 500 ml of saturated aqueous sodium bicarbonate solution, once with 500 ml of water and once with 500 ml of saturated aqueous sodium chloride solution. The organic phase was dried over sodium sulphate and filtered and the filtrate was concentrated under reduced pressure. The crude product was purified by normal phase chromatography (mobile phase: petroleum ether). Yield: 1.30 g (20% of theory).

LC/MS [Method 15]: $R_t$=1.80 min; MS (ESIpos): m/z=328 (M+H)$^+$, $^1$H-NMR (400 MHz, DMSO-d$_6$): δ [ppm]=8.30-7.85 (m, 2H), 7.85-7.59 (m, 1H), $^{19}$F-NMR (376 MHz, DMSO-d$_6$): δ [ppm]=−64.26 (s).

Example 2.14A

2-Bromo-4-chloro-N'-(difluoroacetyl)benzohydrazide

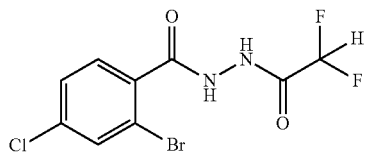 [SMILES: O=C(NNC(=O)C(F)F)c1ccc(Cl)cc1Br]

11.00 g (44.0 mmol) of 2-bromo-4-chlorobenzohydrazide were dissolved in 400 ml of dichloromethane, and 9.98 g (57.3 mmol, 1.3 eq.) of difluoroacetic anhydride were added at 0° C. 7.58 g (74.9 mmol, 1.7 eq.) of triethylamine were then added dropwise at 0° C., and the reaction mixture was stirred at RT for 22 h. The reaction mixture was diluted with dichloromethane (500 ml) and the organic phase was washed twice with in each case 500 ml of saturated aqueous sodium bicarbonate solution and twice with in each case 500 ml of saturated aqueous sodium chloride solution. The organic phase was dried over sodium sulphate and filtered and the filtrate was concentrated under reduced pressure. The product was used in the next step without further purification. Yield: 5.20 g (36% of theory).

LC/MS [Method 16]: $R_t$=0.81 min; MS (ESIpos): m/z=328 (M+H)$^+$, $^1$H-NMR (400 MHz, DMSO-d$_6$): δ [ppm]=11.17 (s, 1H), 10.69 (s, 1H), 7.89 (s, 1H), 7.62-7.59 (m, 1H), 7.48 (d, 1H), 6.42 (t, 1H).

Example 2.14B 2-(2-Bromo-4-chlorophenyl)-5-(difluoromethyl)-1,3,4-oxadiazole

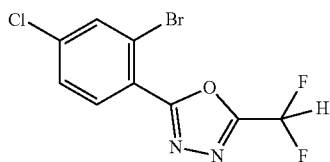 [SMILES: FC(F)c1nnc(-c2ccc(Cl)cc2Br)o1]

2.60 g (7.90 mmol) of 2-bromo-4-chloro-N'-(difluoroacetyl)benzohydrazide were dissolved in 75 ml of thionyl chloride, and the reaction mixture was stirred at 50° C. for 12 h. After cooling to RT, the reaction mixture was concentrated under reduced pressure and the residue was taken up in 100 ml of ethyl acetate. The organic phase was washed once with 100 ml of saturated aqueous sodium bicarbonate solution, once with 100 ml of water and once with 100 ml of saturated aqueous sodium chloride solution. The organic phase was dried over sodium sulphate and filtered and the filtrate was concentrated under reduced pressure. The crude product was purified by normal phase chromatography (mobile phase: petroleum ether/ethyl acetate 20:1). Yield: 1.80 g (71% of theory).

LC/MS [Method 17]: $R_t$=1.60 min; MS (ESIpos): m/z=310 (M+H)$^+$, $^1$H-NMR (400 MHz, DMSO-d$_6$): δ [ppm]=8.12 (s, 1H), 8.01-7.98 (m, 1H), 7.77-7.74 (m, 1H), 7.60 (t, 1H).

Example 2.15A 4-(2-Bromo-4-chlorophenyl)-1-(difluoromethyl)-1H-pyrazole

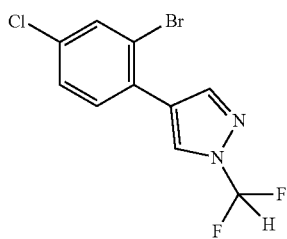 [SMILES: FC(F)n1cc(-c2ccc(Cl)cc2Br)cn1]

Under argon and in a microwave vessel, 610 mg (2.50 mmol) of 1-(difluoromethyl)-4-(4,4,5,5-tetramethyl-1,3,2-dioxaborolan-2-yl)-1H-pyrazole [described in WO2014/159218 A1, paragraph 00218], 662 mg (2.08 mmol) of 2-bromo-4-chloroiodobenzene and 663 mg (6.25 mmol) of sodium carbonate were initially charged in a mixture of 5.57 ml of DMF and 1.73 ml of water, and the solution was flushed with argon. 170 mg (0.21 mmol) of [1,1-bis(diphenylphosphino)ferrocene]dichloropalladium/dichloromethane complex were then added, and the mixture was shaken in a closed vessel at 85° C. overnight. The reaction mixture was diluted with ethyl acetate and water, the phases were separated and the aqueous phase was re-extracted three times with ethyl acetate. The collected organic phases were dried over magnesium sulphate, filtered and concentrated. The residue was purified by flash silica gel chromatography (cyclohexane/ethyl acetate gradient). The crude product obtained in this manner was reacted without further purification. Yield: 401 mg (52% of theory).

LC/MS [Method 10]: $R_t$=2.15 min; MS (ESIpos): m/z=307 (M+H)$^+$.

Example 2.16A 5-(2-Bromo-4-chlorophenyl)-3-methyl-1,2,4-oxadiazole

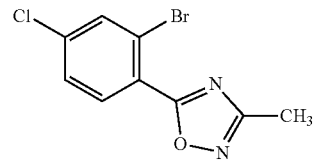

1.00 g (4.25 mmol) of 2-bromo-4-chlorobenzoic acid was initially charged in 20.0 ml of dichloromethane, and 0.445 ml of oxalyl chloride (5.10 mmol) were then added, followed by a few drops (2-3) of DMF. The reaction mixture was stirred at RT for 2 h. Another 0.445 ml of oxalyl chloride were then added, and the mixture was stirred at RT for another 2 h. The mixture was concentrated and a solution of 0.315 g (4.25 mmol) of N-hydroxyacetamidine in 6.0 ml of pyridine was added dropwise to the residue (exothermal reaction). After the addition had ended, stirring was continued under reflux overnight. The mixture obtained in this manner was concentrated and the residue was separated by flash silica gel chromatography (cyclohexane/ethyl acetate gradient). The crude product obtained in this manner was reacted without further purification. Yield: 483 mg (42% of theory).

LC/MS [Method 10]: $R_t$=2.05 min; MS (ESIpos): m/z=273 (M+H)$^+$.

Example 2.17A 4-(2-Bromo-4-chlorophenyl)-1-(2,2,2-trifluoroethyl)-1H-pyrazole

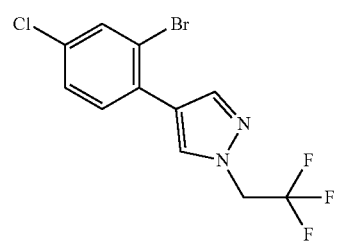 [SMILES: FC(F)(F)Cn1cc(-c2ccc(Cl)cc2Br)cn1]

Analogously to Example 2.15A, 242 mg (0.88 mmol) of 4-(4,4,5,5-tetramethyl-1,3,2-dioxaborolan-2-yl)-1-(2,2,2-trifluoroethyl)-1H-pyrazole [described in WO02015/116886] were reacted with 232 mg (0.73 mmol) of 2-bromo-4-chloroiodobenzene. The crude product obtained in this manner was reacted without further purification. Yield: 137 mg (46% of theory).

LC/MS [Method 10]: $R_t$=2.16 min; MS (ESIpos): m/z=339 (M+H)$^+$.

Example 2.18A

1-Azido-2-bromo-4-chlorobenzene

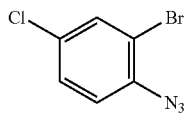

At 0° C., 2.75 g (26.6 mmol) of tert-butyl nitrite were added dropwise to a solution of 5.00 g (24.2 mmol) of 2-bromo-4-chloroaniline and 3.35 g (29.1 mmol) of trimethylsilyl azide in 120.0 ml of acetonitrile. The mixture was then brought to RT and stirred for another 72 hours. The mixture was then concentrated and the residue was purified by flash silica gel chromatography (dichloromethane). Yield: 5.60 g (99% of theory).

$^1$H-NMR (400 MHz, DMSO-$d_6$): δ [ppm]=7.80 (s, 1H), 7.58-7.52 (m, 1H), 7.47-7.44 (m, 1H).

Example 2.18B 1-(2-Bromo-4-chlorophenyl)-4-(trimethylsilyl)-1H-1,2,3-triazole

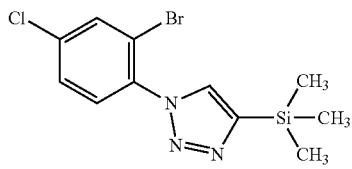 [SMILES: C[Si](C)(C)c1cn(-c2ccc(Cl)cc2Br)nn1]

7.60 g (77.4 mmol) of ethynyl(trimethylsilyl)silane were added to a solution of 6.00 g (25.8 mmol) of 1-azido-2-bromo-4-chlorobenzene in 48.0 ml of toluene, and the mixture was stirred at 110° C. for 12 hours. The mixture was brought to RT and concentrated and the residue was purified by flash silica gel chromatography (petroleum ether/ethyl acetate mixture 10:1). Yield: 7.80 g (91% of theory).

LC/MS [Method 13]: $R_t$=1.21 min; MS (ESIpos): m/z=332 (M+H)$^+$.

$^1$H-NMR (400 MHz, DMSO-$d_6$): δ [ppm]=8.54 (s, 1H), 8.08 (s, 1H), 7.70-7.64 (m, 2H), 0.31 (s, 9H).

Example 2.18C 1-(2-Bromo-4-chlorophenyl)-4-chloro-1H-1,2,3-triazole

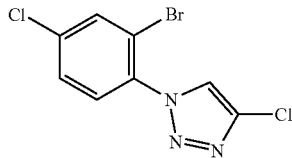 [SMILES: Clc1ccc(-n2cc(Cl)nn2)c(Br)c1]

38.77 g (290.3 mmol) of N-chlorosuccinimide and 8.43 g (145.1 mmol) of potassium fluoride were added to a solution of 8.0 g (24.2 mmol) of 1-(2-bromo-4-chlorophenyl)-4-(trimethylsilyl)-1H-1,2,3-triazole in 250.0 ml of acetonitrile, and the mixture was stirred at 90° C. for 40 hours. The mixture was then filtered at RT, and the filtrate was concentrated and purified by flash silica gel chromatography (petroleum ether/ethyl acetate gradient). Yield: 5.00 g (69% of theory).

LC/MS [Method 14]: $R_t$=1.55 min; MS (ESIpos): m/z=294 (M+H)$^+$.

$^1$H-NMR (400 MHz, DMSO-$d_6$): δ [ppm]=8.88 (s, 1H), 8.12 (s, 1H), 7.77-7.71 (m, 2H).

Example 2.19A 1-(2-Bromo-4-chlorophenyl)-4-(trifluoromethyl)-1H-imidazole

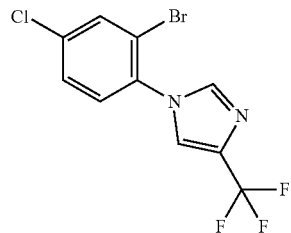 [SMILES: FC(F)(F)c1cn(-c2ccc(Cl)cc2Br)cn1]

93 µl (730 µmol) of 2-bromo-4-chloro-1-fluorobenzene, 100 mg (735 µmol) of 4-(trifluoromethyl)-1H-imidazole, 305 mg (2.20 mmol) of potassium carbonate and 3.7 ml of DMF were stirred in the microwave at 130° C. for 3 hours. After cooling, 40 ml of methyl tert-butyl ether and 15 ml of water were added. After phase separation, the aqueous phase was extracted with methyl-tert-butyl ether. The combined organic phases were dried over sodium sulphate and concentrated under reduced pressure. The residue was purified by preparative HPLC (acetonitrile/water gradient with addition of 0.1% formic acid). Yield: 58 mg (24% of theory).

LC/MS [Method 1]: $R_t$=1.06 min; MS (ESIpos): m/z=327 [M+H]$^+$, $^1$H-NMR (400 MHz, DMSO-$d_6$): δ [ppm]=8.18 (t, 1H), 8.13 (s, 1H), 8.08 (t, 1H), 7.71-7.66 (m, 2H).

Example 2.20A 1-(2-Bromo-4-chlorophenyl)-4-(diethoxymethyl)-1H-1,2,3-triazole

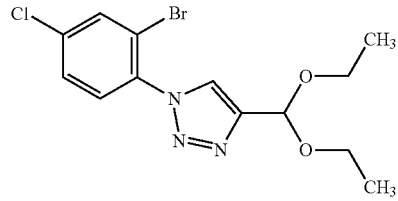 [SMILES: CCOC(OCC)c1cn(-c2ccc(Cl)cc2Br)nn1]

4.96 g (38.7 mmol) of 3,3-diethoxyprop-1-yne were added to a solution of 6.00 g (25.8 mmol) of 1-azido-2-bromo-4-chlorobenzene in 60.0 ml of toluene, and the mixture was stirred at 110° C. for 15 hours. The mixture was brought to RT and concentrated and the residue was purified by flash silica gel chromatography (petroleum ether/ethyl acetate mixture 10:1). Yield: 8.10 g (78% of theory).

LC/MS [Method 13]: $R_t$=1.12 min; MS (ESIpos): m/z=362 (M+H)$^+$.

$^1$H-NMR (300 MHz, DMSO-d$_6$): δ [ppm]=8.49 (s, 1H), 8.11 (s, 1H), 7.72-7.70 (m, 2H), 5.78-5.77 (m, 1H), 3.67-3.57 (m, 4H), 1.17 (t, 6H).

Example 2.20B 1-(2-Bromo-4-chlorophenyl)-1H-1,2,3-triazole-4-carbaldehyde

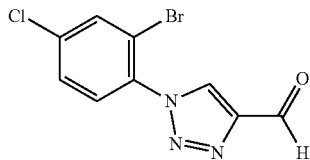 [SMILES: O=Cc1cn(-c2ccc(Cl)cc2Br)nn1]

2.00 g (5.50 mmol) of 1-(2-bromo-4-chlorophenyl)-4-(diethoxymethyl)-1H-1,2,3-triazole were added to a mixture of 13.32 g (221.8 mmol) of acetic acid in 60 ml of water, and the reaction mixture was stirred at RT overnight. The mixture was then diluted with 40 ml of water and extracted with 300 ml of dichloromethane. The organic phase was washed twice with in each case 200 ml of water and twice with in each case 200 ml of saturated aqueous sodium chloride solution, dried over sodium sulphate, filtered and concentrated. The crude product obtained in this manner was reacted without further purification. Yield: 1.50 g (91% of theory).

LC/MS [Method 13]: $R_t$=0.98 min; MS (ESIpos): m/z=288 (M+H)$^+$.

$^1$H-NMR (400 MHz, DMSO-d$_6$): δ [ppm]=10.12 (s, 1H), 9.35 (s, 1H), 8.14 (s, 1H), 7.80-7.74 (m, 2H).

Example 2.20C 1-(2-Bromo-4-chlorophenyl)-4-(difluoromethyl)-1H-1,2,3-triazole

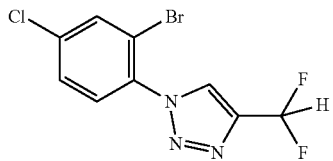 [SMILES: FC(F)c1cn(-c2ccc(Cl)cc2Br)nn1]

3.15 g (19.5 mmol) of diethylaminosulphur trifluoride were added to a solution of 2.80 g (9.8 mmol) of 1-(2-bromo-4-chlorophenyl)-1H-1,2,3-triazole-4-carbaldehyde in 60 ml of dichloromethane, and the reaction mixture was stirred at RT for 2 hours. The mixture was then added to 200 ml of ice-cooled saturated aqueous sodium bicarbonate solution and extracted three times with in each case 200 ml of dichloromethane. The collected organic phases were washed in each case with 500 ml of water and with 500 ml of saturated aqueous sodium chloride solution, dried over sodium sulphate, filtered and concentrated. The crude product obtained in this manner was purified by flash silica gel chromatography (petroleum ether/ethyl acetate mixture 10:1). Yield: 2.07 g (68% of theory).

LC/MS [Method 14]: $R_t$=1.49 min; MS (ESIpos): m/z=310 (M+H)$^+$.

$^1$H-NMR (400 MHz, DMSO-d$_6$): δ [ppm]=9.01 (s, 1H), 8.12 (s, 1H), 7.80-7.72 (m, 2H), 7.34 (t, 1H).

$^{19}$F-NMR (376 MHz, DMSO-d$_6$): δ [ppm]=−112.23 (s, 2F).

Example 2.21A 1-(2-Bromo-4-chlorophenyl)-N-hydroxymethanimine (E/Z Mixture)

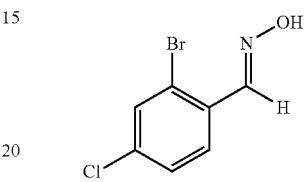

8.00 g (36.4 mmol) of 2-bromo-4-chlorobenzaldehyde were dissolved in 80 ml of methanol, and 5.38 g (65.6 mmol, 1.8 eq.) of sodium acetate were added. 2.79 g (40.1 mmol) of hydroxylamine hydrochloride were then added a little at a time, and the reaction mixture was stirred at RT for 2 h. The reaction mixture was concentrated under reduced pressure and the residue was taken up in 200 ml of dichloromethane. The organic phase was washed with 100 ml of water and 100 ml of saturated aqueous sodium chloride solution, dried over sodium sulphate and filtered. The filtrate was concentrated under reduced pressure. The crude product was reacted in the next step without further purification. Yield: 6.50 g (72% of theory).

LC/MS [Method 18]: $R_t$=0.92 min; MS (ESIpos): m/z=236 (M+H)$^+$, $^1$H-NMR (400 MHz, DMSO-d$_6$): δ [ppm]=11.74 (s, 1H), 8.29 (s, 1H), 7.78-7.72 (m, 2H), 7.50-7.43 (m, 1H).

Example 2.21B

[3-(2-Bromo-4-chlorophenyl)-1,2-oxazol-5-yl]methanol

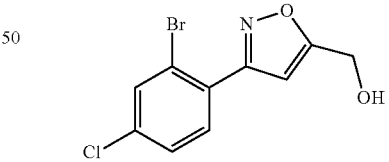

3.00 g (12.8 mmol) of 1-(2-bromo-4-chlorophenyl)-N-hydroxymethanimine (E/Z mixture) were dissolved in 60 ml of dichloromethane, and 17.9 g (19.2 mmol, 1.5 eq.) of 8% strength aqueous sodium hypochlorite solution and 1.44 g (25.6 mmol, 2.0 eq.) of prop-2-yn-1-ol were added. The reaction mixture was stirred at RT for 15 h and then diluted with 100 ml of dichloromethane. The organic phase was twice washed with in each case 100 ml of water and once with 100 ml of aqueous saturated sodium chloride solution, dried over sodium sulphate and filtered, and the filtrate was concentrated under reduced pressure. The crude product was purified by normal phase chromatography (mobile phase: petroleum ether/ethyl acetate 3:1). Yield: 2.74 g (74% of theory).

LC/MS [Method 19]: $R_t$=1.05 min; MS (ESIpos): m/z=290 (M+H)$^+$, $^1$H-NMR (400 MHz, DMSO-d$_6$): δ [ppm]=7.95 (s, 1H), 7.63-7.57 (m, 2H), 6.75 (s, 1H), 5.74 (t, 1H), 4.63 (d, 2H).

Example 2.21C 3-(2-Bromo-4-chlorophenyl)-1,2-oxazole-5-carbaldehyde

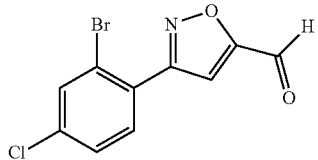 [SMILES: O=Cc1cc(-c2ccc(Cl)cc2Br)no1]

1.20 g (4.20 mmol) of [3-(2-bromo-4-chlorophenyl)-1,2-oxazol-5-yl]methanol were dissolved in 15 ml of dichloromethane, and a solution of 2.3 g (5.4 mmol, 1.3 eq.) of Dess-Martin periodinane in 15 ml of dichloromethane was added dropwise at 0° C. The reaction mixture was stirred at RT for 2 h and then diluted with 50 ml of dichloromethane. The organic phase was washed once with 50 ml of a 1:1 mixture of aqueous saturated sodium thiosulphate solution and aqueous saturated sodium bicarbonate solution, twice with in each case 50 ml of water and once with 50 ml of saturated aqueous sodium chloride solution. The organic phase was then dried over sodium sulphate and filtered and the filtrate was concentrated under reduced pressure. The crude product was used in the next step without further purification. Yield: 1.20 g (99% of theory).

$^1$H-NMR (400 MHz, DMSO-d$_6$): δ [ppm]=9.97 (s, 1H), 8.02 (s, 1H), 7.78 (s, 1H), 7.71-7.64 (m, 2H).

Example 2.21D 3-(2-Bromo-4-chlorophenyl)-5-(difluoromethyl)-1,2-oxazole

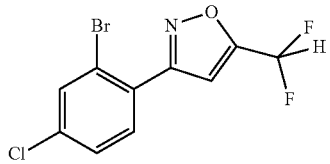 [SMILES: FC(F)c1cc(-c2ccc(Cl)cc2Br)no1]

1.20 g (4.20 mmol) of 3-(2-bromo-4-chlorophenyl)-1,2-oxazole-5-carbaldehyde were dissolved in 24 ml of dichloromethane, and 1.35 g (8.4 mmol, 2.0 eq.) of diethylaminosulphur trifluoride were added. The reaction mixture was stirred at RT for 15 h and then diluted with 60 ml of dichloromethane. The organic phase was twice washed with in each case 60 ml of water and once with 60 ml of aqueous saturated sodium chloride solution, dried over sodium sulphate and filtered, and the filtrate was concentrated under reduced pressure. The crude product was purified by normal phase chromatography (mobile phase: petroleum ether/ethyl acetate 20:1). Yield: 1.21 g (93% of theory).

LC/MS [Method 15]: $R_t$=1.78 min; MS (ESIpos): m/z=310 (M+H)$^+$, $^1$H-NMR (400 MHz, DMSO-d$_6$): δ [ppm]=8.00 (s, 1H), 7.69-7.62 (m, 2H), 7.56-7.30 (m, 2H).

$^{19}$F-NMR (376 MHz, DMSO-d$_6$): δ [ppm]=−118.03 (d).

Example 2.22A 2-(2-Bromo-4-chlorophenyl)-5-(difluoromethyl)-1,3,4-thiadiazole

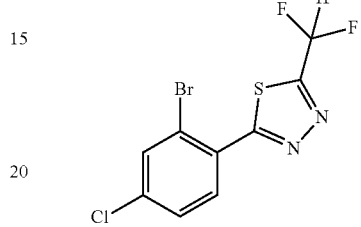

A mixture of 2.60 g (7.9 mmol) of 2-bromo-4-chloro-N'-(difluoroacetyl)benzohydrazide and 3.5 g (15.9 mmol, 2.0 eq.) of phosphorus pentasulfide in 100 ml toluene was heated at 130° C. for 2 h. After cooling to room temperature, the mixture was concentrated under reduced pressure. The residue was partitioned between 500 ml ethyl acetate and 500 ml water. The organic layer was separated, washed with 100 ml 0.78 mM aqueous sodium hypochlorite solution, 100 ml water and twice with 100 ml brine, dried over anhydrous sodium sulfate, filtered and concentrated under reduced pressure. The crude product was purified by flash chromatography on silica gel (eluent: petroleum ether-ethyl acetate 10:1). Yield: 1.28 g (49% of theory).

LC/MS [Method 15]: $R_t$=1.80 min; MS (ESIpos): m/z=327 (M+H)$^+$, $^1$H-NMR (400 MHz, DMSO-d$_6$): δ [ppm]=8.13-8.10 (m, 2H), 7.74-7.71 (m, 1H), 7.69 (t, 1H).

Example 2.23A 4-(2-Bromo-4-chlorophenyl)-1,1,1-trifluoro-4-hydroxybut-3-en-2-one (E/Z Mixture)

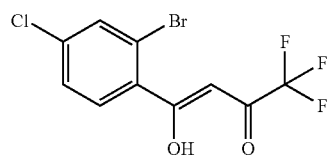 [SMILES: O=C(/C=C(\O)c1ccc(Cl)cc1Br)C(F)(F)F]

To a solution of 1.34 g (9.4 mmol, 1.1 equiv) of ethyl trifluoroacetate in 15 ml methyl tert-butyl ether was added 2.22 g (10.3 mmol, 1.2 equiv) of 25% sodium methoxide in methanol dropwise, and then a solution of 2.00 g (8.6 mmol) of 1-(2-bromo-4-chlorophenyl) ethanone in 5 ml methyl tert-butyl ether was added. After stirring for 15 h at room temperature, the mixture was diluted with 50 ml methyl tert-butyl ether, washed with saturated aqueous sodium bicarbonate solution (30 ml), water (30 ml) and brine (30 ml), dried over anhydrous sodium sulfate, filtered and evaporated under reduced pressure. Yield: 2.57 g (91% of theory).

LC/MS [Method 19]: $R_t$=1.09 min; MS (ESIpos): m/z=330 (M+H)$^+$.

Example 2.23B 3-(2-Bromo-4-chlorophenyl)-5-(trifluoromethyl)-1,2-oxazole

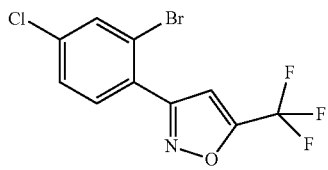 [SMILES: FC(F)(F)c1cc(-c2ccc(Cl)cc2Br)no1]

To a solution of 2.37 g (7.2 mmol) of 1-(2-bromo-4-chlorophenyl)-4,4,4-trifluorobutane-1,3-dione in 10 ml acetic acid was added 0.60 g (8.6 mmol, 1.2 equiv) of hydroxylamine hydrochloride. After stirring for 15 h at 90° C., the mixture was cooled to room temperature and concentrated under reduced pressure. The residue was purified by flash chromatography on silica gel (eluent: petroleum ether-ethyl acetate 20:1). Yield: 2.20 g (94% purity, 88% of theory).

$^1$H-NMR (300 MHz, DMSO-d$_6$): δ [ppm]=8.06 (s, 1H), 7.93 (s, 1H), 7.77-7.67 (m, 2H).

Example 2.24A

2-Bromo-4-chloro-N'-(trifluoroacetyl)benzohydrazide

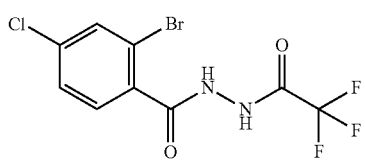 [SMILES: O=C(NNC(=O)C(F)(F)F)c1ccc(Cl)cc1Br]

To a solution of 5.00 g (20.0 mmol) of 2-bromo-4-chlorobenzohydrazide in dichloromethane (100 ml) was added 5.47 g (26.1 mmol) of trifluoroacetic anhydride at 0° C., followed by addition of 3.45 g (34.1 mmol) of triethylamine at the same temperature. After stirring for 22 hours at room temperature, the mixture was diluted with dichloromethane (300 ml), washed with saturated aqueous sodium bicarbonate solution (2×300 ml) and brine (2×300 ml), dried over anhydrous sodium sulfate, filtered and evaporated under reduced pressure to give 5.00 g (69% of theory) of the title compound.

LC/MS [Method 19]: $R_t$=0.94 min; MS (ESIpos): m/z=345 (M+H)$^+$.

$^1$H-NMR (400 MHz, DMSO-d$_6$): δ [ppm]=11.85 (brs, 1H), 10.84 (s, 1H), 7.89 (s, 1H), 7.62-7.59 (m, 1H), 7.49-7.46 (m, 1H).

$^{19}$F-NMR (376 MHz, DMSO-d$_6$): δ [ppm]=−73.73 (s, 3F).

Example 2.24B 2-(2-Bromo-4-chlorophenyl)-5-(trifluoromethyl)-1,3,4-thiadiazole

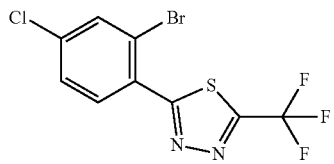 [SMILES: FC(F)(F)c1nnc(-c2ccc(Cl)cc2Br)s1]

A mixture of 2.00 g (5.8 mmol) of 2-bromo-4-chloro-N'-(trifluoroacetyl)benzohydrazide and 2.57 g (11.6 mmol) of phosphorus pentasulfide in toluene (100 ml) was heated at 130° C. for 2 h. After cooled to room temperature, the mixture was concentrated under reduced pressure. The residue was partitioned between ethyl acetate (500 ml) and water (500 ml). The organic layer was separated, washed with 0.78M sodium hypochlorite (200 ml), water (200 ml) and brine (2×200 ml), dried over anhydrous sodium sulfate, filtered and concentrated under reduced pressure. The crude product was purified by flash chromatography on silica gel (eluent: petroleum ether) to give 1.29 g (60% of theory) of the title compound.

LC/MS [Method 20]: $R_t$=1.37 min; MS (ESIpos): m/z=345 (M+H)$^+$.

$^1$H-NMR (400 MHz, DMSO-d$_6$): δ [ppm]=8.34-8.12 (m, 2H), 7.75-7.72 (m, 1H).

$^{19}$F-NMR (376 MHz, DMSO-d$_6$): δ [ppm]=−57.92 (s, 3F).

Example 2.25A

2-Amino-1-(2-bromo-4-chlorophenyl)ethanone hydrochloride

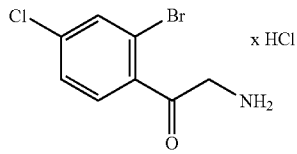 [SMILES: NCC(=O)c1ccc(Cl)cc1Br]

To a solution of 5.00 g (16.0 mmol, 1.0 equiv) of 2-bromo-1-(2-bromo-4-chlorophenyl)ethanone in chloroform (50 ml) was added 2.29 g (16.3 mmol, 1.02 equiv) of hexamethylenetetramine at room temperature. After stirred for 4 hours at room temperature, the solid was collected by filtration, washed with water (50 ml), dried in vacuo to give a solid, which was dissolved in methanol (50 ml), and then 20 ml of concentrated hydrochloric acid was added to the mixture and refluxed for 3 hours. After being cooled to room temperature, the reaction mixture was evaporated under reduced pressure to give 7.00 g of the title compound, which was used for next step directly without further purification.

LC-MS [Method 13]: $R_t$=0.71 min; MS (ESIpos): m/z=250 [M+H]$^+$ $^1$H-NMR (400 MHz, DMSO-d$_6$): δ [ppm]=8.43 (br s, 3H), 7.97-7.94 (m, 2H), 7.70-7.67 (m, 1H), 4.49 (s, 2H).

Example 2.25B

N-[2-(2-Bromo-4-chlorophenyl)-2-oxoethyl]-2,2-difluoroacetamide

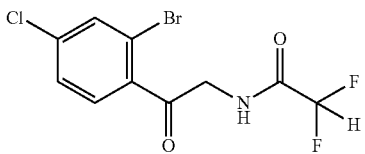 [SMILES: O=C(CNC(=O)C(F)F)c1ccc(Cl)cc1Br]

To a solution of 6.00 g (21.0 mmol, 1.0 equiv) of 2-amino-1-(2-bromo-4-chlorophenyl)ethanone hydrochloride in dichloromethane (200 ml) were added 4.76 g (27.3 mmol, 1.3 equiv) of difluoroacetic anhydride and 3.62 g (35.7 mmol, 1.7 equiv) of triethylamine at 0° C. After stirring for 22 hours at room temperature, the reaction mixture was diluted with dichloromethane (300 ml), washed with saturated sodium bicarbonate solution (2×300 ml) and brine (2×300 ml), dried over anhydrous sodium sulfate, filtered and concentrated under reduced pressure. The residue was purified by flash chromatography on silica gel (eluent: petroleum ether-ethyl acetate 3:1) to give the title compound. Yield: 3.00 g (95% purity, 41% of theory)

LC-MS [Method 13]: $R_t$=1.02 min; MS (ESIpos): m/z=327 [M+H]$^+$ $^1$H-NMR (400 MHz, DMSO-d$_6$): δ [ppm]=9.29 (brs, 1H), 7.91 (s, 1H), 7.79-7.75 (m, 1H), 7.64-7.61 (m, 1H), 6.34 (t, 1H), 4.53 (d, 2H).

Example 2.25C 5-(2-Bromo-4-chlorophenyl)-2-(difluoromethyl)-1,3-oxazole

To a solution of 3.00 g (9.2 mmol, 1.0 equiv) of N-[2-(2-bromo-4-chlorophenyl)-2-oxoethyl]-2,2-difluoroacetamide in chloroform (300 ml) was added 3.91 g (27.5 mmol, 3.0 equiv) of phosphorus pentoxide. The resulting mixture was heated for 24 hours at 60° C. After cooled to room temperature, the reaction mixture was diluted with water (500 ml) and extracted with ethyl acetate (500 ml). The aqueous layer was adjusted to pH=7 with sodium carbonate and extracted with ethyl acetate (2×500 ml). The combined organic layers were washed with brine (2×500 ml), dried over anhydrous sodium sulfate, filtered and concentrated under reduced pressure. The residue was purified by flash chromatography on silica gel (eluent: petroleum ether-ethyl acetate 50:1) to give the title compound. Yield: 1.21 g (42% of theory)

LC-MS [Method 15]: $R_t$=1.77 min; MS (ESIpos): m/z=310 [M+H]$^+$ $^1$H-NMR (400 MHz, DMSO-d$_6$): δ [ppm]=8.00-7.98 (m, 2H), 7.80-7.78 (m, 1H), 7.66-7.63 (m, 1H), 7.31 (t, 1H).

Example 2.26A 1-(2-Bromo-4-chlorophenyl)-4-(trifluoromethyl)-1H-1,2,3-triazole

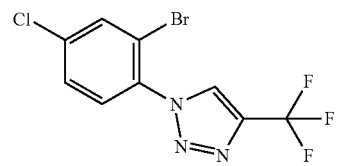 [SMILES: FC(F)(F)c1cn(-c2ccc(Cl)cc2Br)nn1]

(10.4 g, 44.7 mmol) of 1-azido-2-bromo-4-chlorobenzene was dissolved in acetonitrile (600 ml) in a 3-neck flask (equipped with an empty balloon to catch excess gas and avoid pressure build up: it however remained empty during the reaction) and (690 mg, 4.8 mmol) of copper(I)oxide was added. Trifluoropropyne (5 g cylinder) was bubbled gently through the solution for 10-15 minutes until the cylinder was empty. After capping of the flask and 3 days of stirring approximately 80% conversion to product was observed, another 1 g of gas from a second 5 g cylinder was added and the solution was stirred overnight. The solution was concentrated and the residue was filtered over a plug of silica with heptane/DCM 1:1. The eluted material was crystallized from heptane to give a first crop of 9.5 g, another 0.9 g precipitated from the mother liquor. The batches were combined. Yield: 10.4 g (71% of theory).

LC-MS [Method 10]: $R_t$=2.04 min; MS (ESIpos): m/z=328 [M+H]$^+$ $^1$H-NMR (400 MHz, DMSO-d$_6$): δ [ppm]=9.42 (s, 1H), 8.17 (d, 1H), 7.87-7.81 (m, 1H), 7.81-7.76 (m, 1H).

Example 3.1A 2-tert-Butoxyethyl trifluoromethanesulphonate

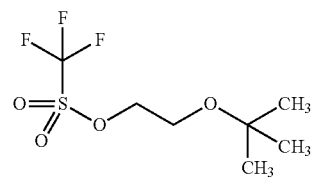

At −78° C., 473 mg (4.00 mmol) of 2-tert-butoxyethanol and 0.75 ml (4.40 mmol, 1.1 eq.) of trifluoromethanesulphonic anhydride in the presence of 0.61 ml (4.4 mmol, 1.1 eq.) of triethylamine were reacted according to General Method 7A. The crude product was reacted in the next step without further purification.

$^1$H-NMR (400 MHz, DMSO-d$_6$): δ [ppm]=4.38 (t, 2H), 3.57 (t, 2H), 1.19 (s, 9H).

Example 3.2A 2-(Trifluoromethoxy)ethyl trifluoromethanesulphonate

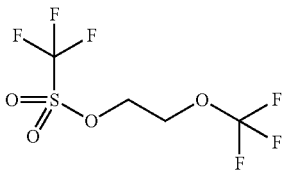 [SMILES: O=S(=O)(OCCOC(F)(F)F)C(F)(F)F]

At −78° C., 200 mg (1.54 mmol) of 2-(trifluoromethoxy)ethanol and 0.29 ml (1.69 mmol, 1.1 eq.) of trifluoromethanesulphonic anhydride in the presence of 0.24 ml (1.69 mmol, 1.1 eq.) of triethylamine were reacted according to General Method 7A. The crude product was reacted in the next step without further purification.

$^1$H-NMR (400 MHz, DMSO-$d_6$): δ [ppm]=4.59-4.52 (m, 2H), 4.41-4.35 (m, 2H).

Example 3.3A

2-[(Benzyloxy)methyl]tetrahydro-2H-pyran (Racemate)

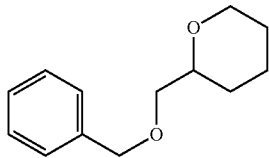 [SMILES: c1ccc(COCC2CCCCO2)cc1]

At 0° C., a solution of 25.0 g (215 mmol) of tetrahydro-2H-pyran-2-ylmethanol (racemate) in 500 ml of THF was slowly added dropwise to a suspension of 9.47 g (237 mmol, 60% in mineral oil) of sodium hydride in 500 ml of THF, and after the addition had ended, the mixture was stirred at 0° C. for another 30 min. 25.7 ml (215 mmol) of benzyl bromide were then added, and the mixture was stirred at 0° C. for another 30 min and at room temperature for another 1 h. The reaction was terminated by addition of 200 ml of saturated aqueous ammonium chloride solution, and the phases were separated. The aqueous phase was extracted twice with 200 ml of methyl tert-butyl ether. The combined organic phases were dried over magnesium sulphate and filtered, and the solvent was removed under reduced pressure. The crude product was purified by column chromatography (ethyl acetate/cyclohexane gradient, 340 g silica cartridge, flow rate 1000 ml/min), giving the title compound. Yield: 41.9 g (94% of theory)

LC/MS [Method 3]: $R_t$=2.18 min; MS (ESIpos): m/z=207 (M+H)$^+$, $^1$H-NMR (400 MHz, DMSO-$d_6$): δ [ppm]=7.37-7.25 (m, 5H), 4.47 (s, 2H), 3.87-3.81 (m, 1H), 3.47-3.28 (m, 4H), 1.80-1.72 (m, 1H), 1.58-1.37 (m, 4H), 1.25-1.13 (m, 1H).

Example 3.3B (S)-2-[(Benzyloxy)methyl]tetrahydro-2H-pyran

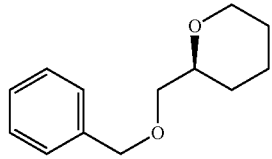 [SMILES: c1ccc(COC[C@@H]2CCCCO2)cc1]

Enantiomer separation of 41.9 g of the racemate from Example 3.3A gave [in addition to 16.7 g of the (R) enantiomer (enantiomer 1): chiral HPLC: $R_t$=5.28 min; 99% ee, purity 93%, optical rotation: $[α]_{589}^{20.0}$=+14.9° (c 0.43 g/100 cm$^3$, chloroform)] 17.0 g of the title compound Example 3.3B (enantiomer 2): chiral HPLC: $R_t$=7.36 min; 96% ee.

optical rotation: $[α]_{589}^{20.0}$=−13.9° (c 0.61 g/100 cm$^3$, chloroform)

Separating method: column: OD-H 5 μm 250 mm×20 mm; mobile phase: 95% isohexane, 5% 2-propanol; temperature: 25° C.; flow rate: 25 ml/min; UV detection: 210 nm.

Analysis: column: OD-H 5 μm 250 mm×4.6 mm; mobile phase: 95% isohexane, 5% 2-propanol; flow rate: 1 ml/min; UV detection: 220 nm.

Example 3.3C (2S)-Tetrahydro-2H-pyran-2-ylmethanol

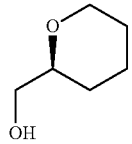

3.51 g (3.30 mmol) of palladium on carbon (10%) were added to a solution of 17.0 g (82.4 mmol) of (S)-2-[(benzyloxy)methyl]tetrahydro-2H-pyran (96% ee, purity 96%) in 120 ml of ethanol, and the mixture was hydrogenated at room temperature and under standard pressure overnight. Another 1.75 g (1.65 mmol) of palladium on carbon (10%) were then added, and the mixture was hydrogenated at room temperature for a further 72 h. Subsequently, the reaction mixture was filtered through Celite and the filtrate was concentrated. The residue was purified chromatographically (silica, dichloromethane/methanol gradient) and the product fractions were freed from the solvent at <25° C. and >50 mbar. Yield: 8.23 g (86% of theory)

optical rotation: $[α]_{589}^{20.0}$=+9.1° (c 0.36 g/100 cm$^3$, chloroform), cf. A. Aponick, B. Biannic, *Org. Lett.* 2011, 13, 1330-1333.

GC/MS [Method 7]: $R_t$=1.82 min; MS: m/z=116 (M)$^+$, $^1$H-NMR (400 MHz, DMSO-$d_6$): δ [ppm]=4.51 (t, 1H), 3.87-3.81 (m, 1H), 3.37-3.18 (m, 4H), 1.80-1.71 (m, 1H), 1.59-1.50 (m, 1H), 1.49-1.36 (m, 3H), 1.19-1.05 (m, 1H).

Example 3.3D (2S)-Tetrahydro-2H-pyran-2-ylmethyl trifluoromethanesulphonate

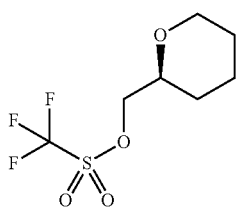 [SMILES: O=S(=O)(OC[C@@H]1CCCCO1)C(F)(F)F]

330 mg (2.84 mmol) of (2S)-tetrahydro-2H-pyran-2-ylmethanol and 0.57 ml (3.41 mmol, 1.2 eq.) of trifluoromethanesulphonic anhydride in the presence of 0.48 ml (3.41 mmol, 1.2 eq.) of triethylamine were reacted according to General Method 7A. The crude product was reacted in the next step without further purification.

$^1$H-NMR (400 MHz, DMSO-d$_6$): δ [ppm]=4.32 (dd, 1H), 4.18 (dd, 1H), 4.00-3.92 (m, 1H), 3.60-3.52 (m, 1H), 3.48-3.39 (m, 1H), 1.85-1.74 (m, 1H), 1.56-1.41 (m, 4H), 1.28-1.14 (m, 1H).

Example 3.4A (R)-2-[(Benzyloxy)methyl]tetrahydro-2H-pyran

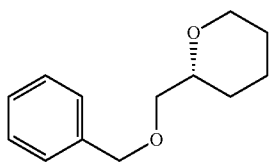 [SMILES: c1ccc(COC[C@H]2CCCCO2)cc1]

Enantiomer separation of 41.9 g of the racemate from Example 3.3A gave 16.7 g of the title compound Example 3.4A (enantiomer 1): chiral HPLC: R$_t$=5.28 min; 99% ee, purity 93%.

optical rotation: [α]$_{5892}^{20.0}$=+14.9° (c 0.43 g/100 cm$^3$, chloroform)

Separating method: column: OD-H 5 μm 250 mm×20 mm; mobile phase: 95% isohexane, 5% 2-propanol; temperature: 25° C.; flow rate: 25 ml/min; UV detection: 210 nm.

Analysis: column: OD-H 5 μm 250 mm×4.6 mm; mobile phase: 95% isohexane, 5% 2-propanol; flow rate: 1 ml/min; UV detection: 220 nm.

Example 3.4B (2R)-Tetrahydro-21H-pyran-2-ylmethanol

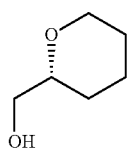

2.06 g (1.94 mmol) of palladium on carbon (10%) were added to a solution of 10.0 g (48.5 mmol) of (R)-2-[(benzyloxy)methyl]tetrahydro-2H-pyran (99% ee) in 70 ml of ethanol, and the mixture was hydrogenated at room temperature and under standard pressure overnight. Another 1.03 g (0.97 mmol) of palladium on carbon (10%) were then added, and the mixture was hydrogenated at room temperature for a further 72 h. Subsequently, the reaction mixture was filtered through Celite and the filtrate was concentrated. The residue was used in the next stage without further purification. Yield: 5.36 g (95% of theory)

$^1$H-NMR (400 MHz, DMSO-d$_6$): δ [ppm]=4.51 (t, 1H), 3.87-3.81 (m, 1H), 3.37-3.18 (m, 4H), 1.80-1.71 (m, 1H), 1.59-1.50 (m, 1H), 1.49-1.36 (m, 3H), 1.19-1.05 (m, 1H).

Example 3.4C (2R)-Tetrahydro-2H-pyran-2-ylmethyl trifluoromethanesulphonate

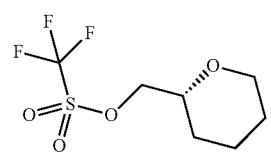 [SMILES: O=S(=O)(OC[C@H]1CCCCO1)C(F)(F)F]

2.50 g (21.5 mmol) of (2R)-tetrahydro-2H-pyran-2-ylmethanol and 3.98 ml (23.7 mmol, 1.1 eq.) of trifluoromethanesulphonic anhydride in the presence of 3.3 ml (23.7 mmol, 1.1 eq.) of triethylamine were reacted according to General Method 7A. The crude product was reacted in the next step without further purification. Yield: 5.4 g (99% of theory).

$^1$H-NMR (400 MHz, DMSO-d$_6$): δ [ppm]=4.32 (dd, 1H), 4.18 (dd, 1H), 4.00-3.92 (m, 1H), 3.60-3.52 (m, 1H), 3.48-3.39 (m, 1H), 1.85-1.74 (m, 1H), 1.56-1.41 (m, 4H), 1.28-1.14 (m, 1H).

Example 3.5A 1,4-Dioxan-2-ylmethyl trifluoromethanesulphonate (Racemate)

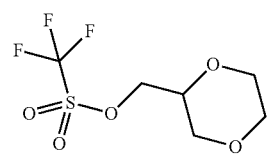 [SMILES: O=S(=O)(OCC1COCCO1)C(F)(F)F]

1.0 g (8.04 mmol) of 1,4-dioxan-2-ylmethanol and 1.42 ml (8.44 mmol, 1.05 eq.) of trifluoromethanesulphonic anhydride in the presence of 1.34 ml (9.65 mmol, 1.2 eq.) of triethylamine were reacted according to General Method 7A. The crude product was reacted in the next step without further purification.

GC/MS [Method 9]: R$_t$=2.91 min; MS: m/z=250 (M)$^+$.

Example 4.1A tert-Butyl (4-bromo-5-methoxy-2-oxopyridin-1(2H)-yl)acetate

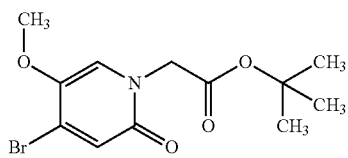 [SMILES: COc1cn(CC(=O)OC(C)(C)C)c(=O)cc1Br]

12.0 g (58.8 mmol) of 4-bromo-5-methoxypyridin-2(1H)-one [described in WO 2014/154794] and 12.2 g (88.2 mmol, 1.5 eq.) of potassium carbonate were initially charged in 267 ml of DMF, 10.6 ml (70.6 mmol, 1.2 eq.) of tert-butyl bromoacetate were added and the mixture was stirred at 50° C. for 80 min. The reaction mixture was then concentrated. 120 ml of water were added, the mixture was stirred for 5 min and filtered off with suction and the product was washed with water, suspended in acetonitrile and concentrated. The crude product was purified by normal phase chromatography (mobile phase: dichloromethane/methanol, 0-12%). Yield: 15.0 g (80% of theory).

LC/MS [Method 10]: $R_t$=1.49 min; MS (ESIpos): m/z=318 (M+H)$^+$, $^1$H-NMR (400 MHz, DMSO-$d_6$): δ [ppm]=7.53 (s, 1H), 6.85 (s, 1H), 4.53 (s, 2H), 3.69 (s, 3H), 1.42 (s, 9H).

Example 4.1B tert-Butyl 2-(4-bromo-5-methoxy-2-oxopyridin-1(2H)-yl)-4-methoxybutanoate (Racemate)

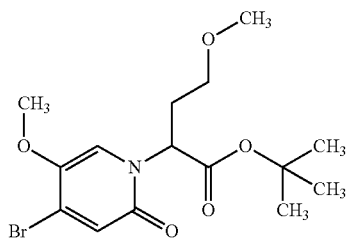 [SMILES: COCCC(C(=O)OC(C)(C)C)n1cc(OC)c(Br)cc1=O]

Under argon and at −70° C., 15 ml (1.0M in THF, 1.35 eq.) of bis(trimethylsilyl)lithium amide were added dropwise to a solution of 3.6 g (10.9 mmol) of tert-butyl (4-bromo-5-methoxy-2-oxopyridin-1(2H)-yl)acetate in 138 ml of tetrahydrofuran, and the mixture was stirred for 20 min. 1.93 ml (12.5 mmol, 1.15 eq.) of 2-methoxyethyl trifluoromethanesulphonate were added dropwise, and the mixture was stirred at −70° C. for 15 min and at RT for 1.5 h. The reaction mixture was cooled to −70° C. again, 4.9 ml (1.0M in THF, 0.45 eq.) of bis(trimethylsilyl)lithium amide were added dropwise followed, after 15 min, by 0.65 ml (4.2 mmol, 0.39 eq.) of 2-methoxyethyl trifluoromethanesulphonate, and the mixture was stirred at −70° C. for 15 min and at RT for 3 h. First 40 ml of saturated aqueous ammonium chloride solution and then 40 ml of water and 350 ml of ethyl acetate were added to the reaction mixture. After phase separation, the organic phase was washed with saturated aqueous sodium chloride solution, dried (sodium sulphate) and concentrated. The crude product was purified by normal phase chromatography (mobile phase: cyclohexane/ethyl acetate, 0-60%). Yield 3.09 g (95% pure, 72% of theory)

LC/MS [Method 1]: $R_t$=0.94 min; MS (ESIpos): m/z=376 (M+H)$^+$, $^1$H-NMR (400 MHz, DMSO-$d_6$): δ [ppm]=7.36 (s, 1H), 6.85 (s, 1H), 5.04 (dd, 1H), 3.71 (s, 3H), 3.39-3.29 (m, 1H), 3.20-3.03 (m, 4H), 2.35-2.20 (m, 2H), 1.38 (s, 9H).

Example 41C tert-Butyl 4-methoxy-2-[5-methoxy-2-oxo-4-(4,4,5,5-tetramethyl-1,3,2-dioxaborolan-2-yl)pyridin-1(2H)-yl]butanoate (Racemate)

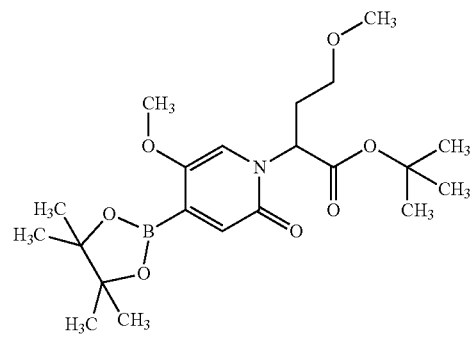 [SMILES: COCCC(C(=O)OC(C)(C)C)n1cc(OC)c(B2OC(C)(C)C(C)(C)O2)cc1=O]

Under argon, 6.00 g (15.5 mmol) of tert-butyl 2-(4-bromo-5-methoxy-2-oxopyridin-1(2H)-yl)-4-methoxybutanoate (racemate), 4.32 g (17.0 mmol, 1.1 eq.) of bis (pinacolato)diboron and 4.55 g (46.4 mmol, 3 eq.) of potassium acetate were initially charged in 84 ml of dioxane, 379 mg (0.464 mmol, 0.03 eq) of [1,1-bis(diphenylphosphino)ferrocene]dichloropalladium-dichloromethane complex were added and the mixture was stirred at 80° C. for 6 h. The reaction mixture was cooled and filtered through kieselguhr, and the filter cake was washed with dioxane. The filtrate was concentrated and dried at 40° C. under high vacuum. Yield: 9.90 g (purity 66%, quant.).

$^1$H-NMR (400 MHz, DMSO-$d_6$): δ [ppm]=7.09 (s, 1H), 6.49 (s, 1H), 5.00 (dd, 1H), 3.60 (s, 3H), 3.36-3.27 (m, 3H), 3.17 (s, 3H), 3.14-3.05 (m, 1H), 2.30-2.21 (m, 2H), 1.37 (s, 9H), 1.27 (s, 12H).

Example 4.2A tert-Butyl 2-(4-bromo-5-methoxy-2-oxopyridin-1(2H)-yl)-4-tert-butoxybutanoate (Racemate)

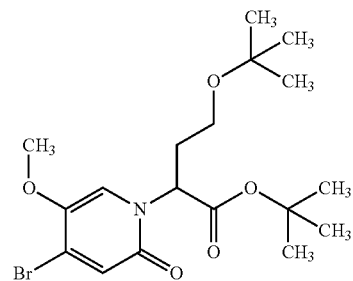 [SMILES: COc1cn(C(CCOC(C)(C)C)C(=O)OC(C)(C)C)c(=O)cc1Br]

Under argon and at −70° C., 22.9 ml (1.0M in THF, 1.35 eq.) of bis(trimethylsilyl)lithium amide were added dropwise to a solution of 5.4 g (16.9 mmol) of tert-butyl (4-bromo-5-methoxy-2-oxopyridin-1(2H)-yl)acetate in 250 ml of tetrahydrofuran, and the mixture was stirred for 20 min. 5.3 g (purity 92%, 19.5 mmol, 1.15 eq.) of 2-tert-butoxyethyl trifluoromethanesulphonate were added dropwise, and the mixture was stirred at −70° C. for 15 min and at RT for 1.5 h. First 100 ml of saturated aqueous ammonium chloride solution and then 100 ml of water and 300 ml of ethyl acetate were added to the reaction mixture. After phase separation, the organic phase was washed with saturated aqueous sodium chloride solution, dried (sodium sulphate) and concentrated. The crude product was purified by normal phase chromatography (mobile phase: cyclohexane/ethyl acetate, 0-50%). Yield: 4.73 g (65% of theory)

LC/MS [Method 1]: $R_t$=1.14 min; MS (ESIpos): m/z=418 (M+H)$^+$, $^1$H-NMR (400 MHz, DMSO-d$_6$): δ [ppm]=7.36 (s, 1H), 6.83 (s, 1H), 5.08 (dd, 1H), 3.72 (s, 3H), 3.37-3.22 (m, 1H), 3.15-3.06 (m, 1H), 2.37-2.15 (m, 2H), 1.38 (s, 9H), 1.04 (s, 9H).

Example 4.2B tert-Butyl 4-tert-butoxy-2-[5-methoxy-2-oxo-4-(4,4,5,5-tetramethyl-1,3,2-dioxaborolan-2-yl)pyridin-1(2H)-yl]butanoate (Racemate)

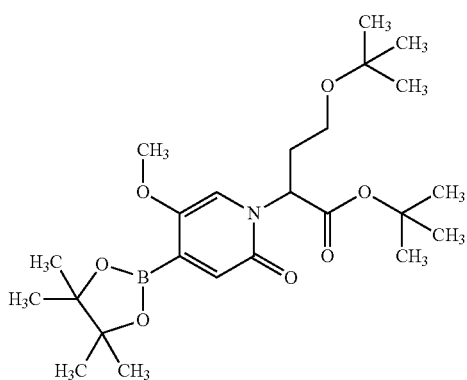 [SMILES: COc1cn(C(CCOC(C)(C)C)C(=O)OC(C)(C)C)c(=O)cc1B1OC(C)(C)C(C)(C)O1]

Under argon, 4.7 g (11.3 mmol) of tert-butyl 2-(4-bromo-5-methoxy-2-oxopyridin-1(2H)-yl)-4-tert-butoxybutanoate (racemate), 3.15 g (12.4 mmol, 1.1 eq.) of bis(pinacolato)diboron and 3.32 g (33.9 mmol, 3 eq.) of potassium acetate were initially charged in 110 ml of dioxane, 277 mg (0.339 mmol, 0.03 eq) of [1,1-bis(diphenylphosphino)ferrocene]dichloropalladium-dichloromethane complex were added and the mixture was stirred at 80° C. for 16 h. The reaction mixture was cooled and filtered through kieselguhr, and the filter cake was washed with dichloromethane and acetonitrile. The filtrate was concentrated and dried at 40° C. under high vacuum. Yield: 7.68 g (purity 68%, quant.).

$^1$H-NMR (400 MHz, DMSO-d$_6$): δ [ppm]=7.08 (s, 1H), 6.48 (s, 1H), 5.03 (dd, 1H), 3.60 (s, 3H), 3.35-3.25 (m, 1H), 3.12-3.04 (m, 1H), 2.31-2.13 (m, 2H), 1.37 (s, 9H), 1.26 (s, 12H), 1.05 (s, 9H).

Example 4.3A tert-Butyl 2-(4-bromo-5-methoxy-2-oxopyridin-1(2H)-yl)-3-(1,4-dioxan-2-yl)propanoate (Diastereomer Mixture)

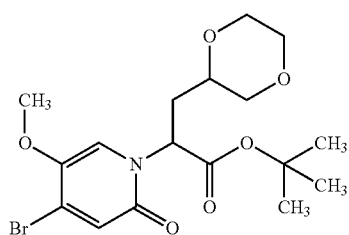

Under argon and at −70° C., 6.7 ml (1.0M in THF, 1.35 eq.) of bis(trimethylsilyl)lithium amide were added dropwise to a solution of 1.64 g (4.95 mmol) of tert-butyl (4-bromo-5-methoxy-2-oxopyridin-1(2H)-yl)acetate in 63 ml of tetrahydrofuran, and the mixture was stirred for 20 min. 1.5 g (5.7 mmol, 1.15 eq.) of 1,4-dioxan-2-ylmethyl trifluoromethanesulphonate were added dropwise, and the mixture was stirred at −70° C. for 15 min and at RT for 1.5 h. First 30 ml of saturated aqueous ammonium chloride solution and then 30 ml of water and 150 ml of ethyl acetate were added to the reaction mixture. After phase separation, the organic phase was washed with saturated aqueous sodium chloride solution, dried (sodium sulphate) and concentrated. The crude product was purified by normal phase chromatography (mobile phase: cyclohexane/ethyl acetate, 0-65%). Yield: 1.59 g (73% of theory)

LC/MS [Method 10]: $R_t$=1.64 min; MS (ESIpos): m/z=420 (M+H)$^+$.

Example 4.3B tert-Butyl 3-(1,4-dioxan-2-yl)-2-[5-methoxy-2-oxo-4-(4,4,5,5-tetramethyl-1,3,2-dioxaborolan-2-yl)pyridin-1(2H)-yl]propanoate (Diastereomer Mixture)

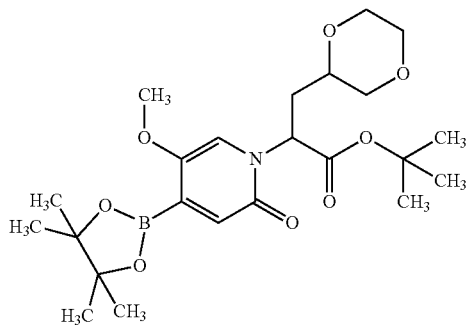 [SMILES: COc1cn(C(CC2COCCO2)C(=O)OC(C)(C)C)c(=O)cc1B1OC(C)(C)C(C)(C)O1]

Under argon, 560 mg (1.3 mmol) of tert-butyl 2-(4-bromo-5-methoxy-2-oxopyridin-1(2H)-yl)-3-(1,4-dioxan-2-yl)propanoate (diastereomer mixture), 366 mg (1.44 mmol, 1.1 eq.) of bis(pinacolato)diboron and 386 mg (3.9 mmol, 3 eq.) of potassium acetate were initially charged in 13.6 ml of dioxane, 32 mg (39 μmol, 0.03 eq) of [1,1-bis(diphenylphosphino)ferrocene]dichloropalladium-dichloromethane complex were added and the mixture was stirred at 80° C.

for 4.5 h. The reaction mixture was cooled and filtered through kieselguhr, and the filter cake was washed with dioxane. The filtrate was concentrated and dried at 40° C. under high vacuum. The crude product was used for the next step without further purification. Yield: 1.13 g (53% purity, 98% of theory).

Example 4.4A tert-Butyl 2-(4-bromo-5-methoxy-2-oxopyridin-1(2H)-yl)-3-[(2S)-tetrahydro-2H-pyran-2-yl]propanoate (Diastereomer Mixture)

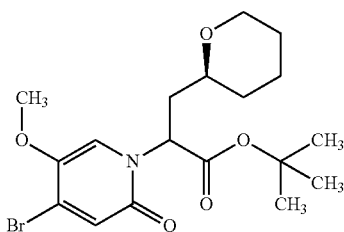 [SMILES: COc1cn(C(C[C@@H]2CCCCO2)C(=O)OC(C)(C)C)c(=O)cc1Br]

Under argon and at −70° C., 7.4 ml (1.0M in THF, 1.35 eq.) of bis(trimethylsilyl)lithium amide were added dropwise to a solution of 1.75 g (5.50 mmol) of tert-butyl (4-bromo-5-methoxy-2-oxopyridin-1(2H)-yl)acetate in 80 ml of tetrahydrofuran, and the mixture was stirred for 20 min. 1.62 g (6.33 mmol, 1.15 eq.) of (2S)-tetrahydro-2H-pyran-2-ylmethyl trifluoromethanesulphonate were added dropwise, and the mixture was stirred at −70° C. for 15 min and at RT for 1.5 h. First 30 ml of saturated aqueous ammonium chloride solution and then 30 ml of water and 100 ml of ethyl acetate were added to the reaction mixture. After phase separation, the organic phase was washed with saturated aqueous sodium chloride solution, dried (sodium sulphate) and concentrated. The crude product was purified by normal phase chromatography (mobile phase: cyclohexane/ethyl acetate, 20-35%). Yield 1.77 g (94% pure, 72% of theory)

LC/MS [Method 1]: $R_t$=1.04 min; MS (ESIpos): m/z=416 (M+H)⁺.

Example 44B tert-Butyl 2-[5-methoxy-2-oxo-4-(4,4,5,5-tetramethyl-1,3,2-dioxaborolan-2-yl)pyridin-1(2H)-yl]-3-[(2S)-tetrahydro-2H-pyran-2-yl]propanoate (Diastereomer Mixture)

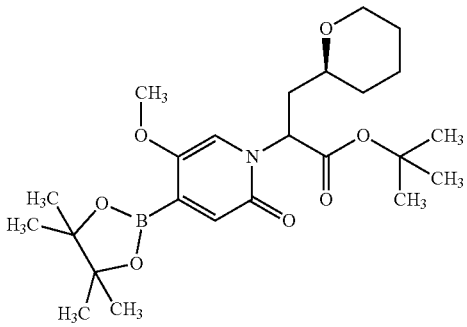 [SMILES: COc1cn(C(C[C@@H]2CCCCO2)C(=O)OC(C)(C)C)c(=O)cc1B1OC(C)(C)C(C)(C)O1]

Under argon, 1.77 g (3.98 mmol, purity 94%) of tert-butyl 2-(4-bromo-5-methoxy-2-oxopyridin-1(2H)-yl)-3-[(2S)-tetrahydro-2H-pyran-2-yl]propanoate (diastereomer mixture), 1.11 g (4.37 mmol, 1.1 eq.) of bis(pinacolato)diboron and 1.17 g (11.9 mmol, 3 eq.) of potassium acetate were initially charged in 40 ml of dioxane, 97.4 mg (119 μmol, 0.03 eq) of [1,1-bis(diphenylphosphino)ferrocene]dichloropalladium-dichloromethane complex were added and the mixture was stirred at 80° C. for 18 h. The reaction mixture was cooled and filtered through kieselguhr, and the filter cake was washed with dioxane. The filtrate was concentrated and dried at 40° C. under high vacuum. The crude product was used for the next step without further purification. Yield: 2.74 g (67% purity, 100% of theory).

Example 4.5A tert-Butyl 2-bromopentanoate (Racemate)

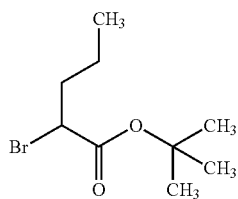

2-Bromopentanoic acid (3.00 g, 16.6 mmol) was dissolved in tert-butyl acetate (56 ml, 410 mmol), and perchloric acid (71 μl, purity 70%, 830 μmol) was added at RT. The reaction mixture was stirred at RT for 16 hours. 75 ml of water were then added. The organic phase was separated off and washed with 50 ml of a 5% strength aqueous sodium carbonate solution and 20 ml of water. The organic phase was then dried over sodium sulphate and concentrated under reduced pressure. The crude product was used for the next step without further purification. Yield: 3.40 g (94% pure, 81% of theory).

LC/MS [Method 9]: $R_t$=2.89 min; MS (EIpos): m/z=221 [M-15]⁺.

Example 4.5B tert-Butyl 2-(4-bromo-5-methoxy-2-oxopyridin-1(2H)-yl)pentanoate (Racemate)

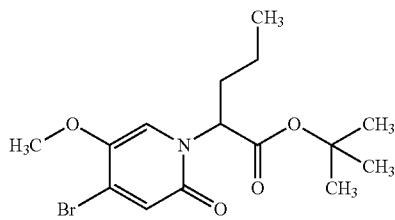 [SMILES: CCCC(C(=O)OC(C)(C)C)n1cc(OC)c(Br)cc1=O]

Under argon and at RT, (3.28 g, 23.7 mmol) of potassium carbonate and tert-butyl 2-bromopentanoate (racemate) (5.00 g, purity 90%, 19.0 mmol) were added to a solution of 4-bromo-5-methoxypyridin-2(1H)-one (3.40 g, purity 95%, 15.8 mmol) [described in WO 2014/154794] in 70 ml of dimethylformamide, and the mixture was then stirred at 50° C. for 70 min. After removal of the dimethylformamide and addition of 120 ml of water and 120 ml of ethyl acetate and phase separation, the organic phase was washed with water and with saturated aqueous sodium chloride solution, dried (sodium sulphate), filtered and concentrated under reduced pressure. The crude product was then purified by normal phase chromatography (cyclohexane/ethyl acetate gradient 0-50%). Yield: 3.10 g (53% of theory).

LC/MS [Method 10]: $R_t$=1.93 min; MS (ESIpos): m/z=360 [M+H]$^+$, $^1$H-NMR (400 MHz, DMSO-d$_6$): δ [ppm]=7.36 (s, 1H), 6.85 (s, 1H), 5.05 (dd, 1H), 3.72 (s, 3H), 2.13-1.94 (m, 2H), 1.38 (s, 9H), 1.27-1.09 (m, 2H), 0.86 (t, 3H).

Example 4.5C tert-Butyl 2-[5-methoxy-2-oxo-4-(4,4,5,5-tetramethyl-1,3,2-dioxaborolan-2-yl)pyridin-1(2H)-yl]pentanoate (Racemate)

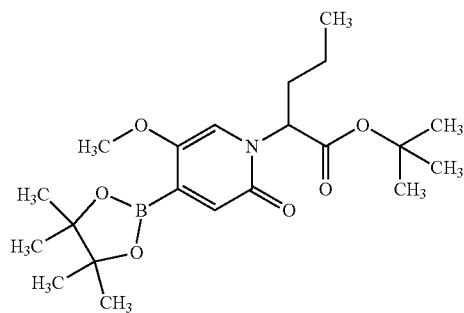 [SMILES: CCCC(C(=O)OC(C)(C)C)n1cc(OC)c(B2OC(C)(C)C(C)(C)O2)cc1=O]

Under argon, 1.55 g (4.22 mmol) of tert-butyl 2-(4-bromo-5-methoxy-2-oxopyridin-1(2H)-yl)pentanoate (racemate), 1.18 g (4.64 mmol, 1.1 eq.) of bis(pinacolato)diboron and 1.24 g (12.7 mmol, 3 eq.) of potassium acetate were initially charged in 42 ml of dioxane, 207 mg (0.253 mmol, 0.03 eq) of [1,1-bis(diphenylphosphino)ferrocene]dichloropalladium-dichloromethane complex were added and the mixture was stirred at 80° C. for 16 h. The reaction mixture was cooled and filtered through kieselguhr, and the filter cake was washed with dioxane. The filtrate was concentrated and dried at 40° C. under high vacuum. Yield: 3.02 g (57% purity, 100% of theory). The crude product was used for the next step without further purification.

Example 4.6A tert-Butyl 2-bromohexanoate (Racemate)

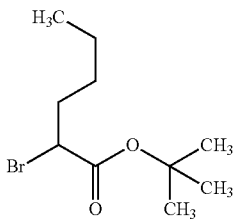

2-Bromohexanoic acid (2.9 ml, 21 mmol) was dissolved in tert-butyl acetate (69 ml, 510 mmol), and perchloric acid (88 µl, purity 70%, 1.0 mmol) was added at RT. The reaction mixture was stirred at RT for 16 hours. 100 ml of water were then added. The organic phase was separated off and washed with 70 ml of a 5% strength aqueous sodium carbonate solution and 20 ml of water. The organic phase was then dried over sodium sulphate and concentrated under reduced pressure. The crude product was used for the next step without further purification. Yield: 5.22 g (95% pure, 96% of theory).

$^1$H-NMR (400 MHz, DMSO-d$_6$): δ [ppm]=4.35 (t, 1H), 2.00-1.89 (m, 1H), 1.88-1.78 (m, 1H), 1.43 (s, 9H), 1.38-1.22 (m, 4H), 0.89-0.84 (m, 3H).

Example 4.6B tert-Butyl 2-(4-bromo-5-methoxy-2-oxopyridin-1(2H)-yl)hexanoate (Racemate)

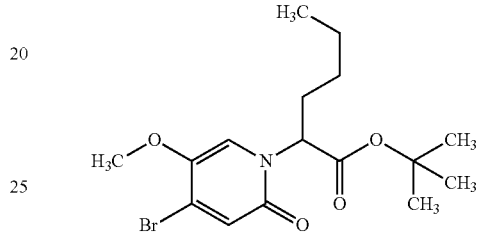

Under argon and at RT, (196 mg, 60% in mineral oil, 4.89 mmol) of sodium hydride were added to a solution of 4-bromo-5-methoxypyridin-2(1H)-one (1.00 g, purity 95%, 4.66 mmol) [described in WO 2014/154794] in 2.4 ml of dimethylformamide and 9.4 ml of 1,2-dimethoxyethane, and the mixture was stirred for 5 min. (809 mg, 9.31 mmol) of lithium bromide were then added and the reaction mixture was treated in an ultrasonic bath for 10 min. A solution of (1.72 g, purity 95%, 6.52 mmol) tert-butyl 2-bromohexanoate (racemate) in 1.8 ml of 1,2-dimethoxyethane was then added dropwise, and the mixture was stirred at 65° C. for 4 hours. After cooling, the dimethylformamide was removed under reduced pressure and the residue was then purified by normal phase chromatography (cyclohexane/ethyl acetate gradient 20-50%). Yield: 1.25 g (72% of theory)

LC/MS [Method 1]: $R_t$=1.08 min; MS (ESIpos): m/z=374 [M+H]$^+$.

Example 4.6.C tert-Butyl 2-[5-methoxy-2-oxo-4-(4,4,5,5-tetramethyl-1,3,2-dioxaborolan-2-yl)pyridin-1(2H)-yl]hexanoate (Racemate)

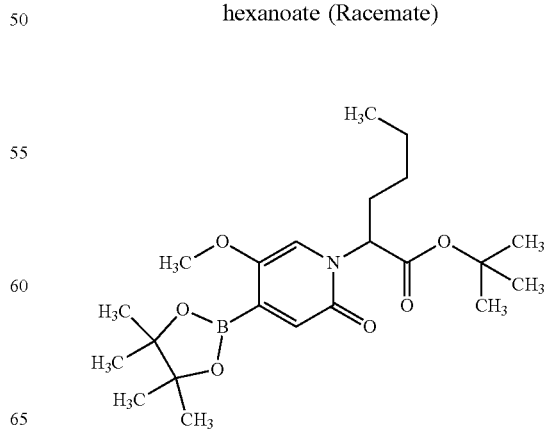

Under argon, 600 mg (1.60 mmol) of tert-butyl 2-(4-bromo-5-methoxy-2-oxopyridin-1(2H)-yl)hexanoate (racemate), 448 mg (1.76 mmol, 1.1 eq.) of bis(pinacolato)diboron and 472 mg (4.81 mmol, 3 eq.) of potassium acetate were initially charged in 16 ml of dioxane, 78.5 mg (96.2 µmol, 0.06 eq) of [1,1-bis(diphenylphosphino)ferrocene]dichloropalladium-dichloromethane complex were added and the mixture was stirred at 80° C. for 16 h. The reaction mixture was cooled and filtered through kieselguhr, and the filter cake was washed with dioxane. The filtrate was concentrated and dried at 40° C. under high vacuum. Yield: 1.16 g (57% purity, 98% of theory). The crude product was used for the next step without further purification.

Example 4.7A tert-Butyl 2-(4-bromo-5-methoxy-2-oxopyridin-1(2H)-yl)butanoate (Racemate)

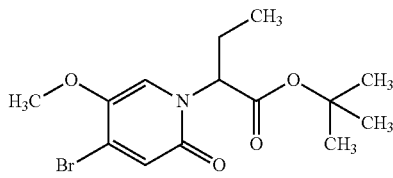 [SMILES: CCC(C(=O)OC(C)(C)C)n1cc(OC)c(Br)cc1=O]

Under argon and at −78° C., 21.22 ml (1.0M in THF, 1.35 eq.) of bis(trimethylsilyl)lithium amide were added dropwise to a solution of 5.00 g (15.72 mmol) of tert-butyl (4-bromo-5-methoxy-2-oxopyridin-1(2H)-yl)acetate in 295 ml of tetrahydrofuran, and the mixture was stirred for 15 min. 2.14 ml (16.50 mmol, 1.05 eq.) of ethyl trifluoromethanesulphonate were added dropwise, and the mixture was stirred at −70° C. for 15 min and at RT overnight. First, 30 ml of saturated aqueous ammonium chloride solution were added, and the reaction mixture was subsequently extracted twice with in each case 20 ml of tert-butyl methyl ether. The collected organic phases were dried over sodium sulphate, filtered and concentrated. The residue was purified by normal phase chromatography (mobile phase: cyclohexane/ethyl acetate gradient). Yield: 3.26 g (60% of theory)

LC/MS [Method 1]: $R_t$=0.99 min; MS (ESIpos): m/z=346 (M+H)$^+$.

Example 4.7B tert-Butyl 2-[5-methoxy-2-oxo-4-(4,4,5,5-tetramethyl-1,3,2-dioxaborolan-2-yl)pyridin-1(2H)-yl]butanoate (Racemate)

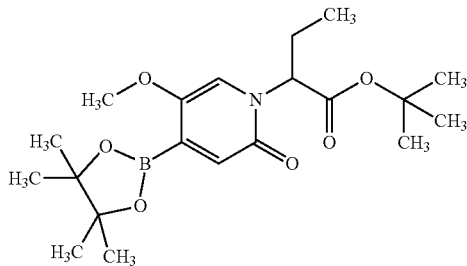 [SMILES: CCC(C(=O)OC(C)(C)C)n1cc(OC)c(B2OC(C)(C)C(C)(C)O2)cc1=O]

Under argon, 5.00 g (14.4 mmol) of tert-butyl 2-(4-bromo-5-methoxy-2-oxopyridin-1(2H)-yl)butanoate (racemate), 4.03 g (15.9 mmol) of bis(pinacolato)diboron and 4.25 g (43.32 mmol) of potassium acetate were initially charged in 105 ml of dioxane, 354 mg (0.433 mmol) of [1,1-bis(diphenylphosphino)ferrocene]dichloropalladium-dichloromethane complex were added and the mixture was stirred at 80° C. for 1.5 h. The reaction mixture was cooled and filtered through kieselguhr, and the filter cake was washed with ethyl acetate. The filtrate was concentrated and dried under high vacuum. Yield: 9.69 g (purity 50%, 58% of theory). The product was used without further purification.

LC/MS [Method 10]: $R_t$=1.24 min; MS (ESIpos): m/z=312 (M+H)$^+$[boronic acid fragment].

Example 4.8A tert-Butyl (2E)-2-(4-bromo-5-methoxy-2-oxopyridin-1(2H)-yl)-3-cyclobutylacrylate (Racemate)

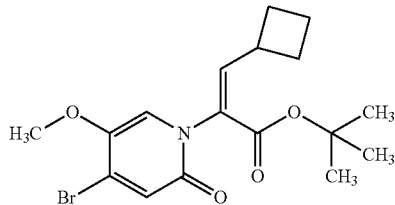 [SMILES: COc1cn(/C(=C/C2CCC2)C(=O)OC(C)(C)C)c(=O)cc1Br]

3.00 g (9.43 mmol) of tert-butyl (4-bromo-5-methoxy-2-oxopyridin-1(2H)-yl)acetate were initially charged in 60.0 ml of THF, the mixture was cooled to −78° C. and 13.20 ml (13.20 mmol) of bis(trimethylsilyl)lithium amide (1M in THF) were then added dropwise at −78° C. The reaction mixture was stirred at −78° C. for 15 min and then brought to RT and stirred at RT overnight. 180 ml of saturated aqueous ammonium chloride solution were added and the reaction mixture was then extracted three times with ethyl acetate. The collected organic phases were washed with saturated aqueous sodium chloride solution, dried over magnesium sulphate, filtered and concentrated. The residue was purified by normal phase chromatography (mobile phase: cyclohexane/ethyl acetate gradient). Yield: 2.27 g (62% of theory).

LC/MS [Method 10]: $R_t$=1.95 min; MS (ESIpos): m/z=384 (M+H)$^+$.

$^1$H-NMR (400 MHz, DMSO-d$_6$): δ [ppm]=7.15 (s, 1H), 6.98 (d, 1H), 6.88 (s, 1H), 3.68 (s, 3H), 3.02-2.90 (m, 1H), 2.15-1.70 (m, 6H), 1.41 (s, 9H).

Example 4.8B tert-Butyl 2-(4-bromo-5-methoxy-2-oxopyridin-1(2H)-yl)-3-cyclobutylpropanoate (Racemate)

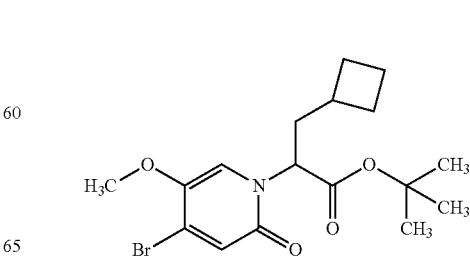

At RT, 5.93 ml of a solution of 1,2-phenylenebis(diphenylphosphine)-hydridocopper complex (1:1) in toluene ["Hot Stryker's" reagent solution, prepared analogously to B. A. Baker et al. *Org. Lett.* 2008, 10, 289-292], were added to 318 mg (0.83 mmol) of tert-butyl (2E)-2-(4-bromo-5-methoxy-2-oxopyridin-1(2H)-yl)-3-cyclobutylacrylate, and the reaction mixture was stirred at RT for 1 h. Saturated aqueous ammonium chloride solution was then added to the mixture, the phases were separated and the aqueous phase was extracted three times with ethyl acetate. The collected organic phases were dried over magnesium sulphate, filtered and concentrated. The residue was purified by normal phase chromatography (mobile phase: cyclohexane/ethyl acetate gradient). Yield: 271 mg (85% of theory).

LC/MS [Method 1]: $R_t$=1.16 min; MS (ESIpos): m/z=386 (M+H)$^+$.

$^1$H-NMR (400 MHz, DMSO-d$_6$): δ [ppm]=7.35 (s, 1H), 6.84 (s, 1H), 5.03-4.88 (m, 1H), 3.72 (s, 3H), 2.29-2.16 (m, 1H), 2.16-2.01 (m, 2H), 1.99-1.88 (m, 1H), 1.84-1.58 (m, 4H), 1.56-1.44 (m, 1H), 1.38 (s, 9H).

Example 4.8C

[1-(1-tert-Butoxy-3-cyclobutyl-1-oxopropan-2-yl)-5-methoxy-2-oxo-1,2-dihydropyridin-4-yl]boric acid (Racemate)

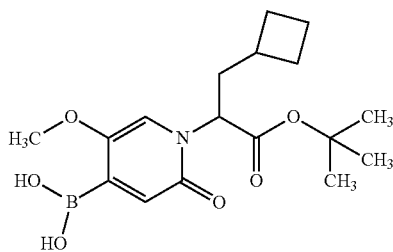 [SMILES: COc1cn(C(CC2CCC2)C(=O)OC(C)(C)C)c(=O)cc1B(O)O]

Under argon, 1.00 g (2.59 mmol) of tert-butyl 2-(4-bromo-5-methoxy-2-oxopyridin-1(2H)-yl)-3-cyclobutylpropanoate (racemate), 723 mg (2.85 mmol) of bis(pinacolato)diboron and 762 mg (7.77 mmol) of potassium acetate were initially charged in 27 ml of dioxane, 63.4 mg (0.078 mmol) of [1,1-bis(diphenylphosphino)ferrocene]dichloropalladium-dichloromethane complex were added and the mixture was stirred at 80° C. for 2 h. The reaction mixture was cooled and filtered through kieselguhr, and the filter cake was washed with dichloromethane and acetonitrile. The filtrate was concentrated and dried under high vacuum. Yield: 1.77 g (purity 51%, quant.). The product was used without further purification.

LC/MS [Method 10]: $R_t$=1.56 min; MS (ESIpos): m/z=352 (M+H)$^+$.

Example 4.9A 2-(4-Bromo-5-methoxy-2-oxopyridin-1(2H)-yl)propanoic acid (Racemate)

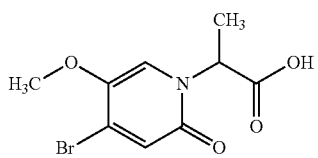

500 mg (2.45 mmol) of 4-bromo-5-methoxypyridin-2 (1H)-one [described in WO 2014/154794], 289 mg (2.57 mmol) of potassium tert-butoxide and 836 mg (4.90 mmol) of magnesium-di-tert-butoxide were initially charged in 10.0 ml of THF, and the mixture was stirred at RT for 10 min. At 0° C., 375 mg (2.45 mmol) of 2-bromopropanoic acid were then added dropwise and the reaction mixture was stirred at RT for 1 h and at 50° C. for 2 days. The mixture was acidified by addition of 4M hydrochloric acid and diluted with 20 ml of ethyl acetate and 20 ml of water. The organic phase was separated off and the aqueous phase was re-extracted with 20 ml of ethyl acetate. The collected organic phases were dried over sodium sulphate, filtered and concentrated. The residue was purified by preparative RP-HPLC (water/acetonitrile gradient). During concentration of the product-containing fractions, crystals formed which were filtered off, washed with water and then dried under reduced pressure at 40° C. Yield: 188 mg (28% of theory).

LC/MS [Method 1]: $R_t$=0.52 min; MS (ESIpos): m/z=276 (M+H)$^+$.

$^1$H-NMR (400 MHz, DMSO-d$_6$): δ [ppm]=12.93 (s, 1H), 7.43 (s, 1H), 6.83 (s, 1H), 5.16-5.05 (m, 1H), 3.73 (s, 3H), 1.56 (d, 3H).

Example 4.9B

Methyl 2-(4-bromo-5-methoxy-2-oxopyridin-1(2H)-yl)propanoate (Racemate)

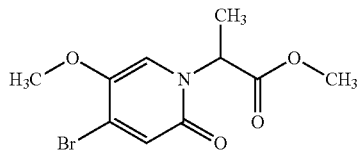

236 mg (0.86 mmol) of 2-(4-bromo-5-methoxy-2-oxopyridin-1(2H)-yl)propanoic acid (racemate) were initially charged in a mixture of 6.00 ml of toluene and 3.00 ml of methanol. 0.86 ml of (diazomethyl)(trimethyl)silane (2.0 M in diethyl ether) was then added, and the reaction mixture was stirred at RT for 30 min. The mixture was then concentrated and the residue was purified by flash silica gel chromatography (cyclohexane/ethyl acetate mixture). Yield: 210 mg (85% of theory).

LC/MS [Method 10]: $R_t$=1.14 min; MS (ESIpos): m/z=290 (M+H)$^+$.

$^1$H-NMR (400 MHz, DMSO-d$_6$): δ [ppm]=7.47 (s, 1H), 6.85 (s, 1H), 5.16-5.06 (m, 1H), 3.73 (s, 3H), 3.63 (s, 3H), 1.55 (d, 3H).

Example 4.9C

Methyl 2-[5-methoxy-2-oxo-4-(4,4,5,5-tetramethyl-1,3,2-dioxaborolan-2-yl)pyridin-1(2H)-yl]propanoate

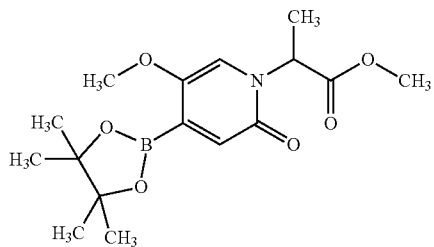

Under argon, 210.0 mg (0.72 mmol) of methyl 4-(4-bromo-5-methoxy-2-oxopyridin-1(2H)-yl)propanoate (racemate), 201.2 mg (0.80 mmol) of bis(pinacolato)diboron and 213.2 mg (2.17 mmol) of potassium acetate were initially charged in 6.91 ml of dioxane, 17.7 mg (0.022 mmol) of [1,1-bis(diphenylphosphino)ferrocene]dichloropalladium-dichloromethane complex were added and the mixture was stirred at 80° C. for 4 h. The reaction mixture was cooled and filtered through kieselguhr, and the filter cake was washed with dichloromethane and acetonitrile. The filtrate was concentrated and dried under high vacuum. Yield: 399 mg (purity 61%, quant.). The crude product was used without further purification.

LC/MS [Method 10]: $R_t$=0.95 min; MS (ESIpos): m/z=256 (M+H)$^+$ [boronic acid fragment].

Example 4.10A tert-Butyl [5-methoxy-2-oxo-4-(4,4,5,5-tetramethyl-1,3,2-dioxaborolan-2-yl)pyridin-1(2H)-yl]acetate

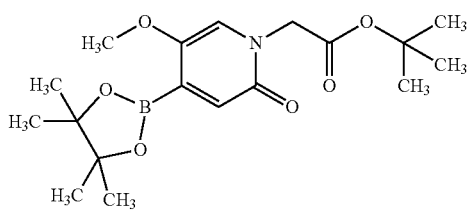 [SMILES: COc1cn(CC(=O)OC(C)(C)C)c(=O)cc1B1OC(C)(C)C(C)(C)O1]

Under argon, 800.0 mg (2.51 mmol) of tert-butyl (4-bromo-5-methoxy-2-oxopyridin-1(2H)-yl)acetate, 702.4 mg (2.77 mmol) of bis(pinacolato)diboron and 740.3 mg (7.54 mmol) of potassium acetate were initially charged in 24.0 ml of dioxane, 61.6 mg (0.075 mmol) of [1,1-bis(diphenylphosphino)ferrocene]dichloropalladium-dichloromethane complex were added and the mixture was stirred at 80° C. for 4 h. The reaction mixture was cooled and filtered through kieselguhr, and the filter cake was washed with dichloromethane and acetonitrile. The filtrate was concentrated and dried under high vacuum. Yield: 1.40 g (purity 51%, quant.). The crude product was used without further purification.

LC/MS [Method 10]: $R_t$=0.95 min; MS (ESIpos): m/z=284 (M+H)$^+$.

Beispiel 4.11A tert-Butyl 2-(4-bromo-5-methoxy-2-oxopyridin-1(2H)-yl)-4,4-difluorobutanoate (Racemate)

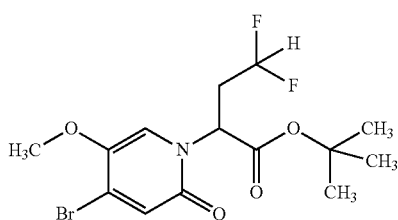 [SMILES: COc1cn(C(CC(F)F)C(=O)OC(C)(C)C)c(=O)cc1Br]

Under argon and at −78° C., 6.20 ml (1.0M in tetrahydrofuran, 1.1 eq.) of bis(trimethylsilyl)lithium amide were added dropwise to a solution of 1.79 g (5.64 mmol) of tert-butyl (4-bromo-5-methoxy-2-oxopyridin-1(2H)-yl)acetate in 43.6 ml of tetrahydrofuran, and the mixture was stirred for 15 min. 1.81 g (8.46 mmol, 1.5 eq.) of 2,2-difluoroethyl trifluoromethanesulfonate (synthesized according to U.S. Pat. No. 6,867,284, page 29) were added dropwise, and the mixture was stirred at −78° C. for 45 min and at RT overnight. Then 50 ml of saturated aqueous ammonium chloride solution were added, and the reaction mixture was subsequently extracted twice with in each case 100 ml of ethyl acetate. The collected organic phases were dried over magnesium sulphate, filtered and concentrated. The residue was purified by normal phase chromatography (mobile phase: cyclohexane/ethyl acetate gradient). Yield: 1.06 g (49% of theory).

LC/MS [Method 10]: $R_t$=1.76 min; MS (ESIpos): m/z=382 (M+H)$^+$.

$^1$H-NMR (400 MHz, DMSO-d$_6$): δ [ppm]=7.48 (s, 1H), 6.87 (s, 1H), 6.32-5.98 (m, 1H), 5.20-5.12 (m, 1H), 3.71 (s, 3H), 2.76-2.60 (m, 2H), 1.37 (s, 9H).

Beispiel 4.11B tert-Butyl 4,4-difluoro-2-[5-methoxy-2-oxo-4-(4,4,5,5-tetramethyl-1,3,2-dioxaborolan-2-yl)-pyridin-1(2H)-yl]butanoate (Racemate)

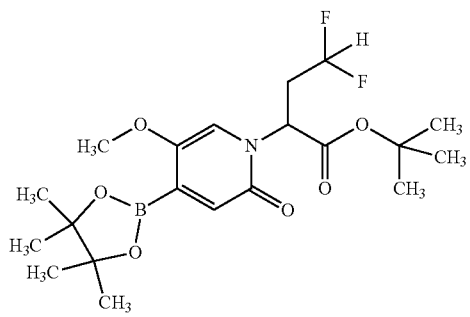 [SMILES: COc1cn(C(CC(F)F)C(=O)OC(C)(C)C)c(=O)cc1B1OC(C)(C)C(C)(C)O1]

Under argon, 1.06 g (2.76 mmol) of tert-butyl 2-(4-bromo-5-methoxy-2-oxopyridin-1(2H)-yl)-4,4-difluorobutanoate (racemate), 0.77 g (3.04 mmol) of bis(pinacolato)diboron and 0.81 g (8.28 mmol) of potassium acetate were initially charged in 26 ml of dioxane, 67.6 mg (0.08 mmol) of [1,1-bis(diphenylphosphino)ferrocene]dichloropalladium-dichloromethane complex were added and the mixture was stirred at 80° C. for 2 h. The reaction mixture was cooled and filtered through Celite, and the filter cake was washed with dichloromethane and acetonitrile. The filtrate was concentrated under reduced pressure and dried under high vacuum to give 1.94 g of the crude product (61% purity) which was used without further purification.

Example 4.12A tert-Butyl 2-(4-bromo-5-methoxy-2-oxopyridin-1(2H)-yl)propanoate (Racemate)

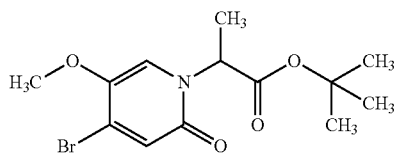 [SMILES: COc1cn(C(C)C(=O)OC(C)(C)C)c(=O)cc1Br]

Under argon, 12.00 g (58.82 mmol) 4-bromo-5-methoxy-pyridin-2(1H)-one [described in WO 2014/154794] were mixed with 20.32 g (147.04 mmol) potassium carbonate in 210 ml DMF. To this suspension, 11.71 ml (7.058 mmol) tert-butyl 2-bromopropanoate (racemate) were added and the mixture was stirred at 50° C. for 2 hours. The reaction mixture was then diluted with 1080 ml 10% aqueous sodium chloride solution and extracted with 480 ml ethyl acetate. The phases were separated and the aqueous phase was again extracted with 480 ml ethyl acetate. The combined organic phases were washed again with 10% aqueous sodium chloride solution, dried and concentrated under reduced pressure. The residue was purified by normal phase chromatography (mobile phase: cyclohexane/ethyl acetate-gradient). Yield: 8.70 g (45% of theory).

LC/MS [Method 10]: $R_t$=2.26 min; MS (ESIpos): m/z=332 (M+H)$^+$.

Example 4.12B tert-Butyl 2-[5-methoxy-2-oxo-4-(4,4,5,5-tetramethyl-1,3,2-dioxaborolan-2-yl)pyridin-1(2H)-yl]propanoate (Racemate)

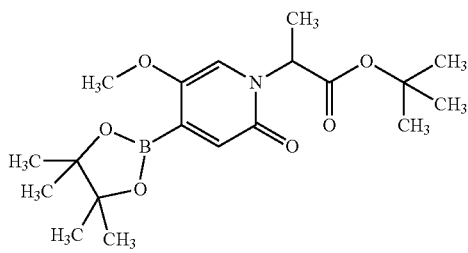 [SMILES: COc1cn(C(C)C(=O)OC(C)(C)C)c(=O)cc1B1OC(C)(C)C(C)(C)O1]

Under argon, 13.0 g (39.13 mmol) tert-butyl 2-(4-bromo-5-methoxy-2-oxopyridin-1(2H)-yl)propanoate (racemate), 10.93 g (43.05 mmol) of bis(pinacolato)diboron and 11.42 g (117.40 mmol) of potassium acetate were initially charged in 284 ml of dioxane. To this suspension, 0.96 g (1.17 mmol) of [1,1-bis(diphenylphosphino)ferrocene]dichloropalladium-dichloromethane complex were added and the mixture was stirred at 80° C. for 1.5 h. The reaction mixture was cooled and filtered through Celite, and the filter cake was washed with 90 ml ethyl acetate. The filtrate was concentrated under reduced pressure and dried under high vacuum to give 1.94 g of the crude product (50% purity) which was used without further purification.

LC/MS [Method 1]: $R_t$=0.61 min; MS (ESIpos): m/z=298 (M+H)$^+$ [boronic acid fragment].

Example 5.1A 2,5-Dimethoxypyridin-4-ylboronic acid

11.53 g (82.9 mmol) of 2,5-dimethoxypyridine were reacted according to General Method 1A. The desired product precipitated out after acidification of the aqueous phase. Yield: 9.53 g (61% of theory)

LC/MS [Method 1]: $R_t$=0.47 min; MS (ESIpos): m/z=184 (M+H)$^+$.

Example 5.1B

4-[5-Chloro-2-(1,3-oxazol-5-yl)phenyl]-2,5-dimethoxypyridine

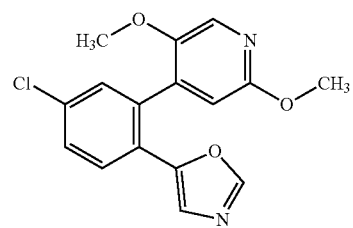 [SMILES: COc1cc(-c2cc(Cl)ccc2-c2cnco2)c(OC)cn1]

2.59 g (10.0 mmol) of 5-(2-bromo-4-chlorophenyl)-1,3-oxazole and 2.38 g (13.0 mmol) of 2,5-dimethoxypyridin-4-ylboronic acid in the presence of 0.08 eq. of [1,1-bis(diphenylphosphino)ferrocene]palladium(II) chloride/dichloromethane monoadduct and 3.0 eq. of potassium carbonate in dioxane were reacted according to General Method 2A. Yield: 1.92 g (61% of theory)

LC/MS [Method 1]: $R_t$=1.00 min; MS (ESIpos): m/z=317 (M+H)$^+$.

Example 5.1C

4-[5-Chloro-2-(1,3-oxazol-5-yl)phenyl]-5-methoxypyridin-2(1H)-one

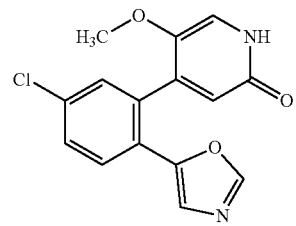 [SMILES: COc1c[nH]c(=O)cc1-c1cc(Cl)ccc1-c1cnco1]

1.92 g (6.07 mmol) of 4-[5-chloro-2-(1,3-oxazol-5-yl)phenyl]-2,5-dimethoxypyridine and 20 eq. of pyridinium hydrochloride in dimethylformamide were reacted according to General Method 3A at 100° C. Yield: 1.67 g (94% of theory)

LC/MS [Method 1]: $R_t$=0.68 min; MS (ESIpos): m/z=303 (M+H)$^+$.

Example 5.1D tert-Butyl {4-[5-chloro-2-(1,3-oxazol-5-yl)phenyl]-5-methoxy-2-oxopyridin-1(2H)-yl}acetate

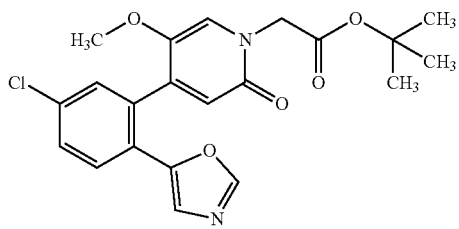 [SMILES: COc1cn(CC(=O)OC(C)(C)C)c(=O)cc1-c1cc(Cl)ccc1-c1cnco1]

1.16 g (3.75 mmol) of 4-[5-chloro-2-(1,3-oxazol-5-yl)phenyl]-5-methoxypyridin-2(1H)-one and 1.2 eq. of tert-butyl bromoacetate in the presence of 1.5 eq. of potassium carbonate in 11 ml of dimethylformamide were reacted according to General Method 4A at 100° C. The crude product was purified by flash chromatography (silica cartridge, dichloromethane/methanol mixture). Yield: 1.19 g (76% of theory)

LC/MS [Method 10]: $R_t$=1.75 min; MS (ESIpos): m/z=417 (M+H)$^+$.

Example 6.1A tert-Butyl 4-tert-butoxy-2-{4-[5-chloro-2-(1,3-oxazol-5-yl)phenyl]-5-methoxy-2-oxopyridin-1(2H)-yl}butanoate (Racemate)

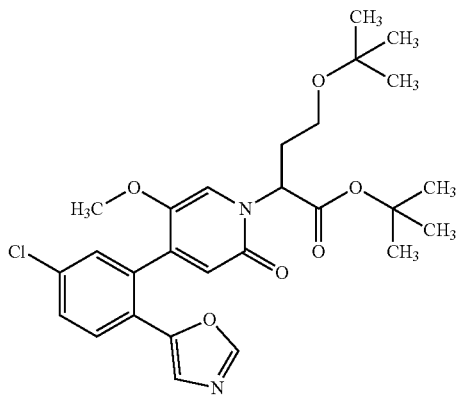 [SMILES: COc1cn(C(CCOC(C)(C)C)C(=O)OC(C)(C)C)c(=O)cc1-c1cc(Cl)ccc1-c1cnco1]

333 mg (0.80 mmol) of tert-butyl {4-[5-chloro-2-(1,3-oxazol-5-yl)phenyl]-5-methoxy-2-oxopyridin-1(2H)-yl}acetate, 320 mg (1.28 mmol, 1.6 eq.) of 2-tert-butoxyethyl trifluoromethanesulphonate and 0.96 ml (0.96 mmol, 1.2 eq.) of bis(trimethylsilyl)lithium amide (1M in THF) in 8 ml of THF were reacted according to General Method 8A. After aqueous work-up, the crude product was purified by flash chromatography (silica cartridge, cyclohexane/ethyl acetate gradient). Yield: 270 mg (65% of theory)

LC/MS [Method 1]: $R_t$=1.18 min; MS (ESIpos): m/z=517 (M+H)$^+$.

Example 6.1B 4-tert-Butoxy-2-{4-[5-chloro-2-(1,3-oxazol-5-yl)phenyl]-5-methoxy-2-oxopyridin-1(2H)-yl}butanoic acid (Racemate)

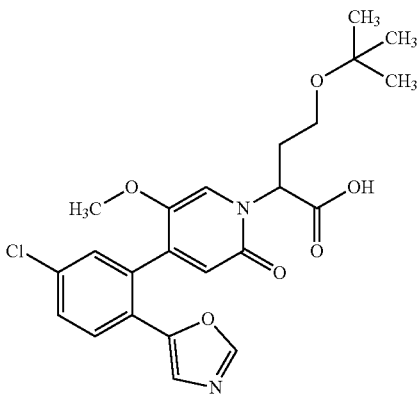 [SMILES: COc1cn(C(CCOC(C)(C)C)C(=O)O)c(=O)cc1-c1cc(Cl)ccc1-c1cnco1]

270 mg (0.52 mmol) of tert-butyl 4-tert-butoxy-2-{4-[5-chloro-2-(1,3-oxazol-5-yl)phenyl]-5-methoxy-2-oxopyridin-1(2H)-yl}butanoic acid (racemate) in 15 ml of ethanol and 7.5 ml of tetrahydrofuran in the presence of 63 mg (2.61 mmol, 5.0 eq.) of lithium hydroxide were reacted according to General Method 6C. Yield: 217 mg (90% of theory)

LC/MS [Method 10]: $R_t$=1.71 min; MS (ESIpos): m/z=461 (M+H)$^+$, $^1$H-NMR (400 MHz, DMSO-d$_6$): δ [ppm]=12.94 (br. s, 1H), 8.37 (s, 1H), 7.77 (d, 1H), 7.62 (dd, 1H), 7.44 (d, 1H), 7.29 (s, 1H), 6.82 (s, 1H), 6.37 (s, 1H), 5.20 (br. s, 1H), 3.42-3.35 (m, 1H), 3.39 (s, 3H), 3.19-3.11 (m, 1H), 2.43-2.35 (m 1H), 2.34-2.23 (m, 1H), 1.10 (s, 9H).

Example 61C

Ethyl 4-[(4-tert-butoxy-2-{4-[5-chloro-2-(1,3-oxazol-5-yl)phenyl]-5-methoxy-2-oxopyridin-1(2H)-yl}butanoyl)amino]benzoate (Racemate)

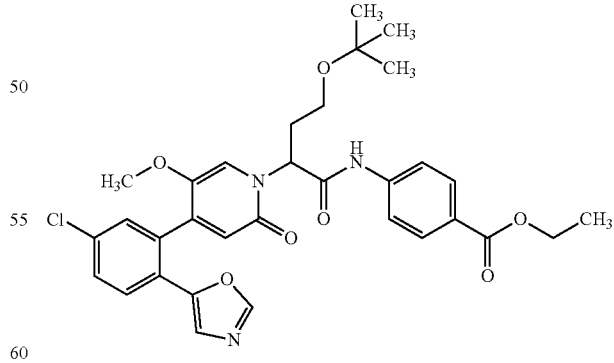

217 mg (0.47 mmol) of 4-tert-butoxy-2-{4-[5-chloro-2-(1,3-oxazol-5-yl)phenyl]-5-methoxy-2-oxopyridin-1(2H)-yl}butanoic acid (racemate) and 86 mg (0.52 mmol, 1.1 eq.) of ethyl 4-aminobenzoate in 8 ml of dimethylformamide were reacted in the presence of 2.2 eq. of N,N-diisopropylethylamine and 1.2 eq. of HATU at RT according to General Method 5B. The crude product was purified by flash chromatography (silica cartridge, cyclohexane/ethyl acetate mixture). Yield: 145 mg (49% of theory)

LC/MS [Method 10]: $R_t$=2.22 min; MS (ESIpos): m/z=608 (M+H)$^+$.

Example 6.2A tert-Butyl 2-{4-[5-chloro-2-(1,3-oxazol-5-yl)phenyl]-5-methoxy-2-oxopyridin-1(2H)-yl}butanoate (Racemate)

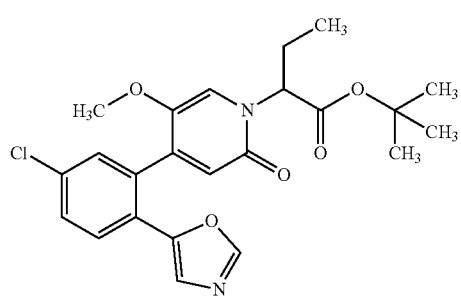 [SMILES: CCC(C(=O)OC(C)(C)C)n1cc(OC)c(-c2cc(Cl)ccc2-c2cnco2)cc1=O]

292 mg (0.70 mmol) of tert-butyl {4-[5-chloro-2-(1,3-oxazol-5-yl)phenyl]-5-methoxy-2-oxopyridin-1(2H)-yl}acetate, 187 mg (1.05 mmol, 1.5 eq.) of ethyl trifluoromethanesulphonate and 0.84 ml (0.84 mmol, 1.2 eq.) of bis(trimethylsilyl)lithium amide (1M in THF) in 7 ml of THF were reacted according to General Method 8A. After aqueous work-up, the crude product was purified by flash chromatography (silica cartridge, cyclohexane/ethyl acetate gradient). Yield: 137 mg (43% of theory)

LC/MS [Method 1]: $R_t$=1.06 min; MS (ESIpos): m/z=445 (M+H)$^+$.

Example 6.2B

2-{4-[5-Chloro-2-(1,3-oxazol-5-yl)phenyl]-5-methoxy-2-oxopyridin-1(2H)-yl}butanoic acid (Racemate)

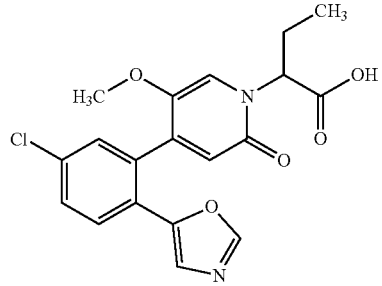 [SMILES: CCC(C(=O)O)n1cc(OC)c(-c2cc(Cl)ccc2-c2cnco2)cc1=O]

137 mg (0.30 mmol) of tert-butyl 2-{4-[5-chloro-2-(1,3-oxazol-5-yl)phenyl]-5-methoxy-2-oxopyridin-1(2H)-yl}butanoic acid (racemate) in 5 ml of dichloromethane in the presence of 0.47 ml (6.04 mmol, 20 eq.) of trifluoroacetic acid were reacted according to General Method 6A. Yield: 150 mg (purity 85%, quant.)

LC/MS [Method 10]: $R_t$=1.45 min; MS (ESIpos): m/z=389 (M+H)$^+$.

Example 6.2C tert-Butyl 4-[(2-{4-[5-chloro-2-(1,3-oxazol-5-yl)phenyl]-5-methoxy-2-oxopyridin-1(2H)-yl}butanoyl)amino]benzoate (Racemate)

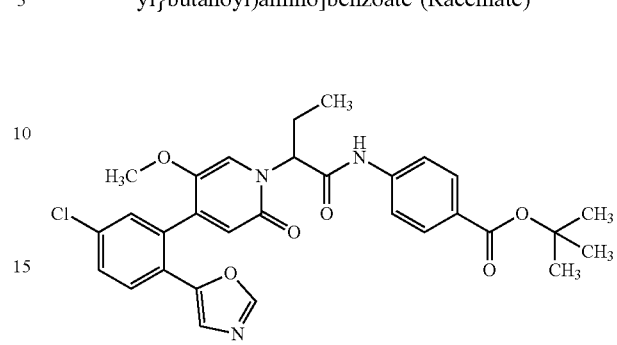

150 mg (purity 85%, 0.33 mmol) of 2-{4-[5-chloro-2-(1,3-oxazol-5-yl)phenyl]-5-methoxy-2-oxopyridin-1(2H)-yl}butanoic acid (racemate) and 69 mg (0.36 mmol, 1.1 eq.) of tert-butyl 4-aminobenzoate in 5 ml of dimethylformamide were reacted in the presence of 2.2 eq. of N,N-diisopropylethylamine and 1.2 eq. of HATU at RT according to General Method 5B. The crude product was purified by RP-HPLC (Reprosil C18, acetonitrile/water gradient). Yield: 138 mg (75% of theory)

LC/MS [Method 10]: $R_t$=2.23 min; MS (ESIpos): m/z=564 (M+H)$^+$.

Example 6.3A tert-Butyl 2-{4-[5-chloro-2-(1,3-oxazol-5-yl)phenyl]-5-methoxy-2-oxopyridin-1(2H)-yl}-4-(trifluoromethoxy)butanoate (Racemate)

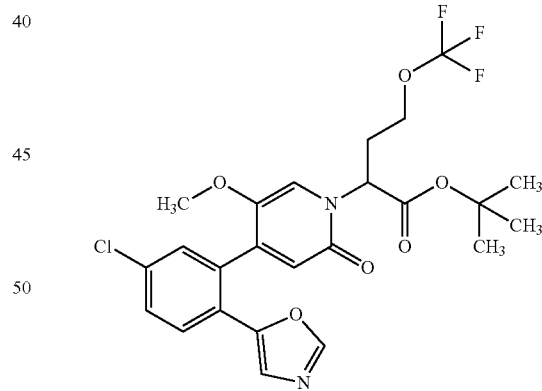

In three batches, a total of 633 mg (1.52 mmol) of tert-butyl {4-[5-chloro-2-(1,3-oxazol-5-yl)phenyl]-5-methoxy-2-oxopyridin-1(2H)-yl}acetate and 617 mg (2.35 mmol, 1.5 eq.) of 2-(trifluoromethoxy)ethyl trifluoromethanesulphonate in the presence of 1.2 eq. of bis(trimethylsilyl)lithium amide (1M in THF) were reacted according to General Method 8A. After aqueous work-up, the combined crude products were purified by flash chromatography (silica cartridge, cyclohexane/ethyl acetate gradient). Yield: 231 mg (28% of theory)

LC/MS [Method 1]: $R_t$=1.12 min; MS (ESIpos): m/z=529 (M+H)$^+$.

Example 6.3B

2-{4-[5-Chloro-2-(1,3-oxazol-5-yl)phenyl]-5-methoxy-2-oxopyridin-1(2H)-yl}-4-(trifluoromethoxy)butanoic acid (Racemate)

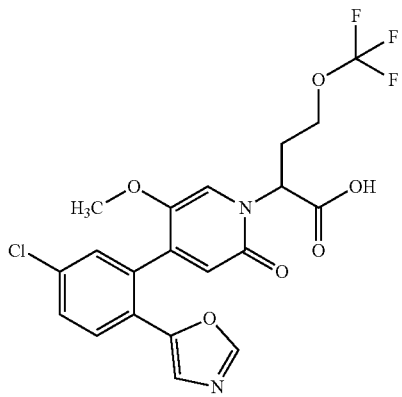 [SMILES: COc1cn(C(CCOC(F)(F)F)C(=O)O)c(=O)cc1-c1cc(Cl)ccc1-c1cnco1]

231 mg (0.42 mmol) of tert-butyl 2-{4-[5-chloro-2-(1,3-oxazol-5-yl)phenyl]-5-methoxy-2-oxopyridin-1(2H)-yl}-4-(trifluoromethoxy)butanoic acid (racemate) in 5 ml of dichloromethane in the presence of 0.65 ml (8.39 mmol, 20 eq.) of trifluoroacetic acid were reacted according to General Method 6A. Yield: 266 mg (quant.)

LC/MS [Method 10]: $R_t$=1.70 min; MS (ESIpos): m/z=473 (M+H)$^+$.

Example 6.3C tert-Butyl 4-{[2-{4-[5-chloro-2-(1,3-oxazol-5-yl)phenyl]-5-methoxy-2-oxopyridin-1(2H)-yl}-4-(trifluoromethoxy)butanoyl]amino}benzoate (Racemate)

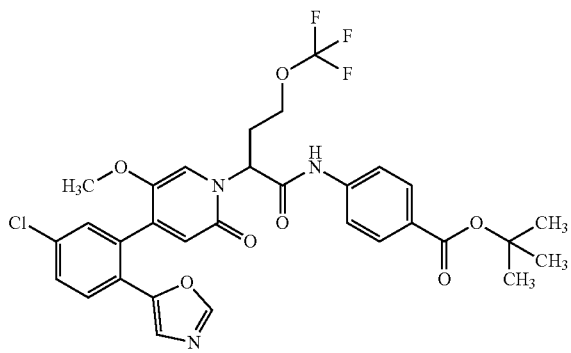 [SMILES: COc1cn(C(CCOC(F)(F)F)C(=O)Nc2ccc(C(=O)OC(C)(C)C)cc2)c(=O)cc1-c1cc(Cl)ccc1-c1cnco1]

266 mg (0.56 mmol) of 2-{4-[5-chloro-2-(1,3-oxazol-5-yl)phenyl]-5-methoxy-2-oxopyridin-1(2H)-yl}-4-(trifluoromethoxy)butanoic acid (racemate) and 120 mg (0.62 mmol, 1.1 eq.) of tert-butyl 4-aminobenzoate in 8 ml of dimethylformamide were reacted in the presence of 2.2 eq. of N,N-diisopropylethylamine and 1.2 eq. of HATU at RT according to General Method 5A. The crude product was purified by flash chromatography (silica cartridge, cyclohexane/ethyl acetate mixture). Yield: 172 mg (purity 94%, 44% of theory)

LC/MS [Method 10]: $R_t$=2.34 min; MS (ESIpos): m/z=648 (M+H)$^+$.

Example 6.4A tert-Butyl 2-{4-[5-chloro-2-(1,3-oxazol-5-yl)phenyl]-5-methoxy-2-oxopyridin-1(2H)-yl}-3-[(2S)-tetrahydro-2H-pyran-2-yl]propanoate (Mixture of Enantiomerically Pure Diastereomers)

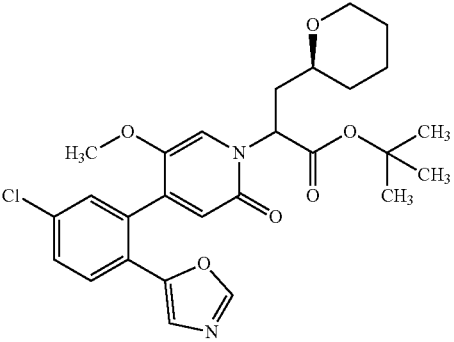 [SMILES: COc1cn(C(C[C@@H]2CCCCO2)C(=O)OC(C)(C)C)c(=O)cc1-c1cc(Cl)ccc1-c1cnco1]

365 mg (0.88 mmol) of tert-butyl {4-[5-chloro-2-(1,3-oxazol-5-yl)phenyl]-5-methoxy-2-oxopyridin-1(2H)-yl}acetate, 386 mg (purity 90%, 1.40 mmol, 1.6 eq.) of (2S)-tetrahydro-2H-pyran-2-ylmethyl trifluoromethanesulphonate and 1.05 ml (1.05 mmol, 1.2 eq.) of bis(trimethylsilyl)lithium amide (1M in THF) in 10 ml of THF were reacted according to General Method 8A. After aqueous work-up, the crude product was purified by flash chromatography (silica cartridge, cyclohexane/ethyl acetate gradient). Yield: 198 mg (43% of theory)

LC/MS [Method 10]: $R_t$=2.17 min; MS (ESIpos): m/z=515 (M+H)$^+$.

Example 6.4B

2-{4-[5-Chloro-2-(1,3-oxazol-5-yl)phenyl]-5-methoxy-2-oxopyridin-1(2H)-yl}-3-[(2S)-tetrahydro-2H-pyran-2-yl]propanoic acid (Mixture of Enantiomerically Pure Diastereomers)

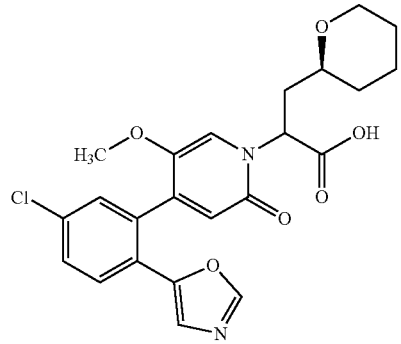 [SMILES: COc1cn(C(C[C@@H]2CCCCO2)C(=O)O)c(=O)cc1-c1cc(Cl)ccc1-c1cnco1]

198 mg (0.37 mmol) of tert-butyl 2-{4-[5-chloro-2-(1,3-oxazol-5-yl)phenyl]-5-methoxy-2-oxopyridin-1(2H)-yl]-3-[(2S)-tetrahydro-2H-pyran-2-yl]propanoate (mixture of enantiornerically pure diastereomers) in 5 ml of dichloromethane in the presence of 0.58 ml (7.46 mmol, 20 eq.) of trifluoroacetic acid were reacted according to General Method 6A. Yield: 222 mg (purity 88%, quant.)

LC/MS [Method 10]: R$_t$=1.61 min/1.64 min; MS (ESIpos): m/z=459 (M+H)$^+$ 459 (M+H)$^+$.

Example 6.4C tert-Butyl 4-[(2-{4-[5-chloro-2-(1,3-oxazol-5-yl)phenyl]-5-methoxy-2-oxopyridin-1(2H)-yl}-3-[(2S)-tetrahydro-2H-pyran-2-yl]propanoyl)amino]benzoate (Mixture of Enantiomerically Pure Diastereomers)

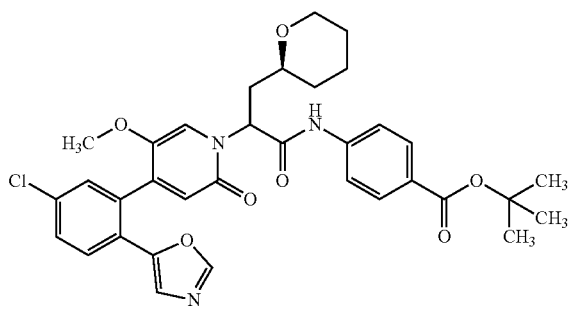 [SMILES: COc1cn(C(C[C@@H]2CCCCO2)C(=O)Nc2ccc(C(=O)OC(C)(C)C)cc2)c(=O)cc1-c1cc(Cl)ccc1-c1cnco1]

222 mg (purity 88%, 0.43 mmol) of 2-{4-[5-chloro-2-(1,3-oxazol-5-yl)phenyl]-5-methoxy-2-oxopyridin-1(2H)-yl}-3-[(2S)-tetrahydro-2H-pyran-2-yl]propanoic acid (mixture of enantiomerically pure diastereomers) and 90 mg (0.47 mmol, 1.1 eq.) of tert-butyl 4-aminobenzoate in 10 ml of dimethylformamide were reacted in the presence of 2.2 eq. of N,N-diisopropylethylamine and 1.2 eq. of HATU at RT according to General Method 5A. The crude product was purified by flash chromatography (silica cartridge, cyclohexane/ethyl acetate mixture). Yield: 241 mg (purity 86%, 77% of theory)

LC/MS [Method 10]: R$_t$=2.38 min/2.42 min; MS (ESIpos): m/z=634 (M+H)$^+$/634 (M+H)$^+$.

Example 6.5A tert-Butyl 2-{4-[5-chloro-2-(1,3-oxazol-5-yl)phenyl]-5-methoxy-2-oxopyridin-1(2H)-yl}-4-methoxybutanoate (Racemate)

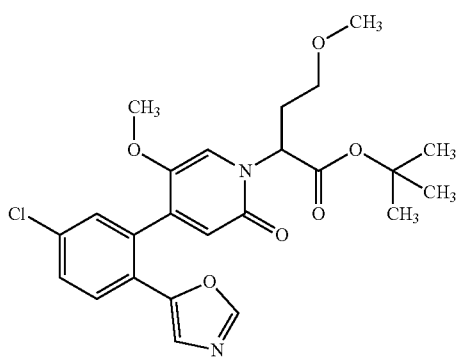 [SMILES: COCCC(C(=O)OC(C)(C)C)n1cc(OC)c(-c2cc(Cl)ccc2-c2cnco2)cc1=O]

20 ml of dioxane were added to 1270 mg (1.95 mmol, purity 65%) of tert-butyl 4-methoxy-2-[5-methoxy-2-oxo-4-(4,4,5,5-tetramethyl-1,3,2-dioxaborolan-2-yl)pyridin-1 (2H)-yl]butanoate (racemate), 504 mg (1.95 mmol, 1 eq.) of 5-(2-bromo-4-chlorophenyl)-1,3-oxazole and 808 mg (5.85 mmol, 3 eq.) of potassium carbonate. For 5 min, argon was passed through the reaction mixture. 48 mg (0.06 mmol, 0.03 eq) of [1,1-bis(diphenylphosphino)ferrocene]dichloropalladium-dichloromethane complex were then added, and the mixture was stirred at 80° C. for 1 day. The reaction mixture was filtered through kieselguhr, washing with dichloromethane/acetonitrile, and the filtrate was concentrated. The crude product was purified by normal phase chromatography (mobile phase: dichloromethane/methanol, 0-6%). The product fractions were combined and purified by preparative HPLC (RP18 column, mobile phase: acetonitrile/water gradient with addition of 0.1% formic acid). Yield: 660 mg (71% of theory)

LC/MS [Method 1]: R$_t$=1.02 min; MS (ESIpos): m/z=475 (M+H)$^+$, $^1$H-NMR (400 MHz, DMSO-d$_6$): δ [ppm]=8.38 (s, 1H), 7.77 (d, 1H), 7.62 (dd, 1H), 7.46 (d, 1H), 7.27 (s, 1H), 6.79 (s, 1H), 6.39 (s, 1H), 5.18-4.95 (m, 1H), 3.45-3.33 (m, 4H), 3.24-3.13 (m, 4H), 2.39-2.27 (m, 2H), 1.42 (s, 9H).

Example 6.5B

2-{4-[5-Chloro-2-(1,3-oxazol-5-yl)phenyl]-5-methoxy-2-oxopyridin-1(2H)-yl}-4-methoxybutanoic acid (Racemate)

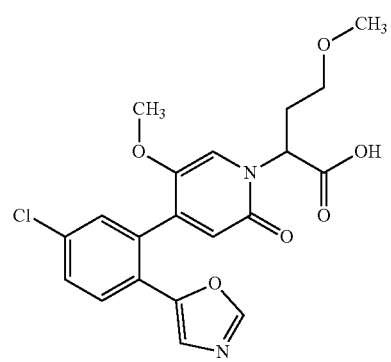 [SMILES: COCCC(C(=O)O)n1cc(OC)c(-c2cc(Cl)ccc2-c2cnco2)cc1=O]

660 mg (1.38 mmol) of tert-butyl 2-{4-[5-chloro-2-(1,3-oxazol-5-yl)phenyl]-5-methoxy-2-oxopyridin-1(2H)-yl}-4-methoxybutanoate (racemate) were reacted in 13.4 ml of a solution of hydrogen chloride in dioxane (4M) according to General Method 6D. Yield: 700 mg (purity 80%, 97% of theory)

LC/MS [Method 10]: R$_t$=1.39 min; MS (ESIpos): m/z=419 (M+H)$^+$, $^1$H-NMR (400 MHz, DMSO-d$_6$): δ [ppm]=8.38 (s, 1H), 7.77 (d, 1H), 7.62 (dd, 1H), 7.48 (d, 1H), 7.30 (s, 1H), 6.83 (s, 1H), 6.37 (s, 1H), 5.14 (br. s, 1H), 4.82 (br. s, 1H), 3.57 (s, 1H), 3.45-3.35 (m, 1H), 3.25-3.11 (m, 4H), 2.45-2.27 (m, 2H).

Example 6.5C tert-Butyl 4-[(2-{4-[5-chloro-2-(1,3-oxazol-5-yl)phenyl]-5-methoxy-2-oxopyridin-1(2H)-yl}-4-methoxybutanoyl)amino]benzoate (Racemate)

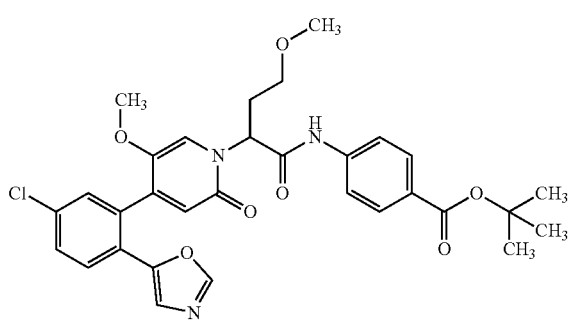 [SMILES: COCCC(C(=O)Nc1ccc(C(=O)OC(C)(C)C)cc1)n1cc(OC)c(-c2cc(Cl)ccc2-c2cnco2)cc1=O]

209 mg (purity 80%, 0.400 mmol) of 2-{4-[5-chloro-2-(1,3-oxazol-5-yl)phenyl]-5-methoxy-2-oxopyridin-1(2H)-yl}-4-methoxybutanoic acid (racemate) and 116 mg (0.600 mmol) of tert-butyl 4-aminobenzoate in 3.3 ml of pyridine were reacted according to General Method 5A. Yield: 210 mg (88% of theory).

LC/MS [Method 1]: $R_t$=1.15 min; MS (ESIpos): m/z=594 (M+H)$^+$,
$^1$H-NMR (400 MHz, DMSO-d$_6$): δ [ppm]=10.71 (br. s, 1H), 8.39 (s, 1H), 7.90-7.84 (m, 2H), 7.80-7.73 (m, 3H), 7.62 (dd, 1H), 7.48 (d, 1H), 7.38 (s, 1H), 6.89 (s, 1H), 6.41 (s, 1H), 5.76 (br. s, 1H), 3.46-3.38 (m, 4H), 3.34-3.26 (m, 1H), 3.23 (s, 3H), 2.46-2.38 (m, 2H), 1.54 (s, 9H).

Example 6.6A tert-Butyl 2-{4-[5-chloro-2-(4,5-dihydro-1,2-oxazol-3-yl)phenyl]-5-methoxy-2-oxopyridin-1(2H)-yl}-4-methoxybutanoate (Racemate)

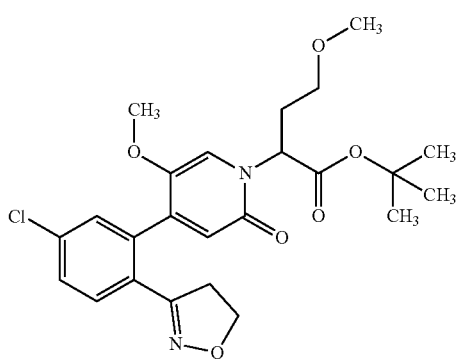 [SMILES: COCCC(C(=O)OC(C)(C)C)n1cc(OC)c(-c2cc(Cl)ccc2C2=NOCC2)cc1=O]

5.5 ml of dioxane were added to 150 mg (0.58 mmol) of 3-(2-bromo-4-chlorophenyl)-4,5-dihydro-1,2-oxazole, 343 mg (0.58 mmol, purity 70%, 1 eq.) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 235 mg (1.70 mmol, 3 eq.) of potassium carbonate. For 5 min, argon was passed through the reaction mixture. 14 mg (0.02 mmol, 0.03 eq) of [1,1-bis(diphenylphosphino)ferrocene]dichloropalladium-dichloromethane complex were then added, and the mixture was stirred at 80° C. overnight. The reaction mixture was filtered through kieselguhr, washing with dichloromethane, and the filtrate was concentrated. The crude product was purified by normal phase chromatography (mobile phase: cyclohexane/ethyl acetate, 50-100%). Yield: 166 mg (95% pure, 58% of theory).

LC/MS [Method 1]: $R_t$=1.02 min; MS (ESIpos): m/z=477 (M+H)$^+$,
$^1$H-NMR (400 MHz, DMSO-d$_6$): δ [ppm]=7.64 (d, 1H), 7.58 (dd, 1H), 7.43 (d, 1H), 7.16 (s, 1H), 6.32 (s, 1H), 5.09-4.98 (m, 1H), 4.33-4.16 (m, 2H), 3.53 (s, 3H), 3.39-3.08 (m, 7H), 2.36-2.18 (m, 2H), 1.40 (s, 9H).

Example 6.6B

2-{4-[5-Chloro-2-(4,5-dihydro-1,2-oxazol-3-yl)phenyl]-5-methoxy-2-oxopyridin-1(2H)-yl}-4-methoxybutanoic acid hydrochloride (Racemate)

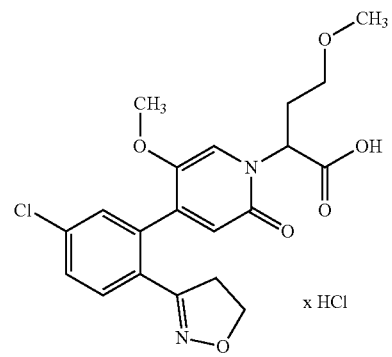 [SMILES: COCCC(C(=O)O)n1cc(OC)c(-c2cc(Cl)ccc2C2=NOCC2)cc1=O]

149 mg (0.297 mmol, purity 95%) of tert-butyl 2-{4-[5-chloro-2-(4,5-dihydro-1,2-oxazol-3-yl)phenyl]-5-methoxy-2-oxopyridin-1(2H)-yl}-4-methoxybutanoate (racemate) were reacted in 3.0 ml of a solution of hydrogen chloride in dioxane (4M) according to General Method 6D. Yield: 134 mg (purity 95%, 94% of theory)

LC/MS [Method 10]: $R_t$=1.33 min; MS (ESIpos): m/z=421 (M+H)$^+$,
$^1$H-NMR (400 MHz, DMSO-d$_6$): δ [ppm]=7.64 (d, 1H), 7.58 (dd, 1H), 7.45 (d, 1H), 7.20 (s, 1H), 6.31 (s, 1H), 5.21-4.92 (m, 1H), 4.33-4.20 (m, 2H), 3.53 (s, 3H), 3.40-3.04 (m, 7H), 2.38-2.25 (m, 2H).

Example 6.6C tert-Butyl 4-[(2-{4-[5-chloro-2-(4,5-dihydro-1,2-oxazol-3-yl)phenyl]-5-methoxy-2-oxopyridin-1(2H)-yl}-4-methoxybutanoyl)amino]benzoate (Racemate)

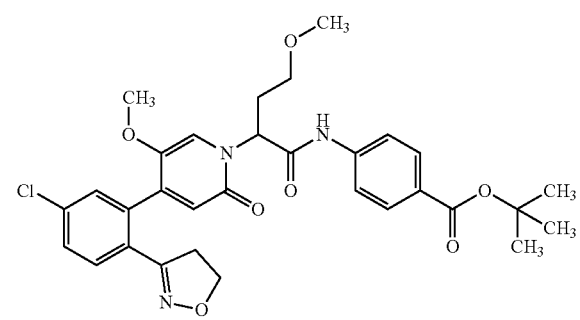 [SMILES: COCCC(C(=O)Nc1ccc(C(=O)OC(C)(C)C)cc1)n1cc(OC)c(-c2cc(Cl)ccc2C2=NOCC2)cc1=O]

66 mg (0.137 mmol) of 2-{4-[5-chloro-2-(4,5-dihydro-1,2-oxazol-3-yl)phenyl]-5-methoxy-2-oxopyridin-1(2H)-yl}-4-methoxybutanoic acid hydrochloride (racemate) and 39.7 mg (0.206 mmol) of tert-butyl 4-aminobenzoate in 1 ml of pyridine were reacted according to General Method 5A. Yield: 69.7 mg (84% of theory).

LC/MS [Method 10]: $R_t$=2.17 min; MS (ESIpos): m/z=596 (M+H)$^+$, $^1$H-NMR (400 MHz, DMSO-d$_6$): δ [ppm]=10.70 (br. s, 1H), 7.90-7.81 (m, 2H), 7.78-7.73 (m, 2H), 7.67-7.57 (m, 2H), 7.44 (d, 1H), 7.32 (s, 1H), 6.35 (s, 1H), 5.78-5.65 (m, 1H), 4.34-4.20 (m, 2H), 3.57 (s, 3H), 3.41-3.33 (m, 1H), 3.29-3.15 (m, 6H), 2.43-2.27 (m, 2H), 1.54 (s, 9H).

Example 6.7A tert-Butyl 2-{4-[5-chloro-2-(5,6-dihydro-1,4,2-dioxazin-3-yl)phenyl]-5-methoxy-2-oxopyridin-1(2H)-yl}-4-methoxybutanoate (Racemate)

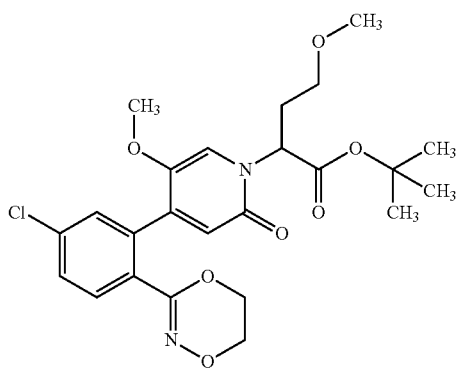 [SMILES: COCCC(C(=O)OC(C)(C)C)n1cc(OC)c(-c2cc(Cl)ccc2C2=NOCCO2)cc1=O]

7.3 ml of dioxane were added to 528 mg (0.72 mmol, purity 58%) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 200 mg (0.72 mmol, 1 eq.) of 3-(2-bromo-4-chlorophenyl)-5,6-dihydro-1,4,2-dioxazine and 300 mg (2.17 mmol, 3 eq.) of potassium carbonate. For 5 min, argon was passed through the reaction mixture. 18 mg (0.02 mmol, 0.03 eq) of [1,1-bis(diphenylphosphino)ferrocene]dichloropalladium-dichloromethane complex were then added, and the mixture was stirred at 80° C. for 1 day. The reaction mixture was filtered through kieselguhr, washing with dichloromethane/acetonitrile, and the filtrate was concentrated. The crude product was purified by normal phase chromatography (mobile phase: cyclohexane/ethyl acetate, 0-100%). Yield: 70 mg (20% of theory).

LC/MS [Method 10]: $R_t$=1.84 min; MS (ESIpos): m/z=493 (M+H)$^+$, $^1$H-NMR (400 MHz, DMSO-d$_6$): δ [ppm]=7.65-7.60 (m, 1H), 7.59-7.54 (m, 1H), 7.44 (d, 1H), 7.16 (s, 1H), 6.28 (s, 1H), 5.11-5.02 (m, 1H), 4.28-4.20 (m, 2H), 4.07-3.95 (m, 2H), 3.56 (s, 3H), 3.40-3.27 (m, 1H), 3.21 (s, 3H), 3.19-3.10 (m, 1H), 2.35-2.26 (m, 2H), 1.41 (s, 9H).

Example 6.7B

2-{4-[5-Chloro-2-(5,6-dihydro-1,4,2-dioxazin-3-yl)phenyl]-5-methoxy-2-oxopyridin-1(2H)-yl}-4-methoxybutanoic acid (Racemate)

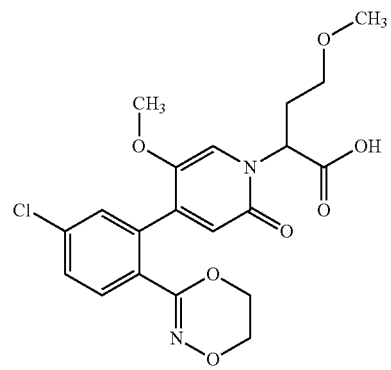 [SMILES: COCCC(C(=O)O)n1cc(OC)c(-c2cc(Cl)ccc2C2=NOCCO2)cc1=O]

1.3 ml of a solution of hydrogen chloride in dioxane (4M) were added to 70 mg (0.142 mmol) of tert-butyl 2-{4-[5-chloro-2-(5,6-dihydro-1,4,2-dioxazin-3-yl)phenyl]-5-methoxy-2-oxopyridin-1(2H)-yl}-4-methoxybutanoate (racemate), and the mixture was stirred at RT for 5 h. The reaction mixture was concentrated and purified by preparative HPLC (RP18 column; mobile phase: acetonitrile/water gradient with addition of 0.1% formic acid). Yield: 36 mg (92% pure, 54% of theory).

LC/MS [Method 10]: $R_t$=1.32 min; MS (ESIpos): m/z=437 (M+H)$^+$, $^1$H-NMR (400 MHz, DMSO-d$_6$): δ [ppm]=12.91 (br. s, 1H), 7.67-7.49 (m, 2H), 7.46 (d, 1H), 7.21 (s, 1H), 6.26 (s, 1H), 5.17-5.04 (m, 1H), 4.28-4.18 (m, 2H), 4.05-3.95 (m, 2H), 3.55 (s, 3H), 3.40-3.27 (m, 1H), 3.24-3.08 (m, 5H), 2.39-2.28 (m, 2H).

Example 6.8A tert-Butyl 2-{4-[5-chloro-2-(1H-tetrazol-1-yl)phenyl]-5-methoxy-2-oxopyridin-1(2N)-yl}-4-methoxybutanoate (Racemate)

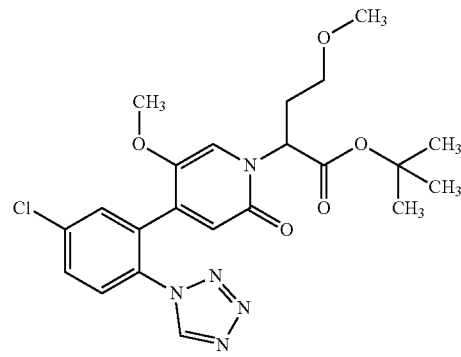 [SMILES: COCCC(C(=O)OC(C)(C)C)n1cc(OC)c(-c2cc(Cl)ccc2-n2cnnn2)cc1=O]

7.0 ml of dioxane were added to 225 mg (0.70 mmol, purity 81%) of 1-(2-bromo-4-chlorophenyl)-1H-tetrazole, 425 mg (0.72 mmol, purity 70%, 1 eq) of tert-butyl 4-methoxy-2-[5-methoxy-2-oxo-4-(4,4,5,5-tetramethyl-1,3, 2-dioxaborolan-2-yl)pyridin-1(2H)-yl]butanoate (racemate) and 291 mg (2.11 mmol, 3 eq.) of potassium carbonate. For 5 min, argon was passed through the reaction mixture. 17 mg (0.02 mmol, 0.03 eq) of [1,1-bis(diphenylphosphino)ferrocene]dichloropalladium-dichloromethane complex were then added, and the mixture was stirred at 80° C. for 3 days. The reaction mixture was filtered through kieselguhr, washing with dichloromethane, and the filtrate was concentrated. The crude product was purified by normal phase chromatography (mobile phase: cyclohexane/ethyl acetate, 50-100%). The product fractions were combined and purified by preparative HPLC (RP18 column, mobile phase: acetonitrile/water gradient with addition of 0.1% formic acid). Yield: 64 mg (19% of theory)

LC/MS [Method 10]: $R_t$=1.73 min; MS (ESIpos): m/z=476 (M+H)$^+$, $^1$H-NMR (400 MHz, DMSO-d$_6$): δ [ppm]=9.64 (s, 1H), 7.86-7.70 (m, 3H), 7.03 (s, 1H), 6.47 (s, 1H), 5.01-4.91 (m, 1H), 3.52-3.20 (m, 6H), 3.17 (s, 3H), 3.09-2.98 (m, 1H), 2.29-2.20 (m, 2H), 1.38 (s, 9H).

Example 6.8B

2-{4-[5-Chloro-2-(1H-tetrazol-1-yl)phenyl]-5-methoxy-2-oxopyridin-1(2H)-yl}-4-methoxybutanoic acid hydrochloride (Racemate)

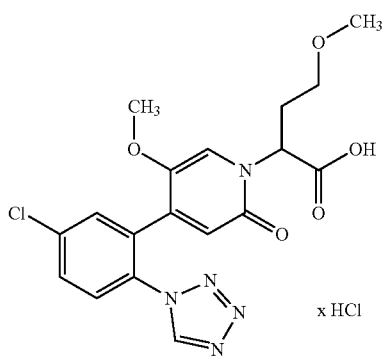 [SMILES: COCCC(C(=O)O)n1cc(OC)c(-c2cc(Cl)ccc2-n2cnnn2)cc1=O]

64 mg (0.134 mmol) of tert-butyl 2-{4-[5-chloro-2-(1H-tetrazol-1-yl)phenyl]-5-methoxy-2-oxopyridin-1(2H)-yl}-4-methoxybutanoate (racemate) were reacted in 1.3 ml of a solution of hydrogen chloride in dioxane (4M) according to General Method 6D. Yield: 58 mg (purity 95%, 90% of theory)

LC/MS [Method 1]: $R_t$=0.70 min; MS (ESIpos): m/z=420 (M+H)$^+$, $^1$H NMR (400 MHz, DMSO-d$_6$): δ [ppm]=9.66 (s, 1H), 7.87-7.73 (m, 3H), 7.07 (s, 1H), 6.46 (s, 1H), 4.61 (br. s, 1H), 3.34-3.25 (m, 1H), 3.23 (s, 3H), 3.16 (s, 3H), 3.04-2.91 (m, 1H), 2.34-2.22 (m, 2H).

Example 6.9A tert-Butyl 2-{4-[5-chloro-2-(1H-imidazol-1-yl)phenyl]-5-methoxy-2-oxopyridin-1(2H)-yl}-4-methoxybutanoate (Racemate)

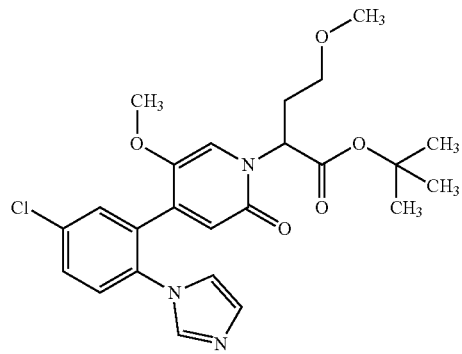 [SMILES: COCCC(C(=O)OC(C)(C)C)n1cc(OC)c(-c2cc(Cl)ccc2-n2ccnc2)cc1=O]

5 ml of dioxane were added to 368 mg (0.504 mmol, purity 58%) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 130 mg (0.504 mmol, 1 eq.) of 1-(2-bromo-4-chlorophenyl)-1H-imidazole and 492 mg (1.51 mmol, 3 eq.) of caesium carbonate. For 5 min, argon was passed through the reaction mixture. 41 mg (0.05 mmol, 0.1 eq) of [1,1-bis(diphenylphosphino)ferrocene]dichloropalladium-dichloromethane complex were then added, and the mixture was stirred at 80° C. overnight. The reaction mixture was filtered through kieselguhr, washing with dichloromethane, and the filtrate was concentrated. The crude product was purified by normal phase chromatography (mobile phase: cyclohexane/ethyl acetate, 30-100%). The product fractions were combined and purified by preparative HPLC (RP18 column, mobile phase: acetonitrile/water gradient with addition of 0.1% formic acid). Yield: 44 mg (18% of theory)

LC/MS [Method 10]: $R_t$=1.33 min; MS (ESIpos): m/z=474 (M+H)$^+$, $^1$H-NMR (400 MHz, DMSO-d$_6$): δ [ppm]=7.67 (dd, 1H), 7.63-7.57 (m, 2H), 7.53 (d, 1H), 7.12 (s, 1H), 7.06 (s, 1H), 6.89 (s, 1H), 6.42 (s, 1H), 5.01-4.92 (m, 1H), 3.36-3.24 (m, 4H), 3.17 (s, 3H), 3.09-2.97 (m, 1H), 2.30-2.19 (m, 2H), 1.38 (s, 9H).

Example 6.9B

2-{4-[5-Chloro-2-(1H-imidazol-1-yl)phenyl]-5-methoxy-2-oxopyridin-1(2H)-yl}-4-methoxybutanoic acid hydrochloride (Racemate)

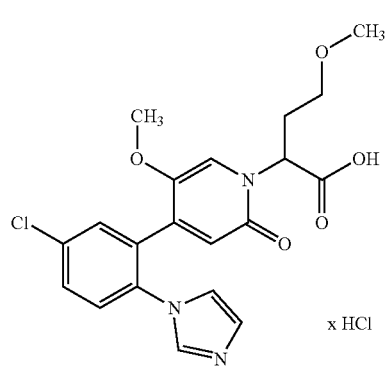 [SMILES: COCCC(C(=O)O)n1cc(OC)c(-c2cc(Cl)ccc2-n2ccnc2)cc1=O]

42 mg (0.089 mmol) of tert-butyl 2-{4-[5-chloro-2-(1H-imidazol-1-yl)phenyl]-5-methoxy-2-oxopyridin-1(2H)-yl}-4-methoxybutanoate (racemate) were reacted in 3.0 ml of a solution of hydrogen chloride in dioxane (4M) according to General Method 6D. Yield: 43 mg (purity 92%, 99% of theory)

LC/MS [Method 1]: $R_t$=0.52 min; MS (ESIpos): m/z=418 (M+H)$^+$, $^1$H-NMR (400 MHz, DMSO-d$_6$): δ [ppm]=9.38 (s, 1H), 7.88-7.71 (m, 5H), 7.15 (s, 1H), 6.51 (s, 1H), 5.02 (br. s, 1H), 3.36-3.25 (m, 4H), 3.15 (s, 3H), 3.03-2.90 (m, 1H), 2.35-2.23 (m, 2H).

Example 69C tert-Butyl 4-[(2-{4-[5-chloro-2-(1H-imidazol-1-yl)phenyl]-5-methoxy-2-oxopyridin-1(2H)-yl}-4-methoxybutanoyl)amino]benzoate (Racemate)

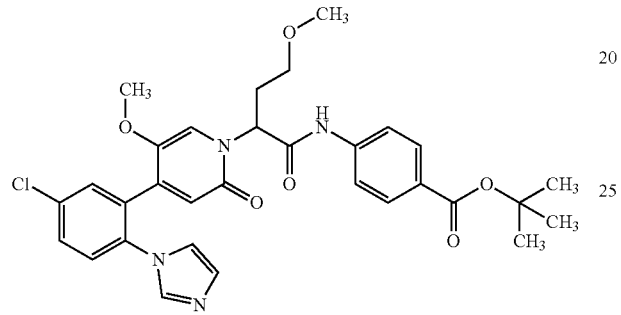

40 mg (purity 92%, 0.081 mmol) of 2-{4-[5-chloro-(1H-imidazol-1-yl)phenyl]-5-methoxy-2-oxopyridin-1(2H)-yl}-4-methoxybutanoic acid hydrochloride (racemate) and 23.5 mg (0.122 mmol) of tert-butyl 4-aminobenzoate in 1 ml of pyridine were reacted according to General Method 5A. Yield: 34.6 mg (72% of theory).

LC/MS [Method 1]: $R_t$=0.93 min; MS (ESIpos): m/z=593 (M+H)$^+$, $^1$H-NMR (400 MHz, DMSO-d$_6$): δ [ppm]=10.65 (br. s, 1H), 7.92-7.81 (m, 2H), 7.77-7.70 (m, 2H), 7.70-7.62 (m, 2H), 7.60 (d, 1H), 7.55 (d, 1H), 7.20 (s, 1H), 7.17-7.13 (m, 1H), 6.92 (s, 1H), 6.44 (s, 1H), 5.72-5.61 (m, 1H), 3.36 (s, 3H), 3.34-3.25 (m, 1H), 3.19 (s, 3H), 3.17-3.09 (m, 1H), 2.39-2.27 (m, 2H), 1.53 (s, 9H).

Example 6.10A tert-Butyl 2-{4-[5-chloro-2-(1,2-oxazol-3-yl)phenyl]-5-methoxy-2-oxopyridin-1(2H)-yl}-4-methoxybutanoate (Racemate)

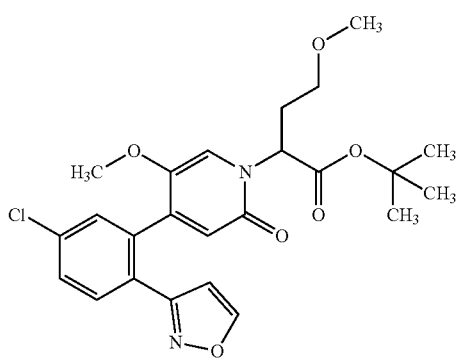 [SMILES: COCCC(C(=O)OC(C)(C)C)n1cc(OC)c(-c2cc(Cl)ccc2-c2ccon2)cc1=O]

3.8 ml of dioxane were added to 2.8 ml of a solution of 264 mg (625 µmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) in dioxane, 170 mg (purity 95%, 625 µmol) of 3-(2-bromo-4-chlorophenyl)-1,2-oxazole and 259 mg (1.87 mmol, 3 eq.) of potassium carbonate. For 5 min, argon was passed through the reaction mixture. 30.6 mg (37.5 µmol) of [1,1-bis(diphenylphosphino)ferrocene]dichloropalladium-dichloromethane complex were then added, and the mixture was stirred at 80° C. overnight. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-70%). Yield: 210 mg (purity 80%, 57% of theory)

LC/MS [Method 1]: $R_t$=1.03 min; MS (ESIpos): m/z=475 (M+H)$^+$,

Example 6.10B

2-{4-[5-Chloro-2-(1,2-oxazol-3-yl)phenyl]-5-methoxy-2-oxopyridin-1(2H)-yl}-4-methoxybutanoic acid (Racemate)

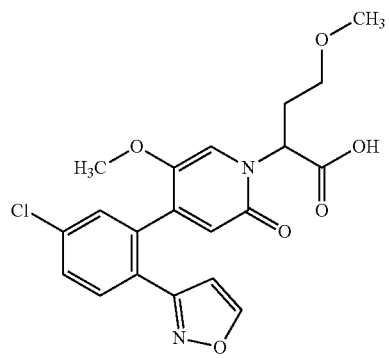 [SMILES: COCCC(C(=O)O)n1cc(OC)c(-c2cc(Cl)ccc2-c2ccon2)cc1=O]

An aqueous lithium hydroxide solution (3.5 ml, 0.50 M, 1.8 mmol) was added to a solution of 210 mg (purity 80%, 354 µmol) of tert-butyl 2-{4-[5-chloro-2-(1,2-oxazol-3-yl)phenyl]-5-methoxy-2-oxopyridin-1(2H)-yl}-4-methoxybutanoate (racemate) in 7.6 ml of tetrahydrofuran, and the mixture was stirred at 35° C. for 20 hours. After cooling, the reaction mixture was neutralized with 1N hydrochloric acid. The mixture was purified by preparative HPLC (RP18 column, mobile phase: acetonitrile/water gradient with addition of 0.1% formic acid). Yield: 140 mg (94% of theory)

LC/MS [Method 1]: $R_t$=0.77 min; MS (ESIpos): m/z=419 (M+H)$^+$,

Example 6.11A tert-Butyl 4-tert-butoxy-2-{4-[5-chloro-2-(1,2-oxazol-3-yl)phenyl]-5-methoxy-2-oxopyridin-1(2H)-yl}butanoate (Racemate)

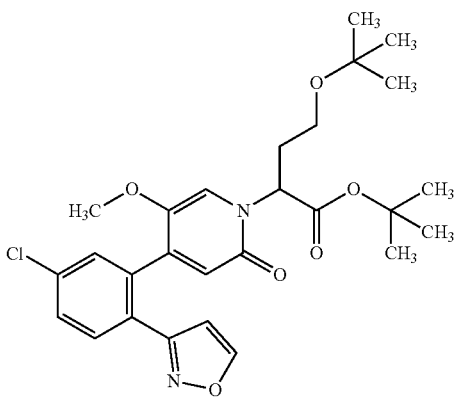 [SMILES: COc1cn(C(CCOC(C)(C)C)C(=O)OC(C)(C)C)c(=O)cc1-c1cc(Cl)ccc1-c1ccon1]

4.6 ml of dioxane were added to 1.7 ml of a solution of 402 mg (purity 68%, 588 µmol) of tert-butyl 4-tert-butoxy-2-[5-methoxy-2-oxo-4-(4,4,5,5-tetramethyl-1,3,2-dioxaborolan-2-yl)pyridin-1(2H)-yl]butanoate (racemate) in dioxane, 160 mg (588 µmol) of 3-(2-bromo-4-chlorophenyl)-1,2-oxazole and 244 mg (1.76 mmol, 3 eq.) of potassium carbonate. For 5 min, argon was passed through the reaction mixture. 28.8 mg (35.3 µmol) of [1,1-bis(diphenylphosphino)ferrocene]-dichloropalladium-dichloromethane complex were then added, and the mixture was stirred at 80° C. overnight. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-35%). Yield: 118 mg (39% of theory)

LC/MS [Method 10]: $R_t$=2.25 min; MS (ESIpos): m/z=517 (M+H)$^+$.

Example 6.11B 4-tert-Butoxy-2-{4-[5-chloro-2-(1,2-oxazol-3-yl)phenyl]-5-methoxy-2-oxopyridin-1(2H)-yl}butanoic acid (Racemate)

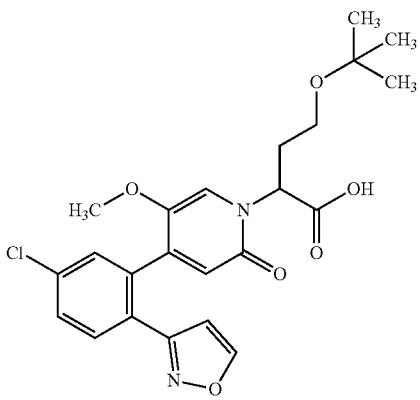 [SMILES: COc1cn(C(CCOC(C)(C)C)C(=O)O)c(=O)cc1-c1cc(Cl)ccc1-c1ccon1]

An aqueous lithium hydroxide solution (1.4 ml, 0.50 M, 700 µmol) was added to a solution of 90.0 mg (purity 80%, 139 µmol) of tert-butyl 4-tert-butoxy-2-{4-[5-chloro-2-(1,2-oxazol-3-yl)phenyl]-5-methoxy-2-oxopyridin-1(2H)-yl}butanoate (racemate) in 3.0 ml of tetrahydrofuran, and the mixture was stirred at RT for 16 hours and then at 40° C. for 2 hours. After cooling, the reaction mixture was neutralized with 1N hydrochloric acid (700 µl, 1.0M, 700 µmol). The mixture was purified by preparative HPLC (RP18 column, mobile phase: acetonitrile/water gradient with addition of 0.1% formic acid). Yield: 56 mg (88% of theory)

LC/MS [Method 1]: $R_t$=0.93 min; MS (ESIpos): m/z=461 (M+H)$^+$.

Example 6.11C

Methyl 4-[(4-tert-butoxy-2-{4-[5-chloro-2-(1,2-oxazol-3-yl)phenyl]-5-methoxy-2-oxopyridin-1(2H)-yl}butanoyl)amino]benzoate (Racemate)

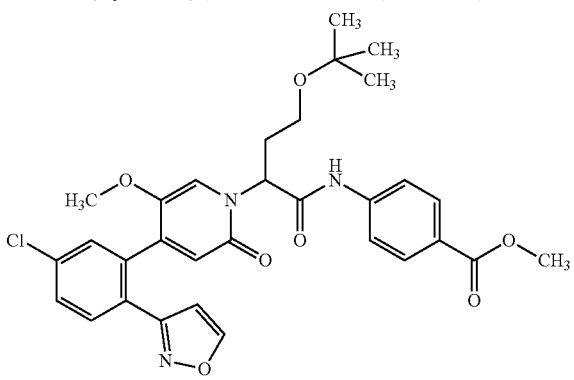

96.0 mg (208 µmol) of 4-tert-butoxy-2-{4-[5-chloro-2-(1,2-oxazol-3-yl)phenyl]-5-methoxy-2-oxopyridin-1(2H)-yl}butanoic acid (racemate) and 48.2 mg (312 µmol) of methyl 4-aminobenzoate in 1.8 ml of pyridine were reacted according to General Method 5A. Yield: 108 mg (87% of theory)

LC/MS [Method 10]: $R_t$=2.15 min; MS (ESIpos): m/z=594 (M+H)$^+$.

Example 6.12A tert-Butyl 2-{4-[5-chloro-2-(1,2-oxazol-3-yl)phenyl]-5-methoxy-2-oxopyridin-1(2H)-yl}-3-[(2S)-tetrahydro-2H-pyran-2-yl]propanoate (Diastereomer Mixture)

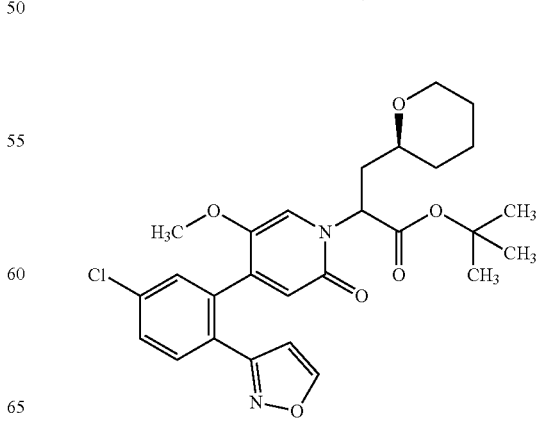

332 mg (2.40 mmol) of potassium carbonate were added to 8.7 ml of a solution of 741 mg (purity 50%, 800 μmol) of tert-butyl 2-[5-methoxy-2-oxo-4-(4,4,5,5-tetramethyl-1,3,2-dioxaborolan-2-yl)pyridin-1(2H)-yl]-3-[(2S)-tetrahydro-2H-pyran-2-yl]propanoate (racemate) in dioxane and 207 mg (800 μmol) of 3-(2-bromo-4-chlorophenyl)-1,2-oxazole. For 5 min, argon was passed through the reaction mixture. 39.2 mg (48.0 μmol) of [1,1-bis(diphenylphosphino)ferrocene]-dichloropalladium-dichloromethane complex were then added, and the mixture was stirred at 80° C. overnight. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-50%). Yield: 350 mg (purity 80%, 68% of theory)

LC/MS [Method 1]: $R_t$=1.19 min; MS (ESIpos): m/z=515 (M+H)$^+$.

Example 612B

2-{4-[5-Chloro-2-(1,2-oxazol-3-yl)phenyl]-5-methoxy-2-oxopyridin-1(2H)-yl}-3-[(2S)-tetrahydro-2H-pyran-2-yl]propanoic acid (Diastereomer Mixture)

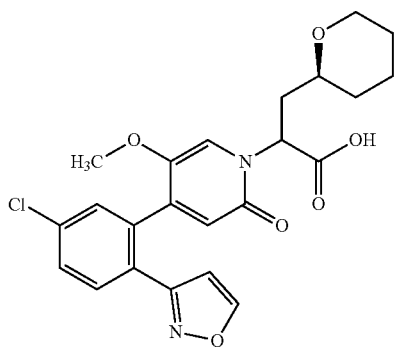 [SMILES: COc1cn(C(C[C@@H]2CCCCO2)C(=O)O)c(=O)cc1-c1cc(Cl)ccc1-c1ccon1]

An aqueous lithium hydroxide solution (5.4 ml, 0.50 M, 2.7 mmol) was added to a solution of 350 mg (purity 80%, 544 μmol) of tert-butyl 2-{4-[5-chloro-2-(1,2-oxazol-3-yl)phenyl]-5-methoxy-2-oxopyridin-1(2H)-yl}-3-[(2S)-tetrahydro-2H-pyran-2-yl]propanoate (diastereomer mixture) in 12 ml of tetrahydrofuran, and the mixture was stirred at 35° C. for 20 hours. After cooling, the reaction mixture was neutralized with 1N hydrochloric acid (2.7 ml, 1.0M, 2.7 mmol). The mixture was purified by preparative HPLC (RP18 column, mobile phase: acetonitrile/water gradient with addition of 0.1% formic acid). Yield: 190 mg (76% of theory)

LC/MS [Method 1]: $R_t$=0.93 min; MS (ESIpos): m/z=459 (M+H)$^+$.

Example 6.13A tert-Butyl 2-{4-[5-chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoate (Diastereomer Mixture)

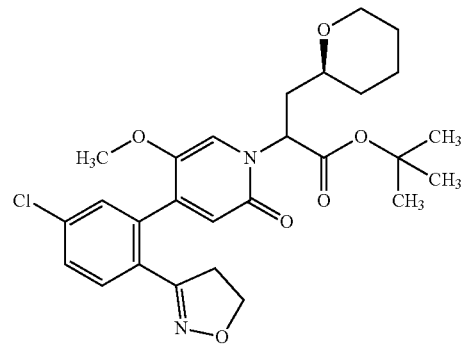 [SMILES: COc1cn(C(C[C@@H]2CCCCO2)C(=O)OC(C)(C)C)c(=O)cc1-c1cc(Cl)ccc1C1=NOCC1]

9 ml of dioxane were added to 5.0 ml of a solution of 899 mg (purity 67%, 1.30 mmol) of tert-butyl 2-[5-methoxy-2-oxo-4-(4,4,5,5-tetramethyl-1,3,2-dioxaborolan-2-yl)pyridin-1(2H)-yl]-3-[(2S)-tetrahydro-2H-pyran-2-yl]propanoate (diastereomer mixture) in dioxane, 339 mg (1.30 mmol) of 3-(2-bromo-4-chlorophenyl)-4,5-dihydro-1,2-oxazole and 539 mg (3.90 mmol, 3 eq.) of potassium carbonate. For 5 min, argon was passed through the reaction mixture. 63.7 mg (78 μmol) of [1,1-bis(diphenylphosphino)ferrocene]dichloropalladium-dichloromethane complex were then added, and the mixture was stirred at 80° C. for 9 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-50%). Yield: 410 mg (purity 80%, 49% of theory)

LC/MS [Method 1]: $R_t$=1.10 min; MS (ESIpos): m/z=517 (M+H)$^+$.

Example 6.13B

2-{4-[5-Chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoic acid (Diastereomer Mixture)

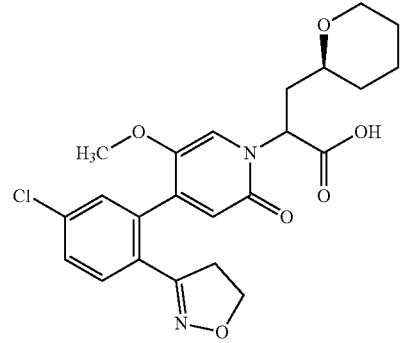 [SMILES: COc1cn(C(C[C@@H]2CCCCO2)C(=O)O)c(=O)cc1-c1cc(Cl)ccc1C1=NOCC1]

450 mg (purity 80%, 696 μmol) of tert-butyl 2-{4-[5-chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoate (diastereomer mixture) were reacted in 25 ml of a solution of hydrogen chloride in dioxane (4M) according to General Method 6D. Yield: 270 mg (84% of theory)

LC/MS [Method 1]: R$_t$=0.88 min; MS (ESIpos): m/z=461 (M+H)$^+$.

Example 6.14A tert-Butyl 2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoate (Diastereomer Mixture)

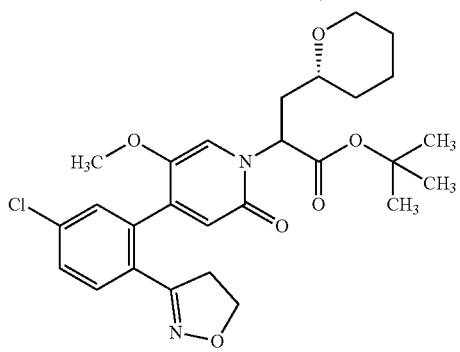

20 ml of dioxane were added to 500 mg (1.92 mmol) of 3-(2-bromo-4-chlorophenyl)-4,5-dihydro-1,2-oxazole, 2.07 g (purity 43%, 1.92 mmol) of tert-butyl 2-[5-methoxy-2-oxo-4-(4,4,5,5-tetramethyl-1,3,2-dioxaborolan-2-yl)pyridin-1(2H)-yl]-3-[(2R)-tetrahydro-2H-pyran-2-yl]propanoate (diastereomer mixture) and 796 mg (5.76 mmol) of potassium carbonate. For 5 min, argon was passed through the reaction mixture. 47.0 mg (57.6 μmol) of [1,1-bis(diphenylphosphino)ferrocene]dichloropalladium-dichloromethane complex were then added, and the mixture was stirred at 80° C. overnight. The reaction mixture was filtered through kieselguhr, washing with dichloromethane, and the filtrate was concentrated. The crude product was purified by normal phase chromatography (mobile phase: cyclohexane/ethyl acetate, 0-50%). Yield: 430 mg (80% pure, 35% of theory).

LC/MS [Method 1]: R$_t$=1.10 min; MS (ESIpos): m/z=517 (M+H)$^+$.

Example 6.14B

2-{4-[5-Chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoic acid (Diastereomer Mixture)

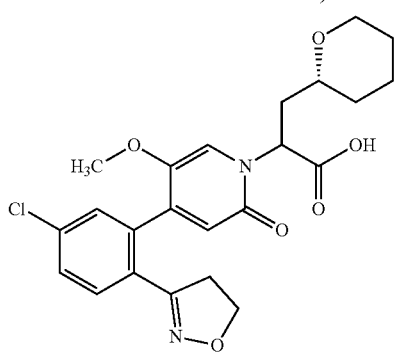

430 mg (purity 80%, 665 μmol) of tert-butyl 2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoate (diastereomer mixture) were reacted in 9.0 ml of a solution of hydrogen chloride in dioxane (4M) according to General Method 6D. Yield: 286 mg (93% of theory)

LC/MS [Method 1]: R$_t$=0.86 min; MS (ESIpos): m/z=461 (M+H)$^+$.

Example 6.14C

Methyl 4-[(2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoyl)amino]benzoate (Diastereomer Mixture)

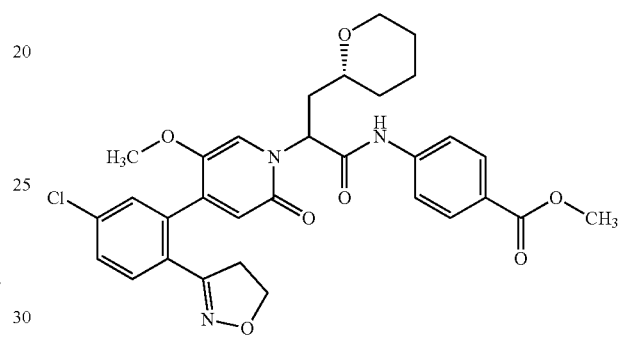

86.0 mg (187 μmol) of 2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoic acid (diastereomer mixture) and 43.2 mg (280 μmol, 1.5 eq.) of methyl 4-aminobenzoate in 2.0 ml of pyridine were reacted according to General Method 5A. Yield: 98 mg (89% of theory).

LC/MS [Method 10]: R$_t$=2.01/2.04 min; MS (ESIpos): m/z=594/594 (M+H)$^+$.

Example 6.15A tert-Butyl 2-{4-[5-chloro-2-(4,5-dihydro-1,2-oxazol-3-yl)phenyl]-5-methoxy-2-oxopyridin-1(2H)-yl}-3-[1,4-dioxan-2-yl]propanoate (Diastereomer Mixture)

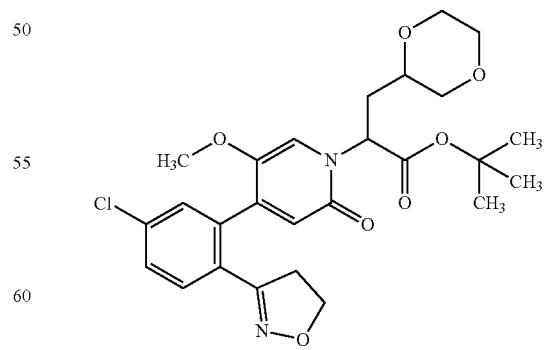

15 ml of dioxane were added to 1.06 g (purity 67%, 1.52 mmol) of tert-butyl 3-[1,4-dioxan-2-yl]-2-[5-methoxy-2-oxo-4-(4,4,5,5-tetramethyl-1,3,2-dioxaborolan-2-yl)pyridin-1(2H)-yl]propanoate (diastereomer mixture), 400 mg (1.52 mmol) of 3-(2-bromo-4-chlorophenyl)-4,5-dihydro-1,2-oxazole and 630 mg (4.56 mmol, 3 eq.) of potassium carbonate. For 5 min, argon was passed through the reaction mixture. 74.5 mg (91.2 µmol) of [1,1-bis(diphenylphosphino)ferrocene]dichloropalladium-dichloromethane complex were then added, and the mixture was stirred at 80° C. for 16 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-50%). Yield: 422 mg (94% pure, 50% of theory).

LC/MS [Method 10]: $R_t$=1.81 min; MS (ESIpos): m/z=519 (M+H)$^+$.

Example 6.15B

2-{4-[5-Chloro-2-(4,5-dihydro-1,2-oxazol-3-yl)phenyl]-5-methoxy-2-oxopyridin-1(2H)-yl}-3-[1,4-dioxan-2-yl]propanoic acid (Diastereomer Mixture)

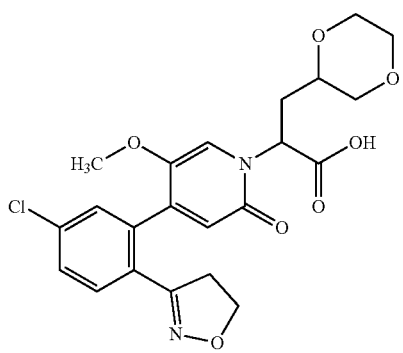 [SMILES: COc1cn(C(CC2COCCO2)C(=O)O)c(=O)cc1-c1cc(Cl)ccc1C1=NOCC1]

421 mg (purity 94%, 763 µmol) of tert-butyl 2-{4-[5-chloro-2-(4,5-dihydro-1,2-oxazol-3-yl)phenyl]-5-methoxy-2-oxopyridin-1(2H)-yl}-3-[1,4-dioxan-2-yl]propanoate (diastereomer mixture) were reacted in 7.6 ml of a solution of hydrogen chloride in dioxane (4M) according to General Method 6D. Yield: 359 mg (purity 85%, 86% of theory)

LC/MS [Method 1]: $R_t$=0.76 min; MS (ESIpos): m/z=463 (M+H)$^+$.

Example 6.15C

Methyl 4-{[2-{4-[5-chloro-2-(4,5-dihydro-1,2-oxazol-3-yl)phenyl]-5-methoxy-2-oxopyridin-1(2H)-yl}-3-(1,4-dioxan-2-yl)propanoyl]amino}benzoate (Diastereomer Mixture)

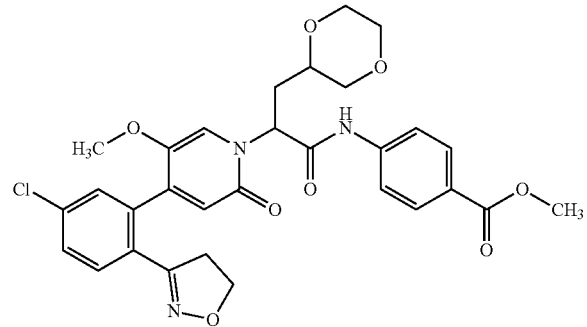 [SMILES: COC(=O)c1ccc(NC(=O)C(CC2COCCO2)n2cc(OC)c(-c3cc(Cl)ccc3C3=NOCC3)cc2=O)cc1]

60.0 mg (purity 85%, 110 µmol) of 2-{4-[5-chloro-2-(4,5-dihydro-1,2-oxazol-3-yl)phenyl]-5-methoxy-2-oxopyridin-1(2H)-yl}-3-(1,4-dioxan-2-yl)propanoic acid (diastereomer mixture) and 25.5 mg (165 µmol, 1.5 eq.) of methyl 4-aminobenzoate in 1.0 ml of pyridine were reacted according to General Method 5A. Yield: 56 mg (84% of theory)

LC/MS [Method 10]: $R_t$=1.78/1.81 min; MS (ESIpos): m/z=596/596 (M+H)$^+$.

Example 6.16A tert-Butyl 4-tert-butoxy-2-{4-[5-chloro-2-(4,5-dihydro-1,2-oxazol-3-yl)phenyl]-5-methoxy-2-oxopyridin-1(2H)-yl}butanoate (Racemate)

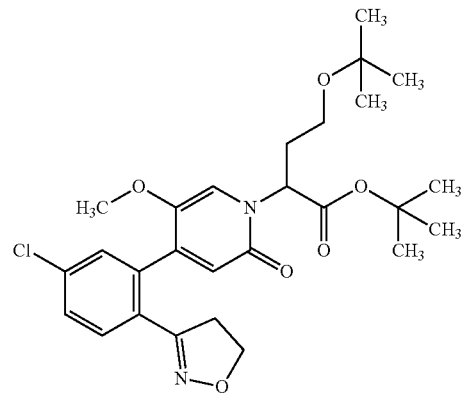 [SMILES: COc1cn(C(CCOC(C)(C)C)C(=O)OC(C)(C)C)c(=O)cc1-c1cc(Cl)ccc1C1=NOCC1]

6.6 ml of dioxane were added to 190 mg (0.73 mmol) of 3-(2-bromo-4-chlorophenyl)-4,5-dihydro-1,2-oxazole, 500 mg (purity 68%, 0.73 mmol) of tert-butyl 4-tert-butoxy-2-[5-methoxy-2-oxo-4-(4,4,5,5-tetramethyl-1,3,2-dioxaborolan-2-yl)pyridin-1(2H)-yl]butanoate (racemate) and 303 mg (2.19 mmol) of potassium carbonate. For 5 min, argon was passed through the reaction mixture. 17.9 mg (0.022 µmol) of [1,1-bis(diphenylphosphino)ferrocene]dichloropalladium-dichloromethane complex were then added, and the mixture was stirred at 80° C. overnight. The reaction mixture was filtered through kieselguhr, washing with ethyl acetate and the filtrate was concentrated. The crude product was purified by normal phase chromatography (cyclohexane/ethyl acetate gradient). Yield: 227 mg (58% of theory).

LC/MS [Method 1]: $R_t$=1.14 min; MS (ESIpos): m/z=519 (M+H)$^+$.

Example 6.16B 4-tert-Butoxy-2-{4-[5-chloro-2-(4,5-dihydro-1,2-oxazol-3-yl)phenyl]-5-methoxy-2-oxopyridin-1(2H)-yl}butanoic acid (Racemate)

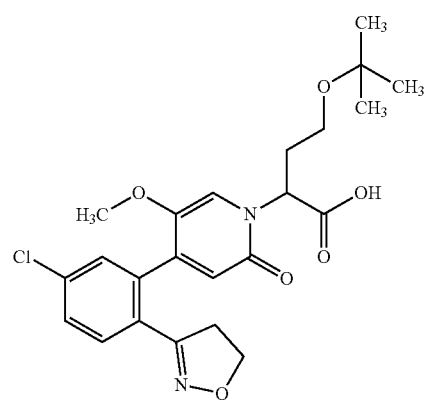 [SMILES: COc1cn(C(CCOC(C)(C)C)C(=O)O)c(=O)cc1-c1cc(Cl)ccc1C1=NOCC1]

225 mg (433 µmol) of tert-butyl 4-tert-butoxy-2-{4-[5-chloro-2-(4,5-dihydro-1,2-oxazol-3-yl)phenyl]-5-methoxy-2-oxopyridin-1(2H)-yl}butanoate (racemate) were reacted in 2.5 ml of a solution of hydrogen chloride in dioxane (4M) according to General Method 6D. Yield: 58 mg (26% of theory).

LC/MS [Method 10]: $R_t$=1.68 min; MS (ESIpos): m/z=463 (M+H)$^+$.

Example 6.16C

Methyl 4-[(4-tert-butoxy-2-{4-[5-chloro-2-(4,5-dihydro-1,2-oxazol-3-yl)phenyl]-5-methoxy-2-oxopyridin-1(2H)-yl}butanoyl)amino]benzoate (Racemate)

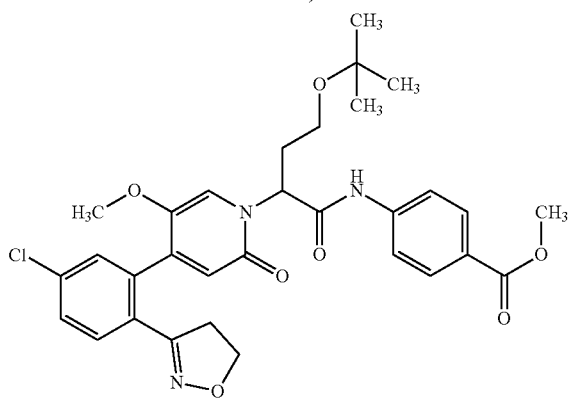

57.0 mg (0.12 mmol) of 4-tert-butoxy-2-{4-[5-chloro-2-(4,5-dihydro-1,2-oxazol-3-yl)phenyl]-5-methoxy-2-oxopyridin-1(2H)-yl}butanoic acid (racemate) and 27.9 mg (0.19 mmol) of methyl 4-aminobenzoate in 0.67 ml of pyridine were reacted according to General Method 5A. Yield: 53 mg (71% of theory).

LC/MS [Method 1]: $R_t$=1.16 min; MS (ESIpos): m/z=596 (M+H)$^+$, $^1$H-NMR (400 MHz, DMSO-$d_6$): δ [ppm]=10.73 (s, 1H), 7.93 (d, 2H), 7.80 (d, 2H), 7.68-7.62 (m, 1H), 7.62-7.55 (m, 1H), 7.40 (br. s., 1H), 7.30 (s, 1H), 6.36 (s, 1H), 5.79-5.69 (m, 1H), 4.32-4.21 (m, 2H), 3.83 (s, 3H), 3.57 (s, 3H), 3.40-3.15 (m, partially hidden), 2.38-2.25 (m, 2H), 1.06 (s, 9H).

Example 6.17A tert-Butyl 2-{4-[5-chloro-2-(4-fluoro-1H-imidazol-1-yl)phenyl]-5-methoxy-2-oxopyridin-1(2H)-yl}-4-methoxybutanoate (Racemate)

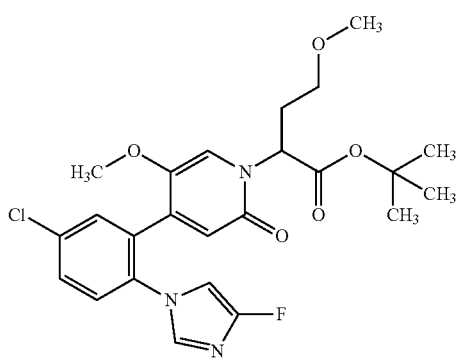 [SMILES: COCCC(C(=O)OC(C)(C)C)n1cc(OC)c(-c2cc(Cl)ccc2-n2cnc(F)c2)cc1=O]

Under argon and in a microwave vessel, 3.5 ml of dioxane were added to 265 mg (purity 55%, 345 mol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 95.0 mg (345 µmol) of 1-(2-bromo-4-chlorophenyl)-4-fluoro-1H-imidazole and 28.2 mg (34.5 µmol) of [1,1-bis(diphenylphosphino)ferrocene]dichloropalladium-dichloromethane complex. 520 µl (2.0 M, 1.0 mmol) of an aqueous sodium carbonate solution were then added, and the mixture was stirred at 100° C. in the microwave for 2 hours. The reaction mixture was filtered through kieselguhr, washing with dichloromethane and acetonitrile, and the filtrate was concentrated. The crude material was combined with a further amount of reaction product prepared from 69.8 mg (purity 55%, 91 µmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 25.0 mg (91 µmol) of 1-(2-bromo-4-chlorophenyl)-4-fluoro-1H-imidazole. The combined crude products were purified by normal phase chromatography (mobile phase: cyclohexane/ethyl acetate, 50-100%). Yield: 212 mg (purity 80%, 78% of theory)

LC/MS [Method 10]: $R_t$=1.85 min; MS (ESIpos): m/z=492 (M+H)$^+$.

Example 6.17B

2-{4-[5-Chloro-2-(4-fluoro-1H-imidazol-1-yl)phenyl]-5-methoxy-2-oxopyridin-1(2H)-yl}-4-methoxybutanoic acid (Racemate)

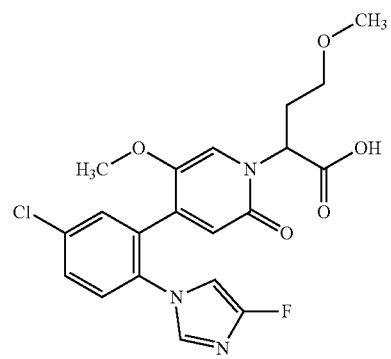 [SMILES: COCCC(C(=O)O)n1cc(OC)c(-c2cc(Cl)ccc2-n2cnc(F)c2)cc1=O]

210 mg (purity 80%, 341 µmol) of tert-butyl 2-{4-[5-chloro-2-(4-fluoro-1H-imidazol-1-yl)phenyl]-5-methoxy-2-oxopyridin-1(2H)-yl}-4-methoxybutanoate (racemate) were reacted in 4.0 ml of a solution of hydrogen chloride in dioxane (4M) according to General Method 6D. Yield: 85.4 mg (57% of theory)

LC/MS [Method 10]: $R_t$=1.33 min; MS (ESIpos): m/z=436 (M+H)$^+$.

Example 6.18A tert-Butyl 2-{4-[5-chloro-2-(4-chloro-1H-imidazol-1-yl)phenyl]-5-methoxy-2-oxopyridin-1(2H)-yl}-4-methoxybutanoate (Racemate)

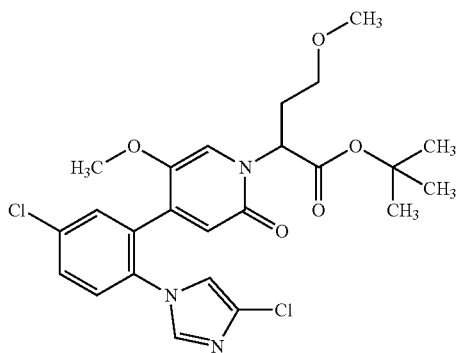 [SMILES: COCCC(C(=O)OC(C)(C)C)n1cc(OC)c(-c2cc(Cl)ccc2-n2cnc(Cl)c2)cc1=O]

16 ml of dioxane were added to 475 mg (1.56 mmol) of 1-(2-bromo-4-chlorophenyl)-4-chloro-1H-imidazole, 1.20 g (purity 55%, 1.56 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 648 mg (4.69 mmol) of potassium carbonate. For 5 min, argon was passed through the reaction mixture. 76.5 mg (94 µmol) of [1,1-bis(diphenylphosphino)ferrocene]dichloropalladium-dichloromethane complex were then added, and the mixture was stirred at 50° C. for 5 hours, at 80° C. for 24 hours and at 90° C. for 24 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 50-100%). Yield: 345 mg (43% of theory).

LC/MS [Method 10]: $R_t$=1.89 min; MS (ESIpos): m/z=508 (M+H)$^+$.

Example 6.18B

2-{4-[5-Chloro-2-(4-chloro-1H-imidazol-1-yl)phenyl]-5-methoxy-2-oxopyridin-1(2H)-yl}-4-methoxybutanoic acid hydrochloride (Racemate)

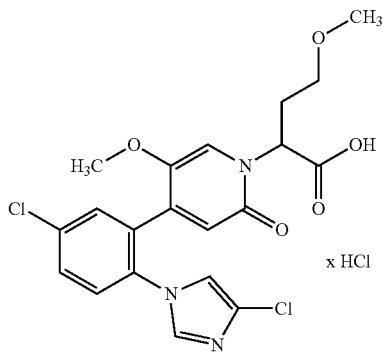 [SMILES: COCCC(C(=O)O)n1cc(OC)c(-c2cc(Cl)ccc2-n2cnc(Cl)c2)cc1=O]

344 mg (670 µmol) of tert-butyl 2-{4-[5-chloro-2-(4-chloro-1H-imidazol-1-yl)phenyl]-5-methoxy-2-oxopyridin-1(2H)-yl}-4-methoxybutanoate (racemate) were reacted in 6.7 ml of a solution of hydrogen chloride in dioxane (4M) according to General Method 6D. Yield: 345 mg (purity 92%, 97% of theory)

LC/MS [Method 10]: $R_t$=1.35 min; MS (ESIpos): m/z=452 (M+H)$^+$.

Example 6.19A tert-Butyl 2-[4-{5-chloro-2-[4-(difluoromethyl)-1H-imidazol-1-yl]phenyl}-5-methoxy-2-oxopyridin-1(2H)-yl]-4-methoxybutanoate (Racemate)

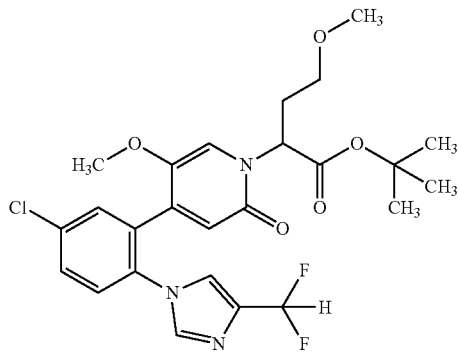 [SMILES: COCCC(C(=O)OC(C)(C)C)n1cc(OC)c(-c2cc(Cl)ccc2-n2cnc(C(F)F)c2)cc1=O]

Under argon and in a microwave vessel, 6.5 ml of dioxane were added to 496 mg (purity 55%, 644 mol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 200 mg (644 µmol) of 1-(2-bromo-4-chlorophenyl)-4-(difluoromethyl)-1H-imidazole and 52.6 mg (64.4 µmol) of [1,1-bis(diphenylphosphino)ferrocene]dichloropalladium-dichloromethane complex. 970 µl (2.0 M, 1.9 mmol) of an aqueous sodium carbonate solution were then added, and the mixture was stirred at 100° C. in the microwave for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 50-100%). Yield: 227 mg (purity 92%, 62% of theory)

LC/MS [Method 10]: $R_t$=1.83 min; MS (ESIpos): m/z=524 (M+H)$^+$.

Example 6.19B

2-[4-{5-Chloro-2-[4-(difluoromethyl)-1H-imidazol-1-yl]phenyl}-5-methoxy-2-oxopyridin-1(2H)-yl]-4-methoxybutanoic acid hydrochloride (Racemate)

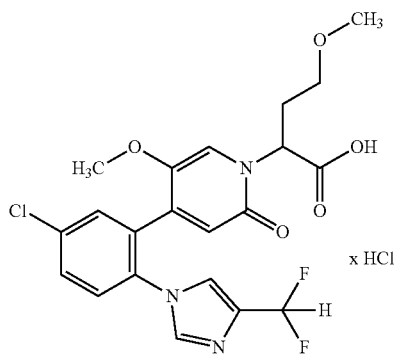 [SMILES: COCCC(C(=O)O)n1cc(OC)c(-c2cc(Cl)ccc2-n2cnc(C(F)F)c2)cc1=O]

227 mg (purity 92%, 399 μmol) of tert-butyl 2-[4-{5-chloro-2-[4-(difluoromethyl)-1H-imidazol-1-yl]phenyl}-5-methoxy-2-oxopyridin-1(2H)-yl]-4-methoxybutanoate (racemate) were reacted in 4.0 ml of a solution of hydrogen chloride in dioxane (4M) according to General Method 6D. Yield: 215 mg (purity 90%, 96% of theory)

LC/MS [Method 1]: $R_t$=0.79 min; MS (ESIpos): m/z=468 (M+H)⁺.

Example 6.20A tert-Butyl 2-[4-{5-chloro-2-[1-(difluoromethyl)-1H-pyrazol-4-yl]phenyl}-5-methoxy-2-oxopyridin-1(2H)-yl]-4-methoxybutanoate (Racemate)

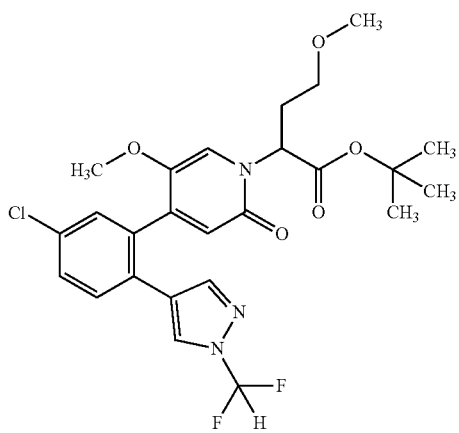 [SMILES: COCCC(C(=O)OC(C)(C)C)n1cc(OC)c(-c2cc(Cl)ccc2-c2cnn(C(F)F)c2)cc1=O]

Under argon and in a microwave vessel, 1.32 g (purity 50%, 1.56 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 401 mg (1.30 mmol) of 4-(2-bromo-4-chlorophenyl)-1-(difluoromethyl)-1H-pyrazole and 414 mg (3.91 mmol) of sodium carbonate were initially charged in a mixture of 3.48 ml of DMF and 1.08 ml of water, and the solution was flushed with argon. 106 mg (0.13 mmol) of [1,1-bis(diphenylphosphino)ferrocene]dichloropalladium/dichloromethane complex were then added, and the mixture was shaken in a closed vessel at 100° C. for 2 hours. The reaction mixture was diluted with ethyl acetate and water, the phases were separated and the aqueous phase was re-extracted three times with ethyl acetate. The collected organic phases were dried over magnesium sulphate, filtered and concentrated. The residue was purified by flash silica gel chromatography (cyclohexane/ethyl acetate gradient). The crude product obtained in this manner was reacted without further purification. Yield: 663 mg (97% of theory).

LC/MS [Method 10]: $R_t$=2.05 min; MS (ESIpos): m/z=524 (M+H)⁺.

Example 6.20B

2-[4-{5-Chloro-2-[1-(difluoromethyl)-1H-pyrazol-4-yl]phenyl}-5-methoxy-2-oxopyridin-1(2H)-yl]-4-methoxybutanoic acid (Racemate)

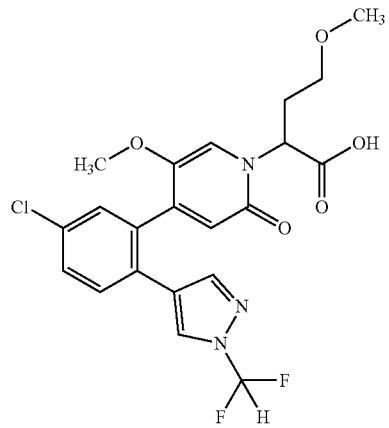 [SMILES: COCCC(C(=O)O)n1cc(OC)c(-c2cc(Cl)ccc2-c2cnn(C(F)F)c2)cc1=O]

661 mg (1.26 mmol) of tert-butyl 2-[4-{5-chloro-2-[1-(difluoromethyl)-1H-pyrazol-4-yl]phenyl}-5-methoxy-2-oxopyridin-1(2H)-yl]-4-methoxybutanoate (racemate) were reacted in 19.0 ml of a solution of hydrogen chloride in dioxane (4M) according to General Method 6D. Yield: 636 mg (99% of theory).

LC/MS [Method 10]: $R_t$=1.54 min; MS (ESIpos): m/z=468 (M+H)⁺.

Example 6.21A tert-Butyl 2-{4-[5-chloro-2-(3-methyl-1,2,4-oxadiazol-5-yl)phenyl]-5-methoxy-2-oxopyridin-1(2H)-yl}-4-methoxybutanoate (Racemate)

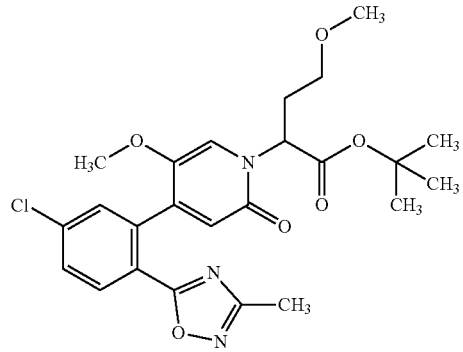 [SMILES: COCCC(C(=O)OC(C)(C)C)n1cc(OC)c(-c2cc(Cl)ccc2-c2nc(C)no2)cc1=O]

Analogously to Example 6.20A, 2.36 g (purity 50%, 2.79 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) were reacted with 636 mg (2.33 mmol) of 5-(2-bromo-4-chlorophenyl)-3-methyl-1,2,4-oxadiazole. The crude product obtained in this manner was reacted without further purification. Yield: 720 mg (63% of theory).

LC/MS [Method 10]: $R_t$=1.99 min; MS (ESIpos): m/z=490 (M+H)⁺.

Example 6.21B

2-{4-[5-Chloro-2-(3-methyl-1,2,4-oxadiazol-5-yl) phenyl]-5-methoxy-2-oxopyridin-1(2H)-yl}-4-methoxybutanoic acid (Racemate)

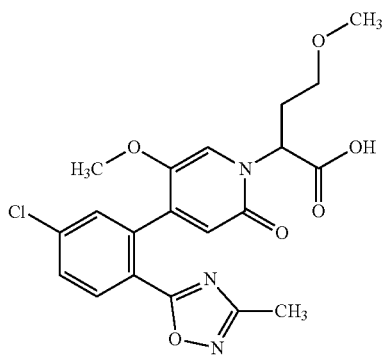 [SMILES: COCCC(C(=O)O)n1cc(OC)c(-c2cc(Cl)ccc2-c2nc(C)no2)cc1=O]

719 mg (1.47 mmol) of tert-butyl 2-{4-[5-chloro-2-(3-methyl-1,2,4-oxadiazol-5-yl)phenyl]-5-methoxy-2-oxopyridin-1(2H)-yl}-4-methoxybutanoate (racemate) were reacted in 22.0 ml of a solution of hydrogen chloride in dioxane (4M) according to General Method 6D. Yield: 505 mg (75% of theory).

LC/MS [Method 1]: $R_t$=0.79 min; MS (ESIpos): m/z=434 (M+H)$^+$.

Example 6.22A tert-Butyl 4-tert-butoxy-2-{4-[5-chloro-2-(3-methyl-1,2,4-oxadiazol-5-yl)phenyl]-5-methoxy-2-oxopyridin-1(2H)-yl}butanoate (Racemate)

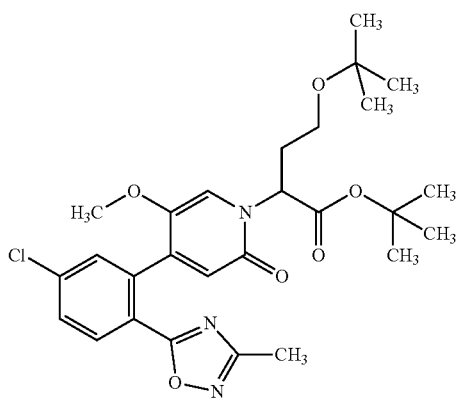 [SMILES: COc1cn(C(CCOC(C)(C)C)C(=O)OC(C)(C)C)c(=O)cc1-c1cc(Cl)ccc1-c1nc(C)no1]

Analogously to Example 6.25A, 749 mg (purity 60%, 0.97 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) were reacted with 240 mg (0.88 mmol) of 5-(2-bromo-4-chlorophenyl)-3-methyl-1,2,4-oxadiazole. Yield: 217 mg (46% of theory).

LC/MS [Method 10]: $R_t$=2.31 min; MS (ESIpos): m/z=532 (M+H)$^+$.

Example 6.22B 4-tert-Butoxy-2-{4-[5-chloro-2-(3-methyl-1,2,4-oxadiazol-5-yl)phenyl]-5-methoxy-2-oxopyridin-1(2H)-yl}butanoic acid (Racemate)

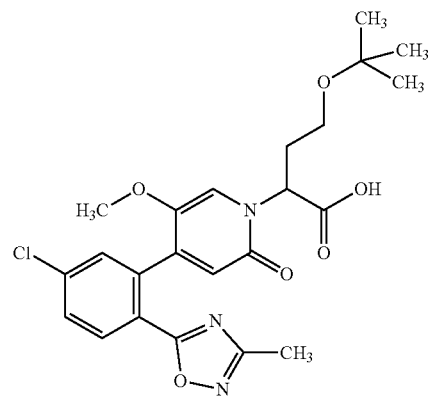 [SMILES: COc1cn(C(CCOC(C)(C)C)C(=O)O)c(=O)cc1-c1cc(Cl)ccc1-c1nc(C)no1]

215 mg (0.40 mmol) of tert-butyl 4-tert-butoxy-2-{4-[5-chloro-2-(3-methyl-1,2,4-oxadiazol-5-yl)phenyl]-5-methoxy-2-oxopyridin-1(2H)-yl}butanoate (racemate) were initially charged in 13 ml of THF, 4.04 ml (1M, 4.04 mmol) of aqueous lithium hydroxide solution were then added and the mixture was stirred at RT for 2 days. Subsequently, the mixture was diluted with 21 ml of saturated aqueous ammonium chloride solution and 31 ml of hydrochloric acid (1M) and extracted three times with in each case 30 ml of ethyl acetate. The collected organic phases were dried over sodium sulphate, filtered and concentrated. Yield: 155 mg (81% of theory).

LC/MS [Method 10]: $R_t$=1.75 min; MS (ESIpos): m/z=476 (M+H)$^+$.

Example 6.23A tert-Butyl 2-[4-{5-chloro-2-[1-(2,2,2-trifluoroethyl)-1H-pyrazol-4-yl]phenyl}-5-methoxy-2-oxopyridin-1(2H)-yl]-4-methoxybutanoate (Racemate)

Analogously to Example 6.20A, 407 mg (purity 50%, 0.48 mmol) of tert-butyl 4-methoxy-2-[5-methoxy-2-oxo-4-

(4,4,5,5-tetramethyl-1,3,2-dioxaborolan-2-yl)pyridin-1(2H)-yl]butanoate (racemate) were reacted with 136 mg (0.40 mmol) of 4-(2-bromo-4-chlorophenyl)-1-(2,2,2-trifluoroethyl)-1H-pyrazole. The crude product obtained in this manner was reacted without further purification. Yield: 191 mg (86% of theory).

LC/MS [Method 10]: $R_t$=2.07 min; MS (ESIpos): m/z=556 (M+H)$^+$.

Example 6.23B

2-[4-{5-Chloro-2-[1-(2,2,2-trifluoroethyl)-1H-pyrazol-4-yl]phenyl}-5-methoxy-2-oxopyridin-1(2H)-yl]-4-methoxybutanoic acid (Racemate)

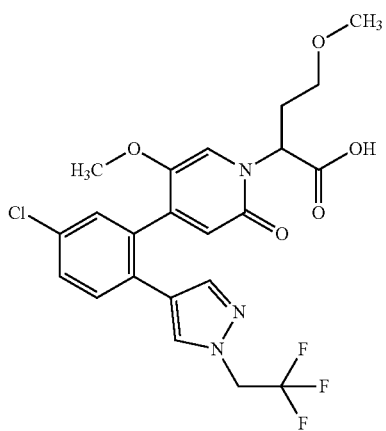 [SMILES: COCCC(C(=O)O)n1cc(OC)c(-c2cc(Cl)ccc2-c2cnn(CC(F)(F)F)c2)cc1=O]

191 mg (0.34 mmol) of tert-butyl 2-[4-{5-chloro-2-[1-(2,2,2-trifluoroethyl)-1H-pyrazol-4-yl]phenyl}-5-methoxy-2-oxopyridin-1(2H)-yl]-4-methoxybutanoate (racemate) were reacted in 5.1 ml of a solution of hydrogen chloride in dioxane (4M) according to General Method 6D. Yield: 177 mg (quantitative)

LC/MS [Method 10]: $R_t$=1.57 min; MS (ESIpos): m/z=500 (M+H)$^+$.

Example 6.24A

2-{4-[5-Chloro-2-(4-chloro-1H-1,2,3-triazol-1-yl)phenyl]-5-methoxy-2-oxopyridin-1(2H)-yl}-4-methoxybutanoic acid (Racemate)

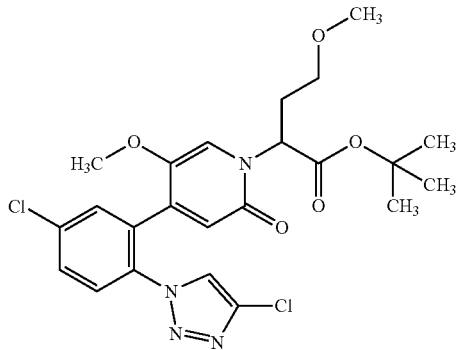

Analogously to Example 6.20A, 1.04 g (purity 50%, 1.23 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) were reacted with 300 mg (1.02 mmol) of 1-(2-bromo-4-chlorophenyl)-4-chloro-1H-1,2,3-triazole. The crude product obtained in this manner was reacted without further purification. Yield: 348 mg (54% of theory)

LC/MS [Method 10]: $R_t$=1.96 min; MS (ESIpos): m/z=509 (M+H)$^+$.

Example 6.24B

2-{4-[5-Chloro-2-(4-chloro-1H-1,2,3-triazol-1-yl)phenyl]-5-methoxy-2-oxopyridin-1(2H)-yl}-4-methoxybutanoic acid (Racemate)

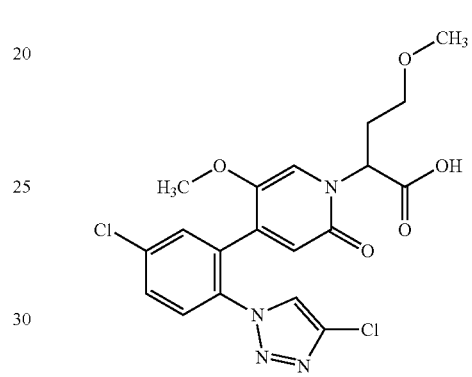

348 mg (purity 81%, 553 µmol) of tert-butyl 2-{4-[5-chloro-2-(4-chloro-1H-1,2,3-triazol-1-yl)phenyl]-5-methoxy-2-oxopyridin-1(2H)-yl}-4-methoxybutanoate (racemate) were reacted in 8.29 ml of a solution of hydrogen chloride in dioxane (4M) according to General Method 6D. Yield: 280 mg (83% of theory).

LC/MS [Method 10]: $R_t$=1.41 min; MS (ESIpos): m/z=453 (M+H)$^+$.

Example 6.25A tert-Butyl 4-tert-butoxy-2-{4-[5-chloro-2-(4-chloro-1H-1,2,3-triazol-1-yl)phenyl]-5-methoxy-2-oxopyridin-1(2H)-yl}butanoate (Racemate)

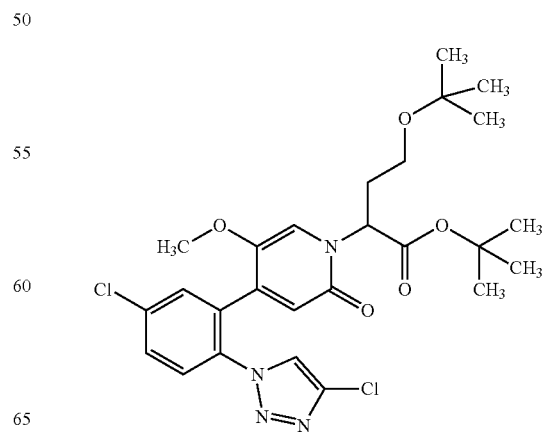

Under argon, 891 mg (purity 50%, 0.95 mmol) of tert-butyl 4-tert-butoxy-2-[5-methoxy-2-oxo-4-(4,4,5,5-tetramethyl-1,3,2-dioxaborolan-2-yl)pyridin-1(2H)-yl]butanoate (racemate), 279 mg (0.95 mmol) of 1-(2-bromo-4-chlorophenyl)-4-chloro-1H-1,2,3-triazole and 395 mg (2.85 mmol) of potassium carbonate were initially charged in 10.0 ml of dioxane, and the solution was flushed with argon. 23.3 mg (0.029 mmol) of [1,1-bis(diphenylphosphino)ferrocene]dichloropalladium/dichloromethane complex were then added, and the mixture was stirred at 80° C. for 2.5 hours and at RT overnight. The reaction mixture was filtered through kieselguhr and the filter residue was washed with dichloromethane. The filtrate was concentrated and the residue was separated by flash silica gel chromatography (cyclohexane/ethyl acetate gradient). Yield: 117 mg (21% of theory).

LC/MS [Method 10]: $R_t$=2.25 min; MS (ESIpos): m/z=551 (M+H)$^+$.

Example 6.25B 4-tert-Butoxy-2-{4-[5-chloro-2-(4-chloro-1H-1,2,3-triazol-1-yl)phenyl]-5-methoxy-2-oxopyridin-1(2H)-yl}butanoic acid (Racemate)

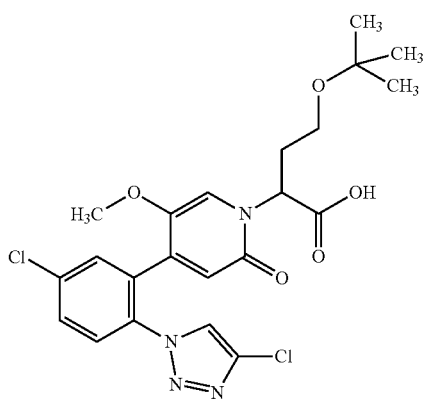 [SMILES: COc1cn(C(CCOC(C)(C)C)C(=O)O)c(=O)cc1-c1cc(Cl)ccc1-n1cc(Cl)nn1]

1.04 ml (1M, 1.04 mmol) of aqueous lithium hydroxide solution were added to a solution of 115 mg (0.21 mmol) of tert-butyl 4-tert-butoxy-2-{4-[5-chloro-2-(4-chloro-1H-1,2,3-triazol-1-yl)phenyl]-5-methoxy-2-oxopyridin-1(2H)-yl}butanoate (racemate) in 1.5 ml of THF, and the mixture was stirred at room temperature for two days. The mixture was then diluted with water, adjusted to pH 4 with aqueous hydrochloric acid solution (1N) and extracted three times with ethyl acetate. The combined organic phases were washed with saturated aqueous sodium chloride solution, dried over sodium sulphate, filtered and concentrated. Yield: 101 mg (93% of theory)

LC/MS [Method 10]: $R_t$=1.73 min; MS (ESIpos): m/z=495 (M+H)$^+$.

Example 6.26A tert-Butyl 2-[4-{5-chloro-2-[5-(difluoromethyl)-1,3,4-thiadiazol-2-yl]phenyl}-5-methoxy-2-oxopyridin-1(2H)-yl]butanoate (Racemat)

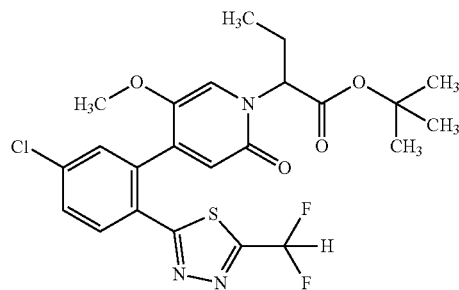 [SMILES: CCC(C(=O)OC(C)(C)C)n1cc(OC)c(-c2cc(Cl)ccc2-c2nnc(C(F)F)s2)cc1=O]

10.0 ml of dioxane were added to 0.30 g (0.92 mmol, 1.0 eq.) of 2-(2-bromo-4-chlorophenyl)-5-(difluoromethyl)-1,3,4-thiadiazole, 1.0 g (1.0 mmol, 40% purity) of tert-butyl 2-[5-methoxy-2-oxo-4-(4,4,5,5-tetramethyl-1,3,2-dioxaborolan-2-yl)pyridin-1(2H)-yl]butanoate (racemate) and 382 mg (2.76 mmol, 3.0 eq.) of potassium carbonate. For 20 min, argon was passed through the reaction mixture. 23 mg (28 μmol, 0.03 eq.) of [1,1-bis(diphenylphosphino)ferrocene]dichloropalladium-dichloromethane complex were then added, and the mixture was stirred at 80° C. for 18 h. The reaction mixture was filtered through kieselguhr, washing with dichloromethane and acetonitrile, and the filtrate was concentrated. The crude product was purified by normal phase chromatography (mobile phase: cyclohexane/ethyl acetate, 1:0 to 1:1). This product was purified by preparative HPLC. Yield: 423 mg (70% purity, 63% of theory).

LC/MS [Method 10]: $R_t$=2.12 min; MS (ESIpos): m/z=512 (M+H)$^+$, $^1$H-NMR (400 MHz, DMSO-d$_6$): δ [ppm]=8.08 (d, 1H), 7.74 (dd, 1H), 7.66 (d, 1H), 7.58 (t, 1H), 7.24-7.20 (m, 1H), 6.54 (s, 1H), 4.99-4.93 (m, 1H), 3.29 (s, 3H), 2.14-2.03 (m, 2H), 1.41 (s, 9H), 0.82 (t, 3H).

Example 6.26B

2-[4-{5-Chloro-2-[5-(difluoromethyl)-1,3,4-thiadiazol-2-yl]phenyl}-5-methoxy-2-oxopyridin-1(2H)-yl]butanoic acid (Racemate)

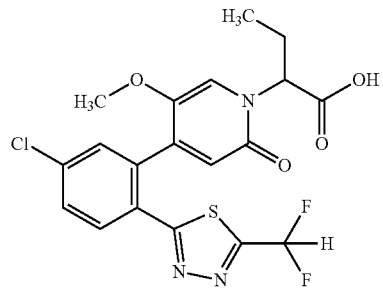 [SMILES: CCC(C(=O)O)n1cc(OC)c(-c2cc(Cl)ccc2-c2nnc(C(F)F)s2)cc1=O]

250 mg (0.342 mmol) of tert-butyl 2-[4-{5-chloro-2-[5-(difluoromethyl)-1,3,4-thiadiazol-2-yl]phenyl}-5-methoxy-2-oxopyridin-1(2H)-yl]butanoate (racemate) were dissolved in 9.8 ml of dichloromethane, and 1.3 ml (17.1 mmol, 50.0 eq.) of trifluoroacetic acid were added. The reaction mixture was stirred at RT for 7 h. The reaction mixture was then concentrated under reduced pressure and purified by column chromatography (125 mm×40 mm, reverse phase, 38 min, 10-90% acetonitrile/water acidified with 0.1% formic acid, 50 ml/min). Yield: 142 mg (91% of theory).

LC/MS [Method 10]: $R_t$=1.57 min; MS (ESIpos): m/z=456 (M+H)$^+$, $^1$H-NMR (400 MHz, DMSO-d$_6$): δ [ppm]=12.96 (brs, 1H), 8.07 (d, 1H), 7.73 (dd, 1H), 7.67 (d, 1H), 7.58 (t, 1H), 7.31-7.20 (m, 1H), 6.53 (s, 1H), 5.37-4.76 (m, 1H), 3.29 (s, 3H), 2.19-2.06 (m, 2H), 0.80 (t, 3H).

Example 6.27A tert-Butyl 2-[4-{5-chloro-2-[5-(trifluoromethyl)-1,2-oxazol-3-yl]phenyl}-5-methoxy-2-oxopyridin-1(2H)-yl]butanoate (Racemate)

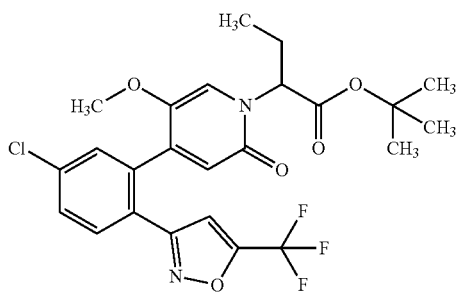 [SMILES: CCC(C(=O)OC(C)(C)C)n1cc(OC)c(-c2cc(Cl)ccc2-c2cc(C(F)(F)F)on2)cc1=O]

9.0 ml of toluene and 0.9 ml of water were added to 0.30 g (0.92 mmol) of 3-(2-bromo-4-chlorophenyl)-5-(trifluoromethyl)-1,2-oxazole, 1.04 g (1.06 mmol, 40% purity, 1.15 eq.) of tert-butyl 2-[5-methoxy-2-oxo-4-(4,4,5,5-tetramethyl-1,3,2-dioxaborolan-2-yl)pyridin-1(2H)-yl]butanoate (racemate) and 381 mg (2.76 mmol, 3.0 eq.) of potassium carbonate. For 10 min, argon was passed through the reaction mixture. 75 mg (92 μmol, 0.1 eq.) of [1,1-bis(diphenylphosphino)ferrocene]dichloropalladium-dichloromethane complex were then added, and the mixture was stirred at 80° C. for 8 h. The reaction mixture was concentrated under reduced pressure. The crude product was purified by normal phase chromatography (mobile phase: cyclohexane/ethyl acetate, 100:1 to 1:1). This product was purified by preparative HPLC. Yield: 290 mg (62% of theory).

LC/MS [Method 10]: $R_t$=2.32 min; MS (ESIpos): m/z=513 (M+H)$^+$, $^1$H-NMR (400 MHz, DMSO-d$_6$): δ [ppm]=7.78 (d, 1H), 7.71 (dd, 1H), 7.62 (d, 1H), 7.45 (s, 1H), 7.12 (s, 1H), 6.44 (s, 1H), 5.01-4.94 (m, 1H), 3.28 (s, 3H), 2.12-2.02 (m, 2H), 1.40 (s, 9H), 0.79 (t, 3H).

Example 6.27B

2-[4-{5-Chloro-2-[5-(trifluoromethyl)-1,2-oxazol-3-yl]phenyl}-5-methoxy-2-oxopyridin-1(2H)-yl]butanoic acid (Racemate)

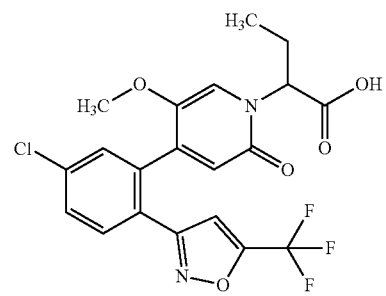 [SMILES: CCC(C(=O)O)n1cc(OC)c(-c2cc(Cl)ccc2-c2cc(C(F)(F)F)on2)cc1=O]

280 mg (0.546 mmol) of tert-butyl 2-[4-{5-chloro-2-[5-(trifluoromethyl)-1,2-oxazol-3-yl]phenyl}-5-methoxy-2-oxopyridin-1(2H)-yl]butanoate (racemate) were dissolved in 14.8 ml of dichloromethane, and 2.1 ml (27.3 mmol, 50.0 eq.) of trifluoroacetic acid were added. The reaction mixture was stirred at RT for 24 h. 4 ml of toluene were added and the reaction mixture was then concentrated under reduced pressure and purified by column chromatography (125 mm×40 mm, reverse phase, 38 min, 10-90% acetonitrile/water acidified with 0.1% formic acid, 50 ml/min). Yield: 200 mg (80% of theory).

LC/MS [Method 10]: $R_t$=1.82 min; MS (ESIpos): m/z=457 (M+H)$^+$, $^1$H-NMR (400 MHz, DMSO-d$_6$): δ [ppm]=12.93 (brs, 1H), 7.79 (d, 1H), 7.70 (dd, 1H), 7.63 (d, 1H), 7.38 (s, 1H), 7.18 (s, 1H), 6.44 (s, 1H), 5.31-4.85 (m, 1H), 3.27 (s, 3H), 2.19-2.03 (m, 2H), 0.77 (t, 3H).

Example 7.1A tert-Butyl 2-{4-[5-chloro-2-(1,3-oxazol-4-yl)phenyl]-5-methoxy-2-oxopyridin-1(2H)-yl}-4-methoxybutanoate (Racemate)

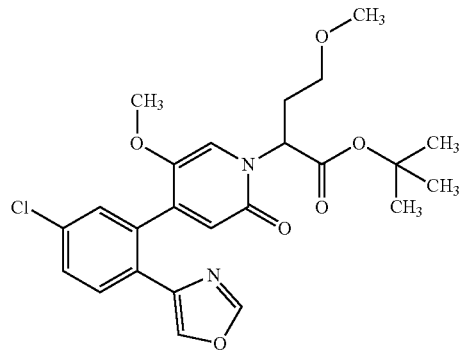 [SMILES: COCCC(C(=O)OC(C)(C)C)n1cc(OC)c(-c2cc(Cl)ccc2-c2cocn2)cc1=O]

11.4 ml of dioxane were added to 719 mg (purity 66%, 1.12 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 290 mg (1.12 mmol) of 4-(2-bromo-4-chlorophenyl)-1,3-oxazole and 465 mg (3.37 mmol) of potassium carbonate. For 5 min, argon was passed through the reaction mixture. 27 mg (0.03 mmol) of [1,1-bis(diphenylphosphino)ferrocene]dichloropalladium-dichloromethane complex were then added, and the mixture was stirred at 80° C. for 18 hours. The reaction mixture was filtered through kieselguhr, washing with dichloromethane/acetonitrile, and the filtrate was concentrated. The crude product was purified by normal phase chromatography (mobile phase: cyclohexane/ethyl acetate gradient). The crude product obtained in this manner was reacted without further purification. Yield: 140 mg (70% pure, 18% of theory).

LC/MS [Method 10]: $R_t$=1.91 min; MS (ESIpos): m/z=475 (M+H)$^+$.

Example 7.1B

2-{4-[5-Chloro-2-(1,3-oxazol-4-yl)phenyl]-5-methoxy-2-oxopyridin-1(2H)-yl}-4-methoxybutanoic acid (Racemate)

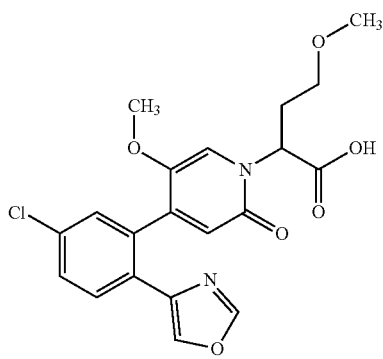 [SMILES: COCCC(C(=O)O)n1cc(OC)c(-c2cc(Cl)ccc2-c2cocn2)cc1=O]

2.3 ml of a solution of hydrogen chloride in dioxane (4M) were added to 140 mg (purity 70%, 0.21 mmol) of tert-butyl 2-{4-[5-chloro-2-(1,3-oxazol-4-yl)phenyl]-5-methoxy-2-oxopyridin-1(2H)-yl}-4-methoxybutanoate (racemate), and the mixture was stirred at RT for 8 h. The reaction mixture was concentrated at temperatures below 25° C. under reduced pressure, THF was added and the mixture was concentrated again at below 25° C. The crude product obtained in this manner was reacted without further purification. Yield: 135 mg (64% pure, 99% of theory).

LC/MS [Method 10]: $R_t$=1.43 min; MS (ESIpos): m/z=419 (M+H)$^+$.

Example 7.1C

Methyl 4-[(2-{4-[5-chloro-2-(1,3-oxazol-4-yl)phenyl]-5-methoxy-2-oxopyridin-1(2H)-yl}-4-methoxybutanoyl)amino]benzoate (Racemate)

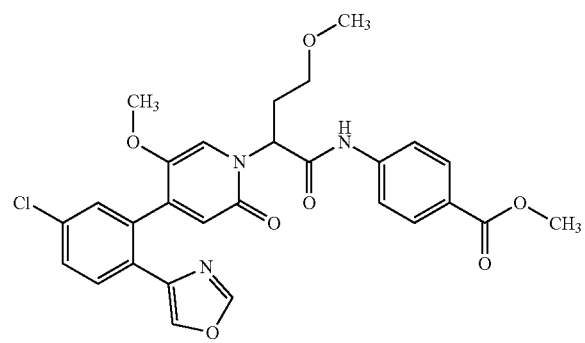 [SMILES: COCCC(C(=O)Nc1ccc(C(=O)OC)cc1)n1cc(OC)c(-c2cc(Cl)ccc2-c2cocn2)cc1=O]

45.0 mg (purity 64%, 0.07 mmol) of 2-{4-[5-chloro-2-(1,3-oxazol-4-yl)phenyl]-5-methoxy-2-oxopyridin-1(2H)-yl}-4-methoxybutanoic acid (racemate) and 15.6 mg (0.10 mmol) of methyl 4-aminobenzoate in 0.57 ml of pyridine were reacted according to General Method 5A. Yield: 26 mg (66% of theory).

LC/MS [Method 10]: $R_t$=1.89 min; MS (ESIpos): m/z=552 (M+H)$^+$, $^1$H-NMR (400 MHz, DMSO-$d_6$): δ [ppm]=10.71 (br. s., 1H), 8.39-8.43 (m, 1H), 7.91-7.97 (m, 2H), 7.88 (d, 1H), 7.76-7.82 (m, 2H), 7.66-7.70 (m, 1H), 7.58 (dd, 1H), 7.40 (d, 1H), 7.35 (s, 1H), 6.36 (s, 1H), 5.69-5.79 (m, 1H), 3.83 (s, 3H), 3.38-3.45 (m, 4H), 3.23 (s, 3H), 2.36-2.44 (m, 2H).

Example 8.1A tert-Butyl 2-{4-[5-chloro-2-(1,3,4-oxadiazol-2-yl)phenyl]-5-methoxy-2-oxopyridin-1(2H)-yl}-4-methoxybutanoate (Racemate)

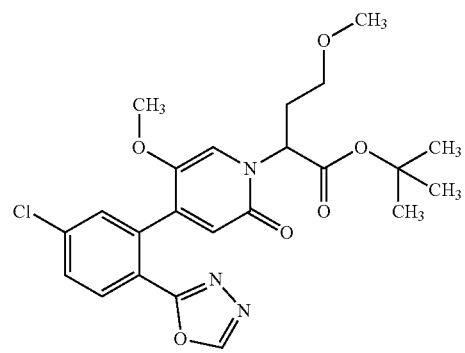 [SMILES: COCCC(C(=O)OC(C)(C)C)n1cc(OC)c(-c2cc(Cl)ccc2-c2nnco2)cc1=O]

11.1 ml of dioxane were added to 704 mg (purity 66%, 1.10 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 300 mg (1.11 mmol) of 2-(2-bromo-4-chlorophenyl)-1,3,4-oxadiazole and 455 mg (3.30 mmol) of potassium carbonate. For 5 min, argon was passed through the reaction mixture. 27 mg (0.03 mmol) of [1,1-bis(diphenylphosphino)ferrocene]dichloropalladium-dichloromethane complex were then added, and the mixture was stirred at 80° C. for 12 hours. The reaction mixture was filtered through kieselguhr, washing with dichloromethane/acetonitrile, and the filtrate was concentrated. The crude product was purified by flash normal phase chromatography (silica gel, dichloromethane/methanol gradient). Yield: 410 mg (70% pure, 55% of theory).

LC/MS [Method 10]: $R_t$=1.76 min; MS (ESIpos): m/z=476 (M+H)$^+$.

Example 8.1B

2-{4-[5-Chloro-2-(1,3,4-oxadiazol-2-yl)phenyl]-5-methoxy-2-oxopyridin-1(2H)-yl}-4-methoxybutanoic acid (Racemate)

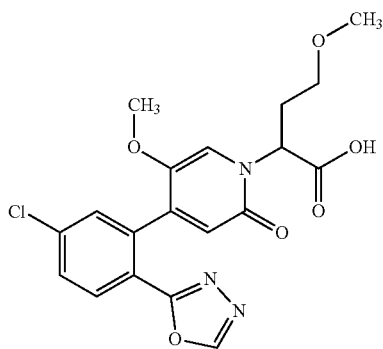 [SMILES: COCCC(C(=O)O)n1cc(OC)c(-c2cc(Cl)ccc2-c2nnco2)cc1=O]

410 mg (purity 70%, 0.60 mmol) of tert-butyl 2-{4-[5-chloro-2-(1,3,4-oxadiazol-2-yl)phenyl]-5-methoxy-2-oxopyridin-1(2H)-yl}-4-methoxybutanoate (racemate) were initially charged in 27 ml of an ethanol/tetrahydrofuran mixture (3:1), and a solution of 127 mg (3.02 mmol) of lithium hydroxide monohydrate in 18 ml of water was then added. The mixture was stirred at RT for 7 hours and then adjusted to pH 7 using hydrochloric acid (1M). The organic solvents were removed under reduced pressure and the residue was extracted twice with ethyl acetate. The collected organic phases were dried over magnesium sulphate and concentrated. The residue was separated by preparative HPLC (RP18 column, mobile phase: acetonitrile/water gradient with addition of 0.1% formic acid). The crude product obtained in this manner was reacted without further purification. Yield: 100 mg (86% pure, 34% of theory).

LC/MS [Method 10]: $R_t$=1.21 min; MS (ESIpos): m/z=420 (M+H)$^+$.

Example 8.1C

Methyl 4-[(2-{4-[5-chloro-2-(1,3,4-oxadiazol-2-yl)phenyl]-5-methoxy-2-oxopyridin-1(2H)-yl}-4-methoxybutanoyl)amino]benzoate (Racemate)

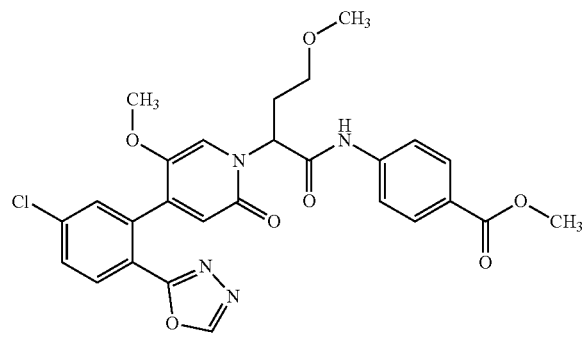 [SMILES: COCCC(C(=O)Nc1ccc(C(=O)OC)cc1)n1cc(OC)c(-c2cc(Cl)ccc2-c2nnco2)cc1=O]

40.0 mg (purity 86%, 0.08 mmol) of 2-{4-[5-chloro-2-(1,3,4-oxadiazol-2-yl)phenyl]-5-methoxy-2-oxopyridin-1(2H)-yl}-4-methoxybutanoic acid (racemate) and 19.0 mg (0.12 mmol) of methyl 4-aminobenzoate in 1.00 ml of pyridine were reacted according to General Method 5A. Yield: 38 mg (84% of theory).

LC/MS [Method 1]: $R_t$=0.93 min; MS (ESIpos): m/z=553 (M+H)$^+$, $^1$H-NMR (400 MHz, DMSO-d$_6$): δ [ppm]=10.71-10.79 (m, 1H), 9.26 (s, 1H), 8.01 (d, 1H), 7.94 (d, 2H), 7.79 (d, 2H), 7.74 (dd, 1H), 7.64 (d, 1H), 7.30 (s, 1H), 6.49 (s, 1H), 5.67-5.80 (m, 1H), 3.83 (s, 3H), 3.36-3.43 (m, 1H), 3.34 (s, 3H), 3.26-3.29 (m, 1H, partially hidden), 3.23 (s, 3H), 2.31-2.42 (m, 2H).

Example 9.1A tert-Butyl 2-[4-(5-chloro-2-fluorophenyl)-5-methoxy-2-oxopyridin-1(2H)-yl]-4-methoxybutanoate (Racemate)

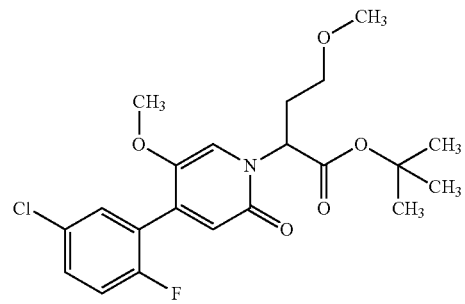 [SMILES: COCCC(C(=O)OC(C)(C)C)n1cc(OC)c(-c2cc(Cl)ccc2F)cc1=O]

8.0 ml of dioxane were added to 496 mg (purity 66%, 0.77 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 165 mg (0.77 mmol) of 2-bromo-4-chloro-1-fluorobenzene and 321 mg (2.32 mmol) of potassium carbonate. For 5 min, argon was passed through the reaction mixture. 19 mg (0.02 mmol) of [1,1-bis(diphenylphosphino)ferrocene]dichloropalladium-dichloromethane complex were then added, and the mixture was stirred at 80° C. for 3 days. The reaction mixture was filtered through kieselguhr, washing with dichloromethane/acetonitrile, and the filtrate was concentrated. The crude product was purified by flash normal phase chromatography (silica gel, cyclohexane/ethyl acetate gradient). Yield: 337 mg (99% of theory).

LC/MS [Method 10]: $R_t$=2.05 min; MS (ESIpos): m/z=426 (M+H)$^+$,

Example 9.1B

2-{4-[5-Chloro-2-(4-fluoro-1H-pyrazol-1-yl)phenyl]-5-methoxy-2-oxopyridin-1(2H)-yl}-4-methoxybutanoic acid (Racemate)

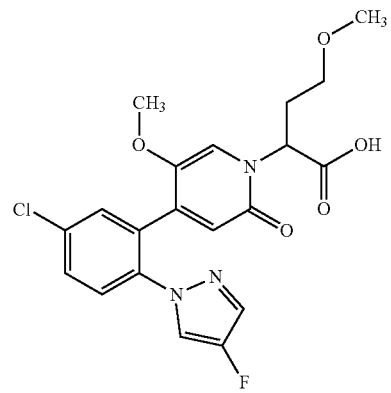 [SMILES: COCCC(C(=O)O)n1cc(OC)c(-c2cc(Cl)ccc2-n2cc(F)cn2)cc1=O]

0.61 ml of N N-dimethylformamide was added to 54 mg (0.12 mmol) of tert-butyl 2-[4-(5-chloro-2-fluorophenyl)-5-methoxy-2-oxopyridin-1(2H)-yl]-4-methoxybutanoate (racemate), 10 mg (0.12 mmol) of 4-fluoro-1H-pyrazole and 51 mg (0.37 mmol) of potassium carbonate, and the mixture was stirred at 120° C. for one hour, at 150° C. for 4 hours and at 200° C. for 4 hours in the microwave. The reaction mixture was brought to RT and separated by preparative HPLC (RP18 column; mobile phase: acetonitrile/water gradient with addition of 0.1% formic acid). Yield: 7 mg (13% of theory).

LC/MS [Method 10]: $R_t$=1.46 min; MS (ESIpos): m/z=436 (M+H)$^+$.

$^1$H-NMR (400 MHz, DMSO-d$_6$): δ [ppm]=12.90 (br. s., 1H), 7.98 (d, 1H), 7.63-7.69 (m, 2H), 7.56-7.62 (m, 2H), 7.12 (s, 1H), 6.33 (s, 1H), 5.04 (br. s., 1H), 3.17 (s, 3H), 3.00-3.07 (m, 1H), 2.26-2.33 (m, 2H).

Example 10.1A tert-Butyl 2-[4-(2-amino-5-chlorophenyl)-5-methoxy-2-oxopyridin-1(2H)-yl]-4-methoxybutanoate (Racemate)

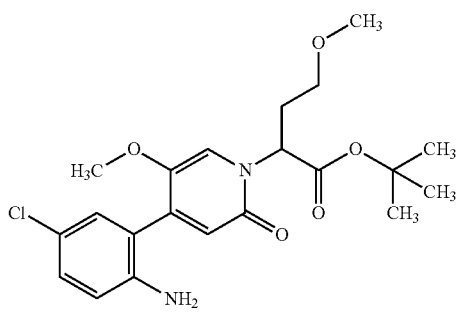 [SMILES: COCCC(C(=O)OC(C)(C)C)n1cc(OC)c(-c2cc(Cl)ccc2N)cc1=O]

18 ml of dioxane were added to 350 mg (1.70 mmol) of 2-bromo-4-chloroaniline, 718 mg (1.70 mmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 703 mg (5.09 mmol) of potassium carbonate. For 5 min, argon was passed through the reaction mixture. 83.1 mg (102 μmol) of [1,1-bis(diphenylphosphino)ferrocene]dichloropalladium-dichloromethane complex were then added, and the mixture was stirred at 80° C. for 3 days. The reaction mixture was filtered through kieselguhr, washing with dichloromethane and acetonitrile, and the filtrate was concentrated. The crude product was purified by normal phase chromatography (mobile phase: cyclohexane/ethyl acetate, 50-100%). Yield: 674 mg (89% pure, 84% of theory).

LC/MS [Method 10]: $R_t$=1.81 min; MS (ESIpos): m/z=423 (M+H)$^+$.

Example 10.1B tert-Butyl 2-{4-[5-chloro-2-(4H-1,2,4-triazol-4-yl)phenyl]-5-methoxy-2-oxopyridin-1(2H)-yl}-4-methoxybutanoate (Racemate)

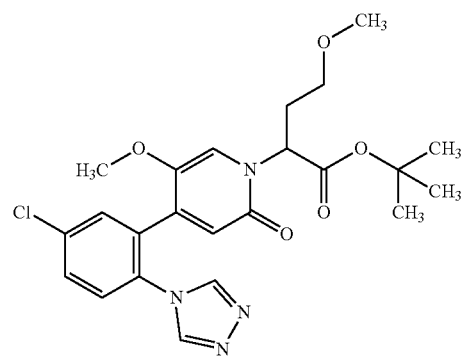 [SMILES: COCCC(C(=O)OC(C)(C)C)n1cc(OC)c(-c2cc(Cl)ccc2-n2cnnc2)cc1=O]

12 ml of pyridine were added to 550 mg (purity 89%, 1.16 mmol) of tert-butyl 2-[4-(2-amino-5-chlorophenyl)-5-methoxy-2-oxopyridin-1(2H)-yl]-4-methoxybutanoate (racemate), 306 mg (3.47 mmol) of N'-formylformic hydrazide and 1.1 ml (8.1 mmol) of triethylamine. 2.2 ml (17 mmol) of chlorotrimethylsilane were then added dropwise, and the suspension was stirred at 100° C. for 5 hours. After cooling, 150 ml of ethyl acetate were added and the organic phase was washed four times with 40 ml of water. The organic phase was then dried over sodium sulphate and concentrated. The residue was purified by normal phase chromatography (mobile phase: dichloromethane/methanol, 0-10%). Yield: 310 mg (94% pure, 53% of theory).

LC/MS [Method 1]: $R_t$=0.87 min; MS (ESIpos): m/z=475 (M+H)$^+$,

Example 10.1C

2-{4-[5-Chloro-2-(4H-1,2,4-triazol-4-yl)phenyl]-5-methoxy-2-oxopyridin-1(2H)-yl}-4-methoxybutanoic acid hydrochloride (Racemate)

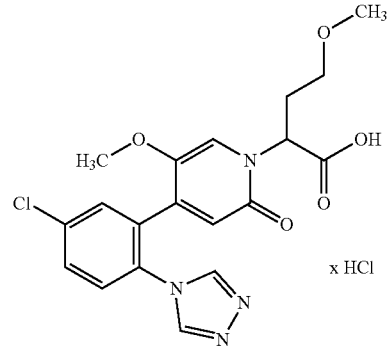 [SMILES: COCCC(C(=O)O)n1cc(OC)c(-c2cc(Cl)ccc2-n2cnnc2)cc1=O]

370 mg (purity 94%, 732 μmol) of tert-butyl 2-{4-[5-chloro-2-(4H-1,2,4-triazol-4-yl)phenyl]-5-methoxy-2-oxopyridin-1(2H)-yl}-4-methoxybutanoate (racemate) were reacted in 18.0 ml of a solution of hydrogen chloride in dioxane (4M) according to General Method 6D. Yield: 378 mg (purity 70%, 79% of theory)

LC/MS [Method 1]: $R_t$=0.64 min; MS (ESIpos): m/z=419 (M+H)$^+$,

Example 111A

Methyl 2-{4-[5-chloro-2-(4-chloro-1H-1,2,3-triazol-1-yl)phenyl]-5-methoxy-2-oxopyridin-1(2H)-yl}propanoate (Racemate)

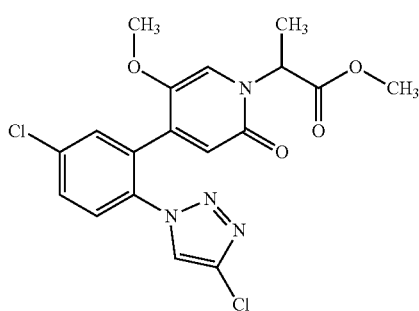 [SMILES: COC(=O)C(C)n1cc(OC)c(-c2cc(Cl)ccc2-n2cc(Cl)nn2)cc1=O]

398.0 mg (purity 61%, 0.72 mmol) of methyl 2-[5-methoxy-2-oxo-4-(4,4,5,5-tetramethyl-1,3,2-dioxaborolan-2-yl)pyridin-1(2H)-yl]propanoate (racemate) were reacted with 210.9 mg (0.72 mmol) of 1-(2-bromo-4-chlorophenyl)-4-chloro-1H-1,2,3-triazole according to General Method 2A. Yield: 139 mg (46% of theory). The crude product was converted without further purification.

LC/MS [Method 1]: $R_t$=0.86 min; MS (ESIpos): m/z=423 (M+H)$^+$.

$^1$H-NMR (400 MHz, DMSO-d$_6$): δ [ppm]=8.64 (s, 1H), 7.82-7.69 (m, 3H), 7.20 (s, 1H), 6.42 (s, 1H), 5.14-5.04 (m, 1H), 3.63 (s, 3H), 3.29 (s, 3H), 1.53 (d, 3H).

Example 11.1B

2-{4-[5-Chloro-2-(4-chloro-1H-1,2,3-triazol-1-yl)phenyl]-5-methoxy-2-oxopyridin-1(2H)-yl}propanoic acid (Racemate)

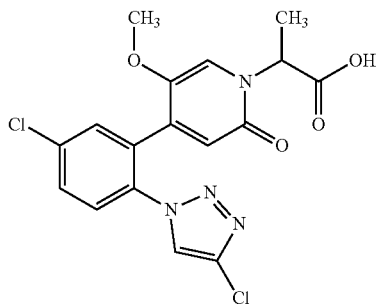 [SMILES: COc1cn(C(C)C(=O)O)c(=O)cc1-c1cc(Cl)ccc1-n1cc(Cl)nn1]

139 mg (0.33 mmol) of methyl 2-{4-[5-chloro-2-(4-chloro-1H-1,2,3-triazol-1-yl)phenyl]-5-methoxy-2-oxopyridin-1(2H)-yl}propanoate (racemate) were initially charged in 9.0 ml of THF, 3.28 ml of aqueous lithium hydroxide solution (1M) were then added and the mixture was stirred at RT for 1.5 h. The reaction mixture was diluted with water and ethyl acetate, the organic phase was separated off and the aqueous phase was extracted twice with ethyl acetate. The combined organic phases were dried over sodium sulphate, filtered and concentrated. The crude product obtained in this manner was reacted without further purification. Yield: 114 mg (85% of theory).

Example 12.1A tert-Butyl 2-{4-[5-chloro-2-(3-methyl-1,2-oxazol-5-yl)phenyl]-5-methoxy-2-oxopyridin-1(2H)-yl}-4-methoxybutanoate (Racemate)

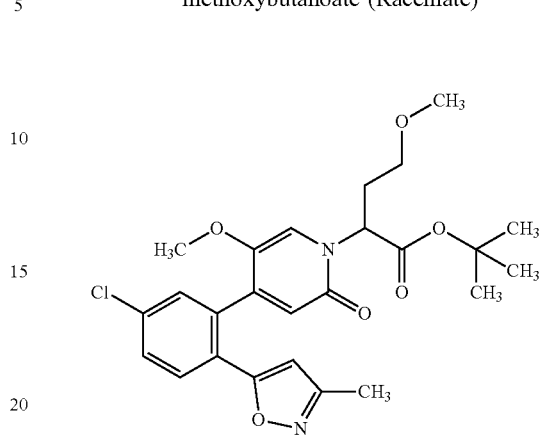

17.2 ml of dioxane were added to 510 mg (1.87 mmol, 1.1 eq.) of 5-(2-bromo-4-chlorophenyl)-3-methyl-1,2-oxazole, 1.60 g (1.70 mmol, purity 45%) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 705 mg (5.10 mmol, 3.0 eq.) of potassium carbonate. For 5 min, argon was passed through the reaction mixture. 41 mg (51 µmol, 0.03 eq.) of [1,1-bis(diphenylphosphino)ferrocene]dichloropalladium-dichloromethane complex were then added, and the mixture was stirred at 80° C. for 20 h. The reaction mixture was filtered through kieselguhr, washing with dichloromethane and acetonitrile, and the filtrate was concentrated. The crude product was purified by normal phase chromatography (mobile phase: cyclohexane/ethyl acetate, 20:1 to 2:1). This product was purified by preparative HPLC. Yield: 220 mg (26% of theory).

LC/MS [Method 8]: $R_t$=1.40 min; MS (ESIneg): m/z=487 (M−H)$^-$, $^1$H-NMR (400 MHz, DMSO-d$_6$): δ [ppm]=7.81 (d, 1H), 7.65 (dd, 1H), 7.52 (d, 1H), 7.21 (s, 1H), 6.39 (s, 1H), 6.17 (s, 1H), 5.10-5.03 (m, 1H), 3.42-3.36 (m, 1H), 3.35 (s, 3H), 3.21 (s, 3H), 3.20-3.13 (m, 1H), 2.35-2.29 (m, 2H), 2.18 (s, 3H), 1.42 (s, 9H).

Example 12.1B

2-{4-[5-Chloro-2-(3-methyl-1,2-oxazol-5-yl)phenyl]-5-methoxy-2-oxopyridin-1(2H)-yl}-4-methoxybutanoic acid (Racemate)

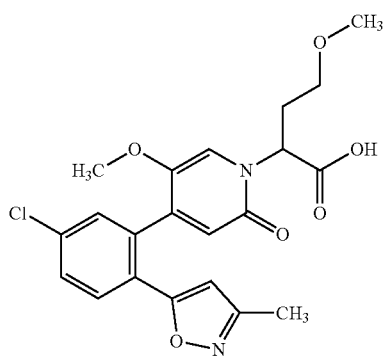 [SMILES: COCCC(C(=O)O)n1cc(OC)c(-c2cc(Cl)ccc2-c2cc(C)no2)cc1=O]

209 mg (0.427 mmol) of tert-butyl 2-{4-[5-chloro-2-(3-methyl-1,2-oxazol-5-yl)phenyl]-5-methoxy-2-oxopyridin-1(2H)-yl}-4-methoxybutanoate (racemate) were reacted in 8 ml of an ethanol/tetrahydrofuran mixture (2:1) according to General Method 6C. Yield: 160 mg (86% of theory).

LC/MS [Method 8]: $R_t$=1.09 min; MS (ESIpos): m/z=433 (M+H)$^+$, $^1$H-NMR (400 MHz, DMSO-d$_6$): δ [ppm]=12.96 (brs, 1H), 7.82 (d, 1H), 7.65 (dd, 1H), 7.54 (d, 1H), 7.25 (s, 1H), 6.38 (s, 1H), 6.16 (s, 1H), 5.23-5.04 (m, 1H), 3.44-3.36 (m, 1H), 3.35 (s, 3H), 3.21 (s, 3H), 3.19-3.10 (m, 1H), 2.40-2.30 (m, 2H), 2.18 (s, 3H).

Example 12.1C

Methyl 4-[(2-{4-[5-chloro-2-(3-methyl-1,2-oxazol-5-yl)phenyl]-5-methoxy-2-oxopyridin-1(2H)-yl}-4-methoxybutanoyl)amino]benzoate (Racemate)

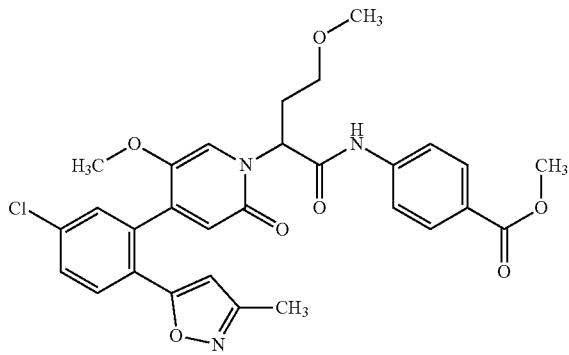 [SMILES: COCCC(C(=O)Nc1ccc(C(=O)OC)cc1)n1cc(OC)c(-c2cc(Cl)ccc2-c2cc(C)no2)cc1=O]

50 mg (0.11 mmol) of 2-{4-[5-chloro-2-(3-methyl-1,2-oxazol-5-yl)phenyl]-5-methoxy-2-oxopyridin-1(2H)-yl}-4-methoxybutanoic acid (racemate) and 25 mg (0.17 mmol, 1.5 eq.) of methyl 4-aminobenzoate were reacted according to General Method 5A. Yield: 60 mg (93% of theory).

LC/MS [Method 10]: $R_t$=1.95 min; MS (ESIpos): m/z=566 (M+H)$^+$, $^1$H-NMR (400 MHz, DMSO-d$_6$): δ [ppm]=10.72 (s, 1H), 7.97-7.91 (m, 2H), 7.84-7.77 (m, 3H), 7.66 (dd, H), 7.53 (d, 1H), 7.33 (s, 1H), 6.42 (s, 1H), 6.21 (s, 1H), 5.83-5.69 (m, 1H), 3.83 (s, 3H), 3.44-3.37 (m, 4H), 3.29-3.25 (m, 1H, partially hidden), 3.23 (s, 3H), 2.44-2.36 (m, 2H), 2.18 (s, 3H).

Example 13.1A tert-Butyl 2-[4-{5-chloro-2-[5-(trifluoromethyl)-1,3,4-oxadiazol-2-yl]phenyl}-5-methoxy-2-oxopyridin-1(2H)-yl]-4-methoxybutanoate (Racemate)

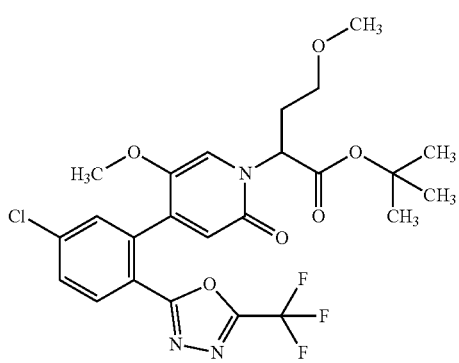 [SMILES: COCCC(C(=O)OC(C)(C)C)n1cc(OC)c(-c2cc(Cl)ccc2-c2nnc(C(F)(F)F)o2)cc1=O]

8.6 ml of dioxane were added to 305 mg (0.931 mmol, 1.1 eq.) of 2-(2-bromo-4-chlorophenyl)-5-(trifluoromethyl)-1,3,4-oxadiazole, 0.796 g (0.85 mmol, purity 45%) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 351 mg (2.54 mmol, 3.0 eq.) of potassium carbonate. For 5 min, argon was passed through the reaction mixture. 21 mg (25 µmol, 0.03 eq.) of [1,1-bis(diphenylphosphino)ferrocene]dichloropalladium-dichloromethane complex were then added, and the mixture was stirred at 80° C. for 20 h. The reaction mixture was filtered through kieselguhr, washing with dichloromethane and acetonitrile, and the filtrate was concentrated. The crude product was purified by normal phase chromatography (mobile phase: cyclohexane/ethyl acetate, 50:1 to 2:1). This product was purified by preparative HPLC. Yield: 430 mg (93% of theory).

LC/MS [Method 10]: $R_t$=2.16 min; MS (ESIpos): m/z=544 (M+H)$^+$.

Example 13.1B

2-[4-{5-Chloro-2-[5-(trifluoromethyl)-1,3,4-oxadiazol-2-yl]phenyl}-5-methoxy-2-oxopyridin-1(2H)-yl]-4-methoxybutanoic acid Racemate)

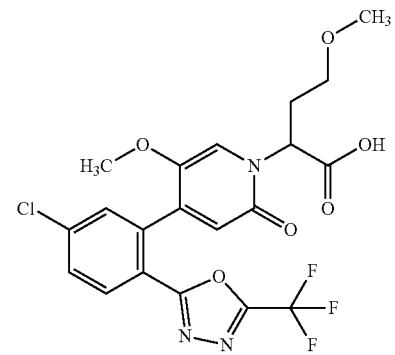 [SMILES: COCCC(C(=O)O)n1cc(OC)c(-c2cc(Cl)ccc2-c2nnc(C(F)(F)F)o2)cc1=O]

400 mg (0.735 mmol) of tert-butyl 2-[4-{5-chloro-2-[5-(trifluoromethyl)-1,3,4-oxadiazol-2-yl]phenyl}-5-methoxy-2-oxopyridin-1(2H)-yl]-4-methoxybutanoate were dissolved in 20 ml of dichloromethane, and 2.8 ml (36.8 mmol, 50.0 eq.) of trifluoroacetic acid were added. The reaction mixture was treated in an ultrasonic bath for 30 min. The reaction mixture was then concentrated under reduced pressure and purified by column chromatography (125 mm×30 mm, reverse phase, 38 min, 10-100% acetonitrile/water acidified with 0.1% formic acid, 50 ml/min). Yield: 212 mg (59% of theory).

LC/MS [Method 8]: $R_t$=1.19 min; MS (ESIpos): m/z=488 (M+H)$^+$, $^1$H-NMR (400 MHz, DMSO-d$_6$): δ [ppm]=12.95 (brs, 1H), 8.10 (d, 1H), 7.80 (dd, 1H), 7.74 (d, 1H), 7.23 (s, 1H), 6.52 (s, 1H), 5.35-4.95 (m, 1H), 3.38-3.33 (m, 1H, partially hidden), 3.30 (s, 3H, partially hidden), 3.21 (s, 3H), 3.18-3.10 (m, 1H), 2.38-2.29 (m, 2H).

Example 14.1A tert-Butyl 2-[4-{5-chloro-2-[5-(difluoromethyl)-1,3,4-oxadiazol-2-yl]phenyl}-5-methoxy-2-oxopyridin-1(2H)-yl]-4-methoxybutanoate (Racemate)

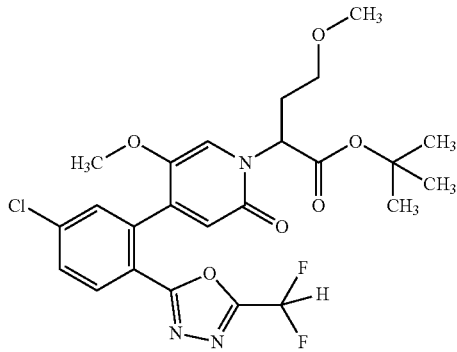 [SMILES: COCCC(C(=O)OC(C)(C)C)n1cc(OC)c(-c2cc(Cl)ccc2-c2nnc(C(F)F)o2)cc1=O]

5.5 ml of dioxane were added to 231 mg (0.597 mmol, purity 80%, 1.1 eq.) of 2-(2-bromo-4-chlorophenyl)-5-(difluoromethyl)-1,3,4-oxadiazole, 0.42 g (0.54 mmol, purity 45%) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 225 mg (1.63 mmol, 3.0 eq.) of potassium carbonate. For 5 min, argon was passed through the reaction mixture. 13 mg (16 µmol, 0.03 eq.) of [1,1-bis(diphenylphosphino)ferrocene]dichloropalladium-dichloromethane complex were then added, and the mixture was stirred at 80° C. After 20 h, 0.42 g (0.54 mmol, purity 45%) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 13 mg (16 µmol, 0.03 eq.) of [1,1-bis(diphenylphosphino)ferrocene]dichloropalladium-dichloromethane complex were added, and the mixture was shaken at 80° C. for 6 h. The reaction mixture was filtered through kieselguhr, washing with dichloromethane and acetonitrile, and the filtrate was concentrated. The crude product was purified by reverse phase chromatography (mobile phase: 10-100% acetonitrile/water, acidified with 0.1% formic acid, 125 mm×40 mm, 100 ml/min, 38 min). Yield: 120 mg (86% pure, 36% of theory).

LC/MS [Method 10]: $R_t$=1.99 min; MS (ESIpos): m/z=526 (M+H)$^+$.

Example 14.1B

2-[4-{5-Chloro-2-[5-(difluoromethyl)-1,3,4-oxadiazol-2-yl]phenyl}-5-methoxy-2-oxopyridin-1(2H)-yl]-4-methoxybutanoic acid (Racemate)

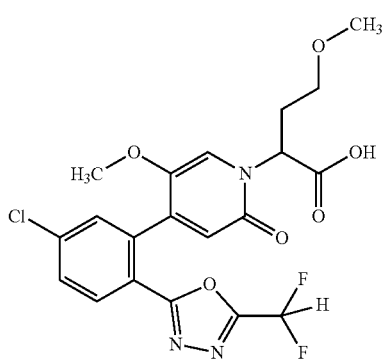 [SMILES: COCCC(C(=O)O)n1cc(OC)c(-c2cc(Cl)ccc2-c2nnc(C(F)F)o2)cc1=O]

120 mg (purity 86%, 0.196 mmol) of tert-butyl 2-[4-{5-chlor-2-[5-(difluormethyl)-1,3,4-oxadiazol-2-yl]phenyl}-5-methoxy-2-oxopyridin-1(2H)-yl]-4-methoxybutanoate (racemate) in 6.2 ml of dichloromethane in the presence of 0.88 ml (11.4 mmol, 50 eq.) of trifluoroacetic acid were reacted according to General Method 6A. Yield: 64 mg (66% of theory).

LC/MS [Method 10]: $R_t$=1.48 min; MS (ESIpos): m/z=470 (M+H)$^+$, $^1$H-NMR (400 MHz, DMSO-$d_6$): δ [ppm]=12.96 (brs, 1H), 8.06 (d, 1H), 7.78 (dd, 1H), 7.71 (d, 1H), 7.47 (t, 1H), 7.20 (s, 1H), 6.50 (s, 1H), 5.40-4.84 (m, 1H), 3.39-3.32 (m, 1H, partially hidden), 3.29 (s, 3H), 3.21 (s, 3H), 3.19-3.12 (m, 1H), 2.38-2.29 (m, 2H).

Example 14.1C tert-Butyl 4-({2-[4-{5-chloro-2-[5-(difluoromethyl)-1,3,4-oxadiazol-2-yl]phenyl}-5-methoxy-2-oxopyridin-1(2H)-yl]-4-methoxybutanoyl}amino)benzoate (Racemate)

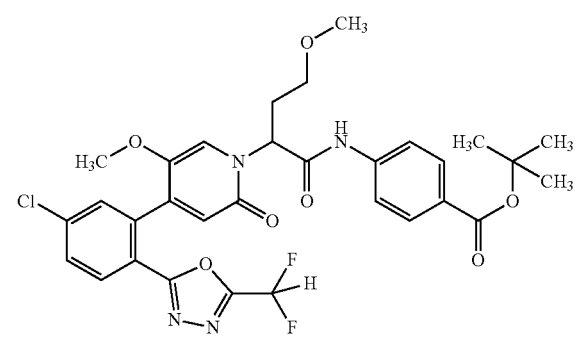 [SMILES: COCCC(C(=O)Nc1ccc(C(=O)OC(C)(C)C)cc1)n1cc(OC)c(-c2cc(Cl)ccc2-c2nnc(C(F)F)o2)cc1=O]

11 mg (purity 80%, 0.019 mmol) of 2-[4-{5-chloro-2-[5-(difluoromethyl)-1,3,4-oxadiazol-2-yl]phenyl}-5-meth oxy-2-oxopyridin-1(2H)-yl]-4-methoxybutanoic acid (racemate) and 5 mg (0.028 mmol, 1.5 eq.) of tert-butyl 4-aminobenzoate in 0.1 ml of pyridine were reacted according to General Method 5A. Yield: 7 mg (93% pure, 54% of theory).

LC/MS [Method 1]: $R_t$=1.17 min; MS (ESIpos): m/z=645 (M+H)$^+$.

Example 15.1A tert-Butyl 2-{4-[5-chloro-2-(4,5-dihydro-1,2-oxazol-3-yl)phenyl]-5-methoxy-2-oxopyridin-1(2H)-yl}pentanoate (Racemate)

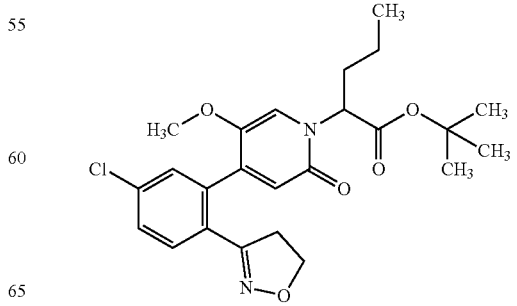

10 ml of dioxane were added to 815 mg (purity 50%, 1.0 mmol) of tert-butyl 2-[5-methoxy-2-oxo-4-(4,4,5,5-tetramethyl-1,3,2-dioxaborolan-2-yl)pyridin-1(2H)-yl]pentanoate (racemate), 415 mg (3.00 mmol) of potassium carbonate and 261 mg (1.0 mmol) of 3-(2-bromo-4-chlorophenyl)-4,5-dihydro-1,2-oxazole. For 5 min, argon was passed through the reaction mixture. 49 mg (60 μmol) of [1,1-bis(diphenylphosphino)ferrocene]dichloropalladium-dichloromethane complex were then added, and the mixture was stirred at 80° C. for 6 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-60%). Yield: 330 mg (75% pure, 54% of theory).

LC/MS [Method 1]: $R_t$=1.08 min; MS (ESIpos): m/z=461 [M+H]$^+$

Example 15.1B

2-{4-[5-Chloro-2-(4,5-dihydro-1,2-oxazol-3-yl)phenyl]-5-methoxy-2-oxopyridin-1(2H)-yl}pentanoic acid (Racemate)

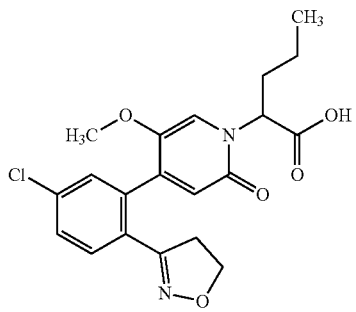 [SMILES: CCCC(C(=O)O)n1cc(OC)c(-c2cc(Cl)ccc2C2=NOCC2)cc1=O]

330 mg (purity 75%, 537 μmol) of tert-butyl 2-{4-[5-chloro-2-(4,5-dihydro-1,2-oxazol-3-yl)phenyl]-5-methoxy-2-oxopyridin-1(2H)-yl}pentanoate (racemate) were reacted in 7.3 ml of a solution of hydrogen chloride in dioxane (4M) according to General Method 6D. Yield: 160 mg (74% of theory).

LC/MS [Method 1]: $R_t$=0.83 min; MS (ESIpos): m/z=405 [M+H]$^+$.

Example 16.1A tert-Butyl 2-{4-[5-chloro-2-(4-fluoro-1H-imidazol-1-yl)phenyl]-5-methoxy-2-oxopyridin-1(2H)-yl}pentanoate (Racemate)

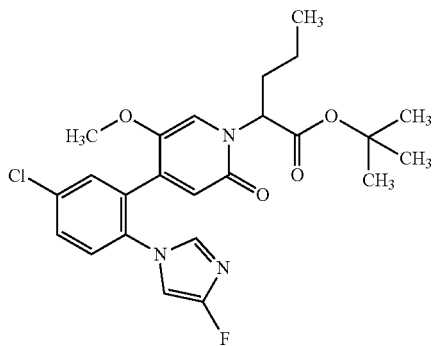 [SMILES: CCCC(C(=O)OC(C)(C)C)n1cc(OC)c(-c2cc(Cl)ccc2-n2cnc(F)c2)cc1=O]

9.7 ml of dioxane were added to 690 mg (purity 57%, 966 μmol) of tert-butyl 2-[5-methoxy-2-oxo-4-(4,4,5,5-tetramethyl-1,3,2-dioxaborolan-2-yl)pyridin-1(2H)-yl]pentanoate (racemate) and 266 mg (966 μmol) of 1-(2-bromo-4-chlorophenyl)-4-fluoro-1H-imidazole. For 5 min, argon was passed through the reaction mixture. 78.9 mg (96.6 μmol) of [1,1-bis(diphenylphosphino)ferrocene]dichloropalladium-dichloromethane complex and 1.4 ml of an aqueous sodium carbonate solution (2.0 M, 2.9 mmol) were then added, and the mixture was stirred at 100 C for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-50%). Yield: 390 mg (purity 70%, 59% of theory)

LC/MS [Method 1]: $R_t$=1.07 min; MS (ESIpos): m/z=476 [M+H]$^+$.

Example 16.1B

2-{4-[5-Chloro-2-(4-fluoro-1H-imidazol-1-yl)phenyl]-5-methoxy-2-oxopyridin-1(2H)-yl}pentanoic acid (Racemate)

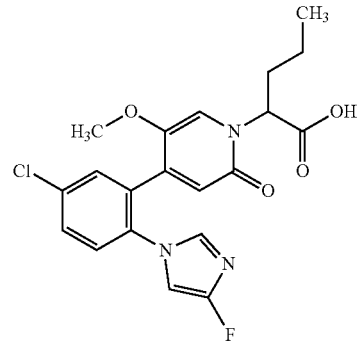 [SMILES: CCCC(C(=O)O)n1cc(OC)c(-c2cc(Cl)ccc2-n2cnc(F)c2)cc1=O]

390 mg (purity 70%, 574 μmol) of tert-butyl 2-{4-[5-chloro-2-(4-fluoro-1H-imidazol-1-yl)phenyl]-5-methoxy-2-oxopyridin-1(2H)-yl}pentanoate (racemate) were reacted in 7.8 ml of a solution of hydrogen chloride in dioxane (4M) according to General Method 6D. Yield: 160 mg (66% of theory)

LC/MS [Method 1]: $R_t$=0.86 min; MS (ESIpos): m/z=420 [M+H]$^+$.

Example 17.1A tert-Butyl 2-{4-[5-chloro-2-(4-chloro-1H-imidazol-1-yl)phenyl]-5-methoxy-2-oxopyridin-1(2H)-yl}pentanoate (Racemate)

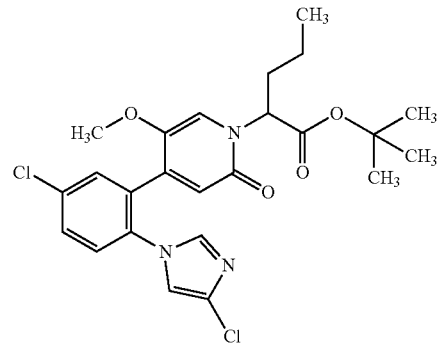 [SMILES: CCCC(C(=O)OC(C)(C)C)n1cc(OC)c(-c2cc(Cl)ccc2-n2cnc(Cl)c2)cc1=O]

9.7 ml of dioxane were added to 690 mg (purity 57%, 966 µmol) of tert-butyl 2-[5-methoxy-2-oxo-4-(4,4,5,5-tetramethyl-1,3,2-dioxaborolan-2-yl)pyridin-1(2H)-yl]pentanoate (racemate) and 282 mg (966 µmol) of 1-(2-bromo-4-chlorophenyl)-4-chloro-1H-imidazole. For 5 min, argon was passed through the reaction mixture. 78.9 mg (96.6 µmol) of [1,1-bis(diphenylphosphino)ferrocene]dichloropalladium-dichloromethane complex and 1.4 ml of an aqueous sodium carbonate solution (2.0 M, 2.9 mmol) were then added, and the mixture was stirred at 100° C. for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-50%). Yield: 400 mg (purity 70%, 59% of theory)

LC/MS [Method 1]: $R_t$=1.09 min; MS (ESIpos): m/z=492 [M+H]$^+$.

Example 17.1B

2-{4-[5-Chloro-2-(4-chloro-1H-imidazol-1-yl)phenyl]-5-methoxy-2-oxopyridin-1(2H)-yl}pentanoic acid (Racemate)

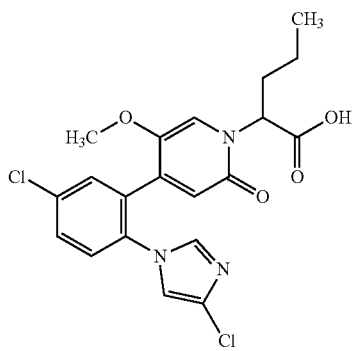 [SMILES: CCCC(C(=O)O)n1cc(OC)c(-c2cc(Cl)ccc2-n2cnc(Cl)c2)cc1=O]

400 mg (purity 70%, 569 µmol) of tert-butyl 2-{4-[5-chloro-2-(4-chloro-1H-imidazol-1-yl)phenyl]-5-methoxy-2-oxopyridin-1(2H)-yl}pentanoate (racemate) were reacted in 8 ml of a solution of hydrogen chloride in dioxane (4M) according to General Method 6D. Yield: 160 mg (64% of theory)

LC/MS [Method 1]: $R_t$=0.87 min; MS (ESIpos): m/z=436 [M+H]$^+$.

Example 18.1A tert-Butyl 2-[4-{5-chloro-2-[4-(trifluoromethyl)-1H-imidazol-1-yl]phenyl}-5-methoxy-2-oxopyridin-1(2H)-yl]-4-methoxybutanoate (Racemate)

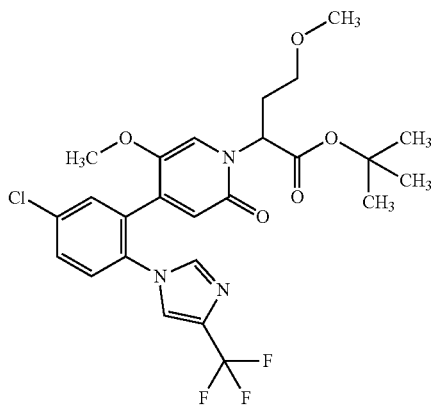 [SMILES: COCCC(C(=O)OC(C)(C)C)n1cc(OC)c(-c2cc(Cl)ccc2-n2cnc(C(F)(F)F)c2)cc1=O]

1.8 ml of dioxane were added to 151 mg (purity 50%, 178 µmol) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 58.0 mg (178 µmol) of 1-(2-bromo-4-chlorophenyl)-4-(trifluoromethyl)-1H-imidazole. For 5 min, argon was passed through the reaction mixture. 14.6 mg (17.8 µmol) of [1,1-bis(diphenylphosphino)ferrocene]dichloropalladium-dichloromethane complex and 270 µl of an aqueous sodium carbonate solution (2.0 M, 530 µmol) were then added, and the mixture was stirred at 100° C. for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 0-60%). Yield: 67.0 mg (purity 80%, 56% of theory)

LC/MS [Method 1]: $R_t$=1.11 min; MS (ESIpos): m/z=542 [M+H]$^+$.

Example 18.1B

2-[4-{5-Chloro-2-[4-(trifluoromethyl)-1H-imidazol-1-yl]phenyl}-5-methoxy-2-oxopyridin-1(2H)-yl]-4-methoxybutanoic acid hydrochloride (Racemate)

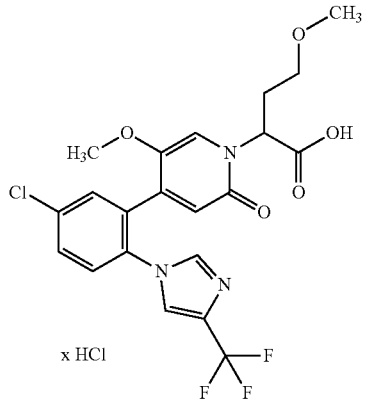 [SMILES: COCCC(C(=O)O)n1cc(OC)c(-c2cc(Cl)ccc2-n2cnc(C(F)(F)F)c2)cc1=O]

67.0 mg (purity 80%, 98.9 µmol) of tert-butyl 2-[4-{5-chloro-2-[4-(trifluoromethyl)-1H-imidazol-1-yl]phenyl}-5-methoxy-2-oxopyridin-1(2H)-yl]-4-methoxybutanoate (racemate) were reacted in 3 ml of a solution of hydrogen chloride in dioxane (4M) according to General Method 6D. Yield: 57.0 mg (80% pure, 88% of theory).

LC/MS [Method 1]: $R_t$=0.86 min; MS (ESIpos): m/z=486 [M+H]$^+$.

Example 19.1A tert-Butyl 2-{4-[5-chloro-2-(1H-tetrazol-1-yl)phenyl]-5-methoxy-2-oxopyridin-1(2H)-yl}pentanoate (Racemate)

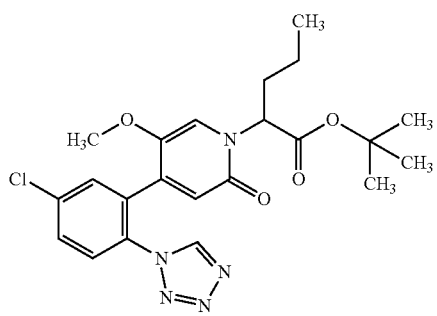 [SMILES: CCCC(C(=O)OC(C)(C)C)n1cc(OC)c(-c2cc(Cl)ccc2-n2cnnn2)cc1=O]

10 ml of dioxane were added to 815 mg (purity 50%, 1.0 mmol) of tert-butyl 2-[5-methoxy-2-oxo-4-(4,4,5,5-tetramethyl-1,3,2-dioxaborolan-2-yl)pyridin-1(2H)-yl]pentanoate (racemate) and 259 mg (1.0 mmol) of 1-(2-bromo-4-chlorophenyl)-1H-tetrazole. For 5 min, argon was passed through the reaction mixture. 81.7 mg (100 μmol) of [1,1-bis(diphenylphosphino)ferrocene]dichloropalladium-dichloromethane complex and 1.5 ml of an aqueous sodium carbonate solution (2.0 M, 3.0 mmol) were then added, and the mixture was stirred at 100° C. for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 20-75%). Yield: 436 mg (purity 94%, 89% of theory)

LC/MS [Method 10]: $R_t$=1.92 min; MS (ESIpos): m/z=460 [M+H]$^+$.

Example 19.1B

2-{4-[5-Chloro-2-(1H-tetrazol-1-yl)phenyl]-5-methoxy-2-oxopyridin-1(2H)-yl}pentanoic acid (Racemate)

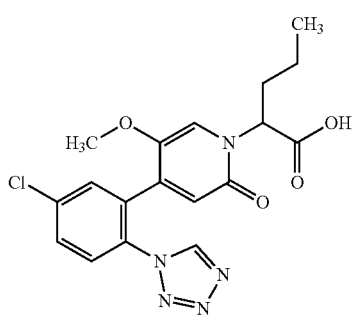 [SMILES: CCCC(C(=O)O)n1cc(OC)c(-c2cc(Cl)ccc2-n2cnnn2)cc1=O]

435 mg (purity 94%, 889 μmol) of tert-butyl 2-{4-[5-chloro-2-(1H-tetrazol-1-yl)phenyl]-5-methoxy-2-oxopyridin-1(2H)-yl}pentanoate (racemate) were reacted in 8.9 ml of a solution of hydrogen chloride in dioxane (4M) according to General Method 6D. Yield: 269 mg (73% of theory).

LC/MS [Method 10]: $R_t$=1.37 min; MS (ESIpos): m/z=404 [M+H]$^+$.

Example 20.1A tert-Butyl 2-[4-{5-chloro-2-[4-(difluoromethyl)-1H-1,2,3-triazol-1-yl]phenyl}-5-methoxy-2-oxopyridin-1(2H)-yl]pentanoate (Racemate)

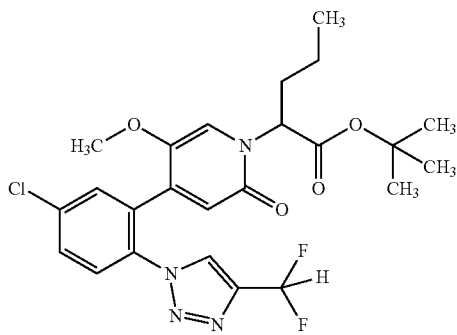 [SMILES: CCCC(C(=O)OC(C)(C)C)n1cc(OC)c(-c2cc(Cl)ccc2-n2cc(C(F)F)nn2)cc1=O]

9.7 ml of dioxane were added to 690 mg (purity 57%, 966 μmol) of tert-butyl 2-[5-methoxy-2-oxo-4-(4,4,5,5-tetramethyl-1,3,2-dioxaborolan-2-yl)pyridin-1(2H)-yl]pentanoate (racemate) and 301 mg (966 μmol) of 1-(2-bromo-4-chlorophenyl)-4-(difluoromethyl)-1H-1,2,3-triazole. For 5 min, argon was passed through the reaction mixture. 78.9 mg (96.6 μmol) of [1,1-bis(diphenylphosphino)ferrocene]dichloropalladium-dichloromethane complex and 1.4 ml of an aqueous sodium carbonate solution (2.0 M, 2.9 mmol) were then added, and the mixture was stirred at 100° C. for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 20-50%). Yield: 123 mg (24% of theory).

LC/MS [Method 10]: $R_t$=2.07 min; MS (ESIpos): m/z=509 [M+H]$^+$.

Example 20.1B

2-[4-{5-Chloro-2-[4-(difluoromethyl)-1H-1,2,3-triazol-1-yl]phenyl}-5-methoxy-2-oxopyridin-1(2H)-yl]pentanoic acid (Racemate)

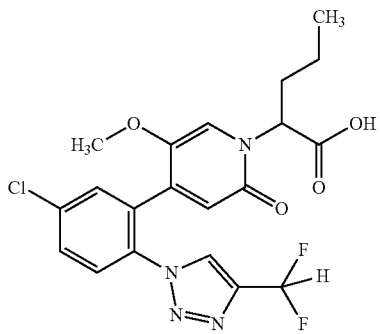 [SMILES: CCCC(C(=O)O)n1cc(OC)c(-c2cc(Cl)ccc2-n2cc(C(F)F)nn2)cc1=O]

120 mg (226 μmol) of tert-butyl 2-[4-{5-chloro-2-[4-(difluoromethyl)-1H-1,2,3-triazol-1-yl]phenyl}-5-methoxy-2-oxopyridin-1(2H)-yl]pentanoate (racemate) were reacted in 2.3 ml of a solution of hydrogen chloride in dioxane (4M) according to General Method 6D. Yield: 119 mg (85% pure, 99% of theory).

LC/MS [Method 10]: $R_t$=1.56 min; MS (ESIpos): m/z=453 [M+H]$^+$.

Example 21.1A tert-Butyl 2-{4-[5-chloro-2-(4-chloro-1H-1,2,3-triazol-1-yl)phenyl]-5-methoxy-2-oxopyridin-1(2H)-yl}pentanoate (Racemate)

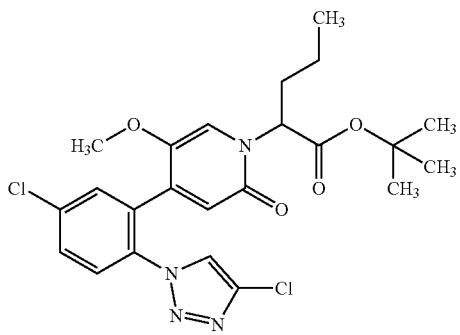 [SMILES: CCCC(C(=O)OC(C)(C)C)n1cc(OC)c(-c2cc(Cl)ccc2-n2cc(Cl)nn2)cc1=O]

10 ml of dioxane were added to 815 mg (purity 50%, 1.0 mmol) of tert-butyl 2-[5-methoxy-2-oxo-4-(4,4,5,5-tetramethyl-1,3,2-dioxaborolan-2-yl)pyridin-1(2H)-yl]pentanoate (racemate) and 299 mg (1.0 mmol) of 1-(2-bromo-4-chlorophenyl)-4-chloro-1H-1,2,3-triazole. For 5 min, argon was passed through the reaction mixture. 81.7 mg (100 µmol) of [1,1-bis(diphenylphosphino)ferrocene]dichloropalladium-dichloromethane complex and 1.5 ml of an aqueous sodium carbonate solution (2.0 M, 3.0 mmol) were then added, and the mixture was stirred at 100° C. for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 20-50%). Yield: 211 mg (43% of theory).

LC/MS [Method 10]: $R_t$=2.12 min; MS (ESIpos): m/z=493 [M+H]$^+$.

Example 21.1B

2-{4-[5-Chloro-2-(4-chloro-1H-1,2,3-triazol-1-yl)phenyl]-5-methoxy-2-oxopyridin-1(2H)-yl}-pentanoic acid (Racemate)

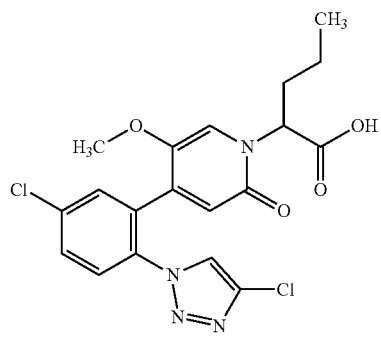 [SMILES: CCCC(C(=O)O)n1cc(OC)c(-c2cc(Cl)ccc2-n2cc(Cl)nn2)cc1=O]

211 mg (428 µmol) of tert-butyl 2-{4-[5-chloro-2-(4-chloro-1H-1,2,3-triazol-1-yl)phenyl]-5-methoxy-2-oxopyridin-1(2H)-yl}pentanoate (racemate) were reacted in 4.3 ml of a solution of hydrogen chloride in dioxane (4M) according to General Method 6D. Yield: 188 mg (100% of theory)

LC/MS [Method 10]: $R_t$=1.55 min; MS (ESIpos): m/z=437 [M+H]$^+$.

Example 22.1A tert-Butyl 2-{4-[5-chloro-2-(1H-tetrazol-1-yl)phenyl]-5-methoxy-2-oxopyridin-1(2H)-yl}hexanoate (Racemate)

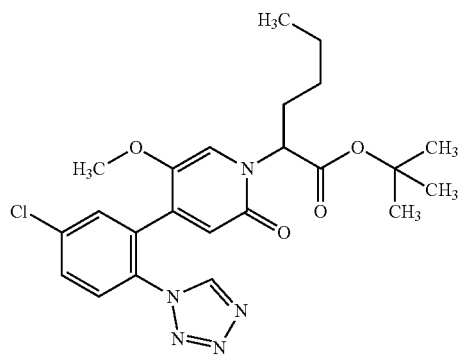 [SMILES: CCCCC(C(=O)OC(C)(C)C)n1cc(OC)c(-c2cc(Cl)ccc2-n2cnnn2)cc1=O]

7.9 ml of dioxane were added to 582 mg (purity 57%, 787 µmol) of tert-butyl 2-[5-methoxy-2-oxo-4-(4,4,5,5-tetramethyl-1,3,2-dioxaborolan-2-yl)pyridin-1(2H)-yl]hexanoate (racemate) and 204 mg (787 µmol) of 1-(2-bromo-4-chlorophenyl)-1H-tetrazole. For 5 min, argon was passed through the reaction mixture. 64.3 mg (78.7 µmol) of [1,1-bis(diphenylphosphino)ferrocene]dichloropalladium-dichloromethane complex and 1.2 ml of an aqueous sodium carbonate solution (2.0 M, 2.4 mmol) were then added, and the mixture was stirred at 100° C. in the microwave for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 20-50%). Yield: 255 mg (purity 91%, 62% of theory)

LC/MS [Method 1]: $R_t$=1.07 min; MS (ESIpos): m/z=474 [M+H]$^+$.

Example 22.1B

2-{4-[5-Chloro-2-(1H-tetrazol-1-yl)phenyl]-5-methoxy-2-oxopyridin-1(2H)-yl}hexanoic acid (Racemate)

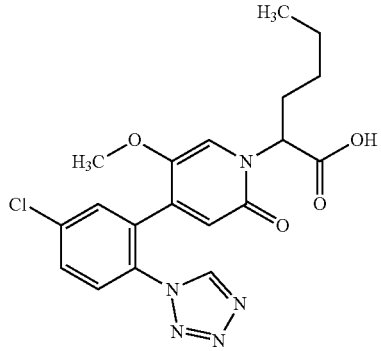 [SMILES: CCCCC(C(=O)O)n1cc(OC)c(-c2cc(Cl)ccc2-n2cnnn2)cc1=O]

254 mg (purity 91%, 485 µmol) of tert-butyl 2-{4-[5-chloro-2-(1H-tetrazol-1-yl)phenyl]-5-methoxy-2-oxopyridin-1(2H)-yl}hexanoate (racemate) were reacted in 4.9 ml of a solution of hydrogen chloride in dioxane (4M) according to General Method 6D. Yield: 209 mg (93% pure, 96% of theory).

LC/MS [Method 10]: $R_t$=1.51 min; MS (ESIpos): m/z=418 [M+H]$^+$.

Example 23.1A tert-Butyl 2-[4-{5-chloro-2-[4-(difluoromethyl)-1H-1,2,3-triazol-1-yl]phenyl}-5-methoxy-2-oxopyridin-1(2H)-yl]hexanoate (Racemate)

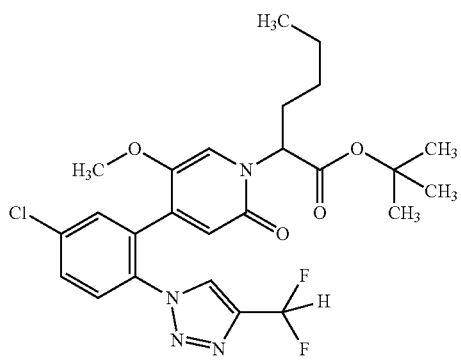 [SMILES: CCCCC(C(=O)OC(C)(C)C)n1cc(OC)c(-c2cc(Cl)ccc2-n2cc(C(F)F)nn2)cc1=O]

7.9 ml of dioxane were added to 582 mg (purity 57%, 787 µmol) of tert-butyl 2-[5-methoxy-2-oxo-4-(4,4,5,5-tetramethyl-1,3,2-dioxaborolan-2-yl)pyridin-1(2H)-yl]hexanoate (racemate) and 245 mg (787 µmol) of 1-(2-bromo-4-chlorophenyl)-4-(difluoromethyl)-1H-1,2,3-triazole. For 5 min, argon was passed through the reaction mixture. 64.3 mg (78.7 µmol) of [1,1-bis(diphenylphosphino)ferrocene]dichloropalladium-dichloromethane complex and 1.2 ml of an aqueous sodium carbonate solution (2.0 M, 2.4 mmol) were then added, and the mixture was stirred at 100° C. in the microwave for 2 hours. The reaction mixture was filtered through kieselguhr, washing with dichloromethane and acetonitrile, and the filtrate was concentrated. The crude product was purified by normal phase chromatography (mobile phase: cyclohexane/ethyl acetate, 20-35%). Yield: 355 mg (purity 86%, 74% of theory)

LC/MS [Method 10]: $R_f$=2.19 min; MS (ESIpos): m/z=523 [M+H]$^+$.

Example 23.1B

2-[4-{5-Chloro-2-[4-(difluoromethyl)-1H-1,2,3-triazol-1-yl]phenyl}-5-methoxy-2-oxopyridin-1(2H)-yl]hexanoic acid (Racemate)

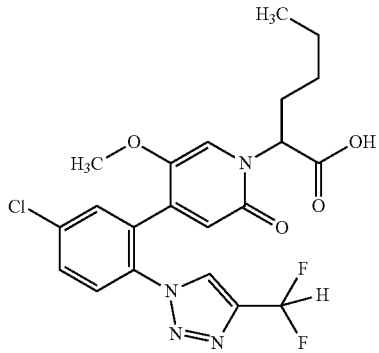 [SMILES: CCCCC(C(=O)O)n1cc(OC)c(-c2cc(Cl)ccc2-n2cc(C(F)F)nn2)cc1=O]

355 mg (purity 86%, 584 µmol) of tert-butyl 2-[4-{5-chloro-2-[4-(difluoromethyl)-1H-1,2,3-triazol-1-yl]phenyl}-5-methoxy-2-oxopyridin-1(2H)-yl]hexanoate (racemate) were reacted in 5.9 ml of a solution of hydrogen chloride in dioxane (4M) according to General Method 6D. Yield: 308 mg (81% pure, 92% of theory).

LC/MS [Method 10]: $R_f$=1.67 min; MS (ESIpos): m/z=467 [M+H]$^+$.

Example 24.1A tert-Butyl 2-[4-{5-chloro-2-[5-(trifluoromethyl)-1,3,4-oxadiazol-2-yl]phenyl}-5-methoxy-2-oxopyridin-1(2H)-yl]butanoate (Racemate)

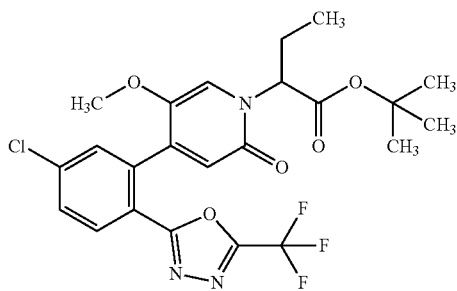 [SMILES: CCC(C(=O)OC(C)(C)C)n1cc(OC)c(-c2cc(Cl)ccc2-c2nnc(C(F)(F)F)o2)cc1=O]

7.3 ml of dioxane were added to 259 mg (0.792 mmol, 1.1 eq.) of 2-(2-bromo-4-chlorophenyl)-5-(trifluoromethyl)-1,3,4-oxadiazole, 0.57 g (0.72 mmol, purity 50%) of tert-butyl 2-[5-methoxy-2-oxo-4-(4,4,5,5-tetramethyl-1,3,2-dioxaborolan-2-yl)pyridin-1(2H)-yl]butanoate (racemate) and 298 mg (2.16 mmol, 3.0 eq.) of potassium carbonate. For 5 min, argon was passed through the reaction mixture. 18 mg (22 µmol, 0.03 eq.) of [1,1-bis(diphenylphosphino)ferrocene]dichloropalladium-dichloromethane complex were then added, and the mixture was stirred at 80° C. for 20 h. The reaction mixture was filtered through kieselguhr, washing with dichloromethane and acetonitrile, and the filtrate was concentrated. The crude product was purified by normal phase chromatography (mobile phase: cyclohexane/ethyl acetate 50:1 to 2:1). This product was purified by preparative HPLC. Yield: 198 mg (50% of theory).

LC/MS [Method 10]: $R_f$=2.24 min; MS (ESIpos): m/z=514 (M+H)$^+$.

$^1$H-NMR (400 MHz, DMSO-d$_6$): δ [ppm]=8.10 (d, 1H), 7.80 (dd, 1H), 7.73 (s, 1H), 7.20 (s, 1H), 6.55 (s, 1H), 5.13-4.89 (m, 1H), 2.17-2.10 (m, 2H), 1.41 (s, 9H), 0.83 (t, 3H).

Example 24.1B

2-[4-{5-Chloro-2-[5-(trifluoromethyl)-1,3,4-oxadiazol-2-yl]phenyl}-5-methoxy-2-oxopyridin-1(2H)-yl]butanoic acid (Racemate)

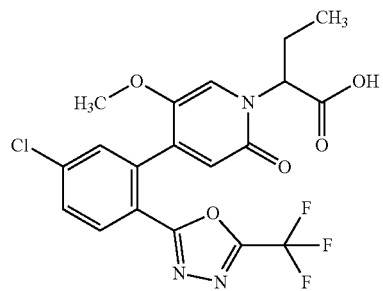 [SMILES: CCC(C(=O)O)n1cc(OC)c(-c2cc(Cl)ccc2-c2nnc(C(F)(F)F)o2)cc1=O]

198 mg (0.385 mmol) of tert-butyl 2-[4-{5-chloro-2-[5-(trifluoromethyl)-1,3,4-oxadiazol-2-yl]phenyl}-5-methoxy-2-oxopyridin-1(2H)-yl]butanoate were dissolved in 10.5 ml of dichloromethane, and 1.5 ml (19.3 mmol, 50.0 eq.) of trifluoroacetic acid were added. The reaction mixture was stirred at RT for 24 h and then concentrated under reduced pressure. The crude product was purified by column chromatography (125 mm×30 mm, reverse phase, 38 min, 10-95% acetonitrile/water acidified with 0.1% formic acid, 50 ml/min). Yield: 120 mg (68% of theory).

LC/MS [Method 8]: $R_f$=1.19 min; MS (ESIpos): m/z=458 (M+H)$^+$, $^1$H-NMR (400 MHz, DMSO-d$_6$): δ [ppm]=12.95 (brs, 1H), 8.11 (d, 1H), 7.80 (dd, 1H), 7.74 (d, 1H), 7.23 (brs, 1H), 6.54 (s, 1H), 5.32-4.85 (m, 1H), 3.30 (s, 3H, partially hidden), 2.18-2.08 (m, 2H), 0.82 (t, 3H).

Example 24.1C tert-Butyl 4-({2-[4-{5-chloro-2-[5-(trifluoromethyl)-1,3,4-oxadiazol-2-yl]phenyl}-5-methoxy-2-oxopyridin-1(2H)-yl]butanoyl}amino)benzoate (Racemate)

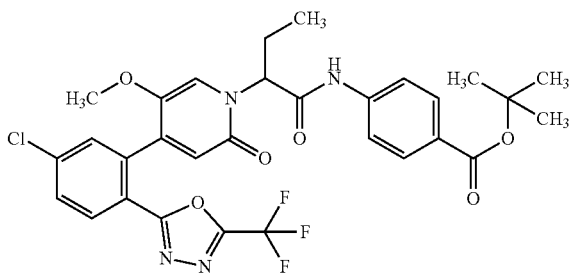 [SMILES: CCC(C(=O)Nc1ccc(C(=O)OC(C)(C)C)cc1)n1cc(OC)c(-c2cc(Cl)ccc2-c2nnc(C(F)(F)F)o2)cc1=O]

15 mg (0.033 mmol) of 2-[4-{5-chloro-2-[5-(trifluoromethyl)-1,3,4-oxadiazol-2-yl]phenyl}-5-methoxy-2-oxopyridin-1(2H)-yl]butanoic acid (racemate) and 10 mg (0.049 mmol, 1.5 eq.) of tert-butyl 4-aminobenzoate were reacted according to General Method 5A. Yield: 11 mg (53% of theory).

LC/MS [Method 8]: $R_t$=1.62 min; MS (ESIneg): m/z=631 (M–H)⁻.

Example 25.1A tert-Butyl 2-[4-{5-chloro-2-[5-(difluoromethyl)-1,3,4-oxadiazol-2-yl]phenyl}-5-methoxy-2-oxopyridin-1(2H)-yl]butanoate (Racemate)

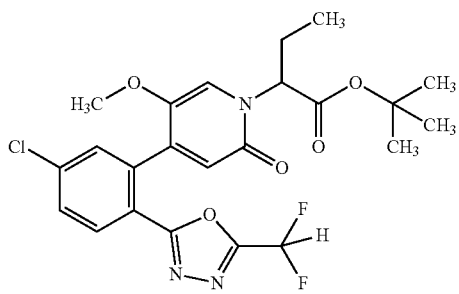 [SMILES: CCC(C(=O)OC(C)(C)C)n1cc(OC)c(-c2cc(Cl)ccc2-c2nnc(C(F)F)o2)cc1=O]

7.3 ml of dioxane were added to 245 mg (0.792 mmol, 1.1 eq.) of 2-(2-bromo-4-chlorophenyl)-5-(difluoromethyl)-1,3,4-oxadiazole, 0.57 g (0.72 mmol, purity 50%) of tert-butyl 2-[5-methoxy-2-oxo-4-(4,4,5,5-tetramethyl-1,3,2-dioxaborolan-2-yl)pyridin-1(2H)-yl]butanoate (racemate) and 298 mg (2.16 mmol, 3.0 eq.) of potassium carbonate. For 5 min, argon was passed through the reaction mixture. 18 mg (22 µmol, 0.03 eq.) of [1,1-bis(diphenylphosphino)ferrocene]dichloropalladium-dichloromethane complex were then added, and the mixture was stirred at 80° C. for 20 h. The reaction mixture was filtered through kieselguhr, washing with dichloromethane and acetonitrile, and the filtrate was concentrated. The crude product was purified by normal phase chromatography (mobile phase: cyclohexane/ethyl acetate, 50:1 to 3:1). This product was purified by preparative HPLC. Yield: 245 mg (67% of theory).

LC/MS [Method 10]: $R_t$=2.06 min; MS (ESIpos): m/z=496 (M+H)⁺.

Example 25.1B

2-[4-{5-Chloro-2-[5-(difluoromethyl)-1,3,4-oxadiazol-2-yl]phenyl}-5-methoxy-2-oxopyridin-1(2H)-yl]butanoic acid (Racemate)

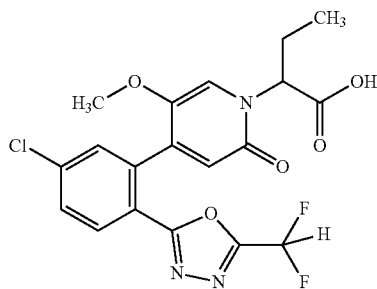 [SMILES: CCC(C(=O)O)n1cc(OC)c(-c2cc(Cl)ccc2-c2nnc(C(F)F)o2)cc1=O]

270 mg (0.544 mmol) of tert-butyl 2-[4-{5-chloro-2-[5-(difluoromethyl)-1,3,4-oxadiazol-2-yl]phenyl}-5-methoxy-2-oxopyridin-1(2H)-yl]butanoate were dissolved in 14.8 ml of dichloromethane, and 2.1 ml (27.2 mmol, 50.0 eq.) of trifluoroacetic acid were added. The reaction mixture was stirred at RT for 24 h and then concentrated under reduced pressure. The crude product was purified by column chromatography (125 mm×30 mm, reverse phase, 38 min, 10-95% acetonitrile/water acidified with 0.1% formic acid, 50 ml/min). Yield: 140 mg (57% of theory).

LC/MS [Method 8]: $R_t$=1.09 min; MS (ESIpos): m/z=440 (M+H)⁺,

¹H-NMR (400 MHz, DMSO-$d_6$): δ [ppm]=12.95 (brs, 1H), 8.08 (d, 1H), 7.78 (dd, 1H), 7.71 (d, 1H), 7.45 (t, 1H), 7.20 (brs, 1H), 6.51 (s, 1H), 5.32-4.80 (m, 1H), 3.29 (s, 3H), 2.19-2.04 (m, 2H), 0.83 (t, 3H).

Example 25.1C tert-Butyl 4-({2-[4-{5-chloro-2-[5-(difluoromethyl)-1,3,4-oxadiazol-2-yl]phenyl}-5-methoxy-2-oxopyridin-1(2H)-yl]butanoyl}amino)benzoate (Racemate)

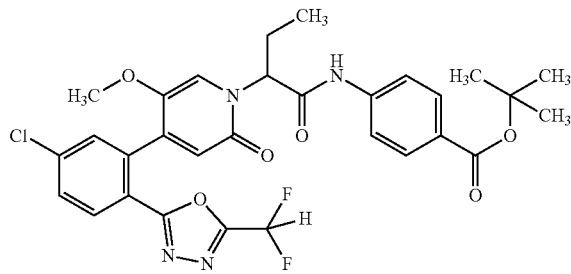 [SMILES: CCC(C(=O)Nc1ccc(C(=O)OC(C)(C)C)cc1)n1cc(OC)c(-c2cc(Cl)ccc2-c2nnc(C(F)F)o2)cc1=O]

15 mg (0.034 mmol) of 2-[4-{5-chloro-2-[5-(difluoromethyl)-1,3,4-oxadiazol-2-yl]phenyl}-5-methoxy-2-oxopyridin-1(2H)-yl]butanoic acid (racemate) and 10 mg (0.051 mmol, 1.5 eq.) of tert-butyl 4-aminobenzoate were reacted according to General Method 5A. Yield: 11 mg (52% of theory).

LC/MS [Method 8]: $R_t$=1.54 min; MS (ESIneg): m/z=613 (M–H)⁻.

Example 26.1A tert-Butyl 2-{4-[5-chloro-2-(4-chloro-1H-1,2,3-triazol-1-yl)phenyl]-5-methoxy-2-oxopyridin-1(2H)-yl}butanoate (Racemate)

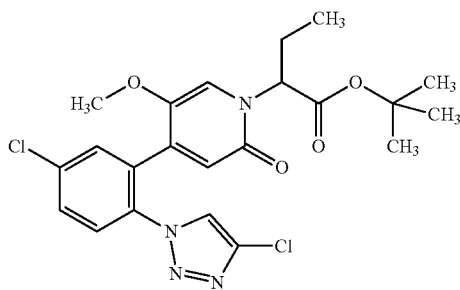 [SMILES: CCC(C(=O)OC(C)(C)C)n1cc(OC)c(-c2cc(Cl)ccc2-n2cc(Cl)nn2)cc1=O]

Under argon, 533 mg (purity 50%, 0.68 mmol) of tert-butyl 2-[5-methoxy-2-oxo-4-(4,4,5,5-tetramethyl-1,3,2-dioxaborolan-2-yl)pyridin-1(2H)-yl]butanoate (racemate), 165 mg (0.57 mmol) of 1-(2-bromo-4-chlorophenyl)-4-chloro-1H-1,2,3-triazole and 180 mg (1.69 mmol) of sodium carbonate were initially charged in 2.0 ml of a DMF/water mixture (3:1) in a microwave vessel, and the solution was flushed with argon. 46.1 mg (0.056 mmol) of [1,1-bis(diphenylphosphino)ferrocene]dichloropalladium/dichloromethane complex were then added, and the mixture was shaken at 100° C. for 2 hours. The reaction mixture was brought to RT, ethyl acetate and water were added and the phases were separated. The aqueous phase was re-extracted three times with ethyl acetate and the collected organic phases were dried over magnesium sulphate, filtered and concentrated. The residue was purified by flash silica gel chromatography (cyclohexane/ethyl acetate gradient). Yield: 148 mg (55% of theory). The crude product was converted without further purification.

LC/MS [Method 10]: $R_t$=2.00 min; MS (ESIpos): m/z=479 (M+H)$^+$.

Example 26.1B

2-{4-[5-Chloro-2-(4-chloro-1H-1,2,3-triazol-1-yl)phenyl]-5-methoxy-2-oxopyridin-1(2H)-yl}butanoic acid (Racemate)

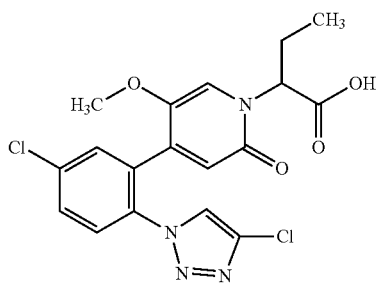 [SMILES: CCC(C(=O)O)n1cc(OC)c(-c2cc(Cl)ccc2-n2cc(Cl)nn2)cc1=O]

11.6 ml of a solution of hydrogen chloride in dioxane (4M) were added to 372 mg (0.78 mmol) of tert-butyl 2-{4-[5-chloro-2-(4-chloro-1H-1,2,3-triazol-1-yl)phenyl]-5-methoxy-2-oxopyridin-1(2H)-yl}butanoate (racemate), and the mixture was stirred at RT overnight. The reaction mixture was concentrated and the residue was dried under high vacuum. The crude product obtained in this manner was reacted without further purification. Yield: 307 mg (87% of theory).

LC/MS [Method 1]: $R_t$=0.79 min; MS (ESIpos): m/z=423 (M+H)$^+$.

Example 27.1A tert-Butyl 2-[4-{5-chloro-2-[4-(difluoromethyl)-1H-1,2,3-triazol-1-yl]phenyl}-5-methoxy-2-oxopyridin-1(2H)-yl]butanoate (Racemate)

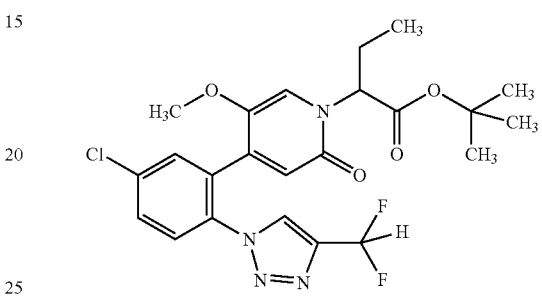

Under argon, 1.25 g (purity 50%, 1.59 mmol) of tert-butyl 2-[5-methoxy-2-oxo-4-(4,4,5,5-tetramethyl-1,3,2-dioxaborolan-2-yl)pyridin-1(2H)-yl]butanoate (racemate), 490 mg (1.59 mmol) of 1-(2-bromo-4-chlorophenyl)-4-(difluoromethyl)-1H-1,2,3-triazole and 659 mg (4.77 mmol) of potassium carbonate were initially charged in 16.7 ml of dioxane, and the solution was flushed with argon. 38.9 mg (0.048 mmol) of [1,1-bis(diphenylphosphino)ferrocene]dichloropalladium/dichloromethane complex were then added, and the mixture was stirred at 80° C. overnight. The reaction mixture was brought to RT, filtered through kieselguhr and washed through with dichloromethane. The filtrate was concentrated and the residue was separated by flash silica gel chromatography (cyclohexane/ethyl acetate gradient). Yield: 417 mg (53% of theory).

LC/MS [Method 10]: $R_t$=1.97 min; MS (ESIpos): m/z=495 (M+H)$^+$.

$^1$H-NMR (400 MHz, DMSO-d$_6$): δ [ppm]=8.71 (s, 1H), 7.79-7.72 (m, 3H), 7.36-6.99 (m, 2H), 6.47 (s, 1H), 4.95-4.86 (m, 1H), 3.22 (s, 3H), 2.09-1.97 (m, 2H), 1.38 (s, 9H), 0.75 (t, 3H).

Example 27.1B

2-[4-{5-Chloro-2-[4-(difluoromethyl)-1H-1,2,3-triazol-1-yl]phenyl}-5-methoxy-2-oxopyridin-1(2H)-yl]butanoic acid (Racemate)

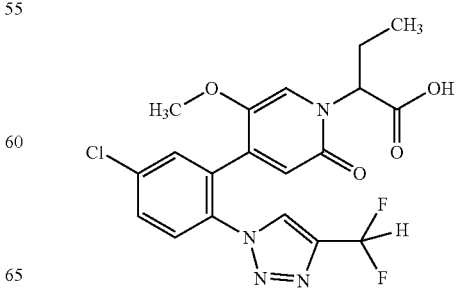

416 mg (0.84 mmol) of tert-butyl 2-[4-{5-chloro-2-[4-(difluoromethyl)-1H-1,2,3-triazol-1-yl]phenyl}-5-methoxy-2-oxopyridin-1(2H)-yl]butanoate (racemate) were initially charged in 0.9 ml of THF, 5.88 ml of an aqueous lithium hydroxide solution (1M) were added and the mixture was stirred at RT overnight. Water was added and the reaction mixture was adjusted to pH 4 with hydrochloric acid (1M). The mixture was then extracted three times with ethyl acetate and the collected organic phases were washed with saturated aqueous sodium chloride solution, dried over sodium sulphate, filtered and concentrated. The crude product obtained in this manner was reacted without further purification. Yield: 372 mg (92% pure, 93% of theory).

LC/MS [Method 1]: $R_t$=0.79 min; MS (ESIpos): m/z=439 (M+H)$^+$.

Example 28.1A tert-Butyl 2-{4-[5-chloro-2-(1H-tetrazol-1-yl)phenyl]-5-methoxy-2-oxopyridin-1(2H)-yl}butanoate (Racemate)

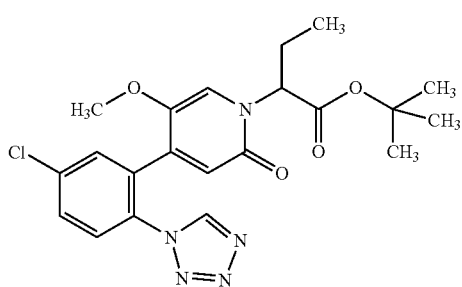 [SMILES: CCC(C(=O)OC(C)(C)C)n1cc(OC)c(-c2cc(Cl)ccc2-n2cnnn2)cc1=O]

Analogously to Example 26.1A, 1.45 g (purity 50%, 1.85 mmol) of tert-butyl 2-[5-methoxy-2-oxo-4-(4,4,5,5-tetramethyl-1,3,2-dioxaborolan-2-yl)pyridin-1(2H)-yl]butanoate (racemate) were reacted with 400 mg (1.54 mmol) of 1-(2-bromo-4-chlorophenyl)-1H-tetrazole. Yield: 313 mg (46% of theory). The crude product was converted without further purification.

LC/MS [Method 10]: $R_t$=1.80 min; MS (ESIpos): m/z=446 (M+H)$^+$.

Example 28.1B

2-{4-[5-Chloro-2-(1H-tetrazol-1-yl)phenyl]-5-methoxy-2-oxopyridin-1(2H)-yl}butanoic acid (Racemate)

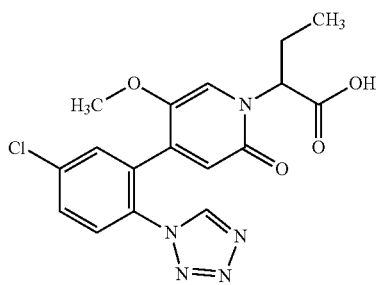 [SMILES: CCC(C(=O)O)n1cc(OC)c(-c2cc(Cl)ccc2-n2cnnn2)cc1=O]

5.0 ml of a solution of hydrogen chloride in dioxane (4M) were added to 313 mg (0.70 mmol) of tert-butyl 2-{4-[5-chloro-2-(4-chloro-1H-1,2,3-triazol-1-yl)phenyl]-5-methoxy-2-oxopyridin-1(2H)-yl}butanoate (racemate), and the mixture was stirred at RT overnight. The precipitated solid was filtered off, washed with in each case 5 ml of dioxane and diethyl ether and dried under high vacuum. The crude product obtained in this manner was reacted without further purification. Yield: 144 mg (53% of theory).

LC/MS [Method 10]: $R_t$=1.26 min; MS (ESIpos): m/z=390 (M+H)$^+$.

Example 29.1A tert-Butyl 2-{4-[5-chloro-2-(4-chloro-1H-1,2,3-triazol-1-yl)phenyl]-5-methoxy-2-oxopyridin-1(2H)-yl}-3-cyclobutylpropanoate (Racemate)

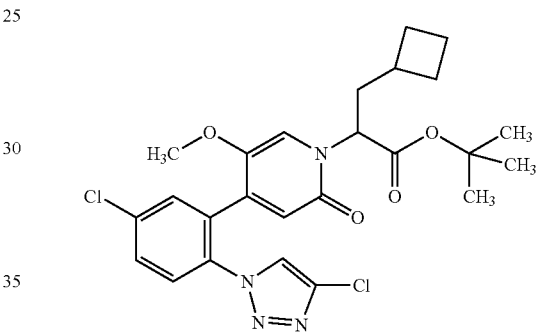

Under argon, 1.00 g (purity 51%, 1.45 mmol) of [1-(1-tert-butoxy-3-cyclobutyl-1-oxopropan-2-yl)-5-methoxy-2-oxo-1,2-dihydropyridin-4-yl]boric acid (racemate), 425 mg (1.45 mmol) of 1-(2-bromo-4-chlorophenyl)-4-chloro-1H-1,2,3-triazole and 602 mg (4.36 mmol) of potassium carbonate were initially charged in 15.3 ml of dioxane, and the solution was flushed with argon. 35.6 mg (0.044 mmol) of [1,1-bis(diphenylphosphino)ferrocene]dichloropalladium/dichloromethane complex were then added, and the mixture was stirred at 80° C. for 2.5 hours. The reaction mixture was brought to RT, filtered through kieselguhr and washed through with dichloromethane. The filtrate was concentrated and the residue was separated by flash silica gel chromatography (cyclohexane/ethyl acetate gradient). Yield: 244 mg (32% of theory).

LC/MS [Method 10]: $R_t$=2.24 min; MS (ESIpos): m/z=519 (M+H)$^+$.

$^1$H-NMR (400 MHz, DMSO-d$_6$): δ [ppm]=8.55 (s, 1H), 7.82-7.68 (m, 3H), 7.05 (s, 1H), 6.40 (s, 1H), 5.00-4.89 (m, 1H), 3.28 (s, 3H), 2.26-2.15 (m, 1H), 2.12-1.87 (m, 4H), 1.85-1.68 (m, 2H), 1.68-1.43 (m, 2H), 1.38 (s, 9H).

Example 29.1B

2-{4-[5-Chloro-2-(4-chloro-1H-1,2,3-triazol-1-yl)phenyl]-5-methoxy-2-oxopyridin-1(2H)-yl}-3-cyclobutylpropanoic acid (Racemate)

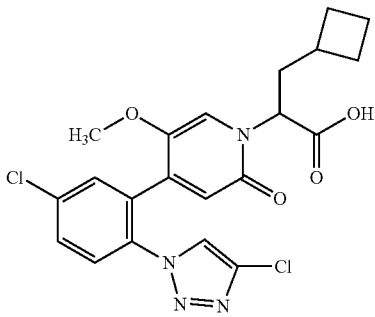 [SMILES: COc1cn(C(CC2CCC2)C(=O)O)c(=O)cc1-c1cc(Cl)ccc1-n1cc(Cl)nn1]

243 mg (0.47 mmol) of tert-butyl 2-{4-[5-chloro-2-(4-chloro-1H-1,2,3-triazol-1-yl)phenyl]-5-methoxy-2-oxopyridin-1(2H)-yl}-3-cyclobutylpropanoate (racemate) were initially charged in 0.9 ml of THF, 4.68 ml of an aqueous lithium hydroxide solution (1M) were added and the mixture was stirred at RT overnight. A further 10.0 eq. of lithium hydroxide were then added, and the mixture was stirred at 50° C. for 7 hours. The reaction mixture was diluted with ethyl acetate and water, the organic phase was separated off and the aqueous phase was re-extracted twice with ethyl acetate. The collected organic phases were washed with saturated aqueous sodium chloride solution, dried over sodium sulphate, filtered and concentrated. The crude product obtained in this manner was reacted without further purification. Yield: 211 mg (92% pure, 89% of theory).

LC/MS [Method 10]: $R_t$=1.71 min; MS (ESIpos): m/z=463 (M+H)$^+$.

Example 30.1A tert-Butyl 2-[4-{5-chloro-2-[5-(difluoromethyl)-1,2-oxazol-3-yl]phenyl}-5-methoxy-2-oxopyridin-1(2H)-yl]butanoate (Racemate)

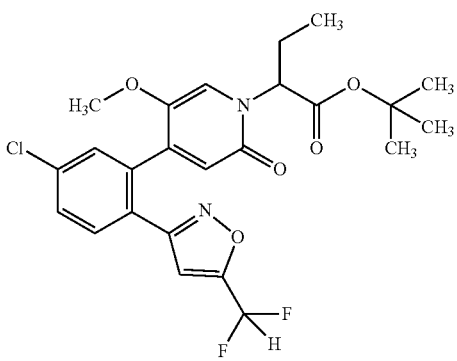 [SMILES: CCC(C(=O)OC(C)(C)C)n1cc(OC)c(-c2cc(Cl)ccc2-c2cc(C(F)F)on2)cc1=O]

10.0 ml of dioxane were added to 300 mg (0.972 mmol, 1.0 eq.) of 3-(2-bromo-4-chlorophenyl)-5-(difluoromethyl)-1,2-oxazole, 0.42 g (1.1 mmol) of tert-butyl 2-[5-methoxy-2-oxo-4-(4,4,5,5-tetramethyl-1,3,2-dioxaborolan-2-yl)pyridin-1(2H)-yl]butanoate (racemate) and 403 mg (2.92 mmol, 3.0 eq.) of potassium carbonate. For 20 min, argon was passed through the reaction mixture. 24 mg (29 μmol, 0.03 eq.) of [1,1-bis(diphenylphosphino)ferrocene]dichloropalladium-dichloromethane complex were then added, argon was passed through the reaction mixture for another 10 min and the mixture was subsequently stirred at 80° C. for 20 h. The reaction mixture was filtered through kieselguhr, washing with dichloromethane and acetonitrile, and the filtrate was concentrated. The crude product was purified by normal phase chromatography (mobile phase: cyclohexane/ethyl acetate 1:0 to 1:1). This product was purified by preparative HPLC. Yield: 292 mg (610% of theory).

LC/MS [Method 10]: $R_t$=2.16 min; MS (ESIpos): m/z=495 (M+H)$^+$.

Example 30.1B

2-[4-{5-Chloro-2-[5-(difluoromethyl)-1,2-oxazol-3-yl]phenyl}-5-methoxy-2-oxopyridin-1(2H)-yl]butanoic acid (Racemate)

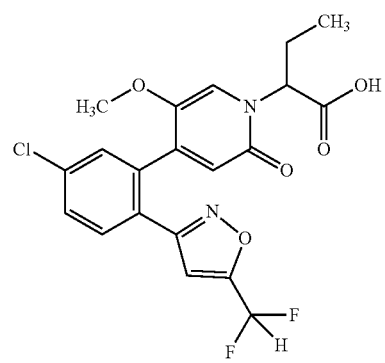 [SMILES: CCC(C(=O)O)n1cc(OC)c(-c2cc(Cl)ccc2-c2cc(C(F)F)on2)cc1=O]

200 mg (0.404 mmol) of tert-butyl 2-[4-{5-chloro-2-[5-(difluormethyl)-1,2-oxazol-3-yl]phenyl}-5-methoxy-2-oxopyridin-1(2H)-yl]butanoate (racemate) in 12 ml of dichloromethane in the presence of 1.6 ml (20.2 mmol, 50 eq.) of trifluoroacetic acid were reacted according to General Method 6A. Yield: 154 mg (87% of theory).

LC/MS [Method 10]: $R_t$=1.65 min; MS (ESIpos): m/z=439 (M+H)$^+$.

Example 31.1A tert-Butyl {4-[5-chloro-2-(1H-tetrazol-1-yl)phenyl]-5-methoxy-2-oxopyridin-1(2H)-yl}acetate

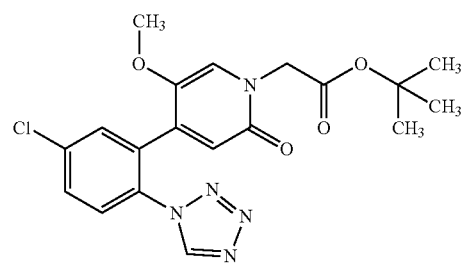 [SMILES: COc1cn(CC(=O)OC(C)(C)C)c(=O)cc1-c1cc(Cl)ccc1-n1cnnn1]

840.0 mg (purity 56%, 1.29 mmol) of tert-butyl [5-methoxy-2-oxo-4-(4,4,5,5-tetramethyl-1,3,2-dioxaborolan-2-yl)pyridin-1(2H)-yl]acetate were reacted with 334.2 mg (1.29 mmol) of 1-(2-bromo-4-chlorophenyl)-1H-tetrazole according to General Method 2A. Yield: 265 mg (92% pure, 45% of theory). The crude product was converted without further purification.

LC/MS [Method 10]: $R_t$=1.59 min; MS (ESIpos): m/z=418 (M+H)⁺.

Example 31.1B

{4-[5-Chloro-2-(1H-tetrazol-1-yl)phenyl]-5-methoxy-2-oxopyridin-1(2H)-yl}acetic acid

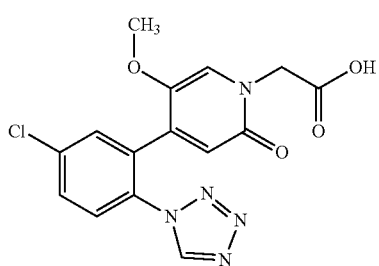 [SMILES: COc1cn(CC(=O)O)c(=O)cc1-c1cc(Cl)ccc1-n1cnnn1]

5.0 ml of a solution of hydrogen chloride in dioxane (4M) were added to 265 mg (0.63 mmol) of tert-butyl {4-[5-chloro-2-(1H-tetrazol-1-yl)phenyl]-5-methoxy-2-oxopyridin-1(2H)-yl}acetate, and the mixture was stirred at RT for 1 h. The reaction mixture was concentrated and the residue was dried under high vacuum. The crude product obtained in this manner was reacted without further purification. Yield: 252 mg (purity 91%, quant.).

LC/MS [Method 1]: $R_t$=0.60 min; MS (ESIpos): m/z=362 (M+H)⁺.

Example 32.1A tert-Butyl 2-[4-{5-chloro-2-[5-(trifluoromethyl)-1,3,4-thiadiazol-2-yl]phenyl}-5-methoxy-2-oxopyridin-1(2H)-yl]butanoate (Racemate)

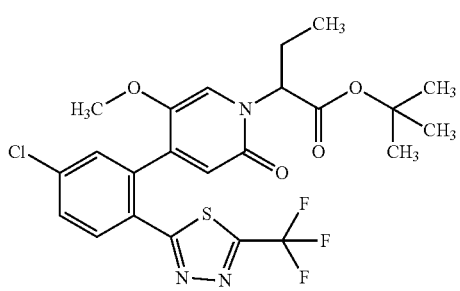 [SMILES: CCC(C(=O)OC(C)(C)C)n1cc(OC)c(-c2cc(Cl)ccc2-c2nnc(C(F)(F)F)s2)cc1=O]

Under argon, 824 mg (50% purity, 1.05 mmol) of tert-butyl 2-[5-methoxy-2-oxo-4-(4,4,5,5-tetramethyl-1,3,2-dioxaborolan-2-yl)pyridin-1(2H)-yl]butanoate (racemate), 300 mg (0.87 mmol) of 2-(2-bromo-4-chlorophenyl)-5-(trifluoromethyl)-1,3,4-thiadiazole and 278 mg (2.62 mmol) of sodium carbonate were initially charged in a mixture of 2.3 ml DMF and 0.7 ml water. The mixture was flushed with argon and 71.3 mg (0.087 mmol) of [1,1-bis(diphenylphosphino)ferrocene]-dichloropalladium dichloromethane complex were then added, and the mixture was shaken at 100° C. for 2 hours. The reaction mixture was brought to RT, diluted with ethyl acetate and water and phases were separated. The aqueous phase was washed three times with ethyl acetate and the combined organic phases were dried (magnesium sulfate), filtered and concentrated under reduced pressure. The residue was purified by normal phase chromatography (mobile phase: cyclohexane/ethyl acetate gradient) to give the title compound. Yield: 220 mg (48% of theory).

LC/MS [Method 10]: $R_t$=2.26 min; MS (ESIpos): m/z=530 (M+H)⁺.

Example 32.1B

2-[4-{5-Chloro-2-[5-(trifluoromethyl)-1,3,4-thiadiazol-2-yl]phenyl}-5-methoxy-2-oxopyridin-1(2H)-yl]butanoic acid (Racemate)

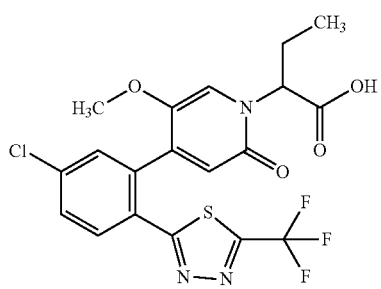 [SMILES: CCC(C(=O)O)n1cc(OC)c(-c2cc(Cl)ccc2-c2nnc(C(F)(F)F)s2)cc1=O]

6.2 ml of a solution of hydrogen chloride in dioxane (4M) were added to 220 mg (0.42 mmol) of tert-butyl 2-[4-{5-chloro-2-[5-(trifluoromethyl)-1,3,4-thiadiazol-2-yl]phenyl}-5-methoxy-2-oxopyridin-1(2H)-yl]butanoate (racemate), and the mixture was stirred at RT overnight. The reaction mixture was concentrated, dried under high vacuum and the crude product obtained in this manner was reacted without further purification. Yield: 209 mg (93% purity, quant.).

LC/MS [Method 10]: $R_t$=1.71 min; MS (ESIpos): m/z=474 (M+H)⁺.

Example 33.1A tert-Butyl 2-{4-[5-chloro-2-(4-chloro-1H-1,2,3-triazol-1-yl)phenyl]-5-methoxy-2-oxopyridin-1(2H)-yl}-4,4-difluorobutanoate (Racemate)

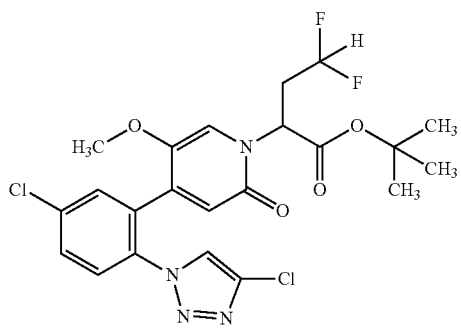 [SMILES: COc1cn(C(CC(F)F)C(=O)OC(C)(C)C)c(=O)cc1-c1cc(Cl)ccc1-n1cc(Cl)nn1]

Under argon, 1.94 g (61% purity, 2.76 mmol) of tert-butyl 4,4-difluoro-2-[5-methoxy-2-oxo-4-(4,4,5,5-tetramethyl-1, 3,2-dioxaborolan-2-yl)pyridin-1(2H)-yl]butanoate (racemate), 808 mg (2.76 mmol) of 1-(2-bromo-4-chlorophenyl)-4-chloro-1H-1,2,3-triazole and 1.14 g (8.28 mmol) of potassium carbonate were initially charged in 34.7 ml dioxane and the mixture was flushed with argon. 225 mg (0.276 mmol) of [1,1-bis(diphenylphosphino)ferrocene]dichloropalladium-dichloromethane complex were then added, and the mixture was stirred at 80° C. overnight. The reaction mixture was brought to RT, filtered through Celite and the residue washed with dichloromethane. The combined filtrate was concentrated under reduced pressure and dried under vacuum. The crude product was taken up in 8 ml dichloromethane and purified by normal phase chromatography (mobile phase: cyclohexane/ethyl acetate gradient). Yield: 926 mg (65% of theory).

LC/MS [Method 10]: $R_t$=1.98 min; MS (ESIpos): m/z=515 (M+H)$^+$.

Example 33.1B

2-{4-[5-Chloro-2-(4-chloro-1H-1,2,3-triazol-1-yl)phenyl]-5-methoxy-2-oxopyridin-1(2H)-yl}-4,4-difluorobutanoic acid (Racemate)

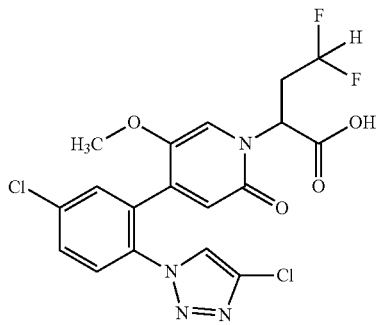 [SMILES: COc1cn(C(CC(F)F)C(=O)O)c(=O)cc1-c1cc(Cl)ccc1-n1cc(Cl)nn1]

28.2 ml of a solution of hydrogen chloride in dioxane (4M) were added to 926 mg (1.80 mmol) of tert-butyl 2-{4-[5-chloro-2-(4-chloro-1H-1,2,3-triazol-1-yl)phenyl]-5-methoxy-2-oxopyridin-1(2H)-yl}-4,4-difluorobutanoate (racemate), and the mixture was stirred at RT overnight. The reaction mixture was concentrated, the residue triturated with 15 ml diethyl ether and the resulting suspension was filtered. The filtered off solids were dried under high vacuum and the crude product obtained in this manner was reacted without further purification. Yield: 499 mg (60% of theory).

LC/MS [Method 10]: $R_t$=1.43 min; MS (ESIpos): m/z=459 (M+H)$^+$.

Example 34.1A tert-Butyl 2-[4-{5-chloro-2-[4-(difluoromethyl)-1H-1,2,3-triazol-1-yl]phenyl}-5-methoxy-2-oxopyridin-1(2H)-yl]propanoate (Racemate)

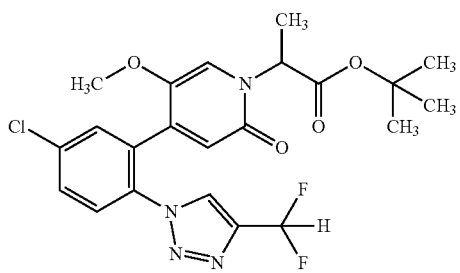 [SMILES: COc1cn(C(C)C(=O)OC(C)(C)C)c(=O)cc1-c1cc(Cl)ccc1-n1cc(C(F)F)nn1]

Under argon, 16.14 g (40% purity, 17.0 mmol) of methyl 2-[5-methoxy-2-oxo-4-(4,4,5,5-tetramethyl-1,3,2-dioxaborolan-2-yl)pyridin-1(2H)-yl]propanoate (racemate) were dissolved in 149 ml dioxane and 5.15 g (48.6 mmol) of sodium carbonate solution (2M in water) was added. 5.00 g (16.2 mmol) of 1-(2-bromo-4-chlorophenyl)-4-(difluoromethyl)-1H-1,2,3-triazole were then added, followed by 1.32 g (1.62 mmol) of [1,1-bis(diphenylphosphino)ferrocene]dichloropalladium dichloromethane complex. The reaction mixture was stirred at 100° C. for 2 hours, then brought to room temperature and poured onto 737 ml water. The resulting mixture was extracted three times with 678 ml methyl tert-butyl ether, and the combined organic phases were dried, filtered and concentrated under reduced pressure. The residue was purified by normal phase chromatography (mobile phase: cyclohexane/ethyl acetate gradient) to give 2.60 g (84% purity) of the crude product which was used in the next step without further purification.

LC/MS [Method 1]: $R_t$=1.00 min; MS (ESIpos): m/z=481 (M+H)$^+$.

Example 34.1B

2-[4-{5-Chloro-2-[4-(difluoromethyl)-1H-1,2,3-triazol-1-yl]phenyl}-5-methoxy-2-oxopyridin-1(2H)-yl]propanoic acid (Racemate)

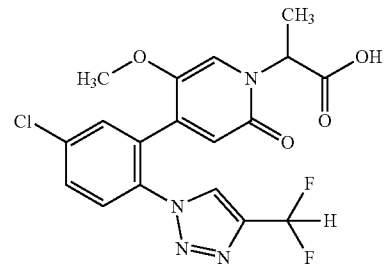

2.60 g (84% purity, 4.51 mmol) of tert-butyl 2-[4-{5-chloro-2-[4-(difluoromethyl)-1H-1,2,3-triazol-1-yl]phenyl}-5-methoxy-2-oxopyridin-1(2H)-yl]propanoate (racemate) were dissolved in 32.7 ml THF and subsequently 22.7 ml aqueous 1M lithium hydroxide was added. The mixture was stirred at RT for 16 h and then 103 ml water were added. The resulting mixture was acidified with 1M hydrochloric acid to pH 4 and then extracted three times with 72 ml ethyl acetate. The combined organic phases were washed with brine, dried (sodium sulfate) and concentrated under reduced pressure. The crude product obtained in this manner was reacted without further purification. Yield: 1.30 g (67% of theory).

LC/MS [Method 1]: $R_t$=0.74 min; MS (ESIpos): m/z=425 (M+H)$^+$.

Example 35.1A tert-Butyl 2-[4-{5-chloro-2-[4-(trifluoromethyl)-1H-1,2,3-triazol-1-yl]phenyl}-5-methoxy-2-oxopyridin-1(2H)-yl]propanoate (Racemate)

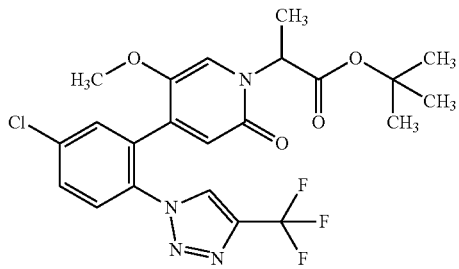 [SMILES: COc1cn(C(C)C(=O)OC(C)(C)C)c(=O)cc1-c1cc(Cl)ccc1-n1cc(C(F)(F)F)nn1]

Under argon, 2.17 g (50% purity, 3.01 mmol) of tert-butyl 2-[5-methoxy-2-oxo-4-(4,4,5,5-tetramethyl-1,3,2-dioxaborolan-2-yl)pyridin-1(2H)-yl]propanoate (racemate), 0.98 g (3.01 mmol) of 1-(2-bromo-4-chlorophenyl)-4-(trifluoromethyl)-1H-1,2,3-triazole and 1.25 g (9.02 mmol) of potassium carbonate and were dissolved in 30.5 ml dioxane. To this mixture, 0.147 g (0.180 mmol) of [1,1-bis(diphenylphosphino)ferrocene]dichloropalladium dichloromethane complex were added and the reaction mixture was stirred at 80° C. for 4 hours. The mixture was then brought to room temperature and filtered through Celite. The remaining solids were washed with dichloromethane/acetonitrile and the combined filtrates were concentrated under reduced pressure. The residue was purified by normal phase chromatography (mobile phase: cyclohexane/ethyl acetate gradient) to give 1.21 g (70% purity) of the product which was used in the next step without further purification.

LC/MS [Method 10]: $R_t$=2.02 min; MS (ESIpos): m/z=499 (M+H)$^+$.

Example 35.1B

2-[4-{5-Chloro-2-[4-(trifluoromethyl)-1H-1,2,3-triazol-1-yl]phenyl}-5-methoxy-2-oxopyridin-1(2H)-yl]propanoic acid

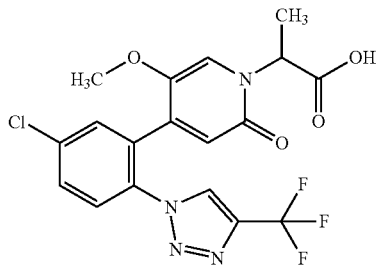

1.19 g (2.39 mmol) of tert-butyl 2-[4-{5-chloro-2-[4-(trifluoromethyl)-1H-1,2,3-triazol-1-yl]phenyl}-5-methoxy-2-oxopyridin-1(2H)-yl]propanoate (racemate) were treated with 31.9 ml of a solution of hydrogen chloride in dioxane (4M) and the mixture stirred overnight at room temperature. The reaction mixture was then concentrated under reduced pressure to give 1.17 g (90% purity, quant.) of the crude product which was used in the next step without further purification.

LC/MS [Method 1]: $R_t$=0.82 min; MS (ESIpos): m/z=443 (M+H)$^+$.

Example 36.1A tert-Butyl 2-[4-{5-chloro-2-[4-(trifluoromethyl)-1H-1,2,3-triazol-1-yl]phenyl}-5-methoxy-2-oxopyridin-1(2H)-yl]butanoate (Racemate)

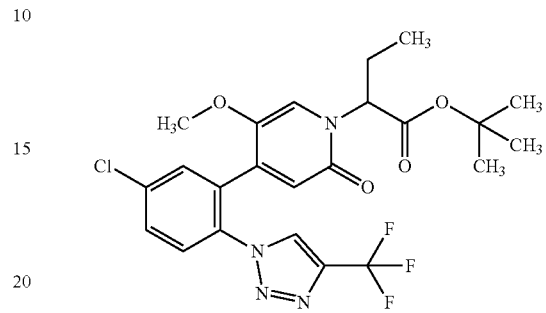

625 mg (50% purity, 795 µmol) of tert-butyl 2-[5-methoxy-2-oxo-4-(4,4,5,5-tetramethyl-1,3,2-dioxaborolan-2-yl)pyridin-1(2H)-yl]butanoate (racemate), 259 mg (795 µmol) of 1-(2-bromo-4-chlorophenyl)-4-(trifluoromethyl)-1H-1,2,3-triazole and 329 mg (2.38 mmol) potassium carbonate were suspended in 8.1 ml of dioxane. Argon was bubbled through this suspension during 5 min and then 38.9 mg, (47.7 µmol) [1,1-bis-(diphenylphosphino)-ferrocene]-dichloropalladiumn dichloromethane complex was added. The reaction mixture was stirred 4 h at 80° C. After cooling down to room temperature, the reaction mixture was filtered over celite and the filter cake was rinsed with dichloromethane and acetonitrile. The filtrate was evaporated and the residue was purified by flash silica-gel chromatography. (cyclohexane/ethyl acetate 0-40% mixture). Yield: 355 mg (70% purity, 61% of theory).

LC-MS [Method 1]: $R_t$=1.15 min; MS (ESIpos): m/z=513 [M+H]$^+$

Example 36.1B

2-[4-{5-Chloro-2-[4-(trifluoromethyl)-1H-1,2,3-triazol-1-yl]phenyl}-5-methoxy-2-oxopyridin-1(2H)-yl]butanoic acid (Racemate)

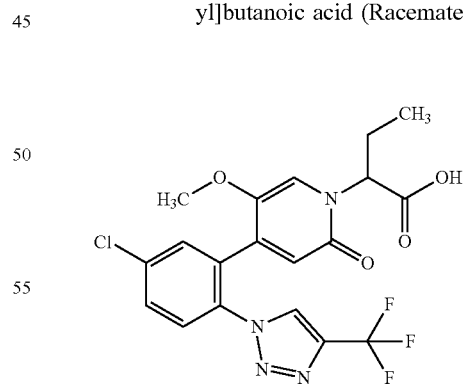

355 mg (83% purity, 574 µmol) of tert-butyl 2-[4-{5-chloro-2-[4-(trifluoromethyl)-1H-1,2,3-triazol-1-yl]phenyl}-5-methoxy-2-oxopyridin-1(2H)-yl]butanoate (racemate) were reacted in 8.3 ml of a solution of hydrogen chloride in dioxane (4M) according to General Method 6D. Yield: 260 mg (99% of theory).

LC-MS [Method 1]: $R_t$=0.90 min; MS (ESIpos): m/z=457 [M+H]$^+$

Example 37.1A tert-Butyl 2-[4-{5-chloro-2-[2-(difluoromethyl)-1,3-oxazol-5-yl]phenyl}-5-methoxy-2-oxopyridin-1(2H)-yl]butanoate (Racemate)

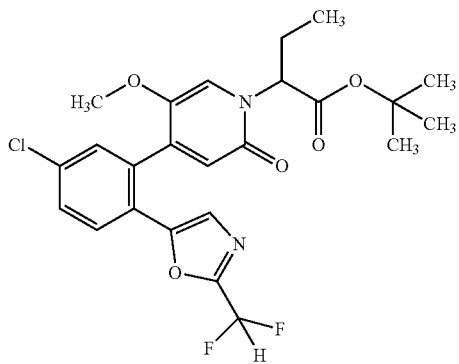 [SMILES: CCC(C(=O)OC(C)(C)C)n1cc(OC)c(-c2cc(Cl)ccc2-c2cnc(C(F)F)o2)cc1=O]

940 mg (60% purity, 1.43 mmol) of tert-butyl 2-[5-methoxy-2-oxo-4-(4,4,5,5-tetramethyl-1,3,2-dioxaborolan-2-yl)pyridin-1(2H)-yl]butanoate (Racemate), 531 mg (1.72 mmol) of 5-(2-bromo-4-chlorophenyl)-2-(difluoromethyl)-1,3-oxazole and 595 mg (4.3 mmol) of potassium carbonate were suspended in 14 ml of dioxane. Argon was bubbled through this suspension during 5 min and then 70.3 mg, (86 μmol) [1,1-bis-(diphenylphosphino)-ferrocene]-dichloropalladium dichloromethane complex was added. The reaction mixture was stirred 2 h at 100° C. in the microwave. After cooling down to room temperature, the reaction mixture was filtered over celite and the filter cake was rinsed with ethyl acetate. The filtrate was washed with brine and after separation, the organic phase was dried over sodium sulphate. After filtration and evaporation, the residue was purified by flash silica-gel chromatography. (cyclohexane/ethyl acetate 20-50% mixture). Yield: 570 mg (79% of theory).

LC-MS [Method 1]: $R_t$=1.15 min; MS (ESIpos): m/z=495 [M+H]$^+$

Example 37.1B

2-[4-{5-Chloro-2-[2-(difluoromethyl)-1,3-oxazol-5-yl]phenyl}-5-methoxy-2-oxopyridin-1(2H)-yl]butanoic acid (Racemate)

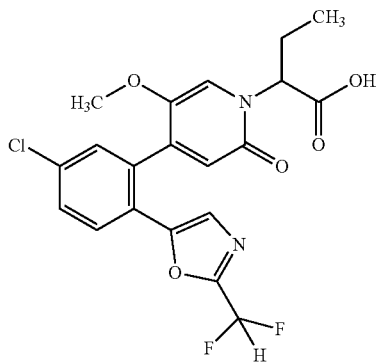 [SMILES: CCC(C(=O)O)n1cc(OC)c(-c2cc(Cl)ccc2-c2cnc(C(F)F)o2)cc1=O]

570 mg (1.13 mmol) of tert-butyl 2-[4-{5-chloro-2-[2-(difluoromethyl)-1,3-oxazol-5-yl]phenyl}-5-methoxy-2-oxopyridin-1(2H)-yl]butanoate (racemate) were reacted in 11 ml of a solution of hydrogen chloride in dioxane (4M) according to General Method 6D. Yield: 489 mg (99% of theory)

LC-MS [Method 10]: $R_t$=1.61 min; MS (ESIpos): m/z=439 [M+H]$^+$

Working Examples

General Method 1: Hydrolysis of a tert-butyl ester or a Boc-Protected Amine Using TFA At RT, TFA (10-20 eq.) was added to a solution of the appropriate tert-butyl ester derivative or a Boc-protected amine (1.0 eq.) in dichloromethane (about 25 ml/mmol), and the mixture was stirred at 0° C. to RT for 1 to 8 h. Subsequently, the reaction mixture was concentrated under reduced pressure. The residue was co-evaporated repeatedly with dichloromethane and/or toluene. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 2: Hydrolysis of a methyl or ethyl ester with Lithium Hydroxide

At RT, lithium hydroxide (2-4 eq.) was added to a solution of the appropriate ester (1.0 eq.) in a mixture of tetrahydrofuran/water (3:1, about 7-15 ml/mmol), and the mixture was stirred at RT. The reaction mixture was then adjusted to pH 1 using aqueous hydrochloric acid solution (1N). After addition of water/ethyl acetate, the aqueous phase was extracted three times with ethyl acetate. The combined organic phases were dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 3: Amide Coupling Using HATU/DIEA

Under argon and at RT, the appropriate amine (1.1-1.2 eq.), N,N-diisopropylethylamine (DIEA) (2.2-3.0 eq.) and a solution of HATU (1.2 eq.) in a little dimethylformamide were added to a solution of the appropriate carboxylic acid (1.0 eq.) in dimethylformamide (about 7-70 ml/mmol). The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by normal phase chromatography (cyclohexane/ethyl acetate mixtures or dichloromethane/methanol mixtures) or preparative RP-HPLC (water/acetonitrile gradient or water/methanol gradient).

General Method 4: Amide Coupling Using T3P/DIEA

Under argon and at 0° C. or RT, N,N-diisopropylethylamine (3 eq.) and propylphosphonic anhydride (T3P, 50% in dimethylformamide or in ethyl acetate, 3 eq.) were added dropwise to a solution of the carboxylic acid and the appropriate amine (1.1-1.5 eq.) in dimethylformamide (0.15-0.05 mmol). The reaction mixture was stirred at RT and then concentrated under reduced pressure. After addition of water/ethyl acetate and phase separation, the aqueous phase was extracted twice with ethyl acetate. The combined organic phases were dried (sodium sulphate or magnesium sulphate), filtered and concentrated under reduced pressure. The crude product was then purified either by flash chromatography (cyclohexane/ethyl acetate mixtures or dichloromethane/methanol mixtures) or preparative HPLC (Reprosil C18, water/acetonitrile gradient or water/methanol gradient).

General Method 5: Amide Coupling Using T3P/pyridine

A solution of the appropriate carboxylic acid (1 eq.) and the appropriate amine (1.1-1.5 eq.) in pyridine (about 0.1M) was heated to 60 to 90° C., and T3P (50% in dimethylformamide or in ethyl acetate, 1.5 to 4 eq.) was added dropwise. Alternatively, T3P (50% in dimethylformamide or in ethyl acetate, 1.5 to 4 eq.) was added at RT and the mixture was then stirred at RT or heated to RT to 90° C. After 1 to 20 h, the reaction mixture was cooled to RT, and water and ethyl acetate were added. The aqueous phase was extracted with ethyl acetate. The combined organic phases were washed with aqueous buffer solution (pH=5), with saturated aqueous sodium bicarbonate solution and with saturated aqueous sodium chloride solution, dried over sodium sulphate and concentrated under reduced pressure. The crude product was then optionally purified either by normal phase chromatography (cyclohexane/ethyl acetate mixtures or dichloromethane/methanol mixtures) or preparative RP-HPLC (water/acetonitrile gradient or water/methanol gradient).

General Method 6: Hydrolysis of a tert-butyl ester Using Hydrogen Chloride in Dioxane A solution of 1.0 eq. of the appropriate tert-butyl ester derivative in 4M hydrogen chloride in dioxane (concentration of the tert-butyl ester derivative about 0.1M) was either stirred at RT for 2 to 48 h or treated in an ultrasonic bath for 2 to 5 h. The reaction mixture was then concentrated under reduced pressure and the residue was co-evaporated repeatedly with tetrahydrofuran and dried under reduced pressure. The crude product was converted without further purification.

Example 1

4-[(4-tert-Butoxy-2-{4-[5-chloro-2-(1,3-oxazol-5-yl)phenyl]-5-methoxy-2-oxopyridin-1(2H)-yl}butanoyl)amino]benzoic acid (Racemate)

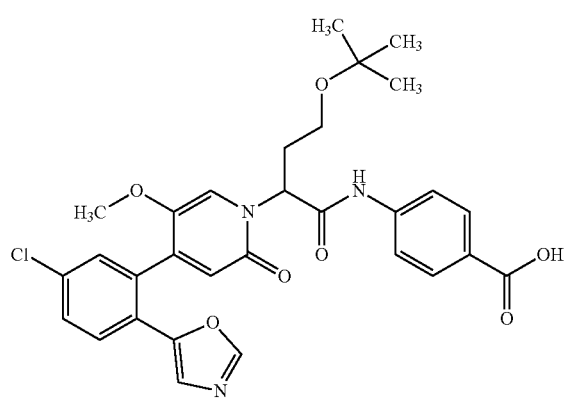 [SMILES: COc1cn(C(CCOC(C)(C)C)C(=O)Nc2ccc(C(=O)O)cc2)c(=O)cc1-c1cc(Cl)ccc1-c1cnco1]

A solution of 145 mg (0.23 mmol) of ethyl 4-[(4-tert-butoxy-2-{4-[5-chloro-2-(1,3-oxazol-5-yl)phenyl]-5-methoxy-2-oxopyridin-1(2H)-yl}butanoyl)amino]benzoate in 3.2 ml of methanol and 0.80 ml of water was stirred in the presence of 151 mg (0.46 mmol, 2 eq.) of caesium carbonate at 60-80° C. for several days. Methanol was then removed under reduced pressure. The aqueous residue was then adjusted to pH 2 using aqueous hydrochloric acid solution (1N), diluted with water and extracted twice with ethyl acetate. The combined organic phases were dried (sodium sulphate), filtered and concentrated under reduced pressure. The crude product was purified by preparative RP-HPLC (Reprosil C18, water/acetonitrile gradient). Yield: 25 mg (18% of theory)

LC/MS [Method 10]: $R_t$=1.87 min; MS (ESIpos): m/z=580 (M+H)$^+$, $^1$H-NMR (400 MHz, DMSO-d$_6$): δ [ppm]=12.73 (s, 1H), 10.69 (s, 1H), 8.38 (s, 1H), 7.91 (d, 2H), 7.81-7.73 (m, 3H), 7.62 (dd, 1H), 7.42 (br. s, 1H), 7.38 (s, 1H), 6.90 (s, 1H), 6.41 (s, 1H), 5.78 (t, 1H), 3.44 (s, 3H), 3.43-3.38 (m, 1H), 2.41-2.31 (m, 2H), 1.09 (s, 9H).

Example 2

4-tert-Butoxy-2-{4-[5-chloro-2-(1,3-oxazol-5-yl)phenyl]-5-methoxy-2-oxopyridin-1(2H)-yl}-N-(2-methyl-2H-indazol-5-yl)butanamide (Racemate)

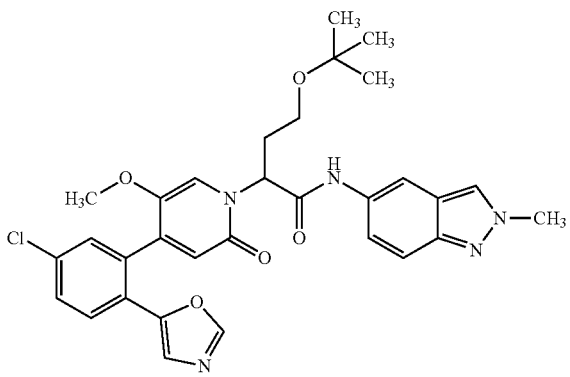 [SMILES: COc1cn(C(CCOC(C)(C)C)C(=O)Nc2ccc3nn(C)cc3c2)c(=O)cc1-c1cc(Cl)ccc1-c1cnco1]

13 mg (0.03 mmol) of 4-tert-butoxy-2-{4-[5-chloro-2-(1,3-oxazol-5-yl)phenyl]-5-methoxy-2-oxopyridin-1(2H)-yl}butanoic acid (racemate) and 5 mg (0.03 mmol, 1.1 eq.) of 2-methyl-2H-indazole-5-amine were reacted at RT in the presence of HATU and N,N-diisopropylethylamine according to General Method 3. After aqueous work-up, water was added to the residue and the product was crystallized in an ultrasonic bath. The precipitate formed was filtered off, washed with water and dried under reduced pressure. Yield: 4 mg (23% of theory)

LC/MS [Method 1]: $R_t$=0.99 min; MS (ESIpos): m/z=590 (M+H)$^+$, $^1$H-NMR (400 MHz, DMSO-d$_6$): δ [ppm]=10.32 (s, 1H), 8.38 (s, 1H), 8.25 (s, 1H), 8.15 (s, 1H), 7.78 (d, 1H), 7.62 (d, 1H), 7.55 (d, 1H), 7.46-7.38 (m, 2H), 7.33 (d, 1H), 6.90 (s, 1H), 6.41 (s, 1H), 5.80 (br. t, 1H), 4.13 (s, 3H), 3.44 (s, 3H), 3.4-3.36 (m, 1H), 2.41-2.30 (m, 2H), 1.09 (s, 9H).

Example 3

4-[(2-{4-[5-Chloro-2-(1,3-oxazol-5-yl)phenyl]-5-methoxy-2-oxopyridin-1(2H)-yl}butanoyl)amino]benzoic acid (Racemate)

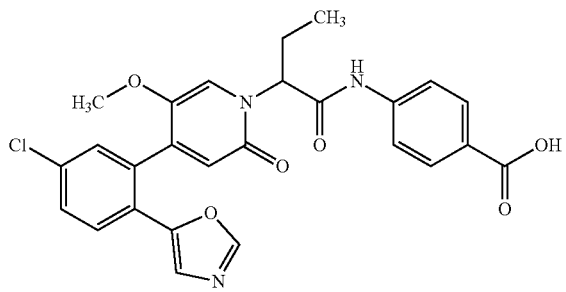 [SMILES: CCC(C(=O)Nc1ccc(C(=O)O)cc1)n1cc(OC)c(-c2cc(Cl)ccc2-c2cnco2)cc1=O]

138 mg (25 mmol) of tert-butyl 4-[(2-{4-[5-chloro-2-(1,3-oxazol-5-yl)phenyl]-5-methoxy-2-oxopyridin-1(2H)-yl}butanoyl)amino]benzoate (racemate) were hydrolysed with 20 eq. of trifluoroacetic acid in 5 ml of dichloromethane according to General Method 1. The crude product was purified by preparative RP-HPLC (Reprosil C18, water/acetonitrile gradient). Yield: 92 mg (74% of theory)

LC/MS [Method 1]: $R_t$=0.90 min; MS (ESIpos): m/z=508 (M+H)$^+$, $^1$H-NMR (400 MHz, DMSO-d$_6$): δ [ppm]=12.75 (s, 1H), 10.75 (s, 1H), 8.38 (s, 1H), 7.92 (d, 2H), 7.81-7.72 (m, 3H), 7.62 (dd, 1H), 7.48 (d, 1H), 7.37 (s, 1H), 6.91 (s, 1H), 6.42 (s, 1H), 5.65 (dd, 1H), 3.43 (s, 3H), 2.25-2.10 (m, 2H), 0.92 (t, 3H).

Example 4

4-{[2-{4-[5-Chloro-2-(1,3-oxazol-5-yl)phenyl]-5-methoxy-2-oxopyridin-1(2H)-yl}-4-(trifluoromethoxy)butanoyl]amino}benzoic acid (Racemate)

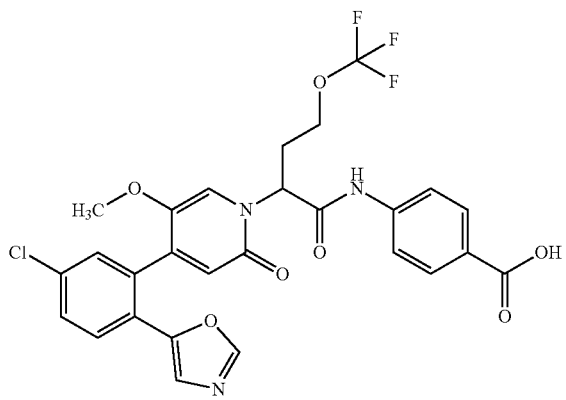 [SMILES: COc1cn(C(CCOC(F)(F)F)C(=O)Nc2ccc(C(=O)O)cc2)c(=O)cc1-c1cc(Cl)ccc1-c1cnco1]

172 mg (purity 94%, 0.25 mmol) of tert-butyl 4-{[2-{4-[5-chloro-2-(1,3-oxazol-5-yl)phenyl]-5-methoxy-2-oxopyridin-1(2H)-yl}-4-(trifluormethoxy)butanoyl]amino}benzoate (racemate) were hydrolysed with 20 eq. of trifluoroacetic acid in 5 ml of dichloromethane according to General Method 1. The crude product was purified by flash chromatography (silica cartridge, cyclohexane/ethyl acetate mixture). Yield: 105 mg (71% of theory)

LC/MS [Method 10]: $R_t$=1.83 min; MS (ESIpos): m/z=592 (M+H)$^+$, $^1$H-NMR (400 MHz, DMSO-d$_6$): δ [ppm]=12.76 (s, 1H), 10.73 (s, 1H), 8.35 (s, 1H), 7.92 (d, 2H), 7.81-7.73 (m, 3H), 7.62 (dd, 1H), 7.44 (d, 1H), 7.37 (s, 1H), 6.94 (s, 1H), 6.44 (s, 1H), 5.80 (t, 1H), 4.24-4.16 (m, 1H), 4.06-3.97 (m, 1H), 3.43 (s, 3H), 2.69-2.57 (m, 2H).

Example 5

4-[(2-{4-[5-Chloro-2-(1,3-oxazol-5-yl)phenyl]-5-methoxy-2-oxopyridin-1(2H)-yl}-3-[(2S)-tetrahydro-2H-pyran-2-yl]propanoyl)amino]benzoic acid (Mixture of Enantiomerically Pure Diastereomers)

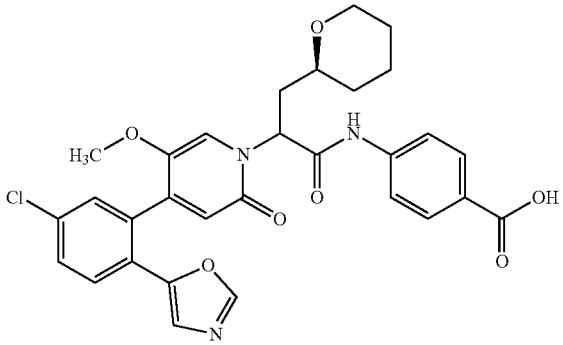 [SMILES: COc1cn(C(C[C@@H]2CCCCO2)C(=O)Nc2ccc(C(=O)O)cc2)c(=O)cc1-c1cc(Cl)ccc1-c1cnco1]

241 mg (purity 86%, 0.33 mmol) of tert-butyl 4-[(2-{4-[5-chloro-2-(1,3-oxazol-5-yl)phenyl]-5-methoxy-2-oxopyridin-1(2H)-yl}-3-[(2S)-tetrahydro-2H-pyran-2-yl]propanoyl)amino]benzoate (mixture of enantiomerically pure diastereomers) were hydrolysed with 20 eq. of trifluoroacetic acid in 7 ml of dichloromethane according to General Method 1. The crude product was purified by preparative RP-HPLC (Reprosil C18, water/acetonitrile gradient). Yield: 81 mg (43% of theory)

LC/MS [Method 10]: $R_t$=1.83 min; MS (ESIpos): m/z=578 (M+H)$^+$, $^1$H-NMR (400 MHz, DMSO-d$_6$): δ [ppm]=12.73 (s, 1H), 10.70 (br. m, 1H), 8.40/8.39 (2×s, 1H), 7.91/7.90 (2×d, 2H), 7.81-7.73 (m, 3H), 7.65-7.60 (2×dd, 1H), 7.49/7.46 (2×d, 1H), 7.41/7.37 (2×s, 1H), 6.85/6.82 (2×, 1H), 6.41/6.40 (2×, 1H), 5.93-5.65 (br. m, 1H), 3.92-3.81 (m, 1H), 3.43 (s, 3H), 3.28-3.18 (m, 1H), 3.14-3.05 (m, 1H), 2.45-2.37 (m, 1H), 2.28-2.15 (m, 1H), 1.83-1.73 (m, 1H), 1.69-1.56 (m, 1H), 1.53-1.39 (m, 3H), 1.34-1.21 (m, 1H).

Example 6

4-[(2-{4-[5-Chloro-2-(1,3-oxazol-5-yl)phenyl]-5-methoxy-2-oxopyridin-1(2H)-yl}-4-methoxy-butanoyl)amino]benzoic acid (Racemate)

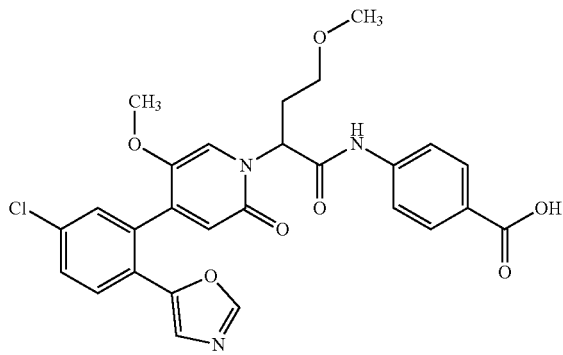 [SMILES: COCCC(C(=O)Nc1ccc(C(=O)O)cc1)n1cc(OC)c(-c2cc(Cl)ccc2-c2cnco2)cc1=O]

210 mg (0.353 mmol) of tert-butyl 4-{[(2-{4-[5-chloro-2-(1,3-oxazol-5-yl)phenyl]-5-methoxy-2-oxopyridin-1(2H)-yl}-4-methoxybutanoyl]amino}benzoate (racemate) were reacted with 25 ml of TFA and 30 ml of dichloromethane according to General Method 1. Yield: 135 mg (71% of theory)

LC/MS [Method 10]: $R_t$=1.60 min; MS (ESIpos): m/z=538 (M+H)$^+$, $^1$H-NMR (400 MHz, DMSO-d$_6$): δ [ppm]=12.74 (br. s, 1H), 10.70 (br. s, 1H), 8.39 (s, 1H), 7.91 (d, 2H), 7.82-7.72 (m, 3H), 7.62 (dd, 1H), 7.48 (d, 1H), 7.39 (s, 1H), 6.90 (s, 1H), 6.41 (s, 1H), 5.85-5.65 (m, 1H), 3.47-3.38 (m, 4H), 3.35-3.26 (m, 1H), 3.24 (s, 3H), 2.46-2.37 (m, 2H).

Example 7

4-{[(2S)-2-{4-[5-Chloro-2-(1,3-oxazol-5-yl)phenyl]-5-methoxy-2-oxopyridin-1(2H)-yl}-4-methoxybutanoyl]amino}benzoic acid (Enantiomer 2)

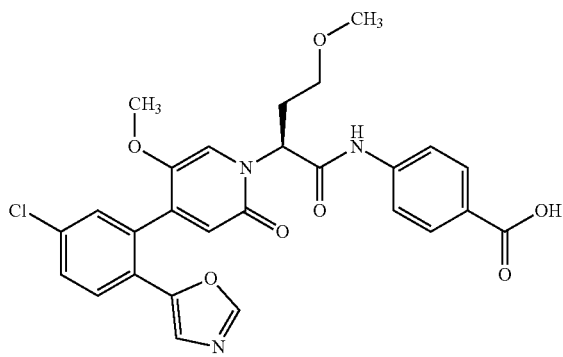 [SMILES: COCC[C@@H](C(=O)Nc1ccc(C(=O)O)cc1)n1cc(OC)c(-c2cc(Cl)ccc2-c2cnco2)cc1=O]

Enantiomer separation of 130 mg of 4-[(2-{4-[5-chloro-2-(1,3-oxazol-5-yl)phenyl]-5-methoxy-2-oxopyridin-1(2H)-yl}-4-methoxybutanoyl)amino]benzoic acid (racemate) gave 39 mg of enantiomer 1 (chiral HPLC: $R_t$=5.1 min) and 29 mg of the title compound Example 7 (enantiomer 2): chiral HPLC: $R_t$=9.00 min; 100% ee.

Separating method: column: Daicel Chiralpak AZ-H SFC 5 μm, 250 mm×30 mm; mobile phase: carbon dioxide 65%/ethanol 35%; temperature: 40° C.; flow rate: 100 ml/min; pressure: 100 bar; UV detection: 210 nm.

Analysis: column: Chiralpak AZ-H SFC 5 μm 250 mm×4.6 mm; mobile phase: 60% carbon dioxide, 40% ethanol; flow rate: 3 ml/min; UV detection: 210 nm.

Example 8

5-[(2-{4-[5-Chloro-2-(1,3-oxazol-5-yl)phenyl]-5-methoxy-2-oxopyridin-1(2H)-yl}-4-methoxybutanoyl)amino]-N-cyclopropylthiophen-2-carboxamide (Racemate)

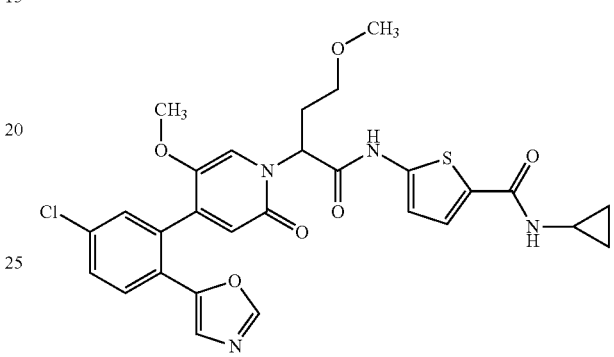

36.6 mg (purity 80%, 0.070 mmol) of 2-{4-[5-chloro-2-(1,3-oxazol-5-yl)phenyl]-5-methoxy-2-oxopyridin-1(2H)-yl}-4-methoxybutanoic acid (racemate) and 22.3 mg (0.105 mmol) of 5-amino-N-cyclopropylthiophene-2-carboxamide in 0.58 ml of pyridine were reacted according to General Method 5. Yield: 30 mg (73% of theory).

LC/MS [Method 10]: $R_t$=1.61 min; MS (ESIpos): m/z=583 (M+H)$^+$, $^1$H-NMR (400 MHz, DMSO-d$_6$): δ [ppm]=11.78 (br. s, 1H), 8.39 (s, 1H), 8.28 (d, 1H), 7.78 (d, 1H), 7.62 (dd, 1H), 7.52-7.45 (m, 2H), 7.38 (s, 1H), 6.92 (s, 1H), 6.74 (d, 1H), 6.41 (s, 1H), 5.85-5.55 (m, 1H), 3.49-3.36 (m, 4H), 3.29-3.16 (m, 4H), 2.79-2.69 (m, 1H), 2.45-2.34 (m, 2H), 0.74-0.60 (m, 2H), 0.59-0.47 (m, 2H).

Example 9

2-{4-[5-Chloro-2-(1,3-oxazol-5-yl)phenyl]-5-methoxy-2-oxopyridin-1(2H)-yl}-4-methoxy-N-(2-methyl-2H-indazol-5-yl)butanamide (Racemate)

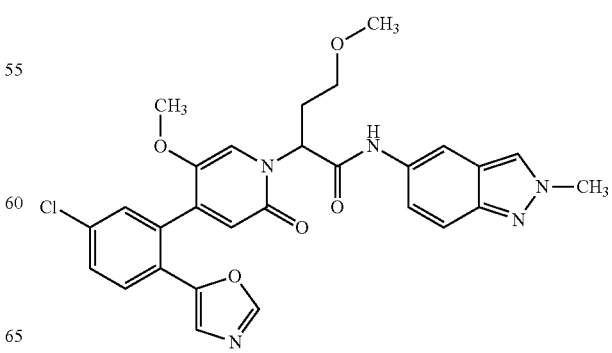

36.6 mg (purity 80%, 0.070 mmol) of 2-{4-[5-chloro-2-(1,3-oxazol-5-yl)phenyl]-5-methoxy-2-oxopyridin-1(2H)-yl}-4-methoxybutanoic acid (racemate) and 17.4 mg (purity 89%, 0.105 mmol) of 2-methyl-2H-indazole-5-amine in 0.58 ml of pyridine were reacted according to General Method 5. Yield: 20 mg (52% of theory).

LC/MS [Method 10]: $R_t$=1.57 min; MS (ESIpos): m/z=548 (M+H)$^+$, $^1$H-NMR (400 MHz, DMSO-d$_6$): δ [ppm]=10.35 (br. s, 1H), 8.39 (s, 1H), 8.26 (s, 1H), 8.16-8.11 (m, 1H), 7.78 (d, 1H), 7.62 (dd, 1H), 7.55 (d, 1H), 7.48 (d, 1H), 7.43 (s, 1H), 7.32 (dd, 1H), 6.90 (s, 1H), 6.41 (s, 1H), 5.87-5.72 (m, 1H), 4.13 (s, 3H), 3.47-3.38 (m, 4H), 3.36-3.26 (m, 1H), 3.24 (s, 3H), 2.44-2.34 (m, 2H).

Example 10

5-[(2-{4-[5-Chloro-2-(1,3-oxazol-5-yl)phenyl]-5-methoxy-2-oxopyridin-1(2H)-yl}-4-methoxybutanoyl)amino]-N-methylpyridine-2-carboxamide (Racemate)

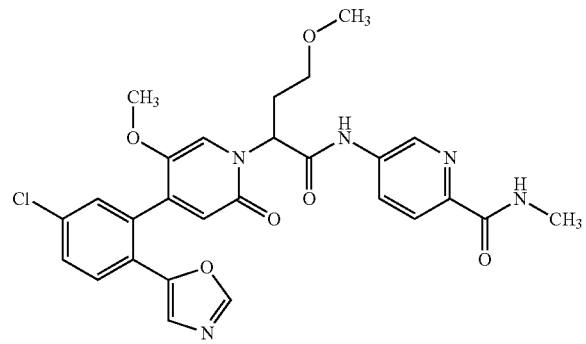 [SMILES: CNC(=O)c1ccc(NC(=O)C(CCOC)n2cc(OC)c(-c3cc(Cl)ccc3-c3cnco3)cc2=O)cn1]

41.9 mg (purity 70%, 0.070 mmol) of 2-{4-[5-chloro-2-(1,3-oxazol-5-yl)phenyl]-5-methoxy-2-oxopyridin-1(2H)-yl}-4-methoxybutanoic acid (racemate) and 16.2 mg (0.105 mmol) of 5-amino-N-methylpyridine-2-carboxamide in 0.58 ml of pyridine were reacted according to General Method 5. Yield: 30 mg (78% of theory).

LC/MS [Method 10]: $R_t$=1.55 min; MS (ESIpos): m/z=552 (M+H)$^+$, $^1$H-NMR (400 MHz, DMSO-d$_6$): δ [ppm]=10.82 (br. s, 1H), 8.87 (d, 1H), 8.74-8.58 (m, 1H), 8.39 (s, 1H), 8.23 (dd, 1H), 8.01 (d, 1H), 7.78 (d, 1H), 7.63 (dd, 1H), 7.47 (d, 1H), 7.38 (s, 1H), 6.91 (s, 1H), 6.42 (s, 1H), 5.82-5.65 (m, 1H), 3.49-3.38 (m, 4H), 3.35-3.26 (m, 1H), 3.24 (s, 3H), 2.80 (d, 3H), 2.47-2.39 (m, 2H).

Example 11

4-[(2-{4-[5-Chloro-2-(1,3-oxazol-5-yl)phenyl]-5-methoxy-2-oxopyridin-1(2H)-yl}-4-methoxybutanoyl)amino]-2-fluorobenzamide (Racemate)

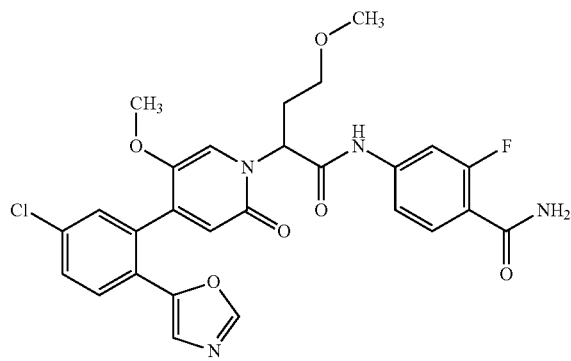 [SMILES: COCCC(C(=O)Nc1ccc(C(N)=O)c(F)c1)n1cc(OC)c(-c2cc(Cl)ccc2-c2cnco2)cc1=O]

41.9 mg (purity 70%, 0.070 mmol) of 2-{4-[5-chloro-2-(1,3-oxazol-5-yl)phenyl]-5-methoxy-2-oxopyridin-1(2H)-yl}-4-methoxybutanoic acid (racemate) and 16.2 mg (0.105 mmol) of 4-amino-2-fluorobenzamide in 0.58 ml of pyridine were reacted according to General Method 4. Yield: 30 mg (77% of theory).

LC/MS [Method 10]: $R_t$=1.54 min; MS (ESIpos): m/z=555 (M+H)$^+$, $^1$H-NMR (400 MHz, DMSO-d$_6$): δ [ppm]=10.76 (br. s, 1H), 8.39 (s, 1H), 7.78 (d, 1H), 7.73-7.58 (m, 3H), 7.58-7.40 (m, 4H), 7.37 (s, 1H), 6.90 (s, 1H), 6.41 (s, 1H), 5.81-5.62 (m, 1H), 3.49-3.36 (m, 4H), 3.32-3.26 (m, 1H), 3.23 (s, 3H), 2.46-2.34 (m, 2H).

Example 12

2-{4-[5-Chloro-2-(4,5-dihydro-1,2-oxazol-3-yl)phenyl]-5-methoxy-2-oxopyridin-1(2H)-yl}-4-methoxy-N-(2-methyl-2H-indazol-5-yl)butanamide (Racemate)

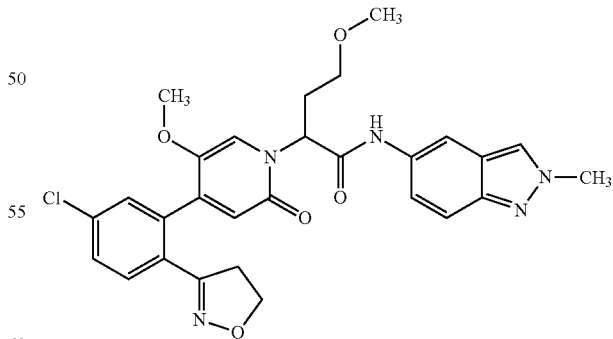

66 mg (0.137 mmol) of 2-{4-[5-chloro-2-(4,5-dihydro-1,2-oxazol-3-yl)phenyl]-5-methoxy-2-oxopyridin-1(2H)-yl}-4-methoxybutanoic acid hydrochloride (racemate) and 30.9 mg (0.206 mmol) of 2-methyl-2H-indazole-5-amine in 1 ml of pyridine were reacted according to General Method 5. Yield: 63.5 mg (83% of theory)

LC/MS [Method 10]: $R_t$=1.55 min; MS (ESIpos): m/z=550 (M+H)$^+$, $^1$H-NMR (400 MHz, DMSO-d$_6$): δ [ppm]=10.34 (s, 1H), 8.25 (s, 1H), 8.13 (d, 1H), 7.70-7.62 (m, 1H), 7.62-7.50 (m, 2H), 7.44 (d, 1H), 7.36 (s, 1H), 7.31 (dd, 1H), 6.36 (s, 1H), 5.81-5.71 (m, 1H), 4.32-4.22 (m, 2H), 4.13 (s, 3H), 3.58 (s, 3H), 3.40-3.18 (m, 7H), 2.43-2.26 (m, 2H).

Example 13

(2S)-2-{4-[5-Chloro-2-(4,5-dihydro-1,2-oxazol-3-yl)phenyl]-5-methoxy-2-oxopyridin-1(2H)-yl}-4-methoxy-N-(2-methyl-2H-indazol-5-yl)butanamide (Enantiomer 2)

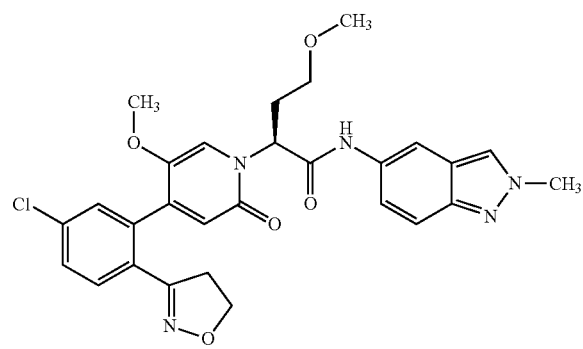 [SMILES: COCC[C@@H](C(=O)Nc1ccc2nn(C)cc2c1)n1cc(OC)c(-c2cc(Cl)ccc2C2=NOCC2)cc1=O]

Enantiomer separation of 69 mg of 2-{4-[5-chloro-2-(4,5-dihydro-1,2-oxazol-3-yl)phenyl]-5-methoxy-2-oxopyridin-1(2H)-yl}-4-methoxy-N-(2-methyl-2H-indazol-5-yl)butanamide (racemate) gave 22 mg of enantiomer 1 (chiral HPLC: $R_t$=6.5 min) and 24 mg of the title compound Example 13 (enantiomer 2): chiral HPLC: $R_t$=9.75 min; 100% ee.

Separating method: column: Daicel Chiralpak IA SFC, 5 μm 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak IA SFC 5 μm 250 mm×4.6 mm; mobile phase: 70% carbon dioxide, 30% ethanol; flow rate: 3 ml/min; UV detection: 210 nm.

LC/MS [Method 1]: $R_t$=0.83 min; MS (ESIpos): m/z=550 (M+H)$^+$, $^1$H-NMR (400 MHz, DMSO-d$_6$): δ [ppm]=10.34 (s, 1H), 8.25 (s, 1H), 8.13 (d, 1H), 7.70-7.62 (m, 1H), 7.62-7.50 (m, 2H), 7.44 (d, 1H), 7.36 (s, 1H), 7.31 (dd, 1H), 6.36 (s, 1H), 5.81-5.71 (m, 1H), 4.32-4.22 (m, 2H), 4.13 (s, 3H), 3.58 (s, 3H), 3.40-3.18 (m, 7H), 2.43-2.26 (m, 2H).

Example 14

4-[(2-{4-[5-Chloro-2-(4,5-dihydro-1,2-oxazol-3-yl)phenyl]-5-methoxy-2-oxopyridin-1(2H)-yl}-4-methoxybutanoyl)amino]-2-fluorobenzamide (Racemate)

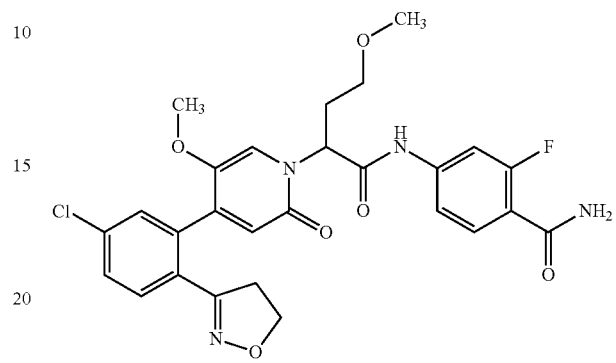

30 mg (purity 93%, 0.061 mmol) of 2-{4-[5-chloro-2-(4,5-dihydro-1,2-oxazol-3-yl)phenyl]-5-methoxy-2-oxopyridin-1(2N)-yl}-4-methoxybutanoic acid hydrochloride (racemate) and 14.1 mg (0.092 mmol) of 4-amino-2-fluorobenzamide in 1 ml of pyridine were reacted according to General Method 5. Yield: 29.4 mg (87% of theory)

LC/MS [Method 1]: $R_t$=0.81 min; MS (ESIpos): m/z=557 (M+H)$^+$, $^1$H-NMR (400 MHz, DMSO-d$_6$): δ [ppm]=10.75 (br. s, 1H), 7.73-7.62 (m, 3H), 7.62-7.57 (m, 1H), 7.56-7.48 (m, 2H), 7.46-7.40 (m, 2H), 7.31 (s, 1H), 6.36 (s, 1H), 5.76-5.61 (m, 1H), 4.35-4.20 (m, 2H), 3.57 (s, 3H), 3.41-3.15 (m, 7H), 2.44-2.26 (m, 2H).

Example 15

4-[(2-{4-[5-Chloro-2-(4,5-dihydro-1,2-oxazol-3-yl)phenyl]-5-methoxy-2-oxopyridin-1(2H)-yl}-4-methoxybutanoyl)amino]benzoic acid (Racemate)

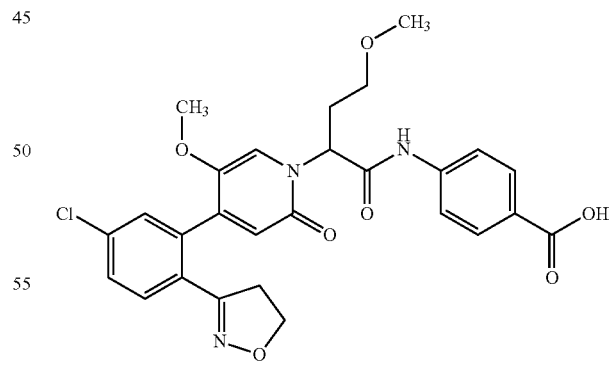

69 mg (0.116 mmol) of tert-butyl 4-[(2-{4-[5-chloro-2-(4,5-dihydro-1,2-oxazol-3-yl)phenyl]-5-methoxy-2-oxopyridin-1(2H)-yl}-4-methoxybutanoyl)amino]benzoate (racemate) were reacted in 1.2 ml of a solution of hydrogen chloride in dioxane (4M) according to General Method 6. The crude product was then purified by preparative HPLC (water/acetonitrile/0.1% formic acid gradient). Yield: 36.8 mg (59% of theory)

LC/MS [Method 10]: R$_t$=1.58 min; MS (ESIpos): m/z=540 (M+H)$^+$, $^1$H-NMR (400 MHz, DMSO-d$_6$): δ [ppm]=12.74 (br. s, 1H), 10.69 (br. s, 1H), 7.94-7.86 (m, 2H), 7.80-7.72 (m, 2H), 7.67-7.56 (m, 2H), 7.44 (d, 1H), 7.32 (s, 1H), 6.36 (s, 1H), 5.78-5.66 (m, 1H), 4.33-4.21 (m, 2H), 3.57 (s, 3H), 3.41-3.14 (m, 7H), 2.41-2.28 (m, 2H).

Example 16

4-[(2-{4-[5-Chloro-2-(4,5-dihydro-1,2-oxazol-3-yl)phenyl]-5-methoxy-2-oxopyridin-1(2H)-yl}-4-methoxybutanoyl)amino]-2-fluoro-N-methylbenzamide (Racemate)

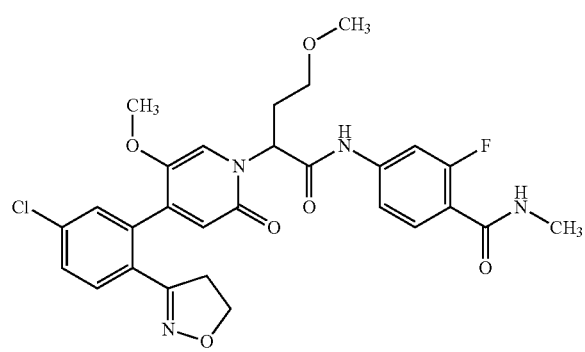 [SMILES: CNC(=O)c1ccc(NC(=O)C(CCOC)n2cc(OC)c(-c3cc(Cl)ccc3C3=NOCC3)cc2=O)cc1F]

30 mg (purity 93%, 0.063 mmol) of 2-{4-[5-chloro-2-(4,5-dihydro-1,2-oxazol-3-yl)phenyl]-5-methoxy-2-oxopyridin-1(2H)-yl}-4-methoxybutanoic acid hydrochloride (racemate) and 16.2 mg (0.094 mmol) of 4-amino-2-fluoro-N-methylbenzamide in 1 ml of pyridine were reacted according to General Method 5. Yield: 29.5 mg (82% of theory).

LC/MS [Method 1]: R$_t$=0.85 min; MS (ESIpos): m/z=571 (M+H)$^+$, $^1$H-NMR (400 MHz, DMSO-d$_6$): δ [ppm]=10.74 (br. s, 1H), 8.13-7.99 (m, 1H), 7.71-7.56 (m, 4H), 7.47-7.38 (m, 2H), 7.30 (s, 1H), 6.36 (s, 1H), 5.77-5.69 (m, 1H), 4.36-4.20 (m, 2H), 3.57 (s, 3H), 3.41-3.12 (m, 7H), 2.76 (d, 3H), 2.43-2.28 (m, 2H).

Example 17

5-[(2-{4-[5-Chloro-2-(5,6-dihydro-1,4,2-dioxazin-3-yl)phenyl]-5-methoxy-2-oxopyridin-1(2H)-yl}-4-methoxybutanoyl)amino]pyridine-2-carboxamide (Racemate)

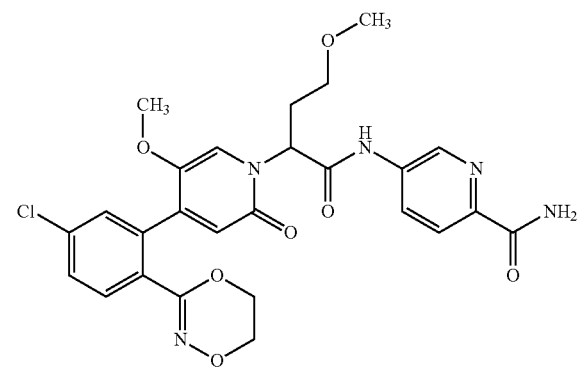 [SMILES: COCCC(C(=O)Nc1ccc(C(N)=O)nc1)n1cc(OC)c(-c2cc(Cl)ccc2C2=NOCCO2)cc1=O]

18 mg (purity 92%, 0.038 mmol) of 2-{4-[5-chloro-2-(5,6-dihydro-1,4,2-dioxazin-3-yl)phenyl]-5-methoxy-2-oxopyridin-1(2H)-yl}-4-methoxybutanoic acid (racemate) and 7.9 mg (0.057 mmol) of 5-aminopyridine-2-carboxamide in 0.7 ml of pyridine were reacted according to General Method 5. Yield: 8.9 mg (94% pure, 40% of theory).

LC/MS [Method 10]: R$_t$=1.40 min; MS (ESIpos): m/z=556 (M+H)$^+$, $^1$H-NMR (400 MHz, DMSO-d$_6$): δ [ppm]=10.86 (br. s, 1H), 8.83 (br. s, 1H), 8.22 (dd, 1H), 8.05-7.92 (m, 2H), 7.66-7.54 (m, 2H), 7.50 (br. s, 1H), 7.45 (d, 1H), 7.33 (s, 1H), 6.32 (s, 1H), 5.77-5.67 (m, 1H), 4.29-4.20 (m, 2H), 4.05-3.97 (m, 2H), 3.60 (s, 3H), 3.44-3.35 (m, 1H), 3.27-3.14 (m, 4H), 2.45-2.30 (m, 2H).

Example 18

2-{4-[5-Chloro-2-(5,6-dihydro-1,4,2-dioxazin-3-yl)phenyl]-5-methoxy-2-oxopyridin-1(2H)-yl}-4-methoxy-N-(2-methyl-2H-indazol-5-yl)butanamide (Racemate)

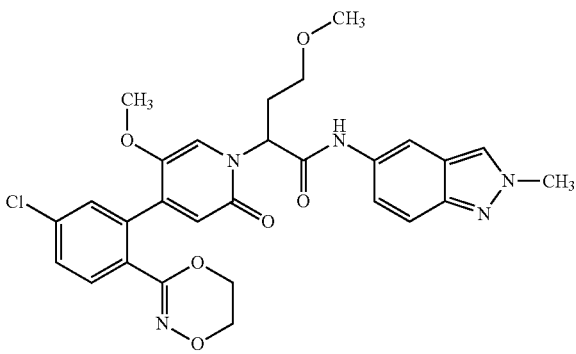 [SMILES: COCCC(C(=O)Nc1ccc2nn(C)cc2c1)n1cc(OC)c(-c2cc(Cl)ccc2C2=NOCCO2)cc1=O]

18 mg (purity 92%, 0.038 mmol) of 2-{4-[5-chloro-2-(5,6-dihydro-1,4,2-dioxazin-3-yl)phenyl]-5-methoxy-2-oxopyridin-1(2H)-yl}-4-methoxybutanoic acid (racemate) and 9.4 mg (0.057 mmol) of 2-methyl-2H-indazole-5-amine in 0.7 ml of pyridine were reacted according to General Method 5. Yield: 8.6 mg (40% of theory).

LC/MS [Method 10]: R$_t$=1.52 min; MS (ESIpos): m/z=566 (M+H)$^+$, $^1$H-NMR (400 MHz, DMSO-d$_6$): δ [ppm]=10.35 (s, 1H), 8.25 (s, 1H), 8.12 (s, 1H), 7.66-7.61 (m, 1H), 7.59-7.51 (m, 2H), 7.45 (d, 1H), 7.36 (s, 1H), 7.31 (d, 1H), 6.32 (s, 1H), 5.82-5.73 (m, 1H), 4.28-4.21 (m, 2H), 4.13 (s, 3H), 4.05-3.98 (m, 2H), 3.60 (s, 3H), 3.43-3.24 (m, 2H), 3.22 (s, 3H), 2.44-2.28 (m, 2H).

Example 19

2-{4-[5-Chloro-2-(1H-tetrazol-1-yl)phenyl]-5-methoxy-2-oxopyridin-1(2H)-yl}-4-methoxy-N-(2-methyl-2H-indazol-5-yl)butanamide (Racemate)

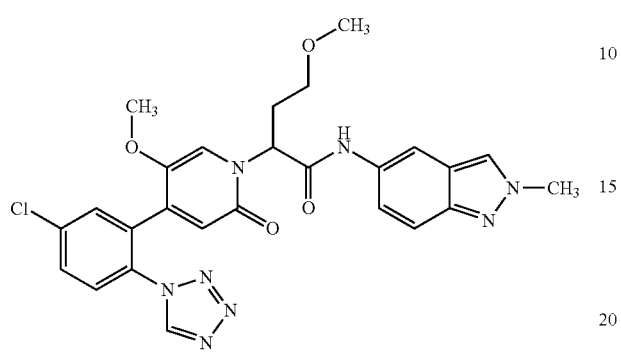

28.5 mg (purity 95%, 0.059 mmol) of 2-{4-[5-chloro-2-(1H-tetrazol-1-yl)phenyl]-5-methoxy-2-oxopyridin-1(2H)-yl}-4-methoxybutanoic acid hydrochloride (racemate) and 14.7 mg (purity 89%, 0.089 mmol) of 2-methyl-2H-indazole-5-amine in 1 ml of pyridine were reacted according to General Method 5. Yield: 20.8 mg (64% of theory).

LC/MS [Method 1]: $R_t$=0.77 min; MS (ESIpos): m/z=549 (M+H)$^+$, $^1$H-NMR (400 MHz, DMSO-d$_6$): δ [ppm]=10.30 (br. s, 1H), 9.68 (s, 1H), 8.24 (s, 1H), 8.10 (s, 1H), 7.85-7.75 (m, 3H), 7.54 (d, 1H), 7.29 (dd, 1H), 7.21 (s, 1H), 6.50 (s, 1H), 5.77-5.63 (m, 1H), 4.13 (s, 3H), 3.35-3.25 (m, 4H), 3.23-3.11 (m, 4H), 2.39-2.22 (m, 2H).

Example 20

4-[(2-{4-[5-Chloro-2-(1H-tetrazol-1-yl)phenyl]-5-methoxy-2-oxopyridin-1(2H)-yl}-4-methoxy-butanoyl)amino]-2-fluorobenzamide (Racemate)

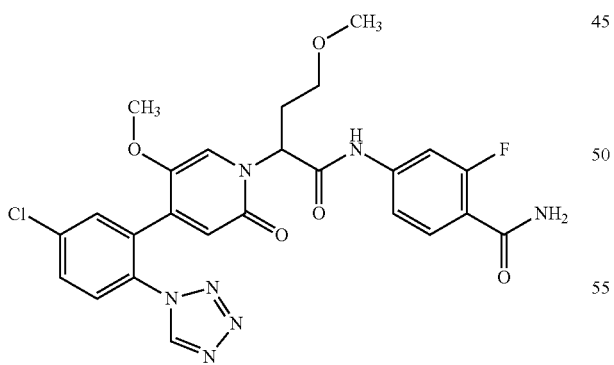

28.5 mg (purity 95%, 0.059 mmol) of 2-{4-[5-chloro-2-(1H-tetrazol-1-yl)phenyl]-5-methoxy-2-oxopyridin-1(2H)-yl}-4-methoxybutanoic acid hydrochloride (racemate) and 13.7 mg (0.089 mmol) of 4-amino-2-fluorobenzamide in 1 ml of pyridine were reacted according to General Method 5. Yield: 20.8 mg (63% of theory).

LC/MS [Method 1]: $R_t$=0.76 min; MS (ESIpos): m/z=556 (M+H)$^+$, $^1$H-NMR (400 MHz, DMSO-d$_6$): δ [ppm]=10.70 (br. s, 1H), 9.68 (s, 1H), 7.85-7.74 (m, 3H), 7.71-7.58 (m, 2H), 7.57-7.45 (m, 2H), 7.41 (dd, 1H), 7.15 (s, 1H), 6.50 (s, 1H), 5.72-5.53 (m, 1H), 3.32-3.23 (m, 4H), 3.22-3.07 (m, 4H), 2.39-2.24 (m, 2H).

Example 21

4-[(2-{4-[5-Chloro-2-(1H-imidazol-1-yl)phenyl]-5-methoxy-2-oxopyridin-1(2H)-yl}-4-methoxy-butanoyl)amino]benzoic acid (Racemate)

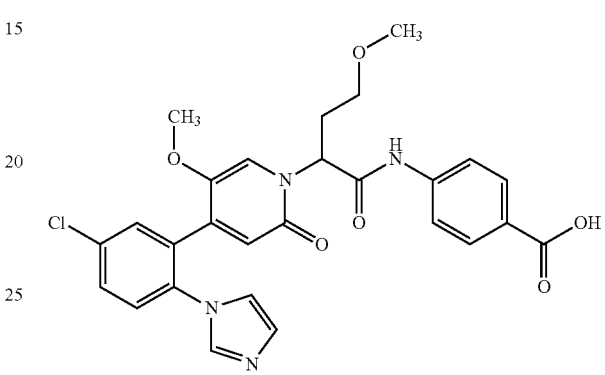

33.3 mg (0.056 mmol) of tert-butyl 4-[(2-{4-[5-chloro-2-(1H-imidazol-1-yl)phenyl]-5-methoxy-2-oxopyridin-1(2H)-yl}-4-methoxybutanoyl)amino]benzoate (racemate) were reacted with 1 ml of a solution of hydrogen chloride in dioxane (4M) according to General Method 6. Yield: 13.3 mg (44% of theory).

LC/MS [Method 1]: $R_t$=0.62 min; MS (ESIpos): m/z=537 (M+H)$^+$, $^1$H-NMR (400 MHz, DMSO-d$_6$): δ [ppm]=12.73 (br. s, 1H), 10.64 (br. s, 1H), 7.92-7.86 (m, 2H), 7.77-7.71 (m, 2H), 7.69-7.59 (m, 3H), 7.55 (d, 1H), 7.20 (s, 1H), 7.17-7.13 (m, 1H), 6.92 (s, 1H), 6.44 (s, 1H), 5.73-5.63 (m, 1H), 3.36 (s, 3H), 3.34-3.26 (m, 1H), 3.22-3.08 (m, 4H), 2.39-2.26 (m, 2H).

Example 22

4-[(2-{4-[5-Chloro-2-(1H-imidazol-1-yl)phenyl]-5-methoxy-2-oxopyridin-1(2H)-yl}-4-methoxy-butanoyl)amino]-2-fluorobenzamide (Racemate)

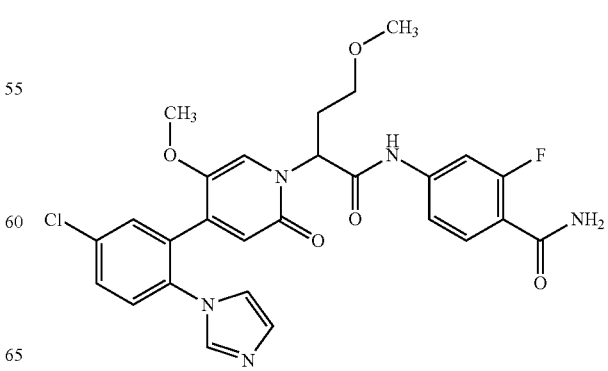

41.0 mg (purity 90%, 0.081 mmol) of 2-{4-[5-chloro-2-(1H-imidazol-1-yl)phenyl]-5-methoxy-2-oxopyridin-1(2H)-yl}-4-methoxybutanoic acid hydrochloride (racemate) and 19.4 mg (0.122 mmol) of 4-amino-2-fluorobenzamide in 0.67 ml of pyridine were reacted according to General Method 5. Yield: 27 mg (60% of theory).

LC/MS [Method 10]: $R_t$=1.02 min; MS (ESIpos): m/z=554 (M+H)$^+$, $^1$H-NMR (400 MHz, DMSO-d$_6$): δ [ppm]=10.69 (br. s, 1H), 7.72-7.59 (m, 5H), 7.58-7.46 (m, 3H), 7.41 (dd, 1H), 7.16 (s, 1H), 7.19 (s, 1H), 6.93 (s, 1H), 6.45 (s, 1H), 5.69-5.57 (m, 1H), 3.36 (s, 3H), 3.34-3.26 (m, 1H), 3.19 (s, 3H), 3.17-3.08 (m, 1H), 2.38-2.27 (m, 2H).

Example 23

2-{4-[5-Chloro-2-(1H-imidazol-1-yl)phenyl]-5-methoxy-2-oxopyridin-1 (2f)-yl}-4-methoxy-N-(2-methyl-2H-indazol-5-yl)butanamide (Racemate)

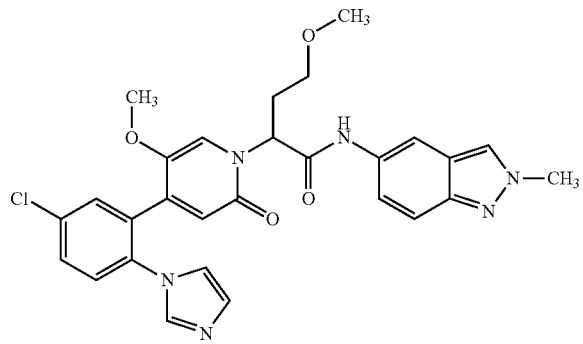 [SMILES: COCCC(C(=O)Nc1ccc2nn(C)cc2c1)n1cc(OC)c(-c2cc(Cl)ccc2-n2ccnc2)cc1=O]

41.0 mg (purity 90%, 0.081 mmol) of 2-{4-[5-chloro-2-(1H-imidazol-1-yl)phenyl]-5-methoxy-2-oxopyridin-1(2H)-yl}-4-methoxybutanoic acid hydrochloride (racemate) and 20.1 mg (purity 89%, 0.122 mmol) of 2-methyl-2H-indazole-5-amine in 0.67 ml of pyridine were reacted according to General Method 5. Yield: 20 mg (44% of theory).

LC/MS [Method 10]: $R_t$=1.05 min; MS (ESIpos): m/z=547 (M+H)$^+$, $^1$H-NMR (400 MHz, DMSO-d$_6$): δ [ppm]=10.30 (s, 1H), 8.24 (s, 1H), 8.14-8.08 (m, 1H), 7.74 (br. s, 1H), 7.68 (dd, 1H), 7.61 (d, 1H), 7.59-7.49 (m, 2H), 7.29 (dd, 1H), 7.25 (s, 1H), 7.19 (s, 1H), 6.97 (s, 1H), 6.45 (s, 1H), 5.79-5.63 (m, 1H), 4.13 (s, 3H), 3.37 (s, 3H), 3.35-3.11 (m, 5H), 2.39-2.21 (m, 2H).

Example 24

4-[(2-{4-[5-Chloro-2-(1,3-oxazol-4-yl)phenyl]-5-methoxy-2-oxopyridin-1 (2N)-yl}-4-methoxybutanoyl)amino]-2-fluorobenzamide (Racemate)

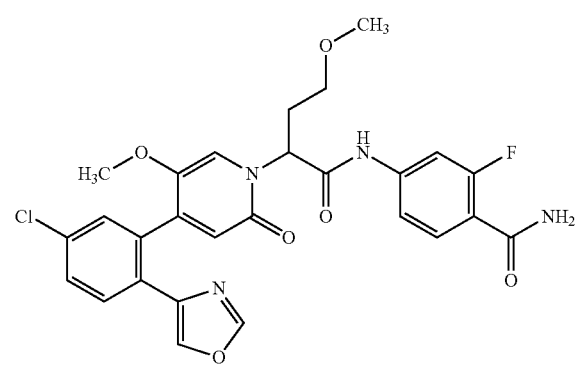 [SMILES: COCCC(C(=O)Nc1ccc(C(N)=O)c(F)c1)n1cc(OC)c(-c2cc(Cl)ccc2-c2cocn2)cc1=O]

45.0 mg (purity 64%, 0.069 mmol) of 2-{4-[5-chloro-2-(1,3-oxazol-4-yl)phenyl]-5-methoxy-2-oxopyridin-1(2H)-yl}-4-methoxybutanoic acid (racemate) and 16.4 mg (0.103 mmol) of 4-amino-2-fluorobenzamide in 0.65 ml of pyridine were reacted according to General Method 5. Yield: 22 mg (57% of theory).

LC/MS [Method 10]: $R_t$=1.55 min; MS (ESIpos): m/z=555 (M+H)$^+$, $^1$H-NMR (400 MHz, DMSO-d$_6$): δ [ppm]=10.73 (br. s., 1H), 8.38-8.44 (m, 1H), 7.88 (d, 1H), 7.63-7.72 (m, 3H), 7.59 (dd, 1H), 7.50-7.56 (m, 2H), 7.42-7.46 (m, 1H), 7.40 (d, 1H), 7.32-7.36 (m, 1H), 6.37 (s, 1H), 5.71 (br. s., 1H), 3.41 (s, 4H), 3.23 (s, 3H), 2.35-2.44 (m, 2H).

Example 25

2-{4-[5-Chloro-2-(1,3-oxazol-4-yl)phenyl]-5-methoxy-2-oxopyridin-1(2H)-yl}-4-methoxy-N-(2-methyl-2H-indazol-5-yl)butanamide (Racemate)

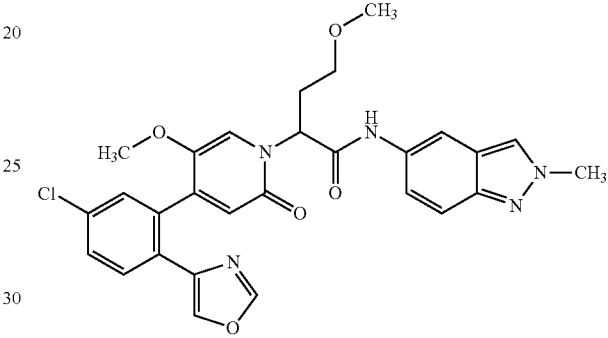

45.0 mg (purity 64%, 0.069 mmol) of 2-{4-[5-chloro-2-(1,3-oxazol-4-yl)phenyl]-5-methoxy-2-oxopyridin-1(2H)-yl}-4-methoxybutanoic acid (racemate) and 17.1 mg (purity 89%, 0.122 mmol) of 2-methyl-2H-indazole-5-amine in 0.57 ml of pyridine were reacted according to General Method 5. Yield: 18 mg (48% of theory).

LC/MS [Method 10]: $R_t$=1.59 min; MS (ESIpos): m/z=548 (M+H)$^+$, $^1$H-NMR (400 MHz, DMSO-d$_6$): δ [ppm]=10.32 (br. s., 1H), 8.39-8.43 (m, 1H), 8.26 (s, 1H), 8.11-8.15 (m, 1H), 7.88 (d, 1H), 7.66-7.70 (m, 1H), 7.52-7.61 (m, 2H), 7.36-7.43 (m, 2H), 7.28-7.34 (m, 1H), 6.36 (s, 1H), 5.73-5.82 (m, 1H), 4.13 (s, 3H), 3.38-3.45 (m, 4H), 3.24 (s, 3H), 2.34-2.43 (m, 2H).

Example 26

4-[(2-{4-[5-Chloro-2-(1,3-oxazol-4-yl)phenyl]-5-methoxy-2-oxopyridin-1(2H)-yl}-4-methoxybutanoyl)amino]benzoic acid (Racemate)

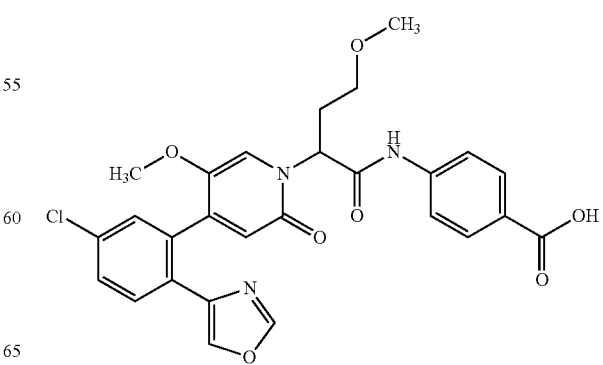

A solution of 26.0 mg (0.047 mmol) of methyl 4-[(2-{4-[5-chloro-2-(1,3-oxazol-4-yl)phenyl]-5-methoxy-2-oxopyridin-1(2H)-yl}-4-methoxybutanoyl)amino]benzoate (Racemate) in 1.2 ml of THF/water (3:1 mixture) was stirred in the presence of 4.0 mg (0.094 mmol) of lithium hydroxide monohydrate at room temperature for 8 hours. The mixture was then adjusted to pH 7 using aqueous hydrochloric acid solution (1N) and the THF was removed under reduced pressure. The aqueous residue was diluted with acetonitrile and purified by preparative RP-HPLC (Reprosil C18, 0.1% strength formic acid/acetonitrile gradient). Yield: 14 mg (53% of theory)

LC/MS [Method 10]: $R_t$=1.58 min; MS (ESIpos): m/z=538 (M+H)$^+$, $^1$H-NMR (400 MHz, DMSO-d$_6$): δ [ppm]=12.75 (br. s., 1H), 10.67 (br. s., 1H), 8.39-8.43 (m, 1H), 7.86-7.94 (m, 3H), 7.76 (d, 2H), 7.65-7.69 (m, 1H), 7.58 (dd, 1H), 7.40 (d, 1H), 7.36 (s, 1H), 6.36 (s, 1H), 5.75 (br. s., 1H), 3.39-3.44 (m, 4H), 3.23 (s, 3H), 2.36-2.44 (m, 2H).

Example 27

4-[(2-{4-[5-Chloro-2-(1,3,4-oxadiazol-2-yl)phenyl]-5-methoxy-2-oxopyridin-1(2H)-yl}-4-methoxybutanoyl)amino]benzoic acid (Racemate)

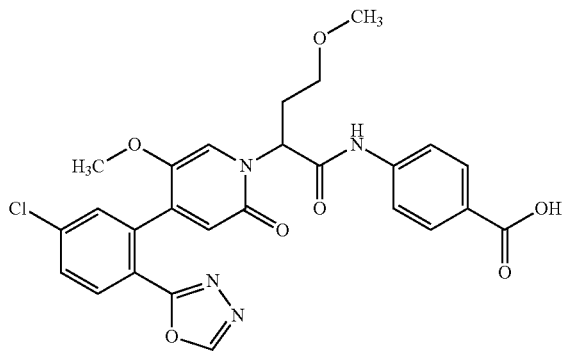 [SMILES: COCCC(C(=O)Nc1ccc(C(=O)O)cc1)n1cc(OC)c(-c2cc(Cl)ccc2-c2nnco2)cc1=O]

A solution of 38.0 mg (0.069 mmol) of methyl 4-[(2-{4-[5-chloro-2-(1,3,4-oxadiazol-2-yl)phenyl]-5-methoxy-2-oxopyridin-1(2H)-yl}-4-methoxybutanoyl)amino]benzoate (Racemate) in 1.8 ml of THF/water (3:1 mixture) was stirred in the presence of 5.8 mg (0.138 mmol) of lithium hydroxide monohydrate at room temperature for 10 hours. The pH was then adjusted to 7 using aqueous hydrochloric acid solution (1N), and the product was purified by preparative RP-HPLC (Reprosil C18, 0.1% strength formic acid/acetonitrile gradient). Yield: 10 mg (27% of theory)

LC/MS [Method 10]: $R_t$=1.44 min; MS (ESIpos): m/z=539 (M+H)$^+$, $^1$H-NMR (400 MHz, DMSO-d$_6$): δ [ppm]=12.75 (br. s., 1H), 10.71 (br. s., 1H), 9.26 (s, 1H), 8.01 (d, 1H), 7.91 (d, 2H), 7.72-7.79 (m, 3H), 7.65 (d, 1H), 7.31 (s, 1H), 6.49 (s, 1H), 5.75 (br. s., 1H), 3.34 (s, 4H), 3.23 (s, 4H), 2.33-2.43 (m, 2H).

Example 28

4-[(2-{4-[5-Chloro-2-(1,3,4-oxadiazol-2-yl)phenyl]-5-methoxy-2-oxopyridin-1(2H)-yl}-4-methoxybutanoyl)amino]-2-fluorobenzamide (Racemate)

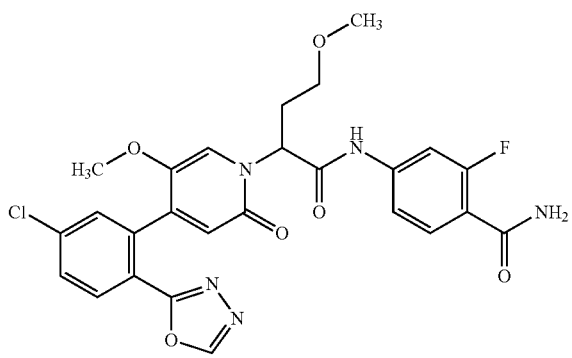 [SMILES: COCCC(C(=O)Nc1ccc(C(N)=O)c(F)c1)n1cc(OC)c(-c2cc(Cl)ccc2-c2nnco2)cc1=O]

30.0 mg (purity 86%, 0.061 mmol) of 2-{4-[5-chloro-2-(1,3,4-oxadiazol-2-yl)phenyl]-5-methoxy-2-oxopyridin-1(2H)-yl}-4-methoxybutanoic acid (racemate) and 14.6 mg (0.092 mmol) of 4-amino-2-fluorobenzamide in 1.00 ml of pyridine were reacted according to General Method 5.

Without further work-up, the reaction mixture was separated by preparative RP-HPLC (Reprosil C18, 0.1% strength formic acid/acetonitrile gradient). The crude product obtained in this manner was then purified by normal phase flash chromatography (silica cartridge, dichloromethane/methanol gradient). Yield: 15 mg (44% of theory)

LC/MS [Method 10]: $R_t$=1.42 min; MS (ESIpos): m/z=556 (M+H)$^+$, $^1$H-NMR (400 MHz, DMSO-d$_6$): δ [ppm]=10.77 (br. s., 1H), 9.27 (s, 1H), 8.01 (d, 1H), 7.75 (dd, 1H), 7.63-7.72 (m, 3H), 7.49-7.57 (m, 2H), 7.44 (dd, 1H), 7.29 (s, 1H), 6.49 (s, 1H), 5.71 (br. s., 1H), 3.36-3.43 (m, 1H), 3.34 (s, 3H), 3.23 (s, 3H), 2.34-2.42 (m, 2H).

Example 29

5-[(2-{4-[5-Chloro-2-(4-fluoro-1H-pyrazol-1-yl)phenyl]-5-methoxy-2-oxopyridin-1(2N)-yl}-4-methoxybutanoyl)amino]-N-methylpyridine-2-carboxamide (Racemate)

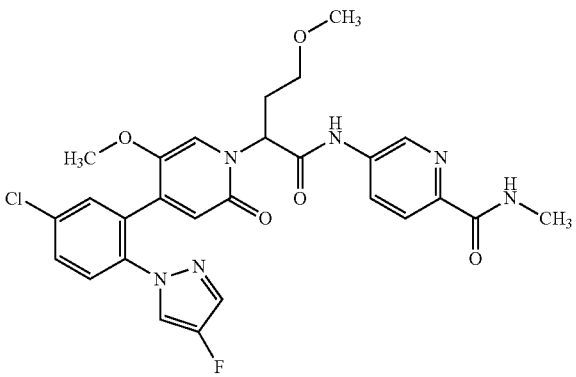 [SMILES: CNC(=O)c1ccc(NC(=O)C(CCOC)n2cc(OC)c(-c3cc(Cl)ccc3-n3cc(F)cn3)cc2=O)cn1]

5.0 mg (0.011 mmol) of 2-{4-[5-chloro-2-(4-fluoro-1H-pyrazol-1-yl)phenyl]-5-methoxy-2-oxopyridin-1(2H)-yl}-4-methoxybutanoic acid (racemate) and 2.6 mg (0.017 mmol) of 5-amino-N-methylpyridine-2-carboxamide in 0.50 ml of pyridine were reacted according to General Method 5.

Without further work-up, the reaction mixture was separated by preparative RP-HPLC (Reprosil C18, 0.1% strength formic acid/acetonitrile gradient). Yield: 3.9 mg (61% of theory)

LC/MS [Method 10]: $R_t$=1.62 min; MS (ESIpos): m/z=569 (M+H)$^+$, $^1$H-NMR (400 MHz, CDCl$_3$): δ [ppm]=9.85 (br. s., 1H), 8.64-8.68 (m, 1H), 8.16 (s, 2H), 7.85-7.91 (m, 1H), 7.45-7.54 (m, 2H), 7.40 (d, 1H), 7.37 (d, 1H), 7.33 (d, 1H), 6.80 (s, 1H), 6.63 (s, 1H), 5.70 (br. s., 1H), 3.48-3.54 (m, 1H), 3.42-3.47 (m, 1H), 3.41 (s, 3H), 3.34 (s, 3H), 3.02 (d, 3H), 2.59-2.67 (m, 1H), 2.18-2.29 (m, 1H).

Example 30

2-{4-[5-Chloro-2-(1,3,4-oxadiazol-2-yl)phenyl]-5-methoxy-2-oxopyridin-1(2H)-yl}-4-methoxy-N-(2-methyl-2H-indazol-5-yl)butanamide (Racemate)

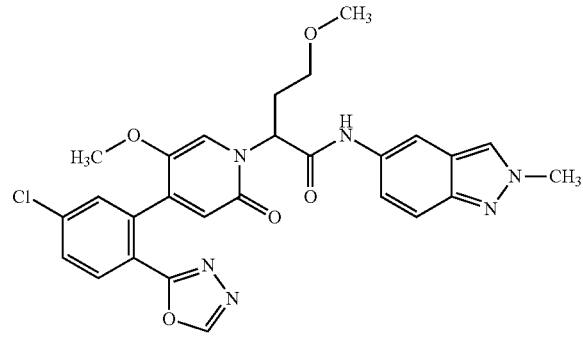 [SMILES: COCCC(C(=O)Nc1ccc2nn(C)cc2c1)n1cc(OC)c(-c2cc(Cl)ccc2-c2nnco2)cc1=O]

30 mg (purity 86%, 0.061 mmol) of 2-{4-[5-chloro-2-(1,3,4-oxadiazol-2-yl)phenyl]-5-methoxy-2-oxopyridin-1(2H)-yl}-4-methoxybutanoic acid (racemate) and 15 mg (purity 89%, 0.092 mmol) of 2-methyl-2H-indazole-5-amine in 1 ml of pyridine were reacted according to General Method 5. Yield: 13 mg (39% of theory).

LC/MS [Method 1]: $R_t$=0.79 min; MS (ESIpos): m/z=549 (M+H)$^+$, $^1$H-NMR (400 MHz, DMSO-d$_6$): δ [ppm]=10.37 (s, 1H), 9.26 (s, 1H), 8.25 (s, 1H), 8.14 (s, 1H), 8.01 (d, 1H), 7.74 (dd, 1H), 7.64 (d, 1H), 7.55 (d, 1H), 7.35 (s, 1H), 7.32 (dd, 1H), 6.49 (s, 1H), 5.82-5.73 (m, 1H), 4.13 (s, 3H), 3.40-3.33 (m, 5H), 3.24 (s, 3H), 2.43-2.28 (m, 2H).

Example 31

N-(Quinoxalin-6-yl)-2-{4-[5-chloro-2-(4,5-dihydro-1,2-oxazol-3-yl)phenyl]-5-methoxy-2-oxopyridin-1(2H)-yl}-3-(1,4-dioxan-2-yl)propanamide (Diastereomer Mixture)

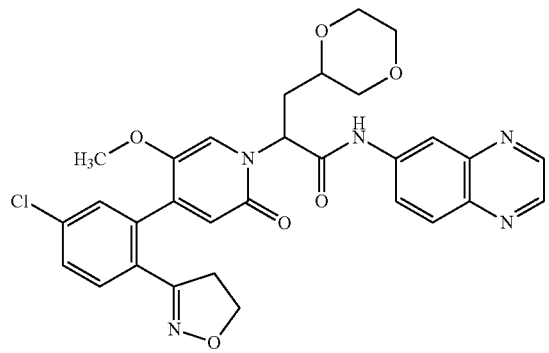 [SMILES: COc1cn(C(CC2COCCO2)C(=O)Nc2ccc3nccnc3c2)c(=O)cc1-c1cc(Cl)ccc1C1=NOCC1]

32.9 mg (purity 85%, 0.060 mmol) of 2-{4-[5-chloro-2-(4,5-dihydro-1,2-oxazol-3-yl)phenyl]-5-methoxy-2-oxopyridin-1(2H)-yl}-3-(1,4-dioxan-2-yl)propanoic acid (diastereomer mixture) and 13 mg (0.091 mmol) of quinoxaline-6-amine in 1 ml of pyridine were reacted according to General Method 5. Yield: 26 mg (72% of theory).

LC/MS [Method 10]: $R_t$=1.53/1.57 min; MS (ESIpos): m/z=590/590 (M+H)$^+$, $^1$H-NMR (400 MHz, DMSO-d$_6$): δ [ppm]=10.96-10.83 (m, 1H), 8.91-8.88 (m, 1H), 8.85-8.82 (m, 1H), 8.56-8.51 (m, 1H), 8.09-7.99 (m, 2H), 7.67-7.57 (m, 2H), 7.47-7.44 (m, 1H), 7.40-7.33 (m, 1H), 6.40-6.37 (m, 1H), 5.87-5.71 (m, 1H), 4.33-4.23 (m, 2H), 3.79-3.54 (m, 7H), 3.54-3.34 (m, 4H), 3.27-3.20 (m, 1H), 2.39-2.27 (m, 1H), 2.23-2.08 (m, 1H). Several signals under water peak.

Example 32

2-{4-[5-Chloro-2-(4,5-dihydro-1,2-oxazol-3-yl)phenyl]-5-methoxy-2-oxopyridin-1(2H)-yl}-3-(1,4-dioxan-2-yl)-N-(2-methyl-2H-indazol-5-yl)propanamide (Diastereomer Mixture)

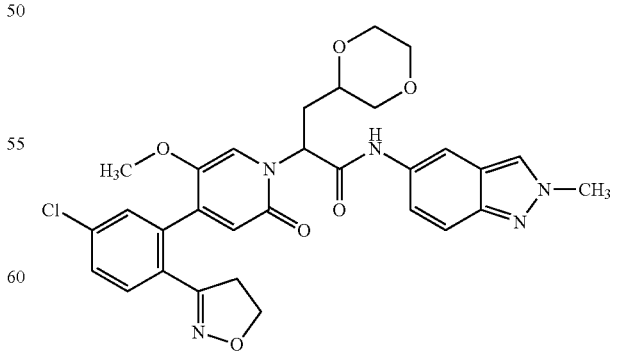

50 mg (purity 85%, 0.092 mmol) of 2-{4-[5-chloro-2-(4,5-dihydro-1,2-oxazol-3-yl)phenyl]-5-methoxy-2-oxopyridin-1(2H)-yl}-3-(1,4-dioxan-2-yl)propanoic acid (diastereomer mixture) and 20 mg (0.138 mmol) of 2-methyl-2H-indazole-5-amine in 1 ml of pyridine were reacted according to General Method 5. Yield: 45 mg (83% of theory).

LC/MS [Method 10]: $R_t$=1.49/1.52 min; MS (ESIpos): m/z=592/592 (M+H)$^+$, $^1$H-NMR (400 MHz, DMSO-d$_6$): δ [ppm]=10.40-10.28 (m, 1H), 8.27-8.23 (m, 1H), 8.14-8.09 (m, 1H), 7.67-7.52 (m, 3H), 7.46-7.43 (m, 1H), 7.40-7.28 (m, 2H), 6.38-6.34 (m, 1H), 5.84-5.70 (m, 1H), 4.34-4.21 (m, 2H), 4.13 (s, 3H), 3.80-3.39 (m, 10H), 3.27-3.20 (m, 2H), 2.33-2.19 (m, 1H), 2.17-2.02 (m, 1H).

Example 33

4-{[2-{4-[5-Chloro-2-(4,5-dihydro-1,2-oxazol-3-yl)phenyl]-5-methoxy-2-oxopyridin-1(2H)-yl}-3-(1,4-dioxan-2-yl)propanoyl]amino}benzoic acid (Diastereomer Mixture)

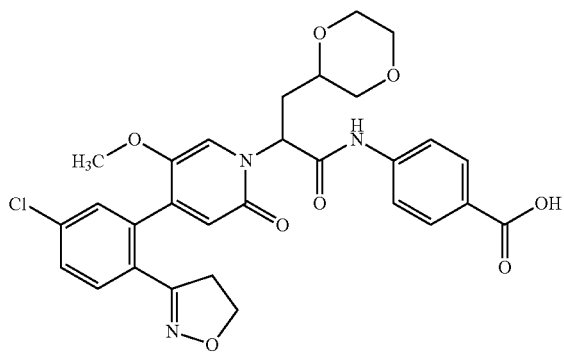 [SMILES: COc1cn(C(CC2COCCO2)C(=O)Nc2ccc(C(=O)O)cc2)c(=O)cc1-c1cc(Cl)ccc1C1=NOCC1]

A solution of 55.0 mg (92.3 μmol) of methyl 4-({2-{4-[5-chloro-2-(4,5-dihydro-1,2-oxazol-3-yl)phenyl]-5-methoxy-2-oxopyridin-1(2H)-yl}-3-[(2R)-1,4-dioxan-2-yl]propanoyl}amino)benzoate (racemate) in 4 ml of THF/water (3:1 mixture) was stirred in the presence of 7.7 mg (185 μmol) of lithium hydroxide monohydrate at room temperature for 18 hours. The mixture was then adjusted to pH 7 using aqueous hydrochloric acid solution (1N) and the THF was removed under reduced pressure. The aqueous residue was diluted with acetonitrile and purified by preparative RP-HPLC (Reprosil C18, 0.1% strength formic acid/acetonitrile gradient). Yield: 37 mg (69% of theory)

LC/MS [Method 10]: $R_t$=1.51/1.54 min; MS (ESIpos): m/z=582/582 (M+H)$^+$, $^1$H-NMR (400 MHz, DMSO-d$_6$): δ [ppm]=12.76 (br s, 1H), 10.75-10.60 (m, 1H), 7.93-7.87 (m, 2H), 7.78-7.71 (m, 2H), 7.68-7.56 (m, 2H), 7.47-7.43 (m, 1H), 7.34 und 7.30 (2×s, 1H), 6.39 und 6.34 (2×s, 1H), 5.82-5.66 (m, 1H), 4.33-4.21 (m, 2H), 3.78-3.39 (m, 10H), 3.28-3.18 (m, 2H), 2.33-2.05 (m, 2H).

Example 34

5-{[2-{4-[5-Chloro-2-(4,5-dihydro-1,2-oxazol-3-yl)phenyl]-5-methoxy-2-oxopyridin-1(2H)-yl}-3-(1,4-dioxan-2-yl)propanoyl]amino}-N-methylpyridine-2-carboxamide (Diastereomer Mixture)

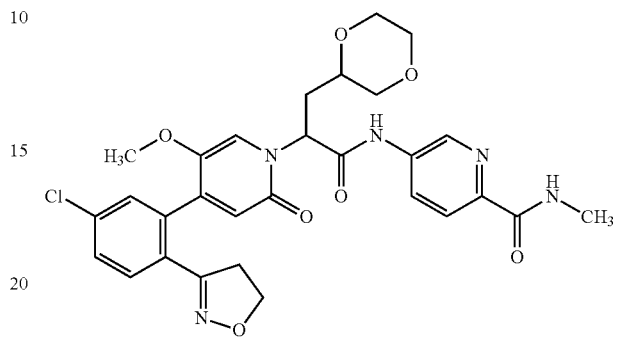

50 mg (purity 85%, 0.092 mmol) of 2-{4-[5-chloro-2-(4,5-dihydro-1,2-oxazol-3-yl)phenyl]-5-methoxy-2-oxopyridin-1(2H)-yl}-3-(1,4-dioxan-2-yl)propanoic acid (diastereomer mixture) and 21 mg (0.138 mmol, 1.5 eq.) of 5-amino-N-methylpyridine-2-carboxamide in 1 ml of pyridine were reacted according to General Method 5. Yield: 46 mg (85% of theory).

LC/MS [Method 10]: $R_t$=1.46/1.49 min; MS (ESIpos): m/z=596/596 (M+H)$^+$, $^1$H-NMR (400 MHz, DMSO-d$_6$): δ [ppm]=10.90-10.72 (m, 1H), 8.88-8.84 (m, 1H), 8.68-8.62 (m, 1H), 8.24-8.18 (m, 1H), 8.02-7.98 (m, 1H), 7.67-7.57 (m, 2H), 7.46-7.43 (m, 1H), 7.34-7.28 (m, 1H), 6.39-6.36 (m, 1H), 5.83-5.61 (m, 1H), 4.32-4.23 (m, 2H), 3.79-3.40 (m, 10H), 3.28-3.19 (m, 2H), 2.80 (d, 3H), 2.37-2.25 (m, 1H), 2.20-2.05 (m, 1H).

Example 35

4-[(2-{4-[5-Chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoyl)amino]benzoic acid (Diastereomer Mixture)

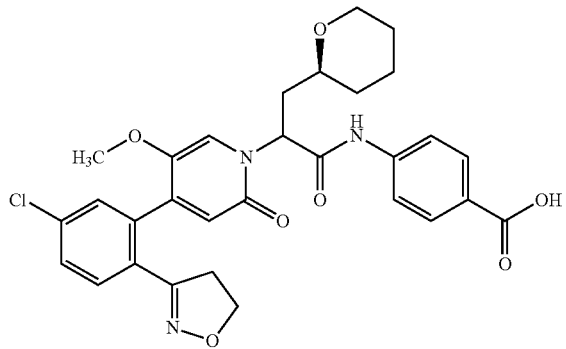 [SMILES: COc1cn(C(C[C@@H]2CCCCO2)C(=O)Nc2ccc(C(=O)O)cc2)c(=O)cc1-c1cc(Cl)ccc1C1=NOCC1]

120 mg (260 μmol) of 2-{4-[5-chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoic acid (diastereomer mixture) and 37.5 mg (273 μmol) of 4-aminobenzoic acid in 1.4 ml of pyridine were reacted according to General Method 5. Yield: 79 mg (52% of theory).

LC/MS [Method 1]: $R_t$=0.96 min; MS (ESIpos): m/z=580 (M+H)$^+$, $^1$H-NMR (400 MHz, DMSO-d$_6$): δ [ppm]=12.74 (br s, 1H), 10.74-10.51 (m, 1H), 7.93-7.87 (m, 2H), 7.79-7.73 (m, 2H), 7.67-7.56 (m, 2H), 7.44 (dd, 1H), 7.34 und 7.29 (2×s, 1H), 6.36 und 6.34 (2×s, 1H), 5.83-5.60 (m, 1H), 4.32-4.22 (m, 2H), 3.89-3.77 (m, 1H), 3.59-3.55 (m, 3H), 3.27-3.02 (m, 4H), 2.37-2.09 (m, 2H), 1.79-1.70 (m, 1H), 1.66-1.54 (m, 1H), 1.47-1.35 (m, 3H), 1.32-1.18 (m, 1H).

Example 36

4-[(2-{4-[5-Chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoyl)amino]benzoic acid (Diastereomer 1)

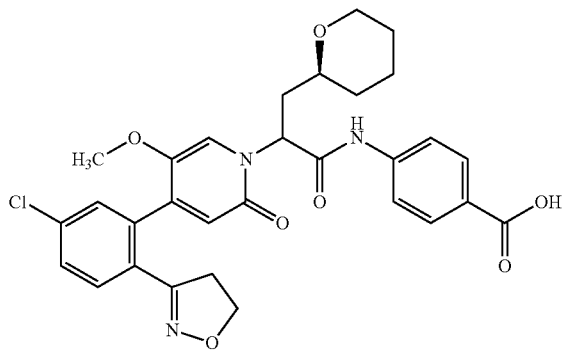 [SMILES: COc1cn(C(C[C@@H]2CCCCO2)C(=O)Nc2ccc(C(=O)O)cc2)c(=O)cc1-c1cc(Cl)ccc1C1=NOCC1]

Diastereomer separation of 97 mg of 4-[(2-{4-[5-chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoyl)amino]benzoic acid (diastereomer mixture) gave 23 mg of diastereomer 2 (chiral HPLC: $R_t$=6.3 min) and 35 mg of the title compound Example 36 (diastereomer 1): chiral HPLC: $R_t$=2.5 min. This product was purified by preparative RP-HPLC (Reprosil C18, 0.1% strength formic acid/acetonitrile gradient). 15 mg, 100% ee.

Separating method: column: Chiralpak AS-H SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AS SFC 3 μm, 100 mm×4.6 mm; mobile phase: 70% carbon dioxide, 30% ethanol; flow rate: 3 ml/min; UV detection: 210 nm.

LC/MS [Method 2]: $R_t$=2.95 min; MS (ESIpos): m/z=580 (M+H)$^+$, $^1$H-NMR (400 MHz, DMSO-d$_6$): δ [ppm]=12.75 (br s, 1H), 10.70 (s, 1H), 7.90 (d, 2H), 7.76 (d, 2H), 7.69-7.61 (m, 1H), 7.61-7.55 (m, 1H), 7.44 (d, 1H), 7.34 (s, 1H), 6.36 (s, 1H), 5.79 (t, 1H), 4.32-4.22 (m, 2H), 3.90-3.83 (m, 1H), 3.57 (s, 3H), 3.24-3.14 (m, 2H), 2.31-2.20 (m, 1H), 2.18-2.05 (m, 1H), 1.80-1.70 (m, 1H), 1.67-1.59 (m, 1H), 1.48-1.36 (m, 3H), 1.32-1.21 (m, 1H).

Example 37

5-[(2-{4-[5-Chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoyl)amino]-N-methylpyridine-2-carboxamide (Diastereomer Mixture)

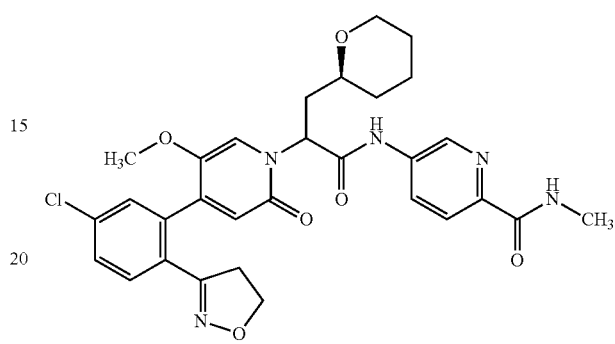

40 mg (0.087 mmol) of 2-{4-[5-chloro-2-(4,5-dihydro-1,2-oxazol-3-yl)phenyl]-5-methoxy-2-oxopyridin-1(2H)-yl}-3-[(2S)-tetrahydro-2H-pyran-2-yl]propanoic acid (diastereomer mixture) and 20 mg (0.130 mmol) of 5-amino-N-methylpyridine-2-carboxamide in 0.77 ml of pyridine were reacted according to General Method 5. Yield: 38 mg (74% of theory).

LC/MS [Method 1]: $R_t$=0.92 min; MS (ESIpos): m/z=594 (M+H)$^+$, $^1$H-NMR (400 MHz, DMSO-d$_6$): δ [ppm]=10.90-10.55 (m, 1H), 8.89-8.85 (m, 1H), 8.68-8.62 (m, 1H), 8.25-8.18 (m, 1H), 8.02-7.97 (m, 1H), 7.67-7.57 (m, 2H), 7.46-7.42 (m, 1H), 7.33 und 7.28 (2×s, 1H), 6.37 und 6.35 (2×s, 1H), 5.82-5.55 (m, 1H), 4.32-4.22 (m, 2H), 3.89-3.77 (m, 1H), 3.57 (2×s, 3H), 3.28-3.00 (m, 4H), 2.80 (d, 3H), 2.38-2.26 (m, 1H), 2.24-2.09 (m, 1H), 1.79-1.70 (m, 1H), 1.68-1.49 (m, 1H), 1.48-1.36 (m, 3H), 1.32-1.19 (m, 1H).

Example 38

2-{4-[5-Chloro-2-(4,5-dihydro-1,2-oxazol-3-yl)phenyl]-5-methoxy-2-oxopyridin-1(2H)-yl}-N-(2-methyl-2H-indazol-5-yl)-3-[(2S)-tetrahydro-2H-pyran-2-yl]propanamide (Diastereomer Mixture)

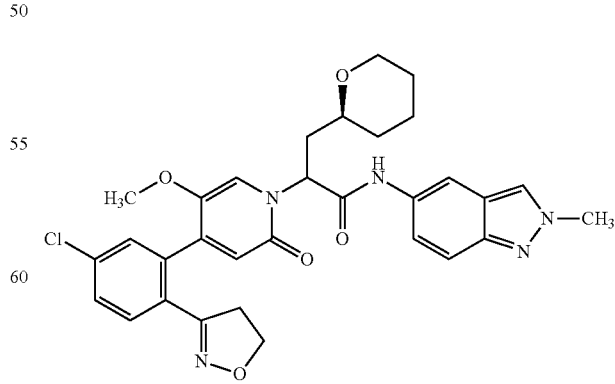

40 mg (0.087 mmol) of 2-{4-[5-chloro-2-(4,5-dihydro-1,2-oxazol-3-yl)phenyl]-5-methoxy-2-oxopyridin-1(2H)-yl}-

3-[(2S)-tetrahydro-2H-pyran-2-yl]propanoic acid (diastereomer mixture) and 19.5 mg (0.130 mmol) of 2-methyl-2H-indazole-5-amine in 0.77 ml of pyridine were reacted according to General Method 5. Yield: 36 mg (70% of theory).

LC/MS [Method 1]: R$_t$=0.93 min; MS (ESIpos): m/z=590 (M+H)$^+$, $^1$H-NMR (400 MHz, DMSO-d$_6$): δ [ppm]=10.36 und 10.26 (2×s, 1H), 8.26-8.23 (m, 1H), 8.15-8.09 (m, 1H), 7.67-7.51 (m, 3H), 7.45-7.30 (m, 3H), 6.37-6.33 (m, 1H), 5.86-5.63 (m, 1H), 4.33-4.22 (m, 2H), 4.13 und 4.12 (2×s, 3H), 3.95-3.78 (m, 1H), 3.57 (2×s, 3H), 3.30-3.03 (m, 4H), 2.34-2.03 (m, 2H), 1.79-1.70 (m, 1H), 1.68-1.54 (m, 1H), 1.49-1.34 (m, 3H), 1.32-1.17 (m, 1H).

Example 39

4-[(2-{4-[5-Chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoyl)amino]benzoic acid (Diastereomer Mixture)

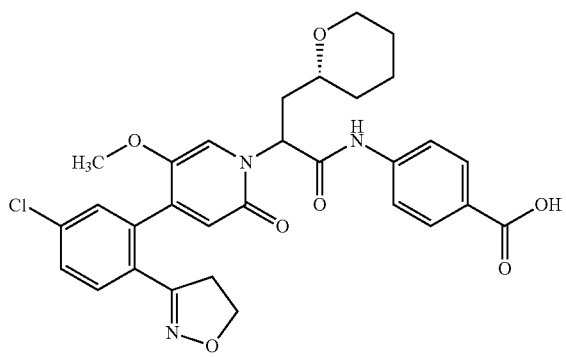 [SMILES: COc1cn(C(C[C@H]2CCCCO2)C(=O)Nc2ccc(C(=O)O)cc2)c(=O)cc1-c1cc(Cl)ccc1C1=NOCC1]

A solution of 96.0 mg (162 µmol) of methyl 4-({2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoyl}-amino)benzoate (diastereomer mixture) in 2.9 ml of THF/water (3:1 mixture) was stirred in the presence of 970 µl (0.50 M, 480 µmol) of a lithium hydroxide monohydrate solution at room temperature for 18 hours. The mixture was then adjusted to pH 7 using aqueous hydrochloric acid solution (1N) and the THF was removed under reduced pressure. The aqueous residue was diluted with acetonitrile and purified by preparative RP-HPLC (Reprosil C18, 0.1% strength formic acid/acetonitrile gradient). Yield: 73 mg (78% of theory)

LC/MS [Method 2]: R$_t$=2.95 min; MS (ESIpos): m/z=580 (M+H)$^+$, $^1$H-NMR (400 MHz, DMSO-d$_6$): δ [ppm]=12.73 (br s, 1H), 10.74-10.50 (m, 1H), 7.93-7.86 (m, 2H), 7.79-7.72 (m, 2H), 7.67-7.57 (m, 2H), 7.44 (dd, 1H), 7.34 und 7.29 (2×s, 1H), 6.36 und 6.34 (2×s, 1H), 5.83-5.58 (m, 1H), 4.33-4.22 (m, 2H), 3.91-3.76 (m, 1H), 3.57 (2×s, 3H), 3.28-3.03 (m, 4H), 2.37-2.08 (m, 2H), 1.78-1.70 (m, 1H), 1.67-1.49 (m, 1H), 1.47-1.36 (m, 3H), 1.35-1.19 (m, 1H).

Example 40

2-{4-[5-Chloro-2-(4,5-dihydro-1,2-oxazol-3-yl)phenyl]-5-methoxy-2-oxopyridin-1(2H)-yl}-N-(2-methyl-2H-indazol-5-yl)-3-[(2R)-tetrahydro-2H-pyran-2-yl]propanamide (Diastereomer Mixture)

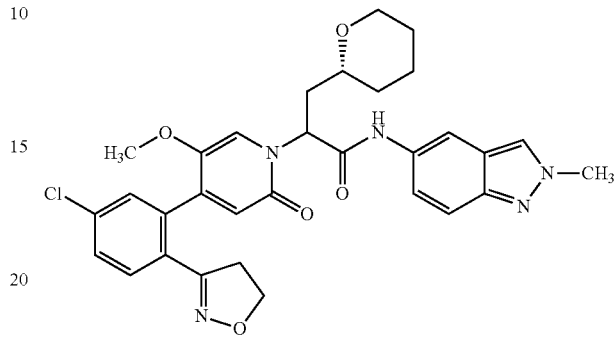

50 mg (0.108 mmol) of 2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoic acid (diastereomer mixture) and 24 mg (0.163 mmol) of 2-methyl-2H-indazole-5-amine in 1 ml of pyridine were reacted according to General Method 5. Yield: 40 mg (62% of theory).

LC/MS [Method 1]: R$_t$=0.93 min; MS (ESIpos): m/z=590 (M+H)$^+$, $^1$H-NMR (400 MHz, DMSO-d$_6$): δ [ppm]=10.36 und 10.25 (2×s, 1H), 8.26-8.23 (m, 1H), 8.15-8.09 (m, 1H), 7.67-7.51 (m, 3H), 7.46-7.43 (m, 1H), 7.40-7.29 (m, 2H), 6.36 und 6.34 (2×s, 1H), 5.86-5.64 (m, 1H), 4.33-4.22 (m, 2H), 4.13 (2×s, 3H), 3.91-3.78 (m, 1H), 3.57 (2×s, 3H), 3.28-3.03 (m, 4H), 2.34-2.06 (m, 2H), 1.79-1.70 (m, 1H), 1.69-1.54 (m, 1H), 1.49-1.36 (m, 3H), 1.32-1.18 (m, 1H).

Example 41

4-[(2-{4-[5-Chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoyl)amino]-2-fluorobenzamide (Diastereomer Mixture)

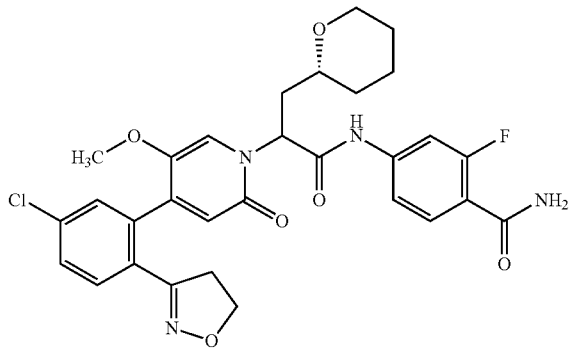 [SMILES: COc1cn(C(C[C@H]2CCCCO2)C(=O)Nc2ccc(C(N)=O)c(F)c2)c(=O)cc1-c1cc(Cl)ccc1C1=NOCC1]

50 mg (0.108 mmol) of 2-{4-[5-chloro-2-(4,5-dihydro-1,2-oxazol-3-yl)phenyl]-5-methoxy-2-oxopyridin-1(2H)-yl}-3-[(2R)-tetrahydro-2H-pyran-2-yl]propanoic acid (diastereomer mixture) and 26 mg (0.163 mmol) of 4-amino-2- fluorobenzamide in 1 ml of pyridine were reacted according to General Method 5. Yield: 37 mg (58% of theory).

LC/MS [Method 2]: $R_t$=2.83 min; MS (ESIpos): m/z=597 (M+H)⁺,

¹H-NMR (400 MHz, DMSO-d₆): δ [ppm]=10.82-10.51 (m, 1H), 7.71-7.62 (m, 3H), 7.61-7.57 (m, 1H), 7.56-7.48 (m, 2H), 7.50-7.42 (m, 2H), 7.33 und 7.27 (2×s, 1H), 6.36 und 6.34 (2×s, 1H), 5.79-5.53 (m, 1H), 4.32-4.23 (m, 2H), 3.89-3.77 (m, 1H), 3.57 (2×s, 3H), 3.27-3.01 (m, 4H), 2.37-2.23 (m, 1H), 2.22-2.07 (m, 1H), 1.79-1.71 (m, 1H), 1.66-1.53 (m, 1H), 1.48-1.35 (m, 3H), 1.32-1.18 (m, 1H).

Example 42

5-[(2-{4-[5-Chloro-2-(1,2-oxazol-3-yl)phenyl]-5-methoxy-2-oxopyridin-1(2H)-yl}-4-methoxybutanoyl)amino]-N-methylpyridin-2-carboxamide (Racemate)

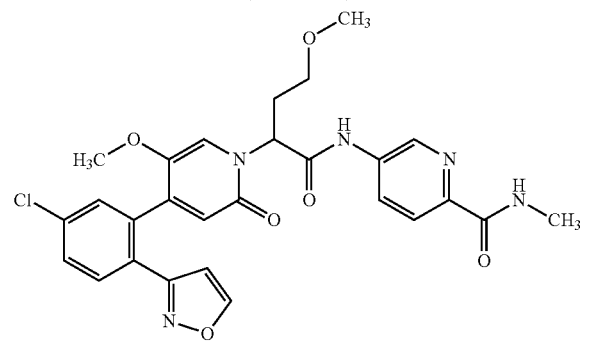 [SMILES: CNC(=O)c1ccc(NC(=O)C(CCOC)n2cc(OC)c(-c3cc(Cl)ccc3-c3ccon3)cc2=O)cn1]

35 mg (0.084 mmol) of 2-{4-[5-chloro-2-(1,2-oxazol-3-yl)phenyl]-5-methoxy-2-oxopyridin-1(2H)-yl}-4-methoxybutanoic acid (racemate) and 19 mg (0.125 mmol) of 5-amino-N-methylpyridine-2-carboxamide in 0.74 ml of pyridine were reacted according to General Method 5. Yield: 35 mg (76% of theory).

LC/MS [Method 1]: $R_t$=0.88 min; MS (ESIpos): m/z=552 (M+H)⁺,

¹H-NMR (500 MHz, DMSO-d₆): δ [ppm]=10.80 (br s, 1H), 8.91 (d, 1H), 8.87 (d, 1H), 8.65 (q, 1H), 8.21 (dd, 1H), 8.00 (d, 1H), 7.74 (d, 1H), 7.65 (dd, 1H), 7.53 (d, 1H), 7.27 (s, 1H), 6.54 (d, 1H), 6.39 (s, 1H), 5.70 (br s, 1H), 3.40-3.33 (m, 4H), 3.26-3.20 (m, 4H), 2.80 (d, 3H), 2.47-2.33 (m, 2H).

Example 43

2-{4-[5-Chloro-2-(1,2-oxazol-3-yl)phenyl]-5-methoxy-2-oxopyridin-1(2H)-yl}-4-methoxy-N-(2-methyl-2H-indazol-5-yl)butanamide (Racemate)

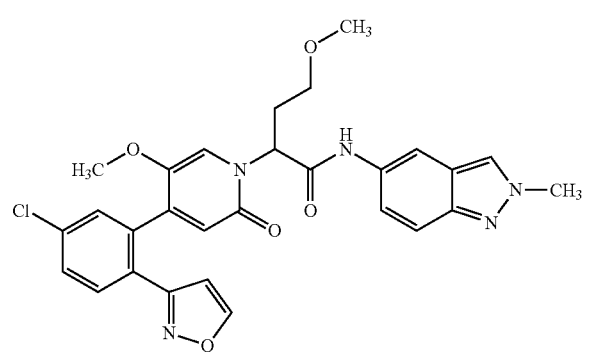 [SMILES: COCCC(C(=O)Nc1ccc2nn(C)cc2c1)n1cc(OC)c(-c2cc(Cl)ccc2-c2ccon2)cc1=O]

35 mg (0.084 mmol) of 2-{4-[5-chloro-2-(1,2-oxazol-3-yl)phenyl]-5-methoxy-2-oxopyridin-1(2H)-yl}-4-methoxybutanoic acid (racemate) and 19 mg (0.125 mmol) of 2-methyl-2H-indazole-5-amine in 0.74 ml of pyridine were reacted according to General Method 5. Yield: 31 mg (68% of theory).

LC/MS [Method 1]: $R_t$=0.91 min; MS (ESIpos): m/z=548 (M+H)⁺,

¹H-NMR (500 MHz, DMSO-d₆): δ [ppm]=10.33 (br s, 1H), 8.91 (d, 1H), 8.25 (s, 1H), 8.12 (d, 1H), 7.74 (d, 1H), 7.64 (dd, 1H), 7.56-7.52 (m, 2H), 7.33-7.29 (m, 2H), 6.53 (d, 1H), 6.38 (s, 1H), 5.76 (br s, 1H), 4.13 (s, 3H), 3.38-3.34 (m, 4H), 3.28-3.20 (m, 4H), 2.42-2.28 (m, 2H).

Example 44

5-[(4-tert-Butoxy-2-{4-[5-chloro-2-(1,2-oxazol-3-yl)phenyl]-5-methoxy-2-oxopyridin-1(2H)-yl}butanoyl)amino]-N-methylpyridine-2-carboxamide (Racemate)

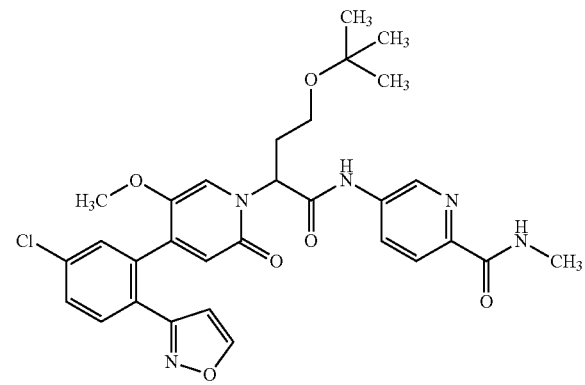 [SMILES: CNC(=O)c1ccc(NC(=O)C(CCOC(C)(C)C)n2cc(OC)c(-c3cc(Cl)ccc3-c3ccon3)cc2=O)cn1]

25 mg (0.054 mmol) of 4-tert-butoxy-2-{4-[5-chloro-2-(1,2-oxazol-3-yl)phenyl]-5-methoxy-2-oxopyridin-1(2H)-yl}butanoic acid (racemate) and 12.5 mg (0.081 mmol) of 5-amino-N-methylpyridine-2-carboxamide in 1 ml of pyridine were reacted according to General Method 5. Yield: 31 mg (96% of theory).

LC/MS [Method 10]: $R_t$=1.83 min; MS (ESIpos): m/z=594 (M+H)⁺,

¹H-NMR (400 MHz, DMSO-d₆): δ [ppm]=10.81 (br s, 1H), 8.90 (d, 1H), 8.88 (d, 1H), 8.65 (q, 1H), 8.22 (dd, 1H), 8.00 (d, 1H), 7.73 (d, 1H), 7.64 (dd, 1H), 7.48 (s, 1H), 7.25 (s, 1H), 6.56 (d, 1H), 6.38 (s, 1H), 5.74 (br s, 1H), 3.42-3.34 (m, 4H), 3.29-3.21 (m, 1H), 2.80 (d, 3H), 2.42-2.29 (m, 2H), 1.07 (s, 9H).

Example 45

4-[(4-tert-Butoxy-2-{4-[5-chloro-2-(1,2-oxazol-3-yl)phenyl]-5-methoxy-2-oxopyridin-1(2H)-yl}butanoyl)amino]benzoic acid (Racemate)

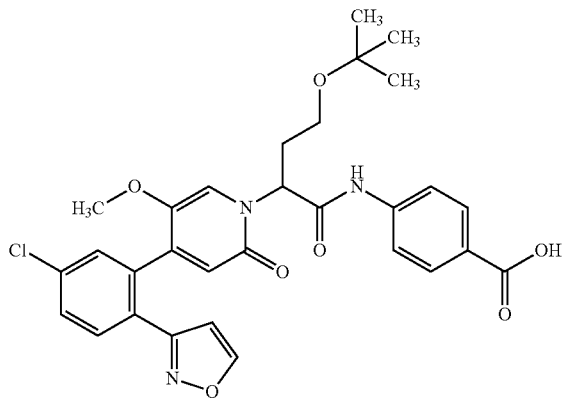 [SMILES: COc1cn(C(CCOC(C)(C)C)C(=O)Nc2ccc(C(=O)O)cc2)c(=O)cc1-c1cc(Cl)ccc1-c1ccon1]

A solution of 107 mg (180 μmol) of methyl 4-{[4-tert-butoxy-2-{4-[5-chloro-2-(1,2-oxazol-3-yl)phenyl]-5-methoxy-2-oxopyridin-1(2H)-yl}butanoyl]amino}benzoate (Racemate) in 3.2 ml of THF/water (3:1 mixture) was stirred in the presence of 1.1 ml (0.50 M, 540 μmol) of a lithium hydroxide monohydrate solution at room temperature for 20 hours and at 40° C. for 3 hours. The mixture was then adjusted to pH 7 using aqueous hydrochloric acid solution (1N) and the THF was removed under reduced pressure. The aqueous residue was diluted with acetonitrile and purified by preparative RP-HPLC (Reprosil C18, 0.1% strength formic acid/acetonitrile gradient). Yield: 82 mg (76% of theory)

LC/MS [Method 1]: $R_t$=1.04 min; MS (ESIpos): m/z=580 (M+H)$^+$, $^1$H-NMR (400 MHz, DMSO-d$_6$): δ [ppm]=12.73 (br s, 1H), 10.67 (s, 1H), 8.90 (d, 1H), 7.90 (d, 2H), 7.79-7.72 (m, 3H), 7.67-7.62 (m, 1H), 7.48 (s, 1H), 7.26 (s, 1H), 6.55 (d, 1H), 6.37 (s, 1H), 5.79-5.69 (m, 1H), 3.40-3.34 (m, 4H), 3.28-3.20 (m, 1H), 2.47-2.27 (m, 2H), 1.08-0.97 (m, 9H).

Example 46

4-{[(2S)-4-tert-Butoxy-2-{4-[5-chloro-2-(1,2-oxazol-3-yl)phenyl]-5-methoxy-2-oxopyridin-1(2H)-yl}butanoyl]amino}benzoic acid (Enantiomer 2)

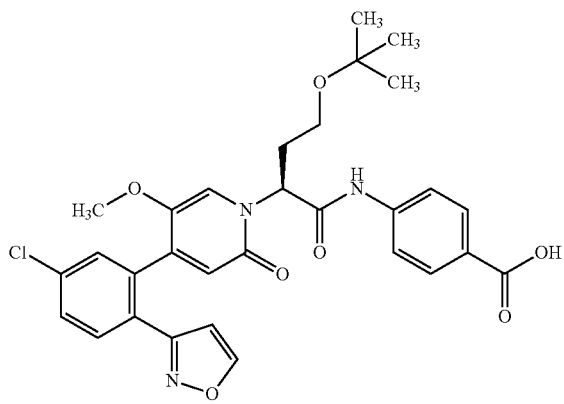 [SMILES: COc1cn([C@@H](CCOC(C)(C)C)C(=O)Nc2ccc(C(=O)O)cc2)c(=O)cc1-c1cc(Cl)ccc1-c1ccon1]

Enantiomer separation of 91 mg of 4-[(4-tert-butoxy-2-{4-[5-chloro-2-(1,2-oxazol-3-yl)phenyl]-5-methoxy-2-oxopyridin-1(2H)-yl}butanoyl)amino]benzoic acid (racemate) gave 36 mg of enantiomer 1 (chiral HPLC: $R_t$=5.6 min) and 30 mg of the title compound Example 46 (enantiomer 2): chiral HPLC: $R_t$=19.3 min; 100% ee, purity 96%.

Separating method: column: Chiralpak AD-H SFC 5 μm, 250 mm×20 mm; mobile phase: carbon dioxide 80%/ethanol 20%; temperature: 40° C.; flow rate: 80 ml/min; pressure: 1000 bar; UV detection: 210 nm.

Analysis: column: Daicel AD-H SFC 3 μm, 100 mm×4.6 mm; mobile phase: 60% carbon dioxide, 40% ethanol; flow rate: 3 ml/min; UV detection: 210 nm.

Example 47

N-(Quinoxalin-6-yl)-2-{4-[5-chloro-2-(1,2-oxazol-3-yl)phenyl]-5-methoxy-2-oxopyridin-1(2H)-yl}-3-[(2S)-tetrahydro-2H-pyran-2-yl]propanamide (Diastereomer Mixture)

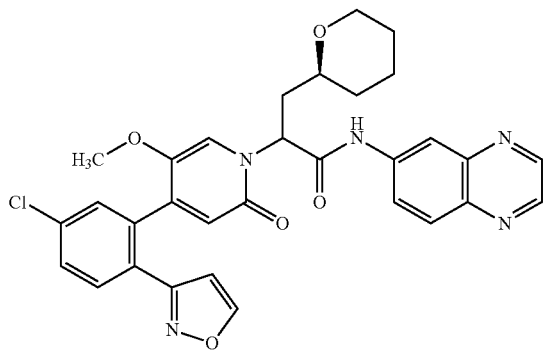 [SMILES: COc1cn(C(C[C@@H]2CCCCO2)C(=O)Nc2ccc3nccnc3c2)c(=O)cc1-c1cc(Cl)ccc1-c1ccon1]

40 mg (0.087 mmol) of 2-{4-[5-chloro-2-(1,2-oxazol-3-yl)phenyl]-5-methoxy-2-oxopyridin-1(2H)-yl}-3-[(2S)-tetrahydro-2H-pyran-2-yl]propanoic acid (diastereomer mixture) and 19 mg (0.131 mmol) of quinoxaline-6-amine in 0.77 ml of pyridine were reacted according to General Method 5. Yield: 35 mg (68% of theory)

LC/MS [Method 1]: $R_t$=1.01/1.03 min; MS (ESIpos): m/z=586/586 (M+H)$^+$, $^1$H-NMR (500 MHz, DMSO-d$_6$): δ [ppm]=10.91 und 10.81 (2×s, 1H), 8.94-8.87 (m, 2H), 8.85-8.82 (m, 1H), 8.56-8.51 (m, 1H), 8.06 (d, 1H), 8.09-7.99 (m, 2H), 7.76-7.73 (m, 1H), 7.66-7.63 (m, 1H), 7.56-7.52 (m, 1H), 7.34 und 7.29 (2×s, 1H), 6.56-6.53 (m, 1H), 6.40-6.38 (m, 1H), 5.92-5.63 (m, 1H), 3.91-3.81 (m, 1H), 3.37 (s, 3H), 3.28-3.03 (m, 2H), 2.41-2.28 (m, 1H), 2.26-2.13 (m, 1H), 1.83-1.73 (m, 1H), 1.68-1.54 (m, 1H), 1.52-1.38 (m, 3H), 1.32-1.22 (m, 1H).

Example 48

4-[(2-{4-[5-Chloro-2-(1,2-oxazol-3-yl)phenyl]-5-methoxy-2-oxopyridin-1(2H)-yl}-3-[(2S)-tetrahydro-2H-pyran-2-yl]propanoyl)amino]benzoic acid (Diastereomer Mixture)

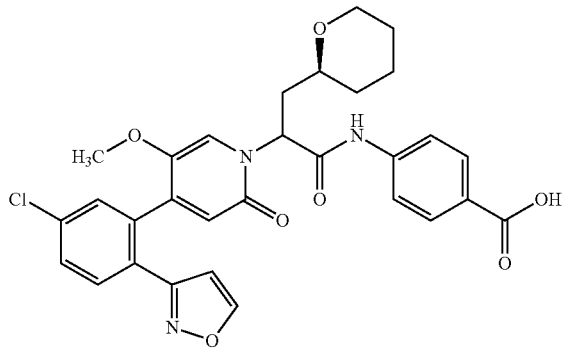 [SMILES: COc1cn(C(C[C@@H]2CCCCO2)C(=O)Nc2ccc(C(=O)O)cc2)c(=O)cc1-c1cc(Cl)ccc1-c1ccon1]

110 mg (240 µmol) of 2-{4-[5-chloro-2-(1,2-oxazol-3-yl)phenyl]-5-methoxy-2-oxopyridin-1(2H)-yl}-3-[(2S)-tetrahydro-2H-pyran-2-yl]propanoic acid (diastereomer mixture) and 34.5 mg (252 mol) of 4-aminobenzoic acid in 1.33 ml of pyridine were reacted according to General Method 5. Yield: 104 mg (75% of theory)

LC/MS [Method 1]: $R_t$=1.00 min; MS (ESIpos): m/z=578 (M+H)$^+$, $^1$H-NMR (500 MHz, DMSO-$d_6$): δ [ppm]=12.74 (br s, 1H), 10.69 und 10.59 (2×, 1H), 8.94-8.89 (m, 1H), 7.93-7.86 (m, 2H), 7.78-7.72 (m, 3H), 7.66-7.62 (m, 1H), 7.55-7.51 (m, 1H), 7.29 und 7.24 (2×s, 1H), 6.55-6.51 (m, 1H), 6.38-6.35 (m, 1H), 5.83-5.59 (m, 1H), 3.89-3.79 (m, 1H), 3.35 (s, 3H), 3.23-3.00 (m, 2H), 2.37-2.09 (m, 2H), 1.81-1.72 (m, 1H), 1.66-1.53 (m, 1H), 1.50-1.37 (m, 3H), 1.33-1.18 (m, 1H).

Example 49

4-[(2-{4-[5-Chloro-2-(1,2-oxazol-3-yl)phenyl]-5-methoxy-2-oxopyridin-1(2H)-yl}-3-[(2S)-tetrahydro-2H-pyran-2-yl]propanoyl)amino]benzoic acid (Diastereomer 1)

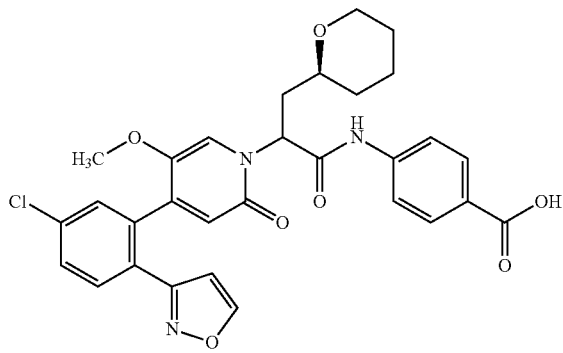 [SMILES: COc1cn(C(C[C@@H]2CCCCO2)C(=O)Nc2ccc(C(=O)O)cc2)c(=O)cc1-c1cc(Cl)ccc1-c1ccon1]

Diastereomer separation of 100 mg of 4-[(2-{4-[5-chloro-2-(1,2-oxazol-3-yl)phenyl]-5-methoxy-2-oxopyridin-1(2H)-yl}-3-[(2S)-tetrahydro-2H-pyran-2-yl]propanoyl) amino]benzoic acid (diastereomer mixture) gave 47 mg of diastereomer 2 (chiral HPLC: $R_t$=9.0 min) and 30 mg of the title compound Example 49 (diastereomer 1): chiral HPLC: $R_t$=3.6 min; 100% ee.

Separating method: column: Chiralpak AS-H SFC 5 µm, 250 mm×20 mm; mobile phase: carbon dioxide 80%/ethanol 20%; temperature: 40° C.; flow rate: 80 ml/min; pressure: 90 bar; UV detection: 210 nm.

Analysis: column: Daicel AS-H SFC 3 µm, 100 mm×4.6 mm; mobile phase: 80% carbon dioxide, 20% ethanol; flow rate: 3 ml/min; UV detection: 210 nm.

LC/MS [Method 1]: $R_t$=1.01 min; MS (ESIpos): m/z=578 (M+H)$^+$, $^1$H-NMR (400 MHz, DMSO-$d_6$): δ [ppm]=12.75 (br s, 1H), 10.69 (s, 1H), 8.90 (d, 1H), 7.94-7.87 (m, 2H), 7.79-7.71 (m, 3H), 7.64 (dd, 1H), 7.52 (d, 1H), 7.29 (s, 1H), 6.52 (d, 1H), 6.38 (s, 1H), 5.83-5.75 (m, 1H), 3.90-3.83 (m, 1H), 3.35 (s, 3H), 3.23-3.14 (m, 1H), 2.28-2.17 (m, 1H), 2.17-2.06 (m, 1H), 1.81-1.72 (m, 1H), 1.67-1.59 (m, 1H), 1.49-1.34 (m, 3H), 1.32-1.19 (m, 1H).

Example 50

2-{4-[5-Chloro-2-(4-fluoro-1H-imidazol-1-yl)phenyl]-5-methoxy-2-oxopyridin-1(2H)-yl}-4-methoxy-N-(2-methyl-2H-indazol-5-yl)butanamide (Racemate)

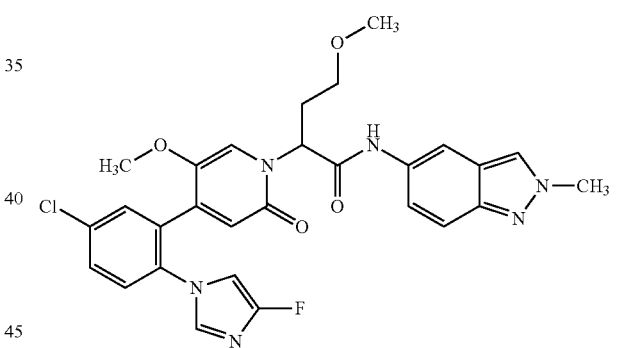

41.0 mg (94.1 µmol) of 2-{4-[5-chloro-2-(4-fluoro-1H-imidazol-1-yl)phenyl]-5-methoxy-2-oxopyridin-1(2H)-yl}-4-methoxybutanoic acid (racemate) and 20.8 mg (141 µmol) of 2-methyl-2H-indazole-5-amine in 1.0 ml of pyridine were reacted according to General Method 5. Yield: 44 mg (82% of theory)

LC/MS [Method 1]: $R_t$=0.83 min; MS (ESIpos): m/z=565 (M+H)$^+$, $^1$H-NMR (400 MHz, DMSO-$d_6$): δ [ppm]=10.29 (s, 1H), 8.24 (s, 1H), 8.12-8.08 (m, 1H), 7.72-7.67 (m, 1H), 7.63-7.52 (m, 3H), 7.40 (t, 1H), 7.32-7.26 (m, 2H), 6.93 (dd, 1H), 6.46 (s, 1H), 5.78-5.63 (m, 1H), 4.13 (s, 3H), 3.41 (s, 3H), 3.22-3.11 (m, 4H), 2.39-2.27 (m, 2H). One proton under water signal.

Example 51

4-[(2-{4-[5-Chloro-2-(4-fluoro-1H-imidazol-1-yl)phenyl]-5-methoxy-2-oxopyridin-1(2H)-yl}-4-methoxybutanoyl)amino]benzoic acid (Racemate)

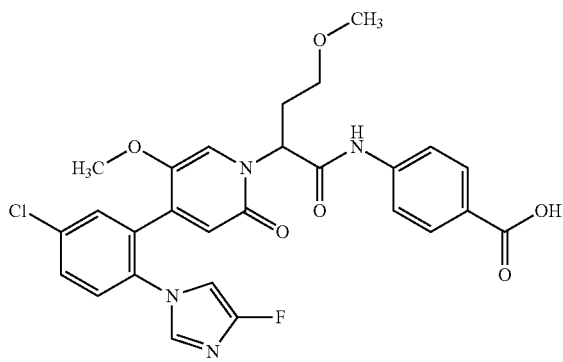

41.0 mg (94.1 µmol) of 2-{4-[5-chloro-2-(4-fluoro-1H-imidazol-1-yl)phenyl]-5-methoxy-2-oxopyridin-1(2H)-yl}-4-methoxybutanoic acid (racemate) and 13.5 mg (99 µmol) of 4-aminobenzoic acid in 0.5 ml of pyridine were reacted according to General Method 5. Yield: 39 mg (76% of theory)

LC/MS [Method 1]: $R_t$=0.84 min; MS (ESIpos): m/z=555 (M+H)$^+$, $^1$H-NMR (400 MHz, DMSO-d$_6$): δ [ppm]=12.75 (br s, 1H), 10.63 (br s, 1H), 7.89 (d, 2H), 7.75-7.67 (m, 3H), 7.63 (d, 1H), 7.58 (d, 1H), 7.39 (t, 1H), 7.23 (s, 1H), 6.92 (dd, 1H), 6.46 (s, 1H), 5.76-5.61 (m, 1H), 3.41 (s, 3H), 3.21-3.08 (m, 4H), 2.40-2.29 (m, 2H).

Example 52

2-{4-[5-Chloro-2-(4-chloro-1H-imidazol-1-yl)phenyl]-5-methoxy-2-oxopyridin-1(2H)-yl}-4-methoxy-N-(2-methyl-2H-indazol-5-yl)butanamide (Racemate)

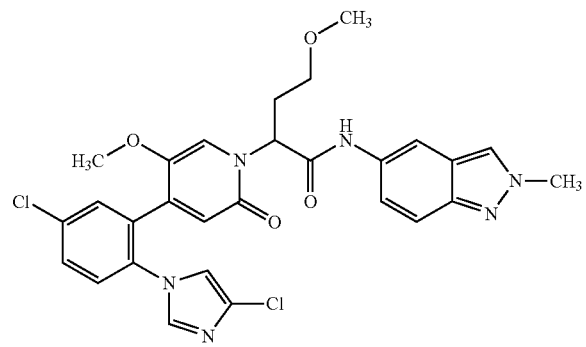 [SMILES: COCCC(C(=O)Nc1ccc2nn(C)cc2c1)n1cc(OC)c(-c2cc(Cl)ccc2-n2cnc(F)c2)cc1=O]

40.0 mg (purity 92%, 75.3 µmol) of 2-{4-[5-chloro-2-(4-chloro-1H-imidazol-1-yl)phenyl]-5-methoxy-2-oxopyridin-1(2H)-yl}-4-methoxybutanoic acid hydrochloride (racemate) and 16.6 mg (113 µmol) of 2-methyl-2H-indazole-5-amine in 1.0 ml of pyridine were reacted according to General Method 5. Yield: 37 mg (purity 92%, 78% of theory)

LC/MS [Method 10]: $R_t$=1.56 min; MS (ESIpos): m/z=581 (M+H)$^+$, $^1$H-NMR (400 MHz, DMSO-d$_6$): δ [ppm]=10.29 (br s, 1H), 8.24 (s, 1H), 8.10 (d, 1H), 7.71-7.67 (m, 1H), 7.66-7.62 (m, 2H), 7.59 (d, 1H), 7.53 (d, 1H), 7.32-7.24 (m, 3H), 6.47 (s, 1H), 5.78-5.66 (m, 1H), 4.12 (s, 3H), 3.39 (s, 3H), 3.36-3.33 (m, 1H), 3.20 (s, 3H), 3.18-3.11 (m, 1H), 2.38-2.28 (m, 2H).

Example 53

4-[(2-{4-[5-Chloro-2-(4-chloro-1H-imidazol-1-yl)phenyl]-5-methoxy-2-oxopyridin-1(2H)-yl}-4-methoxybutanoyl)amino]benzoic acid (Racemate)

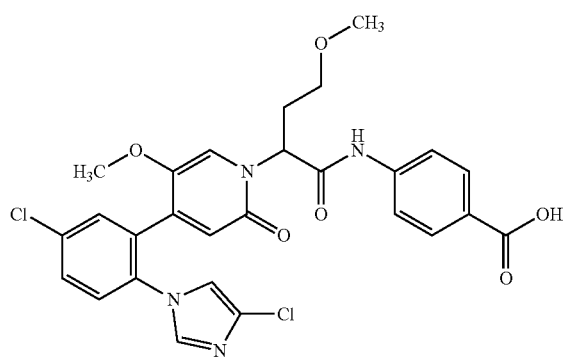 [SMILES: COCCC(C(=O)Nc1ccc(C(=O)O)cc1)n1cc(OC)c(-c2cc(Cl)ccc2-n2cnc(Cl)c2)cc1=O]

41.0 mg (purity 92%, 75 µmol) of 2-{4-[5-chloro-2-(4-chloro-1H-imidazol-1-yl)phenyl]-5-methoxy-2-oxopyridin-1(2H)-yl}-4-methoxybutanoic acid hydrochloride (racemate) and 10.8 mg (79 µmol) of 4-aminobenzoic acid in 0.5 ml of pyridine were reacted according to General Method 5. Yield: 28 mg (purity 90%, 58% of theory)

LC/MS [Method 10]: $R_t$=1.52 min; MS (ESIpos): m/z=585 (M+H)$^+$, $^1$H-NMR (400 MHz, DMSO-d$_6$): δ [ppm]=10.62 (br s, 1H), 7.89 (d, 2H), 7.74-7.67 (m, 3H), 7.64 (dd, 2H), 7.59 (d, 1H), 7.29 (d, 1H), 7.22 (s, 1H), 6.47 (s, 1H), 5.68 (br s, 1H), 3.38 (s, 3H), 3.19 (s, 3H), 3.18-3.09 (m, 2H), 2.39-2.29 (m, 2H).

Example 54

5-[(2-{4-[5-Chloro-2-(4-chloro-1H-imidazol-1-yl)phenyl]-5-methoxy-2-oxopyridin-1(2H)-yl}-4-methoxybutanoyl)amino]-N-methylpyridine-2-carboxamide (Racemate)

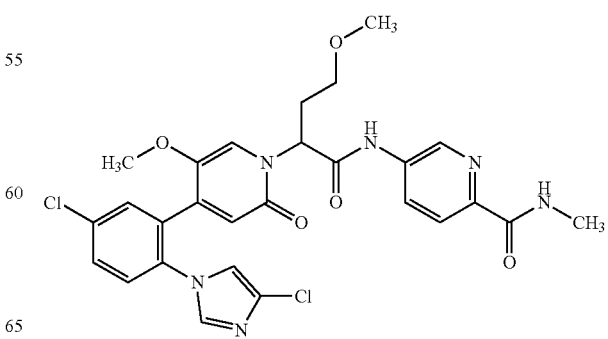

40.0 mg (purity 92%, 75.3 µmol) of 2-{4-[5-chloro-2-(4-chloro-1H-imidazol-1-yl)phenyl]-5-methoxy-2-oxopyridin-1(2H)-yl}-4-methoxybutanoic acid hydrochloride (racemate) and 17.4 mg (113 µmol) of 5-amino-N-methylpyridine-2-carboxamide in 1.0 ml of pyridine were reacted according to General Method 5. Yield: 41 mg (purity 90%, 83% of theory)

LC/MS [Method 10]: $R_t$=1.52 min; MS (ESIpos): m/z=585 (M+H)$^+$, $^1$H-NMR (400 MHz, DMSO-d$_6$): δ [ppm]=10.76 (br s, 1H), 8.86 (d, 1H), 8.65 (q, 1H), 8.21-8.16 (m, 1H), 7.99 (d, 1H), 7.72-7.67 (m, 1H), 7.65 (d, 1H), 7.63 (d, 1H), 7.59 (d, 1H), 7.29 (d, 1H), 7.21 (s, 1H), 6.48 (s, 1H), 5.66 (br s, 1H), 3.38 (s, 3H), 3.37-3.33 (m, 1H), 3.20 (s, 3H), 3.11 (dt, 1H), 2.80 (d, 3H), 2.42-2.34 (m, 2H).

Example 55

N-(Quinoxalin-6-yl)-2-{4-[5-chloro-2-(4-chloro-1H-imidazol-1-yl)phenyl]-5-methoxy-2-oxopyridin-1(2H)-yl}-4-methoxybutanamide (Racemate)

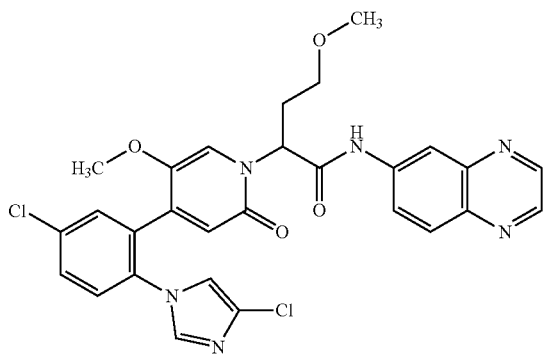 [SMILES: COCCC(C(=O)Nc1ccc2nccnc2c1)n1cc(OC)c(-c2cc(Cl)ccc2-n2cnc(Cl)c2)cc1=O]

40.0 mg (purity 92%, 75.3 µmol) of 2-{4-[5-chloro-2-(4-chloro-1H-imidazol-1-yl)phenyl]-5-methoxy-2-oxopyridin-1(2H)-yl}-4-methoxybutanoic acid hydrochloride (racemate) and 16.4 mg (113 µmol) of quinoxaline-6-amine in 1.0 ml of pyridine were reacted according to General Method 5. Yield: 41 mg (purity 93%, 87% of theory)

LC/MS [Method 10]: $R_t$=1.60 min; MS (ESIpos): m/z=579 (M+H)$^+$, $^1$H-NMR (400 MHz, DMSO-d$_6$): δ [ppm]=10.85 (br s, 1H), 8.89 (d, 1H), 8.83 (d, 1H), 8.52 (d, 1H), 8.08-8.03 (m, 1H), 8.03-7.97 (m, 1H), 7.72-7.67 (m, 1H), 7.67-7.63 (m, 2H), 7.60 (d, 1H), 7.31-7.25 (m, 2H), 6.49 (s, 1H), 5.74 (br s, 1H), 3.41 (s, 3H), 3.39-3.33 (m, 1H), 3.21 (s, 3H), 3.17-3.11 (m, 1H), 2.46-2.36 (m, 2H).

Example 56

4-[(2-{4-[5-Chloro-2-(4H-1,2,4-triazol-4-yl)phenyl]-5-methoxy-2-oxopyridin-1(2H)-yl}-4-methoxybutanoyl)amino]-2-fluorobenzamide (Racemate)

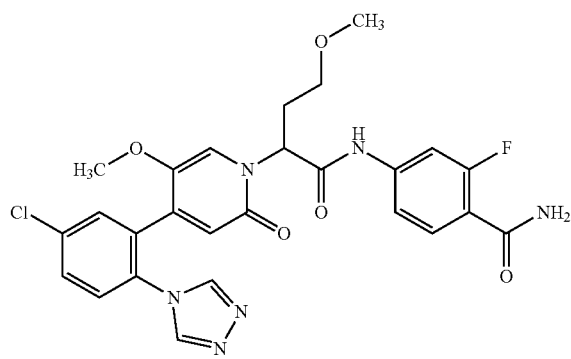 [SMILES: COCCC(C(=O)Nc1ccc(C(N)=O)c(F)c1)n1cc(OC)c(-c2cc(Cl)ccc2-n2cnnc2)cc1=O]

63.0 mg (purity 70%, 97 µmol) of 2-{4-[5-chloro-2-(4H-1,2,4-triazol-4-yl)phenyl]-5-methoxy-2-oxopyridin-1(2H)-yl}-4-methoxybutanoic acid hydrochloride (racemate) and 23.1 mg (145 µmol) of 4-amino-2-fluorobenzamide in 0.8 ml of pyridine were reacted according to General Method 5. Yield: 22 mg (41% of theory)

LC/MS [Method 1]: $R_t$=0.73 min; MS (ESIpos): m/z=555 (M+H)$^+$, $^1$H-NMR (400 MHz, DMSO-d$_6$): δ [ppm]=10.69 (br s, 1H), 8.54 (s, 2H), 7.75-7.71 (m, 1H), 7.71-7.60 (m, 4H), 7.52 (br d, 2H), 7.41 (dd, 1H), 7.17 (s, 1H), 6.49 (s, 1H), 5.63 (br s, 1H), 3.35 (s, 3H), 3.19 (s, 3H), 3.17-3.07 (m, 1H), 2.38-2.27 (m, 2H).

Example 57

N-(Quinoxalin-6-yl)-2-{4-[5-chloro-2-(4H-1,2,4-triazol-4-yl)phenyl]-5-methoxy-2-oxopyridin-1(2H)-yl}-4-methoxybutanamide (Racemate)

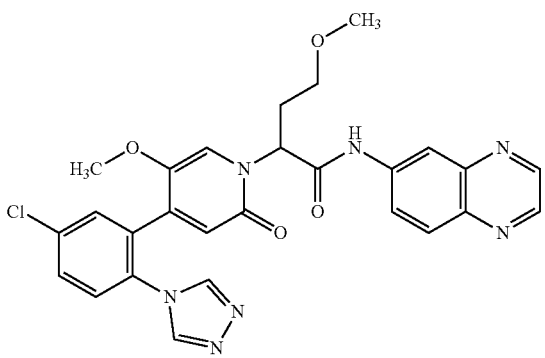 [SMILES: COCCC(C(=O)Nc1ccc2nccnc2c1)n1cc(OC)c(-c2cc(Cl)ccc2-n2cnnc2)cc1=O]

63.0 mg (purity 70%, 97 µmol) of 2-{4-[5-chloro-2-(4H-1,2,4-triazol-4-yl)phenyl]-5-methoxy-2-oxopyridin-1(2H)-yl}-4-methoxybutanoic acid hydrochloride (racemate) and 21.1 mg (145 µmol) of quinoxaline-6-amine in 0.8 ml of pyridine were reacted according to General Method 5. Yield: 39 mg (74% of theory)

LC/MS [Method 1]: $R_t$=0.76 min; MS (ESIpos): m/z=546 (M+H)$^+$,

¹H-NMR (400 MHz, DMSO-d₆): δ [ppm]=10.85 (br s, 1H), 8.89 (d, 1H), 8.83 (d, 1H), 8.56 (s, 2H), 8.51 (d, 1H), 8.08-8.03 (m, 1H), 8.03-7.98 (m, 1H), 7.75-7.71 (m, 1H), 7.69 (d, 1H), 7.67-7.63 (m, 1H), 7.23 (s, 1H), 6.51 (s, 1H), 5.72 (br s, 1H), 3.41-3.33 (m, 4H), 3.23-3.13 (m, 4H), 2.46-2.31 (m, 2H).

Example 58

4-[(2-{4-[5-Chloro-2-(4H-1,2,4-triazol-4-yl)phenyl]-5-methoxy-2-oxopyridin-1(2H)-yl}-4-methoxybutanoyl)amino]benzoic acid (Racemate)

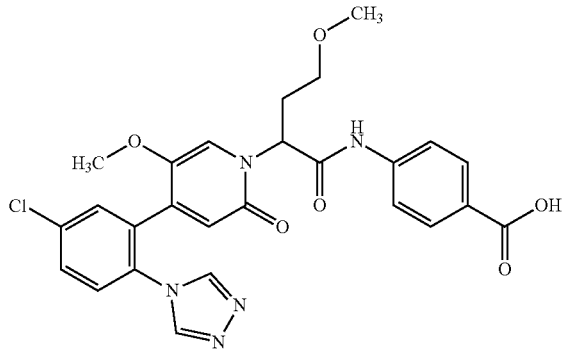 [SMILES: COCCC(C(=O)Nc1ccc(C(=O)O)cc1)n1cc(OC)c(-c2cc(Cl)ccc2-n2cnnc2)cc1=O]

63.0 mg (purity 70%, 97 µmol) of 2-{4-[5-chloro-2-(4H-1,2,4-triazol-4-yl)phenyl]-5-methoxy-2-oxopyridin-1(2H)-yl}-4-methoxybutanoic acid hydrochloride (racemate) and 13.9 mg (102 µmol) of 4-aminobenzoic acid in 0.54 ml of pyridine were reacted according to General Method 5. Yield: 32 mg (61% of theory)

LC/MS [Method 1]: $R_t$=0.76 min; MS (ESIpos): m/z=538 (M+H)⁺,

¹H-NMR (400 MHz, DMSO-d₆): δ [ppm]=12.74 (br s, 1H), 10.63 (br s, 1H), 8.54 (s, 2H), 7.89 (d, 2H), 7.75-7.70 (m, 3H), 7.68 (d, 1H), 7.64 (d, 1H), 7.18 (s, 1H), 6.49 (s, 1H), 5.67 (br s, 1H), 3.35 (m, 3H), 3.29-3.24 (m, 1H), 3.19 (s, 3H), 3.18-3.10 (m, 1H), 2.39-2.26 (m, 2H).

Example 59

2-{4-[5-Chloro-2-(4H-1,2,4-triazol-4-yl)phenyl]-5-methoxy-2-oxopyridin-1(2H)-yl}-4-methoxy-N-(2-methyl-2H-indazol-5-yl)butanamide (Racemate)

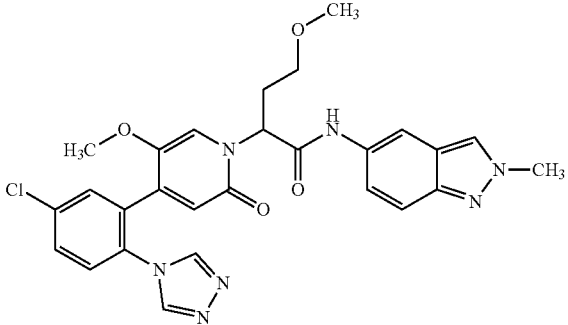 [SMILES: COCCC(C(=O)Nc1ccc2nn(C)cc2c1)n1cc(OC)c(-c2cc(Cl)ccc2-n2cnnc2)cc1=O]

63.0 mg (purity 70%, 97 µmol) of 2-{4-[5-chloro-1,2,4-triazol-4-yl)phenyl]-5-methoxy-2-oxopyridin-1(2H)-yl}-4-methoxybutanoic acid hydrochloride (racemate) and 21.8 mg (145 µmol) of 2-methyl-2H-indazole-5-amine in 0.8 ml of pyridine were reacted according to General Method 5. Yield: 37 mg (70% of theory)

LC/MS [Method 1]: $R_t$=0.75 min; MS (ESIpos): m/z=548 (M+H)⁺,

¹H-NMR (400 MHz, DMSO-d₆): δ [ppm]=10.29 (br s, 1H), 8.55 (s, 2H), 8.24 (s, 1H), 8.11 (d, 1H), 7.75-7.70 (m, 1H), 7.68 (d, 1H), 7.64 (d, 1H), 7.53 (d, 1H), 7.29 (dd, 1H), 7.22 (s, 1H), 6.49 (s, 1H), 5.71 (br s, 1H), 4.12 (s, 3H), 3.36 (s, 3H), 3.29-3.24 (m, 1H), 3.20 (s, 3H), 3.19-3.12 (m, 1H), 2.38-2.23 (m, 2H).

Example 60

N-(Quinoxalin-6-yl)-2-[4-{5-chloro-2-[4-(difluoromethyl)-1H-1,2,3-triazol-1-yl]phenyl}-5-methoxy-2-oxopyridin-1(2H)-yl]pentanamide (Racemate)

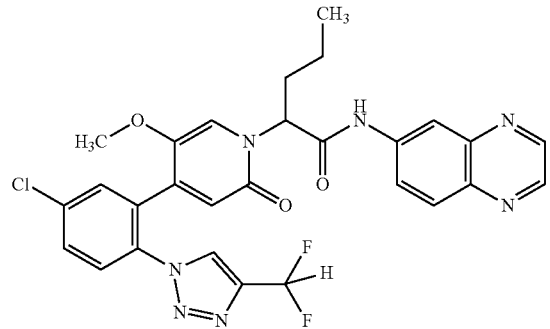 [SMILES: CCCC(C(=O)Nc1ccc2nccnc2c1)n1cc(OC)c(-c2cc(Cl)ccc2-n2cc(C(F)F)nn2)cc1=O]

116 mg (purity 81%, 207 µmol) of 2-[4-{5-chloro-2-[4-(difluoromethyl)-1H-1,2,3-triazol-1-yl]phenyl}-5-methoxy-2-oxopyridin-1(2H)-yl]pentanoic acid (racemate) and 45.0 mg (310 µmol) of quinoxaline-6-amine in 2 ml of pyridine were reacted according to General Method 5. Yield: 100 mg (84% of theory).

LC-MS [Method 10]: $R_t$=1.78 min; MS (ESIpos): m/z=580 [M+H]⁺

1H-NMR (400 MHz, DMSO-d₆): δ [ppm]=10.93 (s, 1H), 8.89 (d, 1H), 8.84 (d, 1H), 8.72 (s, 1H), 8.51 (d, 1H), 8.07 (d, 1H), 7.97 (dd, 1H), 7.82-7.78 (m, 2H), 7.77-7.74 (m, 1H), 7.37-7.07 (m, 2H), 6.52 (s, 1H), 5.72 (br dd, 1H), 3.28 (s, 3H), 2.17-2.02 (m, 2H), 1.31-1.12 (m, 2H), 0.92 (t, 3H).

Example 61

N-(Quinoxalin-6-yl)-2-[4-{5-chloro-2-[4-(difluoromethyl)-1H-imidazol-1-yl]phenyl}-5-methoxy-2-oxopyridin-1(2H)-yl]-4-methoxybutanamide (Racemate)

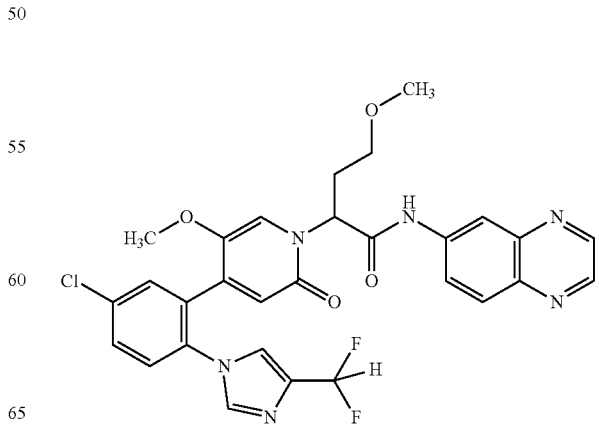

35.0 mg (purity 90%, 62.5 μmol) of 2-[4-{5-chloro-2-[4-(difluoromethyl)-1H-imidazol-1-yl]phenyl}-5-methoxy-2-oxopyridin-1(2H)-yl]-4-methoxybutanoic acid hydrochloride (racemate) and 13.6 mg (93.7 μmol) of quinoxaline-6-amine in 1.0 ml of pyridine were reacted according to General Method 5. Yield: 30 mg (80% of theory)

LC/MS [Method 10]: $R_t$=1.55 min; MS (ESIpos): m/z=595 (M+H)$^+$, $^1$H-NMR (400 MHz, DMSO-d$_6$): δ [ppm]=10.84 (br s, 1H), 8.89 (d, 1H), 8.83 (d, 1H), 8.51 (d, 1H), 8.08-8.03 (m, 1H), 8.01-7.96 (m, 1H), 7.79 (d, 1H), 7.73-7.68 (m, 1H), 7.65 (d, 1H), 7.64-7.60 (m, 1H), 7.55-7.51 (m, 1H), 7.24 (s, 1H), 6.84 (t, 1H), 6.52 (s, 1H), 5.72 (br s, 1H), 3.38-3.32 (m, 4H), 3.20 (s, 3H), 3.16-3.10 (m, 1H), 2.43-2.34 (m, 2H).

Example 62

4-({2-[4-{5-Chloro-2-[4-(difluoromethyl)-1H-imidazol-1-yl]phenyl}-5-methoxy-2-oxopyridin-1(2H)-yl]-4-methoxybutanoyl}amino)benzoic acid (Racemate)

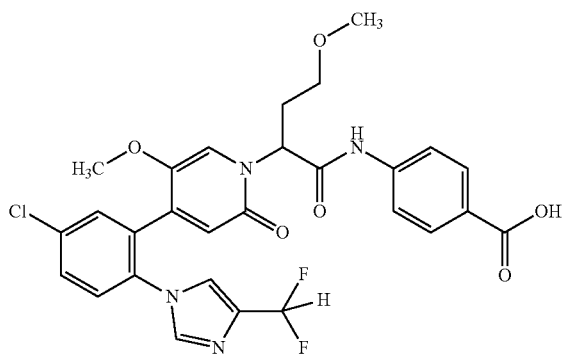 [SMILES: COCCC(C(=O)Nc1ccc(C(=O)O)cc1)n1cc(OC)c(-c2cc(Cl)ccc2-n2cnc(C(F)F)c2)cc1=O]

35.0 mg (purity 90%, 62.5 μmol) of 2-[4-{5-chloro-2-[4-(difluoromethyl)-1H-imidazol-1-yl]phenyl}-5-methoxy-2-oxopyridin-1(2H)-yl]-4-methoxybutanoic acid hydrochloride (racemate) and 9.0 mg (65.6 μmol) of 4-aminobenzoic acid in 0.5 ml of pyridine were reacted according to General Method 5. Yield: 26 mg (70% of theory)

LC/MS [Method 10]: $R_t$=1.52 min; MS (ESIpos): m/z=587 (M+H)$^+$, $^1$H-NMR (400 MHz, DMSO-d$_6$): δ [ppm]=12.74 (br s, 1H), 10.62 (br s, 1H), 7.89 (d, 2H), 7.78 (s, 1H), 7.76-7.67 (m, 3H), 7.66-7.58 (m, 2H), 7.53 (br s, 1H), 7.19 (s, 1H), 6.84 (t, 1H), 6.50 (s, 1H), 5.67 (br s, 1H), 3.34 (s, 3H), 3.18 (s, 3H), 3.15-3.06 (m, 1H), 2.38-2.27 (m, 2H). 1H under water signal.

Example 63

4-({2-[4-{5-Chloro-2-[4-(difluoromethyl)-1H-imidazol-1-yl]phenyl}-5-methoxy-2-oxopyridin-1(2H)-yl]-4-methoxybutanoyl}amino)-2-fluorobenzamide (Racemate)

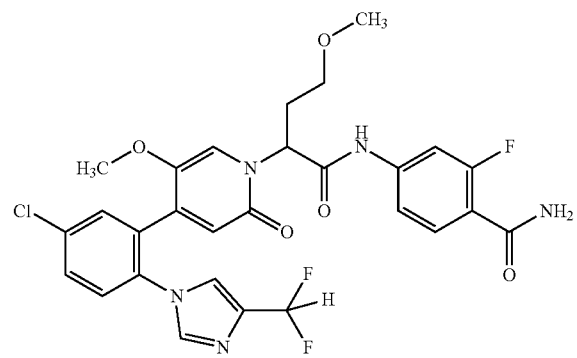 [SMILES: COCCC(C(=O)Nc1ccc(C(N)=O)c(F)c1)n1cc(OC)c(-c2cc(Cl)ccc2-n2cnc(C(F)F)c2)cc1=O]

35.0 mg (purity 90%, 62.5 μmol) of 2-[4-{5-chloro-2-[4-(difluoromethyl)-1H-imidazol-1-yl]phenyl}-5-methoxy-2-oxopyridin-1(2H)-yl]-4-methoxybutanoic acid hydrochloride (racemate) and 14.9 mg (93.7 μmol) of 4-amino-2-fluorobenzamide in 1.0 ml of pyridine were reacted according to General Method 5. Yield: 30 mg (76% of theory)

LC/MS [Method 10]: $R_t$=1.46 min; MS (ESIpos): m/z=604 (M+H)$^+$, $^1$H-NMR (400 MHz, DMSO-d$_6$): δ [ppm]=10.69 (br s, 1H), 7.80-7.76 (m, 1H), 7.73-7.66 (m, 2H), 7.66-7.60 (m, 4H), 7.56-7.48 (m, 3H), 7.41 (dd, 1H), 7.18 (s, 1H), 6.84 (t, 1H), 6.50 (s, 1H), 5.63 (br s, 1H), 3.34 (s, 3H), 3.29-3.24 (m, 1H), 3.18 (s, 3H), 3.14-3.05 (m, 1H), 2.38-2.28 (m, 2H).

Example 64

5-({2-[4-{5-Chloro-2-[4-(difluoromethyl)-1H-imidazol-1-yl]phenyl}-5-methoxy-2-oxopyridin-1(2H)-yl]-4-methoxybutanoyl}amino)pyridine-2-carboxamide (Racemate)

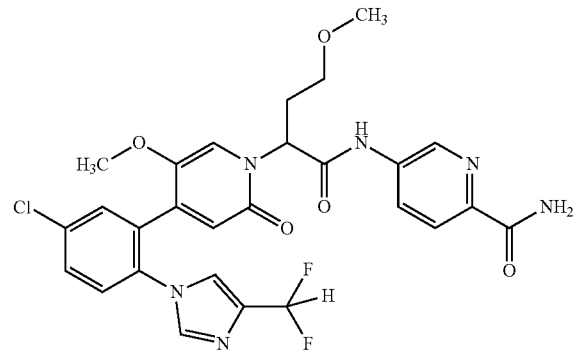 [SMILES: COCCC(C(=O)Nc1ccc(C(N)=O)nc1)n1cc(OC)c(-c2cc(Cl)ccc2-n2cnc(C(F)F)c2)cc1=O]

35.0 mg (purity 90%, 62.5 μmol) of 2-[4-{5-chloro-2-[4-(difluoromethyl)-1H-imidazol-1-yl]phenyl}-5-methoxy-2-oxopyridin-1(2H)-yl]-4-methoxybutanoic acid hydrochloride (racemate) and 13.5 mg (93.7 μmol) of 5-aminopyridine-2-carboxamide in 1.0 ml of pyridine were reacted according to General Method 5. Yield: 31 mg (81% of theory)

LC/MS [Method 10]: $R_t$=1.39 min; MS (ESIpos): m/z=587 (M+H)+, $^1$H-NMR (400 MHz, DMSO-$d_6$): δ [ppm]=10.77 (br s, 1H), 8.84 (d, 1H), 8.19 (dd, 1H), 8.03-7.97 (m, 2H), 7.78 (d, 1H), 7.73-7.68 (m, 1H), 7.64 (d, 1H), 7.63-7.60 (m, 1H), 7.54-7.49 (m, 2H), 7.18 (s, 1H), 6.84 (t, 1H), 6.51 (s, 1H), 5.65 (br s, 1H), 3.34 (s, 3H), 3.18 (s, 3H), 3.14-3.06 (m, 1H), 2.40-2.31 (m, 2H).

Example 65

5-({2-[4-{5-Chloro-2-[4-(difluoromethyl)-1H-imidazol-1-yl]phenyl}-5-methoxy-2-oxopyridin-1(2H)-yl]-4-methoxybutanoyl}amino)-N-methylpyridine-2-carboxamide (Racemate)

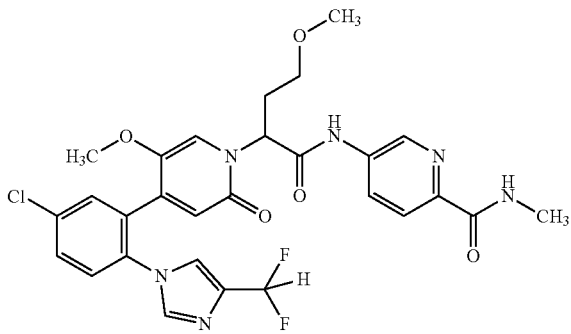 [SMILES: CNC(=O)c1ccc(NC(=O)C(CCOC)n2cc(OC)c(-c3cc(Cl)ccc3-n3cnc(C(F)F)c3)cc2=O)cn1]

35.0 mg (purity 90%, 62.5 μmol) of 2-[4-{5-chloro-2-[4-(difluoromethyl)-1H-imidazol-1-yl]phenyl}-5-methoxy-2-oxopyridin-1(2H)-yl]-4-methoxybutanoic acid hydrochloride (racemate) and 14.5 mg (93.7 μmol) of 5-amino-N-methylpyridine-2-carboxamide in 1.0 ml of pyridine were reacted according to General Method 5. Yield: 31 mg (81% of theory)

LC/MS [Method 10]: $R_t$=1.47 min; MS (ESIpos): m/z=601 (M+H)+, $^1$H-NMR (400 MHz, DMSO-$d_6$): δ [ppm]=10.75 (br s, 1H), 8.86 (d, 1H), 8.65 (q, 1H), 8.20-8.15 (m, 1H), 7.99 (d, 1H), 7.78 (d, 1H), 7.73-7.68 (m, 1H), 7.65-7.60 (m, 2H), 7.55-7.50 (m, 1H), 7.18 (s, 1H), 6.84 (t, 1H), 6.51 (s, 1H), 5.65 (br s, 1H), 3.34 (s, 3H), 3.18 (s, 3H), 3.15-3.06 (m, 1H), 2.80 (d, 3H), 2.42-2.29 (m, 2H). 1H under water signal.

Example 66

2-[4-{5-Chloro-2-[4-(difluoromethyl)-1H-imidazol-1-yl]phenyl}-5-methoxy-2-oxopyridin-1(2H)-yl]-4-methoxy-N-(2-methyl-2H-indazol-5-yl)butanamide (Racemate)

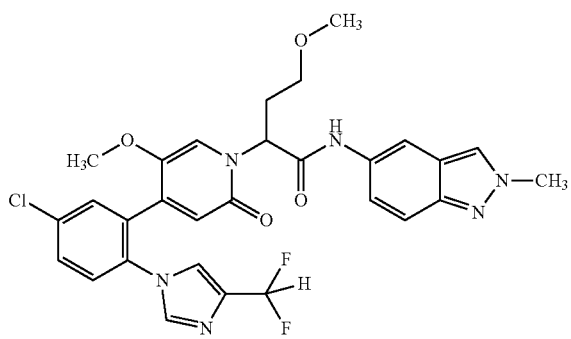 [SMILES: COCCC(C(=O)Nc1ccc2nn(C)cc2c1)n1cc(OC)c(-c2cc(Cl)ccc2-n2cnc(C(F)F)c2)cc1=O]

35.0 mg (purity 90%, 62.5 μmol) of 2-[4-{5-chloro-2-[4-(difluoromethyl)-1H-imidazol-1-yl]phenyl}-5-methoxy-2-oxopyridin-1(2H)-yl]-4-methoxybutanoic acid hydrochloride (racemate) and 13.8 mg (93.7 μmol) of 2-methyl-2H-indazole-5-amine in 1.0 ml of pyridine were reacted according to General Method 5. Yield: 36 mg (97% of theory)

LC/MS [Method 10]: $R_t$=1.50 min; MS (ESIpos): m/z=597 (M+H)+, $^1$H-NMR (400 MHz, DMSO-$d_6$): δ [ppm]=10.28 (br s, 1H), 8.24 (s, 1H), 8.09 (d, 1H), 7.78 (s, 1H), 7.72-7.68 (m, 1H), 7.65-7.59 (m, 2H), 7.55-7.51 (m, 2H), 7.29 (dd, 1H), 7.23 (s, 1H), 6.84 (t, 1H), 6.50 (s, 1H), 5.71 (br s, 1H), 4.12 (s, 3H), 3.35 (s, 3H), 3.30-3.24 (m, 1H), 3.19 (s, 3H), 3.17-3.10 (m, 1H), 2.38-2.25 (m, 2H).

Example 67

4-[(2-{4-[5-Chloro-2-(3-methyl-1,2-oxazol-5-yl)phenyl]-5-methoxy-2-oxopyridin-1(2H)-yl}-4-methoxybutanoyl)amino]benzoic acid (Racemate)

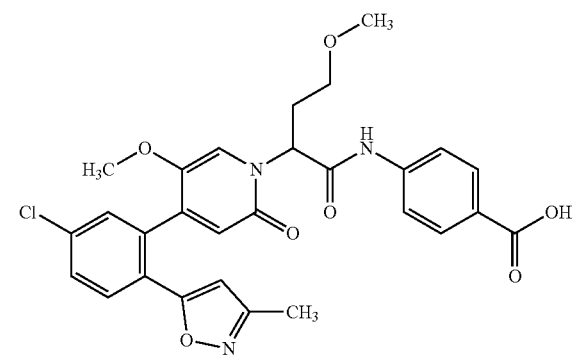 [SMILES: COCCC(C(=O)Nc1ccc(C(=O)O)cc1)n1cc(OC)c(-c2cc(Cl)ccc2-c2cc(C)no2)cc1=O]

60 mg (0.11 mmol) of methyl 4-[(2-{4-[5-chloro-2-(3-methyl-1,2-oxazol-5-yl)phenyl]-5-methoxy-2-oxopyridin-1(2H)-yl}-4-methoxybutanoyl)amino]benzoate (racemate) were reacted according to General Method 2. Yield: 20 mg (33% of theory).

LC/MS [Method 8]: $R_t$=1.20 min; MS (ESIpos): m/z=552 (M+H)+, $^1$H-NMR (400 MHz, DMSO-$d_6$): δ [ppm]=12.82 (brs, 1H), 10.66 (s, 1H), 7.93-7.87 (m, 2H), 7.82 (d, 1H), 7.77-7.71 (m, 2H), 7.65 (dd, 1H), 7.53 (d, 1H), 7.34 (s, 1H), 6.42 (s, 1H), 6.21 (s, 1H), 5.82-5.71 (m, 1H), 3.44-3.37 (m, 4H), 3.23 (s, 3H), 2.44-2.36 (m, 2H), 2.18 (s, 3H).

Example 68

5-[(2-{4-[5-Chloro-2-(3-methyl-1,2-oxazol-5-yl)phenyl]-5-methoxy-2-oxopyridin-1(2H)-yl}-4-methoxybutanoyl)amino]pyridine-2-carboxamide (Racemate)

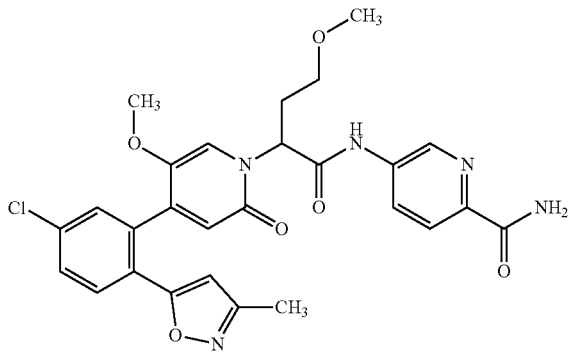 [SMILES: COCCC(C(=O)Nc1ccc(C(N)=O)nc1)n1cc(OC)c(-c2cc(Cl)ccc2-c2cc(C)no2)cc1=O]

20 mg (0.046 mmol) of 2-{4-[5-chloro-2-(3-methyl-1,2-oxazol-5-yl)phenyl]-5-methoxy-2-oxopyridin-1(2H)-yl}-4-methoxybutanoic acid (racemate) and 10 mg (0.069 mmol, 1.5 eq.) of 5-aminopyridine-2-carboxamide were reacted according to General Method 5. Yield: 25 mg (95% of theory).

LC/MS [Method 8]: $R_t$=1.13 min; MS (ESIneg): m/z=550 (M−H)⁻,

¹H-NMR (400 MHz, DMSO-d₆): δ [ppm]=10.84 (brs, 1H), 8.89-8.85 (m, 1H), 8.22 (dd, 1H), 8.05-7.98 (m, 2H), 7.82 (d, 1H), 7.65 (dd, 1H), 7.56-7.49 (m, 2H), 7.33 (s, 1H), 6.43 (s, 1H), 6.22 (s, 1H), 5.84-5.68 (m, 1H), 3.46-3.40 (m, 1H), 3.39 (s, 3H), 3.30-3.26 (m, 1H, partially hidden), 3.24 (s, 3H), 2.47-2.39 (m, 2H), 2.18 (s, 3H).

Example 69

4-[(2-{4-[5-Chloro-2-(3-methyl-1,2-oxazol-5-yl)phenyl]-5-methoxy-2-oxopyridin-1(2H)-yl}-4-methoxybutanoyl)amino]-2-fluorobenzamide (Racemate)

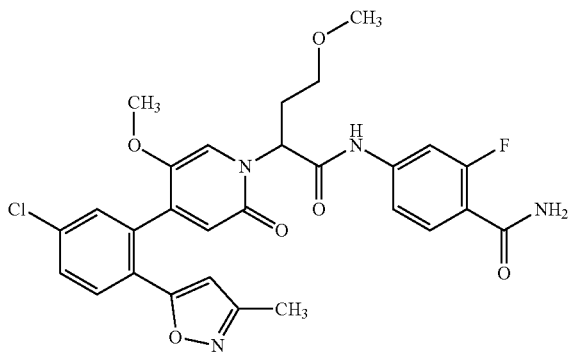 [SMILES: COCCC(C(=O)Nc1ccc(C(N)=O)c(F)c1)n1cc(OC)c(-c2cc(Cl)ccc2-c2cc(C)no2)cc1=O]

20 mg (0.046 mmol) of 2-{4-[5-chloro-2-(3-methyl-1,2-oxazol-5-yl)phenyl]-5-methoxy-2-oxopyridin-1(2H)-yl}-4-methoxybutanoic acid (racemate) and 11 mg (0.069 mmol, 1.5 eq.) of 4-amino-2-fluorobenzamide were reacted according to General Method 5. Yield: 25 mg (95% of theory).

LC/MS [Method 8]: $R_t$=1.17 min; MS (ESIneg): m/z=567 (M−H)⁻,

¹H-NMR (400 MHz, DMSO-d₆): δ [ppm]=10.74 (brs, 1H), 7.33 (d, 1H), 7.73-7.63 (m, 3H), 7.57-7.49 (m, 3H), 7.44 (dd, 1H), 7.32 (s, 1H), 6.43 (s, 1H), 6.22 (s, 1H), 5.78-5.65 (m, 1H), 3.45-3.38 (m, 4H), 3.29-3.25 (m, 1H, partially hidden), 3.23 (s, 3H), 2.44-2.35 (m, 2H), 2.19 (s, 3H).

Example 70

2-{4-[5-Chloro-2-(3-methyl-1,2-oxazol-5-yl)phenyl]-5-methoxy-2-oxopyridin-1(2H)-yl}-4-methoxy-N-(2-methyl-2H-indazol-5-yl)butanamide (Racemate)

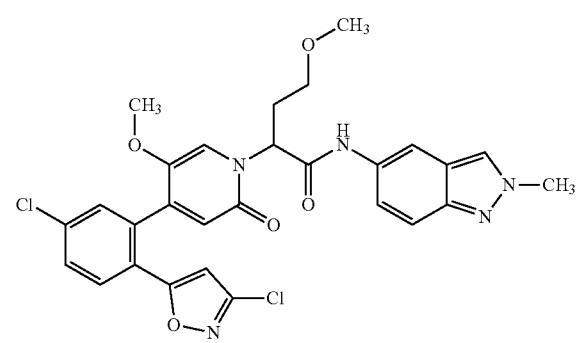 [SMILES: COCCC(C(=O)Nc1ccc2nn(C)cc2c1)n1cc(OC)c(-c2cc(Cl)ccc2-c2cc(Cl)no2)cc1=O]

20 mg (0.046 mmol) of 2-{4-[5-chloro-2-(3-methyl-1,2-oxazol-5-yl)phenyl]-5-methoxy-2-oxopyridin-1(2H)-yl}-4-methoxybutanoic acid (racemate) and 10 mg (0.069 mmol, 1.5 eq.) of 2-methyl-2H-indazole-5-amine were reacted according to General Method 5. Yield: 24 mg (92% of theory).

LC/MS [Method 8]: $R_t$=1.20 min; MS (ESIneg): m/z=560 (M−H)⁻,

¹H-NMR (400 MHz, DMSO-d₆): δ [ppm]=10.33 (brs, 1H), 8.25 (s, 1H), 8.13 (s, 1H), 7.82 (d, 1H), 7.65 (dd, 1H), 7.57-7.52 (m, 2H), 7.37 (s, 1H), 7.31 (dd, 1H), 6.42 (s, 1H), 6.22 (s, 1H), 5.84-5.74 (m, 1H), 4.13 (s, 3H), 3.44-3.37 (m, 4H), 3.24 (s, 3H), 2.43-2.35 (m, 2H), 2.18 (s, 3H).

Example 71

5-[(2-{4-[5-Chloro-2-(3-methyl-1,2-oxazol-5-yl)phenyl]-5-methoxy-2-oxopyridin-1(2H)-yl}-4-methoxybutanoyl)amino]-N-methylpyridine-2-carboxamide (Racemate)

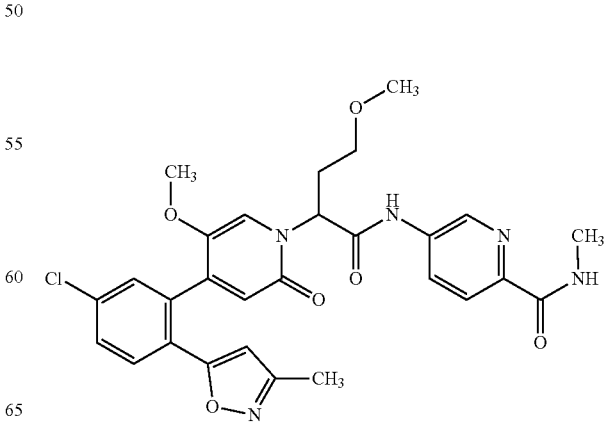

20 mg (46 µmol) of 2-{4-[5-chloro-2-(3-methyl-1,2-oxazol-5-yl)phenyl]-5-methoxy-2-oxopyridin-1(2H)-yl}-4-methoxybutanoic acid (racemate) and 11 mg (69 µmol, 1.5 eq.) of 5-amino-N-methylpyridine-2-carboxamide were reacted according to General Method 5. Yield: 26 mg (99% of theory).

LC/MS [Method 10]: $R_t$=1.63 min; MS (ESIpos): m/z=566 (M+H)$^+$, $^1$H-NMR (400 MHz, DMSO-d$_6$): δ [ppm]=10.81 (brs, 1H), 8.91-8.87 (m, 1H), 8.69-8.62 (m, 1H), 8.21 (dd, 1H), 8.00 (d, 1H), 7.82 (d, 1H), 7.66 (dd, 1H), 7.53 (d, 1H), 7.33 (s, 1H), 6.43 (s, 1H), 6.22 (s, 1H), 5.83-5.67 (m, 1H), 3.46-3.37 (m, 4H), 3.29-3.25 (m, 1H, partially hidden), 3.24 (s, 3H), 2.80 (d, 3H), 2.47-2.39 (m, 2H), 2.18 (s, 3H).

Example 72

N-(Quinoxalin-6-yl)-2-{4-[5-chloro-2-(3-methyl-1,2-oxazol-5-yl)phenyl]-5-methoxy-2-oxopyridin-1(2H)-yl}-4-methoxybutanamide (Racemate)

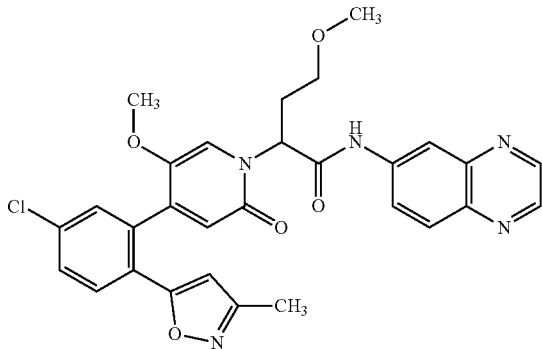 [SMILES: COCCC(C(=O)Nc1ccc2nccnc2c1)n1cc(OC)c(-c2cc(Cl)ccc2-c2cc(C)no2)cc1=O]

20 mg (46 mmol) of 2-{4-[5-chloro-2-(3-methyl-1,2-oxazol-5-yl)phenyl]-5-methoxy-2-oxopyridin-1(2H)-yl}-4-methoxybutanoic acid (racemate) and 10 mg (69 µmol, 1.5 eq.) of quinoxaline-6-amine were reacted according to General Method 5. Yield: 25 mg (93% of theory).

LC/MS [Method 10]: $R_t$=1.72 min; MS (ESIpos): m/z=560 (M+H)$^+$, $^1$H-NMR (400 MHz, DMSO-d$_6$): δ [ppm]=10.90 (brs, 1H), 8.91-8.88 (m, 1H), 8.85-8.83 (m, 1H), 8.57-8.53 (m, 1H), 8.08 (d, 1H), 8.02 (dd, 1H), 7.83 (d, 1H), 7.66 (dd, 1H), 7.55 (d, 1H), 7.38 (s, 1H), 6.45 (d, 1H), 6.23 (s, 1H), 5.89-5.76 (m, 1H), 3.48-3.49 (m, 4H, partially hidden), 3.25 (s, 3H), 2.49-2.42 (m, 2H, partially hidden), 2.19 (s, 3H).

Example 73

5-({2-[4-{5-Chloro-2-[5-(trifluoromethyl)-1,3,4-oxadiazol-2-yl]phenyl}-5-methoxy-2-oxopyridin-1(2H)-yl]-4-methoxybutanoyl}amino)pyridine-2-carboxamide (Racemate)

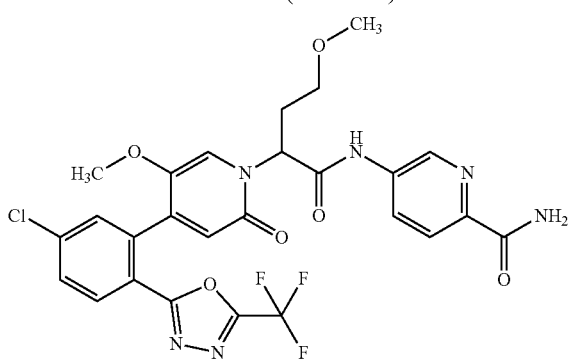

35 mg (0.072 mmol) of 2-[4-{5-chloro-2-[5-(trifluoromethyl)-1,3,4-oxadiazol-2-yl]phenyl}-5-methoxy-2-oxopyridin-1(2H)-yl]-4-methoxybutanoic acid (racemate) and 15 mg (0.11 mmol, 1.5 eq.) of 5-aminopyridine-2-carboxamide were reacted according to General Method 5. Yield: 35 mg (80% of theory).

LC/MS [Method 10]: $R_t$=1.69 min; MS (ESIpos): m/z=607 (M+H)$^+$, $^1$H-NMR (400 MHz, DMSO-d$_6$): δ [ppm]=10.98-10.74 (m, 1H), 8.86 (d, 1H), 8.22 (dd, 1H), 8.11 (d, 1H), 8.03-7.99 (m, 2H), 7.81 (dd, 1H), 7.73 (d, 1H), 7.52 (brs, 1H), 7.33 (s, 1H), 6.58 (s, 1H), 5.91-5.59 (m, 1H), 3.43-3.37 (m, 1H, partially hidden), 3.35 (s, 3H, partially hidden), 3.29-3.24 (m, 1H, partially hidden), 3.23 (s, 3H), 2.46-2.27 (m, 2H).

Example 74

4-({2-[4-{5-Chloro-2-[5-(trifluoromethyl)-1,3,4-oxadiazol-2-yl]phenyl}-5-methoxy-2-oxopyridin-1(2H)-yl]-4-methoxybutanoyl}amino)-2-fluorobenzamide (Racemate)

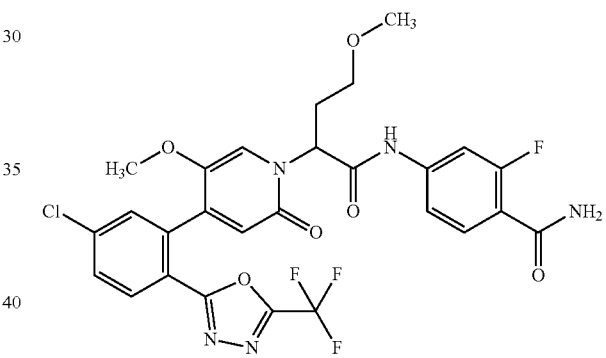

35 mg (0.072 mmol) of 2-[4-{5-chloro-2-[5-(trifluoromethyl)-1,3,4-oxadiazol-2-yl]phenyl}-5-methoxy-2-oxopyridin-1(2H)-yl]-4-methoxybutanoic acid (racemate) and 17 mg (0.11 mmol, 1.5 eq.) of 4-amino-2-fluorobenzamide were reacted according to General Method 5. Yield: 18 mg (45% of theory).

LC/MS [Method 10]: $R_t$=1.76 min; MS (ESIpos): m/z=624 (M+H)$^+$, $^1$H-NMR (400 MHz, DMSO-d$_6$): δ [ppm]=10.90-10.63 (m, 1H), 8.11 (d, 1H), 7.81 (dd, 1H), 7.73 (d, 1H), 7.71-7.63 (m, 2H), 7.57-7.49 (m, 2H), 7.43 (dd, 1H), 7.32 (s, 1H), 6.58 (s, 1H), 5.86-5.55 (m, 1H), 3.41-3.36 (m, 1H, partially hidden), 3.35 (s, 3H, partially hidden), 3.29-3.23 (m, 1H, partially hidden), 3.22 (s, 3H), 2.42-2.34 (m, 2H).

Example 75

2-[4-{5-Chloro-2-[5-(trifluoromethyl)-1,3,4-oxadiazol-2-yl]phenyl}-5-methoxy-2-oxopyridin-1(2H)-yl]-4-methoxy-N-(2-methyl-2H-indazol-5-yl)butanamide (Racemate)

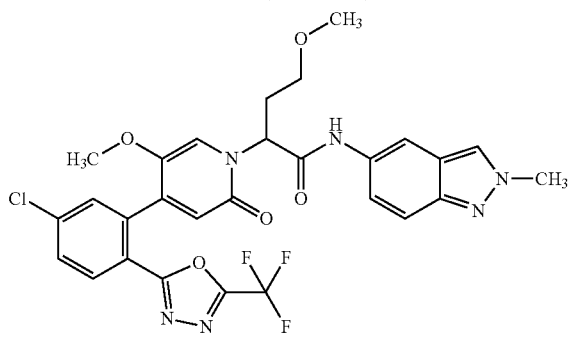 [SMILES: COCCC(C(=O)Nc1ccc2nn(C)cc2c1)n1cc(OC)c(-c2cc(Cl)ccc2-c2nnc(C(F)(F)F)o2)cc1=O]

35 mg (0.072 mmol) of 2-[4-{5-chloro-2-[5-(trifluoromethyl)-1,3,4-oxadiazol-2-yl]phenyl}-5-methoxy-2-oxopyridin-1(2H)-yl]-4-methoxybutanoic acid (racemate) and 16 mg (0.11 mmol, 1.5 eq.) of 2-methyl-2H-indazole-5-amine were reacted according to General Method 5. Yield: 42 mg (95% of theory).

LC/MS [Method 10]: $R_t$=1.79 min; MS (ESIpos): m/z=617 (M+H)$^+$, $^1$H-NMR (400 MHz, DMSO-d$_6$): δ [ppm]=10.45-10.28 (m, 1H), 8.25 (s, 1H), 8.15-8.07 (m, 2H), 7.81 (dd, 1H), 7.73 (d, 1H), 7.54 (d, 1H), 7.38 (s, 1H), 7.31 (dd, 1H), 6.57 (s, 1H), 5.92-5.69 (m, 1H), 3.24 (s, 3H), 3.30-3.25 (m, 1H, partially hidden), 3.23 (s, 3H), 2.42-2.34 (m, 2H). (s, 3H), 2.77 (d, 3H), 2.22-2.03 (m, 2H), 0.90 (t, 3H).

Example 76

(2S)-2-[4-{5-Chloro-2-[5-(trifluoromethyl)-1,3,4-oxadiazol-2-yl]phenyl}-5-methoxy-2-oxopyridin-1(2H)-yl]-4-methoxy-N-(2-methyl-2H-indazol-5-yl)butanamide (Enantiomer 2)

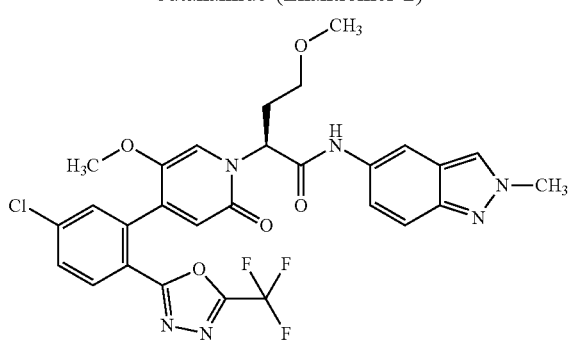

Enantiomer separation of 2-[4-{5-chloro-2-[5-(trifluoromethyl)-1,3,4-oxadiazol-2-yl]phenyl}-5-methoxy-2-oxopyridin-1(2H)-yl]-4-methoxy-N-(2-methyl-2H-indazol-5-yl)butanamide (35.0 mg, 72 μmol) (racemate) gave 12.3 mg of enantiomer 1 (chiral HPLC: $R_t$=2.5 min) and 12.4 mg of the title compound Example 76 (enantiomer 2): chiral HPLC: $R_t$=3.2 min; 95% ee.

Separating method: column: Daicel Chiralpak IA SFC, 5 μm 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak IA SFC 3 μm 100 mm×4.6 mm; mobile phase: 70% carbon dioxide, 30% ethanol; flow rate: 3 ml/min; UV detection: 210 nm.

LC/MS (Method 8): $R_t$=1.28 min; MS (ESIneg): m/z=615 [M–H]$^−$.

Example 77

5-({2-[4-{5-Chloro-2-[5-(trifluoromethyl)-1,3,4-oxadiazol-2-yl]phenyl}-5-methoxy-2-oxopyridin-1(2H)-yl]-4-methoxybutanoyl}amino)-N-methylpyridine-2-carboxamide (Racemate)

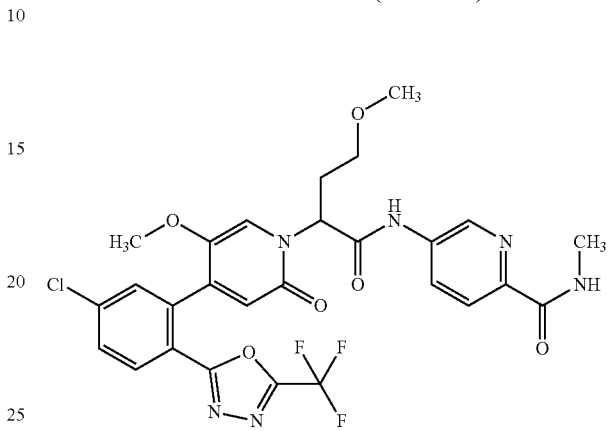

35 mg (72 μmol) of 2-[4-{5-chloro-2-[5-(trifluoromethyl)-1,3,4-oxadiazol-2-yl]phenyl}-5-methoxy-2-oxopyridin-1(2H)-yl]-4-methoxybutanoic acid (racemate) and 16 mg (0.11 mmol, 1.5 eq.) of 5-amino-N-methylpyridine-2-carboxamide were reacted according to General Method 5. Yield: 39 mg (82% of theory).

LC/MS [Method 10]: $R_t$=1.76 min; MS (ESIpos): m/z=621 (M+H)$^+$, $^1$H-NMR (400 MHz, DMSO-d$_6$): δ [ppm]=10.99-10.72 (m, 1H), 8.89 (d, 1H), 8.69-8.64 (m, 1H), 8.20 (dd, 1H), 8.11 (d, 1H), 8.00 (d, 1H), 7.81 (dd, 1H), 7.73 (d, 1H), 7.32 (s, 1H), 6.58 (s, 1H), 5.90-5.60 (m, 1H), 3.43-3.36 (m, 1H), 3.35 (s, 3H), 3.29-3.24 (m, 1H, partially hidden), 3.23 (s, 3H), 2.80 (d, 3H), 2.46-2.39 (m, 2H).

Example 78

N-(Quinoxalin-6-yl)-2-[4-{5-chloro-2-[5-(trifluoromethyl)-1,3,4-oxadiazol-2-yl]phenyl}-5-methoxy-2-oxopyridin-1(2H)-yl]-4-methoxybutanamide (Racemate)

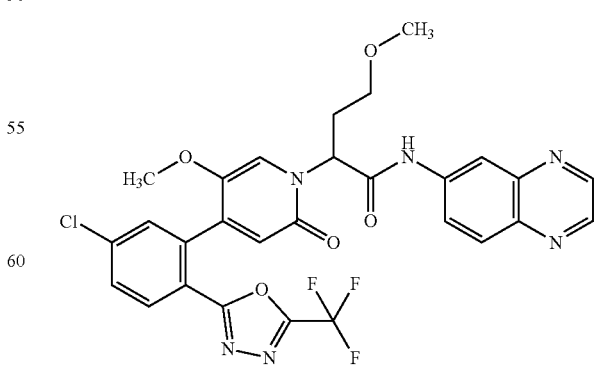

35 mg (72 μmol) of 2-[4-{5-chloro-2-[5-(trifluoromethyl)-1,3,4-oxadiazol-2-yl]phenyl}-5-methoxy-2-oxopyridin-1(2H)-yl]-4-methoxybutanoic acid (racemate) and 16 mg (0.11 mmol, 1.5 eq.) of quinoxaline-6-amine were reacted according to General Method 5. Yield: 42 mg (95% of theory).

LC/MS [Method 10]: $R_t$=1.85 min; MS (ESIpos): m/z=615 (M+H)$^+$, $^1$H-NMR (400 MHz, DMSO-d$_6$): δ [ppm]=11.04-10.80 (m, 1H), 8.90 (d, 1H), 8.84 (d, 1H), 8.57-8.53 (m, 1H), 8.13-8.05 (m, 2H), 8.03-7.98 (m, 1H), 7.81 (dd, 1H), 7.74 (d, 1H), 7.38 (s, 1H), 6.59 (1H), 5.95-5.71 (m, 1H), 3.45-3.39 (m, 1H, partially hidden), 3.38 (s, 3H, partially hidden), 3.24 (s, 3H), 2.47-2.39 (m, 2H, partially hidden).

Example 79

N-(Quinoxalin-6-yl)-(2S)-2-[4-{5-chloro-2-[5-(trifluoromethyl)-1,3,4-oxadiazol-2-yl]phenyl}-5-methoxy-2-oxopyridin-1(2H)-yl]-4-methoxybutanamide (Enantiomer 2)

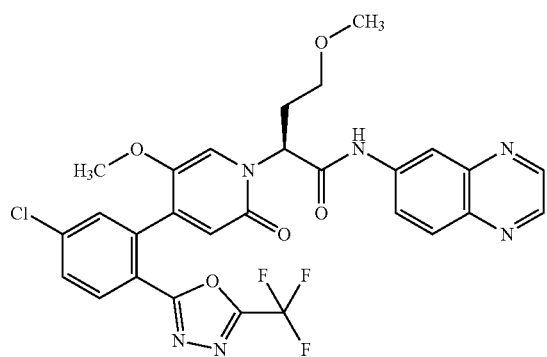 [SMILES: COCC[C@@H](C(=O)Nc1ccc2nccnc2c1)n1cc(OC)c(-c2cc(Cl)ccc2-c2nnc(C(F)(F)F)o2)cc1=O]

Enantiomer separation of N-(quinoxalin-6-yl)-2-[4-{5-chloro-2-[5-(trifluoromethyl)-1,3,4-oxadiazol-2-yl]phenyl}-5-methoxy-2-oxopyridin-1(2H)-yl]-4-methoxybutanamide (35.0 mg, 72 µmol) (Racemate) gave 10.2 mg of enantiomer 1 (chiral HPLC: $R_t$=3.7 min) and 8.9 mg of the title compound Example 79 (enantiomer 2): chiral HPLC: $R_t$=4.9 min; 99% ee.

Separating method: column: Daicel Chiralpak OJ-H SFC 5 µm, 250 mm×20 mm; mobile phase: carbon dioxide 90%/methanol 10%; temperature: 40° C.; flow rate: 80 ml/min; pressure: 100 bar; UV detection: 210 nm.

Analysis: column: Chiralpak OJ-H SFC 3 µm 100 mm×4.6 mm; mobile phase: 90% carbon dioxide, 10% methanol; flow rate: 3 ml/min; UV detection: 210 nm.

LC/MS (Method 10): $R_t$=1.86 min; MS (ESIpos): m/z=615 [M+H]$^+$.

Example 80

4-({2-[4-{5-Chloro-2-[5-(difluoromethyl)-1,3,4-oxadiazol-2-yl]phenyl}-5-methoxy-2-oxopyridin-1(2H)-yl]-4-methoxybutanoyl}amino)benzoic acid (Racemate)

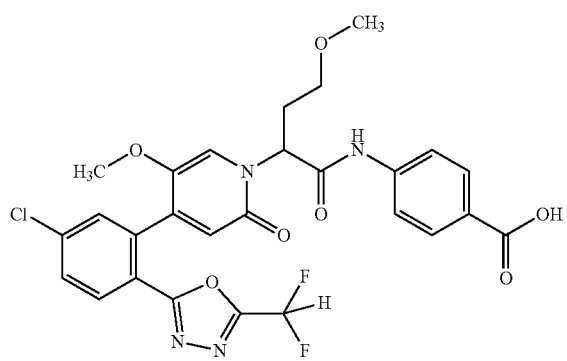 [SMILES: COCCC(C(=O)Nc1ccc(C(=O)O)cc1)n1cc(OC)c(-c2cc(Cl)ccc2-c2nnc(C(F)F)o2)cc1=O]

7 mg (0.011 mmol) of tert-butyl 4-({2-[4-{5-chloro-2-[5-(difluoromethyl)-1,3,4-oxadiazol-2-yl]-phenyl}-5-methoxy-2-oxopyridin-1(2H)-yl]-4-methoxybutanoyl}amino)benzoate were dissolved in 0.3 ml of dichloromethane, and 42 µl (0.54 mmol, 50.0 eq.) of trifluoroacetic acid were added. The reaction mixture was treated in an ultrasonic bath for 2 h. The reaction mixture was then concentrated under reduced pressure and purified by column chromatography (250 mm×20 mm, reverse phase, 38 min, 10-100% acetonitrile/water acidified with 0.1% formic acid, 25 ml/min). Yield: 5 mg (76% of theory).

LC/MS [Method 10]: $R_t$=1.67 min; MS (ESIpos): m/z=589 (M+H)$^+$, $^1$H-NMR (400 MHz, DMSO-d$_6$): δ [ppm]=12.82 (brs, 1H), 10.74 (brs, 1H), 8.07 (d, 1H), 7.92-7.86 (m, 2H), 7.80-7.69 (m, 4H), 7.48 (t, 1H), 7.31 (s, 1H), 6.55 (s, 1H), 5.91-5.72 (m, 1H), 3.41-3.35 (m, 1H, partially hidden), 3.34 (s, 3H, partially hidden), 3.23 (s, 3H), 2.41-2.34 (m, 2H).

Example 81

5-({2-[4-{5-Chloro-2-[5-(difluoromethyl)-1,3,4-oxadiazol-2-yl]phenyl}-5-methoxy-2-oxopyridin-1(2H)-yl]-4-methoxybutanoyl}amino)pyridine-2-carboxamide (Racemate)

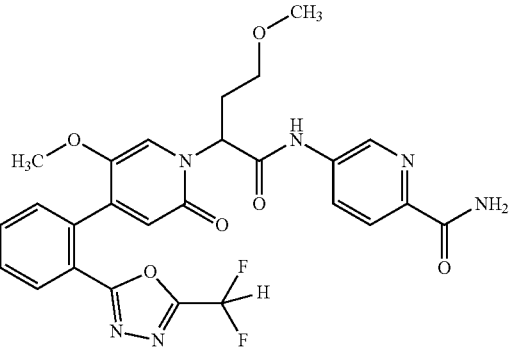

12 mg (0.026 mmol) of 2-[4-{5-chloro-2-[5-(difluoromethyl)-1,3,4-oxadiazol-2-yl]phenyl}-5-methoxy-2-oxopyridin-1(2H)-yl]-4-methoxybutanoic acid (racemate) and 5 mg (0.038 mmol, 1.5 eq.) of 5-aminopyridine-2-carboxamide were reacted according to General Method 5. Yield: 10 mg (66% of theory).

LC/MS [Method 10]: $R_t$=1.52 min; MS (ESIpos): m/z=589 (M+H)$^+$, $^1$H-NMR (400 MHz, DMSO-d$_6$): δ [ppm]=10.93 (brs, 1H), 8.86 (d, 1H), 8.22 (dd, 1H), 8.08 (d, 1H), 8.04-7.98 (m, 2H), 7.79 (dd, 1H), 7.70 (d, 1H), 7.52 (s, 1H), 7.48 (t, 1H), 7.30 (s, 1H), 6.56 (s, 1H), 5.90-5.61 (m, 1H), 3.43-3.36 (m, 1H), 3.34 (s, 3H, partially hidden), 3.23 (s, 3H), 2.45-2.36 (m, 2H, partially hidden).

Example 82

4-({2-[4-{5-Chloro-2-[5-(difluoromethyl)-1,3,4-oxadiazol-2-yl]phenyl}-5-methoxy-2-oxopyridin-1(2H)-yl]-4-methoxybutanoyl}amino)-2-fluorobenzamide (Racemate)

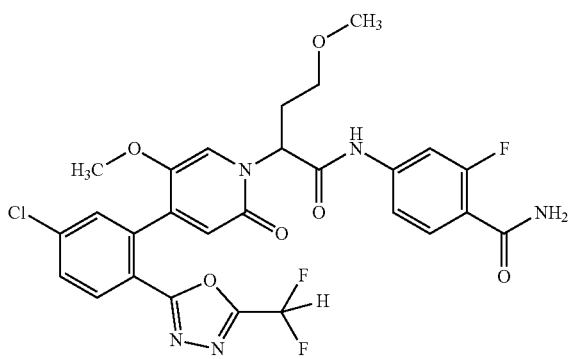 [SMILES: COCCC(C(=O)Nc1ccc(C(N)=O)c(F)c1)n1cc(OC)c(-c2cc(Cl)ccc2-c2nnc(C(F)F)o2)cc1=O]

12 mg (0.026 mmol) of 2-[4-{5-chloro-2-[5-(difluoromethyl)-1,3,4-oxadiazol-2-yl]phenyl}-5-methoxy-2-oxopyridin-1(2H)-yl]-4-methoxybutanoic acid (racemate) and 6 mg (0.038 mmol, 1.5 eq.) of 4-amino-2-fluorobenzamide were reacted according to General Method 5. Yield: 10 mg (62% of theory).

LC/MS [Method 10]: $R_t$=1.61 min; MS (ESIpos): m/z=606 (M+H)$^+$, $^1$H-NMR (400 MHz, DMSO-d$_6$): δ [ppm]=10.84 (brs, 1H), 8.08 (d, 1H), 7.79 (dd, 1H), 7.72-7.64 (m, 3H), 7.56-7.49 (m, 2H), 7.50 (t, 1H, partially hidden), 7.43 (dd, 1H), 7.30 (s, 1H), 6.56 (s, 1H), 5.89-5.62 (m, 1H), 3.42-3.35 (m, 1H, partially hidden), 3.34 (s, 3H, partially hidden), 3.23 (s, 3H), 2.42-2.34 (m, 2H).

Example 83

2-[4-{5-Chloro-2-[5-(difluoromethyl)-1,3,4-oxadiazol-2-yl]phenyl}-5-methoxy-2-oxopyridin-1(2H)-yl]-4-methoxy-N-(2-methyl-2H-indazol-5-yl)butanamide (Racemate)

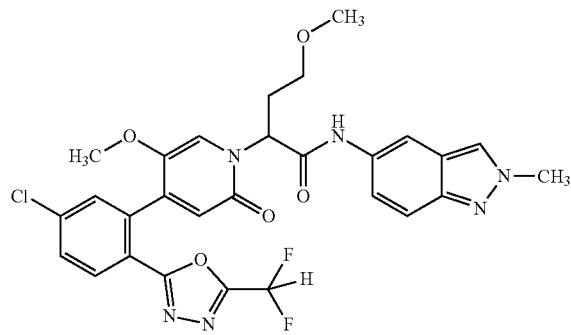 [SMILES: COCCC(C(=O)Nc1ccc2nn(C)cc2c1)n1cc(OC)c(-c2cc(Cl)ccc2-c2nnc(C(F)F)o2)cc1=O]

12 mg (0.026 mmol) of 2-[4-{5-chloro-2-[5-(difluoromethyl)-1,3,4-oxadiazol-2-yl]phenyl}-5-methoxy-2-oxopyridin-1(2H)-yl]-4-methoxybutanoic acid (racemate) and 6 mg (0.038 mmol, 1.5 eq.) of 2-methyl-2H-indazole-5-amine were reacted according to General Method 5. Yield: 11 mg (72% of theory).

LC/MS [Method 10]: $R_t$=1.65 min; MS (ESIpos): m/z=599 (M+H)$^+$, $^1$H-NMR (400 MHz, DMSO-d$_6$): δ [ppm]=10.36 (brs, 1H), 8.25 (s, 1H), 8.14-8.11 (m, 1H), 8.08 (d, 1H), 7.78 (dd, 1H), 7.70 (d, 1H), 7.54 (d, 1H), 7.48 (t, 1H, partially hidden), 7.35 (s, 1H), 7.31 (dd, 1H), 6.55 (s, 1H), 5.90-5.68 (m, 1H), 4.13 (s, 3H), 3.42-3.35 (m, 1H, partially hidden), 3.34 (s, 3H, partially hidden), 3.24 (s, 3H), 2.42-2.31 (m, 2H).

Example 84

5-({2-[4-{5-Chloro-2-[5-(difluoromethyl)-1,3,4-oxadiazol-2-yl]phenyl}-5-methoxy-2-oxopyridin-1(2H)-yl]-4-methoxybutanoyl}amino)-N-methylpyridine-2-carboxamide (Racemate)

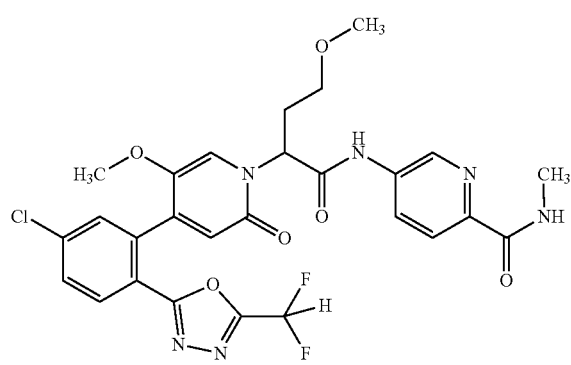 [SMILES: CNC(=O)c1ccc(NC(=O)C(CCOC)n2cc(OC)c(-c3cc(Cl)ccc3-c3nnc(C(F)F)o3)cc2=O)cn1]

12 mg (26 μmol) of 2-[4-{5-chloro-2-[5-(difluoromethyl)-1,3,4-oxadiazol-2-yl]phenyl}-5-methoxy-2-oxopyridin-1(2H)-yl]-4-methoxybutanoic acid (racemate) and 6 mg (0.038 mmol, 1.5 eq.) of 5-amino-N-methylpyridine-2-carboxamide were reacted according to General Method 5. Yield: 14 mg (91% of theory).

LC/MS [Method 10]: R$_t$=1.62 min; MS (ESIpos): m/z=603 (M+H)$^+$,
PURITY $^1$H-NMR (400 MHz, DMSO-d$_6$): δ [ppm]=10.84 (brs, 1H), 8.88 (d, 1H), 8.69-8.62 (m, 1H), 8.21 (dd, 1H), 8.08 (d, 1H), 8.00 (d, 1H), 7.78 (dd, 1H), 7.70 (d, 1H), 7.47 (t, 1H), 7.30 (s, 1H), 6.56 (s, 1H), 5.91-5.66 (m, 1H), 3.43-3.36 (m, 1H, partially hidden), 3.34 (s, 3H), 3.31-3.26 (m, 1H), 3.23 (s, 3H), 2.80 (d, 3H), 2.45-2.36 (m, 2H).

Example 85

N-(Quinoxalin-6-yl)-2-[4-{5-chloro-2-[5-(difluoromethyl)-1,3,4-oxadiazol-2-yl]phenyl}-5-methoxy-2-oxopyridin-1(2H)-yl]-4-methoxybutanamide (Racemate)

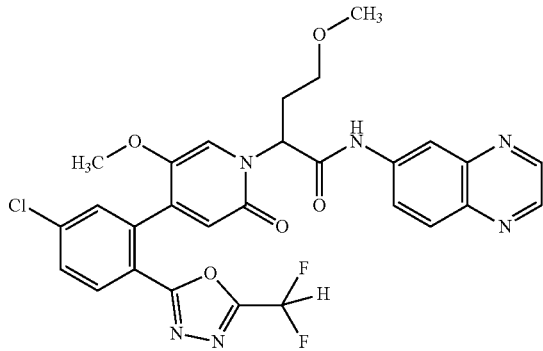 [SMILES: COCCC(C(=O)Nc1ccc2nccnc2c1)n1cc(OC)c(-c2cc(Cl)ccc2-c2nnc(C(F)F)o2)cc1=O]

12 mg (26 μmol) of 2-[4-{5-chloro-2-[5-(diifluoromethyl)-1,3,4-oxadiazol-2-yl]phenyl}-5-methoxy-2-oxopyridin-1(2H)-yl]-4-methoxybutanoic acid (racemate) and 6 mg (0.038 mmol, 1.5 eq.) of quinoxaline-6-amine were reacted according to General Method 5. Yield: 14 mg (92% of theory).
LC/MS [Method 10]: R$_t$=1.70 min; MS (ESIpos): m/z=597 (M+H)$^+$,
$^1$H-NMR (400 MHz, DMSO-d$_6$): δ [ppm]=10.97 (brs, 1H), 8.89 (d, 1H), 8.84 (d, 1H), 8.54 (d, 1H), 8.11-8.05 (m, 2H), 8.01 (dd, 1H), 7.79 (dd, 1H), 7.72 (d, 1H), 7.49 (t, 1H), 7.36 (s, 1H), 6.57 (s, 1H), 5.99-5.75 (m, 1H), 3.45-3.39 (m, 1H), 3.36 (s, 3H), 3.24 (s, 3H), 2.46-2.39 (m, 2H).

Example 86

4-({2-[4-{5-Chloro-2-[1-(difluoromethyl)-1H-pyrazol-4-yl]phenyl}-5-methoxy-2-oxopyridin-1(2H)-yl]-4-methoxybutanoyl}amino)benzoic acid (Racemate)

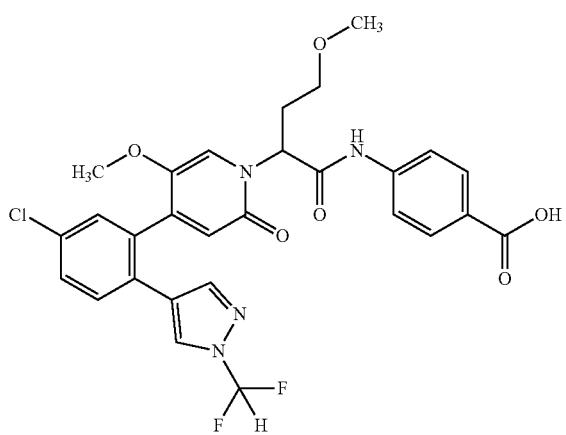 [SMILES: COCCC(C(=O)Nc1ccc(C(=O)O)cc1)n1cc(OC)c(-c2cc(Cl)ccc2-c2cnn(C(F)F)c2)cc1=O]

100 mg (0.214 mmol) of 2-[4-{5-chloro-2-[1-(difluoromethyl)-1H-pyrazol-4-yl]phenyl}-5-methoxy-2-oxopyridin-1(2H)-yl]-4-methoxybutanoic acid (racemate) and 32.2 mg (0.235 mmol) of 4-aminobenzoic acid in 2.5 ml of pyridine were reacted according to General Method 5. Yield: 54 mg (42% of theory).
LC/MS [Method 10]: R$_t$=1.72 min; MS (ESIpos): m/z=587 (M+H)$^+$,
$^1$H-NMR (400 MHz, DMSO-d$_6$): δ [ppm]=12.72 (br. s., 1H), 10.73 (br. s., 1H), 8.11 (s, 1H), 7.90 (d, 2H), 7.75 (d, 2H), 7.69 (s, 1H), 7.62-7.57 (m, 1H), 7.56-7.52 (m, 1H), 7.44-7.40 (m, 1H), 7.31 (s, 1H), 6.40 (s, 1H), 5.79 (br. s., 1H), 3.38-3.27 (m, partially hidden), 3.21 (s, 3H), 2.42-2.33 (m, 2H).

Example 87

2-[4-{5-Chloro-2-[1-(difluoromethyl)-1H-pyrazol-4-yl]phenyl}-5-methoxy-2-oxopyridin-1(2H)-yl]-4-methoxy-N-(2-methyl-2H-indazol-5-yl)butanamide (Racemate)

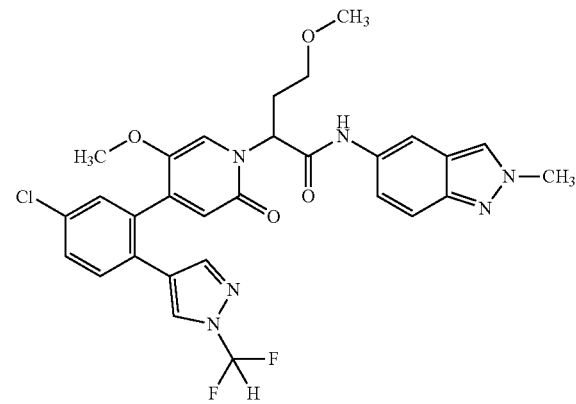 [SMILES: COCCC(C(=O)Nc1ccc2nn(C)cc2c1)n1cc(OC)c(-c2cc(Cl)ccc2-c2cnn(C(F)F)c2)cc1=O]

50.0 mg (0.107 mmol) of 2-[4-{5-chloro-2-[1-(difluoromethyl)-1H-pyrazol-4-yl]phenyl}-5-methoxy-2-oxopyridin-1(2H)-yl]-4-methoxybutanoic acid (racemate) and 26.5 mg (purity 89%, 0.160 mmol) of 2-methyl-2H-indazole-5-amine in 0.6 ml of pyridine were reacted according to General Method 5. Yield: 31 mg (48% of theory).
LC/MS [Method 10]: R$_t$=1.71 min; MS (ESIpos): m/z=597 (M+H)$^+$,
$^1$H-NMR (400 MHz, DMSO-d$_6$): δ [ppm]=10.35 (br. s., 1H), 8.25 (s, 1H), 8.11 (s, 2H), 7.89-7.73 (m, 1H), 7.69 (s, 1H), 7.63-7.58 (m, 1H), 7.57-7.52 (m, 2H), 7.43-7.40 (m, 1H), 7.36-7.28 (m, 2H), 6.40 (s, 1H), 5.80 (br. s., 1H), 4.13 (s, 3H), 3.45-3.31 (m, partially hidden), 3.30-3.23 (m, 1H), 3.22 (s, 3H), 2.40-2.33 (m, 2H).

Example 88

5-({2-[4-{5-Chloro-2-[1-(difluoromethyl)-1H-pyrazol-4-yl]phenyl}-5-methoxy-2-oxopyridin-1(2H)-yl]-4-methoxybutanoyl}amino)pyridine-2-carboxamide (Racemate)

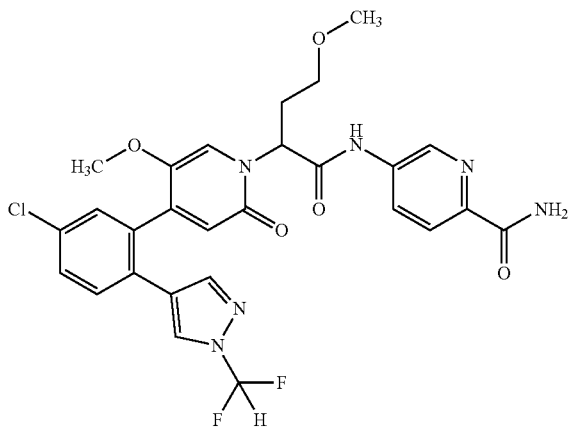 [SMILES: COCCC(C(=O)Nc1ccc(C(N)=O)nc1)n1cc(OC)c(-c2cc(Cl)ccc2-c2cnn(C(F)F)c2)cc1=O]

50.0 mg (0.107 mmol) of 2-[4-{5-chloro-2-[1-(difluoromethyl)-1H-pyrazol-4-yl]phenyl}-5-methoxy-2-oxopyridin-1(2H)-yl]-4-methoxybutanoic acid (racemate) and 22.7 mg (0.160 mmol) of 5-aminopyridine-2-carboxamide in 0.6 ml of pyridine were reacted according to General Method 5. Yield: 26 mg (40% of theory).

LC/MS [Method 10]: $R_t$=1.62 min; MS (ESIpos): m/z=587 (M+H)$^+$, $^1$H-NMR (400 MHz, DMSO-d$_6$): δ [ppm]=10.89 (br. s., 1H), 8.88-8.84 (m, 1H), 8.24-8.17 (m, 1H), 8.13-8.07 (m, 1H), 8.04-7.98 (m, 2H), 7.93-7.72 (m, 1H), 7.70 (s, 1H), 7.62-7.49 (m, 3H), 7.45-7.40 (m, 1H), 7.34-7.25 (m, 1H), 6.41 (s, 1H), 5.78 (br. s., 1H), 3.41-3.23 (m, partially hidden), 3.22 (s, 3H), 2.45-2.34 (m, 2H).

Example 89

4-[(2-{4-[5-Chloro-2-(3-methyl-1,2,4-oxadiazol-5-yl)phenyl]-5-methoxy-2-oxopyridin-1(2H)-yl}-4-methoxybutanoyl)amino]-2-fluorobenzamide (Racemate)

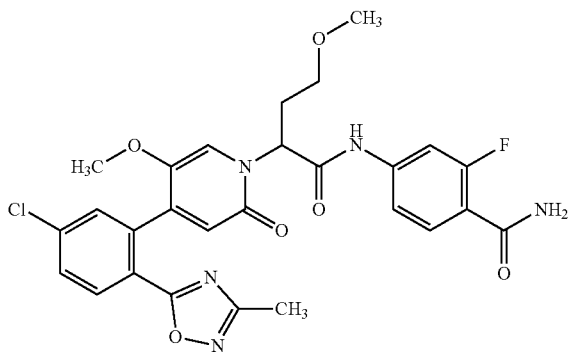 [SMILES: COCCC(C(=O)Nc1ccc(C(N)=O)c(F)c1)n1cc(OC)c(-c2cc(Cl)ccc2-c2nc(C)no2)cc1=O]

50.0 mg (115 μmol) of 2-{4-[5-chloro-2-(3-methyl-1,2,4-oxadiazol-5-yl)phenyl]-5-methoxy-2-oxopyridin-(2H)-yl}-4-methoxybutanoic acid (racemate) and 26.6 mg (173 μmol) of 4-amino-2-fluorobenzamide in 0.6 ml of pyridine were reacted according to General Method 5. Yield: 58 mg (87% of theory).

LC/MS [Method 10]: $R_t$=1.61 min; MS (ESIpos): m/z=570 (M+H)$^+$, $^1$H-NMR (400 MHz, DMSO-d$_6$): δ [ppm]=10.87-10.70 (m, 1H), 8.07 (d, 1H), 7.75 (dd, 1H), 7.72-7.63 (m, 3H), 7.58-7.48 (m, 2H), 7.47-7.40 (m, 1H), 7.29 (s, 1H), 6.51 (s, 1H), 5.78 (br. s., 1H), 3.45-3.37 (m, 1H), 3.40-3.20 (m, partially hidden), 2.45-2.35 (m, 2H), 2.34 (s, 3H).

Example 90

4-[(2-{4-[5-Chloro-2-(3-methyl-1,2,4-oxadiazol-5-yl)phenyl]-5-methoxy-2-oxopyridin-1(2H)-yl}-4-methoxybutanoyl)amino]benzoic acid (Racemate)

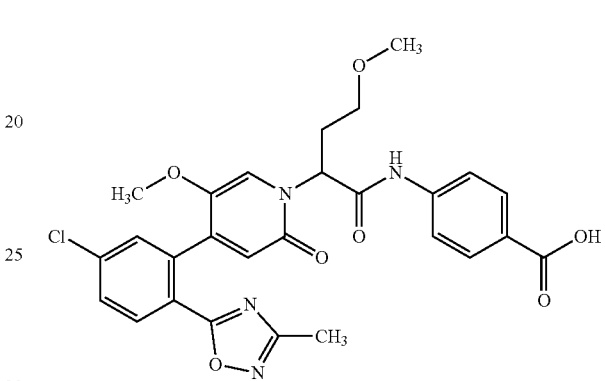

50.0 mg (115 μmol) of 2-{4-[5-chloro-2-(3-methyl-1,2,4-oxadiazol-5-yl)phenyl]-5-methoxy-2-oxopyridin-1(2H)-yl}-4-methoxybutanoic acid (racemate) and 17.4 mg (0.127 mmol) of 4-aminobenzoic acid in 1.4 ml of pyridine were reacted according to General Method 5. Yield: 24 mg (37% of theory).

LC/MS [Method 10]: $R_t$=1.67 min; MS (ESIpos): m/z=553 (M+H)$^+$, $^1$H-NMR (400 MHz, DMSO-d$_6$): δ [ppm]=12.72 (br. s., 1H), 10.72 (br. s., 1H), 8.07 (d, 1H), 7.91 (d, 2H), 7.79-7.72 (m, 3H), 7.69-7.65 (m, 1H), 7.30 (s, 1H), 6.51 (s, 1H), 5.79 (br. s., 1H), 3.45-3.36 (m, 1H), 3.35-3.20 (m, partially hidden), 2.44-2.36 (m, 2H), 2.33 (s, 3H).

Example 91

2-{4-[5-Chloro-2-(3-methyl-1,2,4-oxadiazol-5-yl)phenyl]-5-methoxy-2-oxopyridin-1(2H)-yl}-4-methoxy-N-(2-methyl-2H-indazol-5-yl)butanamide (Racemate)

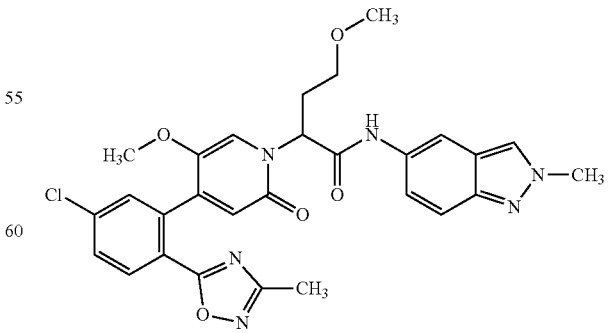

50.0 mg (0.12 mmol) of 2-{4-[5-chloro-2-(3-methyl-1,2,4-oxadiazol-5-yl)phenyl]-5-methoxy-2-oxopyridin-1(2H)-yl}-4-methoxybutanoic acid (racemate) and 28.6 mg (purity 89%, 0.46 mmol) of 2-methyl-2H-indazole-5-amine in 0.6 ml of pyridine were reacted according to General Method 5. Yield: 29 mg (44% of theory).

LC/MS [Method 10]: $R_t$=1.65 min; MS (ESIpos): m/z=563 (M+H)$^+$, $^1$H-NMR (400 MHz, DMSO-d$_6$): δ [ppm]=10.36 (br. s., 1H), 8.25 (s, 1H), 8.13 (d, 1H), 8.07 (d, 1H), 7.78-7.72 (m, 1H), 7.67 (d, 1H), 7.58-7.51 (m, 1H), 7.37-7.27 (m, 2H), 6.51 (s, 1H), 5.81 (br. s., 1H), 4.13 (s, 3H), 3.43-3.36 (m, 1H), 3.35-3.20 (m, partially hidden), 2.41-2.28 (m, 5H).

Example 92

4-tert-Butoxy-N-(quinoxalin-6-yl)-2-{4-[5-chloro-2-(3-methyl-1,2,4-oxadiazol-5-yl)phenyl]-5-methoxy-2-oxopyridin-1(2H)-yl}butanamide (Racemate)

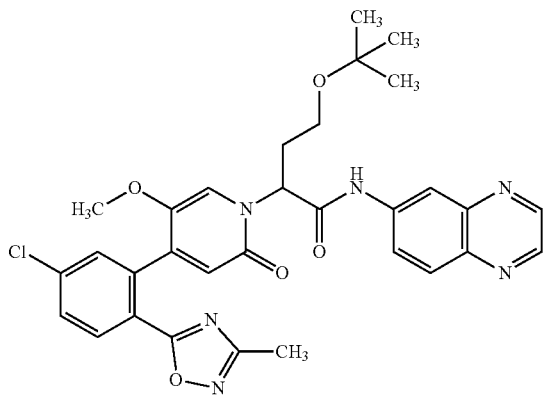 [SMILES: COc1cn(C(CCOC(C)(C)C)C(=O)Nc2ccc3nccnc3c2)c(=O)cc1-c1cc(Cl)ccc1-c1nc(C)no1]

38.8 mg (81 μmol) of 4-tert-butoxy-2-{4-[5-chloro-2-(3-methyl-1,2,4-oxadiazol-5-yl)phenyl]-5-methoxy-2-oxopyridin-1(2H)-yl}butanoic acid (racemate) and 15.4 mg (106 μmol) of quinoxaline-6-amine with 2.0 ml of pyridine were reacted according to General Method 5. Yield: 25 mg (52% of theory)

LC/MS [Method 10]: $R_t$=1.04 min; MS (ESIpos): m/z=603 (M+H)$^+$, $^1$H-NMR (400 MHz, DMSO-d$_6$): δ [ppm]=10.94 (br. s., 1H), 8.91-8.81 (m, 1H), 8.59-8.53 (m, 1H), 8.10-8.00 (m, 3H), 7.78-7.72 (m, 1H), 7.64 (br. s., 1H), 7.33 (s, 1H), 6.54 (s, 1H), 5.88 (br. s., 1H), 3.48-3.39 (m, 1H), 3.35 (s, 3H), 2.45-2.30 (m, 5H), 1.09 (s, 9H).

Example 93

4-[(4-tert-Butoxy-2-{4-[5-chloro-2-(3-methyl-1,2,4-oxadiazol-5-yl)phenyl]-5-methoxy-2-oxopyridin-1(2H)-yl}butanoyl)amino]-2-fluorobenzamide (Racemate)

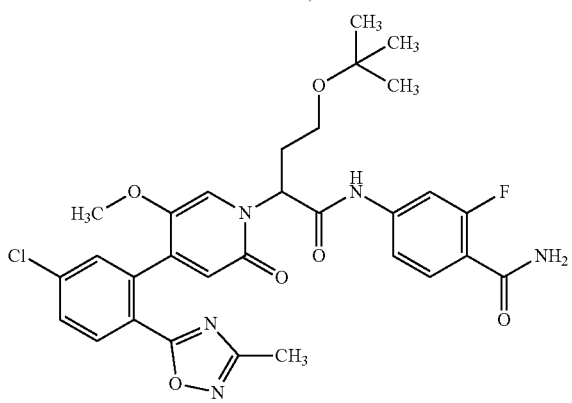 [SMILES: COc1cn(C(CCOC(C)(C)C)C(=O)Nc2ccc(C(N)=O)c(F)c2)c(=O)cc1-c1cc(Cl)ccc1-c1nc(C)no1]

38.8 mg (81 μmol) of 4-tert-butoxy-2-{4-[5-chloro-2-(3-methyl-1,2,4-oxadiazol-5-yl)phenyl]-5-methoxy-2-oxopyridin-1(2H)-yl}butanoic acid (racemate) and 16.3 mg (106 μmol) of 4-amino-2-fluorobenzamide with 2.0 ml of pyridine were reacted according to General Method 5. Yield: 23 mg (45% of theory).

LC/MS [Method 1]: $R_t$=0.99 min; MS (ESIpos): m/z=612 (M+H)$^+$, $^1$H-NMR (400 MHz, DMSO-d$_6$): δ [ppm]=10.79 (br. s., 1H), 8.06 (d, 1H), 7.76 (d, 1H), 7.71-7.59 (m, 3H), 7.57-7.49 (m, 2H), 7.48-7.43 (m, 1H), 7.27 (s, 1H), 6.53 (s, 1H), 5.79 (br. s., 1H), 3.45-3.37 (m, 1H), 3.33 (s, 3H), 3.27-3.22 (m, 1H), 2.34-2.32 (m, 5H), 1.08 (s, 9H).

Example 94

4-[(4-tert-Butoxy-2-{4-[5-chloro-2-(3-methyl-1,2,4-oxadiazol-5-yl)phenyl]-5-methoxy-2-oxopyridin-1(2H)-yl}butanoyl)amino]benzoic acid (Racemate)

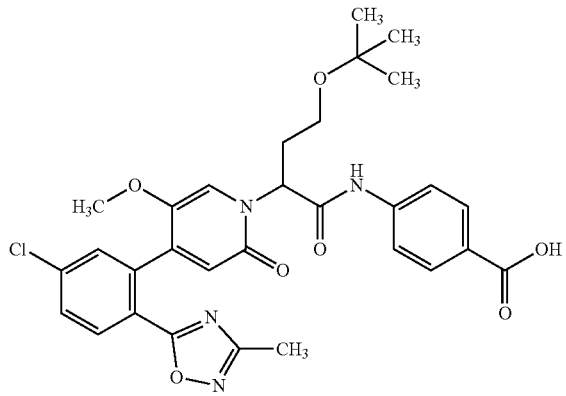 [SMILES: COc1cn(C(CCOC(C)(C)C)C(=O)Nc2ccc(C(=O)O)cc2)c(=O)cc1-c1cc(Cl)ccc1-c1nc(C)no1]

38.8 mg (81 μmol) of 4-tert-butoxy-2-{4-[5-chloro-2-(3-methyl-1,2,4-oxadiazol-5-yl)phenyl]-5-methoxy-2-oxopyridin-1(2H)-yl}butanoic acid (racemate) and 14.5 mg (106 μmol) of 4-aminobenzoic acid in 2.0 ml of pyridine were reacted according to General Method 5. Yield: 23 mg (47% of theory).

LC/MS [Method 1]: $R_t$=1.02 min; MS (ESIpos): m/z=595 (M+H)$^+$, $^1$H-NMR (400 MHz, DMSO-d$_6$): δ [ppm]=12.74 (br. s., 1H), 10.71 (br. s., 1H), 8.06 (d, 1H), 7.90 (d, 2H), 7.80-7.71 (m, 3H), 7.63 (br. s., 1H), 7.28 (s, 1H), 6.52 (s, 1H), 5.82 (br. s., 1H), 3.45-3.36 (m, 1H), 3.35-3.20 (m, partially hidden), 2.41-2.27 (m, 5H), 1.08 (s, 9H).

Example 95

4-tert-Butoxy-2-{4-[5-chloro-2-(3-methyl-1,2,4-oxadiazol-5-yl)phenyl]-5-methoxy-2-oxopyridin-1(2H)-yl}-N-(2-methyl-2H-indazol-5-yl)butanamide (Racemate)

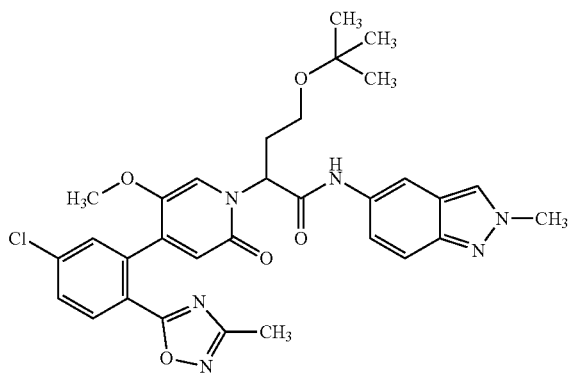 [SMILES: COc1cn(C(CCOC(C)(C)C)C(=O)Nc2ccc3nn(C)cc3c2)c(=O)cc1-c1cc(Cl)ccc1-c1nc(C)no1]

38.7 mg (81 µmol) of 4-tert-butoxy-2-{4-[5-chloro-2-(3-methyl-1,2,4-oxadiazol-5-yl)phenyl]-5-methoxy-2-oxopyridin-1(2H)-yl}butanoic acid (racemate) and 15.6 mg (106 µmol) of 2-methyl-2H-indazole-5-amine with 2.0 ml of pyridine were reacted according to General Method 5. Yield: 26 mg (49% of theory).

LC/MS [Method 1]: $R_t$=1.02 min; MS (ESIpos): m/z=605 (M+H)$^+$, $^1$H-NMR (400 MHz, DMSO-d$_6$): δ [ppm]=10.34 (br. s., 1H), 8.25 (s, 1H), 8.14 (d, 1H), 8.06 (d, 1H), 7.75 (dd, 1H), 7.63 (br. s., 1H), 7.54 (d, 1H), 7.38-7.26 (m, 2H), 6.52 (s, 1H), 5.82 (br. s., 1H), 4.13 (s, 3H), 3.44-3.36 (m, 1H), 3.35-3.20 (m, partially hidden), 2.40-2.25 (m, 5H), 1.09 (s, 9H).

Example 96

4-({2-[4-{5-Chloro-2-[1-(2,2,2-trifluoroethyl)-1H-pyrazol-4-yl]phenyl}-5-methoxy-2-oxopyridin-1(2H)-yl]-4-methoxybutanoyl}amino)benzoic acid (Racemate)

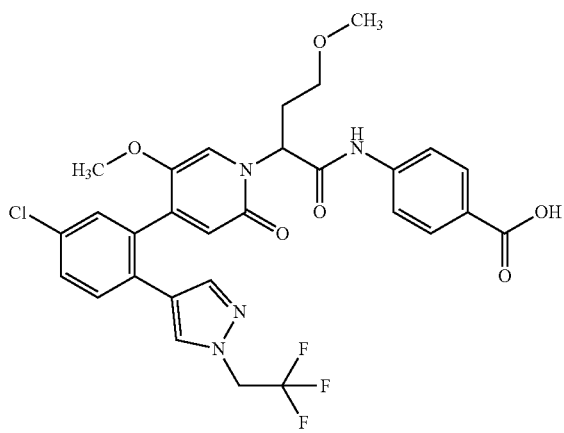 [SMILES: COCCC(C(=O)Nc1ccc(C(=O)O)cc1)n1cc(OC)c(-c2cc(Cl)ccc2-c2cnn(CC(F)(F)F)c2)cc1=O]

35.3 mg (0.07 mmol) of 2-[4-{5-chloro-2-[1-(2,2,2-trifluoroethyl)-1H-pyrazol-4-yl]phenyl}-5-methoxy-2-oxopyridin-1(2H)-yl]-4-methoxybutanoic acid (racemate) and 10.7 mg (0.08 mmol) of 4-aminobenzoic acid in 0.83 ml of pyridine were reacted according to General Method 5. Yield: 22 mg (50% of theory).

LC/MS [Method 10]: $R_t$=1.74 min; MS (ESIpos): m/z=619 (M+H)$^+$, $^1$H-NMR (400 MHz, DMSO-d$_6$): δ [ppm]=12.76 (br. s., 1H), 10.71 (br. s., 1H), 7.90 (d, 2H), 7.75 (d, 2H), 7.69 (br. s., 1H), 7.59-7.48 (m, 3H), 7.37 (d, 1H), 7.30 (s, 1H), 6.38 (s, 1H), 5.76 (br. s., 1H), 5.05 (br. s., 2H), 3.41-3.25 (m, partially hidden), 3.23 (s, 3H), 2.44-2.27 (m, 2H).

Example 97

5-({2-[4-{5-Chloro-2-[1-(2,2,2-trifluoroethyl)-1H-pyrazol-4-yl]phenyl}-5-methoxy-2-oxopyridin-1(2H)-yl]-4-methoxybutanoyl}amino)-N-methylpyridine-2-carboxamide (Racemate)

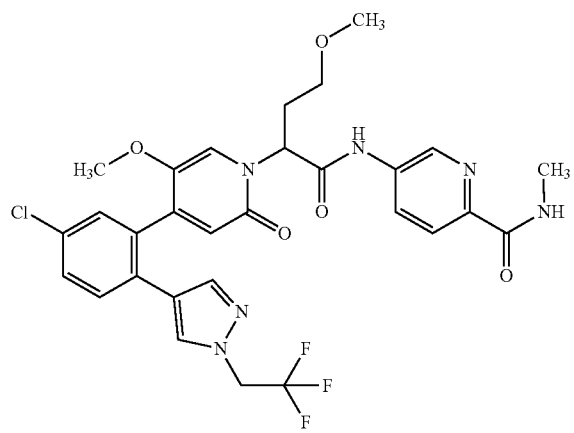 [SMILES: CNC(=O)c1ccc(NC(=O)C(CCOC)n2cc(OC)c(-c3cc(Cl)ccc3-c3cnn(CC(F)(F)F)c3)cc2=O)cn1]

35.3 mg (0.07 mmol) of 2-[4-{5-chloro-2-[1-(2,2,2-trifluoroethyl)-1H-pyrazol-4-yl]phenyl}-5-methoxy-2-oxopyridin-1(2H)-yl]-4-methoxybutanoic acid (racemate) and 16.0 mg (0.11 mmol) of 5-amino-N-methylpyridine-2-carboxamide in 0.38 ml of pyridine were reacted according to General Method 5. Yield: 22 mg (48% of theory).

LC/MS [Method 10]: $R_t$=1.69 min; MS (ESIpos): m/z=633 (M+H)$^+$, $^1$H-NMR (400 MHz, DMSO-d$_6$): δ [ppm]=10.97-10.65 (m, 1H), 8.89-8.85 (m, 1H), 8.68-8.61 (m, 1H), 8.24-8.17 (m, 1H), 8.00 (d, 1H), 7.76-7.64 (m, 1H), 7.58-7.48 (m, 3H), 7.39-7.34 (m, 1H), 7.32-7.25 (m, 1H), 6.39 (s, 1H), 5.75 (br. s., 1H), 5.05 (br. s., 2H), 3.45-3.24 (m, partially hidden), 3.23 (s, 3H), 2.80 (d, 3H), 2.46-2.28 (m, 2H).

Example 98

2-[4-{5-Chloro-2-[1-(2,2,2-trifluoroethyl)-1H-pyrazol-4-yl]phenyl}-5-methoxy-2-oxopyridin-1(2H)-yl]-4-methoxy-N-(2-methyl-2H-indazol-5-yl)butanamide (Racemate)

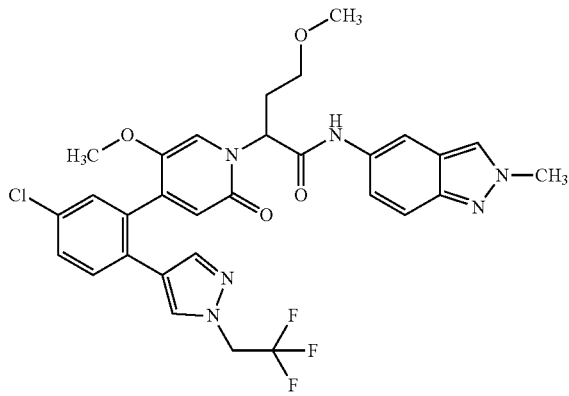 [SMILES: COCCC(C(=O)Nc1ccc2nn(C)cc2c1)n1cc(OC)c(-c2cc(Cl)ccc2-c2cnn(CC(F)(F)F)c2)cc1=O]

35.3 mg (0.07 mmol) of 2-[4-{5-chloro-2-[1-(2,2,2-trifluoroethyl)-1H-pyrazol-4-yl]phenyl}-5-methoxy-2-oxopyridin-1(2H)-yl]-4-methoxybutanoic acid (racemate) and 17.5 mg (purity 89%, 0.11 mmol) of 2-methyl-2H-indazole-5-amine in 0.38 ml of pyridine were reacted according to General Method 5. Yield: 13 mg (30% of theory).

LC/MS [Method 10]: $R_t$=1.73 min; MS (ESIpos): m/z=629 (M+H)$^+$, $^1$H-NMR (400 MHz, DMSO-d$_6$): δ [ppm]=10.34 (br. s., 1H), 8.27-8.20 (m, 1H), 8.14-8.09 (m, 1H), 7.69 (br. s., 1H), 7.61-7.46 (m, 4H), 7.39-7.26 (m, 42), 6.39 (s, 1H), 5.79 (br. s., 1H), 5.05 (br. s., 2H), 4.13 (s, 3H), 3.43-3.25 (m, partially hidden), 3.24 (s, 3H), 2.43-2.24 (m, 2H).

Example 99

2-{4-[5-Chloro-2-(4-chloro-1H-1,2,3-triazol-1-yl)phenyl]-5-methoxy-2-oxopyridin-1(2H)-yl}-4-methoxy-N-(2-methyl-2H-indazol-5-yl)butanamide (Racemate)

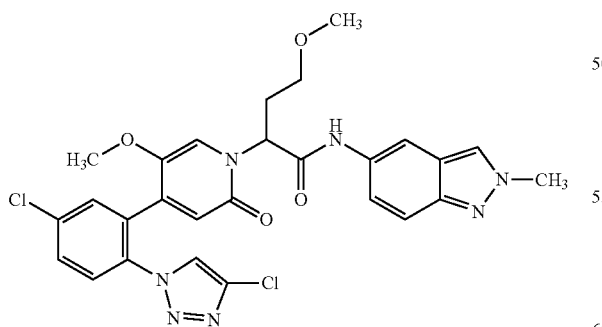

83.3 mg (purity 81%, 0.15 mmol) of 2-{4-[5-chloro-2-(4-chloro-1H-1,2,3-triazol-1-yl)phenyl]-5-methoxy-2-oxopyridin-1(2H)-yl}-4-methoxybutanoic acid (racemate) and 36.9 mg (purity 89%, 0.22 mmol) of 2-methyl-2H-indazole-5-amine in 0.80 ml of pyridine were reacted according to General Method 5. Yield: 34 mg (38% of theory).

LC/MS [Method 10]: $R_t$=1.58 min; MS (ESIpos): m/z=582 (M+H)$^+$, $^1$H-NMR (400 MHz, DMSO-d$_6$): δ [ppm]=10.29 (br. s., 1H), 8.63 (s, 1H), 8.25 (s, 1H), 8.12-8.09 (m, 1H), 7.81-7.71 (m, 3H), 7.54 (d, 1H), 7.30 (dd, 1H), 7.24 (s, 1H), 6.46 (s, 1H), 5.76-5.65 (m, 1H), 4.13 (s, 3H), 3.40-3.28 (m, partially hidden), 3.21 (s, 3H), 3.19-3.13 (m, 1H), 2.38-2.26 (m, 2H).

Example 100

4-[(2-{4-[5-Chloro-2-(4-chloro-1H-1,2,3-triazol-1-yl)phenyl]-5-methoxy-2-oxopyridin-1(2H)-yl}-4-methoxybutanoyl)amino]-2-fluorobenzamide (Racemate)

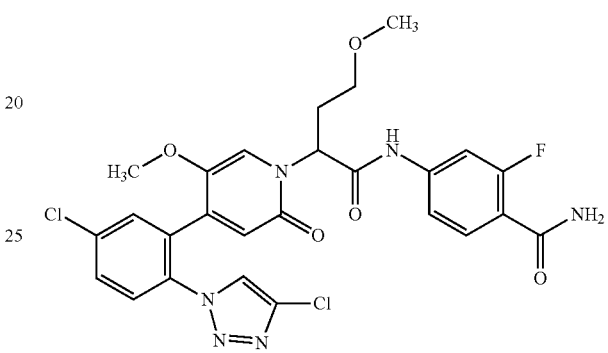

83.3 mg (purity 81%, 0.15 mmol) of 2-{4-[5-chloro-2-(4-chloro-1H-1,2,3-triazol-1-yl)phenyl]-5-methoxy-2-oxopyridin-1(2H)-yl}-4-methoxybutanoic acid (racemate) and 34.4 mg (0.22 mmol) of 4-amino-2-fluorobenzamide in 0.8 ml of pyridine were reacted according to General Method 5. Yield: 21 mg (22% of theory).

LC/MS [Method 10]: $R_t$=1.53 min; MS (ESIpos): m/z=589 (M+H)$^+$, $^1$H-NMR (400 MHz, DMSO-d$_6$): δ [ppm]=10.70 (br. s., 1H), 8.63 (s, 1H), 7.81-7.72 (m, 3H), 7.71-7.61 (m, 2H), 7.55-7.47 (m, 2H), 7.42 (dd, 1H), 7.19 (s, 1H), 6.46 (s, 1H), 5.63 (br. s., 1H), 3.40-3.25 (m, partially hidden), 3.20 (s, 3H), 3.17-3.10 (m, 1H), 2.38-2.29 (m, 2H).

Example 101

4-[(2-{4-[5-Chloro-2-(4-chloro-1H-1,2,3-triazol-1-yl)phenyl]-5-methoxy-2-oxopyridin-1(2H)-yl}-4-methoxybutanoyl)amino]benzoic acid (Racemate)

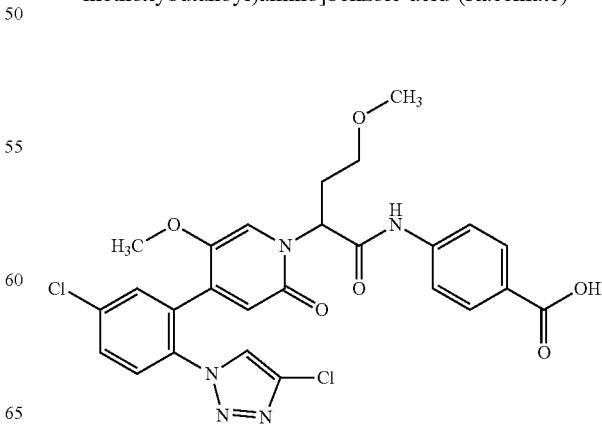

83.3 mg (purity 81%, 0.15 mmol) of 2-{4-[5-chloro-2-(4-chloro-1H-1,2,3-triazol-1-yl)phenyl]-5-methoxy-2-oxopyridin-1(2H)-yl}-4-methoxybutanoic acid (racemate) and 22.5 mg (0.16 mmol) of 4-aminobenzoic acid in 1.75 ml of pyridine were reacted according to General Method 5. Yield: 3 mg (3% of theory).

LC/MS [Method 10]: $R_t$=1.59 min; MS (ESIpos): m/z=572 (M+H)$^+$, $^1$H-NMR (400 MHz, DMSO-d$_6$): δ [ppm]=10.47 (br. s., 1H), 8.63 (s, 1H), 7.90-7.83 (m, 2H), 7.81-7.72 (m, 3H), 7.65-7.58 (m, 2H), 7.21 (s, 1H), 6.45 (s, 1H), 5.68 (br. s., 1H), 3.42-3.25 (m, partially hidden), 3.20 (s, 3H), 3.18-3.11 (m, 2H), 2.36-2.28 (m, 2H).

Example 102

4-[(4-tert-Butoxy-2-{4-[5-chloro-2-(4-chloro-1H-1,2,3-triazol-1-yl)phenyl]-5-methoxy-2-oxopyridin-1(2H)-yl}butanoyl)amino]-2-fluorobenzamide (Racemate)

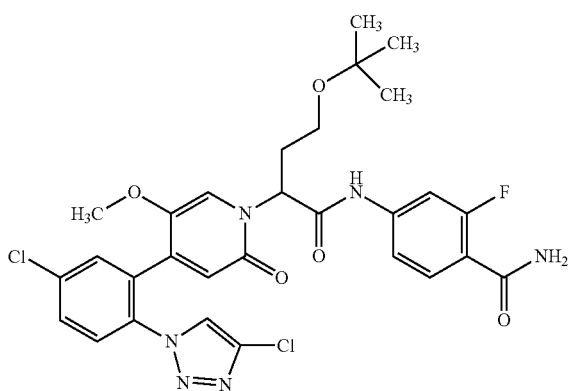 [SMILES: COc1cn(C(CCOC(C)(C)C)C(=O)Nc2ccc(C(N)=O)c(F)c2)c(=O)cc1-c1cc(Cl)ccc1-n1cc(Cl)nn1]

48 mg (97 μmol) of 4-tert-butoxy-2-{4-[5-chloro-2-(4-chloro-1H-1,2,3-triazol-1-yl)phenyl]-5-methoxy-2-oxopyridin-1(2H)-yl}butanoic acid (racemate) and 19 mg (126 μmol) of 4-amino-2-fluorobenzamide in 1 ml of pyridine were reacted according to General Method 5. Yield: 24 mg (35% of theory).

LC/MS [Method 1]: $R_t$=0.97 min; MS (ESIpos): m/z=631 (M+H)$^+$, $^1$H-NMR (400 MHz, DMSO-d$_6$): δ [ppm]=10.70 (br. s., 1H), 8.64 (s, 1H), 7.81-7.72 (m, 1H), 7.71-7.62 (m, 1H), 7.56-7.47 (m, 1H), 7.43 (d, 1H), 7.18 (s, 1H), 6.46 (s, 1H), 5.72-5.61 (m, 1H), 3.40-3.25 (m, partially hidden), 3.20-3.10 (m, 1H), 2.35-2.25 (m, 2H), 1.05 (s, 9H).

Example 103

4-tert-Butoxy-2-{4-[5-chloro-2-(4-chloro-1H-1,2,3-triazol-1-yl)phenyl]-5-methoxy-2-oxopyridin-1(2H)-yl}-N-(2-methyl-2H-indazol-5-yl)butanamide (Racemate)

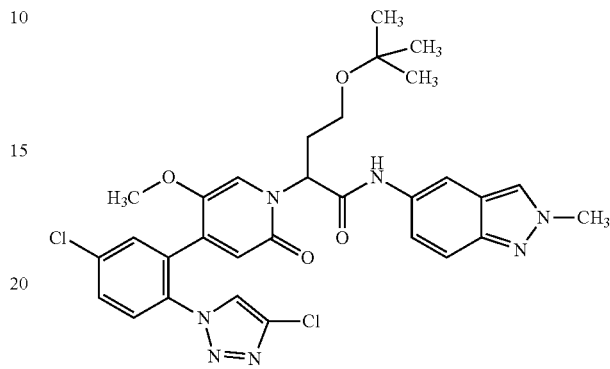

48.0 mg (97 μmol) of 4-tert-butoxy-2-{4-[5-chloro-2-(4-chloro-1H-1,2,3-triazol-1-yl)phenyl]-5-methoxy-2-oxopyridin-1(2H)-yl}butanoic acid (racemate) and 18.5 mg (126 μmol) of 2-methyl-2H-indazole-5-amine in 1 ml of pyridine were reacted according to General Method 5. Yield: 40 mg (63% of theory).

LC/MS [Method 1]: $R_t$=0.99 min; MS (ESIpos): m/z=624 (M+H)$^+$, $^1$H-NMR (400 MHz, DMSO-d$_6$): δ [ppm]=10.27 (s, 1H), 8.64 (s, 1H), 8.24 (s, 1H), 8.11 (s, 1H), 7.82-7.72 (m, 2H), 7.68 (s, 1H), 7.53 (d, 1H), 7.31 (d, 1H), 7.23 (s, 1H), 6.45 (s, 1H), 5.77-5.66 (m, 1H), 4.12 (s, 3H), 3.23-3.11 (m, 1H), 2.32-2.21 (m, 2H), 1.06 (s, 9H).

Example 104

4-{[2-{4-[5-Chloro-2-(4-fluoro-1H-imidazol-1-yl)phenyl]-5-methoxy-2-oxopyridin-1(2H)-yl}pentanoyl]amino}benzoic acid (Racemate)

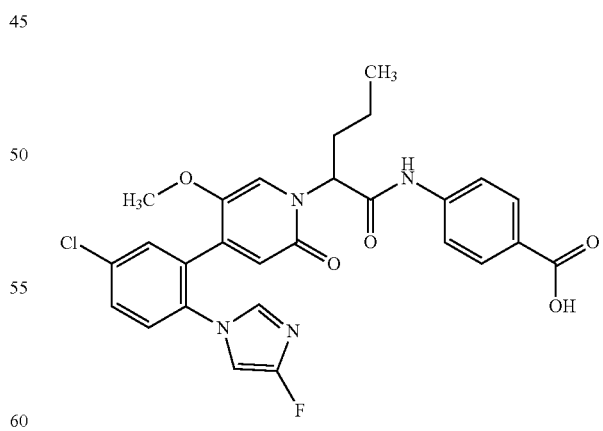

30.0 mg (71.5 μmol) of 2-{4-[5-chloro-2-(4-fluoro-1H-imidazol-1-yl)phenyl]-5-methoxy-2-oxopyridin-1(2H)-yl}pentanoic acid (racemate) and 10.3 mg (75.0 μmol) of 4-aminobenzoic acid in 0.4 ml of pyridine were reacted according to General Method 5. Yield: 27 mg (81% pure, 57% of theory).

LC/MS [Method 1]: $R_t$=0.97 min; MS (ESIpos): m/z=539 [M+H]$^+$ $^1$H-NMR (400 MHz, DMSO-d$_6$): δ [ppm]=12.76 (br s, 1H), 10.71 (s, 1H), 7.90 (d, 2H), 7.75-7.67 (m, 3H), 7.63 (d, 1H), 7.58 (d, 1H), 7.39 (t, 1H), 7.23 (s, 1H), 6.90 (dd, 1H), 6.46 (s, 1H), 5.72-5.63 (m, 1H), 3.41 (s, 3H), 2.13-1.98 (m, 2H), 1.28-1.12 (m, 2H), 0.90 (t, 3H).

Example 105

N-(Quinoxalin-6-yl)-2-{4-[5-chloro-2-(4-fluoro-1H-imidazol-1-yl)phenyl]-5-methoxy-2-oxopyridin-1(2H)-yl}pentanamide (Racemate)

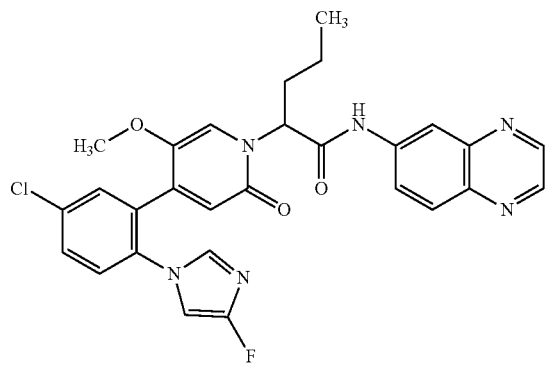 [SMILES: CCCC(C(=O)Nc1ccc2nccnc2c1)n1cc(OC)c(-c2cc(Cl)ccc2-n2cnc(F)c2)cc1=O]

30.0 mg (71.5 μmol) of 2-{4-[5-chloro-2-(4-fluoro-1H-imidazol-1-yl)phenyl]-5-methoxy-2-oxopyridin-1(2H)-yl}pentanoic acid (racemate) and 15.6 mg (107 μmol) of quinoxaline-6-amine with 590 μl of pyridine were reacted according to General Method 5. Yield: 28.0 mg (purity 83%, 59% of theory)

LC/MS [Method 2]: $R_t$=2.86 min; MS (ESIpos): m/z=547 [M+H]$^+$ $^1$H-NMR (400 MHz, DMSO-d$_6$): δ [ppm]=10.93 (s, 1H), 8.89 (d, 1H), 8.84 (d, 1H), 8.53-8.50 (m, 1H), 8.09-8.05 (m, 1H), 7.99-7.94 (m, 1H), 7.71-7.66 (m, 1H), 7.64 (d, 1H), 7.59 (d, 1H), 7.40 (t, 1H), 7.28 (s, 1H), 6.91 (dd, 1H), 6.48 (s, 1H), 5.77-5.69 (m, 1H), 3.43 (s, 3H), 2.20-2.06 (m, 2H), 1.31-1.16 (m, 2H), 0.92 (t, 3H).

Example 106

2-{4-[5-Chloro-2-(4-fluoro-1H-imidazol-1-yl)phenyl]-5-methoxy-2-oxopyridin-1(2H)-yl}-N-(2-methyl-2H-indazol-5-yl)pentanamide (Racemate)

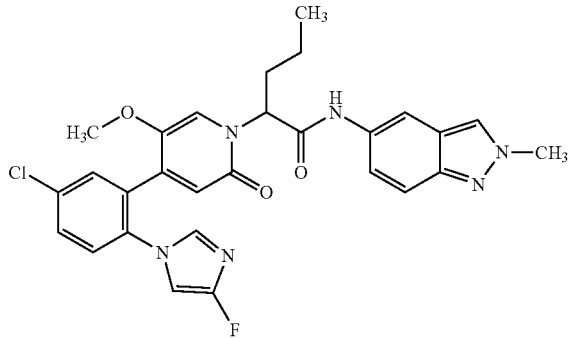 [SMILES: CCCC(C(=O)Nc1ccc2nn(C)cc2c1)n1cc(OC)c(-c2cc(Cl)ccc2-n2cnc(Cl)c2)cc1=O]

30.0 mg (71.5 μmol) of 2-{4-[5-chloro-2-(4-fluoro-1H-imidazol-1-yl)phenyl]-5-methoxy-2-oxopyridin-1(2H)-yl}pentanoic acid (racemate) and 16.1 mg (107 μmol) of 2-methyl-2H-indazole-5-amine in 590 μl of pyridine were reacted according to General Method 5. Yield: 27.0 mg (69% of theory).

LC/MS [Method 1]: $R_t$=0.94 min; MS (ESIpos): m/z=549 [M+H]$^+$ $^1$H-NMR (400 MHz, DMSO-d$_6$): δ [ppm]=10.36 (s, 1H), 8.24 (s, 1H), 8.12 (s, 1H), 7.72-7.66 (m, 1H), 7.63 (d, 1H), 7.61-7.53 (m, 2H), 7.39 (t, 1H), 7.30-7.25 (m, 2H), 6.91 (dd, 1H), 6.46 (s, 1H), 5.74-5.65 (m, 1H), 4.13 (s, 3H), 3.41 (s, 3H), 2.09-1.98 (m, 2H), 1.30-1.13 (m, 2H), 0.91 (t, 3H).

Example 107

5-{[2-{4-[5-Chloro-2-(4-chloro-1H-imidazol-1-yl)phenyl]-5-methoxy-2-oxopyridin-1(2H)-yl}pentanoyl]amino}pyridine-2-carboxamide (Racemate)

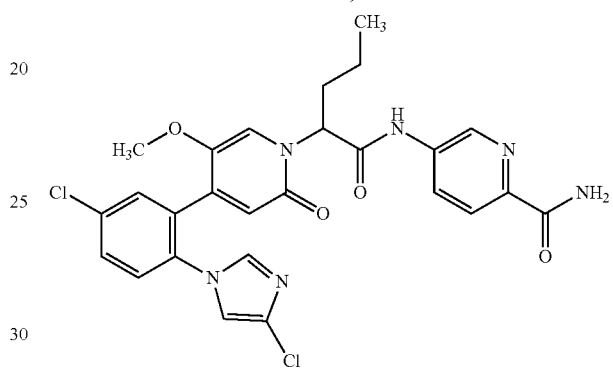

30.0 mg (68.8 μmol) of 2-{4-[5-chloro-2-(4-chloro-1H-imidazol-1-yl)phenyl]-5-methoxy-2-oxopyridin-1(2H)-yl}pentanoic acid (racemate) and 14.6 mg (103 μmol) of 5-aminopyridine-2-carboxamide were reacted according to General Method 5. Yield: 28.0 mg (71% of theory).

LC/MS [Method 1]: $R_t$=0.86 min; MS (ESIpos): m/z=555 [M+H]$^+$ $^1$H-NMR (400 MHz, DMSO-d$_6$): δ [ppm]=10.86 (s, 1H), 8.83 (d, 1H), 8.20 (dd, 1H), 8.04-7.98 (m, 2H), 7.72-7.67 (m, 1H), 7.66 (d, 1H), 7.64 (d, 1H), 7.59 (d, 1H), 7.52 (br s, 1H), 7.25 (d, 1H), 7.22 (s, 1H), 6.48 (s, 1H), 5.68 (br dd, 1H), 3.38 (s, 3H), 2.18-2.01 (m, 2H), 1.30-1.12 (m, 2H), 0.95-0.88 (m, 3H).

Example 108

2-{4-[5-Chloro-2-(4-chloro-1H-imidazol-1-yl)phenyl]-5-methoxy-2-oxopyridin-1(2H)-yl}-N-(2-methyl-2H-indazol-5-yl)pentanamide (Racemate)

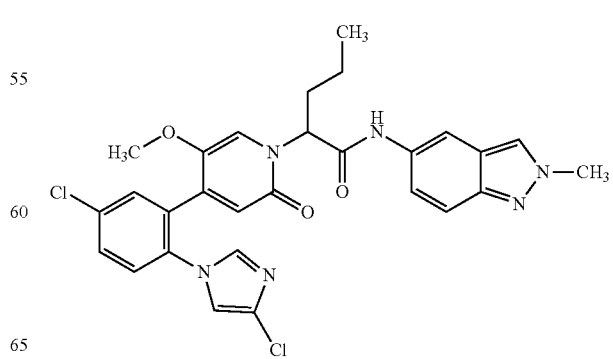

30.0 mg (68.8 μmol) of 2-{4-[5-chloro-2-(4-fluoro-1H-imidazol-1-yl)phenyl]-5-methoxy-2-oxopyridin-1(2H)-yl}pentanoic acid (racemate) and 15.5 mg (103 μmol) of 2-methyl-2H-indazole-5-amine were reacted according to General Method 5. Yield: 29 mg (75% of theory).

LC/MS [Method 1]: $R_t$=0.95 min; MS (ESIpos): m/z=565 [M+H]$^+$ $^1$H-NMR (400 MHz, DMSO-d$_6$): δ [ppm]=10.35 (s, 1H), 8.24 (s, 1H), 8.11 (s, 1H), 7.71-7.67 (m, 1H), 7.65 (dd, 2H), 7.59 (d, 1H), 7.54 (d, 1H), 7.29-7.24 (m, 3H), 6.47 (s, 1H), 5.74-5.67 (m, 1H), 4.13 (s, 3H), 3.39 (s, 3H), 2.10-1.98 (m, 2H), 1.21 (br d, 2H), 0.92 (t, 3H).

Example 109

4-{[2-{4-[5-Chloro-2-(4-chloro-1H-imidazol-1-yl)phenyl]-5-methoxy-2-oxopyridin-1(2H)-yl}pentanoyl]amino}benzoic acid (Racemate)

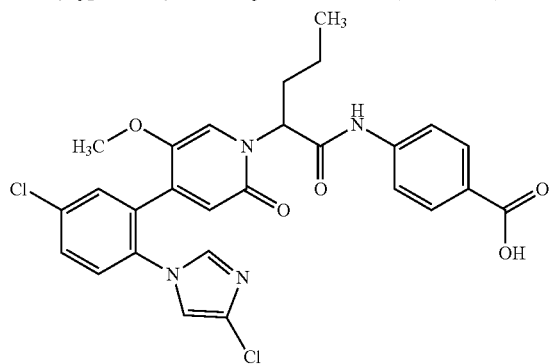

30.0 mg (68.8 μmol) of 2-{4-[5-chloro-2-(4-chloro-1H-imidazol-1-yl)phenyl]-5-methoxy-2-oxopyridin-1(2H)-yl}pentanoic acid (racemate) and 9.9 mg (72.2 μmol) of 4-aminobenzoic acid were reacted according to General Method 5. Yield: 26.0 mg (95% pure, 65% of theory).

LC/MS [Method 1]: $R_t$=0.98 min; MS (ESIpos): m/z=555 [M+H]$^+$ $^1$H-NMR (400 MHz, DMSO-d$_6$): δ [ppm]=12.76 (br s, 1H), 10.70 (s, 1H), 7.90 (d, 2H), 7.74-7.68 (m, 3H), 7.66-7.63 (m, 2H), 7.59 (d, 1H), 7.25 (d, 1H), 7.22 (s, 1H), 6.47 (s, 1H), 5.72-5.66 (m, 1H), 3.38 (m, 3H), 2.14-1.99 (m, 2H), 1.27-1.12 (m, 2H), 0.91 (t, 3H).

Example 110

4-({2-[4-{5-Chloro-2-[4-(trifluoromethyl)-1H-imidazol-1-yl]phenyl}-5-methoxy-2-oxopyridin-1(2H)-yl]-4-methoxybutanoyl}amino)-2-fluorobenzamide (Racemate)

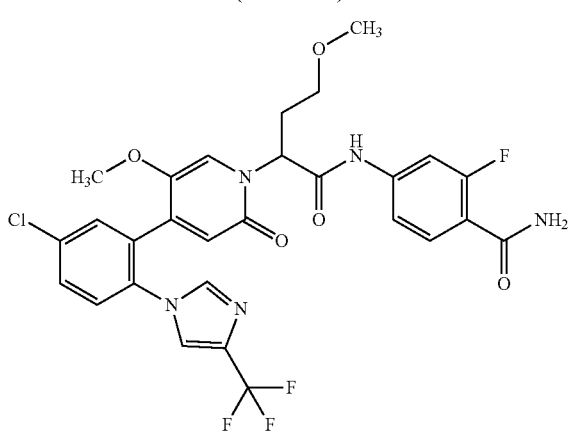

28.0 mg (purity 80%, 42.9 μmol) of 2-[4-{5-chloro-2-[4-(trifluoromethyl)-1H-imidazol-1-yl]phenyl}-5-methoxypyridin-1(2H)-yl]-4-methoxybutanoic acid hydrochloride (Racemate) and 10.2 mg (64.3 μmol) of 4-amino-2-fluorobenzamide in 350 μl of pyridine were reacted according to General Method 5. Yield: 14.0 mg (52% of theory).

LC/MS [Method 1]: $R_t$=0.87 min; MS (ESIpos): m/z=622 [M+H]$^+$ $^1$H-NMR (400 MHz, DMSO-d$_6$): δ [ppm]=10.69 (br s, 1H), 7.89 (s, 1H), 7.85 (s, 1H), 7.75-7.71 (m, 1H), 7.71-7.61 (m, 4H), 7.55-7.48 (m, 2H), 7.40 (dd, 1H), 7.17 (s, 1H), 6.52 (s, 1H), 5.64 (br s, 1H), 3.33 (s, 3H), 3.30-3.26 (m, 1H), 3.17 (s, 3H), 3.15-3.02 (m, 1H), 2.39-2.27 (m, 2H).

Example 111

2-[4-{5-Chloro-2-[4-(trifluoromethyl)-1H-imidazol-1-yl]phenyl}-5-methoxy-2-oxopyridin-1(2H)-yl]-4-methoxy-N-(2-methyl-2H-indazol-5-yl)butanamide (Racemate)

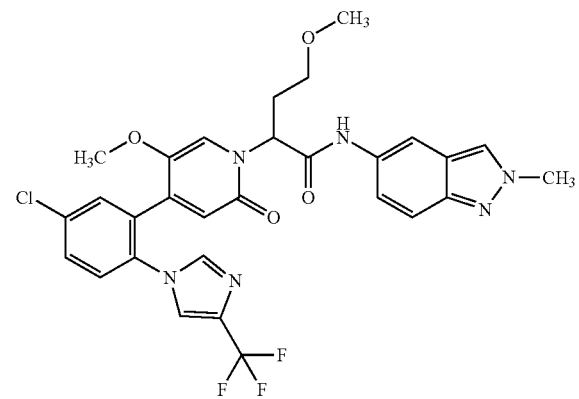 [SMILES: COCCC(C(=O)Nc1ccc2nn(C)cc2c1)n1cc(OC)c(-c2cc(Cl)ccc2-n2cnc(C(F)(F)F)c2)cc1=O]

28.0 mg (purity 80%, 42.9 μmol) of 2-[4-{5-Chloro-2-[4-(trifluoromethyl)-1H-imidazol-1-yl]phenyl}-5-methoxy-2-oxopyridin-1(2H)-yl]-4-methoxybutanoic acid hydrochloride (racemate) and 9.66 mg (64.3 μmol) of 2-methyl-2H-indazole-5-amine in 350 μl of pyridine were reacted according to General Method 5. Yield: 12.0 mg (45% of theory).

LC/MS [Method 1]: $R_t$=0.89 min; MS (ESIpos): m/z=615 [M+H]$^+$ $^1$H-NMR (400 MHz, DMSO-d$_6$): δ [ppm]=10.28 (br s, 1H), 8.24 (s, 1H), 8.09 (s, 1H), 7.89 (s, 1H), 7.86 (s, 1H), 7.75-7.70 (m, 1H), 7.70-7.65 (m, 2H), 7.53 (d, 1H), 7.29 (dd, 1H), 7.22 (s, 1H), 6.51 (s, 1H), 5.71 (br s, 1H), 4.12 (s, 3H), 3.34 (s, 3H), 3.29-3.24 (m, 1H), 3.18 (s, 3H), 3.15-3.05 (m, 1H), 2.37-2.26 (m, 2H).

Example 112

4-{[2-{4-[5-Chloro-2-(1H-tetrazol-1-yl)phenyl]-5-methoxy-2-oxopyridin-1(2H)-yl}pentanoyl]amino}benzoic acid (Racemate)

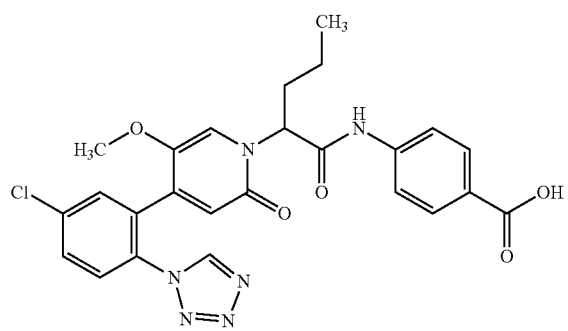 [SMILES: CCCC(C(=O)Nc1ccc(C(=O)O)cc1)n1cc(OC)c(-c2cc(Cl)ccc2-n2cnnn2)cc1=O]

40.0 mg (95.1 µmol) of 2-{4-[5-chloro-2-(1H-tetrazol-1-yl)phenyl]-5-methoxy-2-oxopyridin-1(2H)-yl}pentanoic acid (racemate) and 13.7 mg (99.8 µmol) of 4-aminobenzoic acid in 500 µl of pyridine were reacted according to General Method 5. Yield: 37.4 mg (75% of theory).

LC/MS [Method 10]: $R_t$=1.59 min; MS (ESIpos): m/z=523 [M+H]$^+$ $^1$H-NMR (400 MHz, DMSO-d$_6$): δ [ppm]=12.74 (s, 1H), 10.73 (s, 1H), 9.67 (s, 1H), 7.90 (d, 2H), 7.83-7.81 (m, 2H), 7.79-7.77 (m, 1H), 7.73 (d, 2H), 7.16 (s, 1H), 6.50 (s, 1H), 5.67 (dd, 1H), 3.29 (s, 3H), 2.09-1.98 (m, 2H), 1.28-1.11 (m, 2H), 0.91 (t, 3H).

Example 113

4-{[2-{4-[5-Chloro-2-(1H-tetrazol-1-yl)phenyl]-5-methoxy-2-oxopyridin-1(2H)-yl}pentanoyl]amino}-2-fluorobenzamide (Racemate)

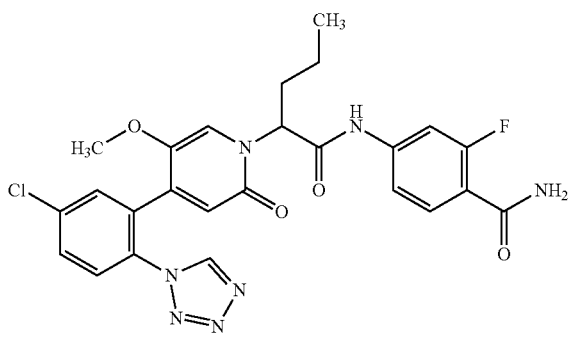 [SMILES: CCCC(C(=O)Nc1ccc(C(N)=O)c(F)c1)n1cc(OC)c(-c2cc(Cl)ccc2-n2cnnn2)cc1=O]

40.0 mg (95.1 µmol) of 2-{4-[5-chloro-2-(1H-tetrazol-1-yl)phenyl]-5-methoxy-2-oxopyridin-1(2H)-yl}pentanoic acid (racemate) and 22.7 mg (143 µmol) of 4-amino-2-fluorobenzamide in 1 ml of pyridine were reacted according to General Method 5. Yield: 41.3 mg (80% of theory).

LC/MS [Method 10]: $R_t$=1.53 min; MS (ESIpos): m/z=540 [M+H]$^+$ $^1$H-NMR (400 MHz, DMSO-d$_6$): δ [ppm]=10.79 (s, 1H), 9.68 (s, 1H), 7.82 (d, 2H), 7.78 (t, 1H), 7.69 (t, 1H), 7.63 (dd, 1H), 7.57-7.48 (m, 2H), 7.39 (dd, 1H), 7.15 (s, 1H), 6.51 (s, 1H), 5.63 (dd, 1H), 3.29-3.28 (m, 3H), 2.10-1.98 (m, 2H), 1.27-1.11 (m, 2H), 0.90 (t, 3H).

Example 114

4-{[(2S)-2-{4-[5-Chloro-2-(1H-tetrazol-1-yl)phenyl]-5-methoxy-2-oxopyridin-1(2H)-yl}pentanoyl]amino}-2-fluorobenzamide (Enantiomer 1)

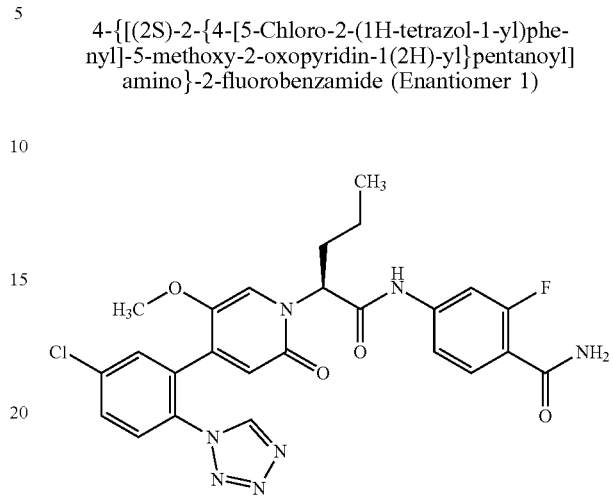

Enantiomer separation of 96.4 mg of 4-{[2-{4-[5-chloro-2-(1H-tetrazol-1-yl)phenyl]-5-methoxy-2-oxopyridin-1(2H)-yl}pentanoyl]amino}-2-fluorobenzamide (racemate) gave 42.8 mg of enantiomer 2 (chiral HPLC: $R_t$=14.0 min) and 41.2 mg of the title compound Example 114 (enantiomer 1): chiral HPLC: $R_t$=8.0 min; 100% ee.

Separating method: column: Daicel Chiralpak IC SFC 5 µm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak IC SFC 5 µm, 250 mm×4.6 mm; mobile phase: 70% carbon dioxide, 30% ethanol; flow rate: 3 ml/min; UV detection: 210 nm.

LC/MS [Method 10]: $R_t$=1.51 min; MS (ESIpos): m/z=540 [M+H]$^+$

Example 115

5-{[2-{4-[5-Chloro-2-(1H-tetrazol-1-yl)phenyl]-5-methoxy-2-oxopyridin-1(2H)-yl}pentanoyl]amino}pyridine-2-carboxamide (Racemate)

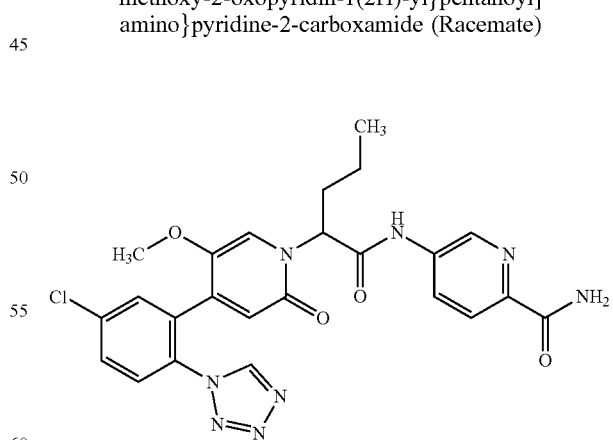

40.0 mg (95.1 µmol) of 2-{4-[5-chloro-2-(1H-tetrazol-1-yl)phenyl]-5-methoxy-2-oxopyridin-1(2H)-yl}pentanoic acid (racemate) and 20.6 mg (purity 95%, 143 µmol) of 5-aminopyridine-2-carboxamide in 1 ml of pyridine were reacted according to General Method 5. Yield: 40.2 mg (81% of theory).

LC/MS [Method 10]: R$_t$=1.45 min; MS (ESIpos): m/z=523 [M+H]$^+$ $^1$H-NMR (400 MHz, DMSO-d$_6$): δ [ppm]=10.88 (s, 1H), 9.68 (s, 1H), 8.82 (d, 1H), 8.21 (dd, 1H), 8.05-7.97 (m, 2H), 7.85-7.81 (m, 2H), 7.78 (t, 1H), 7.52 (br s, 1H), 7.16 (s, 1H), 6.52 (s, 1H), 5.66 (dd, 1H), 3.29 (s, 3H), 2.12-2.00 (m, 2H), 1.29-1.12 (m, 2H), 0.91 (t, 3H).

Example 116

5-{[2-{4-[5-Chloro-2-(1H-tetrazol-1-yl)phenyl]-5-methoxy-2-oxopyridin-1(2H)-yl}pentanoyl]-amino}-N-methylpyridine-2-carboxamide (Racemate)

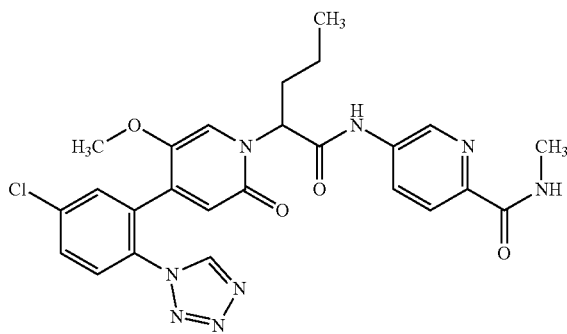 [SMILES: CCCC(C(=O)Nc1ccc(C(=O)NC)nc1)n1cc(OC)c(-c2cc(Cl)ccc2-n2cnnn2)cc1=O]

40.0 mg (95.1 μmol) of 2-{4-[5-chloro-2-(1H-tetrazol-1-yl)phenyl]-5-methoxy-2-oxopyridin-1(2H)-yl}pentanoic acid (racemate) and 22 mg (143 μmol) of 5-amino-N-methylpyridine-2-carboxamide in 1 ml of pyridine were reacted according to General Method 5. Yield: 39.6 mg (78% of theory).

LC/MS [Method 10]: R$_t$=1.53 min; MS (ESIpos): m/z=537 [M+H]$^+$ $^1$H-NMR (400 MHz, DMSO-d$_6$): δ [ppm]=10.87 (s, 1H), 9.68 (s, 1H), 8.83 (d, 1H), 8.68-8.62 (m, 1H), 8.19 (dd, 1H), 8.00 (d, 1H), 7.84-7.81 (m, 2H), 7.78 (t, 1H), 7.16 (s, 1H), 6.51 (s, 1H), 5.68-5.62 (m, 1H), 3.29 (s, 3H), 2.80 (d, 3H), 2.12-2.00 (m, 2H), 1.28-1.12 (m, 2H), 0.91 (t, 3H).

Example 117

N-(Quinoxalin-6-yl)-2-{4-[5-chloro-2-(1H-tetrazol-1-yl)phenyl]-5-methoxy-2-oxopyridin-1(2H)-yl}pentanamide (Racemate)

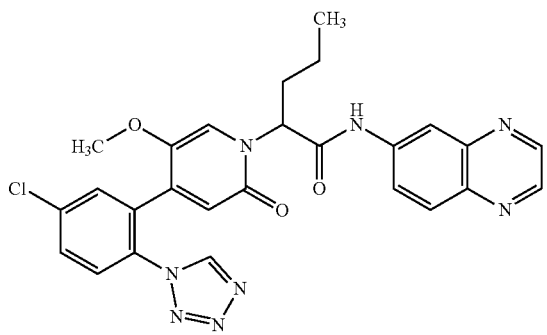 [SMILES: CCCC(C(=O)Nc1ccc2nccnc2c1)n1cc(OC)c(-c2cc(Cl)ccc2-n2cnnn2)cc1=O]

40.0 mg (95.1 μmol) of 2-{4-[5-chloro-2-(1H-tetrazol-1-yl)phenyl]-5-methoxy-2-oxopyridin-1(2H)-yl}pentanoic acid (racemate) and 20.7 mg (143 μmol) of quinoxaline-6-amine in 1 ml of pyridine were reacted according to General Method 5. Yield: 37.4 mg (74% of theory).

LC/MS [Method 10]: R$_t$=1.62 min; MS (ESIpos): m/z=531 [M+H]$^+$ $^1$H-NMR (400 MHz, DMSO-d$_6$): δ [ppm]=10.94 (s, 1H), 9.69 (s, 1H), 8.89 (d, 1H), 8.84 (d, 1H), 8.51 (d, 1H), 8.07 (d, 1H), 7.97 (dd, 1H), 7.84-7.81 (m, 2H), 7.80-7.78 (m, 1H), 7.21 (s, 1H), 6.52 (s, 1H), 5.75-5.69 (m, 1H), 3.31 (s, 3H), 2.15-2.04 (m, 2H), 1.32-1.15 (m, 2H), 0.93 (t, 3H).

Example 118

N-(Quinoxalin-6-yl)-(2S)-2-{4-[5-chloro-2-(1H-tetrazol-1-yl)phenyl]-5-methoxy-2-oxopyridin-1(2H)-yl}pentanamide (Enantiomer 2)

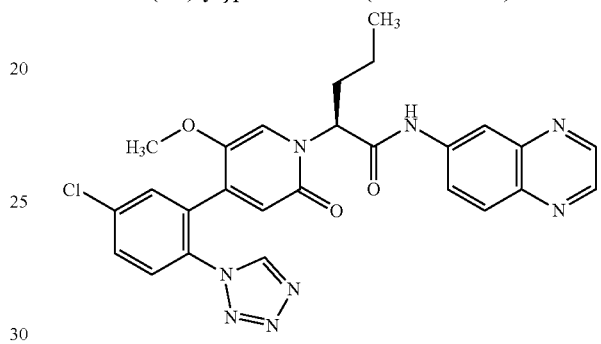

Enantiomer separation of 103 mg of N-(quinoxalin-6-yl)-2-{4-[5-chloro-2-(1H-tetrazol-1-yl)phenyl]-5-methoxy-2-oxopyridin-1(2H)-yl}pentanamide (racemate) gave 47.3 mg of enantiomer 1 (chiral HPLC: R$_t$=7.1 min) and 40.0 mg of the title compound Example 118 (enantiomer 2): chiral HPLC: R$_t$=11.6 min; 100% ee.

Separating method: column: Daicel Chiralpak ID SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak ID SFC 3 μm, 100 mm×4.6 mm; mobile phase: 70% carbon dioxide, 30% ethanol; flow rate: 3 ml/min; UV detection: 210 nm.

LC/MS [Method 10]: R$_t$=1.62 min; MS (ESIpos): m/z=531 [M+H]$^+$

Example 119

2-{4-[5-Chloro-2-(1H-tetrazol-1-yl)phenyl]-5-methoxy-2-oxopyridin-1(2H)-yl}-N-(2-methyl-2H-indazol-5-yl)pentanamide (Racemate)

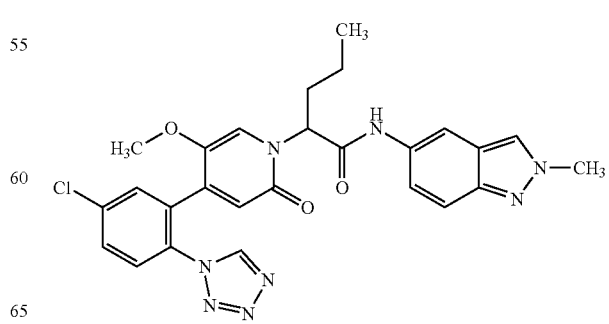

35 mg (83.2 µmol) of 2-{4-[5-chloro-2-(1H-tetrazol-1-yl)phenyl]-5-methoxy-2-oxopyridin-1(2H)-yl}pentanoic acid (racemate) and 18.4 mg (125 µmol) of 2-methyl-2H-indazole-5-amine in 1 ml of pyridine were reacted according to General Method 5. Yield: 34 mg (77% of theory).

LC/MS [Method 10]: $R_t$=1.57 min; MS (ESIpos): m/z=533 [M+H]$^+$ $^1$H-NMR (400 MHz, DMSO-d$_6$): δ [ppm]=10.37 (s, 1H), 9.68 (s, 1H), 8.24 (s, 1H), 8.13-8.11 (m, 1H), 7.83-7.81 (m, 2H), 7.80-7.77 (m, 1H), 7.54 (d, 1H), 7.27 (dd, 1H), 7.21 (s, 1H), 6.50 (s, 1H), 5.69 (t, 1H), 4.13 (s, 3H), 3.29 (s, 3H), 2.01 (q, 2H), 1.21 (td, 2H), 0.94-0.89 (m, 3H).

Example 120

(2S)-2-{4-[5-Chloro-2-(1H-tetrazol-1-yl)phenyl]-5-methoxy-2-oxopyridin-1(2H)-yl}-N-(2-methyl-2H-indazol-5-yl)pentanamide (Enantiomer 2)

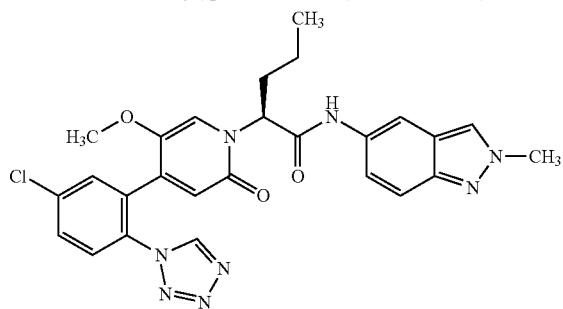 [SMILES: CCC[C@@H](C(=O)Nc1ccc2nn(C)cc2c1)n1cc(OC)c(-c2cc(Cl)ccc2-n2cnnn2)cc1=O]

Enantiomer separation of 2-{4-[5-chloro-2-(1H-tetrazol-1-yl)phenyl]-5-methoxy-2-oxopyridin-1(2H)-yl}-N-(2-methyl-2H-indazol-5-yl)pentanamide (90.0 mg, 169 µmol) (racemate) gave 41.1 mg of enantiomer 1 (chiral HPLC: $R_t$=4.8 min) and 43.0 mg of the title compound Example 120 (enantiomer 2): chiral HPLC: $R_t$=7.7 min; 100% ee.

Separating method: column: Daicel Chiralpak AZ-H SFC 5 µm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak AZ SFC 3 µm, 100 mm×4.6 mm; mobile phase: 70% carbon dioxide, 30% ethanol; flow rate: 3 ml/min; UV detection: 210 nm.

LC/MS [Method 10]: $R_t$=1.56 min; MS (ESIpos): m/z=533 [M+H]$^+$

Example 121

4-({2-[4-{5-Chloro-2-[4-(difluoromethyl)-1H-1,2,3-triazol-1-yl]phenyl}-5-methoxy-2-oxopyridin-1(2H)-yl]pentanoyl}amino)-2-fluorobenzamide (Racemate)

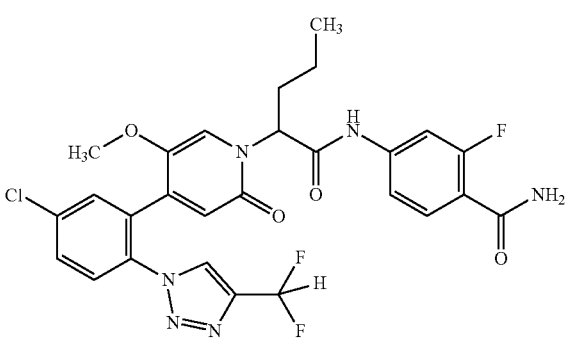 [SMILES: CCCC(C(=O)Nc1ccc(C(N)=O)c(F)c1)n1cc(OC)c(-c2cc(Cl)ccc2-n2cc(C(F)F)nn2)cc1=O]

39.0 mg (purity 85%, 73.2 µmol) of 2-[4-{5-chloro-2-[4-(difluoromethyl)-1H-1,2,3-triazol-1-yl]phenyl}-5-methoxy-2-oxopyridin-1(2H)-yl]pentanoic acid (racemate) and 17.4 mg (110 µmol) of 4-amino-2-fluorobenzamide were mixed in 1.0 ml of pyridine. 139 µl (0.22 mmol) propylphosphonic anhydride (T3P, 50% solution in ethyl acetate) were then added dropwise at room temperature and the mixture was stirred additional 1 h at 50° C. The reaction mixture was brought to room temperature and then purified by preparative RP-HPLC (0.1% formic acid/acetonitrile gradient). Yield: 36 mg (84% of theory).

LC/MS [Method 10]: $R_t$=1.66 min; MS (ESIpos): m/z=589 [M+H]$^+$ $^1$H-NMR (400 MHz, DMSO-d$_6$): δ [ppm]=10.78 (s, 1H), 8.70 (s, 1H), 7.79 (s, 2H), 7.74 (s, 1H), 7.72-7.61 (m, 2H), 7.57-7.48 (m, 2H), 7.38 (dd, 1H), 7.21 (t, 1H), 7.15 (s, 1H), 6.50 (s, 1H), 5.63 (dd, 1H), 3.26 (s, 3H), 2.12-1.96 (m, 2H), 1.27-1.08 (m, 2H), 0.93-0.86 (m, 3H).

Example 122

2-[4-{5-Chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)pentanamide (Racemate)

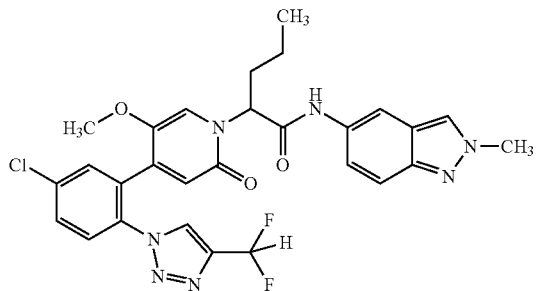 [SMILES: CCCC(C(=O)Nc1ccc2nn(C)cc2c1)n1cc(OC)c(-c2cc(Cl)ccc2-n2cc(C(F)F)nn2)cc1=O]

39.0 mg (purity 85%, 73.2 µmol) of 2-[4-{5-chloro-2-[4-(difluoromethyl)-1H-1,2,3-triazol-1-yl]phenyl}-5-methoxy-2-oxopyridin-1(2H)-yl]pentanoic acid (racemate) and 16.2 mg (110 µmol) of 2-methyl-2H-indazole-5-amine in 1 ml of pyridine were reacted according to General Method 5. Yield: 38.4 mg (90% of theory).

LC/MS [Method 10]: $R_t$=1.72 min; MS (ESIpos): m/z=582 [M+H]$^+$ $^1$H-NMR (400 MHz, DMSO-d$_6$): δ [ppm]=10.35 (s, 1H), 8.71 (s, 1H), 8.24 (s, 1H), 8.10 (s, 1H), 7.81-7.76 (m, 2H), 7.74 (s, 1H), 7.54 (d, 1H), 7.36-7.07 (m, 3H), 6.50 (s, 1H), 5.69 (t, 1H), 4.13 (s, 3H), 3.27 (s, 3H), 2.01 (q, 2H), 1.28-1.11 (m, 2H), 0.90 (t, 3H).

Example 123

(2S)-2-[4-{5-Chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)pentanamide (Enantiomer 2)

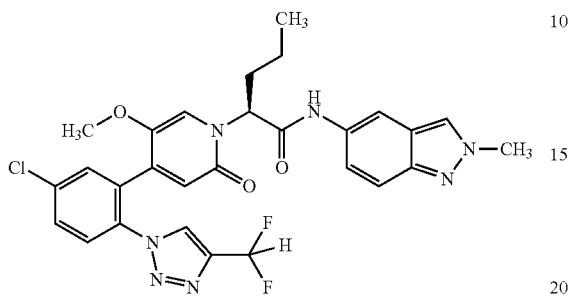

Enantiomer separation of 96.4 mg of 2-[4-{5-chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)pentanamide (racemate) gave 43.4 mg of enantiomer 1 (chiral HPLC: $R_t$=3.5 min) and 35.1 mg of the title compound Example 123 (enantiomer 2): chiral HPLC: $R_t$=5.1 min; 100% ee.

Separating method: column: Daicel Chiralpak IA SFC, 5 μm 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak IA SFC 3 μm, 100 mm×4.6 mm; mobile phase: 70% carbon dioxide, 30% ethanol; flow rate: 3 ml/min; UV detection: 210 nm.

LC/MS [Method 1]: $R_t$=0.93 min; MS (ESIpos): m/z=582 [M+H]$^+$

Example 124

5-({2-[4-{5-Chloro-2-[4-(difluoromethyl)-1H-1,2,3-triazol-1-yl]phenyl}-5-methoxy-2-oxopyridin-1(2H)-yl]pentanoyl}amino)-N-methylpyridine-2-carboxamide (Racemate)

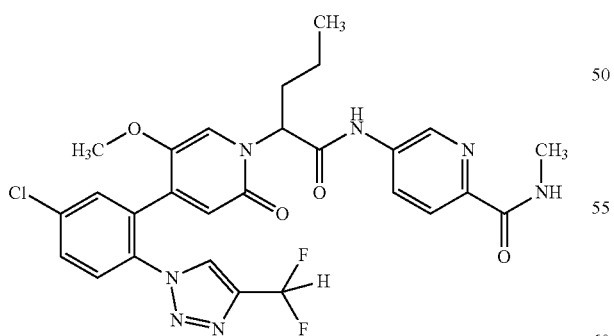

39.0 mg (purity 85%, 73.2 μmol) of 2-[4-{5-chloro-2-[4-(difluoromethyl)-1H-1,2,3-triazol-1-yl]phenyl}-5-methoxy-2-oxopyridin-1(2H)-yl]pentanoic acid (racemate) and 16.9 mg (110 μmol) of 5-amino-N-methylpyridine-2-carboxamide in 1 ml of pyridine were reacted according to General Method 5. Yield: 36.2 mg (84% of theory).

LC/MS [Method 10]: $R_t$=1.68 min; MS (ESIpos): m/z=586 [M+H]$^+$ $^1$H-NMR (400 MHz, DMSO-d$_6$): δ [ppm]=10.86 (br s, 1H), 8.85 (d, 1H), 8.70 (s, 1H), 8.65 (q, 1H), 8.18 (dd, 1H), 8.00 (d, 1H), 7.81-7.76 (m, 2H), 7.74 (t, 1H), 7.15 (s, 1H), 6.51 (s, 1H), 5.65 (dd, 1H), 3.26 (s, 3H), 2.80 (d, 3H), 2.14-1.99 (m, 2H), 1.27-1.08 (m, 2H), 0.90 (t, 3H).

Example 125

4-{[2-{4-[5-Chloro-2-(4-chloro-1H-1,2,3-triazol-1-yl)phenyl]-5-methoxy-2-oxopyridin-1(2H)-yl}pentanoyl]amino}-2-fluorobenzamide (Racemate)

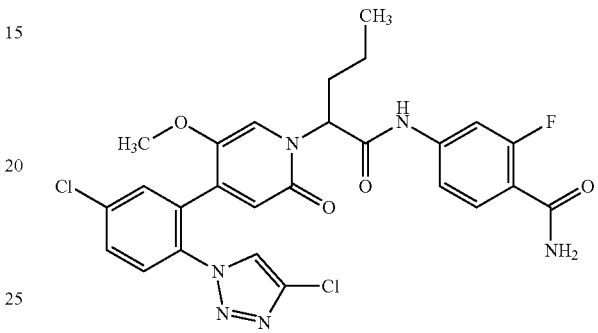

35.0 mg (76.8 μmol) of 2-{4-[5-chloro-2-(4-chloro-1H-1,2,3-triazol-1-yl)phenyl]-5-methoxy-2-oxopyridin-1(2H)-yl}pentanoic acid (racemate) and 18.3 mg (115 μmol) of 4-amino-2-fluorobenzamide were mixed in 1.0 ml of pyridine. 137 μl (0.23 mmol) propylphosphonic anhydride (T3P, 50% solution in ethyl acetate) were then added dropwise at room temperature and the mixture was stirred additional 1 h at 50° C. The reaction mixture was brought to room temperature and then purified by preparative RP-HPLC (0.1% formic acid/acetonitrile gradient). Yield: 33.1 mg (75% of theory).

LC/MS [Method 10]: $R_t$=1.70 min; MS (ESIpos): m/z=573 [M+H]$^+$, $^1$H-NMR (400 MHz, DMSO-d$_6$): δ [ppm]=10.78 (s, 1H), 8.59 (s, 1H), 7.81-7.72 (m, 3H), 7.72-7.61 (m, 2H), 7.57-7.49 (m, 2H), 7.39 (dd, 1H), 7.18 (s, 1H), 6.47 (s, 1H), 5.64 (br dd, 1H), 3.31 (s, 3H), 2.13-1.97 (m, 2H), 1.27-1.12 (m, 2H), 0.91 (t, 3H).

Example 126

N-(Quinoxalin-6-yl)-2-{4-[5-chloro-2-(4-chloro-1H-1,2,3-triazol-1-yl)phenyl]-5-methoxy-2-oxopyridin-1(2H)-yl}pentanamide (Racemate)

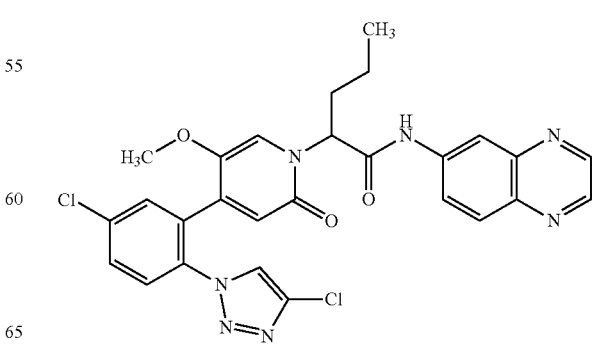

35.0 mg (76.8 µmol) of 2-{4-[5-chloro-2-(4-chloro-1H-1,2,3-triazol-1-yl)phenyl]-5-methoxy-2-oxopyridin-1(2H)-yl}pentanoic acid (racemate) and 16.7 mg (115 µmol) of quinoxaline-6-amine in 1 ml of pyridine were reacted according to General Method 5. Yield: 37.3 mg (86% of theory).

LC/MS [Method 10]: $R_t$=1.81 min; MS (ESIpos): m/z=564 [M+H]$^+$ $^1$H-NMR (400 MHz, DMSO-d$_6$): δ [ppm]=10.93 (s, 1H), 8.89 (d, 1H), 8.84 (d, 1H), 8.60 (s, 1H), 8.52 (d, 1H), 8.07 (d, 1H), 7.97 (dd, 1H), 7.81-7.72 (m, 3H), 7.24 (s, 1H), 6.48 (s, 1H), 5.73 (dd, 1H), 3.34 (s, 3H), 2.19-2.04 (m, 2H), 1.31-1.15 (m, 2H), 0.93 (t, 3H).

Example 127

5-{[2-{4-[5-Chloro-2-(4-chloro-1H-1,2,3-triazol-1-yl)phenyl]-5-methoxy-2-oxopyridin-1(2H)-yl}pentanoyl]amino}-N-methylpyridine-2-carboxamide (Racemate)

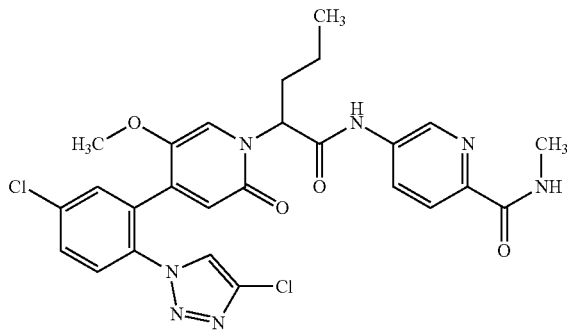 [SMILES: CCCC(C(=O)Nc1ccc(C(=O)NC)nc1)n1cc(OC)c(-c2cc(Cl)ccc2-n2cc(Cl)nn2)cc1=O]

35.0 mg (76.8 µmol) of 2-{4-[5-chloro-2-(4-chloro-1H-1,2,3-triazol-1-yl)phenyl]-5-methoxy-2-oxopyridin-1(2H)-yl}pentanoic acid (racemate) and 17.8 mg (115 µmol) of 5-amino-N-methylpyridine-2-carboxamide in 1 ml of pyridine were reacted according to General Method 5. Yield: 36.8 mg (84% of theory).

LC/MS [Method 10]: $R_t$=1.71 min; MS (ESIpos): m/z=570 [M+H]$^+$ $^1$H-NMR (400 MHz, DMSO-d$_6$): δ [ppm]=10.85 (s, 1H), 8.85 (d, 1H), 8.68-8.62 (m, 1H), 8.59 (s, 1H), 8.19 (dd, 1H), 8.00 (d, 1H), 7.81-7.73 (m, 3H), 7.19 (s, 1H), 6.47 (s, 1H), 5.66 (dd, 1H), 3.31 (s, 3H), 2.80 (d, 3H), 2.16-2.02 (m, 2H), 1.28-1.13 (m, 2H), 0.92 (t, 3H).

Example 128

5-{[(2S)-2-{4-[5-Chloro-2-(4-chloro-1H-1,2,3-triazol-1-yl)phenyl]-5-methoxy-2-oxopyridin-1(2H)-yl}pentanoyl]amino}-N-methylpyridine-2-carboxamide (Enantiomer 2)

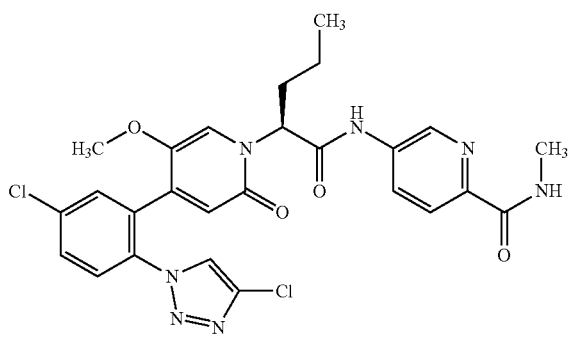

Enantiomer separation of 5-{[2-{4-[5-chloro-2-(4-chloro-1H-1,2,3-triazol-1-yl)phenyl]-5-methoxy-2-oxopyridin-1(2H)-yl}pentanoyl]amino}-N-methylpyridine-2-carboxamide (122 mg, 214 µmol) (racemate) gave 51.8 mg of enantiomer 1 (chiral HPLC: $R_t$=4.1 min) and 52.7 mg (purity 100%, 43% of theory) of the title compound Example 128 (enantiomer 2): chiral HPLC: $R_t$=7.1 min; 100% ee.

Separating method: column: Daicel Chiralpak IA SFC, 5 µm 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak IA SFC 3 µm, 100 mm×4.6 mm; mobile phase: 70% carbon dioxide, 30% ethanol; flow rate: 3 ml/min; UV detection: 210 nm.

LC/MS [Method 10]: $R_t$=1.72 min; MS (ESIpos): m/z=570 [M+H]$^+$.

Example 129

2-{4-[5-Chloro-2-(4-chloro-1H-1,2,3-triazol-1-yl)phenyl]-5-methoxy-2-oxopyridin-1(2H)-yl}-N-(2-methyl-2H-indazol-5-yl)pentanamide (Racemate)

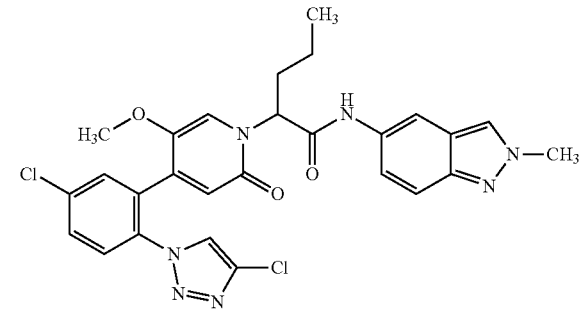 [SMILES: CCCC(C(=O)Nc1ccc2nn(C)cc2c1)n1cc(OC)c(-c2cc(Cl)ccc2-n2cc(Cl)nn2)cc1=O]

35.0 mg (76.8 µmol) of 2-{4-[5-chloro-2-(4-chloro-1H-1,2,3-triazol-1-yl)phenyl]-5-methoxy-2-oxopyridin-1(2H)-yl}pentanoic acid (racemate) and 17.0 mg (115 µmol) of 2-methyl-2H-indazole-5-amine in 1 ml of pyridine were reacted according to General Method 5. Yield: 34.4 mg (78% of theory).

LC/MS [Method 10]: $R_t$=1.75 min; MS (ESIpos): m/z=566 [M+H]$^+$ $^1$H-NMR (400 MHz, DMSO-d$_6$): δ [ppm]=10.35 (s, 1H), 8.60 (s, 1H), 8.24 (s, 1H), 8.11 (d, 1H), 7.81-7.72 (m, 3H), 7.55 (d, 1H), 7.28 (dd, 1H), 7.24 (s, 1H), 6.46 (s, 1H), 5.70 (t, 1H), 4.13 (s, 3H), 3.31 (s, 3H), 2.08-1.98 (m, 2H), 1.30-1.07 (m, 2H), 0.92 (t, 3H).

Example 130

(2S)-2-{4-[5-Chloro-2-(4-chloro-1H-1,2,3-triazol-1-yl)phenyl]-5-methoxy-2-oxopyridin-1(2H)-yl}-N-(2-methyl-2H-indazol-5-yl)pentanamide (Enantiomer 2)

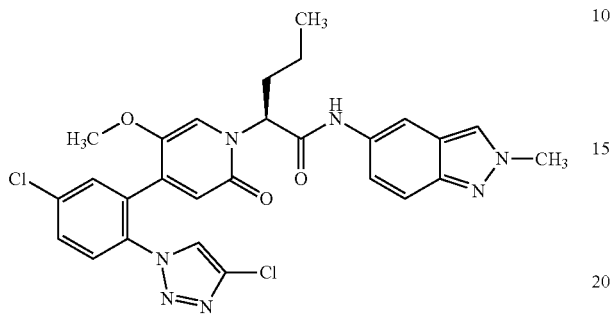

Enantiomer separation of 122 mg of 2-{4-[5-chloro-2-(4-chloro-1H-1,2,3-triazol-1-yl)phenyl]-5-methoxy-2-oxopyridin-1(2H)-yl}-N-(2-methyl-2H-indazol-5-yl)pentanamide (racemate) gave 50.1 mg of enantiomer 1 (chiral HPLC: $R_t$=3.9 min) and 48.4 mg of the title compound Example 130 (enantiomer 2): chiral HPLC: $R_t$=5.65 min; 100% ee.

Separating method: column: Daicel Chiralpak IA SFC, 5 μm 250 mm×20 mm; mobile phase: carbon dioxide 70%/methanol 30%; temperature: 40° C.; flow rate: 80 ml/min; pressure: 100 bar; UV detection: 210 nm.

Analysis: column: Chiralpak IA SFC 3 μm, 100 mm×4.6 mm; mobile phase: 70% carbon dioxide, 30% methanol; flow rate: 3 ml/min; UV detection: 210 nm.

LC/MS [Method 10]: $R_t$=1.74 min; MS (ESIpos): m/z=566 [M+H]$^+$

Example 131

5-{[2-{4-[5-Chloro-2-(4,5-dihydro-1,2-oxazol-3-yl)phenyl]-5-methoxy-2-oxopyridin-1(2H)-yl}pentanoyl]amino}-N-methylpyridine-2-carboxamide (Racemate)

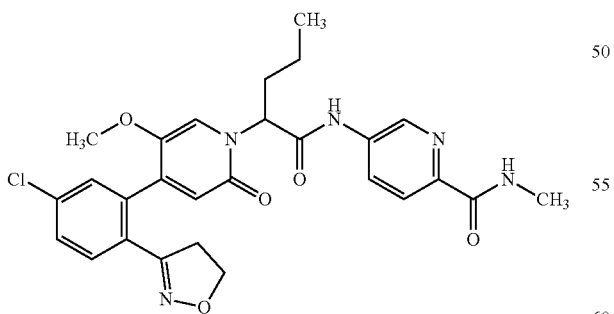

32.0 mg (79.0 μmol) of 2-{4-[5-chloro-2-(4,5-dihydro-1,2-oxazol-3-yl)phenyl]-5-methoxy-2-oxopyridin-1(2H)-yl}pentanoic acid (racemate) and 18.3 mg (119 μmol) of 5-amino-N-methylpyridine-2-carboxamide in 0.65 ml of pyridine were reacted according to General Method 5. Yield: 33 mg (78% of theory).

LC/MS [Method 1]: $R_t$=0.90 min; MS (ESIpos): m/z=538 [M+H]$^+$ $^1$H-NMR (400 MHz, DMSO-d$_6$): δ [ppm]=10.92 (s, 1H), 8.86 (d, 1H), 8.66 (q, 1H), 8.22 (dd, 1H), 8.01 (d, 1H), 7.66-7.57 (m, 2H), 7.44 (d, 1H), 7.31 (s, 1H), 6.37 (s, 1H), 5.74-5.67 (m, 1H), 4.32-4.22 (m, 2H), 3.58 (s, 3H), 3.29-3.12 (m, 2H), 2.80 (d, 3H), 2.17-2.05 (m, 2H), 1.38-1.19 (m, 2H), 0.94 (t, 3H).

Example 132

2-{4-[5-Chloro-2-(4,5-dihydro-1,2-oxazol-3-yl)phenyl]-5-methoxy-2-oxopyridin-1(2H)-yl}-N-(2-methyl-2H-indazol-5-yl)pentanamide (Racemate)

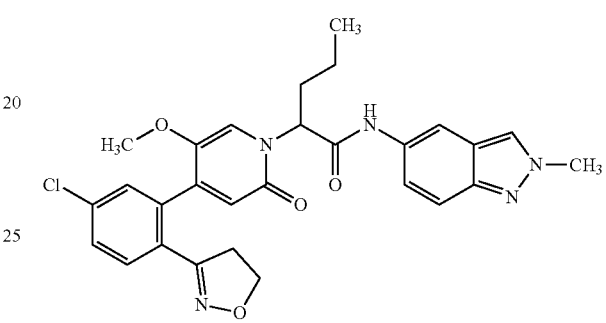

32.0 mg (79.0 μmol) of 2-{4-[5-chloro-2-(4,5-dihydro-1,2-oxazol-3-yl)phenyl]-5-methoxy-2-oxopyridin-1(2H)-yl}pentanoic acid (racemate) and 17.8 mg (119 μmol) of 5-amino-2-methyl-2H-indazole in 0.65 ml of pyridine were reacted according to General Method 5. Yield: 33 mg (78% of theory).

LC/MS [Method 1]: $R_t$=0.91 min; MS (ESIpos): m/z=534 [M+H]$^+$ $^1$H-NMR (400 MHz, DMSO-d$_6$): δ [ppm]=10.41 (s, 1H), 8.25 (s, 1H), 8.14 (d, 1H), 7.66-7.62 (m, 1H), 7.61-7.57 (m, 1H), 7.55 (d, 1H), 7.44 (d, 1H), 7.38 (s, 1H), 7.29 (dd, 1H), 6.36 (s, 1H), 5.77-5.71 (m, 1H), 4.32-4.22 (m, 2H), 4.13 (s, 3H), 3.58 (s, 3H), 3.29-3.12 (m, 2H), 2.11-2.01 (m, 2H), 1.37-1.20 (m, 2H), 0.94 (t, 3H).

Example 133

4-{[2-{4-[5-Chloro-2-(4,5-dihydro-1,2-oxazol-3-yl)phenyl]-5-methoxy-2-oxopyridin-1(2H)-yl}pentanoyl]amino}-2-fluorobenzamide (Racemate)

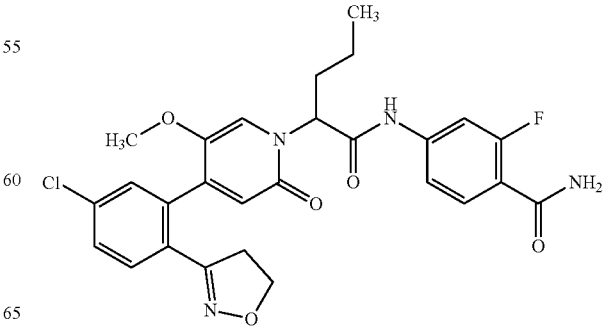

32.0 mg (79.0 μmol) of 2-{4-[5-chloro-2-(4,5-dihydro-1,2-oxazol-3-yl)phenyl]-5-methoxy-2-oxopyridin-1(2H)-yl}pentanoic acid (racemate) and 18.8 mg (119 μmol) of 4-amino-2-fluorobenzamide in 0.65 ml of pyridine were reacted according to General Method 5. Yield: 29 mg (68% of theory).

LC/MS [Method 1]: $R_t$=0.89 min; MS (ESIpos): m/z=541 [M+H]$^+$ $^1$H-NMR (400 MHz, DMSO-d$_6$): δ [ppm]=10.84 (s, 1H), 7.72-7.63 (m, 3H), 7.61-7.57 (m, 1H), 7.56-7.48 (m, 2H), 7.44 (d, 1H), 7.41 (dd, 1H), 7.31 (s, 1H), 6.37 (s, 1H), 5.68 (dd, 1H), 4.32-4.23 (m, 2H), 3.58 (s, 3H), 3.29-3.13 (m, 2H), 2.15-2.01 (m, 2H), 1.36-1.18 (m, 2H), 0.93 (t, 3H).

Example 134

N-(Quinoxalin-6-yl)-2-{4-[5-chloro-2-(4,5-dihydro-1,2-oxazol-3-yl)phenyl]-5-methoxy-2-oxopyridin-1(2H)-yl}pentanamide (Racemate)

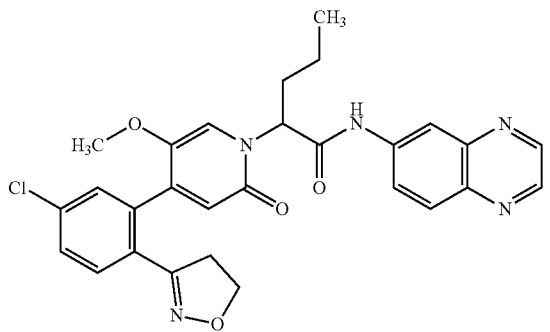 [SMILES: CCCC(C(=O)Nc1ccc2nccnc2c1)n1cc(OC)c(-c2cc(Cl)ccc2C2=NOCC2)cc1=O]

32.0 mg (79.0 μmol) of 2-{4-[5-chloro-2-(4,5-dihydro-1,2-oxazol-3-yl)phenyl]-5-methoxy-2-oxopyridin-1(2H)-yl}pentanoic acid (racemate) and 17.2 mg (119 μmol) of quinoxaline-6-amine in 0.65 ml of pyridine were reacted according to General Method 5. Yield: 30 mg (71% of theory).

LC/MS [Method 1]: $R_t$=0.94 min; MS (ESIpos): m/z=532 [M+H]$^+$ $^1$H-NMR (400 MHz, DMSO-d$_6$): δ [ppm]=10.99 (s, 1H), 8.90 (d, 1H), 8.84 (d, 1H), 8.54 (d, 1H), 8.08 (d, 1H), 7.99 (dd, 1H), 7.67-7.63 (m, 1H), 7.61-7.57 (m, 1H), 7.46 (d, 1H), 7.37 (s, 1H), 6.38 (s, 1H), 5.78 (t, 1H), 4.33-4.23 (m, 2H), 3.60 (s, 3H), 3.29-3.13 (m, 2H), 2.14 (q, 2H), 1.40-1.23 (m, 2H), 0.96 (t, 3H).

Example 135

5-{[2-{4-[5-Chloro-2-(4,5-dihydro-1,2-oxazol-3-yl)phenyl]-5-methoxy-2-oxopyridin-1(2H)-yl}pentanoyl]amino}pyridine-2-carboxamide (Racemate)

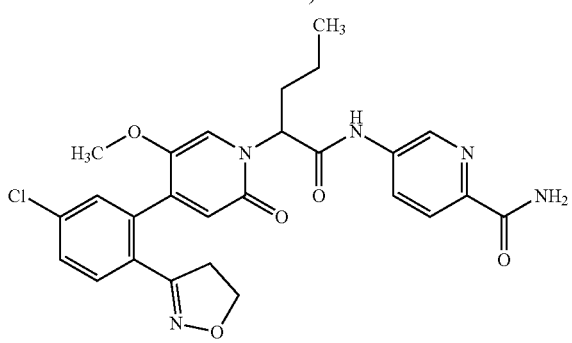

32.0 mg (79.0 μmol) of 2-{4-[5-chloro-2-(4,5-dihydro-1,2-oxazol-3-yl)phenyl]-5-methoxy-2-oxopyridin-1(2H)-yl}pentanoic acid (racemate) and 16.8 mg (119 μmol) of 5-aminopyridine-2-carboxamide in 0.65 ml of pyridine were reacted according to General Method 5. Yield: 31 mg (75% of theory).

LC/MS [Method 1]: $R_t$=0.86 min; MS (ESIpos): m/z=524 [M+H]$^+$ $^1$H-NMR (400 MHz, DMSO-d$_6$): δ [ppm]=10.93 (s, 1H), 8.84 (d, 1H), 8.23 (dd, 1H), 8.04-7.99 (m, 2H), 7.66-7.63 (m, 1H), 7.61-7.57 (m, 1H), 7.52 (br s, 1H), 7.45 (d, 1H), 7.32 (s, 1H), 6.37 (s, 1H), 5.71 (dd, 1H), 4.32-4.23 (m, 2H), 3.58 (s, 3H), 3.29-3.12 (m, 2H), 2.17-2.06 (m, 2H), 1.37-1.20 (m, 2H), 0.94 (t, 3H).

Example 136

5-{[2-{4-[5-Chloro-2-(1H-tetrazol-1-yl)phenyl]-5-methoxy-2-oxopyridin-1(2H)-yl}hexanoyl]amino}pyridine-2-carboxamide (Racemate)

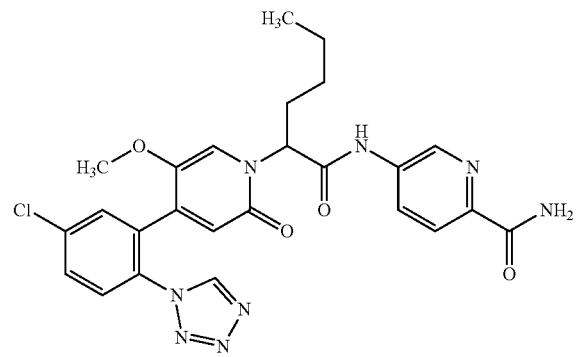 [SMILES: CCCCC(C(=O)Nc1ccc(C(N)=O)nc1)n1cc(OC)c(-c2cc(Cl)ccc2-n2cnnn2)cc1=O]

35.0 mg (purity 93%, 77.9 μmol) of 2-{4-[5-chloro-2-(1H-tetrazol-1-yl)phenyl]-5-methoxy-2-oxopyridin-1(2H)-yl}hexanoic acid (racemate) and 16.9 mg (purity 95%, 117 μmol) of 5-aminopyridine-2-carboxamide in 1.0 ml of pyridine were reacted according to General Method 5. Yield: 32 mg (77% of theory).

LC/MS [Method 10]: $R_t$=1.55 min; MS (ESIpos): m/z=537 [M+H]$^+$ $^1$H-NMR (400 MHz, DMSO-d$_6$): δ [ppm]=10.87 (s, 1H), 9.67 (s, 1H), 8.82 (d, 1H), 8.20 (dd, 1H), 8.04-7.97 (m, 2H), 7.85-7.80 (m, 2H), 7.80-7.77 (m, 1H), 7.52 (br s, 1H), 7.16 (s, 1H), 6.52 (s, 1H), 5.63 (t, 1H), 3.28 (s, 3H), 2.08 (q, 2H), 1.39-1.22 (m, 2H), 1.22-1.07 (m, 2H), 0.88 (t, 3H).

Example 137

4-{[2-{4-[5-Chloro-2-(1H-tetrazol-1-yl)phenyl]-5-methoxy-2-oxopyridin-1(2H)-yl}hexanoyl]amino}-2-fluorobenzamide (Racemate)

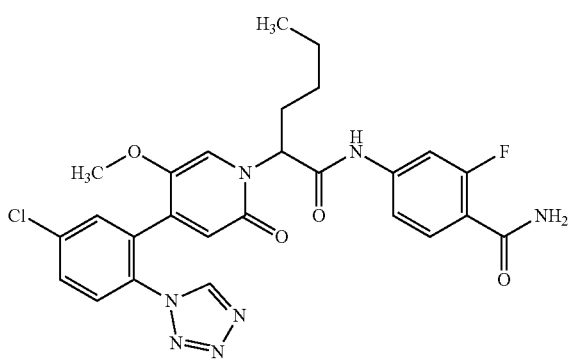 [SMILES: CCCCC(C(=O)Nc1ccc(C(N)=O)c(F)c1)n1cc(OC)c(-c2cc(Cl)ccc2-n2cnnn2)cc1=O]

35.0 mg (purity 93%, 77.9 µmol) of 2-{4-[5-chloro-2-(1H-tetrazol-1-yl)phenyl]-5-methoxy-2-oxopyridin-1(2H)-yl}hexanoic acid (racemate) and 18.6 mg (117 µmol) of 4-amino-2-fluorobenzamide in 1.0 ml of pyridine were reacted according to General Method 5. Yield: 31 mg (72% of theory).

LC/MS [Method 10]: $R_t$=1.62 min; MS (ESIpos): m/z=554 [M+H]$^+$ $^1$H-NMR (400 MHz, DMSO-d$_6$): δ [ppm]=10.78 (s, 1H), 9.67 (s, 1H), 7.84-7.80 (m, 2H), 7.79-7.77 (m, 1H), 7.68 (t, 1H), 7.66-7.61 (m, 1H), 7.57-7.48 (m, 2H), 7.39 (dd, 1H), 7.15 (s, 1H), 6.51 (s, 1H), 5.60 (t, 1H), 3.28 (s, 3H), 2.05 (q, 2H), 1.36-1.23 (m, 2H), 1.21-1.05 (m, 2H), 0.88 (t, 3H).

Example 138

4-{[2-{4-[5-Chloro-2-(1H-tetrazol-1-yl)phenyl]-5-methoxy-2-oxopyridin-1(2H)-yl}hexanoyl]amino}benzoic acid (Racemate)

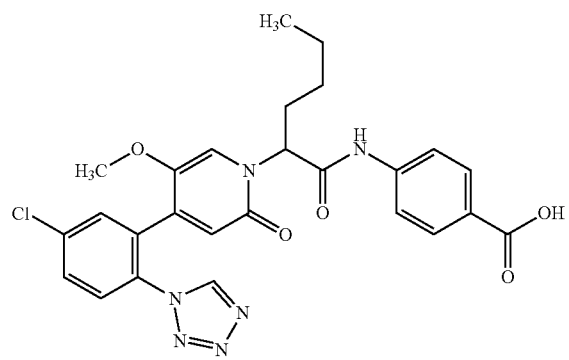 [SMILES: CCCCC(C(=O)Nc1ccc(C(=O)O)cc1)n1cc(OC)c(-c2cc(Cl)ccc2-n2cnnn2)cc1=O]

35.0 mg (purity 93%, 77.9 µmol) of 2-{4-[5-chloro-2-(1H-tetrazol-1-yl)phenyl]-5-methoxy-2-oxopyridin-1(2H)-yl}hexanoic acid (racemate) and 11.2 mg (81.8 µmol) of 4-aminobenzoic acid in 0.5 ml of pyridine were reacted according to General Method 5. Yield: 31.7 mg (74% of theory).

LC/MS [Method 10]: $R_t$=1.68 min; MS (ESIpos): m/z=537 [M+H]$^+$ $^1$H-NMR (400 MHz, DMSO-d$_6$): δ [ppm]=12.75 (br s, 1H), 10.72 (s, 1H), 9.67 (s, 1H), 7.92-7.87 (m, 2H), 7.84-7.81 (m, 2H), 7.80-7.77 (m, 1H), 7.75-7.69 (m, 2H), 7.16 (s, 1H), 6.51 (s, 1H), 5.65 (t, 1H), 3.28 (s, 3H), 2.05 (q, 2H), 1.36-1.24 (m, 2H), 1.21-1.07 (m, 2H), 0.88 (t, 3H).

Example 139

2-{4-[5-Chloro-2-(1H-tetrazol-1-yl)phenyl]-5-methoxy-2-oxopyridin-1(2H)-yl}-N-(2-methyl-2H-indazol-5-yl)hexanamide (Racemate)

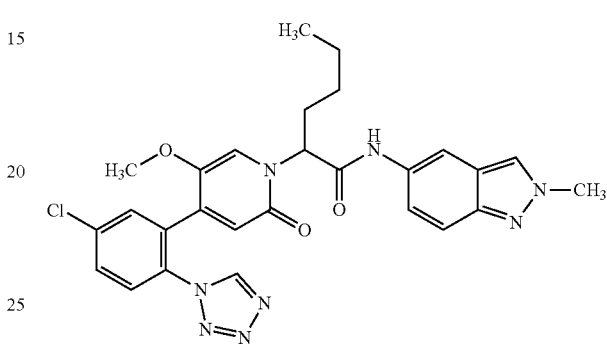

35.0 mg (purity 93%, 77.9 µmol) of 2-{4-[5-chloro-2-(1H-tetrazol-1-yl)phenyl]-5-methoxy-2-oxopyridin-1(2H)-yl}hexanoic acid (racemate) and 17.2 mg (117 µmol) of 2-methyl-2H-indazole-5-amine in 1.0 ml of pyridine were reacted according to General Method 5. Yield: 32.8 mg (75% of theory).

LC/MS [Method 10]: $R_t$=1.68 min; MS (ESIpos): m/z=547 [M+H]$^+$ $^1$H-NMR (400 MHz, DMSO-d$_6$): δ [ppm]=10.36 (s, 1H), 9.67 (s, 1H), 8.24 (s, 1H), 8.12 (s, 1H), 7.84-7.80 (m, 2H), 7.80-7.77 (m, 1H), 7.54 (d, 1H), 7.27 (d, 1H), 7.21 (s, 1H), 6.50 (s, 1H), 5.70-5.64 (m, 1H), 4.13 (s, 3H), 3.29 (s, 3H), 2.09-1.95 (m, 2H), 1.37-1.24 (m, 2H), 1.23-1.07 (m, 2H), 0.88 (t, 3H).

Example 140

N-(Quinoxalin-6-yl)-2-{4-[5-chloro-2-(1H-tetrazol-1-yl)phenyl]-5-methoxy-2-oxopyridin-1(2H)-yl}hexanamide (Racemate)

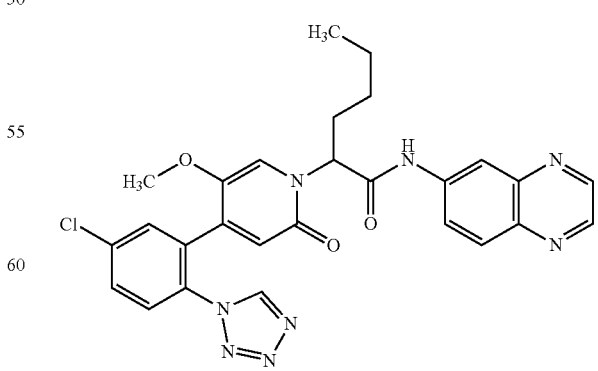

35.0 mg (purity 93%, 77.9 µmol) of 2-{4-[5-chloro-2-(1H-tetrazol-1-yl)phenyl]-5-methoxy-2-oxopyridin-1(2H)- yl}hexanoic acid (racemate) and 17.0 mg (117 μmol) of quinoxaline-6-amine in 1.0 ml of pyridine were reacted according to General Method 5. Yield: 34.5 mg (80% of theory).

LC/MS [Method 10]: $R_t$=1.73 min; MS (ESIpos): m/z=545 [M+H]$^+$ $^1$H-NMR (400 MHz, DMSO-d$_6$): δ [ppm]=10.94 (s, 1H), 9.68 (s, 1H), 8.89 (d, 1H), 8.84 (d, 1H), 8.51 (d, 1H), 8.07 (d, 1H), 7.97 (dd, 1H), 7.84-7.82 (m, 2H), 7.80-7.79 (m, 1H), 7.21 (s, 1H), 6.53 (s, 1H), 5.74-5.66 (m, 1H), 3.31 (s, 3H), 2.11 (q, 2H), 1.38-1.25 (m, 2H), 1.25-1.09 (m, 2H), 0.89 (t, 3H).

Example 141

5-{[2-{4-[5-Chloro-2-(1H-tetrazol-1-yl)phenyl]-5-methoxy-2-oxopyridin-1(2H)-yl}hexanoyl]amino}-N-methylpyridine-2-carboxamide (Racemate)

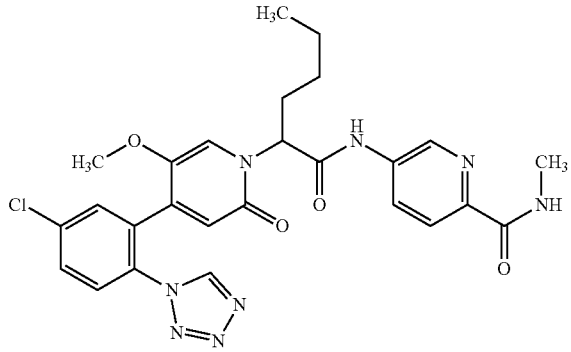 [SMILES: CCCCC(C(=O)Nc1ccc(C(=O)NC)nc1)n1cc(OC)c(-c2cc(Cl)ccc2-n2cnnn2)cc1=O]

35.0 mg (purity 93%, 77.9 μmol) of 2-{4-[5-chloro-2-(1H-tetrazol-1-yl)phenyl]-5-methoxy-2-oxopyridin-1(2H)-yl}hexanoic acid (racemate) and 18.0 mg (117 μmol) of 5-amino-N-methylpyridine-2-carboxamide in 1.0 ml of pyridine were reacted according to General Method 5. Yield: 32.7 mg (76% of theory).

LC/MS [Method 10]: $R_t$=1.64 min; MS (ESIpos): m/z=551 [M+H]$^+$ $^1$H-NMR (400 MHz, DMSO-d$_6$): δ [ppm]=10.85 (s, 1H), 9.67 (s, 1H), 8.84 (d, 1H), 8.65 (q, 1H), 8.19 (dd, 1H), 8.00 (d, 1H), 7.84-7.81 (m, 2H), 7.79-7.77 (m, 1H), 7.16 (s, 1H), 6.52 (s, 1H), 5.66-5.59 (m, 1H), 3.28 (s, 3H), 2.80 (d, 3H), 2.08 (q, 2H), 1.36-1.24 (m, 2H), 1.22-1.07 (m, 2H), 0.88 (t, 3H).

Example 142

4-({2-[4-{5-Chloro-2-[4-(difluoromethyl)-1H-1,2,3-triazol-1-yl]phenyl}-5-methoxy-2-oxopyridin-1(2H)-yl]hexanoyl}amino)benzoic acid (Racemate)

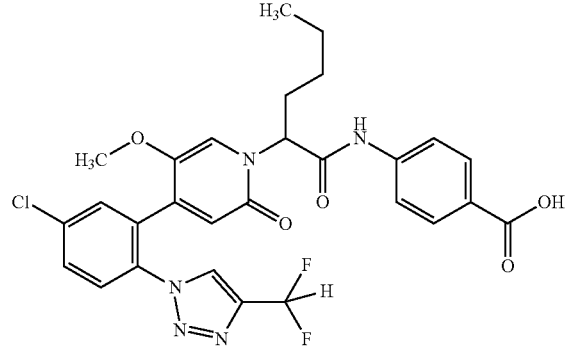 [SMILES: CCCCC(C(=O)Nc1ccc(C(=O)O)cc1)n1cc(OC)c(-c2cc(Cl)ccc2-n2cc(C(F)F)nn2)cc1=O]

50.0 mg (purity 81%, 86.7 μmol) of 2-[4-{5-chloro-2-[4-(difluoromethyl)-1H-1,2,3-triazol-1-yl]phenyl}-5-methoxy-2-oxopyridin-1(2H)-yl]hexanoic acid (racemate) and 12.5 mg (91.1 μmol) of 4-aminobenzoic acid in 0.5 ml of pyridine were reacted according to General Method 5. Yield: 31.8 mg (62% of theory).

LC/MS [Method 10]: $R_t$=1.83 min; MS (ESIpos): m/z=586 [M+H]$^+$ $^1$H-NMR (400 MHz, DMSO-d$_6$): δ [ppm]=12.75 (br s, 1H), 10.71 (s, 1H), 8.73 (s, 1H), 7.90 (d, 2H), 7.78 (s, 2H), 7.76-7.70 (m, 3H), 7.36-7.06 (m, 2H), 6.50 (s, 1H), 5.67-5.61 (m, 1H), 3.26 (s, 3H), 2.05 (q, 2H), 1.36-1.23 (m, 2H), 1.22-1.07 (m, 2H), 0.87 (t, 3H).

Example 143

5-({2-[4-{5-Chloro-2-[4-(difluoromethyl)-1H-1,2,3-triazol-1-yl]phenyl}-5-methoxy-2-oxopyridin-1(2H)-yl]hexanoyl}amino)pyridine-2-carboxamide (Racemate)

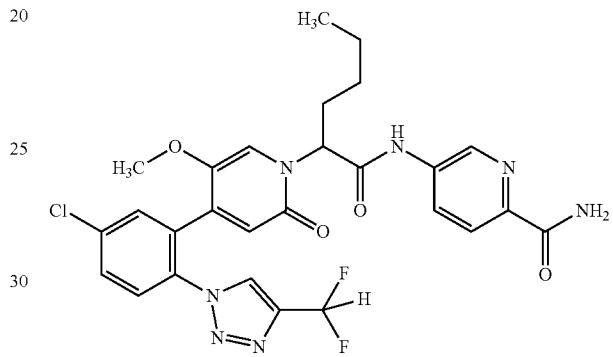

50.0 mg (purity 81%, 86.7 μmol) of 2-[4-{5-chloro-2-[4-(difluoromethyl)-1H-1,2,3-triazol-1-yl]phenyl}-5-methoxy-2-oxopyridin-1(2H)-yl]hexanoic acid (racemate) and 18.8 mg (purity 95%, 130 μmol) of 5-aminopyridine-2-carboxamide in 1.0 ml of pyridine were reacted according to General Method 5. Yield: 35.8 mg (70% of theory).

LC/MS [Method 10]: $R_t$=1.71 min; MS (ESIpos): m/z=586 [M+H]$^+$ $^1$H-NMR (400 MHz, DMSO-d$_6$): δ [ppm]=10.87 (s, 1H), 8.83 (d, 1H), 8.73 (s, 1H), 8.19 (dd, 1H), 8.05-7.97 (m, 2H), 7.81-7.74 (m, 3H), 7.52 (br s, 1H), 7.36-7.06 (m, 2H), 6.51 (s, 1H), 5.68-5.58 (m, 1H), 3.26 (s, 3H), 2.08 (q, 2H), 1.36-1.25 (m, 2H), 1.22-1.08 (m, 2H), 0.87 (t, 3H).

Example 144

4-({2-[4-{5-Chloro-2-[4-(difluoromethyl)-1H-1,2,3-triazol-1-yl]phenyl}-5-methoxy-2-oxopyridin-1(2H)-yl]hexanoyl}amino)-2-fluorobenzamide (Racemate)

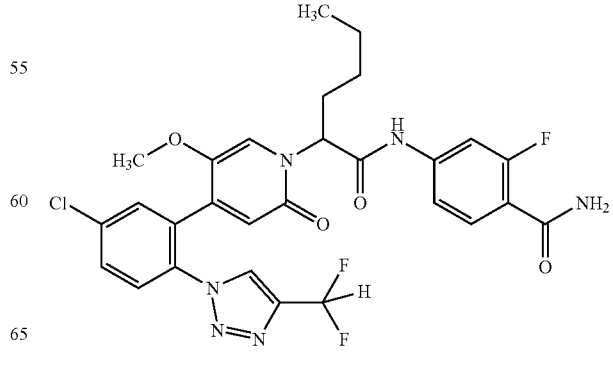

50.0 mg (purity 81%, 86.7 µmol) of 2-[4-{5-chloro-2-[4-(difluoromethyl)-1H-1,2,3-triazol-1-yl]phenyl}-5-methoxy-2-oxopyridin-1(2H)-yl]hexanoic acid (racemate) and 20.7 mg (130 µmol) of 4-amino-2-fluorobenzamide in 1.0 ml of pyridine were reacted according to General Method 5. Yield: 42.7 mg (81% of theory).

LC/MS [Method 10]: $R_t$=1.78 min; MS (ESIpos): m/z=603 [M+H]$^+$ $^1$H-NMR (400 MHz, DMSO-d$_6$): δ [ppm]=10.78 (s, 1H), 8.72 (s, 1H), 7.81-7.76 (m, 2H), 7.76-7.73 (m, 1H), 7.68 (t, 1H), 7.63 (dd, 1H), 7.52 (br d, 2H), 7.38 (dd, 1H), 7.35-7.06 (m, 2H), 6.51 (s, 1H), 5.64-5.57 (m, 1H), 3.26 (s, 3H), 2.11-2.00 (m, 2H), 1.36-1.25 (m, 2H), 1.14 (dt, 2H), 0.87 (t, 3H).

Example 145

2-[4-{5-Chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)hexanamide (Racemate)

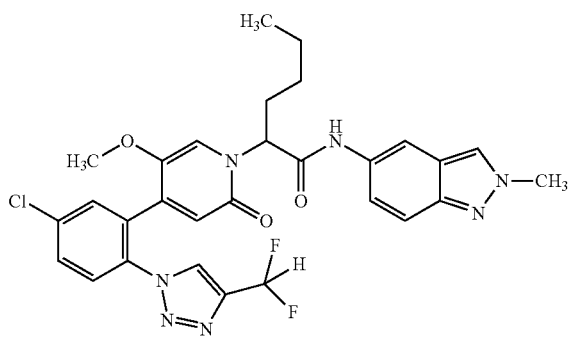 [SMILES: CCCCC(C(=O)Nc1ccc2nn(C)cc2c1)n1cc(OC)c(-c2cc(Cl)ccc2-n2cc(C(F)F)nn2)cc1=O]

50.0 mg (purity 81%, 86.7 µmol) of 2-[4-{5-chloro-2-[4-(difluoromethyl)-1H-1,2,3-triazol-1-yl]phenyl}-5-methoxy-2-oxopyridin-1(2H)-yl]hexanoic acid (racemate) and 19.2 mg (130 µmol) of 2-methyl-2H-indazole-5-amine in 1.0 ml of pyridine were reacted according to General Method 5. Yield: 22.9 mg (44% of theory).

LC/MS [Method 10]: $R_t$=1.83 min; MS (ESIpos): m/z=596 [M+H]$^+$ $^1$H-NMR (400 MHz, DMSO-d$_6$): δ [ppm]=10.35 (s, 1H), 8.73 (s, 1H), 8.24 (s, 1H), 8.10 (d, 1H), 7.80-7.76 (m, 2H), 7.75-7.73 (m, 1H), 7.54 (d, 1H), 7.27 (dd, 1H), 7.36-7.06 (m, 2H), 6.50 (s, 1H), 5.70-5.64 (m, 1H), 4.12 (s, 3H), 3.26 (s, 3H), 2.04 (br s, 2H), 1.37-1.25 (m, 2H), 1.20-1.09 (m, 2H), 0.87 (t, 3H).

Example 146

N-(Quinoxalin-6-yl)-2-[4-{5-chloro-2-[4-(difluoromethyl)-1H-1,2,3-triazol-1-yl]phenyl}-5-methoxy-2-oxopyridin-1(2H)-yl]hexanamide (Racemate)

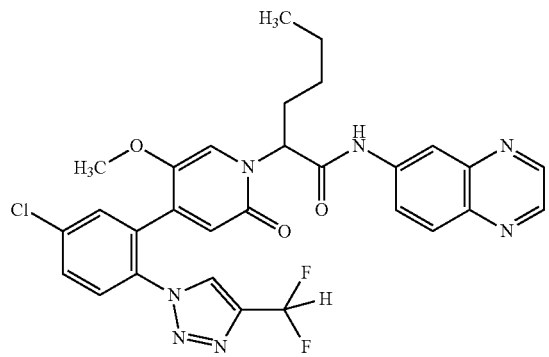 [SMILES: CCCCC(C(=O)Nc1ccc2nccnc2c1)n1cc(OC)c(-c2cc(Cl)ccc2-n2cc(C(F)F)nn2)cc1=O]

50.0 mg (purity 81%, 86.7 µmol) of 2-[4-{5-chloro-2-[4-(difluoromethyl)-1H-1,2,3-triazol-1-yl]phenyl}-5-methoxy-2-oxopyridin-1(2H)-yl]hexanoic acid (racemate) and 18.9 mg (130 µmol) of quinoxaline-6-amine in 1.0 ml of pyridine were reacted according to General Method 5. Yield: 36.6 mg (71% of theory).

LC/MS [Method 1]: $R_t$=1.00 min; MS (ESIpos): m/z=594 [M+H]$^+$ $^1$H-NMR (400 MHz, DMSO-d$_6$): δ [ppm]=10.93 (s, 1H), 8.89 (d, 1H), 8.84 (d, 1H), 8.74 (s, 1H), 8.51 (d, 1H), 8.07 (d, 1H), 7.96 (dd, 1H), 7.81-7.77 (m, 2H), 7.77-7.74 (m, 1H), 7.36-7.06 (m, 2H), 6.52 (s, 1H), 5.73-5.66 (m, 1H), 3.28 (s, 3H), 2.11 (q, 2H), 1.39-1.26 (m, 2H), 1.25-1.10 (m, 2H), 0.88 (t, 3H).

Example 147

5-({2-[4-{5-Chloro-2-[4-(difluoromethyl)-1H-1,2,3-triazol-1-yl]phenyl}-5-methoxy-2-oxopyridin-1(2H)-yl]hexanoyl}amino)-N-methylpyridine-2-carboxamide (Racemate)

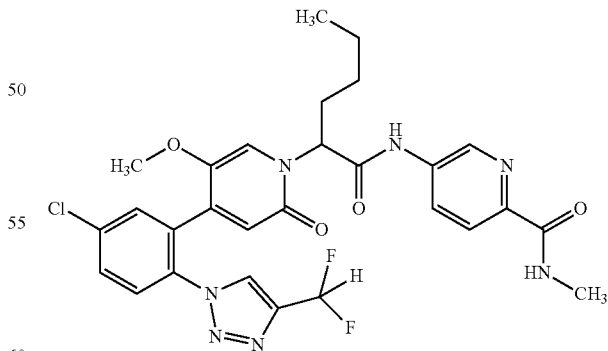

50.0 mg (purity 81%, 86.7 µmol) of 2-[4-{5-chloro-2-[4-(difluoromethyl)-1H-1,2,3-triazol-1-yl]phenyl}-5-methoxy-2-oxopyridin-1(2H)-yl]hexanoic acid (racemate) and 20.1 mg (130 µmol) of 5-amino-N-methylpyridine-2-carboxamide in 1.0 ml of pyridine were reacted according to General Method 5. Yield: 34.7 mg (67% of theory).

LC/MS [Method 10]: R$_t$=1.79 min; MS (ESIpos): m/z=600 [M+H]$^+$
$^1$H-NMR (400 MHz, DMSO-d$_6$): δ [ppm]=10.85 (br s, 1H), 8.85 (d, 1H), 8.74-8.71 (m, 1H), 8.65 (d, 1H), 8.17 (dd, 1H), 8.00 (d, 1H), 7.80-7.76 (m, 2H), 7.74 (s, 1H), 7.35-7.06 (m, 2H), 6.51 (s, 1H), 5.65-5.59 (m, 1H), 3.26 (s, 3H), 2.80 (d, 3H), 2.12-2.04 (m, 2H), 1.37-1.23 (m, 2H), 1.22-1.08 (m, 2H), 0.87 (t, 3H).

Example 148

4-({2-[4-{5-Chloro-2-[5-(trifluoromethyl)-1,3,4-oxadiazol-2-yl]phenyl}-5-methoxy-2-oxopyridin-1(2H)-yl]butanoyl}amino)benzoic acid (Racemate)

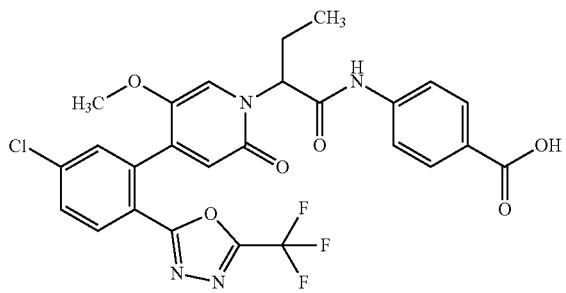 [SMILES: CCC(C(=O)Nc1ccc(C(=O)O)cc1)n1cc(OC)c(-c2cc(Cl)ccc2-c2nnc(C(F)(F)F)o2)cc1=O]

11 mg (0.017 mmol) of tert-butyl 4-({2-[4-{5-chloro-2-[5-(trifluoromethyl)-1,3,4-oxadiazol-2-yl]phenyl}-5-methoxy-2-oxopyridin-1(2H)-yl]butanoyl}amino)benzoate (racemate) were reacted according to General Method 1. Yield: 5 mg (47% of theory).
LC/MS [Method 8]: R$_t$=1.31 min; MS (ESIneg): m/z=575 (M−H)$^-$,
$^1$H-NMR (400 MHz, DMSO-d$_6$): δ [ppm]=10.73 (brs, 1H), 8.13-8.09 (m, 1H), 7.92-7.89 (m, 2H), 7.81 (dd, 1H), 7.75-7.70 (m, 3H), 7.33 (s, 1H), 6.58 (s, 1H), 5.79-5.55 (m, 1H), 3.36 (s, 3H), 2.21-2.06 (m, 2H), 0.89 (t, 3H).

Example 149

5-({2-[4-{5-Chloro-2-[5-(trifluoromethyl)-1,3,4-oxadiazol-2-yl]phenyl}-5-methoxy-2-oxopyridin-1(2H)-yl]butanoyl}amino)pyridine-2-carboxamide (Racemate)

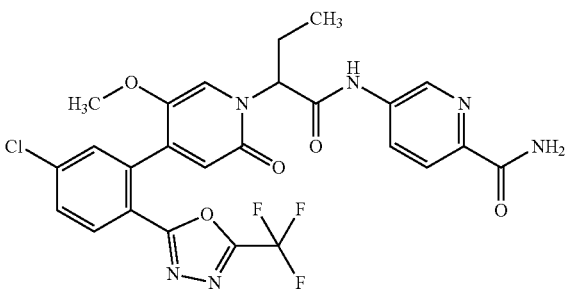 [SMILES: CCC(C(=O)Nc1ccc(C(N)=O)nc1)n1cc(OC)c(-c2cc(Cl)ccc2-c2nnc(C(F)(F)F)o2)cc1=O]

10 mg (0.022 mmol) of 2-[4-{5-chloro-2-[5-(trifluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of 5-aminopyridine-2-carboxamide were reacted according to General Method 5. Yield: 8 mg (63% of theory).

LC/MS [Method 8]: R$_t$=1.22 min; MS (ESIneg): m/z=575 (M−H)$^-$,
$^1$H-NMR (400 MHz, DMSO-d$_6$): δ [ppm]=10.95 (brs, 1H), 8.85 (s, 1H), 8.21 (dd, 1H), 8.12 (d, 1H), 8.05-7.98 (m, 2H), 7.81 (dd, 1H), 7.74 (d, 1H), 7.53 (brs, 1H), 7.32 (s, 1H), 6.59 (s, 1H), 5.78-5.49 (m, 1H), 3.36 (s, 3H), 2.29-2.02 (m, 2H), 0.90 (t, 3H).

Example 150

4-({2-[4-{5-Chloro-2-[5-(trifluoromethyl)-1,3,4-oxadiazol-2-yl]phenyl}-5-methoxy-2-oxopyridin-1(2H)-yl]butanoyl}amino)-2-fluorobenzamide (Racemate)

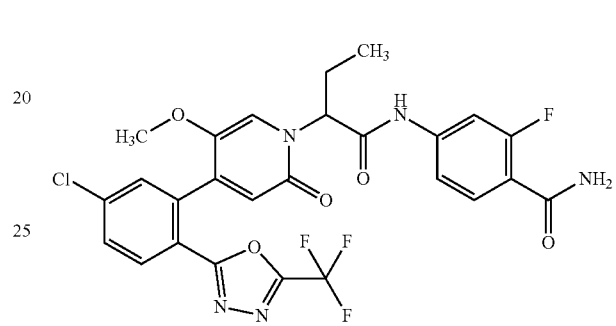

10 mg (0.022 mmol) of 2-[4-{5-chloro-2-[5-(trifluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of 4-amino-2-fluorobenzamide were reacted according to General Method 5. Yield: 8 mg (58% of theory).
LC/MS [Method 8]: R$_t$=1.26 min; MS (ESIneg): m/z=592 (M−H)$^-$,
$^1$H-NMR (400 MHz, DMSO-d$_6$): δ [ppm]=10.85 (brs, 1H), 8.12 (d, 1H), 7.81 (dd, 1H), 7.74 (d, 1H), 7.73-7.62 (m, 2H), 7.57-7.49 (m, 2H), 7.39 (dd, 1H), 7.31 (s, 1H), 6.58 (s, 1H), 5.71-5.53 (m, 1H), 3.36 (s, 3H, partially hidden), 2.23-2.04 (m, 2H), 0.89 (t, 3H).

Example 151

2-[4-{5-Chloro-2-[5-(trifluoromethyl)-1,3,4-oxadiazol-2-yl]phenyl}-5-methoxy-2-oxopyridin-1(2H)-yl]-N-(2-methyl-2H-indazol-5-yl)butanamide (Racemate)

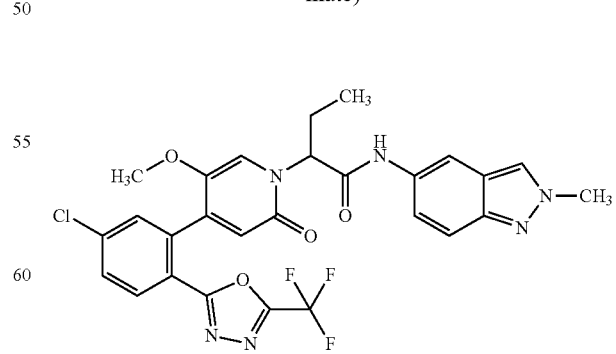

10 mg (0.022 mmol) of 2-[4-{5-chloro-2-[5-(trifluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of 2-methyl-2H-indazole-5-amine were reacted according to General Method 5. Yield: 8 mg (62% of theory).

LC/MS [Method 8]: $R_t$=1.31 min; MS (ESIneg): m/z=585 (M–H)⁻,

¹H-NMR (400 MHz, DMSO-d₆): δ [ppm]=10.40 (brs, 1H), 8.25 (s, 1H), 8.16-8.07 (m, 2H), 7.81 (dd, 1H), 7.73 (d, 1H), 7.55 (d, 1H), 7.38 (s, 1H), 7.28 (dd, 1H), 6.58 (s, 1H), 5.74-5.62 (m, 1H), 4.13 (s, 3H), 3.36 (s, 3H), 2.22-2.01 (m, 2H), 0.90 (t, 3H).

Example 152

N-(Quinoxalin-6-yl)-2-[4-{5-chloro-2-[5-(trifluoromethyl)-1,3,4-oxadiazol-2-yl]phenyl}-5-methoxy-2-oxopyridin-1(2H)-yl]butanamide (Racemate)

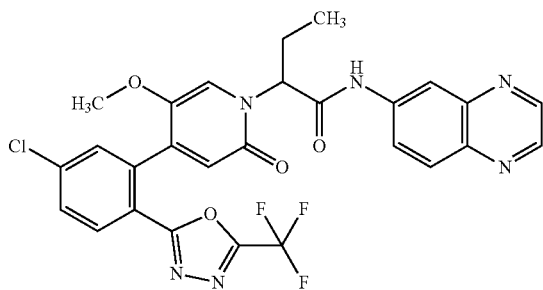 [SMILES: CCC(C(=O)Nc1ccc2nccnc2c1)n1cc(OC)c(-c2cc(Cl)ccc2-c2nnc(C(F)(F)F)o2)cc1=O]

10 mg (22 μmol) of 2-[4-{5-chloro-2-[5-(trifluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of quinoxaline-6-amine were reacted according to General Method 5. Yield: 11 mg (99% of theory).

LC/MS [Method 8]: $R_t$=1.34 min; MS (ESIneg): m/z=583 (M–H)⁻,

¹H-NMR (400 MHz, DMSO-d₆): δ [ppm]=10.99 (brs, 1H), 8.90 (d, 1H), 8.84 (d, 1H), 8.56-8.52 (m, 1H), 8.15-8.05 (m, 2H), 7.97 (dd, 1H), 7.81 (dd, 1H), 7.75 (d, 1H), 7.37 (s, 1H), 6.60 (s, 1H), 5.79-5.63 (m, 1H), 3.38 (s, 3H), 2.28-2.09 (m, 2H), 0.92 (t, 3H).

Example 153

4-({2-[4-{5-Chloro-2-[5-(trifluoromethyl)-1,3,4-oxadiazol-2-yl]phenyl}-5-methoxy-2-oxopyridin-1(2H)-yl]butanoyl}amino)-2-fluoro-N-methylbenzamide (Racemate)

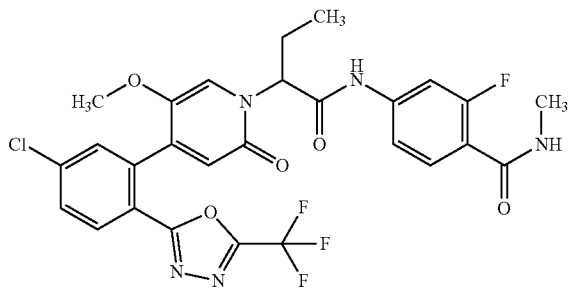 [SMILES: CCC(C(=O)Nc1ccc(C(=O)NC)c(F)c1)n1cc(OC)c(-c2cc(Cl)ccc2-c2nnc(C(F)(F)F)o2)cc1=O]

10 mg (22 μmol) of 2-[4-{5-chloro-2-[5-(trifluoromethyl)-1,3,4-oxadiazol-2-yl]phenyl}-5-methoxy-2-oxopyridin-1(2H)-yl]butanoic acid (racemate) and 6 mg (0.03 mmol, 1.5 eq.) of 4-amino-2-fluoro-N-methylbenzamide were reacted according to General Method 5. Yield: 8 mg (59% of theory).

LC/MS [Method 8]: $R_t$=1.32 min; MS (ESIneg): m/z=606 (M–H)⁻,

¹H-NMR (400 MHz, DMSO-d₆): δ [ppm]=10.84 (brs, 1H), 8.15-8.03 (m, 2H), 7.81 (dd, 1H), 7.73 (d, 1H), 7.70-7.61 (m, 2H), 7.39 (dd, 1H), 7.31 (s, 1H), 6.58 (s, 1H), 5.70-5.52 (m, 1H), 3.36 (s, 3H), 2.76 (d, 3H), 2.22-2.05 (m, 2H), 0.89 (t, 3H).

Example 154

4-({2-[4-{5-Chloro-2-[5-(difluoromethyl)-1,3,4-oxadiazol-2-yl]phenyl}-5-methoxy-2-oxopyridin-1(2H)-yl]butanoyl}amino)benzoic acid (Racemate)

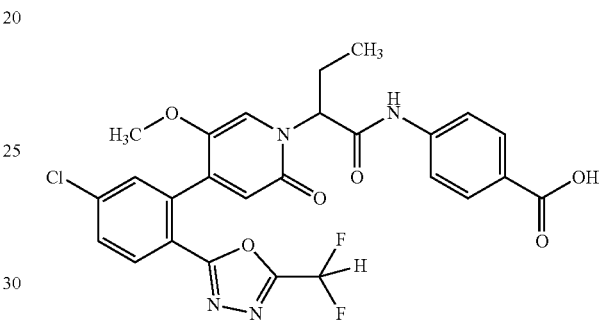

11 mg (0.018 mmol) of tert-butyl 4-({2-[4-{5-chloro-2-[5-(difluoromethyl)-1,3,4-oxadiazol-2-yl]phenyl}-5-methoxy-2-oxopyridin-1(2H)-yl]butanoyl}amino)benzoate (racemate) were reacted according to General Method 1. Yield: 2 mg (20% of theory).

LC/MS [Method 10]: $R_t$=1.72 min; MS (ESIneg): m/z=557 (M–H)⁻,

¹H-NMR (400 MHz, DMSO-d₆): δ [ppm]=12.74 (brs, 1H), 10.76 (brs, 1H), 8.08 (d, 1H), 7.94-7.88 (m, 2H), 7.78 (dd, 1H), 7.76-7.69 (m, 3H), 7.47 (t, 1H), 7.30 (s, 1H), 6.56 (s, 1H), 5.74-5.57 (m, 1H), 3.34 (s, 3H), 2.20-2.04 (m, 2H), 0.90 (t, 3H).

Example 155

5-({2-[4-{5-Chloro-2-[5-(difluoromethyl)-1,3,4-oxadiazol-2-yl]phenyl}-5-methoxy-2-oxopyridin-1(2H)-yl]butanoyl}amino)pyridine-2-carboxamide (Racemate)

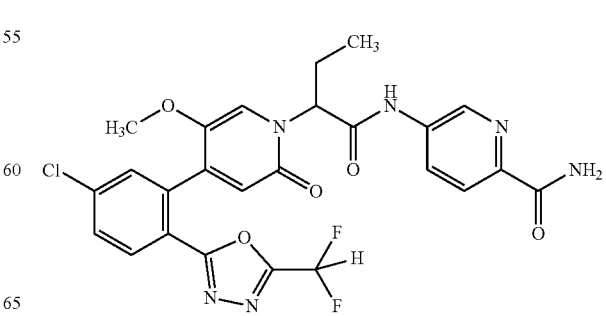

10 mg (0.023 mmol) of 2-[4-{5-chloro-2-[5-(difluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of 5-aminopyridine-2-carboxamide were reacted according to General Method 5. Yield: 8 mg (63% of theory).

LC/MS [Method 8]: $R_t$=1.13 min; MS (ESIneg): m/z=557 (M−H)⁻,

¹H-NMR (400 MHz, DMSO-d₆): δ [ppm]=10.93 (brs, 1H), 8.85 (d, 1H), 8.21 (dd, 1H), 8.08 (d, 1H), 8.04-7.99 (m, 2H), 7.78 (dd, 1H), 7.71 (d, 1H), 7.62-7.42 (m, 2H), 7.30 (s, 1H), 6.57 (s, 1H), 5.74-5.56 (m, 1H), 3.34 (s, 3H), 2.25-2.07 (m, 2H), 0.91 (t, 3H).

Example 156

4-({2-[4-{5-Chloro-2-[5-(difluoromethyl)-1,3,4-oxadiazol-2-yl]phenyl}-5-methoxy-2-oxopyridin-1(2H)-yl]butanoyl}amino)-2-fluorobenzamide (Racemate)

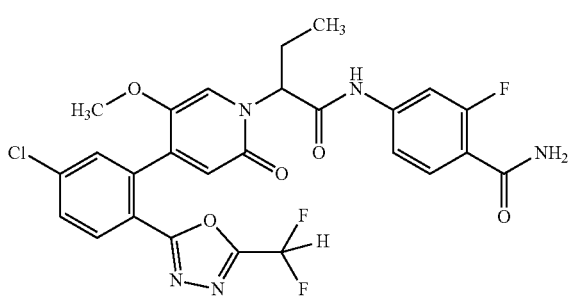 [SMILES: CCC(C(=O)Nc1ccc(C(N)=O)c(F)c1)n1cc(OC)c(-c2cc(Cl)ccc2-c2nnc(C(F)F)o2)cc1=O]

10 mg (0.023 mmol) of 2-[4-{5-chloro-2-[5-(difluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of 4-amino-2-fluorobenzamide were reacted according to General Method 5. Yield: 9 mg (69% of theory).

LC/MS [Method 8]: $R_t$=1.19 min; MS (ESIneg): m/z=574 (M−H)⁻,

¹H-NMR (400 MHz, DMSO-d₆): δ [ppm]=10.85 (brs, 1H), 8.08 (d, 1H), 7.78 (dd, 1H), 7.74-7.62 (m, 3H), 7.60-7.33 (m, 4H), 7.29 (s, 1H), 6.56 (s, 1H), 5.71-5.55 (m, 1H), 3.34 (s, 3H), 2.21-2.06 (m, 2H), 0.90 (t, 3H).

Example 157

2-[4-{5-Chloro-2-[5-(difluoromethyl)-1,3,4-oxadiazol-2-yl]phenyl}-5-methoxy-2-oxopyridin-1(2H)-yl]-N-(2-methyl-2H-indazol-5-yl)butanamide (Racemate)

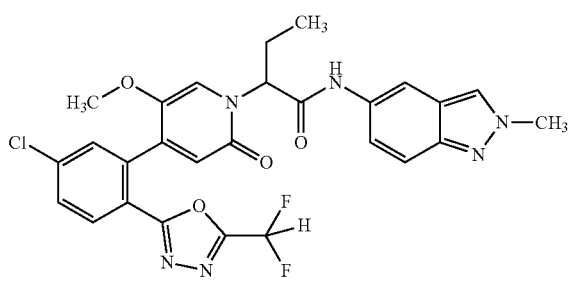 [SMILES: CCC(C(=O)Nc1ccc2nn(C)cc2c1)n1cc(OC)c(-c2cc(Cl)ccc2-c2nnc(C(F)F)o2)cc1=O]

10 mg (0.023 mmol) of 2-[4-{5-chloro-2-[5-(difluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of 2-methyl-2H-indazole-5-amine were reacted according to General Method 5. Yield: 7 mg (54% of theory).

LC/MS [Method 8]: $R_t$=1.22 min; MS (ESIneg): m/z=567 (M−H)⁻,

¹H-NMR (400 MHz, DMSO-d₆): δ [ppm]=10.4 (s, 1H), 8.25 (s, 1H), 8.13 (s, 1H), 8.08 (d, 1H), 7.78 (dd, 1H), 7.71 (d, 1H), 7.55 (d, 1H), 7.47 (t, 1H), 7.35 (s, 1H), 7.29 (dd, 1H), 6.56 (s, 1H), 5.73-5.61 (m, 1H), 4.13 (s, 3H), 3.34 (s, 3H), 2.22-1.98 (m, 2H), 0.91 (t, 3H).

Example 158

N-(Quinoxalin-6-yl)-2-[4-{5-chloro-2-[5-(difluoromethyl)-1,3,4-oxadiazol-2-yl]phenyl}-5-methoxy-2-oxopyridin-1(2H)-yl]butanamide (Racemate)

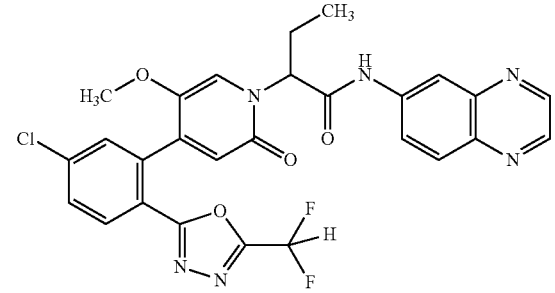 [SMILES: CCC(C(=O)Nc1ccc2nccnc2c1)n1cc(OC)c(-c2cc(Cl)ccc2-c2nnc(C(F)F)o2)cc1=O]

10 mg (23 μmol) of 2-[4-{5-chloro-2-[5-(difluoromethyl)-1,3,4-oxadiazol-2-yl]phenyl}-5-methoxy-2-oxopyridin-1(2H)-yl]butanoic acid (racemate) and 5 mg (0.03 mmol, 1.5 eq.) of quinoxaline-6-amine were reacted according to General Method 5. Yield: 11 mg (85% of theory).

LC/MS [Method 10]: $R_t$=1.75 min; MS (ESIpos): m/z=567 (M+H)⁺,

¹H-NMR (400 MHz, DMSO-d₆): δ [ppm]=10.98 (brs, 1H), 8.90 (d, 1H), 8.84 (d, 1H), 8.54 (d, 1H), 8.12-8.05 (m, 2H), 7.98 (dd, 1H), 7.79 (dd, 1H), 7.72 (d, 1H), 7.47 (t, 1H), 7.35 (s, 1H), 6.58 (s, 1H), 5.80-5.64 (m, 1H), 3.37 (s, 3H), 2.29-2.08 (m, 2H), 0.93 (t, 3H).

Example 159

4-({2-[4-{5-Chloro-2-[5-(difluoromethyl)-1,3,4-oxadiazol-2-yl]phenyl}-5-methoxy-2-oxopyridin-1(2H)-yl]butanoyl}amino)-2-fluoro-N-methylbenzamide (Racemate)

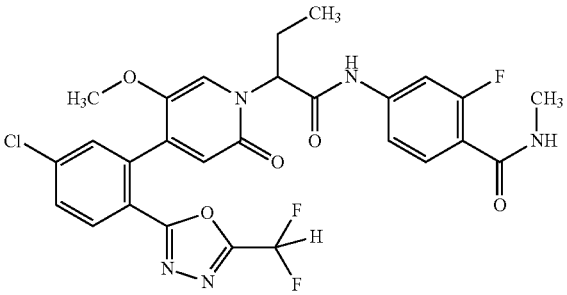 [SMILES: CCC(C(=O)Nc1ccc(C(=O)NC)c(F)c1)n1cc(OC)c(-c2cc(Cl)ccc2-c2nnc(C(F)F)o2)cc1=O]

10 mg (23 μmol) of 2-[4-{5-chloro-2-[5-(difluoromethyl)-1,3,4-oxadiazol-2-yl]phenyl}-5-methoxy-2-oxopyridin-1(2H)-yl]butanoic acid (racemate) and 6 mg (0.03 mmol, 1.5 eq.) of 4-amino-2-fluoro-N-methylbenzamide were reacted according to General Method 5. Yield: 7 mg (52% of theory).

LC/MS [Method 8]: R$_t$=1.24 min; MS (ESIneg): m/z=588 (M−H)⁻,

¹H-NMR (400 MHz, DMSO-d$_6$): δ [ppm]=10.84 (brs, 1H), 8.11-8.04 (m, 2H), 7.79 (dd, 1H), 7.72-7.62 (m, 3H), 7.47 (t, 1H), 7.40 (dd, 1H), 7.29 (s, 1H), 6.56 (s, 1H), 5.70-5.50 (m, 1H), 3.34 (s, 3H), 2.77 (d, 3H), 2.22-2.03 (m, 2H), 0.90 (t, 3H).

Example 160

4-({2-[4-{5-Chloro-2-[4-(difluoromethyl)-1H-1,2,3-triazol-1-yl]phenyl}-5-methoxy-2-oxopyridin-1(2H)-yl]butanoyl}amino)-2-fluorobenzamide (Racemate)

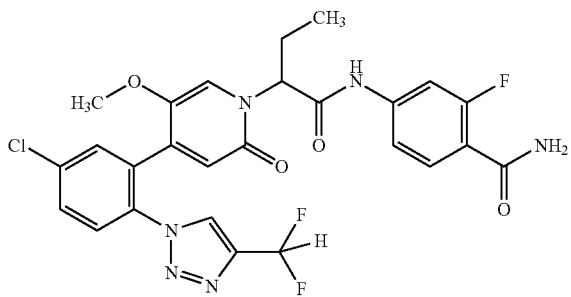 [SMILES: CCC(C(=O)Nc1ccc(C(N)=O)c(F)c1)n1cc(OC)c(-c2cc(Cl)ccc2-n2cc(C(F)F)nn2)cc1=O]

122.0 mg (0.28 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 64.3 mg (0.42 mmol) of 4-amino-2-fluorobenzamide in 2.3 ml of pyridine were reacted according to General Method 5. Yield: 30 mg (18% of theory).

LC/MS [Method 10]: R$_t$=1.58 min; MS (ESIpos): m/z=575 (M+H)⁺,

Alternatively the compound was prepared according to the following procedure:

350.0 mg (0.80 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) were dissolved in 16.7 ml of pyridine and 0.76 ml (1.28 mmol) propylphosphonic anhydride (T3P, 50% solution in ethyl acetate) were added. The mixture was heated to 40° C. and then 159.8 mg (1.04 mmol) of 4-amino-2-fluorobenzamide were added. The reaction mixture was stirred additional 15 min at 40° C. and then immediately concentrated under reduced pressure. The residue was taken up in 10 ml acetonitrile, acidified with 3 ml hydrochloric acid (1M) and then purified by preparative RP-HPLC (0.1% formic acid/acetonitrile gradient). Yield: 270 mg (59% of theory).

LC/MS [Method 1]: R$_t$=0.85 min; MS (ESIpos): m/z=575 (M+H)⁺,

¹H-NMR (400 MHz, DMSO-d$_6$): δ [ppm]=10.78 (br. s., 1H), 8.72 (s, 1H), 7.82-7.73 (m, 3H), 7.72-7.60 (m, 2H), 7.56-7.48 (m, 2H), 7.40-7.33 (m, 1H), 7.23-7.05 (m, 2H), 6.51 (s, 1H), 5.57-5.48 (m, 1H), 3.26 (s, 3H), 2.16-2.01 (m, 2H), 0.80 (t, 3H).

Example 161

4-({(2S)-2-[4-{5-Chloro-2-[4-(difluoromethyl)-1H-1,2,3-triazol-1-yl]phenyl}-5-methoxy-2-oxopyridin-1(2H)-yl]butanoyl}amino)-2-fluorobenzamide (Enantiomer 2)

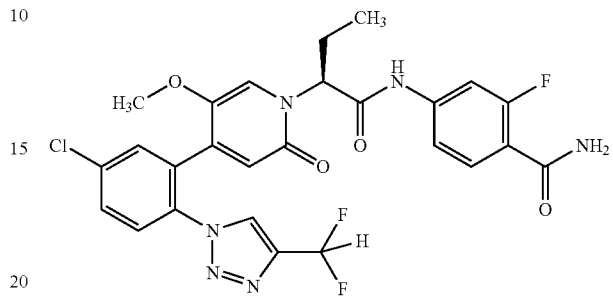

Enantiomer separation of 122 mg of 4-({2-[4-{5-chloro-2-[4-(difluoromethyl)-1H-1,2,3-triazol-1-yl]phenyl}-5-methoxy-2-oxopyridin-1(2H)-yl]butanoyl}amino)-2-fluorobenzamide (racemate) gave 11.3 mg of the title compound Example 161 (enantiomer 2): chiral HPLC: R$_t$=2.2 min; 100% ee, purity 100%.

Separating method: column: Chiralpak AS-H SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AS SFC 3 μm, 100 mm×4.6 mm; mobile phase: carbon dioxide 70%/ethanol 30%; temperature: 40° C.; flow rate: 3 ml/min; UV detection: 210 nm.

Example 162

N-(Quinoxalin-6-yl)-2-[4-{5-chloro-2-[4-(difluoromethyl)-1H-1,2,3-triazol-1-yl]phenyl}-5-methoxy-2-oxopyridin-1(2H)-yl]butanamide (Racemate)

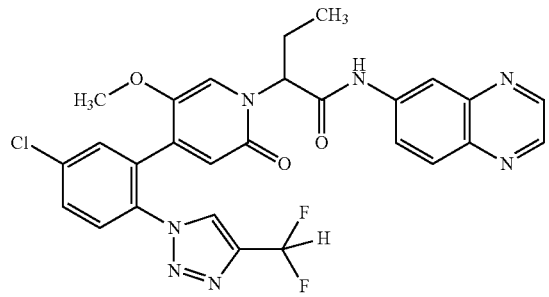 [SMILES: CCC(C(=O)Nc1ccc2nccnc2c1)n1cc(OC)c(-c2cc(Cl)ccc2-n2cc(C(F)F)nn2)cc1=O]

122.0 mg (0.28 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 60.5 mg (0.42 mmol) of quinoxaline-6-amine in 2.3 ml of pyridine were reacted according to General Method 5. Yield: 115 mg (73% of theory).

LC/MS [Method 1]: R$_t$=0.89 min; MS (ESIpos): m/z=566 (M+H)⁺,

¹H-NMR (400 MHz, DMSO-d$_6$): δ [ppm]=10.93 (s, 1H), 8.92-8.81 (m, 2H), 8.74 (s, 1H), 8.51 (d, 1H), 8.07 (d, 1H), 7.97 (d, 1H), 7.83-7.72 (m, 3H), 7.39-7.05 (m, 2H), 6.53 (s, 1H), 5.67-5.58 (m, 1H), 3.28 (s, 3H), 2.25-2.04 (m, 2H), 0.84 (t, 3H).

Example 163

N-(Quinoxalin-6-yl)-(2S)-2-[4-{5-chloro-2-[4-(difluoromethyl)-1H-1,2,3-triazol-1-yl]phenyl}-5-methoxy-2-oxopyridin-1(2H)-yl]butanamide (Enantiomer 2)

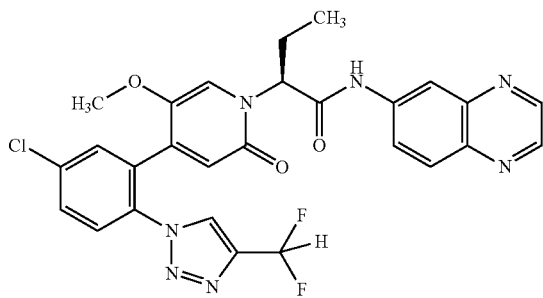 [SMILES: CC[C@@H](C(=O)Nc1ccc2nccnc2c1)n1cc(OC)c(-c2cc(Cl)ccc2-n2cc(C(F)F)nn2)cc1=O]

Enantiomer separation of 115 mg of N-(quinoxalin-6-yl)-2-[4-{5-chloro-2-[4-(difluoromethyl)-1H-1,2,3-triazol-1-yl]phenyl}-5-methoxy-2-oxopyridin-1(2H)-yl]butanamide (racemate) gave 42.2 mg of the title compound Example 163 (enantiomer 2): chiral HPLC: $R_t$=4.6 min; 100% ee, purity 100%.

Separating method: column: Chiralpak AD SFC 5 µm, 250 mm×20 mm; mobile phase: carbon dioxide 70%/methanol 30%; temperature: 40° C.; flow rate: 80 ml/min; pressure: 100 bar; UV detection: 210 nm.

Analysis: column: Daicel AD SFC 3 µm, 100 mm×4.6 mm; mobile phase: carbon dioxide 70%/methanol 30%; temperature: 40° C.; flow rate: 3 ml/min; UV detection: 210 nm.

Example 164

2-[4-{5-Chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)butanamide (Racemate)

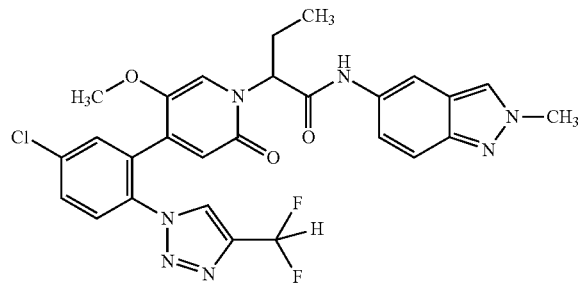 [SMILES: CCC(C(=O)Nc1ccc2nn(C)cc2c1)n1cc(OC)c(-c2cc(Cl)ccc2-n2cc(C(F)F)nn2)cc1=O]

122.0 mg (0.28 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 61.4 mg (0.42 mmol) of 2-methyl-2H-indazole-5-amine in 1.5 ml of pyridine were reacted according to General Method 5. Yield: 111 mg (73% of theory).

LC/MS [Method 10]: $R_t$=1.63 min; MS (ESIpos): m/z=568 (M+H)⁺.

¹H-NMR (400 MHz, DMSO-d₆): δ [ppm]=10.35 (s, 1H), 8.73 (s, 1H), 8.24 (s, 1H), 8.11 (d, 1H), 7.80-7.72 (m, 3H), 7.54 (d, 1H), 7.37-7.06 (m, 3H), 6.50 (s, 1H), 5.64-5.55 (m, 1H), 4.13 (s, 3H), 3.27 (s, 3H), 2.17-1.95 (m, 2H), 0.81 (t, 3H).

Example 165

(2S)-2-[4-{5-Chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)butanamide (Enantiomer 2)

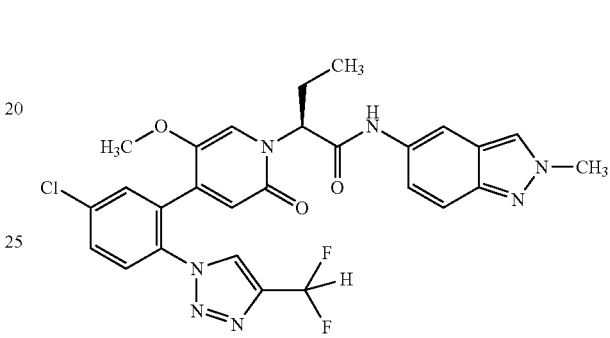

Enantiomer separation of 110 mg of 2-[4-{5-chloro-2-[4-(difluoromethyl)-1H-1,2,3-triazol-1-yl]phenyl}-5-methoxy-2-oxopyridin-1(2H)-yl]-N-(2-methyl-2H-indazol-5-yl)butanamide (racemate) gave 42.7 mg of the title compound Example 165 (enantiomer 2): chiral HPLC: $R_t$=2.9 min; 100% ee, purity 100%.

Separating method: column: Chiralpak AD SFC 5 µm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AD SFC 3 µm, 100 mm×4.6 mm; mobile phase: carbon dioxide 70%/ethanol 30%; temperature: 40° C.; flow rate: 3 ml/min; UV detection: 210 nm.

Example 166

4-({2-[4-{5-Chloro-2-[4-(difluoromethyl)-1H-1,2,3-triazol-1-yl]phenyl}-5-methoxy-2-oxopyridin-1(2H)-yl]butanoyl}amino)benzoic acid (Racemate)

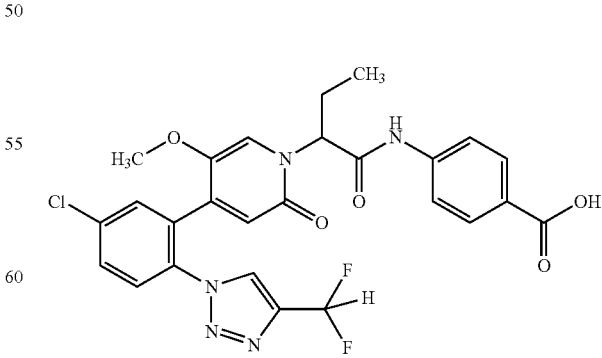

48.3 mg (0.11 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 16.6 mg (0.12 mmol) of 4-aminobenzoic acid in 1.3 ml of pyridine were reacted according to General Method 5. Yield: 14 mg (22% of theory).

LC/MS [Method 10]: R$_t$=1.64 min; MS (ESIpos): m/z=558 (M+H)$^+$, $^1$H-NMR (400 MHz, DMSO-d$_6$): δ [ppm]=12.80 (br. s., 1H), 10.69 (s, 1H), 8.73 (s, 1H), 7.89 (d, 2H), 7.81-7.66 (m, 5H), 7.38-7.06 (m, 2H), 6.51 (s, 1H), 5.61-5.52 (m, 1H), 3.26 (s, 3H), 2.18-1.97 (m, 2H), 0.81 (t, 3H).

Example 167

2-{4-[5-Chloro-2-(4-chloro-1H-1,2,3-triazol-1-yl) phenyl]-5-methoxy-2-oxopyridin-1(2H)-yl}-N-(2-methyl-2H-indazol-5-yl)butanamide (Racemate)

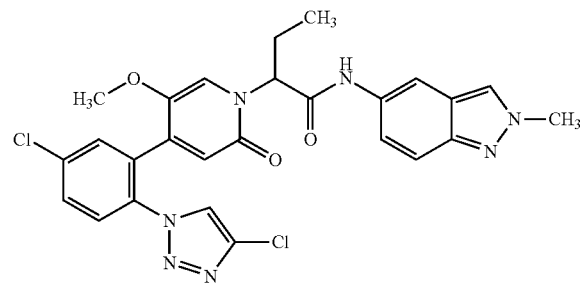 [SMILES: CCC(C(=O)Nc1ccc2nn(C)cc2c1)n1cc(OC)c(-c2cc(Cl)ccc2-n2cc(Cl)nn2)cc1=O]

101.0 mg (0.24 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 45.7 mg (0.31 mmol) of 2-methyl-2H-indazole-5-amine in 6.3 ml of pyridine were reacted according to General Method 5. Yield: 93 mg (70% of theory).

LC/MS [Method 10]: R$_t$=1.65 min; MS (ESIneg): m/z=550 (M−H)$^-$, $^1$H-NMR (400 MHz, DMSO-d$_6$): δ [ppm]=10.35 (s, 1H), 8.63 (s, 1H), 8.25 (s, 1H), 8.13-8.10 (m, 1H), 7.82-7.72 (m, 3H), 7.55 (d, 1H), 7.29-7.22 (m, 2H), 6.47 (s, 1H), 5.64-5.57 (m, 1H), 4.13 (s, 3H), 3.32 (s, 3H, partially hidden), 2.17-1.98 (m, 2H), 0.83 (t, 3H).

Example 168

(2S)-2-{4-[5-Chloro-2-(4-chloro-1H-1,2,3-triazol-1-yl)phenyl]-5-methoxy-2-oxopyridin-1(2H)-yl}-N-(2-methyl-2H-indazol-5-yl)butanamide (Enantiomer 2)

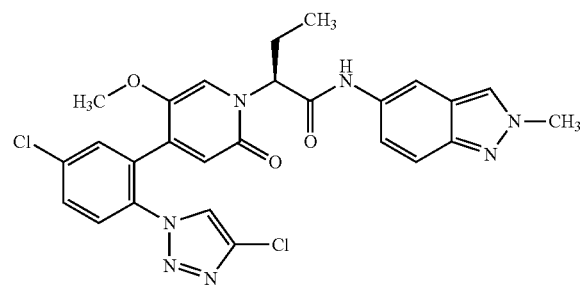 [SMILES: CC[C@@H](C(=O)Nc1ccc2nn(C)cc2c1)n1cc(OC)c(-c2cc(Cl)ccc2-n2cc(Cl)nn2)cc1=O]

Enantiomer separation of 101 mg of 2-{4-[5-chloro-2-(4-chloro-1H-1,2,3-triazol-1-yl)phenyl]-5-methoxy-2-oxopyridin-1(2H)-yl}-N-(2-methyl-2H-indazol-5-yl)butanamide (racemate) gave 33.9 mg of the title compound Example 168 (enantiomer 2): chiral HPLC: R$_t$=3.6 min; 100% ee, purity 100%.

Separating method: column: Chiralpak AD-H SFC 5 μm, 250 mm×20 mm; mobile phase: carbon dioxide 70%/methanol 30%; temperature: 40° C.; flow rate: 80 ml/min pressure: 100 bar; UV detection: 210 nm.

Analysis: column: Daicel AD SFC 3 μm, 100 mm×4.6 mm; mobile phase: carbon dioxide 60%/methanol 40%; temperature: 40° C.; flow rate: 3 ml/min; UV detection: 210 nm.

Example 169

N-(Quinoxalin-6-yl)-2-{4-[5-chloro-2-(4-chloro-1H-1,2,3-triazol-1-yl)phenyl]-5-methoxy-2-oxopyridin-1(2H)-yl}butanamide (Racemate)

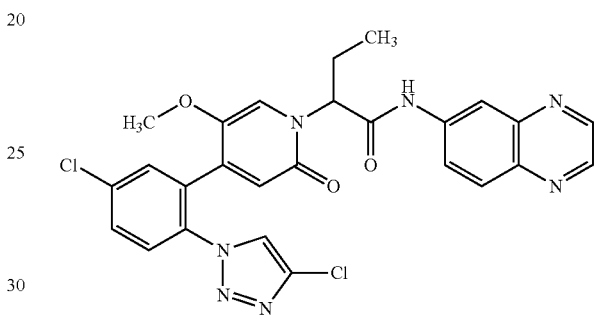

101.0 mg (0.24 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 52.0 mg (0.36 mmol) of quinoxaline-6-amine in 2.0 ml of pyridine were reacted according to General Method 5. Yield: 102 mg (78% of theory).

LC/MS [Method 1]: R$_t$=0.90 min; MS (ESIpos): m/z=550 (M+H)$^+$, $^1$H-NMR (400 MHz, DMSO-d$_6$): δ [ppm]=10.93 (s, 1H), 8.90-8.83 (m, 2H), 8.63 (s, 1H), 8.52 (d, 1H), 8.10-8.05 (m, 1H), 7.97 (dd, 1H), 7.82-7.73 (m, 3H), 7.24 (s, 1H), 6.49 (s, 1H), 5.67-5.59 (m, 1H), 3.34 (s, 3H), 2.24-2.08 (m, 2H), 0.86 (t, 3H).

Example 170

N-(Quinoxalin-6-yl)-(2S)-2-{4-[5-chloro-2-(4-chloro-1H-1,2,3-triazol-1-yl)phenyl]-5-methoxy-2-oxopyridin-1(2H)-yl}butanamide (Enantiomer 2)

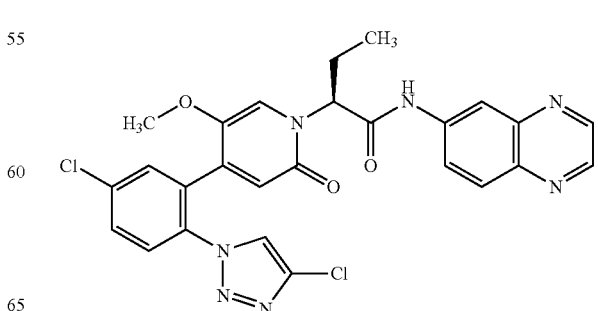

Enantiomer separation of 101 mg of N-(quinoxalin-6-yl)-2-{4-[5-chloro-2-(4-chloro-1H-1,2,3-triazol-1-yl)phenyl]-5-methoxy-2-oxopyridin-1(2H)-yl}butanamide (Racemate) gave 35.0 mg of the title compound Example 170 (enantiomer 2): chiral HPLC: $R_t$=2.2 min; 100% ee, purity 98%.

Separating method: column: Chiralpak AD-H SFC, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AD SFC 3 μm, 100 mm×4.6 mm; mobile phase: carbon dioxide 70%/ethanol 30%; temperature: 40° C.; flow rate: 3 ml/min; UV detection: 210 nm.

Example 171

4-[(2-{4-[5-Chloro-2-(4-chloro-1H-1,2,3-triazol-1-yl)phenyl]-5-methoxy-2-oxopyridin-1(2H)-yl}butanoyl)amino]-2-fluorobenzamide (Racemate)

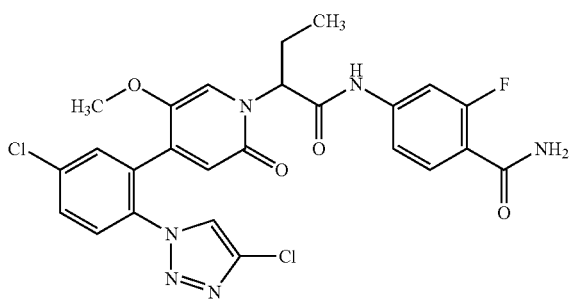 [SMILES: CCC(C(=O)Nc1ccc(C(N)=O)c(F)c1)n1cc(OC)c(-c2cc(Cl)ccc2-n2cc(Cl)nn2)cc1=O]

101.0 mg (0.24 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 47.8 mg (0.31 mmol) of 4-amino-2-fluorobenzamide in 6.3 ml of pyridine were reacted according to General Method 5. Yield: 28 mg (20% of theory).

Alternatively the compound was prepared according to the following procedure:

239 mg (0.57 mmol) of 2-{4-[5-chloro-2-(4-chloro-1H-1,2,3-triazol-1-yl)phenyl]-5-methoxy-2-oxopyridin-1(2H)-yl}butanoic acid (racemate) were dissolved in 15.0 ml pyridine and then 605 μl (1.02 mmol) propylphosphonic anhydride (T3P, 50% solution in ethyl acetate) were added. The mixture was heated to 50° C. and then 113 mg (0.74 mmol) of 4-amino-2-fluorobenzamide were added. The reaction mixture was stirred additional 1 h at 50° C. and then brought to room temperature. The mixture was diluted with 5 ml acetonitrile/water (1:1) and purified by preparative RP-HPLC (0.1% formic acid/acetonitrile gradient). Yield: 180 mg (57% of theory).

LC/MS [Method 10]: $R_t$=1.60 min; MS (ESIpos): m/z=559 (M+H)$^+$, $^1$H-NMR (400 MHz, DMSO-d$_6$): δ [ppm]=10.78 (s, 1H), 8.62 (s, 1H), 7.82-7.73 (m, 3H), 7.72-7.61 (m, 2H), 7.57-7.48 (m, 2H), 7.41-7.35 (m, 1H), 7.18 (s, 1H), 6.48 (s, 1H), 5.58-5.49 (m, 1H), 2.18-2.02 (m, 2H), 0.82 (t, 3H).

Example 172

2-{4-[5-Chloro-2-(1H-tetrazol-1-yl)phenyl]-5-methoxy-2-oxopyridin-(2H)-yl}-N-(2-methyl-2H-indazol-5-yl)butanamide (Racemate)

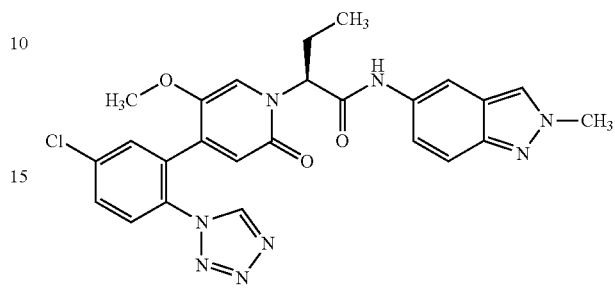

48.1 mg (0.12 mmol) of 2-{4-[5-chloro-2-(1H-tetrazol-1-yl)phenyl]-5-methoxy-2-oxopyridin-1(2H)-yl}butanoic acid (racemate) and 27.2 mg (0.19 mmol) of 2-methyl-2H-indazole-5-amine in 0.7 ml of pyridine were reacted according to General Method 5. Yield: 41 mg (63% of theory).

LC/MS [Method 10]: $R_t$=1.45 min; MS (ESIneg): m/z=517 (M−H)$^-$, $^1$H-NMR (400 MHz, DMSO-d$_6$): δ [ppm]=10.36 (s, 1H), 9.68 (s, 1H), 8.24 (s, 1H), 8.12 (s, 1H), 7.84-7.76 (m, 3H), 7.55 (d, 1H), 7.27 (dd, 1H), 7.20 (s, 1H), 6.51 (s, 1H), 5.65-5.55 (m, 1H), 4.13 (s, 3H), 3.29 (s, 3H), 2.17-1.93 (m, 2H), 0.82 (t, 3H).

Example 173

N-(Quinoxalin-6-yl)-2-{4-[5-chloro-2-(4-chloro-1H-1,2,3-triazol-1-yl)phenyl]-5-methoxy-2-oxopyridin-1(2H)-yl}-3-cyclobutylpropanamide (Racemate)

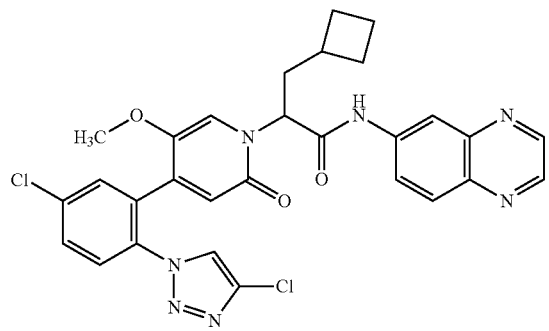 [SMILES: COc1cn(C(CC2CCC2)C(=O)Nc2ccc3nccnc3c2)c(=O)cc1-c1cc(Cl)ccc1-n1cc(Cl)nn1]

70.0 mg (0.15 mmol) of 2-{4-[5-chloro-2-(4-chloro-1H-1,2,3-triazol-1-yl)phenyl]-5-methoxy-2-oxopyridin-1(2H)-yl}-3-cyclobutylpropanoic acid (racemate) and 28.5 mg (0.20 mmol) of quinoxaline-6-amine in 4.0 ml of pyridine were reacted according to General Method 5. Yield: 40 mg (44% of theory).

LC/MS [Method 10]: $R_t$=1.94 min; MS (ESIpos): m/z=590 (M+H)$^+$, $^1$H-NMR (400 MHz, DMSO-d$_6$): δ [ppm]=10.90 (s, 1H), 8.92-8.80 (m, 2H), 8.59 (s, 1H), 8.51 (d, 1H), 8.11-8.05 (m, 1H), 8.02-7.95 (m, 1H), 7.84-7.70 (m, 3H), 7.27 (s, 1H), 6.46 (s, 1H), 5.74-5.63 (m, 1H), 3.36 (s, 3H), 2.31-2.11 (m, 3H), 1.98-1.69 (m, 6H), 1.65-1.52 (m, 1H).

Example 174

5-({2-[4-{5-Chloro-2-[5-(difluoromethyl)-1,2-oxazol-3-yl]phenyl}-5-methoxy-2-oxopyridin-1(2H)-yl]butanoyl}amino)pyridine-2-carboxamide (Racemate)

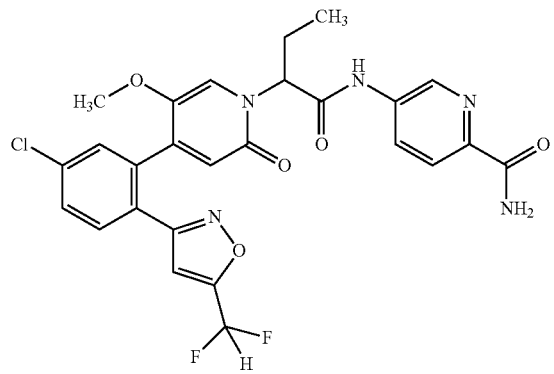 [SMILES: CCC(C(=O)Nc1ccc(C(N)=O)nc1)n1cc(OC)c(-c2cc(Cl)ccc2-c2cc(C(F)F)on2)cc1=O]

10 mg (23 µmol) of 2-[4-{5-chloro-2-[5-(difluoromethyl)-1,2-oxazol-3-yl]phenyl}-5-methoxy-2-oxopyridin-1(2H)-yl]butanoic acid (racemate) and 5 mg (0.03 mmol, 1.5 eq.) of 5-aminopyridine-2-carboxamide were reacted according to General Method 5. Yield: 10 mg (78% of theory).

LC/MS [Method 10]: $R_t$=1.70 min; MS (ESIpos): m/z=558 (M+H)$^+$,
$^1$H-NMR (400 MHz, DMSO-d$_6$): δ [ppm]=10.88 (brs, 1H), 8.85 (d, 1H), 8.20 (dd, 1H), 8.05-7.98 (m, 2H), 7.79 (d, 1H), 7.68 (dd, 1H), 7.60 (d, 1H), 7.54-7.49 (m, 1H), 7.32 (t, 1H), 7.26 (s, 1H), 6.97-6.93 (s, 1H), 6.47 (s, 1H), 5.65-5.56 (m, 1H), 3.34 (s, 3H), 2.24-2.09 (m, 2H), 0.87 (t, 3H).

Example 175

4-({2-[4-{5-Chloro-2-[5-(difluoromethyl)-1,2-oxazol-3-yl]phenyl}-5-methoxy-2-oxopyridin-1(2H)-yl]butanoyl}amino)-2-fluorobenzamide (Racemate)

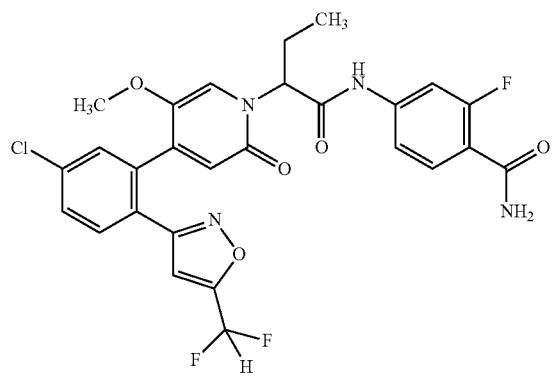 [SMILES: CCC(C(=O)Nc1ccc(C(N)=O)c(F)c1)n1cc(OC)c(-c2cc(Cl)ccc2-c2cc(C(F)F)on2)cc1=O]

10 mg (0.023 mmol) of 2-[4-{5-chloro-2-[5-(difluoromethyl)-1,2-oxazol-3-yl]phenyl}-5-methoxy-2-oxopyridin-1(2H)-yl]butanoic acid (racemate) and 5 mg (0.03 mmol, 1.5 eq.) of 4-amino-2-fluorobenzamide were reacted according to General Method 5. Yield: 8 mg (59% of theory).

LC/MS [Method 10]: $R_t$=1.77 min; MS (ESIneg): m/z=573 (M–H)$^-$,
$^1$H-NMR (400 MHz, DMSO-d$_6$): δ [ppm]=10.80 (brs, 1H), 7.78 (d, 1H), 7.72-7.63 (m, 3H), 7.59 (d, 1H), 7.56-7.49 (m, 2H), 7.39 (dd, 1H), 7.32 (t, 1H), 7.25 (s, 1H), 6.95 (s, 1H), 6.46 (s, 1H), 5.62-5.54 (m, 1H), 3.34 (s, 3H), 2.19-2.07 (m, 2H), 0.86 (t, 3H).

Example 176

2-[4-{5-Chloro-2-[5-(difluoromethyl)-1,2-oxazol-3-yl]phenyl}-5-methoxy-2-oxopyridin-1(2H)-yl]-N-(2-methyl-2H-indazol-5-yl)butanamide (Racemate)

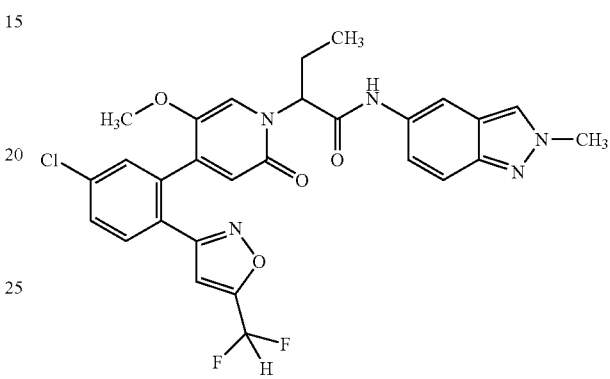

10 mg (0.022 mmol) of 2-[4-{5-chloro-2-[5-(difluoromethyl)-1,2-oxazol-3-yl]phenyl}-5-methoxy-2-oxopyridin-1(2H)-yl]butanoic acid (racemate) and 5 mg (0.03 mmol, 1.5 eq.) of 2-methyl-2H-indazole-5-amine were reacted according to General Method 5. Yield: 12 mg (90% of theory).

LC/MS [Method 10]: $R_t$=1.81 min; MS (ESIpos): m/z=568 (M+H)$^+$,
$^1$H-NMR (400 MHz, DMSO-d$_6$): δ [ppm]=10.37 (brs, 1H), 8.25 (s, 1H), 8.13 (d, 1H), 7.78 (d, 1H), 7.68 (dd, 1H), 7.59 (d, 1H), 7.55 (d, 1H), 7.32 (t, 1H, partially hidden), 7.32-7.26 (m, 2H, partially hidden), 6.98-6.94 (m, 1H), 6.45 (s, 1H), 5.68-5.60 (m, 1H), 4.13 (s, 3H), 3.34 (s, 3H), 2.20-2.00 (m, 2H), 0.87 (t, 3H).

Example 177

4-({2-[4-{5-Chloro-2-[5-(difluoromethyl)-1,2-oxazol-3-yl]phenyl}-5-methoxy-2-oxopyridin-1(2H)-yl]butanoyl}amino)-2-fluoro-N-methylbenzamide (Racemate)

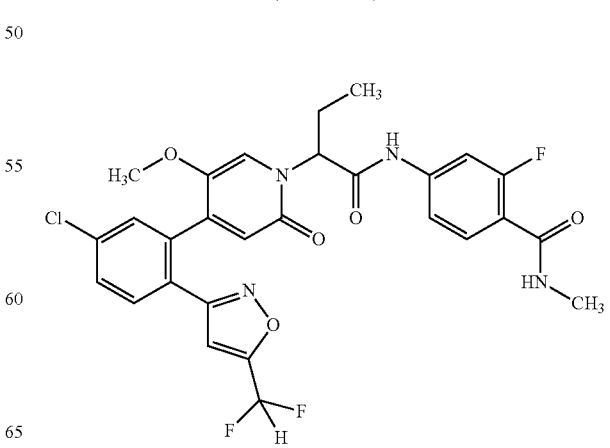

10 mg (23 µmol) of 2-[4-{5-chloro-2-[5-(difluoromethyl)-1,2-oxazol-3-yl]phenyl}-5-methoxy-2-oxopyridin-1(2H)-yl]butanoic acid (racemate) and 6 mg (0.03 mmol, 1.5 eq.) of 4-amino-2-fluoro-N-methylbenzamide were reacted according to General Method 5. Yield: 12 mg (86% of theory).

LC/MS [Method 10]: $R_t$=1.84 min; MS (ESIpos): m/z=589 (M+H)$^+$, $^1$H-NMR (400 MHz, DMSO-d$_6$): δ [ppm]=10.79 (brs, 1H), 8.09-8.04 (m, 1H), 7.79 (d, 1H), 7.70-7.62 (m, 3H), 7.59 (d, 1H), 7.39 (dd, 1H), 7.32 (t, 1H), 7.25 (s, 1H), 6.95 (s, 1H), 6.46 (s, 1H), 5.63-5.53 (m, 1H), 3.34 (s, 3H), 2.77 (d, 3H), 2.19-2.06 (m, 2H), 0.86 (t, 3H).

Example 178

N-(Quinoxalin-6-yl)-2-[4-{5-chloro-2-[5-(difluoromethyl)-1,2-oxazol-3-yl]phenyl}-5-methoxy-2-oxopyridin-1(2H)-yl]butanamide (Racemate)

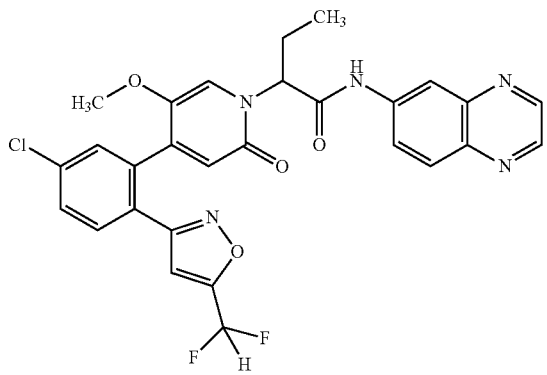 [SMILES: CCC(C(=O)Nc1ccc2nccnc2c1)n1cc(OC)c(-c2cc(Cl)ccc2-c2cc(C(F)F)on2)cc1=O]

10 mg (23 µmol) of 2-[4-{5-chloro-2-[5-(difluoromethyl)-1,2-oxazol-3-yl]phenyl}-5-methoxy-2-oxopyridin-1(2H)-yl]butanoic acid (racemate) and 5 mg (0.03 mmol, 1.5 eq.) of quinoxaline-6-amine were reacted according to General Method 5. Yield: 8 mg (60% of theory).

LC/MS [Method 10]: $R_t$=1.87 min; MS (ESIpos): m/z=566 (M+H)$^+$, $^1$H-NMR (400 MHz, DMSO-d$_6$): δ [ppm]=10.94 (brs, 1H), 8.90 (d, 1H), 8.84 (d, 1H), 8.54 (d, 1H), 8.08 (d, 1H), 7.97 (dd, 1H), 7.79 (d, 1H), 7.69 (dd, 1H), 7.60 (d, 1H), 7.33-7.32 (m, 1H, partially hidden), 7.32 (t, 1H, partially hidden), 6.97 (s, 1H), 6.48 (s, 1H), 5.71-5.64 (m, 1H), 3.36 (s, 3H), 2.27-2.12 (m, 2H), 0.89 (t, 3H).

Example 179

4-[(4-tert-Butoxy-2-{4-[5-chloro-2-(4,5-dihydro-1,2-oxazol-3-yl)phenyl]-5-methoxy-2-oxopyridin-1(2H)-yl}butanoyl)amino]benzoic acid (Racemate)

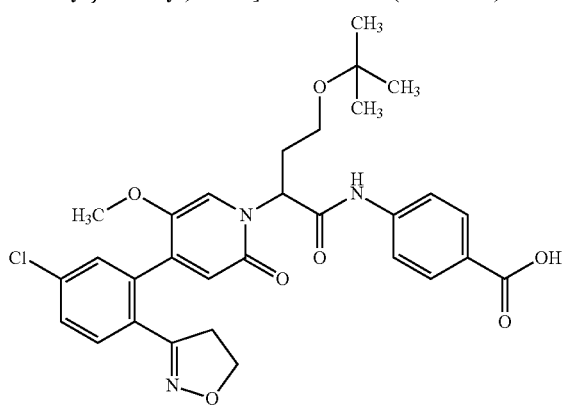

51 mg (0.086 mmol) of methyl 4-[(4-tert-butoxy-2-{4-[5-chloro-2-(4,5-dihydro-1,2-oxazol-3-yl)phenyl]-5-methoxy-2-oxopyridin-1(2H)-yl}butanoyl)amino]benzoate (racemate) were reacted with 0.86 ml of aqueous lithium hydroxide solution (1M) in 2.48 ml of THF according to General Method 2. Yield: 31 mg (62% of theory).

LC/MS [Method 10]: $R_t$=1.82 min; MS (ESIpos): m/z=582 (M+H)$^+$, $^1$H-NMR (400 MHz, DMSO-d$_6$): δ [ppm]=12.74 (br. s., 1H), 10.68 (s, 1H), 7.90 (d, 2H), 7.77 (d, 2H), 7.68-7.62 (m, 1H), 7.61-7.55 (m, 1H), 7.40 (br. s., 1H), 7.30 (s, 1H), 6.36 (s, 1H), 5.80-5.70 (m, 1H), 4.33-4.21 (m, 2H), 3.57 (s, 3H), 3.40-3.10 (m, partially hidden), 2.40-2.26 (m, 2H), 1.06 (s, 9H).

Example 180

4-({(2S)-2-[4-{5-Chloro-2-[1-(difluoromethyl)-1H-pyrazol-4-yl]phenyl}-5-methoxy-2-oxopyridin-1(2H)-yl]-4-methoxybutanoyl}amino)benzoic acid (Enantiomer 2)

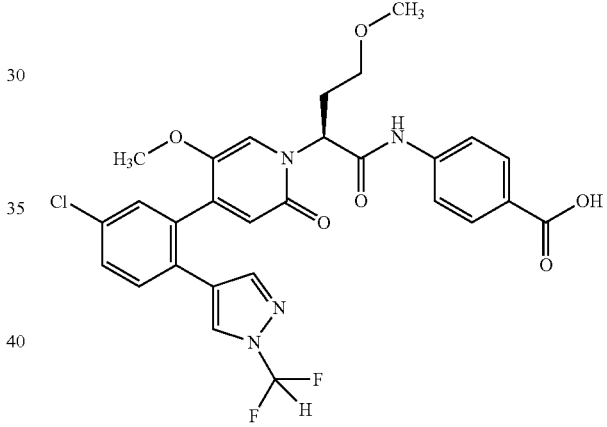

Enantiomer separation of 32.6 mg of 4-({2-[4-{5-chloro-2-[1-(difluoromethyl)-1H-pyrazol-4-yl]phenyl}-5-methoxy-2-oxopyridin-1(2H)-yl]-4-methoxybutanoyl}amino)benzoic acid (racemate) (Example 86) gave 3.3 mg of the title compound Example 180 (enantiomer 2): chiral HPLC: $R_t$=2.6 min; 100% ee, purity 95%.

Separating method: column: Daicel Chiralcel OX-H SFC 5 µm, 250 mm×20 mm; mobile phase: carbon dioxide 83%/ethanol 17%; temperature: 40° C.; flow rate: 80 ml/min; pressure: 100 bar; UV detection: 210 nm.

Analysis: column: OX 20 SFC 3 µm, 100 mm×4.6 mm; mobile phase: carbon dioxide 80%/ethanol 20%; temperature: 40° C.; flow rate: 3 ml/min; UV detection: 210 nm.

Example 181

4-({(2S)-2-[4-{5-Chloro-2-[5-(trifluoromethyl)-1,3,4-oxadiazol-2-yl]phenyl}-5-methoxy-2-oxopyridin-1(2H)-yl]-4-methoxybutanoyl}amino)-2-fluorobenzamide (Enantiomer 2)

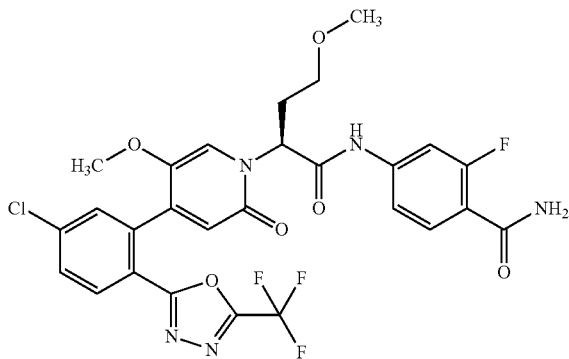 [SMILES: COCC[C@@H](C(=O)Nc1ccc(C(N)=O)c(F)c1)n1cc(OC)c(-c2cc(Cl)ccc2-c2nnc(C(F)(F)F)o2)cc1=O]

Enantiomer separation of 4-({2-[4-{5-chloro-2-[5-(trifluoromethyl)-1,3,4-oxadiazol-2-yl]phenyl}-5-methoxy-2-oxopyridin-1(2H)-yl]-4-methoxybutanoyl}amino)-2-fluorobenzamide (14.5 mg, 23 mol) (racemate) (Example 74) gave 3.4 mg of enantiomer 1 (chiral HPLC: $R_t$=2.8 min) and 2.0 mg of the title compound Example 181 (enantiomer 2): chiral HPLC: $R_t$=4.9 min; 98% ee.

Separating method: column: Daicel Chiralpak AD-H SFC 5 μm 250 mm×20 mm; mobile phase: carbon dioxide 80%/methanol 20%; temperature: 40° C.; flow rate: 80 ml/min; pressure: 100 bar; UV detection: 210 nm.

Analysis: column: Chiralpak AD SFC 3 μm, 100 mm×4.6 mm; mobile phase: 70% carbon dioxide, 30% methanol; flow rate: 3 ml/min; UV detection: 210 nm.

LC/MS (Method 10): $R_t$=1.76 min; MS (ESIneg): m/z=622 [M−H]$^−$.

Example 182

4-({(2S)-2-[4-{5-Chloro-2-[4-(difluoromethyl)-1H-1,2,3-triazol-1-yl]phenyl}-5-methoxy-2-oxopyridin-1(2H)-yl]pentanoyl}amino)-2-fluorobenzamide (Enantiomer 2)

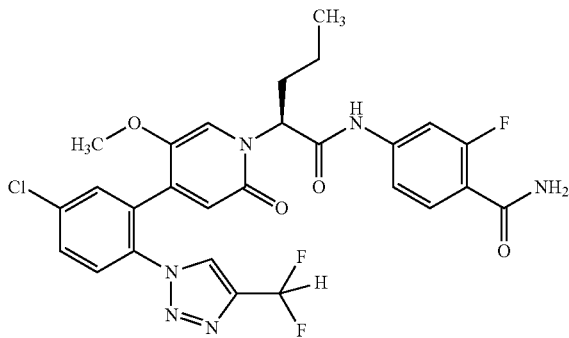 [SMILES: CCC[C@@H](C(=O)Nc1ccc(C(N)=O)c(F)c1)n1cc(OC)c(-c2cc(Cl)ccc2-n2cc(C(F)F)nn2)cc1=O]

Enantiomer separation of 85.8 mg of 4-({2-[4-{5-chloro-2-[4-(difluoromethyl)-1H-1,2,3-triazol-1-yl]phenyl}-5-methoxy-2-oxopyridin-1(2H)-yl]pentanoyl}amino)-2-fluorobenzamide (racemate) (Example 121) gave 39.3 mg of enantiomer 1 (chiral HPLC: $R_t$=2.3 min) and 32.5 mg of the title compound Example 182 (enantiomer 2): chiral HPLC: $R_t$=12.6 min; 100% ee.

Separating method: column: Daicel Chiralpak AS-H SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AS SFC 3 μm, 100 mm×4.6 mm; mobile phase: 70% carbon dioxide, 30% ethanol; flow rate: 3 ml/min; UV detection: 210 nm.

LC/MS [Method 1]: $R_t$=0.90 min; MS (ESIpos): m/z=589 [M+H]$^+$.

Example 183

5-({(2S)-2-[4-{5-Chloro-2-[4-(difluoromethyl)-1H-1,2,3-triazol-1-yl]phenyl}-5-methoxy-2-oxopyridin-1(2H)-yl]pentanoyl}amino)-N-methylpyridine-2-carboxamide (Enantiomer 2)

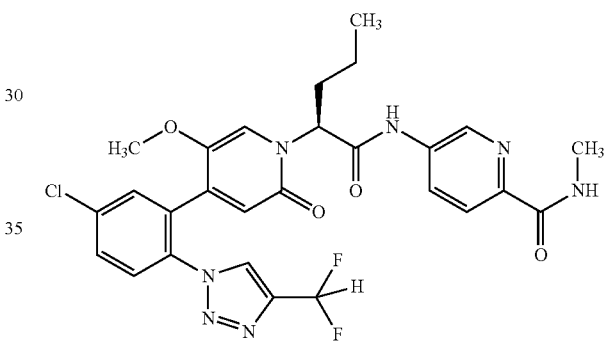

Enantiomer separation of 104 mg of 5-({2-[4-{5-chloro-2-[4-(difluoromethyl)-1H-1,2,3-triazol-1-yl]phenyl}-5-methoxy-2-oxopyridin-1(2H)-yl]pentanoyl}amino)-N-methylpyridine-2-carboxamide (racemate) (Example 124) gave 43.4 mg of enantiomer 1 (chiral HPLC: $R_t$=4.6 min) and 36.2 mg of the title compound Example 183 (enantiomer 2): chiral HPLC: $R_t$=7.2 min; 100% ee.

Separating method: column: Daicel Chiralpak ID SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Chiralpak ID SFC 3 μm, 100 mm×4.6 mm; mobile phase: 70% carbon dioxide, 30% ethanol; flow rate: 3 ml/min; UV detection: 210 nm.

LC/MS [Method 1]: $R_t$=0.91 min; MS (ESIpos): m/z=586 [M+H]$^+$.

Example 184

4-[(2-{4-[5-Chloro-2-(4-chloro-1H-1,2,3-triazol-1-yl)phenyl]-5-methoxy-2-oxopyridin-1(2H)-yl}propanoyl)amino]-2-fluorobenzamide (Racemate)

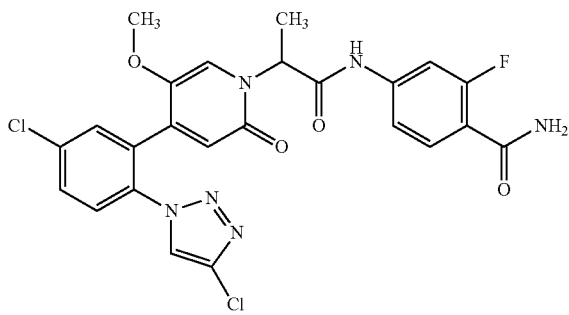 [SMILES: COc1cn(C(C)C(=O)Nc2ccc(C(N)=O)c(F)c2)c(=O)cc1-c1cc(Cl)ccc1-n1cc(Cl)nn1]

38.0 mg (0.093 mmol) of 2-{4-[5-chloro-2-(4-chloro-1H-1,2,3-triazol-1-yl)phenyl]-5-methoxy-2-oxopyridin-1(2H)-yl}propanoic acid (racemate) and 18.6 mg (0.121 mmol) of 4-amino-2-fluorobenzamide in 2.5 ml of pyridine were reacted according to General Method 5. Yield: 33.0 mg (65% of theory)

Alternatively the compound was prepared according to the following procedure:

300 mg (86% purity, 0.63 mmol) of 2-{4-[5-chloro-2-(4-chloro-1H-1,2,3-triazol-1-yl)phenyl]-5-methoxy-2-oxopyridin-1(2H)-yl}propanoic acid (racemate) were dissolved in 16.7 ml pyridine and then 600 µl (1.01 mmol) propylphosphonic anhydride (T3P, 50% solution in ethyl acetate) were added. The mixture was heated to 50° C. and then 126 mg (0.82 mmol) of 4-amino-2-fluorobenzamide were added. The reaction mixture was stirred additional 1 h at 50° C. and then brought to room temperature. The mixture was diluted with 5 ml acetonitrile/water (1:1) and purified by preparative RP-HPLC (0.1% formic acid/acetonitrile gradient). Yield: 234 mg (68% of theory)

LC/MS [Method 1]: $R_t$=0.80 min; MS (ESIpos): m/z=545 (M+H)$^+$, $^1$H-NMR (400 MHz, DMSO-d$_6$): δ [ppm]=10.68 (s, 1H), 8.67 (s, 1H), 7.81-7.60 (m, 5H), 7.56-7.48 (m, 2H), 7.41-7.34 (m, 1H), 7.16 (s, 1H), 6.46 (s, 1H), 5.55-5.46 (m, 1H), 3.33 (s, 3H), 1.64 (d, 3H).

Example 185

N-(Quinoxalin-6-yl)-2-{4-[5-chloro-2-(4-chloro-1H-1,2,3-triazol-1-yl)phenyl]-5-methoxy-2-oxopyridin-1(2H)-yl}propanamide (Racemate)

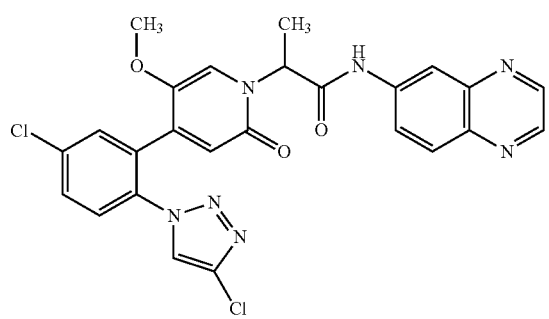 [SMILES: COc1cn(C(C)C(=O)Nc2ccc3nccnc3c2)c(=O)cc1-c1cc(Cl)ccc1-n1cc(Cl)nn1]

38.0 mg (0.093 mmol) of 2-{4-[5-chloro-2-(4-chloro-1H-1,2,3-triazol-1-yl)phenyl]-5-methoxy-2-oxopyridin-1(2H)-yl}propanoic acid (racemate) and 17.5 mg (0.121 mmol) of quinoxaline-6-amine in 2.5 ml of pyridine were reacted according to General Method 5. Yield: 34.2 mg (69% of theory).

LC/MS [Method 1]: $R_t$=0.87 min; MS (ESIpos): m/z=536 (M+H)$^+$, $^1$H-NMR (400 MHz, DMSO-d$_6$): δ [ppm]=10.84 (s, 1H), 8.89 (d, 1H), 8.83 (d, 1H), 8.67 (s, 1H), 8.51 (d, 1H), 8.11-8.04 (m, 1H), 7.98 (d, 1H), 7.82-7.71 (m, 3H), 7.22 (s, 1H), 6.48 (s, 1H), 5.64-5.55 (m, 1H), 3.35 (s, 3H), 1.70 (d, 3H).

Example 186

2-{4-[5-Chloro-2-(4-chloro-1H-1,2,3-triazol-1-yl)phenyl]-5-methoxy-2-oxopyridin-1(2H)-yl}-N-(2-methyl-2H-indazol-5-yl)propanamide (Racemate)

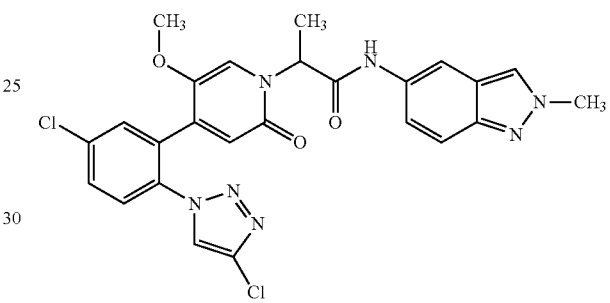

Yield: 26.7 mg (52% of theory).

LC/MS [Method 1]: $R_t$=0.85 min; MS (ESIpos): m/z=538 (M+H)$^+$, $^1$H-NMR (400 MHz, DMSO-d$_6$): δ [ppm]=10.24 (s, 1H), 8.67 (s, 1H), 8.25 (s, 1H), 8.10 (s, 1H), 7.81-7.73 (m, 2H), 7.71 (d, 1H), 7.55 (d, 1H), 7.27 (dd, 1H), 7.21 (s, 1H), 6.45 (s, 1H), 5.65-5.57 (m, 1H), 4.13 (s, 3H), 3.34 (s, 3H), 1.63 (d, 3H).

Example 187

2-{4-[5-Chloro-2-(1H-tetrazol-1-yl)phenyl]-5-methoxy-2-oxopyridin-1(2H)-yl}-N-(2-methyl-2H-indazol-5-yl)acetamide

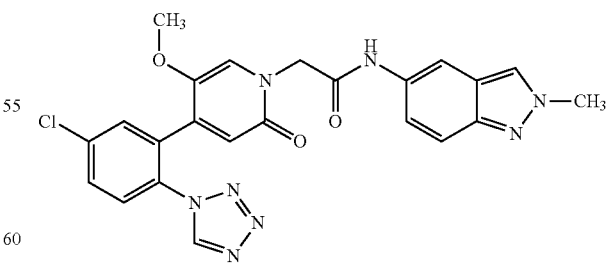

50.0 mg (0.138 mmol) of 2-{4-[5-chloro-2-(1H-tetrazol-1-yl)phenyl]-5-methoxy-2-oxopyridin-1(2H)-yl}acetic acid and 26.4 mg (0.180 mmol) of 2-methyl-2H-indazole-5-amine in 3.7 ml of pyridine were reacted according to General Method 5. Yield: 19.3 mg (29% of theory).

LC/MS [Method 1]: R$_t$=0.69 min; MS (ESIpos): m/z=491 (M+H)$^+$, $^1$H-NMR (400 MHz, DMSO-d$_6$): δ [ppm]=10.23 (s, 1H), 9.68 (s, 1H), 8.24 (s, 1H), 8.12-8.08 (m, 1H), 7.84-7.81 (m, 2H), 7.76 (s, 1H), 7.55 (d, 1H), 7.30-7.22 (m, 2H), 6.49 (s, 1H), 4.70 (br. s., 2H), 4.12 (s, 3H), 3.24 (s, 3H).

Example 188

5-[({4-[5-Chloro-2-(1H-tetrazol-1-yl)phenyl]-5-methoxy-2-oxopyridin-1(2H)-yl}acetyl)amino]-N-methylpyridine-2-carboxamide

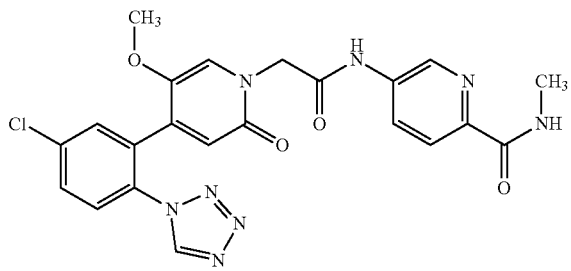 [SMILES: CNC(=O)c1ccc(NC(=O)Cn2cc(OC)c(-c3cc(Cl)ccc3-n3cnnn3)cc2=O)cn1]

50.0 mg (0.138 mmol) of 2-{4-[5-chloro-2-(1H-tetrazol-1-yl)phenyl]-5-methoxy-2-oxopyridin-1(2H)-yl}acetic acid and 27.2 mg (0.180 mmol) of 5-amino-N-methylpyridine-2-carboxamide in 3.7 ml of pyridine were reacted according to General Method 5. Yield: 26.5 mg (39% of theory).

LC/MS [Method 1]: R$_t$=0.68 min; MS (ESIpos): m/z=495 (M+H)$^+$, $^1$H-NMR (400 MHz, DMSO-d$_6$): δ [ppm]=10.82 (s, 1H), 9.69 (s, 1H), 8.91-8.81 (m, 1H), 8.71-8.58 (m, 1H), 8.13 (dd, 1H), 8.00 (d, 1H), 7.83 (s, 2H), 7.76 (s, 1H), 7.28 (s, 1H), 6.51 (s, 1H), 4.75 (br. s., 2H), 3.24 (s, 3H), 2.80 (d, 3H).

Example 189

N-(Quinoxalin-6-yl)-2-{4-[5-chloro-2-(1H-tetrazol-1-yl)phenyl]-5-methoxy-2-oxopyridin-1(2H)-yl}acetamide

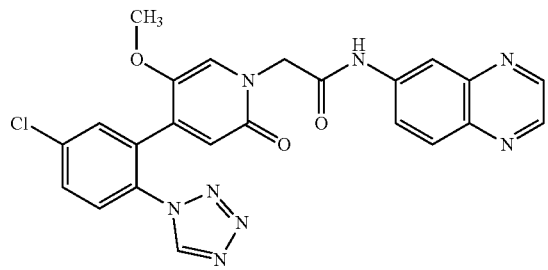 [SMILES: COc1cn(CC(=O)Nc2ccc3nccnc3c2)c(=O)cc1-c1cc(Cl)ccc1-n1cnnn1]

50.0 mg (0.138 mmol) of 2-{4-[5-chloro-2-(1H-tetrazol-1-yl)phenyl]-5-methoxy-2-oxopyridin-1(2H)-yl}acetic acid and 26.1 mg (0.180 mmol) of quinoxaline-6-amine in 3.7 ml of pyridine were reacted according to General Method 5. Yield: 32.3 mg (48% of theory).

LC/MS [Method 10]: R$_t$=1.26 min; MS (ESIpos): m/z=489 (M+H)$^+$, $^1$H-NMR (400 MHz, DMSO-d$_6$): δ [ppm]=10.88 (s, 1H), 9.70 (s, 1H), 8.91-8.80 (m, 2H), 8.49 (d, 1H), 8.08 (d, 1H), 7.97-7.89 (m, 1H), 7.85-7.76 (m, 3H), 7.31 (s, 1H), 6.52 (s, 1H), 4.80 (br. s., 2H), 3.26 (s, 3H).

Example 190

4-[({4-[5-Chloro-2-(1H-tetrazol-1-yl)phenyl]-5-methoxy-2-oxopyridin-1(2H)-yl}acetyl)amino]benzoic acid

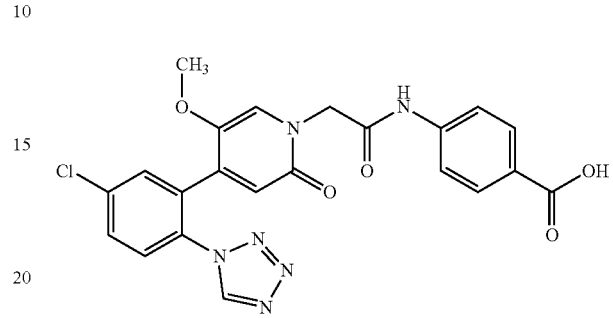

50.0 mg (0.138 mmol) of 2-{4-[5-chloro-2-(1H-tetrazol-1-yl)phenyl]-5-methoxy-2-oxopyridin-1(2H)-yl}acetic acid and 24.6 mg (0.180 mmol) of 4-aminobenzoic acid in 3.7 ml of pyridine were reacted according to General Method 5. Yield: 16.2 mg (24% of theory).

LC/MS [Method 1]: R$_t$=0.70 min; MS (ESIpos): m/z=481 (M+H)$^+$, $^1$H-NMR (400 MHz, DMSO-d$_6$): δ [ppm]=12.72 (br. s., 1H), 10.64 (s, 1H), 9.68 (s, 1H), 7.91 (d, 2H), 7.83 (s, 2H), 7.78-7.75 (m, 1H), 7.70 (d, 2H), 7.27 (s, 1H), 6.50 (s, 1H), 4.77-4.66 (m, 2H), 3.24 (s, 3H).

Example 191

4-[({4-[5-Chloro-2-(1H-tetrazol-1-yl)phenyl]-5-methoxy-2-oxopyridin-1(2H)-yl}acetyl)amino]-2-fluorobenzamide

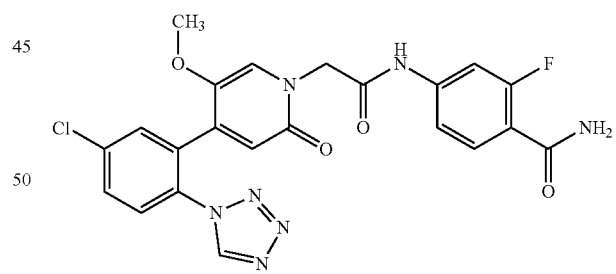

50.0 mg (0.138 mmol) of 2-{4-[5-chloro-2-(1H-tetrazol-1-yl)phenyl]-5-methoxy-2-oxopyridin-1(2H)-yl}acetic acid and 27.7 mg (0.180 mmol) of 4-amino-2-fluorobenzamide in 3.7 ml of pyridine were reacted according to General Method 5. Yield: 15.5 mg (22% of theory).

LC/MS [Method 1]: R$_t$=0.67 min; MS (ESIpos): m/z=498 (M+H)$^+$, $^1$H-NMR (400 MHz, DMSO-d$_6$): δ [ppm]=10.75 (s, 1H), 9.69 (s, 1H), 7.85-7.81 (m, 2H), 7.76 (s, 1H), 7.69 (t, 1H), 7.65-7.59 (m, 1H), 7.53 (br. s., 2H), 7.36-7.31 (m, 1H), 7.29-7.24 (m, 1H), 6.50 (s, 1H), 4.71 (br. s., 2H), 3.24 (s, 3H).

Example 192

5-({2-[4-{5-Chloro-2-[5-(difluoromethyl)-1,3,4-thiadiazol-2-yl]phenyl}-5-methoxy-2-oxopyridin-1(2H)-yl]butanoyl}amino)pyridine-2-carboxamide (Racemate)

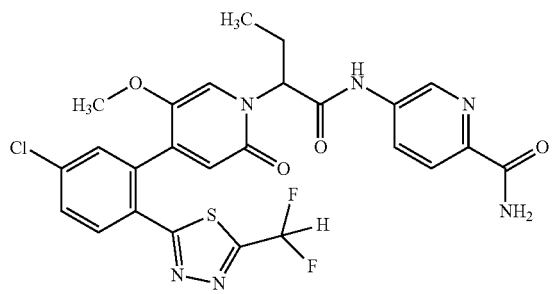 [SMILES: CCC(C(=O)Nc1ccc(C(N)=O)nc1)n1cc(OC)c(-c2cc(Cl)ccc2-c2nnc(C(F)F)s2)cc1=O]

23 mg (50 µmol) of 2-[4-{5-chloro-2-[5-(difluoromethyl)-1,3,4-thiadiazol-2-yl]phenyl}-5-methoxy-2-oxopyridin-1(2H)-yl]butanoic acid (racemate) and 10 mg (0.076 mmol, 1.5 eq.) of 5-aminopyridine-2-carboxamide in 0.25 ml of pyridine were reacted according to General Method 5. Yield: 23 mg (81% of theory).

LC/MS [Method 10]: $R_t$=1.63 min; MS (ESIpos): m/z=575 (M+H)$^+$, $^1$H-NMR (400 MHz, DMSO-$d_6$): δ [ppm]=10.92 (brs, 1H), 8.85 (d, 1H), 8.21 (dd, 1H), 8.08 (d, 1H), 8.04-7.98 (m, 2H), 7.74 (dd, 1H), 7.67 (d, 1H), 7.58 (t, 1H), 7.55-7.51 (m, 1H), 7.32 (s, 1H), 6.59 (s, 1H), 5.79-5.53 (m, 1H), 3.34 (s, 3H), 2.24-2.13 (m, 2H), 0.88 (t, 3H).

Example 193

4-({2-[4-{5-Chloro-2-[5-(difluoromethyl)-1,3,4-thiadiazol-2-yl]phenyl}-5-methoxy-2-oxopyridin-1(2H)-yl]butanoyl}amino)-2-fluorobenzamide (Racemate)

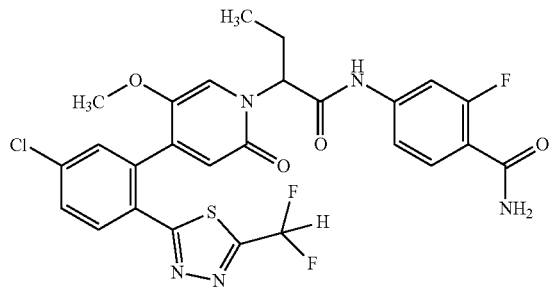 [SMILES: CCC(C(=O)Nc1ccc(C(N)=O)c(F)c1)n1cc(OC)c(-c2cc(Cl)ccc2-c2nnc(C(F)F)s2)cc1=O]

23.0 mg (0.050 mmol) of 2-[4-{5-chloro-2-[5-(difluoromethyl)-1,3,4-thiadiazol-2-yl]phenyl}-5-methoxy-2-oxopyridin-1(2H)-yl]butanoic acid (racemate) and 12 mg (0.076 mmol, 1.5 eq.) of 4-amino-2-fluorobenzamide in 0.25 ml of pyridine were reacted according to General Method 5. Yield: 22.0 mg (75% of theory)

LC/MS [Method 10]: $R_t$=1.70 min; MS (ESIpos): m/z=592 (M+H)$^+$, $^1$H-NMR (400 MHz, DMSO-$d_6$): δ [ppm]=10.81 (brs, 1H), 8.08 (d, 1H), 7.75 (dd, 1H), 7.73-7.64 (m, 3H), 7.59 (t, 1H, partially hidden), 7.56-7.50 (m, 2H), 7.39 (dd, 1H), 7.31 (s, 1H), 6.58 (s, 1H), 5.68-5.53 (m, 1H), 3.34 (s, 3H), 2.21-2.10 (m, 2H), 0.87 (t, 3H).

Example 194

2-[4-{5-Chloro-2-[5-(difluoroethyl)-1,3,4-thiadiazol-2-yl]phenyl}-5-methoxy-2-oxopyridin-1(2H)-yl]-N-(2-methyl-2H-indazol-5-yl)butanamide (Racemate)

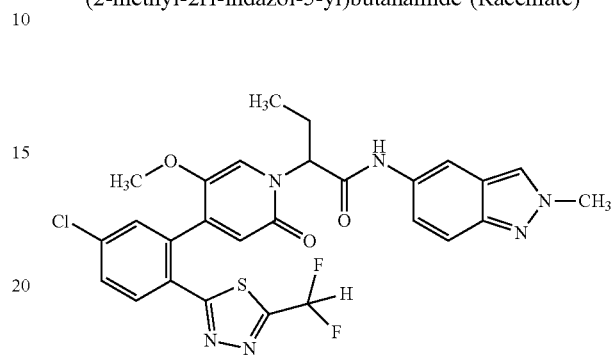

23.0 mg (0.050 mmol) of 2-[4-{5-chloro-2-[5-(difluoromethyl)-1,3,4-thiadiazol-2-yl]phenyl}-5-methoxy-2-oxopyridin-1(2H)-yl]butanoic acid (racemate) and 11 mg (0.076 mmol, 1.5 eq.) of 2-methyl-2H-indazole-5-amine in 0.25 ml of pyridine were reacted according to General Method 5. Yield: 23 mg (78% of theory).

LC/MS [Method 10]: $R_t$=1.75 min; MS (ESIpos): m/z=585 (M+H)$^+$, $^1$H-NMR (400 MHz, DMSO-$d_6$): δ [ppm]=10.38 (s, 1H), 8.25 (s, 1H), 8.13 (d, 1H), 8.08 (d, 1H), 7.74 (dd, 1H), 7.67 (d, 1H), 7.57 (d, 1H), 7.54 (t, 1H), 7.37 (s, 1H), 7.28 (dd, 1H), 6.57 (s, 1H), 5.73-5.61 (m, 1H), 4.13 (s, 3H), 3.34 (s, 3H), 2.22-2.05 (m, 2H), 0.88 (t, 3H).

Example 195

4-({2-[4-{5-Chloro-2-[5-(difluoromethyl)-1,3,4-thiadiazol-2-yl]phenyl}-5-methoxy-2-oxopyridin-1(2H)-yl]butanoyl}amino)-2-fluoro-N-methylbenzamide (Racemate)

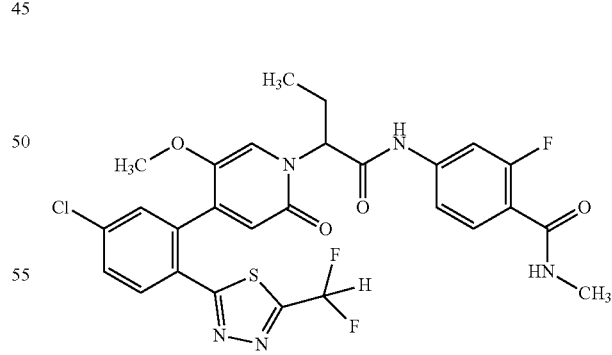

23 mg (0.050 mmol) of 2-[4-{5-chloro-2-[5-(difluoromethyl)-1,3,4-thiadiazol-2-yl]phenyl}-5-methoxy-2-oxopyridin-1(2H)-yl]butanoic acid (racemate) and 13 mg (0.076 mmol) of 4-amino-2-fluoro-N-methylbenzamide in 0.25 ml of pyridine were reacted according to General Method 5. Yield: 23 mg (74% of theory).

LC/MS [Method 10]: $R_t$=1.78 min; MS (ESIpos): m/z=606 (M+H)$^+$,

¹H-NMR (400 MHz, DMSO-d₆): δ [ppm]=10.81 (brs, 1H), 8.11-8.04 (m, 2H), 7.75 (dd, 1H), 7.70-7.62 (m, 3H), 7.58 (t, 1H), 7.38 (dd, 1H), 7.31 (s, 1H), 6.58 (s, 1H), 5.68-5.53 (m, 1H), 3.34 (s, 3H), 2.76 (d, 3H), 2.20-2.10 (m, 2H), 0.87 (t, 3H).

Example 196

2-[4-{5-Chloro-2-[5-(difluoromethyl)-1,3,4-thiadiazol-2-yl]phenyl}-5-methoxy-2-oxopyridin-1(2H)-yl]-N-(quinoxalin-6-yl)butanamide (Racemate)

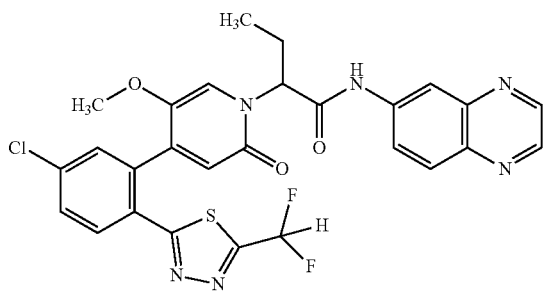 [SMILES: CCC(C(=O)Nc1ccc2nccnc2c1)n1cc(OC)c(-c2cc(Cl)ccc2-c2nnc(C(F)F)s2)cc1=O]

23 mg (0.050 mmol) of 2-[4-{5-chloro-2-[5-(difluoromethyl)-1,3,4-thiadiazol-2-yl]phenyl}-5-methoxy-2-oxopyridin-1(2H)-yl]butanoic acid and 11 mg (0.076 mmol) of quinoxaline-6-amine in 0.25 ml of pyridine were reacted according to General Method 5. Yield: 24 mg (83% of theory).

LC/MS [Method 10]: $R_t$=1.80 min; MS (ESIpos): m/z=583 (M+H)⁺,

¹H-NMR (400 MHz, DMSO-d₆): δ [ppm]=10.97 (brs, 1H), 8.90 (d, 1H), 8.84 (d, 1H), 8.54 (d, 1H), 8.10-8.06 (m, 2H), 7.97 (dd, 1H), 7.75 (dd, 1H), 7.68 (d, 1H), 7.59 (t, 1H, partially hidden), 7.37 (s, 1H), 6.60 (s, 1H), 5.81-5.56 (m, 1H), 3.36 (s, 3H), 2.28-2.15 (m, 2H), 0.91 (t, 3H).

Example 197

4-({2-[4-{5-Chloro-2-[5-(trifluoromethyl)-1,2-oxazol-3-yl]phenyl}-5-methoxy-2-oxopyridin-1(2H)-yl]butanoyl}amino)-2-fluorobenzamide (Racemate)

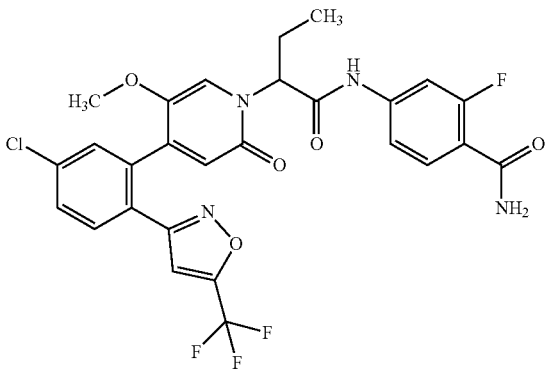 [SMILES: CCC(C(=O)Nc1ccc(C(N)=O)c(F)c1)n1cc(OC)c(-c2cc(Cl)ccc2-c2cc(C(F)(F)F)on2)cc1=O]

28 mg (61 µmol) of 2-[4-{5-chloro-2-[5-(trifluoromethyl)-1,2-oxazol-3-yl]phenyl}-5-methoxy-2-oxopyridin-1(2H)-yl]butanoic acid (racemate) and 14 mg (0.092 mmol, 1.5 eq.) of 4-amino-2-fluorobenzamide in 0.34 ml of pyridine were reacted according to General Method 5. Yield: 34 mg (92% of theory).

LC/MS [Method 8]: $R_t$=1.32 min; MS (ESIneg): m/z=591 (M−H)⁻,

¹H-NMR (400 MHz, DMSO-d₆): δ [ppm]=10.78 (brs, 1H), 7.81 (d, 1H), 7.73-7.62 (m, 4H), 7.56-7.49 (m, 2H), 7.44-7.41 (m, 1H), 7.39 (dd, 1H), 7.24 (s, 1H), 6.49 (s, 1H), 5.61-5.51 (m, 1H), 3.32 (s, 3H), 2.19-2.08 (m, 2H), 0.85 (t, 3H).

Example 198

2-[4-{5-Chloro-2-[5-(trifluoromethyl)-1,2-oxazol-3-yl]phenyl}-5-methoxy-2-oxopyridin-1(2H)-yl]-N-(2-methyl-2H-indazol-5-yl)butanamide (Racemate)

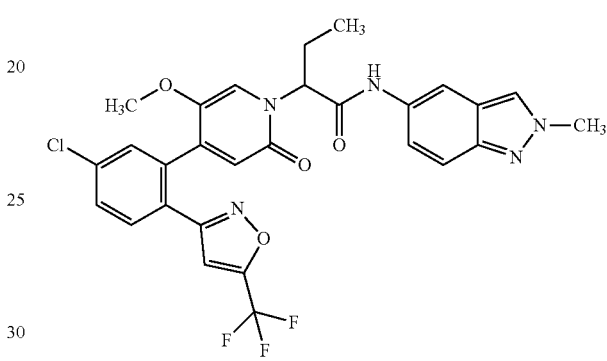

28 mg (61 µmol) of 2-[4-{5-chloro-2-[5-(trifluoromethyl)-1,2-oxazol-3-yl]phenyl}-5-methoxy-2-oxopyridin-1 (2H)-yl]butanoic acid (racemate) and 14 mg (0.092 mmol, 1.5 eq.) of 2-methyl-2H-indazole-5-amine in 0.34 ml of pyridine were reacted according to General Method 5. Yield: 33 mg (92% of theory).

LC/MS [Method 10]: $R_t$=1.95 min; MS (ESIpos): m/z=586 (M+H)⁺,

¹H-NMR (400 MHz, DMSO-d₆): δ [ppm]=10.36 (brs, 1H), 8.25 (s, 1H), 8.14-8.11 (m, 1H), 7.81 (d, 1H), 7.71 (dd, 1H), 7.63 (d, 1H), 7.55 (d, 1H), 7.45 (s, 1H), 7.31-7.26 (m, 2H), 6.48 (s, 1H), 5.68-5.61 (m, 1H), 4.13 (s, 3H), 3.33 (s, 3H), 2.20-2.02 (m, 2H), 0.86 (t, 3H).

Example 199

6-[(2-{4-[5-Chloro-2-(4-chloro-1H-1,2,3-triazol-1-yl)phenyl]-5-methoxy-2-oxopyridin-1(2H)-yl}butanoyl)amino]quinolin-2-aminium formate (Racemate)

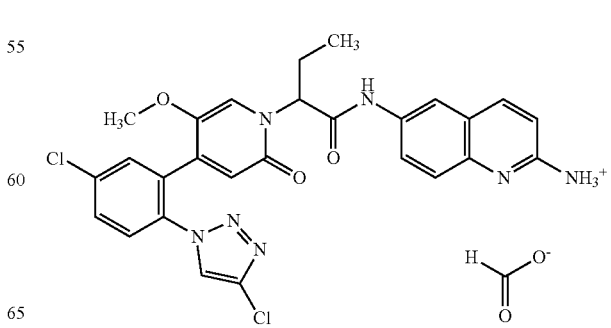

40 mg (95 µmol) of 2-{4-[5-chloro-2-(4-chloro-1H-1,2,3-triazol-1-yl)phenyl]-5-methoxy-2-oxopyridin-1(2H)-yl}butanoic acid (racemate) and 23 mg (0.142 mmol, 1.5 eq.) of quinoline-2,6-diamine in 0.52 ml of pyridine were reacted according to General Method 5. Yield: 4 mg (7% of theory).

LC/MS [Method 10]: $R_t$=1.23 min; MS (ESIpos): m/z=564 (M+H)$^+$, $^1$H-NMR (400 MHz, DMSO-d$_6$): δ [ppm]=10.46 (s, 1H), 8.64 (s, 1H), 8.17 (s, 1H), 8.02 (s, 1H), 7.86-7.71 (m, 4H), 7.58-7.53 (m, 1H), 7.43-7.38 (m, 1H), 7.23 (s, 1H), 6.73 (d, 1H), 6.48 (s, 1H), 6.37 (brs, 1H), 5.63-5.57 (m, 1H), 3.32 (s, 3H), 2.17-1.99 (m, 2H), 0.83 (t, 3H).

Example 200

2-{4-[5-Chloro-2-(4-chloro-1H-1,2,3-triazol-1-yl)phenyl]-5-methoxy-2-oxopyridin-1(2H)-yl}-N-(3-methylquinoxalin-6-yl)butanamide (Racemate)

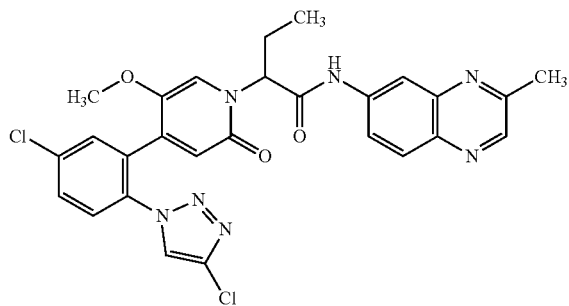 [SMILES: CCC(C(=O)Nc1ccc2ncc(C)nc2c1)n1cc(OC)c(-c2cc(Cl)ccc2-n2cc(Cl)nn2)cc1=O]

130 mg (307 µmol) of 2-{4-[5-chloro-2-(4-chloro-1H-1,2,3-triazol-1-yl)phenyl]-5-methoxy-2-oxopyridin-1(2H)-yl}butanoic acid (racemate) and 73 mg (0.46 mmol, 1.5 eq.) of 3-methylquinoxalin-6-amine in 1.5 ml of pyridine were reacted according to General Method 5. Yield: 126 mg (73% of theory).

LC/MS [Method 8]: $R_t$=1.23 min; MS (ESIneg): m/z=562 (M−H)$^-$, $^1$H-NMR (400 MHz, DMSO-d$_6$): δ [ppm]=10.87 (s, 1H), 8.73 (s, 1H), 8.63 (s, 1H), 8.38 (d, 1H), 8.01 (d, 1H), 7.90 (dd, 1H), 7.83-7.72 (m, 3H), 7.24 (s, 1H), 6.49 (s, 1H), 5.67-5.57 (m, 1H), 3.34 (s, 3H), 2.68 (s, 3H), 2.23-2.05 (m, 2H), 0.85 (t, 3H).

Example 201

(S)-2-{4-[5-Chloro-2-(4-chloro-1H-1,2,3-triazol-1-yl)phenyl]-5-methoxy-2-oxopyridin-1(2H)-yl}-N-(3-methylquinoxalin-6-yl)butanamide (Enantiomer 2)

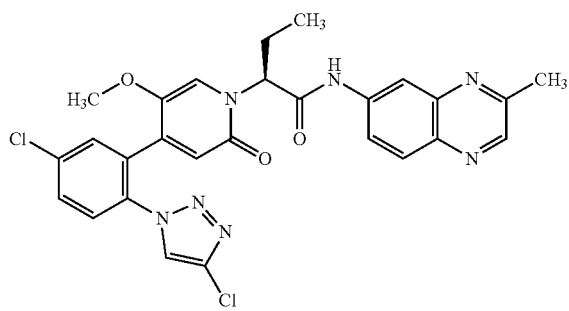 [SMILES: CC[C@@H](C(=O)Nc1ccc2ncc(C)nc2c1)n1cc(OC)c(-c2cc(Cl)ccc2-n2cc(Cl)nn2)cc1=O]

Enantiomer separation of 2-{4-[5-chloro-2-(4-chloro-1H-1,2,3-triazol-1-yl)phenyl]-5-methoxy-2-oxopyridin-1(2H)-yl}-N-(3-methylquinoxalin-6-yl)butanamide (114 mg, 0.202 mmol) (racemate) (Example 200) gave 49 mg of enantiomer 1 (chiral HPLC: $R_t$=3.3 min) and 50 mg of the title compound Example 201 (enantiomer 2): chiral HPLC: $R_t$=6.4 min; 100% ee.

Separating method: column: Daicel Chiralpak AD-H SFC 5 µm 250 mm×20 mm; mobile phase: carbon dioxide 70%/ethanol 30%; temperature: 40° C.; flow rate: 70 ml/min; pressure: 100 bar; UV detection: 210 nm.

Analysis: column: Chiralpak AD SFC 3 µm, 100 mm×4.6 mm; mobile phase: 70% carbon dioxide, 30% ethanol; flow rate: 3 ml/min; UV detection: 210 nm.

LC/MS (Method 10): $R_t$=1.75 min; MS (ESIpos): m/z=564 [M+H]$^+$.

Example 202

4-{[(2S)-2-{4-[5-Chloro-2-(4-chloro-1H-1,2,3-triazol-1-yl)phenyl]-5-methoxy-2-oxopyridin-1(2H)-yl}pentanoyl]amino}-2-fluorobenzamide (Enantiomer 2)

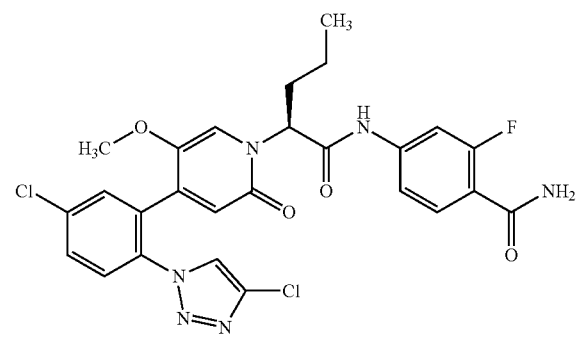 [SMILES: CCC[C@@H](C(=O)Nc1ccc(C(N)=O)c(F)c1)n1cc(OC)c(-c2cc(Cl)ccc2-n2cc(Cl)nn2)cc1=O]

Enantiomer separation of 25 mg of 4-{[2-{4-[5-chloro-2-(4-chloro-1H-1,2,3-triazol-1-yl)phenyl]-5-methoxy-2-oxopyridin-1(2H)-yl}pentanoyl]amino}-2-fluorobenzamide (racemate) (Example 125) gave 10.6 mg of enantiomer 1 (chiral HPLC: $R_t$=4.6 min) and 9.9 mg of the title compound (enantiomer 2): chiral HPLC: $R_t$=7.3 min; 100% ee.

Separating method: column: Chiralpak AD-H SFC, 5 µm 250 mm×20 mm; mobile phase: carbon dioxide 78%/ethanol 22%; temperature: 40° C.; flow rate: 70 ml/min; pressure: 100 bar; UV detection: 210 nm.

Analysis: column: Daicel AD SFC 3 µm, 100 mm×4.6 mm; mobile phase: 70% carbon dioxide, 30% ethanol; flow rate: 3 ml/min; UV detection: 210 nm.

LC-MS [Method 1]: $R_t$=0.92 min; MS (ESIpos): m/z=573 [M+H]$^+$

Example 203

2-{4-[5-Chloro-2-(4-chloro-1H-H-1,2,3-triazol-1-yl)phenyl]-5-methoxy-2-oxopyridin-1(2H)-yl}-N-[3-(trifluoromethyl)quinoxalin-6-yl]butanamide (Racemate)

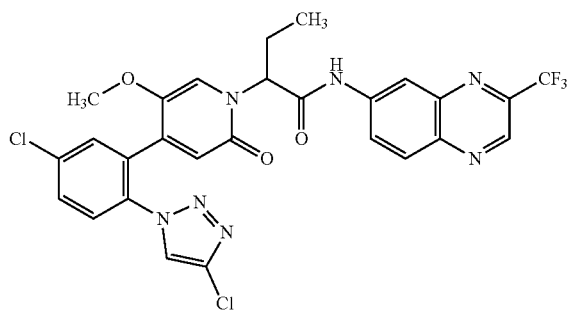 [SMILES: CCC(C(=O)Nc1ccc2ncc(C(F)(F)F)nc2c1)n1cc(OC)c(-c2cc(Cl)ccc2-n2cc(Cl)nn2)cc1=O]

20 mg (47 µmol) of 2-{4-[5-chloro-2-(4-chloro-1H-1,2,3-triazol-1-yl)phenyl]-5-methoxy-2-oxopyridin-1(2H)-yl}butanoic acid (racemate) and 11 mg (0.052 mmol, 1.1 eq.) of 3-(trifluoromethyl)quinoxalin-6-amine in 0.23 ml of pyridine were reacted according to General Method 5. Yield: 24 mg (82% of theory).

LC/MS [Method 8]: $R_t$=1.43 min; MS (ESIneg): m/z=616 (M−H)$^-$, $^1$H-NMR (400 MHz, DMSO-d$_6$): δ [ppm]=11.10 (s, 1H), 9.31 (s, 1H), 8.65-8.61 (m, 2H), 8.25 (d, 1H), 8.15 (dd, 1H), 7.82-7.73 (m, 3H), 7.24 (s, 1H), 6.50 (s, 1H), 5.69-5.59 (m, 1H), 3.34 (s, 3H), 2.26-2.08 (m, 2H), 0.86 (t, 3H).

Example 204

2-{4-[5-Chloro-2-(4-chloro-1H-1,2,3-triazol-1-yl)phenyl]-5-methoxy-2-oxopyridin-1(2H)-yl}-N-[2-(trifluoromethyl)quinoxalin-6-yl]butanamide (Racemate)

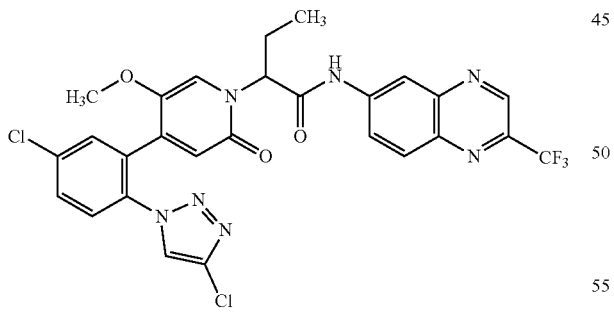

20 mg (47 µmol) of 2-{4-[5-chloro-2-(4-chloro-1H-1,2,3-triazol-1-yl)phenyl]-5-methoxy-2-oxopyridin-1(2H)-yl}butanoic acid (racemate) and 11 mg (0.052 mmol, 1.1 eq.) of 2-(trifluoromethyl)quinoxalin-6-amine in 0.23 ml of pyridine were reacted according to General Method 5. Yield: 24 mg (82% of theory).

LC/MS [Method 8]: $R_t$=1.43 min; MS (ESIneg): m/z=616 (M−H)$^-$, $^1$H-NMR (400 MHz, DMSO-d$_6$): δ [ppm]=11.12 (s, 1H), 9.36 (s, 1H), 8.70-8.66 (m, 1H), 8.63 (s, 1H), 8.25 (d, 1H), 8.10 (dd, 1H), 7.82-7.73 (m, 3H), 7.23 (s, 1H), 6.50 (s, 1H), 5.69-5.59 (m, 1H), 3.34 (s, 3H), 2.26-2.08 (m, 2H), 0.87 (t, 3H).

Example 205

2-[4-{5-Chloro-2-[4-(trifluoromethyl)-1H-1,2,3-triazol-1-yl]phenyl}-5-methoxy-2-oxopyridin-1(2H)-yl]-N-[3-(trifluoromethyl)quinoxalin-6-yl]butanamide (Racemate)

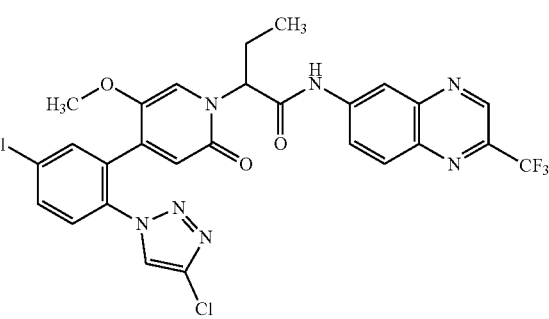

20 mg (31 µmol, 70% purity) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) and 7 mg (0.034 mmol, 1.1 eq.) of 3-(trifluoromethyl)quinoxalin-6-amine in 0.15 ml of pyridine were reacted according to General Method 5. Yield: 17 mg (85% of theory).

LC/MS [Method 8]: $R_t$=1.48 min; MS (ESIneg): m/z=650 (M−H)$^-$, $^1$H-NMR (400 MHz, DMSO-d$_6$): δ [ppm]=11.08 (s, 1H), 9.30 (s, 1H), 9.14 (s, 1H), 8.63-8.59 (m, 1H), 8.25 (d, 1H), 8.14 (dd, 1H), 7.87-7.78 (m, 3H), 7.19 (s, 1H), 6.55 (s, 1H), 5.66-5.58 (m, 1H), 3.29 (s, 3H), 2.25-2.08 (m, 2H), 0.83 (t, 3H).

Example 206

2-[4-{5-Chloro-2-[4-(trifluoromethyl)-1H-1,2,3-triazol-1-yl]phenyl}-5-methoxy-2-oxopyridin-1(2H)-yl]-N-[2-(trifluoromethyl)quinoxalin-6-yl]butanamide (Racemate)

20 mg (31 µmol, 70% purity) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) and 7 mg (0.034 mmol, 1.1 eq.) of 2-(trifluoromethyl)

quinoxalin-6-amine in 0.15 ml of pyridine were reacted according to General Method 5. Yield: 17 mg (82% of theory).

LC/MS [Method 8]: R$_t$=1.48 min; MS (ESIneg): m/z=650 (M−H)$^-$, $^1$H-NMR (400 MHz, DMSO-d$_6$): δ [ppm]=11.11 (s, 1H), 9.36 (s, 1H), 9.14 (s, 1H), 8.69-8.66 (m, 1H), 8.25 (d, 1H), 8.09 (dd, 1H), 7.88-7.78 (m, 3H), 7.19 (s, 1H), 6.55 (s, 1H), 5.66-5.58 (m, 1H), 3.28 (s, 3H), 2.24-2.09 (m, 2H), 0.83 (t, 3H).

Example 207

2-{4-[5-Chloro-2-(4-chloro-1H-1,2,3-triazol-1-yl)phenyl]-5-methoxy-2-oxopyridin-1(2H)-yl}-N-(phthalazin-6-yl)butanamide (Racemate)

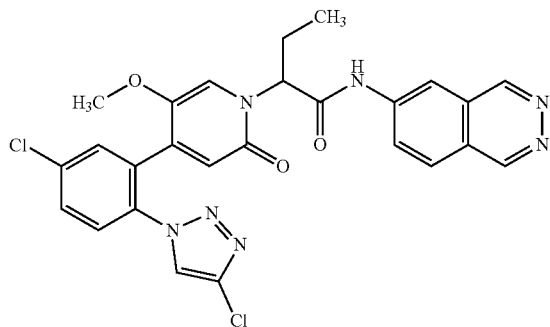 [SMILES: CCC(C(=O)Nc1ccc2cnncc2c1)n1cc(OC)c(-c2cc(Cl)ccc2-n2cc(Cl)nn2)cc1=O]

20 mg (47 µmol) of 2-{4-[5-chloro-2-(4-chloro-1H-1,2,3-triazol-1-yl)phenyl]-5-methoxy-2-oxopyridin-1(2H)-yl}butanoic acid (racemate) and 9 mg (0.052 mmol, 1.1 eq.) of phthalazin-6-aminium chloride in 0.23 ml of pyridine were reacted according to General Method 5. Yield: 25 mg (96% of theory).

LC/MS [Method 8]: R$_t$=1.10 min; MS (ESIneg): m/z=548 (M−H)$^-$, $^1$H-NMR (400 MHz, DMSO-d$_6$): δ [ppm]=11.06 (s, 1H), 9.64 (s, 1H), 9.55 (s, 1H), 8.64 (s, 1H), 8.56 (s, 1H), 8.14 (d, 1H), 8.06-8.01 (m, 1H), 7.82-7.72 (m, 3H), 7.22 (s, 1H), 6.49 (s, 1H), 5.66-5.59 (m, 1H), 3.34 (s, 3H), 2.24-2.06 (m, 2H), 0.86 (t, 3H).

Example 208

2-[4-{5-Chloro-2-[4-(trifluoromethyl)-1H-1,2,3-triazol-1-yl]phenyl}-5-methoxy-2-oxopyridin-1(2H)-yl]-N-(phthalazin-6-yl)butanamide (Racemate)

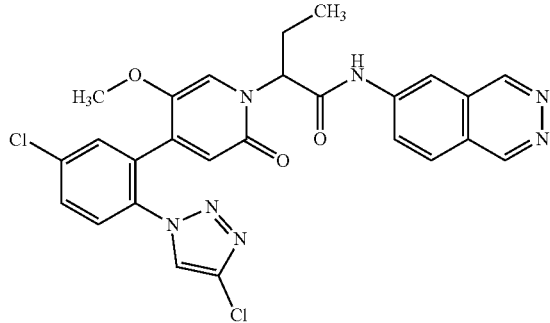 [SMILES: CCC(C(=O)Nc1ccc2cnncc2c1)n1cc(OC)c(-c2cc(Cl)ccc2-n2cc(Cl)nn2)cc1=O]

30 mg (46 µmol, 70% purity) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) and 9 mg (0.051 mmol, 1.1 eq.) of phthalazin-6-aminium chloride in 0.23 ml of pyridine were reacted according to General Method 5. Yield: 16 mg (60% of theory).

LC/MS [Method 8]: R$_t$=1.17 min; MS (ESIneg): m/z=582 (M−H)$^-$, $^1$H-NMR (400 MHz, DMSO-d$_6$): δ [ppm]=11.04 (s, 1H), 9.62 (s, 1H), 9.55 (s, 1H), 9.16 (s, 1H), 8.54 (s, 1H), 8.14 (d, 1H), 8.05-8.00 (m, 1H), 7.89-7.76 (m, 3H), 7.18 (s, 1H), 6.55 (s, 1H), 5.66-5.57 (m, 1H), 3.28 (s, 3H), 2.22-2.07 (m, 2H), 0.82 (t, 3H).

Example 209

2-[4-{5-Chloro-2-[4-(difluoromethyl)-1H-1,2,3-triazol-1-yl]phenyl}-5-methoxy-2-oxopyridin-1(2H)-yl]-N-[2-(difluoromethyl)-2H-indazol-5-yl]butanamide (Racemate)

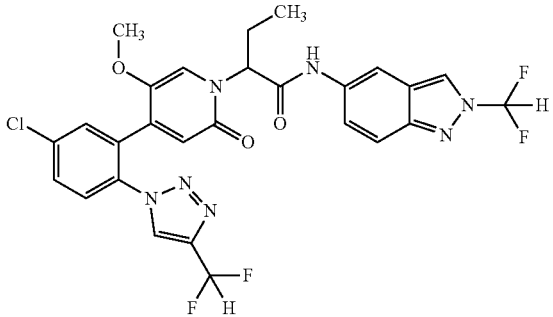 [SMILES: CCC(C(=O)Nc1ccc2nn(C(F)F)cc2c1)n1cc(OC)c(-c2cc(Cl)ccc2-n2cc(C(F)F)nn2)cc1=O]

160.0 mg (80% purity, 0.292 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 85.4 mg (90% purity, 0.350 mmol) of 2-(difluoromethyl)-2H-indazol-5-amine hydrochloride in 2.0 ml of pyridine were reacted at room temperature according to General Method 5. Yield: 138 mg (79% of theory).

LC/MS [Method 10]: R$_t$=1.82 min; MS (ESIpos): m/z=604 (M+H)$^+$, $^1$H-NMR (400 MHz, DMSO-d$_6$): δ [ppm]=10.50 (s, 1H), 8.79 (d, 1H), 8.74 (s, 1H), 7.91-8.28 (m, 2H), 7.65-7.83 (m, 4H), 7.38-7.46 (m, 1H), 7.05-7.37 (m, 2H), 6.51 (s, 1H), 5.51-5.68 (m, 1H), 3.27 (s, 3H), 1.96-2.19 (m, 2H), 0.74-0.89 (m, 3H).

Example 210

(2S)-2-[4-{5-Chloro-2-[4-(difluoromethyl)-1H-1,2,3-triazol-1-yl]phenyl}-5-methoxy-2-oxopyridin-1(2H)-yl]-N-[2-(difluoromethyl)-2H-indazol-5-yl]butanamide (Enantiomer 2)

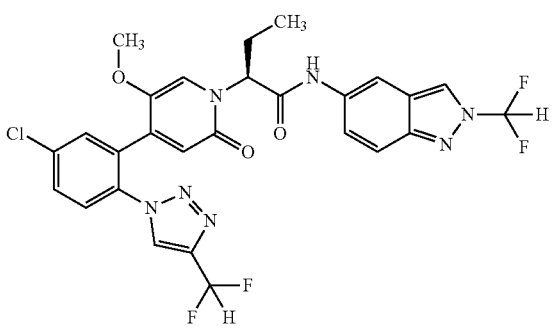 [SMILES: CC[C@@H](C(=O)Nc1ccc2nn(C(F)F)cc2c1)n1cc(OC)c(-c2cc(Cl)ccc2-n2cc(C(F)F)nn2)cc1=O]

Enantiomer separation of 127 mg of 2-[4-{5-chloro-2-[4-(difluoromethyl)-1H-1,2,3-triazol-1-yl]phenyl}-5-methoxy-2-oxopyridin-1(2H)-yl]-N-[2-(difluoromethyl)-2H-indazol-5-yl]butanamide (racemate) (Example 209) gave 49 mg of enantiomer 1 (chiral HPLC: $R_t$=1.1 min) and 46 mg of the title compound (enantiomer 2): chiral HPLC: $R_t$=2.2 min; 100% ee.

Separating method: column: Daicel Chiralpak AD-H SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AD SFC 3 μm, 100 mm×4.6 mm; mobile phase: 70% carbon dioxide, 30% ethanol; flow rate: 3 ml/min; UV detection: 210 nm.

LC/MS [Method 10]: $R_t$=1.82 min; MS (ESIpos): m/z=604 [M+H]$^+$.

Example 211

2-{4-[5-Chloro-2-(4-chloro-1H-1,2,3-triazol-1-yl)phenyl]-5-methoxy-2-oxopyridin-1(2H)-yl}-N-[2-(difluoromethyl)-2H-indazol-5-yl]butanamide (Racemate)

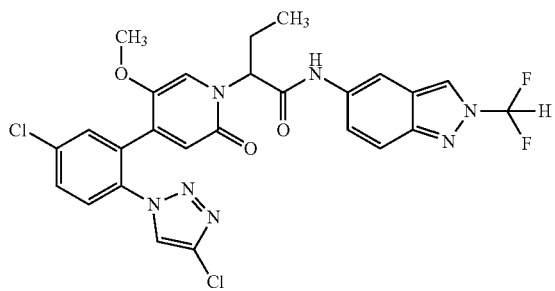 [SMILES: CCC(C(=O)Nc1ccc2nn(C(F)F)cc2c1)n1cc(OC)c(-c2cc(Cl)ccc2-n2cc(Cl)nn2)cc1=O]

100.0 mg (0.236 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 69.2 mg (90% purity, 0.284 mmol) of 2-(difluoromethyl)-2H-indazol-5-amine hydrochloride in 1.8 ml of pyridine were reacted at room temperature according to General Method 5. Yield: 104 mg (75% of theory).

LC/MS [Method 10]: $R_t$=1.84 min; MS (ESIpos): m/z=588 (M+H)$^+$, $^1$H-NMR (400 MHz, DMSO-$d_6$): δ [ppm]=10.50 (s, 1H), 8.80 (s, 1H), 8.63 (s, 1H), 7.92-8.29 (m, 2H), 7.66-7.83 (m, 4H), 7.42 (dd, 1H), 7.23 (s, 1H), 6.48 (s, 1H), 5.56-5.66 (m, 1H), 3.32 (s, 3H), 1.99-2.20 (m, 2H), 0.78-0.89 (m, 3H).

Example 212

(2S)-2-{4-[5-Chloro-2-(4-chloro-1H-1,2,3-triazol-1-yl)phenyl]-5-methoxy-2-oxopyridin-1(2H)-yl}-N-[2-(difluoromethyl)-2H-indazol-5-yl]butanamide (Enantiomer 2)

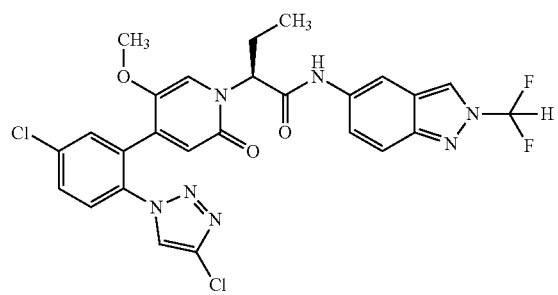 [SMILES: CC[C@@H](C(=O)Nc1ccc2nn(C(F)F)cc2c1)n1cc(OC)c(-c2cc(Cl)ccc2-n2cc(Cl)nn2)cc1=O]

Enantiomer separation of 248 mg of 2-{4-[5-chloro-2-(4-chloro-1H-1,2,3-triazol-1-yl)phenyl]-5-methoxy-2-oxopyridin-1(2H)-yl}-N-[2-(difluoromethyl)-2H-indazol-5-yl]butanamide (racemate) (Example 211) gave 98 mg of enantiomer 1 (chiral HPLC: $R_t$=3.8 min) and 97 mg of the title compound (enantiomer 2): chiral HPLC: $R_t$=8.4 min; 100% ee.

Separating method: column: Daicel Chiralpak AD-H SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AD SFC 3 μm, 100 mm×4.6 mm; mobile phase: 70% carbon dioxide, 30% ethanol; flow rate: 3 ml/min; UV detection: 210 nm.

LC/MS [Method 1]: $R_t$=0.98 min; MS (ESIpos): m/z=588 [M+H]$^+$.

Example 213

2-{4-[5-Chloro-2-(4-chloro-1H-1,2,3-triazol-1-yl)phenyl]-5-methoxy-2-oxopyridin-1(2H)-yl}-N-[2-(cyclopropylmethyl)-2H-indazol-5-yl]butanamide (Racemate)

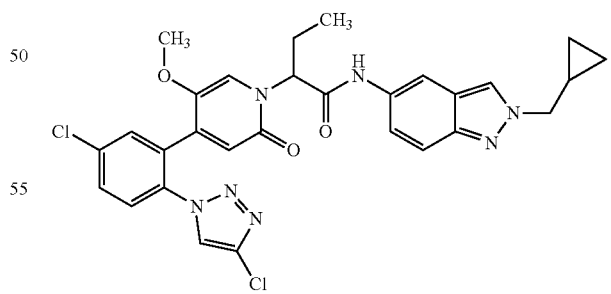

50.0 mg (0.118 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 37.3 mg (85% purity, 0.142 mmol) of 2-(cyclopropylmethyl)-2H-indazol-5-amine hydrochloride in 0.9 ml of pyridine were reacted at room temperature according to General Method 5. Yield: 23 mg (31% of theory).

LC/MS [Method 10]: $R_t$=1.85 min; MS (ESIpos): m/z=592 (M+H)$^+$, $^1$H-NMR (400 MHz, DMSO-d$_6$): δ [ppm]=10.35 (s, 1H), 8.63 (s, 1H), 8.32 (s, 1H), 8.10-8.14 (m, 1H), 7.72-7.82 (m, 3H), 7.54-7.60 (m, 1H), 7.26-7.31 (m, 1H), 7.22-7.25 (m, 1H), 6.47 (s, 1H), 5.57-5.65 (m, 1H), 4.24 (d, 2H), 3.32 (s, 3H), 1.98-2.19 (m, 2H), 1.31-1.43 (m, 1H), 0.79-0.87 (m, 3H), 0.53-0.60 (m, 2H), 0.40-0.46 (m, 2H).

Example 214

4-[(2-{4-[5-Chloro-2-(4-chloro-1H-1,2,3-triazol-1-yl)phenyl]-5-methoxy-2-oxopyridin-1(2H)-yl}-4,4-difluorobutanoyl)amino]-2-fluorobenzamide (Racemate)

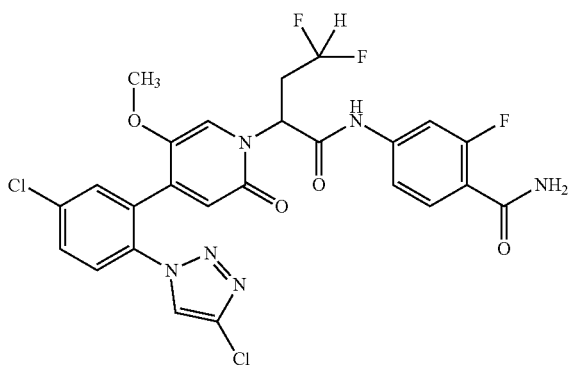 [SMILES: COc1cn(C(CC(F)F)C(=O)Nc2ccc(C(N)=O)c(F)c2)c(=O)cc1-c1cc(Cl)ccc1-n1cc(Cl)nn1]

100.0 mg (0.218 mmol) of 2-{4-[5-chloro-2-(4-chloro-1H-1,2,3-triazol-1-yl)phenyl]-5-methoxy-2-oxopyridin-1(2H)-yl}-4,4-difluorobutanoic acid (racemate) and 43.6 mg (0.283 mmol) of 4-amino-2-fluorobenzamide in 5.8 ml of pyridine were reacted at 50° C. according to General Method 5. Yield: 86 mg (67% of theory).

LC/MS [Method 1]: $R_t$=0.86 min; MS (ESIpos): m/z=595 (M+H)$^+$, $^1$H-NMR (400 MHz, DMSO-d$_6$): δ [ppm]=10.65 (br s, 1H), 8.56 (s, 1H), 7.74-7.82 (m, 2H), 7.66-7.72 (m, 2H), 7.60-7.65 (m, 1H), 7.50-7.57 (m, 2H), 7.38-7.44 (m, 1H), 7.25 (s, 1H), 6.50 (s, 1H), 5.86-6.20 (m, 1H), 5.73-5.84 (m, 1H), 3.30 (s, 3H), 2.69-2.87 (m, 2H).

Example 215

5-({2-[4-{5-Chloro-2-[5-(trifluoromethyl)-1,3,4-thiadiazol-2-yl]phenyl}-5-methoxy-2-oxopyridin-1(2H)-yl]butanoyl}amino)-N-methylpyridine-2-carboxamide (Racemate)

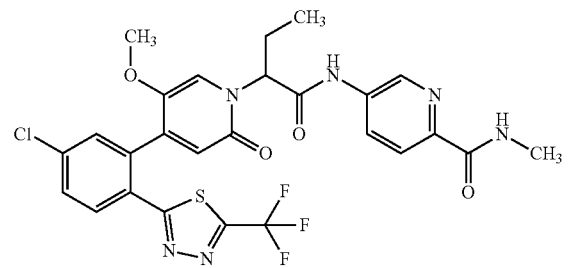 [SMILES: CCC(C(=O)Nc1ccc(C(=O)NC)nc1)n1cc(OC)c(-c2cc(Cl)ccc2-c2nnc(C(F)(F)F)s2)cc1=O]

52.0 mg (0.110 mmol) of 2-[4-{5-chloro-2-[5-(trifluoromethyl)-1,3,4-thiadiazol-2-yl]phenyl}-5-methoxy-2-oxopyridin-1(2H)-yl]butanoic acid (racemate) and 24.9 mg (0.165 mmol) of 5-amino-N-methylpyridine-2-carboxamide in 0.9 ml of pyridine were reacted at 50° C. according to General Method 5. Yield: 51 mg (77% of theory).

LC/MS [Method 1]: $R_t$=0.99 min; MS (ESIpos): m/z=607 (M+H)$^+$, $^1$H-NMR (400 MHz, DMSO-d$_6$): δ [ppm]=10.76-11.01 (m, 1H), 8.87 (d, 1H), 8.61-8.71 (m, 1H), 8.18 (dd, 1H), 8.11 (d, 1H), 8.01 (d, 1H), 7.74-7.82 (m, 1H), 7.68-7.73 (m, 1H), 7.32 (s, 1H), 6.61 (s, 1H), 5.51-5.72 (m, 1H), 3.33-3.36 (m, 3H), 2.77-2.83 (m, 3H), 2.13-2.26 (m, 2H), 0.80-0.95 (m, 3H).

Example 216

2-{4-[5-Chloro-2-(4-chloro-1H-1,2,3-triazol-1-yl)phenyl]-5-methoxy-2-oxopyridin-1(2H)-yl}-N-[2-(difluoromethyl)-2H-indazol-5-yl]-4,4-difluorobutanamide (Racemate)

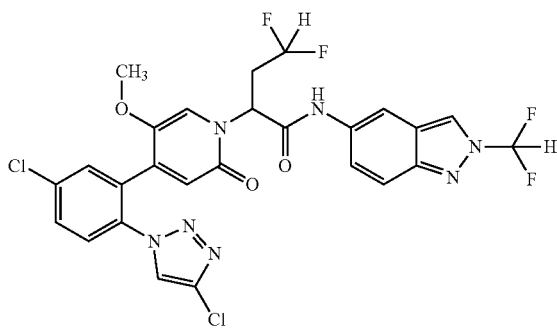 [SMILES: COc1cn(C(CC(F)F)C(=O)Nc2ccc3nn(C(F)F)cc3c2)c(=O)cc1-c1cc(Cl)ccc1-n1cc(Cl)nn1]

100.0 mg (0.218 mmol) of 2-{4-[5-chloro-2-(4-chloro-1H-1,2,3-triazol-1-yl)phenyl]-5-methoxy-2-oxopyridin-1(2H)-yl}-4,4-difluorobutanoic acid (racemate) and 63.4 mg (0.283 mmol) of 2-(difluoromethyl)-2H-indazol-5-amine hydrochloride in 5.8 ml of pyridine were reacted at 50° C. according to General Method 5. Yield: 75 mg (55% of theory).

LC/MS [Method 1]: $R_t$=0.98 min; MS (ESIpos): m/z=624 (M+H)$^+$, $^1$H-NMR (400 MHz, DMSO-d$_6$): δ [ppm]=10.45-10.54 (m, 1H), 8.80 (s, 1H), 8.57 (s, 1H), 7.91-8.25 (m, 2H), 7.69-7.82 (m, 4H), 7.29 (s, 1H), 7.20-7.26 (m, 1H), 6.50 (s, 1H), 5.81-6.20 (m, 2H), 3.3 (s, partly covered by solvent signal), 2.72-2.90 (m, 2H).

Example 217

2-{4-[5-Chloro-2-(4-chloro-1H-1,2,3-triazol-1-yl)
phenyl]-5-methoxy-2-oxopyridin-1(2H)-yl}-4,4-
difluoro-N-(quinoxalin-6-yl)butanamide (Racemate)

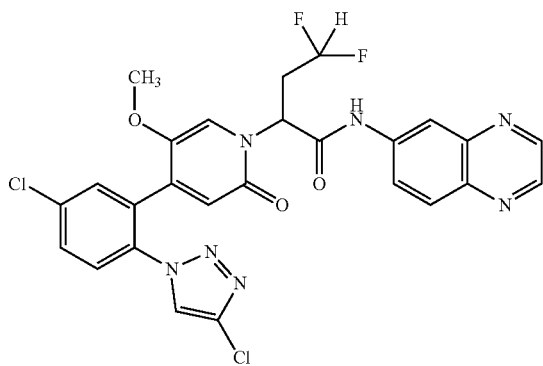 [SMILES: COc1cn(C(CC(F)F)C(=O)Nc2ccc3nccnc3c2)c(=O)cc1-c1cc(Cl)ccc1-n1cc(Cl)nn1]

100.0 mg (0.218 mmol) of 2-{4-[5-chloro-2-(4-chloro-1H-1,2,3-triazol-1-yl)phenyl]-5-methoxy-2-oxopyridin-1(2H)-yl}-4,4-difluorobutanoic acid (racemate) and 41.1 mg (0.283 mmol) of quinoxalin-6-amine in 5.8 ml of pyridine were reacted at 50° C. according to General Method 5. Yield: 34 mg (27% of theory).

LC/MS [Method 1]: $R_t$=0.91 min; MS (ESIpos): m/z=586 (M+H)$^+$, $^1$H-NMR (400 MHz, DMSO-d$_6$): δ [ppm]=10.82 (br s, 1H), 8.88-8.93 (m, 1H), 8.83-8.86 (m, 1H), 8.57 (s, 1H), 8.48-8.53 (m, 1H), 8.06-8.12 (m, 1H), 7.95-8.02 (m, 1H), 7.70-7.83 (m, 3H), 7.31 (s, 1H), 6.51 (s, 1H), 5.82-6.23 (m, 2H), 3.32 (s, 3H), 2.76-2.93 (m, 2H).

Example 218

2-{4-[5-Chloro-2-(4-chloro-1H-1,2,3-triazol-1-yl)
phenyl]-5-methoxy-2-oxopyridin-1(2H)-yl}-4,4-
difluoro-N-(2-methyl-2H-indazol-5-yl)butanamide
(Racemate)

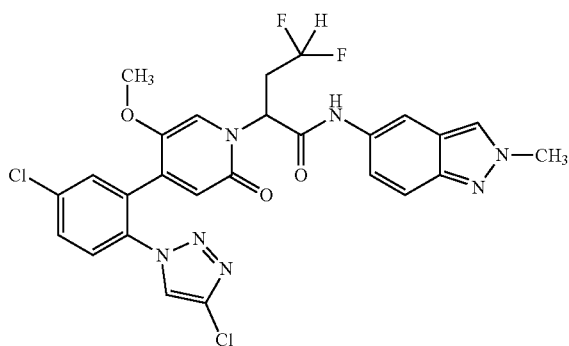 [SMILES: COc1cn(C(CC(F)F)C(=O)Nc2ccc3nn(C)cc3c2)c(=O)cc1-c1cc(Cl)ccc1-n1cc(Cl)nn1]

100.0 mg (0.218 mmol) of 2-{4-[5-chloro-2-(4-chloro-1H-1,2,3-triazol-1-yl)phenyl]-5-methoxy-2-oxopyridin-1(2H)-yl}-4,4-difluorobutanoic acid (racemate) and 41.7 mg (0.283 mmol) of 2-methyl-2H-indazol-5-amine in 5.8 ml of pyridine were reacted at 50° C. according to General Method 5. Yield: 40 mg (30% of theory).

LC/MS [Method 10]: $R_t$=1.65 min; MS (ESIpos): m/z=588 (M+H)$^+$, $^1$H-NMR (400 MHz, DMSO-d$_6$): δ [ppm]=10.27 (s, 1H), 8.58 (s, 1H), 8.26 (s, 1H), 8.05-8.10 (m, 1H), 7.76-7.83 (m, 2H), 7.68-7.73 (m, 1H), 7.55 (d, 1H), 7.25-7.31 (m, 2H), 6.49 (s, 1H), 5.81-6.20 (m, 2H), 4.13 (s, 3H), 2.69-2.86 (m, 2H).

Example 219

4-({2-[4-{5-Chloro-2-[5-(trifluoromethyl)-1,3,4-
thiadiazol-2-yl]phenyl}-5-methoxy-2-oxopyridin-1
(2H)-yl]butanoyl}amino)-2-fluorobenzamide (Racemate)

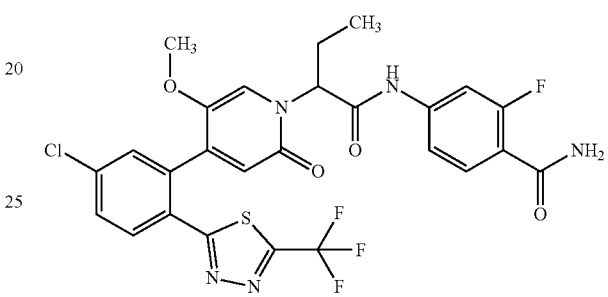

52.0 mg (0.110 mmol) of 2-[4-{5-chloro-2-[5-(trifluoromethyl)-1,3,4-thiadiazol-2-yl]phenyl}-5-methoxy-2-oxopyridin-1(2H)-yl]butanoic acid (racemate) and 25.4 mg (0.165 mmol) of 4-amino-2-fluorobenzamide in 0.9 ml of pyridine were reacted at 50° C. according to General Method 5. Yield: 40 mg (60% of theory).

LC/MS [Method 1]: $R_t$=0.98 min; MS (ESIpos): m/z=610 (M+H)$^+$, $^1$H-NMR (400 MHz, DMSO-d$_6$): δ [ppm]=10.81 (br s, 1H), 8.11 (d, 1H), 7.77 (dd, 1H), 7.63-7.73 (m, 3H), 7.49-7.58 (m, 2H), 7.35-7.42 (m, 1H), 7.31 (s, 1H), 6.60 (s, 1H), 5.60 (br s, 1H), 3.34 (s, 3H), 2.10-2.23 (m, 2H), 0.82-0.94 (m, 3H).

Example 220

2-[4-{5-Chloro-2-[5-(trifluoromethyl)-1,3,4-thiadi-
azol-2-yl]phenyl}-5-methoxy-2-oxopyridin-1(2H)-
yl]-N-(2-methyl-2H-indazol-5-yl)butanamide (Racemate)

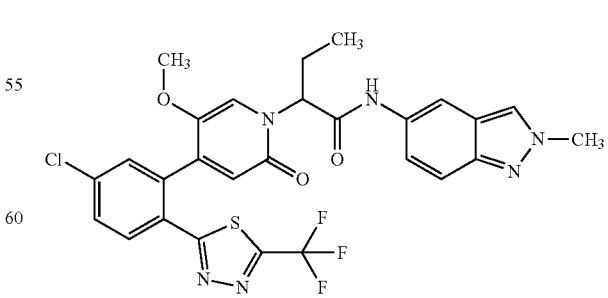

52.0 mg (0.110 mmol) of 2-[4-{5-chloro-2-[5-(trifluoromethyl)-1,3,4-thiadiazol-2-yl]phenyl}-5-methoxy-2-oxopyridin-1(2H)-yl]butanoic acid (racemate) and 21.0 mg (0.143 mmol) of 2-methyl-2H-indazol-5-amine in 2.9 ml of pyridine were reacted at 50° C. according to General Method 5. Yield: 50 mg (76% of theory).

LC/MS [Method 1]: $R_t$=1.01 min; MS (ESIpos): m/z=603 (M+H)⁺,

¹H-NMR (400 MHz, DMSO-d₆): δ [ppm]=10.38 (br s, 1H), 8.25 (s, 1H), 8.08-8.16 (m, 2H), 7.74-7.81 (m, 1H), 7.69-7.73 (m, 1H), 7.52-7.59 (m, 1H), 7.37 (s, 1H), 7.23-7.32 (m, 1H), 6.60 (s, 1H), 5.67 (br s, 1H), 4.13 (s, 3H), 3.35 (s, 3H), 2.06-2.23 (m, 2H), 0.80-0.96 (m, 3H).

Example 221

2-{4-[5-Chloro-2-(4-chloro-1H-1,2,3-triazol-1-yl)phenyl]-5-methoxy-2-oxopyridin-1(2H)-yl}-N-(2-methylquinoxalin-6-yl)butanamide (Racemate)

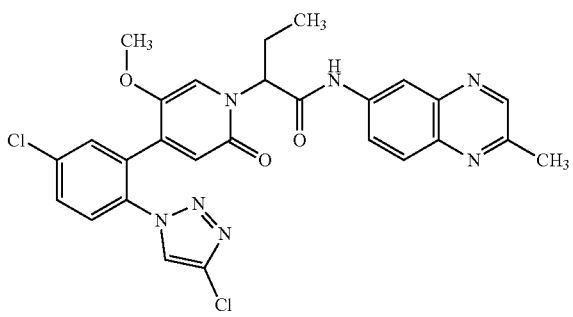 [SMILES: CCC(C(=O)Nc1ccc2nc(C)cnc2c1)n1cc(OC)c(-c2cc(Cl)ccc2-n2cc(Cl)nn2)cc1=O]

50.0 mg (0.118 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 28.2 mg (0.177 mmol) of 2-methylquinoxalin-6-amine in 1.8 ml of pyridine were reacted at 50° C. according to General Method 5. Yield: 11 mg (16% of theory).

LC/MS [Method 1]: $R_t$=0.93 min; MS (ESIpos): m/z=564 (M+H)⁺,

¹H-NMR (400 MHz, DMSO-d₆): δ [ppm]=10.85 (s, 1H), 8.80 (s, 1H), 8.63 (s, 1H), 8.46 (d, 1H), 7.94-7.99 (m, 1H), 7.88-7.94 (m, 1H), 7.73-7.82 (m, 3H), 7.24 (s, 1H), 6.49 (s, 1H), 5.58-5.66 (m, 1H), 3.33 (s, 3H), 2.67 (s, 3H), 2.05-2.26 (m, 2H), 0.82-0.91 (m, 3H).

Example 222

2-{4-[5-Chloro-2-(4-chloro-1H-1,2,3-triazol-1-yl)phenyl]-5-methoxy-2-oxopyridin-1(2H)-yl}-N-(2,3-dimethylquinoxalin-6-yl)butanamide (Racemate)

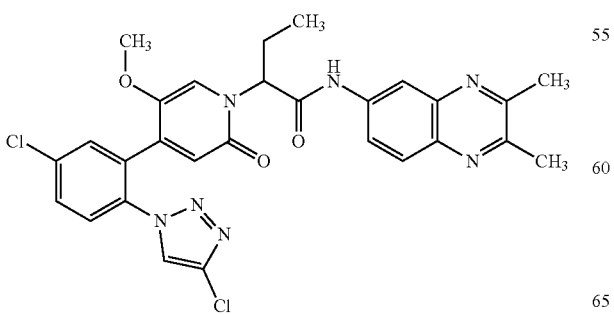

33.0 mg (0.078 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 20.3 mg (0.117 mmol) of 2,3-dimethylquinoxalin-6-amine in 0.6 ml of pyridine were reacted at 50° C. according to General Method 5. Yield: 31 mg (69% of theory).

LC/MS [Method 1]: $R_t$=0.95 min; MS (ESIpos): m/z=578 (M+H)⁺,

¹H-NMR (400 MHz, DMSO-d₆): δ [ppm]=10.80 (s, 1H), 8.63 (s, 1H), 8.34 (d, 1H), 7.89-7.94 (m, 1H), 7.73-7.86 (m, 4H), 7.24 (s, 1H), 6.49 (s, 1H), 5.58-5.67 (m, 1H), 3.33 (s, 3H), 2.65 (d, 6H), 2.05-2.22 (m, 2H), 0.81-0.89 (m, 3H).

Example 223

2-{4-[5-Chloro-2-(4-chloro-1H-1,2,3-triazol-1-yl)phenyl]-5-methoxy-2-oxopyridin-1(2H)-yl}-N-(quinolin-6-yl)butanamide (Racemate)

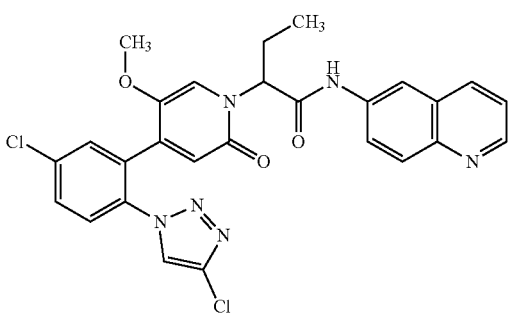 [SMILES: CCC(C(=O)Nc1ccc2ncccc2c1)n1cc(OC)c(-c2cc(Cl)ccc2-n2cc(Cl)nn2)cc1=O]

33.0 mg (0.078 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 16.9 mg (0.117 mmol) of quinolin-6-amine in 0.6 ml of pyridine were reacted at 50° C. according to General Method 5. Yield: 22 mg (51% of theory).

LC/MS [Method 1]: $R_t$=0.84 min; MS (ESIpos): m/z=549 (M+H)⁺,

¹H-NMR (400 MHz, DMSO-d₆): δ [ppm]=10.76 (s, 1H), 8.77-8.82 (m, 1H), 8.64 (s, 1H), 8.37-8.43 (m, 1H), 8.29 (d, 1H), 7.99 (d, 1H), 7.72-7.86 (m, 4H), 7.45-7.53 (m, 1H), 7.24 (s, 1H), 6.49 (s, 1H), 5.60-5.69 (m, 1H), 3.33 (s, 3H), 2.03-2.25 (m, 2H), 0.81-0.90 (m, 3H).

Example 224

2-{4-[5-Chloro-2-(4-chloro-1H-1,2,3-triazol-1-yl)phenyl]-5-methoxy-2-oxopyridin-1(2H)-yl}-N-(quinolin-7-yl)butanamide (Racemate)

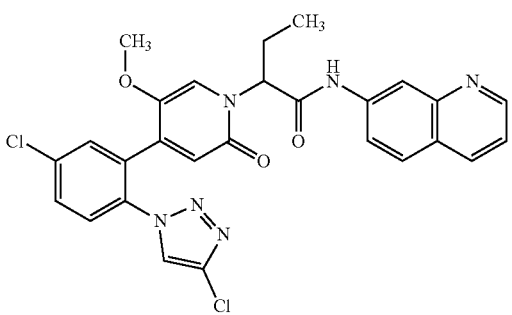 [SMILES: CCC(C(=O)Nc1ccc2cccnc2c1)n1cc(OC)c(-c2cc(Cl)ccc2-n2cc(Cl)nn2)cc1=O]

33.9 mg (0.080 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 17.3 mg (0.120 mmol) of quinolin-7-amine in 0.7 ml of pyridine were reacted at 50° C. according to General Method 5. Yield: 23 mg (52% of theory).

LC/MS [Method 10]: $R_t$=1.51 min; MS (ESIpos): m/z=549 (M+H)$^+$, $^1$H-NMR (400 MHz, DMSO-d$_6$): δ [ppm]=10.77 (s, 1H), 8.82-8.88 (m, 1H), 8.63 (s, 1H), 8.40-8.45 (m, 1H), 8.27-8.33 (m, 1H), 7.95 (d, 1H), 7.73-7.82 (m, 4H), 7.41-7.46 (m, 1H), 7.24 (s, 1H), 6.49 (s, 1H), 5.59-5.68 (m, 1H), 3.34 (s, 3H), 2.04-2.23 (m, 2H), 0.80-0.91 (m, 3H).

Example 225

2-{4-[5-Chloro-2-(4-chloro-1H-1,2,3-triazol-1-yl)phenyl]-5-methoxy-2-oxopyridin-1(2H)-yl}-N-[2-(trideutero)methyl-2H-indazol-5-yl]butanamide (Racemate)

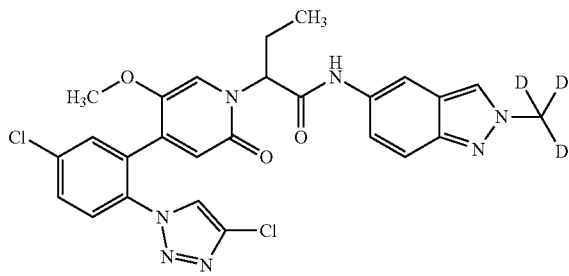 [SMILES: [2H]C([2H])([2H])n1cc2cc(NC(=O)C(CC)n3cc(OC)c(-c4cc(Cl)ccc4-n4cc(Cl)nn4)cc3=O)ccc2n1]

100.0 mg (0.236 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 35.5 mg (0.236 mmol) of 2-(trideutero)methyl-2H-indazol-6-amine in 1.8 ml of pyridine were reacted at 50° C. according to General Method 5. Yield: 54 mg (40% of theory).

LC/MS [Method 1]: $R_t$=0.89 min; MS (ESIpos): m/z=555 (M+H)$^+$, $^1$H-NMR (400 MHz, DMSO-d$_6$): δ [ppm]=10.35 (s, 1H), 8.63 (s, 1H), 8.24 (s, 1H), 8.08-8.15 (m, 1H), 7.71-7.83 (m, 3H), 7.51-7.58 (m, 1H), 7.21-7.30 (m, 2H), 6.47 (s, 1H), 5.51-5.66 (m, 1H), 3.32 (s, 3H), 1.98-2.19 (m, 2H), 0.75-0.88 (m, 3H).

Example 226

2-{4-[5-Chloro-2-(4-chloro-1H-1,2,3-triazol-1-yl)phenyl]-5-methoxy-2-oxopyridin-1(2H)-yl}-N-[2-(2,2-difluoroethyl)-2H-indazol-5-yl]butanamide (Racemate)

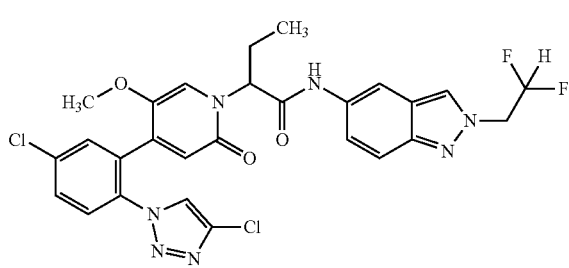 [SMILES: CCC(C(=O)Nc1ccc2nn(CC(F)F)cc2c1)n1cc(OC)c(-c2cc(Cl)ccc2-n2cc(Cl)nn2)cc1=O]

100.0 mg (0.236 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 46.6 mg (0.236 mmol) of 2-(2,2-difluoroethyl)-2H-indazol-5-amine in 1.8 ml of pyridine were reacted at 50° C. according to General Method 5. Yield: 33 mg (21% of theory).

LC/MS [Method 1]: $R_t$=0.95 min; MS (ESIpos): m/z=602 (M+H)$^+$, $^1$H-NMR (400 MHz, DMSO-d$_6$): δ [ppm]=10.40 (s, 1H), 8.63 (s, 1H), 8.36 (s, 1H), 8.16 (s, 1H), 7.72-7.83 (m, 3H), 7.60 (d, 1H), 7.32 (dd, 1H), 7.24 (s, 1H), 6.35-6.68 (m, 2H), 5.56-5.65 (m, 1H), 4.87-4.98 (m, 2H), 3.32 (s, 3H), 1.98-2.18 (m, 2H), 0.79-0.87 (m, 3H).

Example 227

2-{4-[5-Chloro-2-(4-chloro-1H-1,2,3-triazol-1-yl)phenyl]-5-methoxy-2-oxopyridin-1(2H)-yl}-N-[2-(2,2,2-trifluoroethyl)-2H-indazol-5-yl]butanamide (Racemate)

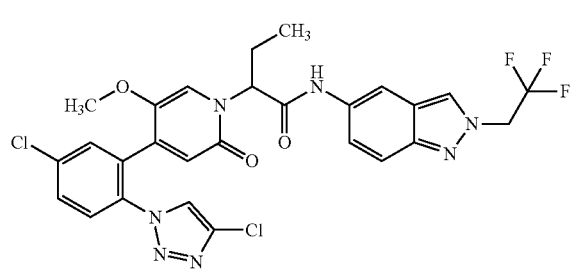 [SMILES: CCC(C(=O)Nc1ccc2nn(CC(F)(F)F)cc2c1)n1cc(OC)c(-c2cc(Cl)ccc2-n2cc(Cl)nn2)cc1=O]

100.0 mg (0.236 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 50.8 mg (0.236 mmol) of 2-(2,2,2-trifluoroethyl)-2H-indazol-5-amine in 1.8 ml of pyridine were reacted at 50° C. according to General Method 5. Yield: 35 mg (23% of theory).

LC/MS [Method 1]: $R_t$=0.99 min; MS (ESIpos): m/z=620 (M+H)$^+$, $^1$H-NMR (400 MHz, DMSO-d$_6$): δ [ppm]=10.42 (s, 1H), 8.63 (s, 1H), 8.42 (s, 1H), 8.18 (s, 1H), 7.72-7.83 (m, 3H), 7.63 (d, 1H), 7.34 (dd, 1H), 7.23 (s, 1H), 6.47 (s, 1H), 5.61 (dd, 1H), 5.45 (q, 2H), 3.32 (s, 3H), 1.98-2.18 (m, 2H), 0.78-0.90 (m, 3H).

Example 228

2-{4-[5-Chloro-2-(4-chloro-1H-1,2,3-triazol-1-yl)phenyl]-5-methoxy-2-oxopyridin-1(2H)-yl}-N-(2-methylquinolin-6-yl)butanamide (Racemate)

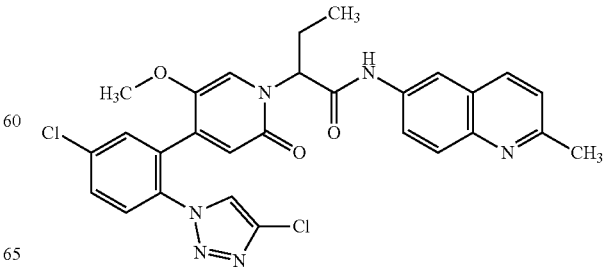

150.0 mg (0.354 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 84.1 mg (0.532 mmol) of 2-methylquinolin-6-amine in 2.9 ml of pyridine were reacted at 50° C. according to General Method 5. Yield: 41 mg (20% of theory).

LC/MS [Method 1]: $R_t$=0.79 min; MS (ESIpos): m/z=563 (M+H)$^+$, $^1$H-NMR (400 MHz, DMSO-d$_6$): δ [ppm]=10.69 (s, 1H), 8.64 (s, 1H), 8.33 (d, 1H), 8.17 (d, 1H), 7.88 (d, 1H), 7.71-7.82 (m, 4H), 7.37 (d, 1H), 7.23 (s, 1H), 6.48 (s, 1H), 5.63 (dd, 1H), 3.33 (s, 3H), 2.62 (s, 3H), 2.02-2.22 (m, 2H), 0.81-0.88 (m, 3H).

Example 229

2-[4-{5-Chloro-2-[4-(difluoromethyl)-1H-1,2,3-triazol-1-yl]phenyl}-5-methoxy-2-oxopyridin-1(2H)-yl]-N-(2-methylquinolin-6-yl)butanamide (Racemate)

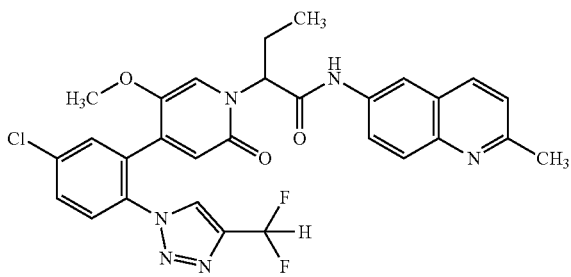 [SMILES: CCC(C(=O)Nc1ccc2nc(C)ccc2c1)n1cc(OC)c(-c2cc(Cl)ccc2-n2cc(C(F)F)nn2)cc1=O]

150.0 mg (0.342 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 81.1 mg (0.513 mmol) of 2-methylquinolin-6-amine in 2.8 ml of pyridine were reacted at 50° C. according to General Method 5. Yield: 40 mg (20% of theory).

LC/MS [Method 1]: $R_t$=0.78 min; MS (ESIpos): m/z=579 (M+H)$^+$, $^1$H-NMR (400 MHz, DMSO-d$_6$): δ [ppm]=10.69 (s, 1H), 8.74 (s, 1H), 8.29-8.35 (m, 1H), 8.11-8.20 (m, 1H), 7.84-7.91 (m, 1H), 7.72-7.81 (m, 4H), 7.08-7.41 (m, 3H), 6.52 (s, 1H), 5.56-5.68 (m, 1H), 3.28 (s, 3H), 2.62 (s, 3H), 1.99-2.22 (m, 2H), 0.80-0.89 (m, 3H).

Example 230

4-({2-[4-{5-Chloro-2-[4-(difluoromethyl)-1H-1,2,3-triazol-1-yl]phenyl}-5-methoxy-2-oxopyridin-1(2H)-yl]propanoyl}amino)-2-fluorobenzamide (Racemate)

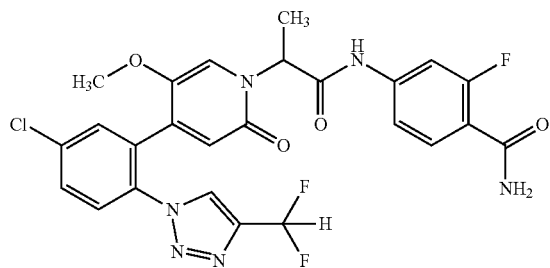 [SMILES: COc1cn(C(C)C(=O)Nc2ccc(C(N)=O)c(F)c2)c(=O)cc1-c1cc(Cl)ccc1-n1cc(C(F)F)nn1]

400 mg (0.94 mmol) of 2-[4-{5-chloro-2-[4-(difluoromethyl)-1H-1,2,3-triazol-1-yl]phenyl}-5-methoxy-2-oxopyridin-1(2H)-yl]propanoic acid (racemate) were dissolved in 24.9 ml of pyridine and then 896 μl (1.51 mmol) propylphosphonic anhydride (T3P, 50% solution in ethyl acetate) were added. The mixture was heated to 50° C. and then 189 mg (1.22 mmol) of 4-amino-2-fluorobenzamide were added. The reaction mixture was stirred additional 1 h at 50° C. and then brought to room temperature. The mixture was diluted with 5 ml acetonitrile/water (1:1) and purified by preparative RP-HPLC (0.1% formic acid/acetonitrile gradient). Yield: 229 mg (43% of theory).

LC/MS [Method 1]: $R_t$=0.80 min; MS (ESIpos): m/z=561 (M+H)$^+$, $^1$H-NMR (400 MHz, DMSO-d$_6$): δ [ppm]=10.68 (s, 1H), 8.77 (s, 1H), 7.75-7.83 (m, 2H), 7.59-7.73 (m, 3H), 7.47-7.57 (m, 2H), 7.32-7.40 (m, 1H), 7.24 (s, 1H), 7.07-7.15 (m, 1H), 6.49 (s, 1H), 5.45-5.57 (m, 1H), 3.27 (s, 3H), 1.63 (d, 3H).

Example 231

(2S)-2-[4-{5-Chloro-2-[4-(difluoromethyl)-1H-1,2,3-triazol-1-yl]phenyl}-5-methoxy-2-oxopyridin-1(2H)-yl]-N-(quinoxalin-6-yl)pentanamide (Enantiomer 2)

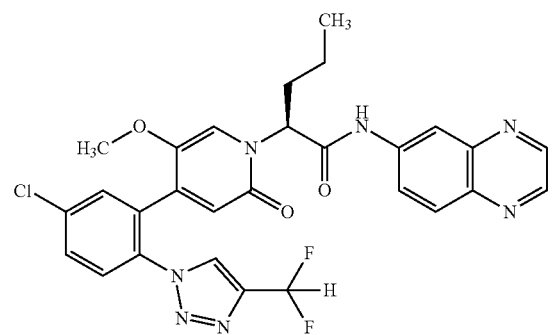 [SMILES: CCC[C@@H](C(=O)Nc1ccc2nccnc2c1)n1cc(OC)c(-c2cc(Cl)ccc2-n2cc(C(F)F)nn2)cc1=O]

Enantiomer separation of 96 mg of 2-[4-{5-chloro-2-[4-(difluoromethyl)-1H-1,2,3-triazol-1-yl]phenyl}-5-methoxy-2-oxopyridin-1(2H)-yl]-N-(quinoxalin-6-yl)pentanamide (racemate) gave 40.5 mg of enantiomer 1 (chiral HPLC: $R_t$=9.6 min) and 40 mg of the title compound (enantiomer 2): chiral HPLC: $R_t$=16.1 min; 100% ee.

Separating method: column: Chiralpak AD-H SFC, 5 μm 250 mm×20 mm; mobile phase: carbon dioxide 70%/ethanol 30%; temperature: 40° C.; flow rate: 50 ml/min; pressure: 100 bar; UV detection: 210 nm.

Analysis: column: Daicel AD SFC 3 μm, 100 mm×4.6 mm; mobile phase: 70% carbon dioxide, 30% ethanol; flow rate: 3 ml/min; UV detection: 210 nm.

LC-MS [Method 10]: $R_t$=1.75 min; MS (ESIpos): m/z=580 [M+H]$^+$ $^1$H-NMR (400 MHz, DMSO-d$_6$): δ [ppm]=10.93 (s, 1H), 8.89 (d, 1H), 8.84 (d, 1H), 8.72 (s, 1H), 8.51 (d, 1H), 8.07 (d, 1H), 7.97 (dd, 1H), 7.82-7.78 (m, 2H), 7.77-7.74 (m, 1H), 7.37-7.07 (m, 2H), 6.52 (s, 1H), 5.72 (br dd, 1H), 3.28 (s, 3H), 2.17-2.02 (m, 2H), 1.31-1.12 (m, 2H), 0.92 (t, 3H).

Example 232

2-[4-{5-Chloro-2-[4-(trifluoromethyl)-1H-1,2,3-triazol-1-yl]phenyl}-5-methoxy-2-oxopyridin-1(2H)-yl]-N-(2-methyl-2H-indazol-5-yl)butanamide (Racemate)

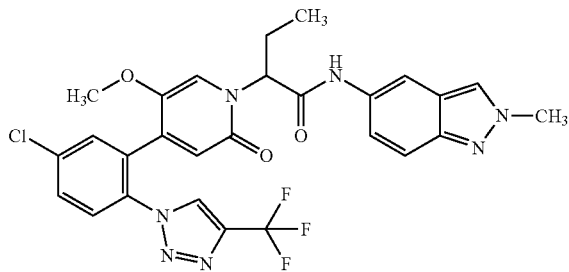 [SMILES: CCC(C(=O)Nc1ccc2nn(C)cc2c1)n1cc(OC)c(-c2cc(Cl)ccc2-n2cc(C(F)(F)F)nn2)cc1=O]

86.0 mg (188 µmol) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) and 42.4 mg (282 µmol) of 2-methyl-2H-indazol-5-amine in 1.5 ml of pyridine were reacted according to General Method 5. Yield: 87 mg (77% of theory).

LC-MS [Method 1]: $R_t$=0.94 min; MS (ESIneg): m/z=584 [M−H]⁻

$^1$H-NMR (400 MHz, DMSO-$d_6$): δ [ppm]=10.34 (s, 1H), 9.14 (s, 1H), 8.24 (s, 1H), 8.10 (d, 1H), 7.86-7.79 (m, 2H), 7.78 (d, 1H), 7.54 (d, 1H), 7.26 (dd, 1H), 7.19 (s, 1H), 6.52 (s, 1H), 5.59 (dd, 1H), 4.12 (s, 3H), 3.26 (s, 3H), 2.15-1.97 (m, 2H), 0.79 (t, 3H).

Example 233

(2S)-2-[4-{5-Chloro-2-[4-(trifluoromethyl)-1H-1,2,3-triazol-1-yl]phenyl}-5-methoxy-2-oxopyridin-1(2H)-yl]-N-(2-methyl-2H-indazol-5-yl)butanamide (Enantiomer 2)

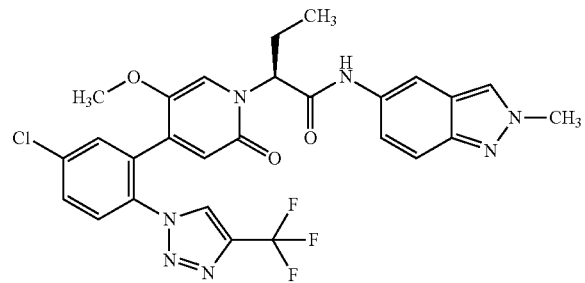 [SMILES: CC[C@@H](C(=O)Nc1ccc2nn(C)cc2c1)n1cc(OC)c(-c2cc(Cl)ccc2-n2cc(C(F)(F)F)nn2)cc1=O]

Enantiomer separation of 84 mg of 2-[4-{5-chloro-2-[4-(trifluoromethyl)-1H-1,2,3-triazol-1-yl]phenyl}-5-methoxy-2-oxopyridin-1(2H)-yl]-N-(2-methyl-2H-indazol-5-yl)butanamide (racemate) gave 29 mg of enantiomer 1 (chiral HPLC: $R_t$=2.8 min) and 31 mg of the title compound (enantiomer 2): chiral HPLC: $R_t$=4.7 min; 100% ee.

Separating method: column: Chiralpak AD-H SFC, 5 µm 250 mm×20 mm; mobile phase: carbon dioxide 75%/ethanol 25%; temperature: 40° C.; flow rate: 80 ml/min; pressure: 100 bar; UV detection: 210 nm.

Analysis: column: Daicel AD SFC 3 µm, 100 mm×4.6 mm; mobile phase: 75% carbon dioxide, 25% ethanol; flow rate: 3 ml/min; UV detection: 210 nm.

LC-MS [Method 1]: $R_t$=0.94 min; MS (ESIpos): m/z=586 [M+H]⁺

Example 234

4-({2-[4-{5-Chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (Racemate)

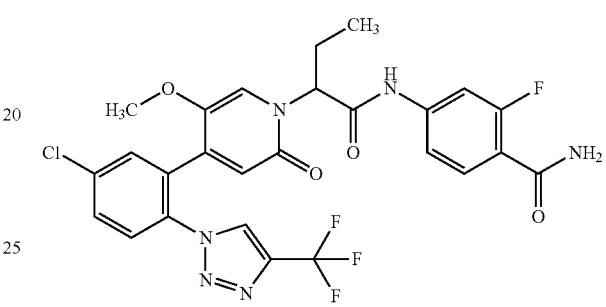

86.0 mg (188 µmol) of 2-[4-{5-chloro-2-[4-(trifluoromethyl)-NH-1,2,3-triazol-1-yl]phenyl}-5-methoxy-2-oxopyridin-1(2H)-yl]butanoic acid (racemate) and 44.9 mg (282 µmol) of 4-amino-2-fluorobenzamide were mixed in 1.5 ml of pyridine. 336 µl (0.57 mmol) propylphosphonic anhydride (T3P, 50% solution in ethyl acetate) were then added dropwise at room temperature and the mixture was stirred additional 30 min at 50° C. The reaction mixture was brought to room temperature and then purified by preparative RP-HPLC (0.1% formic acid/acetonitrile gradient). Yield: 60 mg (54% of theory).

Alternatively the compound was prepared according to the following procedure:

1.00 g (73% purity, 1.60 mmol) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) were dissolved in 13.1 ml of pyridine and 1.52 ml (2.56 mmol) propylphosphonic anhydride (T3P, 50% solution in ethyl acetate) were added. The mixture was heated to 40° C. and then 0.32 g (2.08 mmol) of 4-amino-2-fluorobenzamide were added. The reaction mixture was stirred additional 15 min at 40° C. and then immediately concentrated under reduced pressure. The residue was taken up in 10 ml acetonitrile, acidified with 3 ml hydrochloric acid (1M) and then purified by preparative RP-HPLC (0.1% formic acid/acetonitrile gradient). Yield: 794 mg (84% of theory).

LC-MS [Method 1]: $R_t$=0.92 min; MS (ESIpos): m/z=593 [M+H]⁺

$^1$H-NMR (400 MHz, DMSO-$d_6$): δ [ppm]=10.76 (br s, 1H), 9.13 (s, 1H), 7.86-7.80 (m, 2H), 7.79-7.77 (m, 1H), 7.69 (t, 1H), 7.66-7.61 (m, 1H), 7.56-7.49 (m, 2H), 7.37 (dd, 1H), 7.13 (s, 1H), 6.53 (s, 1H), 5.55-5.49 (m, 1H), 3.26 (s, 3H), 2.14-2.02 (m, 2H), 0.79 (t, 3H).

Example 235

4-({(2S)-2-[4-{5-Chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (Enantiomer 2)

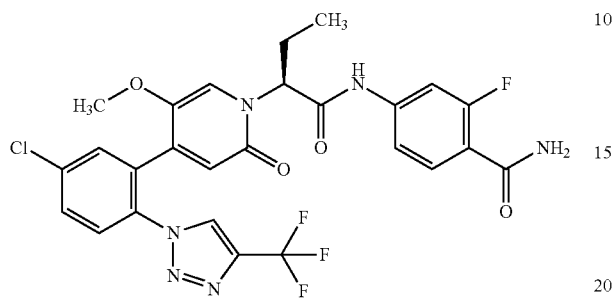

Enantiomer separation of 63 mg of 4-({2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (racemate) gave 25 mg of enantiomer 1 (chiral HPLC: $R_t$=2.6 min) and 26 mg of the title compound (enantiomer 2): chiral HPLC: $R_t$=3.6 min; 100% ee.

Separating method: column: Chiralpak AD-H SFC, 5 μm 250 mm×20 mm; mobile phase: carbon dioxide 75%/ethanol 25%; temperature: 40° C.; flow rate: 80 ml/min; pressure: 100 bar; UV detection: 210 nm.

Analysis: column: Daicel AD SFC 3 μm, 100 mm×4.6 mm; mobile phase: 75% carbon dioxide, 25% ethanol; flow rate: 3 ml/min; UV detection: 210 nm.

LC-MS [Method 1]: $R_t$=0.92 min; MS (ESIpos): m/z=593 [M+H]$^+$

Example 236

2-[4-{5-Chloro-2-[4-(trifluoromethyl)-1H-1,2,3-triazol-1-yl]phenyl}-5-methoxy-2-oxopyridin-1(2H)-yl]-N-(2,3-dimethylquinoxalin-6-yl)butanamide (Racemate)

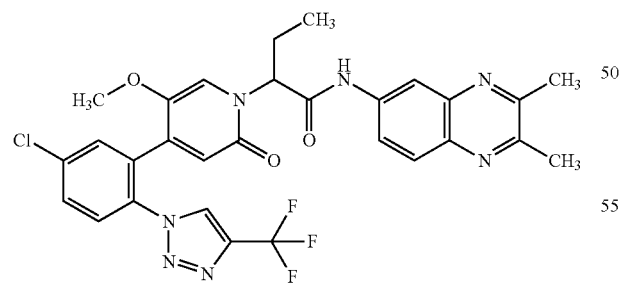

86.0 mg (188 μmol) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) and 48.9 mg (282 μmol) of 2,3-dimethylquinoxalin-6-amine in 1.5 ml of pyridine were reacted according to General Method 5. Yield: 100 mg (87% of theory).

LC-MS [Method 1]: $R_t$=1.02 min; MS (ESIpos): m/z=612 [M+H]$^+$ $^1$H-NMR (400 MHz, DMSO-d$_6$): δ [ppm]=10.78 (s, 1H), 9.14 (s, 1H), 8.33 (d, 1H), 7.92-7.89 (m, 1H), 7.87-7.81 (m, 3H), 7.80-7.78 (m, 1H), 7.19 (s, 1H), 6.54 (s, 1H), 5.61 (dd, 1H), 3.29-3.27 (m, 3H), 2.65 (s, 3H), 2.64 (s, 3H), 2.20-2.05 (m, 2H), 0.81 (t, 3H).

Example 237

(2S)-2-[4-{5-Chloro-2-[4-(trifluoromethyl)-1H-1,2,3-triazol-1-yl]phenyl}-5-methoxy-2-oxopyridin-1(2H)-yl]-N-(2,3-dimethylquinoxalin-6-yl)butanamide (Enantiomer 2)

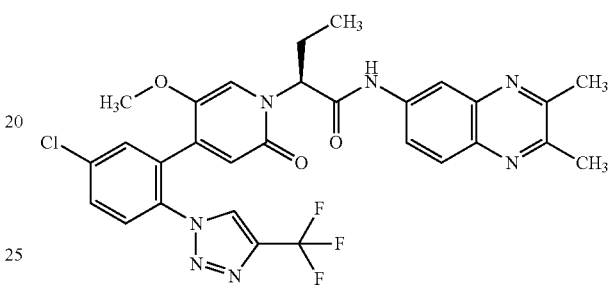

Enantiomer separation of 88 mg of 2-[4-{5-chloro-2-[4-(trifluoromethyl)-1H-1,2,3-triazol-1-yl]phenyl}-5-methoxy-2-oxopyridin-1(2H)-yl]-N-(2,3-dimethylquinoxalin-6-yl)butanamide (racemate) gave 34 mg of enantiomer 1 (chiral HPLC: $R_t$=2.9 min) and 34 mg of the title compound (enantiomer 2): chiral HPLC: $R_t$=6.1 min; 100% ee.

Separating method: column: Chiralpak AD-H SFC, 5 μm 250 mm×20 mm; mobile phase: carbon dioxide 75%/ethanol 25%; temperature: 40° C.; flow rate: 80 ml/min; pressure: 100 bar; UV detection: 210 nm.

Analysis: column: Daicel AD SFC 3 μm, 100 mm×4.6 mm; mobile phase: 75% carbon dioxide, 25% ethanol; flow rate: 3 ml/min; UV detection: 210 nm.

LC-MS [Method 1]: $R_t$=1.02 min; MS (ESIpos): m/z=612 [M+H]$^+$

Example 238

4-({2-[4-{5-Chloro-2-[2-(difluoromethyl)-1,3-oxazol-5-yl]phenyl}-5-methoxy-2-oxopyridin-1(2H)-yl]butanoyl}amino)benzoic acid (Racemate)

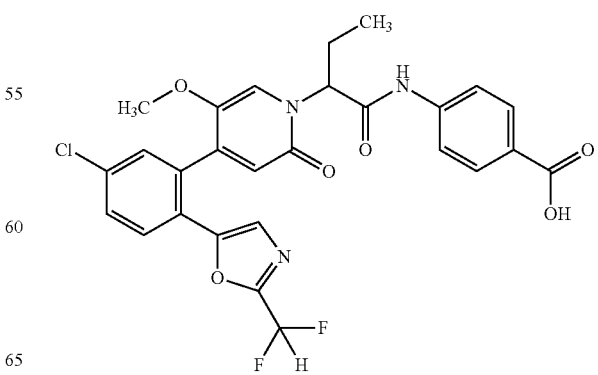

50.0 mg (114 µmol) of 2-[4-{5-chloro-2-[2-(difluoromethyl)-1,3-oxazol-5-yl]phenyl}-5-methoxy-2-oxopyridin-1(2H)-yl]butanoic acid (racemate) and 16.4 mg (120 µmol) of 4-aminobenzoic acid in 0.5 ml of pyridine were reacted according to General Method 5. Yield: 40 mg (63% of theory).

LC-MS [Method 10]: $R_t$=1.77 min; MS (ESIpos): m/z=558 [M+H]$^+$ $^1$H-NMR (400 MHz, DMSO-d$_6$): δ [ppm]=12.75 (br s, 1H), 10.75 (br s, 1H), 7.95-7.88 (m, 2H), 7.83 (d, 1H), 7.78-7.72 (m, 2H), 7.67 (dd, 1H), 7.55 (d, 1H), 7.34 (s, 1H), 7.04 (t, 1H), 6.46 (s, 1H), 5.71-5.60 (m, 1H), 3.40 (s, 3H), 2.23-2.07 (m, 2H), 0.92 (t, 3H).

Example 239

4-({2-[4-{5-Chloro-2-[4-(trifluoromethyl)-1H-1,2,3-triazol-1-yl]phenyl}-5-methoxy-2-oxopyridin-1(2H)-yl]propanoyl}amino)-2-fluorobenzamide (Racemate)

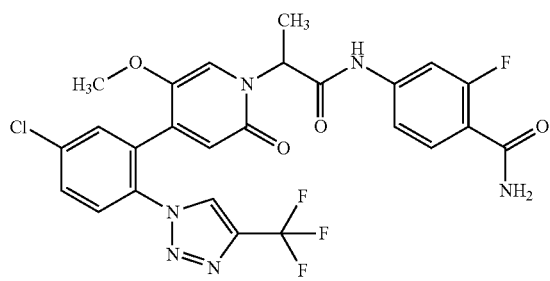 [SMILES: COc1cn(C(C)C(=O)Nc2ccc(C(N)=O)c(F)c2)c(=O)cc1-c1cc(Cl)ccc1-n1cc(C(F)(F)F)nn1]

400 mg (90% pure, 0.81 mmol) 2-[4-{5-chloro-2-[4-(trifluoromethyl)-1H-1,2,3-triazol-1-yl]phenyl}-5-methoxy-2-oxopyridin-1(2H)-yl]propanoic acid were dissolved in 21.5 ml pyridine and subsequently 0.77 ml propylphosphonic anhydride (T3P, 50% solution in ethyl acetate) were added. The reaction mixture was heated to 40° C. and then 163 mg (1.06 mmol) 4-amino-2-fluorobenzamide were added. After addition, the mixture was stirred additional 25 min at 40° C., then brought to room temperature and concentrated under reduced pressure. The residue was taken up in 10 ml acetonitrile, acidified with 1M hydrochloric acid and then purified by preparative RP-HPLC (0.1% formic acid/acetonitrile gradient). Yield: 231 mg (49% of theory).

LC/MS [Method 1]: $R_t$=0.87 min; MS (ESIpos): m/z=579 (M+H)$^+$, $^1$H-NMR (400 MHz, DMSO-d$_6$): δ [ppm]=10.67 (s, 1H), 9.17 (s, 1H), 7.80-7.86 (m, 2H), 7.75 (s, 1H), 7.59-7.72 (m, 2H), 7.48-7.56 (m, 2H), 7.36 (dd, 1H), 7.12 (s, 1H), 6.51 (s, 1H), 5.46-5.56 (m, 1H), 3.27 (s, 3H), 1.63 (d, 3H).

Example 240

4-{[(2S)-2-{4-[5-Chloro-2-(4-chloro-1H-1,2,3-triazol-1-yl)phenyl]-5-methoxy-2-oxopyridin-1(2H)-yl}propanoyl]amino}-2-fluorobenzamide (Enantiomer 2)

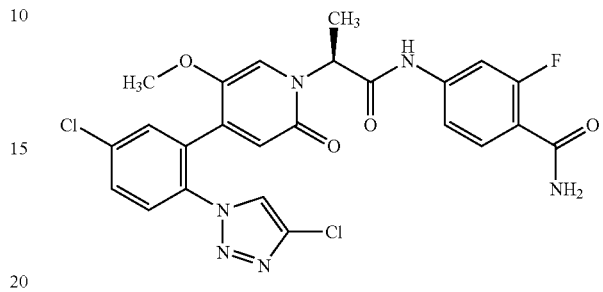

Enantiomer separation of 38 mg of 4-[(2-{4-[5-chloro-2-(4-chloro-1H-1,2,3-triazol-1-yl)phenyl]-5-methoxy-2-oxopyridin-1(2H)-yl}propanoyl)amino]-2-fluorobenzamide (racemate) (Example 184) gave 4.7 mg of enantiomer 1 (chiral HPLC: $R_t$=1.9 min) and 4.8 mg of the title compound (enantiomer 2): chiral HPLC: $R_t$=5.2 min; 100% ee.

Separating method: column: Daicel Chiralpak AD-H SFC 5 µm, 250 mm×20 mm; mobile phase: carbon dioxide 75%/ethanol 25%; temperature: 40° C.; flow rate: 80 ml/min; pressure: 100 bar; UV detection: 210 nm.

Analysis: column: Daicel AD SFC 3 µm, 100 mm×4.6 mm; mobile phase: 70% carbon dioxide, 30% ethanol; flow rate: 3 ml/min; UV detection: 210 nm.

LC/MS [Method 10]: $R_t$=1.49 min; MS (ESIpos): m/z=545 [M+H]$^+$.

Example 241

4-({(2S)-2-[4-{5-Chloro-2-[4-(difluoromethyl)-1H-1,2,3-triazol-1-yl]phenyl}-5-methoxy-2-oxopyridin-1(2H)-yl]propanoyl}amino)-2-fluorobenzamide (Enantiomer 2)

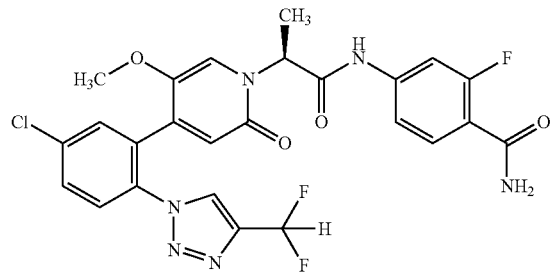 [SMILES: COc1cn([C@@H](C)C(=O)Nc2ccc(C(N)=O)c(F)c2)c(=O)cc1-c1cc(Cl)ccc1-n1cc(C(F)F)nn1]

Enantiomer separation of 229 mg of 4-({2-[4-{5-chloro-2-[4-(difluoromethyl)-1H-1,2,3-triazol-1-yl]phenyl}-5-methoxy-2-oxopyridin-1(2H)-yl]propanoyl}amino)-2-fluorobenzamide (racemate) (Example 230) gave 93 mg of enantiomer 1 (chiral HPLC: $R_t$=2.3 min) and 92 mg of the title compound (enantiomer 2): chiral HPLC: $R_t$=4.2 min; 100% ee.

Separating method: column: Daicel Chiralpak AD-H SFC 5 µm, 250 mm×20 mm; mobile phase: carbon dioxide 80%/ethanol 20%; temperature: 40° C.; flow rate: 80 ml/min; pressure: 100 bar; UV detection: 210 nm.

Analysis: column: Daicel AD SFC 3 μm, 100 mm×4.6 mm; mobile phase: 75% carbon dioxide, 25% ethanol; flow rate: 3 ml/min; UV detection: 210 nm.

LC/MS [Method 1]: $R_t$=0.81 min; MS (ESIpos): m/z=561 [M+H]$^+$.

Example 242

4-{[(2S)-2-{4-[5-Chloro-2-(4-chloro-1H-1,2,3-triazol-1-yl)phenyl]-5-methoxy-2-oxopyridin-1(2H)-yl}butanoyl]amino}-2-fluorobenzamide (Enantiomer 2)

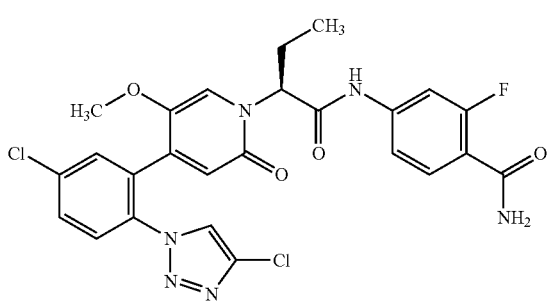 [SMILES: CC[C@@H](C(=O)Nc1ccc(C(N)=O)c(F)c1)n1cc(OC)c(-c2cc(Cl)ccc2-n2cc(Cl)nn2)cc1=O]

Enantiomer separation of 170 mg of 4-[(2-{4-[5-chloro-2-(4-chloro-1H-1,2,3-triazol-1-yl)phenyl]-5-methoxy-2-oxopyridin-1(2H)-yl}butanoyl)amino]-2-fluorobenzamide (racemate) (Example 171) gave 68 mg of enantiomer 1 (chiral HPLC: $R_t$=1.3 min) and 68 mg of the title compound (enantiomer 2): chiral HPLC: $R_t$=1.6 min; 100% ee.

Separating method: column: Daicel Chiralpak AD-H SFC 5 μm, 250 mm×20 mm; mobile phase: carbon dioxide 75%/ethanol 25%; temperature: 40° C.; flow rate: 80 ml/min; pressure: 100 bar; UV detection: 210 nm.

Analysis: column: Daicel AD SFC 3 μm, 100 mm×4.6 mm; mobile phase: 70% carbon dioxide, 30% ethanol; flow rate: 3 ml/min; UV detection: 210 nm.

LC/MS [Method 10]: $R_t$=1.59 min; MS (ESIpos): m/z=559 [M+H]$^+$.

Example 243

(2S)-2-[4-{5-Chloro-2-[4-(difluoromethyl)-1H-1,2,3-triazol-1-yl]phenyl}-5-methoxy-2-oxopyridin-1(2H)-yl]-N-(2-methylquinolin-6-yl)butanamide (Enantiomer 2)

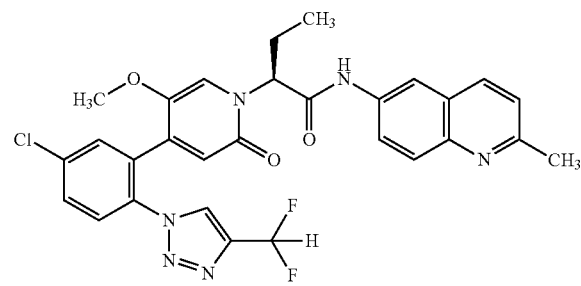 [SMILES: CC[C@@H](C(=O)Nc1ccc2nc(C)ccc2c1)n1cc(OC)c(-c2cc(Cl)ccc2-n2cc(C(F)F)nn2)cc1=O]

Enantiomer separation of 110 mg of 2-[4-{5-chloro-2-[4-(difluoromethyl)-1H-1,2,3-triazol-1-yl]phenyl}-5-methoxy-2-oxopyridin-1(2H)-yl]-N-(2-methylquinolin-6-yl)butanamide (racemate) (Example 229) gave 44 mg of enantiomer 1 (chiral HPLC: $R_t$=1.6 min) and 42 mg of the title compound Example 243 (enantiomer 2): chiral HPLC: $R_t$=3.5 min; 100% ee.

Separating method: column: Daicel Chiralpak AZ-H SFC 5 mm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AZ SFC 3 μm, 100 mm×4.6 mm; mobile phase: 60% carbon dioxide, 40% ethanol; flow rate: 3 ml/min; UV detection: 210 nm.

LC/MS [Method 10]: $R_t$=1.41 min; MS (ESIpos): m/z=579 [M+H]$^+$.

Example 244

(2S)-2-{4-[5-Chloro-2-(4-chloro-1H-1,2,3-triazol-1-yl)phenyl]-5-methoxy-2-oxopyridin-1(2H)-yl}-N-(2-methylquinolin-6-yl)butanamide (Enantiomer 2)

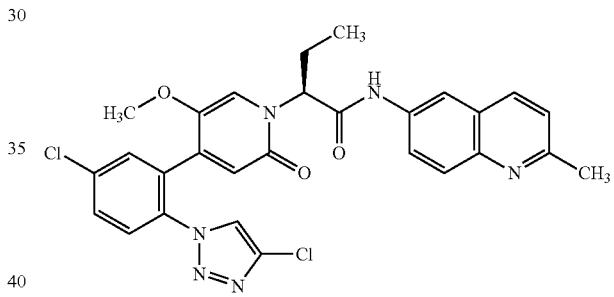

Enantiomer separation of 75 mg of 2-{4-[5-chloro-2-(4-chloro-1H-1,2,3-triazol-1-yl)phenyl]-5-methoxy-2-oxopyridin-1(2H)-yl}-N-(2-methylquinolin-6-yl)butanamide (racemate) (Example 228) gave 31 mg of enantiomer 1 (chiral HPLC: $R_t$=2.4 min) and 27 mg of the title compound Example 244 (enantiomer 2): chiral HPLC: $R_t$=6.6 min; 100% ee.

Separating method: column: Daicel Chiralpak AZ-H SFC 5 μm, 250 mm×20 mm; mobile phase: carbon dioxide 70%/ethanol 30%; temperature: 40° C.; flow rate: 80 ml/min; pressure: 100 bar; UV detection: 210 nm.

Analysis: column: Daicel AZ SFC 3 μm, 100 mm×4.6 mm; mobile phase: 60% carbon dioxide, 40% ethanol; flow rate: 3 ml/min; UV detection: 210 nm.

LC/MS [Method 10]: $R_t$=1.43 min; MS (ESIpos): m/z=563 [M+H]$^+$.

Example 245

2-{4-[5-Chloro-2-(4-chloro-1H-1,2,3-triazol-1-yl)phenyl]-5-methoxy-2-oxopyridin-1(2H)-yl}-N-(2,3-dimethyl-2H-indazol-5-yl)butanamide (Racemate)

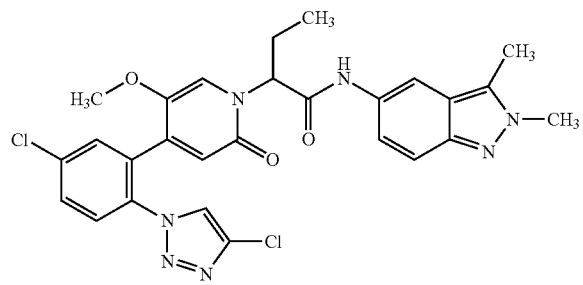 [SMILES: CCC(C(=O)Nc1ccc2nn(C)c(C)c2c1)n1cc(OC)c(-c2cc(Cl)ccc2-n2cc(Cl)nn2)cc1=O]

50.0 mg (70% purity, 0.12 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 28.6 mg (0.18 mmol) of 2,3-dimethyl-2H-indazol-5-amine in 0.98 ml of pyridine were reacted according to General Method 5. Yield: 50 mg (74% of theory).

LC-MS [Method 10]: $R_t$=1.69 min; MS (ESIneg): m/z=566 [M−H]⁻,

¹H-NMR (400 MHz, DMSO-d₆): δ [ppm]=10.32 (s, 1H), 8.63 (s, 1H), 8.08-8.03 (m, 1H), 7.82-7.71 (m, 3H), 7.46 (d, 1H), 7.26-7.18 (m, 2H), 6.47 (s, 1H), 5.65-5.55 (m, 1H), 4.02 (s, 3H), 3.32 (s, 3H), 2.20-1.96 (m, 2H), 0.90-0.79 (m, 3H).

Example 246

2-[4-{5-Chloro-2-[4-(trifluoromethyl)-1H-1,2,3-triazol-1-yl]phenyl}-5-methoxy-2-oxopyridin-1(2H)-yl]-N-(2,3-dimethyl-2H-indazol-5-yl)butanamide (Racemate)

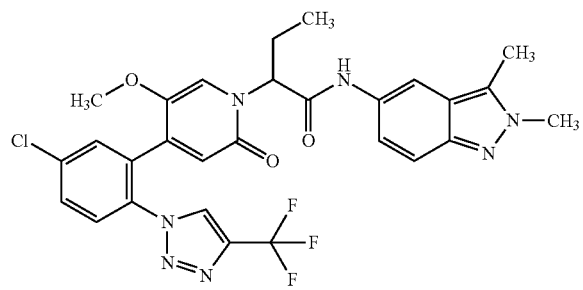 [SMILES: CCC(C(=O)Nc1ccc2nn(C)c(C)c2c1)n1cc(OC)c(-c2cc(Cl)ccc2-n2cc(C(F)(F)F)nn2)cc1=O]

60.0 mg (70% purity, 0.09 mmol) of 2-[4-{5-chloro-2-[4-(trifluoromethyl)-1H-1,2,3-triazol-1-yl]phenyl}-5-methoxy-2-oxopyridin-1(2H)-yl]butanoic acid (racemate) and 22.2 mg (0.14 mmol) of 2,3-dimethyl-2H-indazol-5-amine in 0.76 ml of pyridine were reacted according to General Method 5. Yield: 51 mg (55% of theory).

LC-MS [Method 10]: $R_t$=1.80 min; MS (ESIneg): m/z=600 [M−H]⁻,

¹H-NMR (400 MHz, DMSO-d₆): δ [ppm]=10.31 (s, 1H), 9.13 (d, 1H), 8.05 (d, 1H), 7.88-7.79 (m, 2H), 7.79-7.75 (m, 1H), 7.46 (d, 1H), 7.24-7.14 (m, 2H), 6.52 (s, 1H), 5.63-5.54 (m, 1H), 4.02 (s, 3H), 3.27 (s, 3H), 2.53 (s, 3H), 2.18-1.96 (m, 2H), 0.85-0.75 (m, 3H).

Example 247

2-{4-[5-Chloro-2-(4-chloro-1H-1,2,3-triazol-1-yl)phenyl]-5-methoxy-2-oxopyridin-1(2H)-yl}-N-[2-(trifluoromethyl)quinolin-6-yl]butanamide (Racemate)

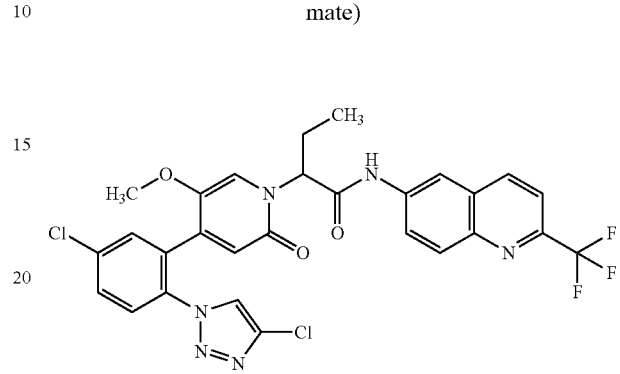

110.0 mg (0.26 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 82.7 mg (0.39 mmol) of 2-(trifluoromethyl)quinolin-6-amine in 2.2 ml of pyridine were reacted according to General Method 5. Yield: 125 mg (77% of theory).

LC/MS [Method 10]: $R_t$=2.15 min; MS (ESIneg): m/z=615 (M−H)⁻,

¹H-NMR (400 MHz, DMSO-d₆): δ [ppm]=10.93 (s, 1H), 8.62-8.68 (m, 2H), 8.57-8.61 (m, 1H), 8.15 (d, 1H), 7.89-7.99 (m, 2H), 7.73-7.83 (m, 3H), 7.23 (s, 1H), 6.49 (s, 1H), 5.59-5.70 (m, 1H), 3.34 (s, 3H), 2.05-2.25 (m, 2H), 0.82-0.91 (m, 3H).

Example 248

2-[4-{5-Chloro-2-[4-(difluoromethyl)-1H-1,2,3-triazol-1-yl]phenyl}-5-methoxy-2-oxopyridin-1(2H)-yl]-N-[2-(trifluoromethyl)quinolin-6-yl]butanamide (Racemate)

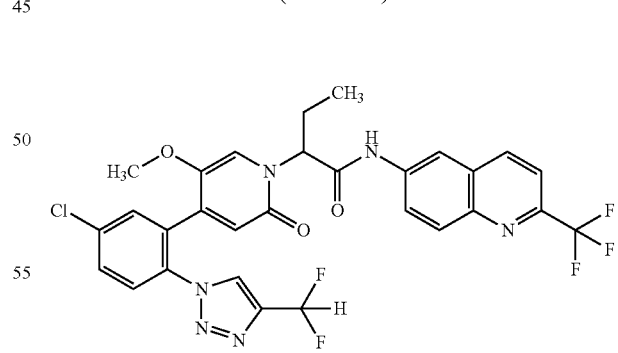

110.0 mg (0.25 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 79.8 mg (0.38 mmol) of 2-(trifluoromethyl)quinolin-6-amine in 2.1 ml of pyridine were reacted according to General Method 5. Yield: 106 mg (66% of theory).

LC/MS [Method 10]: $R_t$=2.12 min; MS (ESIpos): m/z=633 (M+H)⁺, $^1$H-NMR (400 MHz, DMSO-d$_6$): δ [ppm]=10.93 (s, 1H), 8.75 (s, 1H), 8.64 (d, 1H), 8.55-8.60 (m, 1H), 8.15 (d, 1H), 7.88-8.00 (m, 2H), 7.72-7.82 (m, 3H), 7.06-7.38 (m, 2H), 6.53 (s, 1H), 5.58-5.68 (m, 1H), 3.28 (s, 3H), 2.04-2.23 (m, 2H), 0.79-0.91 (m, 3H).

Example 249

2-{4-[5-Chloro-2-(4-chloro-1H-1,2,3-triazol-1-yl)phenyl]-5-methoxy-2-oxopyridin-1(2H)-yl}-N-(2-methyl-2H-benzotriazol-5-yl)butanamide (Racemate)

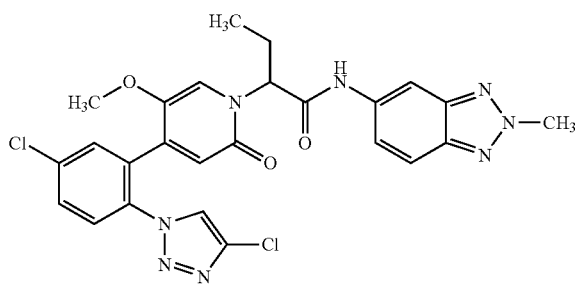 [SMILES: CCC(C(=O)Nc1ccc2nn(C)nc2c1)n1cc(OC)c(-c2cc(Cl)ccc2-n2cc(Cl)nn2)cc1=O]

100 mg (0.22 mmol) 2-{4-[5-chloro-2-(4-chloro-1H-1,2,3-triazol-1-yl)phenyl]-5-methoxy-2-oxopyridin-1(2H)-yl}butanoic acid (racemate) were dissolved in 5 ml pyridine and subsequently 0.52 ml propylphosphonic anhydride (T3P. 50% solution in ethyl acetate) were added. The reaction mixture was heated to 50° C. and then 42 mg (0.28 mmol) 2-methyl-2H-benzotriazol-5-amine were added. After addition, the mixture was stirred for one hour at 50° C., then brought to room temperature and concentrated under reduced pressure. The residue was purified by preparative RP-HPLC (Column: Chromatorex C18 10 μm 250 mm×30 mm; eluent A: water, eluent B: acetonitrile; gradient: 0.0 min 30% B; 4.5 min 50% B; 11.5 min 70% B; 12 min 100% B; 14.75 min 30% B; flow: 50 ml/min). Yield: 90 mg (75% of theory).

LC/MS [Method 1]: R$_t$=0.94 min; MS (ESIpos): m/z=553 (M+H)$^+$, $^1$H-NMR (400 MHz, DMSO-d$_6$): δ [ppm]=10.64 (s, 1H), 8.62 (s, 1H), 8.34 (d, 1H), 7.87 (d, 1H), 7.81-7.74 (m, 3H), 7.46 (dd, 1H), 7.23 (s, 1H), 6.48 (s, 1H), 5.60 (dd, 1H), 4.45 (s, 3H), 3.37 (s, 3H), 2.19-2.05 (m, 2H), 0.84 (t, 3H).

Example 250

2-{4-[5-Chloro-2-(4-chloro-1H-1,2,3-triazol-1-yl)phenyl]-5-methoxy-2-oxopyridin-1(2H)-yl}-N-(2-ethyl-2H-indazol-5-yl)butanamide (Racemate)

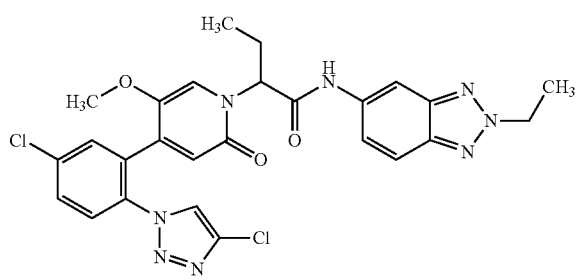 [SMILES: CCC(C(=O)Nc1ccc2nn(CC)nc2c1)n1cc(OC)c(-c2cc(Cl)ccc2-n2cc(Cl)nn2)cc1=O]

100 mg (0.22 mmol) 2-{4-[5-chloro-2-(4-chloro-1H-1,2,3-triazol-1-yl)phenyl]-5-methoxy-2-oxopyridin-1(2H)-yl}butanoic acid (racemate) were dissolved in 5 ml pyridine and subsequently 0.52 ml propylphosphonic anhydride (T3P. 50% solution in ethyl acetate) were added. The reaction mixture was heated to 50° C. and then 46 mg (0.28 mmol) 2-ethyl-2H-indazol-5-amine were added. After addition, the mixture was stirred for one hour at 50° C., then brought to room temperature and concentrated under reduced pressure. The residue was purified by preparative RP-HPLC (Column: Chromatorex C18 10 μm 250 mm×30 mm; eluent A: water, eluent B: acetonitrile; gradient: 0.0 min 30% B; 4.5 min 50% B; 11.5 min 70% B; 12 min 100% B; 14.75 min 30% B; flow: 50 ml/min). Yield: 95 mg (77% of theory).

LC/MS [Method 19]: R$_t$=1.75 min; MS (ESIpos): m/z=566 (M+H)$^+$, $^1$H-NMR (400 MHz, DMSO-d$_6$): δ [ppm]=10.36 (s, 1H), 8.63 (s, 1H), 8.29 (s, 1H), 8.12 (d, 1H), 7.81-7.74 (m, 3H), 7.56 (d, 1H), 7.27 (dd, 1H), 7.24 (s, 1H), 6.47 (s, 1H), 5.60 (dd, 1H), 4.41 (q, 2H), 3.32 (s, 3H), 2.18-1.98 (m, 2H), 1.49 (t, 3H), 0.83 (t, 3H).

Example 251

4-({(2S)-2-[4-{5-Chloro-2-[4-(trifluoromethyl)-1H-1,2,3-triazol-1-yl]phenyl}-5-methoxy-2-oxopyridin-1(2H)-yl]propanoyl}amino)-2-fluorobenzamide (Enantiomer 2)

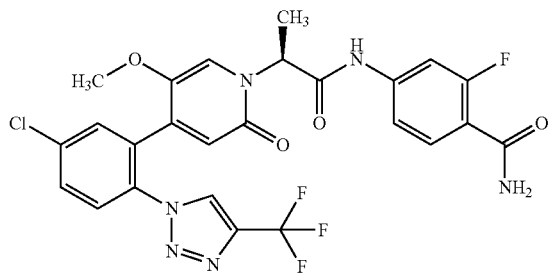 [SMILES: COc1cn([C@@H](C)C(=O)Nc2ccc(C(N)=O)c(F)c2)c(=O)cc1-c1cc(Cl)ccc1-n1cc(C(F)(F)F)nn1]

Enantiomer separation of 230 mg of 4-({2-[4-{5-chloro-2-[4-(trifluoromethyl)-1H-1,2,3-triazol-1-yl]phenyl}-5-methoxy-2-oxopyridin-1(2H)-yl]propanoyl}amino)-2-fluorobenzamide (racemate) (Example 239) gave 106 mg of enantiomer 1 (chiral HPLC: R$_t$=1.0 min) and 96 mg of the title compound (enantiomer 2): chiral HPLC: R$_t$=1.8 min; 100% ee.

Separating method: column: Daicel Chiralpak AD-H SFC 5 μm, 250 mm×20 mm; mobile phase: carbon dioxide 80%/ethanol 20%; temperature: 40° C.; flow rate: 80 ml/min; pressure: 100 bar; UV detection: 210 nm.

Analysis: column: Daicel AD SFC 3 μm, 100 mm×4.6 mm; mobile phase: 70% carbon dioxide, 30% ethanol; flow rate: 3 ml/min; UV detection: 210 nm.

LC/MS [Method 10]: R$_t$=1.62 min; MS (ESIpos): m/z=579 [M+H]$^+$.

Example 252

2-[4-{5-Chloro-2-[4-(difluoromethyl)-1H-1,2,3-triazol-1-yl]phenyl}-5-methoxy-2-oxopyridin-1(2H)-yl]-N-(2-cyanoquinolin-6-yl)butanamide (Racemate)

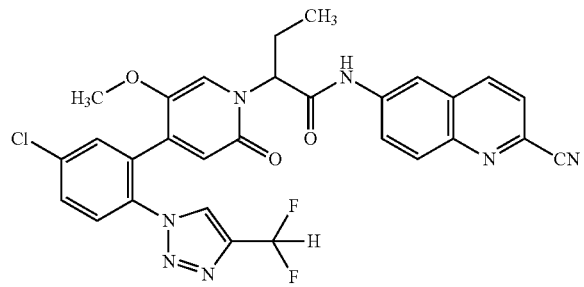 [SMILES: CCC(C(=O)Nc1ccc2nc(C#N)ccc2c1)n1cc(OC)c(-c2cc(Cl)ccc2-n2cc(C(F)F)nn2)cc1=O]

100.0 mg (0.23 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 57.8 mg (0.34 mmol) of 6-aminoquinoline-2-carbonitrile in 1.0 ml of pyridine were reacted according to General Method 5. Yield: 82 mg (61% of theory).

LC/MS [Method 10]: $R_t$=1.92 min; MS (ESIpos): m/z=590 (M+H)$^+$, $^1$H-NMR (400 MHz, DMSO-d$_6$): δ [ppm]=10.97 (s, 1H), 8.75 (s, 1H), 8.61-8.54 (m, 2H), 8.12 (d, 1H), 8.01-7.93 (m, 2H), 7.79 (s, 2H), 7.76-7.73 (m, 1H), 7.38-7.08 (m, 2H), 6.53 (s, 1H), 5.67-5.58 (m, 1H), 2.24-2.02 (m, 2H), 0.87-0.80 (m, 3H).

Example 253

2-{4-[5-Chloro-2-(4-chloro-1H-1,2,3-triazol-1-yl)phenyl]-5-methoxy-2-oxopyridin-1(2H)-yl}-N-(2-cyanoquinolin-6-yl)butanamide (Racemate)

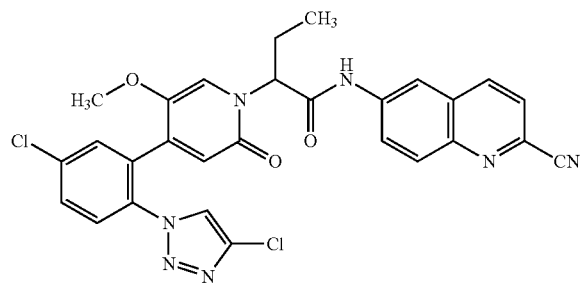 [SMILES: CCC(C(=O)Nc1ccc2nc(C#N)ccc2c1)n1cc(OC)c(-c2cc(Cl)ccc2-n2cc(Cl)nn2)cc1=O]

100.0 mg (0.24 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 60.0 mg (0.35 mmol) of 6-aminoquinoline-2-carbonitrile in 1.0 ml of pyridine were reacted according to General Method 5. Yield: 103 mg (75% of theory).

LC/MS [Method 10]: $R_t$=1.95 min; MS (ESIpos): m/z=574 (M+H)$^+$, $^1$H-NMR (400 MHz, DMSO-d$_6$): δ [ppm]=10.98 (s, 1H), 8.67-8.54 (m, 3H), 8.12 (d, 1H), 8.01-7.93 (m, 2H), 7.83-7.71 (m, 3H), 7.22 (s, 1H), 6.49 (s, 1H), 5.69-5.58 (m, 1H), 2.26-2.04 (m, 2H), 0.91-0.80 (m, 3H).

Example 254

2-{4-[5-Chloro-2-(4-chloro-1H-1,2,3-triazol-1-yl)phenyl]-5-methoxy-2-oxopyridin-1(2H)-yl}-N-[2-(2-hydroxyethyl)-2H-indazol-5-yl]butanamide (Racemate)

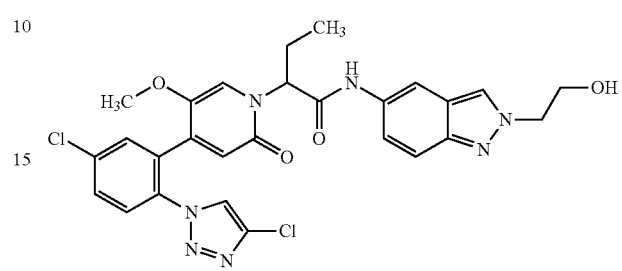

50.0 mg (0.12 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 25.1 mg (0.14 mmol) of 2-(5-amino-2H-indazol-2-yl)ethanol in 0.5 ml of pyridine were reacted according to General Method 5. Yield: 24 mg (35% of theory).

LC/MS [Method 10]: $R_t$=1.52 min; MS (ESIpos): m/z=582 (M+H)$^+$,

H-NMR (600 MHz, DMSO-d$_6$): δ [ppm]=10.37 (s, 1H), 8.64 (s, 1H), 8.27 (s, 1H), 8.13 (s, 1H), 7.82-7.73 (m, 3H), 7.56 (d, 1H), 7.31-7.26 (m, 1H), 7.24 (s, 1H), 6.48 (s, 1H), 5.66-5.57 (m, 1H), 4.97 (br s, 1H), 4.45-4.37 (m, 2H), 3.89-3.82 (m, 2H), 3.32 (s, 3H), 2.18-1.99 (m, 2H), 0.87-0.79 (m, 3H).

Example 255

2-[4-{5-Chloro-2-[4-(difluoromethyl)-1H-1,2,3-triazol-1-yl]phenyl}-5-methoxy-2-oxopyridin-1(2H)-yl]-N-[2-(2-hydroxyethyl)-2H-indazol-5-yl]butanamide (Racemate)

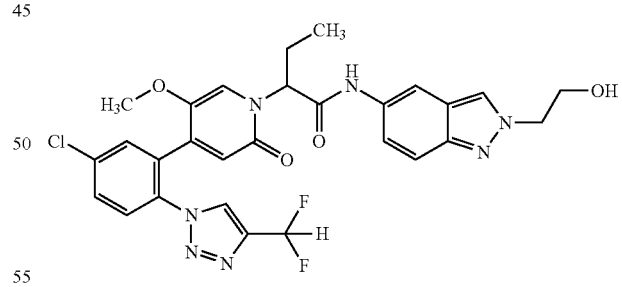

50.0 mg (0.11 mmol) of 2-[4-{5-chloro-2-[4-(difluoromethyl)-1H-1,2,3-triazol-1-yl]phenyl}-5-methoxy-2-oxopyridin-1(2H)-yl]butanoic acid (racemate) and 24.2 mg (0.14 mmol) of 2-(5-amino-2H-indazol-2-yl)ethanol in 0.5 ml of pyridine were reacted according to General Method 5. Yield: 26 mg (38% of theory).

LC/MS [Method 10]: $R_t$=1.51 min; MS (ESIpos): m/z=598 (M+H)$^+$, $^1$H-NMR (600 MHz, DMSO-d$_6$): δ [ppm]=10.37 (s, 1H), 8.75 (s, 1H), 8.27 (s, 1H), 8.12 (d, 1H), 7.82-7.77 (m, 2H), 7.75 (s, 1H), 7.56 (d, 1H), 7.34-7.12 (m, 3H), 6.51 (s, 1H), 5.64-5.56 (m, 1H), 5.01-4.94 (m, 1H), 4.44-4.38 (m, 2H), 3.89-3.83 (m, 2H), 3.26 (s, 3H), 2.16-1.96 (m, 2H), 0.85-0.77 (m, 3H).

Example 256

2-{4-[5-Chloro-2-(4-chloro-1H-1,2,3-triazol-1-yl)phenyl]-5-methoxy-2-oxopyridin-1(2H)-yl}-N-[3-(trifluoromethyl)-1H-indazol-5-yl]butanamide (Racemate)

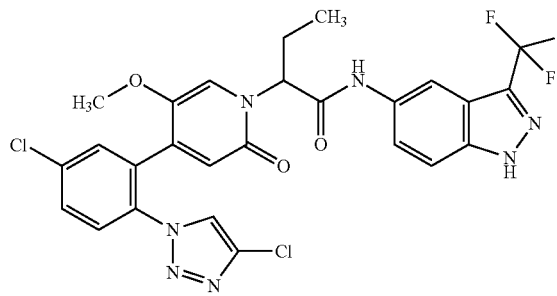

50.0 mg (0.12 mmol) of 2-{4-[5-chloro-2-(4-chloro-1H-1,2,3-triazol-1-yl)phenyl]-5-methoxy-2-oxopyridin-1(2H)-yl}butanoic acid (racemate) and 44.6 mg (0.18 mmol) of 3-(trifluoromethyl)-1H-indazol-5-amine in 1.0 ml of pyridine were reacted according to General Method 5. Yield: 44 mg (61% of theory).

LC/MS [Method 10]: $R_t$=1.92 min; MS (ESIneg): m/z=604 (M−H)⁻,

¹H-NMR (400 MHz, DMSO-d$_6$): δ [ppm]=13.96 (br s, 1H), 10.61 (s, 1H), 8.61 (s, 1H), 8.31 (s, 1H), 7.82-7.72 (m, 3H), 7.71-7.66 (m, 1H), 7.61-7.55 (m, 1H), 7.22 (s, 1H), 6.47 (s, 1H), 5.62-5.55 (m, 1H), 3.33 (s, 3H), 2.21-2.02 (m, 2H), 0.88-0.80 (m, 3H).

Example 257

(2S)-2-{4-[5-Chloro-2-(4-chloro-1H-1,2,3-triazol-1-yl)phenyl]-5-methoxy-2-oxopyridin-1(2H)-yl}-4,4-difluoro-N-(quinoxalin-6-yl)butanamide (Enantiomer 2)

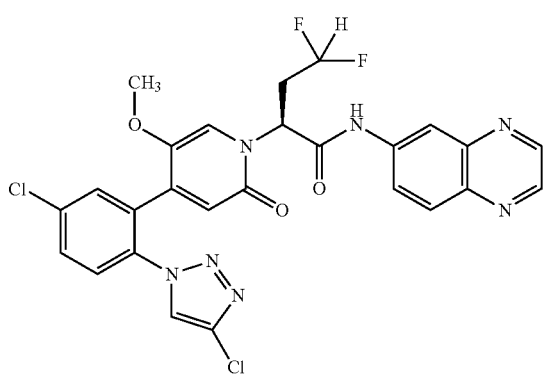 [SMILES: COc1cn([C@@H](CC(F)F)C(=O)Nc2ccc3nccnc3c2)c(=O)cc1-c1cc(Cl)ccc1-n1cc(Cl)nn1]

Enantiomer separation of 32 mg of 2-{4-[5-chloro-2-(4-chloro-1H-1,2,3-triazol-1-yl)phenyl]-5-methoxy-2-oxopyridin-1(2H)-yl}-4,4-difluoro-N-(quinoxalin-6-yl)butanamide (racemate) gave 9 mg of enantiomer 1 (chiral HPLC: $R_t$=2.2 min) and 10 mg of the title compound (enantiomer 2): chiral HPLC: $R_t$=4.9 min; 100% ee.

Separating method: column: Daicel Chiralpak OJ-H SFC 5 μm, 250 mm×20 mm; mobile phase: carbon dioxide 75%/methanol 25%; temperature: 40° C.; flow rate: 80 ml/min; pressure: 100 bar; UV detection: 210 nm.

Analysis: column: Daicel OJ SFC 3 μm, 100 mm×4.6 mm; mobile phase: 80% carbon dioxide, 20% methanol; flow rate: 3 ml/min; UV detection: 210 nm.

LC/MS [Method 1]: $R_t$=0.91 min; MS (ESIpos): m/z=586 [M+H]⁺.

Example 258

4-({2-[4-{5-Chloro-2-[4-(trifluoromethyl)-1H-1,2,3-triazol-1-yl]phenyl}-5-methoxy-2-oxopyridin-1(2H)-yl]pentanoyl}amino)-2-fluorobenzamide (Racemate)

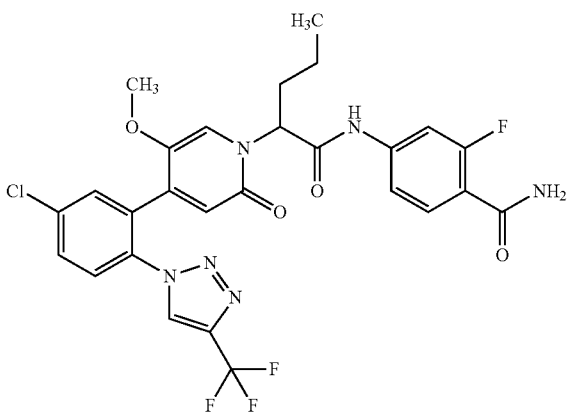 [SMILES: CCCC(C(=O)Nc1ccc(C(N)=O)c(F)c1)n1cc(OC)c(-c2cc(Cl)ccc2-n2cc(C(F)(F)F)nn2)cc1=O]

300 mg (71% purity, 0.45 mmol) of 2-[4-{5-chloro-2-[4-(trifluoromethyl)-1H-1,2,3-triazol-1-yl]phenyl}-5-methoxy-2-oxopyridin-1(2H)-yl]pentanoic acid (racemate) were dissolved in 2.4 ml pyridine and then 430 μl (0.72 mmol) propylphosphonic anhydride (T3P, 50% solution in ethyl acetate) were added. The mixture was heated to 40° C. and then 91 mg (0.59 mmol) of 4-amino-2-fluorobenzamide were added. The reaction mixture was stirred additional 10 min at 40° C. and then brought to room temperature. The mixture was diluted with 2 ml DMF and purified by preparative RP-HPLC (0.1% formic acid/acetonitrile gradient). Yield: 184 mg (67% of theory).

LC/MS [Method 10]: $R_t$=1.81 min; MS (ESIpos): m/z=607 (M+H)⁺,

¹H-NMR (400 MHz, DMSO-d$_6$): δ [ppm]=10.76 (br s, 1H), 9.11 (s, 1H), 7.87-7.80 (m, 2H), 7.79-7.77 (m, 1H), 7.72-7.60 (m, 2H), 7.57-7.49 (m, 2H), 7.37 (dd, 1H), 7.14 (s, 1H), 6.52 (s, 1H), 5.68-5.59 (m, 1H), 3.26 (s, 3H), 2.17-1.94 (m, 2H), 1.23-1.09 (m, 2H), 0.94-0.85 (m, 3H).

Example 259

4-({(2S)-2-[4-{5-Chloro-2-[4-(trifluoromethyl)-1H-1,2,3-triazol-1-yl]phenyl}-5-methoxy-2-oxopyridin-1(2H)-yl]pentanoyl}amino)-2-fluorobenzamide (Enantiomer 2)

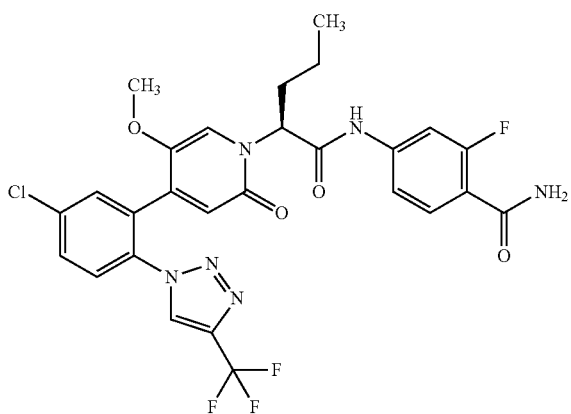 [SMILES: CCC[C@@H](C(=O)Nc1ccc(C(N)=O)c(F)c1)n1cc(OC)c(-c2cc(Cl)ccc2-n2cc(C(F)(F)F)nn2)cc1=O]

Enantiomer separation of 4-({2-[4-{5-chloro-2-[4-(trifluoromethyl)-1H-1,2,3-triazol-1-yl]phenyl}-5-methoxy-2-oxopyridin-1(2H)-yl]pentanoyl}amino)-2-fluorobenzamide (177 mg, 0.292 mmol) (racemate) (Example 258) gave 82 mg of enantiomer 1 (analysis chiral HPLC: $R_t$=1.15 min) and 72 mg of the title compound Example 259 (enantiomer 2): analysis chiral HPLC: $R_t$=1.75 min; 100% ee.

Separating method: column: Daicel Chiralpak AD-H SFC 5 μm 250 mm×20 mm; mobile phase: carbon dioxide 75%/ethanol 25%; temperature: 40° C.; flow rate: 80 ml/min; pressure: 100 bar; UV detection: 210 nm.

Analysis: column: Chiralpak AD SFC 3 μm, 100 mm×4.6 mm; mobile phase: 75% carbon dioxide, 25% ethanol; flow rate: 3 ml/min; UV detection: 210 nm.

LC/MS (Method 10): $R_t$=1.81 min; MS (ESIpos): m/z=607 [M+H]$^+$.

B) ASSESSMENT OF PHYSIOLOGICAL EFFICACY

The suitability of the compounds according to the invention for treating thromboembolic disorders can be demonstrated in the following assay systems:

a) Test Descriptions (In Vitro)

a.1) Measurement of FXIa Inhibition

The factor XIa inhibition of the substances according to the invention is determined using a biochemical test system which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 μM to 0.0078 μM; resulting final concentrations in the test: 50 μM to 0.00013 μM). In each case 1 μl of the diluted substance solutions is placed into the wells of white microtitre plates from Greiner (384 wells). 20 μl of assay buffer (50 mM of Tris/HCl pH 7.4; 100 mM of sodium chloride; 5 mM of calcium chloride; 0.1% of bovine serum albumin) and 20 μl of factor XIa from Kordia (0.45 nM in assay buffer) are then added successively. After 15 min of incubation, the enzyme reaction is started by addition of 20 μl of the factor XIa substrate Boc-Glu(OBzl)-Ala-Arg-AMC dissolved in assay buffer (10 μM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table A below (some as mean values from multiple independent individual determinations):

TABLE A

| Example No. | $IC_{50}$ [nM] | Example No. | $IC_{50}$ [nM] |
| --- | --- | --- | --- |
| 1 | 1.8 | 2 | 9.6 |
| 3 | 4.1 | 4 | 3.6 |
| 5 | 1.6 | 6 | 1.1 |
| 7 | 0.4 | 8 | 9.6 |
| 9 | 2.9 | 10 | 4.0 |
| 11 | 4.5 | 12 | 4.5 |
| 13 | 4.3 | 14 | 9.0 |
| 15 | 1.3 | 16 | 9.9 |
| 17 | 22 | 18 | 15 |
| 19 | 0.26 | 20 | 0.34 |
| 21 | 1.3 | 22 | 3.7 |
| 23 | 1.8 | 24 | 88 |
| 25 | 39 | 26 | 10 |
| 27 | 0.7 | 28 | 5.7 |
| 29 | 37 | 30 | 4.0 |
| 31 | 4.1 | 32 | 4.7 |
| 33 | 2.1 | 34 | 6.1 |
| 35 | 0.83 | 36 | 1.4 |
| 37 | 3.1 | 38 | 1.9 |
| 39 | 4.3 | 40 | 11 |
| 41 | 16 | 42 | 2.5 |
| 43 | 2.3 | 44 | 2.6 |
| 45 | 1.5 | 46 | 0.53 |
| 47 | 4.3 | 48 | 1.0 |
| 49 | 0.36 | 50 | 17 |
| 51 | 1.5 | 52 | 3.4 |
| 53 | 1.7 | 54 | 4.8 |
| 55 | 3.2 | 56 | 4.7 |
| 57 | 2.7 | 58 | 1.8 |
| 59 | 4.8 | 60 | 1.8 |
| 61 | 5.9 | 62 | 3.2 |
| 63 | 22 | 64 | 22 |
| 65 | 20 | 66 | 8.2 |
| 67 | 1.2 | 68 | 4.4 |
| 69 | 6.4 | 70 | 2.7 |
| 71 | 4.0 | 72 | 4.5 |
| 73 | 5.3 | 74 | 4.6 |
| 75 | 2.1 | 76 | 2.6 |
| 77 | 3.7 | 78 | 3.0 |
| 79 | 1.6 | 80 | 1.3 |
| 81 | 6.0 | 82 | 6.3 |
| 83 | 2.8 | 84 | 5.7 |
| 85 | 1.8 | 86 | 1.1 |
| 87 | 4.7 | 88 | 7.4 |
| 89 | 7.2 | 90 | 0.92 |
| 91 | 3.2 | 92 | 7.8 |
| 93 | 9.9 | 94 | 1.4 |
| 95 | 3.7 | 96 | 6.0 |
| 97 | 39 | 98 | 22 |
| 99 | 0.96 | 100 | 1.1 |
| 101 | 1.0 | 102 | 1.4 |
| 103 | 1.5 | 104 | 3.7 |
| 105 | 14 | 106 | 18 |
| 107 | 22 | 108 | 15 |
| 109 | 3.6 | 110 | 21 |
| 111 | 8.3 | 112 | 0.36 |
| 113 | 0.55 | 114 | 0.31 |
| 115 | 0.46 | 116 | 0.66 |

TABLE A-continued

| Example No. | IC$_{50}$ [nM] | Example No. | IC$_{50}$ [nM] |
|---|---|---|---|
| 117 | 0.56 | 118 | 0.26 |
| 119 | 0.50 | 120 | 0.34 |
| 121 | 6.1 | 122 | 3.6 |
| 123 | 1.4 | 124 | 5.7 |
| 125 | 2.3 | 126 | 1.4 |
| 127 | 2.1 | 128 | 1.3 |
| 129 | 2.1 | 130 | 0.84 |
| 131 | 33 | 132 | 15 |
| 133 | 38 | 134 | 18 |
| 135 | 30 | 136 | 0.72 |
| 137 | 0.84 | 138 | 0.36 |
| 139 | 0.59 | 140 | 0.76 |
| 141 | 0.71 | 142 | 0.71 |
| 143 | 3.0 | 144 | 4.7 |
| 145 | 2.1 | 146 | 2.0 |
| 147 | 2.7 | 148 | 2.0 |
| 149 | 13 | 150 | 12 |
| 151 | 6.7 | 152 | 6.2 |
| 153 | 16 | 154 | 2.0 |
| 155 | 9.2 | 156 | 15 |
| 157 | 8.1 | 158 | 7.6 |
| 159 | 24 | 160 | 2.7 |
| 161 | 2.9 | 162 | 1.4 |
| 163 | 0.70 | 164 | 1.9 |
| 165 | 0.86 | 166 | 0.62 |
| 167 | 1.4 | 168 | 0.78 |
| 169 | 1.4 | 170 | 0.55 |
| 171 | 1.6 | 172 | 0.82 |
| 173 | 3.9 | 174 | 2.9 |
| 175 | 6.4 | 176 | 4.2 |
| 177 | 7.7 | 178 | 9.4 |
| 179 | 5.6 | 180 | 1.2 |
| 181 | 1.7 | 182 | 3.1 |
| 183 | 2.7 | 184 | 1.4 |
| 185 | 0.75 | 186 | 0.65 |
| 187 | 1.1 | 188 | 1.7 |
| 189 | 0.73 | 190 | 0.65 |
| 191 | 1.9 | 192 | 4.6 |
| 193 | 10 | 194 | 5.9 |
| 195 | 10 | 196 | 3.6 |
| 197 | 6.5 | 198 | 4.6 |
| 199 | 1.3 | 200 | 1.1 |
| 201 | 1.1 | 202 | 1.7 |
| 203 | 11 | 204 | 3.5 |
| 205 | 17 | 206 | 5.0 |
| 207 | 2.0 | 208 | 1.9 |
| 209 | 1.7 | 210 | 0.78 |
| 211 | 1.4 | 212 | 0.98 |
| 213 | 3.8 | 214 | 2.8 |
| 215 | 4.6 | 216 | 7.6 |
| 217 | 1.7 | 218 | 2.2 |
| 219 | 6.5 | 220 | 3.5 |
| 221 | 1.0 | 222 | 1.2 |
| 223 | 1.3 | 224 | 3.4 |
| 225 | 1.0 | 226 | 1.8 |
| 227 | 1.8 | 228 | 1.6 |
| 229 | 1.1 | 230 | 2.8 |
| 231 | 1.1 | 232 | 1.1 |
| 233 | 0.79 | 234 | 1.5 |
| 235 | 0.92 | 236 | 1.8 |
| 237 | 0.89 | 238 | 10 |
| 239 | 0.89 | 240 | 0.64 |
| 241 | 0.98 | 242 | 0.89 |
| 243 | 0.87 | 244 | 0.65 |
| 245 | 2.0 | 246 | 1.7 |
| 247 | 6.9 | 248 | 7.9 |
| 249 | 4.1 | 250 | 1.3 |
| 251 | 0.74 | 252 | 3.0 |
| 253 | 2.3 | 254 | 0.81 |
| 255 | 1.7 | 256 | 6.3 |
| 257 | 0.85 | 258 | 4.6 | a.2) Determination of the Selectivity

To demonstrate the selectivity of the substances with respect to FXIa inhibition, the test substances are examined for their inhibition of other human serine proteases, such as factor Xa, trypsin and plasmin. To determine the enzymatic activity of factor Xa (1.3 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of NaCl, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 µmol/l of Boc-Ile-Glu-Gly-Arg-AMC from Bachem for factor Xa and trypsin, 50 µmol/l of MeOSuc-Ala-Phe-Lys-AMC from Bachem for plasmin). After an incubation time of 30 min at 22° C., fluorescence is measured (excitation: 360 nm, emission: 460 nm). The measured emissions of the test mixtures with test substance are compared to the control mixtures without test substance (only dimethyl sulphoxide instead of test substance in dimethyl sulphoxide) and IC$_{50}$ values are calculated from the concentration/activity relationships.

a.3) Thrombin Generation Assay (Thromboramn)

The effect of the test substances on the thrombogram (thrombin generation assay according to Hemker) is determined in vitro in human plasma (Octaplas® from Octapharma).

In the thrombin generation assay according to Hemker, the activity of thrombin in coagulating plasma is determined by measuring the fluorescent cleavage products of the substrate I-1140 (Z-Gly-Gly-Arg-AMC, Bachem). The reactions are carried out in the presence of varying concentrations of test substance or the corresponding solvent. To start the reaction, reagents from Thrombinoscope (30 pM or 0.1 pM recombinant tissue factor, 24 µM phospholipids in HEPES) are used. In addition, a thrombin calibrator from Thrombinoscope is used whose amidolytic activity is required for calculating the thrombin activity in a sample containing an unknown amount of thrombin. The test is carried out according to the manufacturer's instructions (Thrombinoscope BV): 4 µl of test substance or of the solvent, 76 µl of plasma and 20 µl of PPP reagent or thrombin calibrator are incubated at 37° C. for 5 min. After addition of 20 µl of 2.5 mM thrombin substrate in 20 mM Hepes, 60 mg/ml of BSA, 102 mM of calcium chloride, the thrombin generation is measured every 20 s over a period of 120 min. Measurement is carried out using a fluorometer (Fluoroskan Ascent) from Thermo Electron fitted with a 390/460 nm filter pair and a dispenser.

Using the Thrombinoscope software, the thrombogram is calculated and represented graphically. The following parameters are calculated: lag time, time to peak, peak, ETP (endogenous thrombin potential) and start tail.

a.4) Determination of Anticoagulatory Activity

The anticoagulatory activity of the test substances is determined in vitro in human plasma and rat plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions is placed into the wells of white microtitre plates from Greiner (384 wells). 20 µl of assay buffer (50 mM Tris/HCl pH 7.4; 100 mM sodium chloride solution; 5 mM of calcium chloride solution; 0.1% of bovine serum albumin) and 20 µl of plasma kallikrein from Kordia (0.6 nM in assay buffer) are then added successively. After 15 min of incubation, the enzyme reaction is started by addition of 20 µl of the substrate H-Pro-Phe-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table B below (some as mean values from multiple independent individual determinations):

TABLE B

| Example No. | $IC_{50}$ [nM] | Example No. | $IC_{50}$ [nM] |
| --- | --- | --- | --- |
| 1 | 41 | 2 | 29 |
| 3 | 110 | 4 | 53 |
| 5 | 53 | 6 | 31 |
| 7 | 13 | 8 | 21 |
| 9 | 11 | 10 | 21 |
| 11 | 19 | 12 | 34 |
| 13 | 34 | 14 | 85 |
| 15 | 85 | 16 | 99 |
| 17 | 500 | 18 | 150 |
| 19 | 1.1 | 20 | 1.4 |
| 21 | 69 | 22 | 31 |
| 23 | 12 | 24 | 360 |
| 25 | 170 | 26 | 510 |
| 27 | 18 | 28 | 20 |
| 29 | 870 | 30 | 11 |
| 31 | 21 | 32 | 51 |
| 33 | 170 | 34 | 140 |
| 35 | 83 | 36 | 96 |
| 37 | 100 | 38 | 46 |
| 39 | 570 | 40 | 130 |
| 41 | 220 | 42 | 24 |
| 43 | 18 | 44 | 18 |
| 45 | 28 | 46 | 15 |
| 47 | 25 | 48 | 49 |
| 49 | 17 | 50 | 95 |
| 51 | 56 | 52 | 19 |
| 53 | 37 | 54 | 44 |
| 55 | 12 | 56 | 26 |
| 57 | 8.7 | 58 | 47 |
| 59 | 15 | 60 | 6.6 |
| 61 | 15 | 62 | 140 |
| 63 | 170 | 64 | 180 |
| 65 | 93 | 66 | 43 |
| 67 | 45 | 68 | 51 |
| 69 | 58 | 70 | 21 |
| 71 | 35 | 72 | 18 |
| 73 | 110 | 74 | 98 |
| 75 | 28 | 76 | 23 |
| 77 | 47 | 78 | 14 |
| 79 | 9.8 | 80 | 78 |
| 81 | 100 | 82 | 67 |
| 83 | 21 | 84 | 49 |
| 85 | 9.6 | 86 | 88 |
| 87 | 41 | 88 | 110 |
| 89 | 58 | 90 | 54 |
| 91 | 25 | 92 | 24 |
| 93 | 87 | 94 | 40 |
| 95 | 51 | 96 | 230 |
| 97 | 190 | 98 | 100 |
| 99 | 3.2 | 100 | 5.0 |
| 101 | 6.0 | 102 | 4.4 |
| 103 | 4.3 | 104 | 250 |
| 105 | 47 | 106 | 85 |
| 107 | 200 | 108 | 67 |
| 109 | 180 | 110 | 330 |
| 111 | 120 | 112 | 2.9 |
| 113 | 3.7 | 114 | 1.3 |
| 115 | 1.9 | 116 | 1.8 |
| 117 | 0.97 | 118 | 0.57 |
| 119 | 1.1 | 120 | 0.78 |
| 121 | 39 | 122 | 16 |
| 123 | 4.5 | 124 | 24 |
| 125 | 13 | 126 | 3.8 |
| 127 | 7.5 | 128 | 4.6 |
| 129 | 6.8 | 130 | 3.1 |
| 131 | 250 | 132 | 110 |
| 133 | 460 | 134 | 45 |
| 135 | 380 | 136 | 2.5 |
| 137 | 2.1 | 138 | 1.8 |
| 139 | 1.0 | 140 | 1.5 |
| 141 | 1.4 | 142 | 11 |
| 143 | 21 | 144 | 30 |
| 145 | 7.3 | 146 | 5.6 |
| 147 | 13 | 148 | 200 |
| 149 | 210 | 150 | 210 |
| 151 | 71 | 152 | 40 |
| 153 | 270 | 154 | 170 |
| 155 | 140 | 156 | 170 |
| 157 | 65 | 158 | 32 |
| 159 | 230 | 160 | 18 |
| 161 | 14 | 162 | 5.9 |
| 163 | 1.7 | 164 | 8.2 |
| 165 | 3.2 | 166 | 20 |
| 167 | 6.3 | 168 | 2.1 |
| 169 | 3.8 | 170 | 1.5 |
| 171 | 9.6 | 172 | 1.7 |
| 173 | 5.9 | 174 | 15 |
| 175 | 38 | 176 | 14 |
| 177 | 43 | 178 | 24 |
| 179 | 260 | 180 | 71 |
| 181 | 31 | 182 | 19 |
| 183 | 9.6 | 184 | 9.0 |
| 185 | 1.5 | 186 | 3.0 |
| 187 | 2.7 | 188 | 5.4 |
| 189 | 1.0 | 190 | 9.4 |
| 191 | 7.9 | 192 | 32 |
| 193 | 56 | 194 | 23 |

TABLE B-continued

| Example No. | IC$_{50}$ [nM] | Example No. | IC$_{50}$ [nM] |
|---|---|---|---|
| 195 | 72 | 196 | 11 |
| 197 | 34 | 198 | 20 |
| 199 | 3.6 | 200 | 2.4 |
| 201 | 2.2 | 202 | 9.8 |
| 203 | 29 | 204 | 10 |
| 205 | 47 | 206 | 24 |
| 207 | 3.5 | 208 | 4.4 |
| 209 | 9.1 | 210 | 3.5 |
| 211 | 5.4 | 212 | 1.5 |
| 213 | 12 | 214 | 21 |
| 215 | 20 | 216 | 10 |
| 217 | 4.9 | 218 | 10 |
| 219 | 43 | 220 | 14 |
| 221 | 2.8 | 222 | 2.4 |
| 223 | 3.6 | 224 | 4.6 |
| 225 | 3.5 | 226 | 6.0 |
| 227 | 6.0 | 228 | 2.9 |
| 229 | 3.9 | 230 | 17 |
| 231 | 3.3 | 232 | 5.2 |
| 233 | 3.5 | 234 | 14 |
| 235 | 5.7 | 236 | 5.8 |
| 237 | 2.4 | 238 | 850 |
| 239 | 6.9 | 240 | 3.5 |
| 241 | 6.0 | 242 | 5.4 |
| 243 | 1.7 | 244 | 1.4 |
| 245 | 5.8 | 246 | 7.8 |
| 247 | 17 | 248 | 21 |
| 249 | 7.6 | 250 | 4.7 |
| 251 | 4.6 | 252 | 11 |
| 253 | 6.8 | 254 | 3.5 |
| 255 | 8.9 | 256 | 17 |
| 257 | 2.7 | 258 | 34 | a.6) Determination of Endothelium Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, N.Y.), it is possible to measure continuously variations in the transendothelial electrical resistance (TEER) across an endothelial cell monolayer plated over gold electrodes. HUVECs are sown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1 \times 10^{-10}$ to $1 \times 10^{-6}$ M.

a.7) Determination of the In Vitro Permeability of Endothelial Cells

In a further hyperpermeability model, the activity of the substances on the modulation of macromolecular permeability is determined. HUVECs are sown on a fibronectin-coated Transwell filter membrane (24-well plates, 6.5 mm insert with 0.4 µM polycarbonate membrane; Costar #3413). The filter membrane separates the upper from the lower cell culture space, with the confluent endothelial cell layer on the floor of the upper cell culture space. 250 g/ml of 40 kDa FITC dextan (Invitrogen, D1844) are added to the medium of the upper chamber. Hyperpermeability of the monolayer is induced by stimulation with kininogen, prekallikrein and factor XII (100 nM each). Every 30 min, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1 \times 10^{-10}$ to $1 \times 10^{-6}$ M.

b) Determination of Antithrombotic Activity (In Vivo)

b.1) Arterial Thrombosis Model (Iron(II) Chloride-Induced Thrombosis) in Combination with Ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined.

Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the vessel injury is then caused by wrapping a piece of filter paper (10 mm×10 mm) on a Parafilm® strip (25 mm×12 mm) around the carotid artery without disturbing the blood flow. The filter paper contains 100 µL of a 13% strength solution of iron(II) chloride (Sigma) in water. After 5 min, the filter paper is removed and the vessel is rinsed twice with aqueous 0.9% strength sodium chloride solution. 30 min after the injury the injured region of the carotid artery is extracted surgically and any thrombotic material is removed and weighed.

The test substances are administered either intravenously to the anaesthetized animals via the femoral vein or orally to the awake animals via gavage, in each case 5 min and 2 h, respectively, before the injury.

Ear bleeding time is determined 2 min after injury to the carotid artery. To this end, the left ear is shaved and a defined 3-mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Oedema Formation and/or Neovascularization in the Eye (In Vivo)

c.1) Test of the Efficacy of Substances in the Laser-Induced Choroidal Neovascularization Model This study serves to investigate the efficacy of a test substance on reduction of extravasation/oedema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine). Following instillation of a drop of a 0.5% strength tropicamide solution to dilate the pupils, choroidal neovascularization is triggered on six defined locations around the optical nerve using a 532 nm argon laser photocoagulator (diameter 50-75 nm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 min later, pictures of the eye background are taken. The degree of extravasation/the oedema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and $\mu m^3$, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57Bl/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% Formalin. After washing in phosphate-buffered saline, the retina is excised, a flat preparation thereof is produced and this is stained with isolectin B4 antibody. Quantification of neovascularization is carried out using a Zeiss ApoTome.

d) Determination of Permeability (Caco Assay)

The Caco cells (obtained from the Deutsche Sammlung für Mikroorganismen and Zellkulturen, DSMZ) are cultivated in 24-well Transwell plates for 15 or 16 days. The test is carried out using a Hamilton robot. The density of the cell monolayers is ensured by measuring the Lucifer yellow permeability. The test compounds are dissolved in DMSO and then diluted with assay buffer to a concentration of 2 $\mu M$ (final DMSO concentration 1%). The permeability is examined in both directions by addition of the substance solutions to the apical or basolateral compartment. The covered plates are incubated at 37° C. for 2 hours. The concentrations in the two compartments are determined by LC-MS/MS and the Papp values are calculated according to Artursson and Karlsson (PMID: 1673839).

e) Determination of Pharmacokinetic Parameters Following Intravenous Administration To examine the pharmacokinetic properties of a test substance, the respective test substances are administered to animals as a bolus injection, infusion or via oral administration. In the case of rats, the preferred formulation for intravenous administration of the test substances is plasma/dimethyl sulphoxide in a ratio of 99:1. The infusion solution of the test substance in the case of dogs and monkeys consists of polyethylene glycol/ethanol/water in a ratio of 50/10/40. Formulations for oral administration can be polyethylene glycol/ethanol/water or solutol/ethanol/water in a ratio of 50/10/40, or other formulations as appropriate (e.g. water, tylose, self-emulsifying drug dispering systems, etc.). The administration volume for rats is 2-10 ml/kg, for dogs and monkeys 0.5-5 ml/kg.

Blood samples are removed from the test animals into sodium EDTA (or other anticoagulant)-containing tubes: in the case of bolus administration, blood samples are usually taken at 0.033, 0.083, 0.167, 0.25, 0.283, 0.333, 0.5, 0.75, 1, 2, 3, 5, 7, 24 hours after administration of the test substance. In the case of infusions, blood samples are usually taken at 0.083, 0.167, 0.25, 0.283, 0.333, 0.5, 0.75, 1, 2, 3, 5, 7, 24 hours after administration of the test substance. In the case of oral administration, blood samples are usually taken at 0.083, 0.25, 0.5, 0.75, 1, 2, 3, 5, 7, 24 hours after administration of the test substance. Other time points might be chosen as appropriate.

After removal, the blood samples are centrifuged at 1280 g for 10 minutes. The supernatant (plasma) is taken off and either directly processed further or frozen for later sample preparation. For sample preparation, 50 µl of plasma are mixed with 250 µl of acetonitrile (the precipitating agent acetonitrile also contains the internal standard ISTD for later analytical determination) and then allowed to stand at room temperature for 5 minutes. The mixture is then centrifuged at 16 000 g for 3 minutes. The supernatant is taken off, and 500 µl of a buffer suitable for the mobile phase are added. The samples are then examined by LC-MS/MS analysis (e.g. liquid chromatography using a Gemini 5 µM C18 110A 50 mm×3 mm (or 150 mm×3 mm) column from Phenomenex; by mass spectrometry using an API 5500 or API 6500; SCIEX, Canada) to determine the concentration of the test substance in the individual samples.

In addition to the the plasma concentrations, the concentration ratio whole blood to plasma for the test substance in question is determined. To this end, the test substance is incubated at a certain concentration in whole blood for 20 minutes. The samples are then processed as described above to determine the concentration of the test substance in the plasma. The concentration set divided by the concentration measured in the plasma gives the parameter Cb/Cp.

The pharmacokinetic parameters are calculated by non-compartmental analysis (NCA). The algorithms for calculating the parameters are defined in an internal process description and are based on rules published in general textbooks of pharmacokinetics.

The primary pharmacokinetic parameters clearance (CL) and distribution volume (Vss) are calculated as follows:

| Parameter | Formula |
|---|---|
| CLplasma (plasma clearance) | CLplasma = dose/AUC (AUC = area under the curve) |
| CLblood (blood clearance) | CLblood = CLplasma/(Cb/Cp) |
| Vss | Vss = CLplasma * MRTiv |
| MRTiv | MRTiv = AUMC/AUC |
| AUMC | AUMC = AUMC(0-$t_{last}$) + $t_{last}$ * $C_{last,calculated}$/$\lambda_z$ + $C_{last,calculated}$/$\lambda_z^2$ |
| $\lambda_z$ | Rate constant for the terminal phase; calculated from the logarithmic-linear regression of unweighted data from the terminal phase with data points above the detection limit |
| AUC | AUC = AUC(0-tlast) + $C_{last,calculated}$/$\lambda_z$ |
| AUCnorm | AUC divided by dose (mg) per kg body weight |

Pharmacokinetic Parameters from this Test are Listed in Table C Below:

TABLE C

| Example No. | AUCnorm [kg · h/L] rat | CLblood [L/h/kg] rat | AUCnorm [kg · h/L] monkey | CLblood [L/h/kg] monkey |
|---|---|---|---|---|
| 235 | 2.16* | 0.83* | 9.27** | 0.12** |
| 242 | 1.96* | 0.80* | 4.22*** | 0.33*** |

*0.3 mg/kg i.v. bolus;
**0.21 mg/kg i.v. infusion over 15 min;
***0.3 mg/kg i.v. infusion over 15 min For comparative purposes selected compounds described in Int. Pat. Appl. WO02014/154794 and WO2016/046164 were also tested in the FXIa inhibition assay described under a.1) above. The $IC_{50}$ values for FXIa inhibition for these compounds as well as the pharmacokinetic parameters obtained from the assay described under e) above are listed in Table D below:

TABLE D

| Int. Pat. Appl. | Example No. | $IC_{50}$ [nM] | AUCnorm [kg · h/L] rat | CLblood [L/h/kg] rat | AUCnorm [kg · h/L] monkey | CLblood [L/h/kg] monkey |
|---|---|---|---|---|---|---|
| WO2014/154794 | 103 | 0.5 | 1.02* | 1.54* | 0.76*** | 2.33*** |
| WO2016/046164 | 7 | 25 | 0.43* | 2.64* | n.m. | n.m. |
| WO2016/046164 | 24 | 27 | 0.73* | 2.45* | n.m. | n.m. |
| present invention | 235 | 0.92 | 2.16* | 0.83* | 9.27** | 0.12** |
| present invention | 242 | 0.89 | 1.96* | 0.80* | 4.22*** | 0.33*** |

*0.3 mg/kg i.v. bolus;
**0.21 mg/kg i.v. infusion over 15 min;
***0.3 mg/kg i.v. infusion over 15 min;
n.m.: not measured The results shown in Table D demonstrate that the compounds of the present invention are more potent Factor XIa inhibitors and have a lower blood clearance (CLblood) and, correspondingly, a higher AUC norm value than the comparison compounds which results in a longer exposure of such a compound in the blood above the minimal effective concentration within a given dosing interval. Such a profile results in an improved peak-to-trough ratio (quotient of maximum to minimum concentration) within a given dosing interval, which has the advantage that the compound can be administered less frequently and at a significantly lower dose to achieve an effect.

C) WORKING EXAMPLES OF PHARMACEUTICAL COMPOSITIONS

The substances according to the invention can be converted to pharmaceutical preparations as follows:
Tablet:
Composition:
100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.
Production:
The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).
Oral Suspension:
Composition:
1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.
Production:
The Rhodigel is suspended in ethanol, and the compound of Example 1 is added to the suspension. The water is added while stirring. The mixture is stirred for about 6 h until swelling of the Rhodigel is complete.
Solution or Suspension for Topical Administration to the Eye (Eye Drops):
A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkoniumn chloride, thiomersal or phenylmercury nitrate in a concentration range of from 0.001 to 1 percent by weight.

The invention claimed is:
1. A compound of the formula

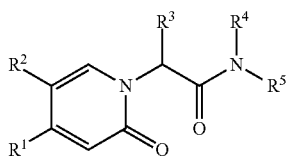

(I)

wherein
R¹ represents a group of the formula

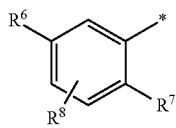

wherein * is the point of attachment to the oxopyridine ring,
R⁶ represents chlorine,
R⁷ represents 1,2,3-triazolyl,
wherein the 1,2,3-triazolyl is substituted by a substituent selected from the group consisting of chlorine, difluoromethyl and trifluoromethyl,
R⁸ represents hydrogen,
R² represents methoxy,
R³ represents methyl, ethyl or n-propyl,
R⁴ represents hydrogen,
R⁵ represents a group of the formula

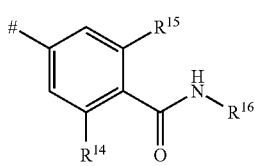

wherein # is the point of attachment to the nitrogen atom,
R¹⁴ represents fluorine,
R¹⁵ represents hydrogen,
R¹⁶ represents hydrogen,
or a salt thereof.
2. A compound according to claim 1, wherein
R¹ represents a group of the formula

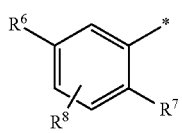

wherein * is the point of attachment to the oxopyridine ring,
R⁶ represents chlorine,
R⁷ represents 1,2,3-triazolyl,
wherein the 1,2,3-triazolyl is substituted by a substituent selected from the group consisting of chlorine and trifluoromethyl,
R⁸ represents hydrogen,
R² represents methoxy,
R³ represents ethyl,
R⁴ represents hydrogen,
R⁵ represents a group of the formula

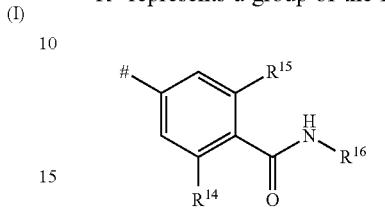

wherein # is the point of attachment to the nitrogen atom,
R¹⁴ represents fluorine,
R¹⁵ represents hydrogen,
R¹⁶ represents hydrogen,
or a salt thereof.
3. 4-({(2S)-2-[4-{5-Chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (enantiomer 2) according to claim 1 of the formula below:

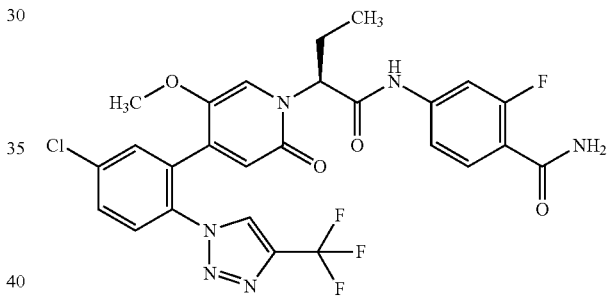

or a salt thereof.
4. 4-{[(2S)-2-{4-[5-Chloro-2-(4-chloro-1H-1,2,3-triazol-1-yl)phenyl]-5-methoxy-2-oxopyridin-1(2H)-yl}butanoyl]amino}-2-fluorobenzamide (enantiomer 2) according to claim 1 of the formula below:

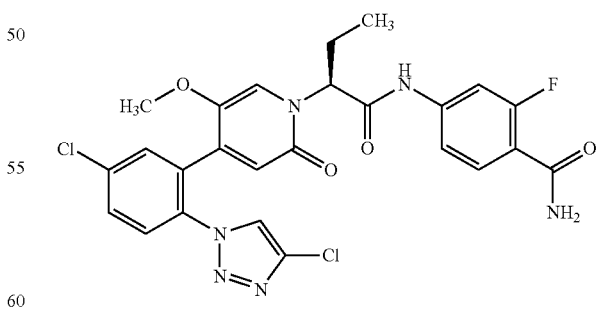

or a salt thereof.
5. A composition comprising a compound according to claim 1 in combination with a pharmaceutically suitable excipient.
6. 4-({(2S)-2-[4-{5-Chloro-2-[4-(trifluoromethyl)-1H-1,2,3-triazol-1-yl]phenyl}-5-methoxy-2-oxopyridin-1(2H)-yl]

butanoyl}amino)-2-fluorobenzamide (enantiomer 2) according to claim 1 of the formula below:

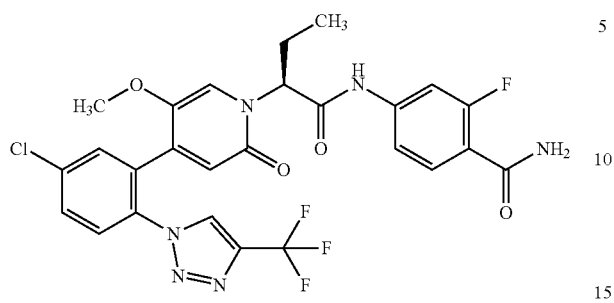

7. A composition comprising a compound according to claim 2 in combination with a pharmaceutically suitable excipient.

8. A composition comprising a compound according to claim 3 in combination with a pharmaceutically suitable excipient.

9. A composition comprising a compound according to claim 4 in combination with a pharmaceutically suitable excipient.

* * * * *